US007348324B2

(12) United States Patent
Imamura et al.

(10) Patent No.: US 7,348,324 B2
(45) Date of Patent: Mar. 25, 2008

(54) CYCLIC AMINE COMPOUNDS AS CCR5 ANTAGONISTS

(75) Inventors: Shinichi Imamura, Osaka (JP); Shohei Hashiguchi, Toyonaka (JP); Taeko Hattori, Osaka (JP); Osamu Nishimura, Kawanishi (JP); Naoyuki Kanzaki, Ibaraki (JP); Masanori Baba, Kagoshima (JP); Yoshihiro Sugihara, Ikoma (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 684 days.

(21) Appl. No.: 10/273,111

(22) Filed: Oct. 18, 2002

(65) Prior Publication Data

US 2003/0114443 A1 Jun. 19, 2003

Related U.S. Application Data

(62) Division of application No. 10/089,374, filed as application No. PCT/JP00/06755 on Sep. 29, 2000, now Pat. No. 6,562,978.

(30) Foreign Application Priority Data

Oct. 1, 1999 (JP) .................................. 11/282088
Feb. 18, 2000 (JP) .................................. 2000/46749

(51) Int. Cl.
| | | |
|---|---|---|
| *A61P 31/18* | (2006.01) | |
| *A61K 31/535* | (2006.01) | |
| *A61K 31/4965* | (2006.01) | |
| *A61K 31/44* | (2006.01) | |
| *A61K 31/47* | (2006.01) | |
| *C07D 413/00* | (2006.01) | |
| *C07D 241/00* | (2006.01) | |
| *C07D 211/00* | (2006.01) | |

(52) U.S. Cl. .............. 514/238.2; 514/249; 514/255.05; 514/293; 514/300; 514/303; 514/312; 514/316; 544/129; 544/336; 544/350; 544/355; 546/82; 546/120; 546/121; 546/187; 546/188; 546/189; 546/190

(58) Field of Classification Search ............ 514/238.2, 514/249, 255.05, 293, 300, 303, 312, 316; 544/129, 336, 350, 355; 546/82, 120, 121, 546/187, 188, 189, 190
See application file for complete search history.

(56) References Cited

U.S. PATENT DOCUMENTS 4,203,988 A 5/1980 Bolhofer et al. ............ 424/266
6,833,457 B1* 12/2004 Miki et al. .................. 546/189

FOREIGN PATENT DOCUMENTS

| JP | 62-89679 | 4/1987 |
|---|---|---|
| WO | 94/22861 | 10/1994 |
| WO | 99/04794 | 2/1999 |
| WO | 99/17773 | 4/1999 |
| WO | 99/38514 | 8/1999 |

OTHER PUBLICATIONS

Singh, No Vaccine Against HIV Yet-Are We Not Perfectly Equipped?, Aug. 29, 2006, Virology Journal, vol. 3, No. 60, pp. 1-7.*
D. Bhuniya et al., "Homochiral Lithium Amides: Enantioselective Deprotonation of Cyclohexene Oxide", Synth. Commun., vol. 24, No. 3, pp. 375-385, 1994.

* cited by examiner

*Primary Examiner*—Brenda L Coleman
(74) *Attorney, Agent, or Firm*—Wenderoth, Lind & Ponack, L.L.P.

(57) ABSTRACT

A compound of formula (I) (wherein $R^1$ is a hydrogen atom, a hydrocarbon group which may be substituted, a non-aromatic heterocyclic group which may be substituted, $R^2$ is a hydrocarbon group which may be substituted, a non-aromatic heterocyclic group which may be substituted, or $R^1$ and $R^2$ may combine to each other together with A to form a heterocyclic group which may be substituted; A is N or $N^+$—$R^5$.$Y^-$ ($R^5$ is a hydrocarbon group; $Y^-$ is a counter anion); $R^3$ is a cyclic hydrocarbon group which may be substituted or a heterocyclic group which may be substituted; n is 0 or 1; $R^4$ is a hydrogen atom, a hydrocarbon group which may be substituted, a heterocyclic group which may be substituted, an alkoxy group which may be substituted, an aryloxy group which may be substituted, or an amino group which may be substituted, E is a divalent aliphatic hydrocarbon group which may be substituted by group(s) other than oxo; $G^1$ is a bond, CO or $SO_2$; $G^2$ is CO, $SO_2$, NHCO, CONH or OCO; J is methine or a nitrogen atom; and each of Q and R is a bond or a divalent $C_{1-3}$ aliphatic hydrocarbon which may be substituted; provided that J is methine when $G_2$ is OCO, that one of Q and R is not a bond when the other is a bond and that each of Q and R is not substituted by oxo group(s) when $G^1$ is a bond) or a salt thereof has a potent CCR5 antagonistic activity and can be advantageously used for the treatment or prevention of infectious disease of various HIV in human (e.g. AIDS).

35 Claims, No Drawings

CYCLIC AMINE COMPOUNDS AS CCR5 ANTAGONISTS

This application is a divisional of Ser. No. 10/089,374 filed Mar. 29, 2002 now U.S. Pat. No. 6,562,978, which is a U.S. national stage of PCT/JP00/06755 filed Sep. 29, 2000.

TECHNICAL FIELD

The present invention relates to cyclic amine compounds, which are useful for the treatment of acquired immunodeficiency syndrome (AIDS), their production and use and pharmaceutical compositions containing them.

BACKGROUND ART

HIV (human immunodeficiency virus) protease inhibitors have been developed for the treatment of AIDS and use of the protease inhibitors in combination with two conventional HIV reverse transcriptase inhibitors has provided further progress in the treatment of AIDS. However, these drugs and their combination use are not sufficient to eradicate AIDS, and new anti-AIDS drugs having different activities and mechanisms are therefore required.

CD4 is a known receptor from which HIV invades a target cell. Recently, CCR5 has been discovered as a second receptor of macrophage-tropic HIV. CCR5 is a G protein-coupled chemokine receptor having seven transmembrane domains. This chemokine receptor is thought to play an essential role in establishment and spread of HIV infection. In fact, it is reported that a person who is resistant to HIV infection in spite of several exposures retains mutation of homo deletion of CCR5 gene. Therefore, a CCR5 antagonist is expected to be a new anti-HIV drug.

As chemokine receptor antagonists, there are known aromatic urea derivatives (J. Biol. Chem., 1998, 273, 10095-10098.), benzodiazepine derivatives (Japanese unexamined patent publication No. 9-249570), cyclam derivatives (Nat. Med., 1998, 4, 72-77.), spiro piperidine derivatives (WO98/25604,25605,), acridine derivatives (WO98/30218), xanthene derivatives (WO98/04554), haloperidol derivatives (J. Biol. Chem., 1998,273,15687-15692., WO98/24325, 02151.), benzazocine-type compound (Japanese unexamined patent publication No. 9-25572), benzimidazole derivatives (WO98/06703), piperazine and diazepine derivatives (WO97/44329), 3-di-substituted piperidine derivatives (Japanese unexamined patent publication No. 9-249566), 4-substituted piperidine derivatives (WO99/04794), substituted pyrrolidine derivatives (WO99/09984, WO99/38514), etc. However, so far, there has been no report that a CCR5 antagonist is developed as a therapeutic agent of AIDS.

DISCLOSURE OF INVENTION

In order to investigate an anti-AIDS drug having CCR5 antagonistic activity, it is necessary to clone CCR5 gene from human tissue derived cDNA library, to ligate said gene with a vector for expression in animal cells, to introduce said gene into animal cells and to obtain cells expressing CCR5. In addition, with using this transformant, it is necessary to screen a compound which strongly inhibits binding of CC chemokine RANTES, natural ligand, to CCR5 (which strongly antagonizes CCR5). However, so far there has been no report on a low molecule compound having CCR5 antagonistic activity.

The present inventors diligently made extensive studies on compounds having CCR5 antagonistic activity and, as a result, they found that a compound shown be the formula (I) or a salt thereof unexpectedly possesses potent CCR5 antagonistic activity and inhibition of HIV infection to human peripheral mononuclear cells (especially AIDS), and also that the compound has superior absorbability when orally administered. Based on the finding, the present invention was accomplished.

More specifically, the present invention relates to:

(1) A compound of the formula:

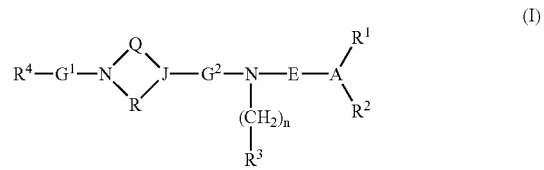

(I)

(wherein $R^1$ is a hydrogen atom, a hydrocarbon group which may be substituted, a non-aromatic heterocyclic group which may be substituted, $R^2$ is a hydrocarbon group which maybe substituted, a non-aromatic heterocyclic group which may be substituted, or $R^1$ and $R^2$ may combine to each other together with A to form a heterocyclic group which may be substituted; A is N or $N^+$—$R^5$. $Y^-$ ($R^5$ is a hydrocarbon group; $Y^-$ is a counter anion); $R^3$ is a cyclic hydrocarbon group which may be substituted or a heterocyclic group which may be substituted; n is 0 or 1; $R^4$ is a hydrogen atom, a hydrocarbon group which may be substituted, a heterocyclic group which may be substituted, an alkoxy group which may be substituted, an aryloxy group which may be substituted, or an amino group which may be substituted, E is a divalent aliphatic hydrocarbon group which may be substituted by a group other than an oxo group; $G^1$ is a bond, CO or $SO_2$; $G^2$ is CO, $SO_2$, NHCO, CONH or OCO; J is methine or a nitrogen atom; and each of Q and R is a bond or a divalent $C_{1-3}$ aliphatic hydrocarbon which may be substituted; provided that J is methine when $G_2$ is OCO, that one of Q and R is not a bond when the other is a bond and that each of Q and R is not substituted by an oxo group when $G^1$ is a bond) or a salt thereof.

(2) A compound as shown in the above (1), wherein $R^1$ is a hydrogen atom, a hydrocarbon group selected from Group 2 which may be substituted by member(s) selected from Group 1, a 3- to 8-membered saturated or unsaturated non-aromatic heterocyclic group which may be substituted by member(s) selected from Group 1; $R^2$ is a hydrocarbon group selected from Group 2 which may be substituted by member(s) selected from Group 1 or a 3- to 8-membered saturated or unsaturated non-aromatic heterocyclic group which may be substituted by member(s) selected from Group 1, or $R^1$ and $R^2$ may combine each other together with A to form a heterocyclic group selected from Group 4 which may be substituted by member(s) selected from Group 3; A is N or $N^+$—$R^5$.$Y^-$ ($Y^-$ is $Cl^-$, $Br^-$, $I^-$, $NO_3^-$, $SO_4^{2-}$, $PO_4^{3-}$ or $CH_3SO_3^-$; $R^5$ is a hydrocarbon group selected from Group 2); $R^3$ is a cyclic hydrocarbon group selected from Group 5 which may be substituted by member(s) selected from Group 1 or a heterocyclic group selected from Group 6 which may be substituted by member(s) selected from Group 1; $R^4$ is a hydrogen atom, a hydrocarbon group selected from Group 2 which may be substituted by member(s) selected from Group 1, a heterocyclic group, selected from Group 6 which may be substituted by member(s) selected from Group 1, a $C_{1-6}$ alkoxy group which may be substituted by member(s) selected from Group 7, a $C_{6-14}$ aryloxy group which may be substituted by member(s) selected from Group 8, an amino group which may be substituted by member(s) selected from Group 9 or a cyclic-amino group selected from Group 10; E is a divalent aliphatic hydrocarbon group selected from Group 12 which may be substituted by member(s) other than oxo group(s) and selected from Group 11; each of Q and R is a bond or a divalent $C_{1-3}$ aliphatic hydrocarbon group selected from Group 13 which may be substituted by member(s) selected from Group 11.

Group 1

(1) a $C_{1-6}$ alkyl group which may be substituted by member(s) selected from Group 14, (2) a $C_{2-6}$ alkenyl group which may be substituted by member(s) selected from Group 14, (3) a $C_{2-6}$ alkynyl group which may be substituted by member(s) selected from Group 14, (4) a $C_{6-14}$ aryl group which may be substituted by member(s) selected from Group 14, (5) a $C_{3-7}$ cycloalkyl group which may be substituted by member(s) selected from Group 14, (6) a $C_{3-6}$ cycloalkenyl group which may be substituted by member(s) selected from Group 14, (7) a heterocyclic group selected from Group 16 which may be substituted by member(s) selected from Group 15, (8) an amino group which may be substituted by a $C_{1-6}$ alkyl-imidoyl(s), formyl-imidoyl(s), amidino(s) or member(s) selected from Group 17, (9) a cyclic-amino group which may be substituted by member(s) selected from Group 10, (10) an imidoyl group which may be substituted by member(s) selected from Group 17, (11) an amidino group which may be substituted by member(s) selected from Group 17, (12) a hydroxyl group which may be substituted by a member selected from Group 17, (13) a thiol group which may be substituted by a member selected from Group 17, (14) a carboxyl group, (15) a $C_{1-6}$ alkoxy-carbonyl group which may be substituted by member(s) selected from Group 18, (16) a $C_{7-12}$ aryloxy-carbonyl group which may be substituted by member(s) selected from Group 18, (17) a $C_{7-10}$ aralkyl-oxy-carbonyl group which may be substituted by member(s) selected from Group 18, (18) a carbamoyl group, (19) a mono-substituted carbamoyl group which may be substituted by a member selected from Group 19, (20) a di-substituted carbamoyl group substituted by a member selected from Group 19 and a member selected from Group 20, (21) a cyclic-aminocarbamoyl group selected from Group 21, (22) a thiocarbamoyl group, (23) a mono-substituted thiocarbamoyl group which may be substituted by a member selected from Group 19, (24) a di-substituted thiocarbamoyl group substituted by a member selected from Group 19 and a member selected from Group 20, (25) a cyclic-aminothiocarbamoyl group which may be substituted by member(s) selected from Group 21, (26) a sulfamoyl group, (27) a N-mono-substituted sulfamoyl group substituted by a member selected from Group 19, (28) a N,N-di-substituted sulfamoyl group substituted by a member selected from Group 19 and a member selected from Group 20, (29) a cyclic-amino-sulfonyl group selected from Group 22, (30) a halogen atom, (31) a cyano group, (32) a nitro group, (33) an acyl group derived from a sulfonic acid selected from Group 22, (34) a formyl group, (35) a $C_{2-6}$ alkanoyl group, (36) a $C_{7-12}$ aryl-carbonyl group, (37) a $C_{1-6}$ alkyl-sulfinyl group which may be substituted by member(s) selected from Group 23 and (38) a $C_{6-14}$ aryl-sulfinyl group which may be substituted by member(s) selected from Group 23

Group 2

(1) a $C_{1-10}$ alkyl group, (2) a $C_{2-6}$ alkenyl group, (3) a $C_{2-6}$ alkynyl group, (4) a $C_{3-9}$ cycloalkyl group which may be condensed with benzene, (5) a $C_{3-6}$ cycloalkenyl group, (6) a $C_{4-6}$ cycloalkadienyl group and (7) a $C_{6-14}$ aryl group Group 3

(1) a hydroxy group, (2) a cyano group, (3) a nitro group, (4) an amino group, (5) an oxo group, (6) a halogen atom and (7) a group represented by the formula: —B$^1$R$^a$ [wherein R$^a$ is a hydrocarbon group selected from Group 2 which maybe substituted by member(s) selected from Group 1, or a heterocyclic group selected from Group 6 which may be substituted by member(s) selected from Group 1, B$^1$ is a bond, —CR$^b$R$^c$—, —COO—, —CO—, —CR$^b$(OH)—, —CR$^b$R$^c$—S—, —CR$^b$R$^c$—SO$_2$—, —CO—NR$^b$—, —CS—NR$^b$—, —CO—S—, —CS—S—, —CO—NR$^b$—CO—NR$^c$—, —C(=NH)—NR$^b$—, —NR$^b$—, —NR$^b$—CO—, —NR$^b$—CS—, —NR$^b$—CO—NR$^c$—, —NR$^b$—CS—NR$^c$—, —NR$^b$—CO—O—, —NR$^b$—CS—O—, —NR$^b$—CO—S—, —NR$^b$—CS—S—, —NR$^b$—C(=NH)—NR$^c$—, —NR$^b$—SO$_2$—, —NR$^b$—NR$^c$—, —O—, —O—CO—, —O—CS—, —O—CO—O, —O—CO—NR$^b$—, —O—C(=NH)—NR$^b$—, —S—, —SO—, —SO$_2$—, —SO$_2$—NR$^b$—, —S—CO—, —S—CS—, —S—CO—NR$^b$—, —S—CS—NR$^b$— and —S—C(=NH)—NR$^b$— (wherein each of R$^b$ and R$^c$ is a hydrogen atom, a $C_{1-6}$ alkyl group which may be substituted by member(s) selected from Group 14, a $C_{2-6}$ alkenyl group which may be substituted by member(s) selected from Group 14, a $C_{2-6}$ alkynyl group which may be substituted by member(s) selected from Group 14, a $C_{6-14}$ aryl group which may be substituted by member(s) selected from Group 14, a $C_{3-7}$ cycloalkyl group which may be substituted by member(s) selected from Group 14, a $C_{3-6}$ cycloalkenyl group which may be substituted by member(s) selected from Group 14, a heterocyclic group selected from Group 6 which may be substituted by member(s) selected from Group 1, an acyl group derived from a sulfonic acid selected from Group 22, a $C_{1-6}$ alkanoyl, a $C_{7-12}$ aryl-carbonyl group)]

Group 4

(1) a monocyclic heterocyclic group, (2) a heterocyclic group condensed with benzene and (3) a heterocyclic spiro compound, each of which contains one nitrogen atom and may further contain one or more atoms selected from the group consisting of a nitrogen atom, a oxygen atom and a sulfur atom Group 5

(1) a $C_{3-9}$ cycloalkyl which may be condensed with benzene, (2) a $C_{3-6}$ cycloalkenyl group, (3) a $C_{4-6}$ cycloalkadienyl group and (4) a $C_{6-14}$ aryl group Group 6

(1) a 5- to 6-membered aromatic monocyclic heterocyclic group selected from Group 24, (2) a 8- to 12-membered aromatic condensed heterocyclic group selected from Group 26 and (3) a 3- to 8-membered saturated or unsaturated non-aromatic heterocyclic group (aliphatic heterocyclic group) selected from Group 25, each of which contains at least one hetero atom selected from the group consisting of an oxygen atom, a sulfur atom and a nitrogen atom Group 7 a $C_{3-6}$ cycloalkyl group which may be substituted by member(s) selected from Group 18, a $C_{6-10}$ aryl group which may be substituted by member(s) selected from Group 18, a $C_{7-10}$ aralkyl group which may be substituted by member(s) selected from Group 18 and a heterocyclic group selected from Group 16 which may be substituted by member(s) selected from Group 18

Group 8 a $C_{1-6}$ alkoxy group, a halogen atom, a $C_{1-6}$ alkyl group, an amino group, a hydroxyl group, a cyano group and an amidino group Group 9

(1) a $C_{1-6}$ alkyl group, (2) a $C_{1-6}$ alkanoyl, (3) benzoyl, (4) a $C_{1-6}$ alkoxy-carbonyl group which may be substituted by halogen(s), (5) a $C_{1-6}$ alkyl-imidoyl, (6) formyl-imidoyl and (7) amidino Group 10

(1) 1-azetidinyl, (2) 1-pyrrolidinyl, (3) 1-piperidinyl, (4) 4-morpholinyl and (5) a 1-piperazinyl which may be substituted by member(s) selected from Group 27

Group 11

(1) a $C_{1-6}$ alkyl group which may be substituted by member(s) selected from Group 14, (2) a $C_{6-14}$ aryl group which may be substituted by member(s) selected from Group 14, (3) a $C_{3-7}$ cycloalkyl group which may be substituted by member(s) selected from Group 14, (4) a $C_{3-6}$ cycloalkenyl group which may be substituted by member(s) selected from Group 14, (5) a carboxyl group, (6) a $C_{1-6}$ alkoxy-carbonyl group which may be substituted by member(s) selected from Group 18, (7) a $C_{7-12}$ aryloxy-carbonyl group which may be substituted by member(s) selected from Group 18, (8) a $C_{7-10}$ aralkyl-oxy-carbonyl group which may be substituted by member(s) selected from Group 18, (9) a carbamoyl group, (10) a mono-substituted carbamoyl group which may be substituted by a member selected from Group 19, (11) a di-substituted carbamoyl group substituted by a member selected from Group 19 and a member selected from Group 20, (12) a cyclic-aminocarbamoyl group selected from Group 21, (13) a thiocarbamoyl group, (14) a mono-substituted thiocarbamoyl group which may be substituted by a member selected from Group 19, (15) a di-substituted thiocarbamoyl group substituted by a member selected from Group 19 and a member selected from Group 20, (16) a cyclic-aminothiocarbamoyl group selected from Group 21, (17) an amino group which may be substituted by a $C_{1-6}$ alkyl-imidoyl(s), formyl-imidoyl(s), amidino(s) or member(s) selected from Group 17, (18) a cyclic-amino group selected from Group 10, (19) a hydroxyl group which may be substituted by a member selected from Group 17, (20) a thiol group which may be substituted by a member selected from Group 17, (21) a $C_{1-6}$ alkanoyl group, (22) a $C_{7-12}$ aryl-carbonyl group, (23) an acyl group derived from a sulfonic acid selected from Group 22, (24) a halogen atom, (25) nitro and (26) cyano Group 12 a $C_{1-6}$ alkylene, a $C_{2-6}$ alkenylene and a $C_{2-6}$ alkynylene

Group 13 a $C_{1-3}$ alkylene, a $C_{2-3}$ alkenylene and a $C_{2-3}$ alkynylene

Group 14

(1) a $C_{1-6}$ alkoxy group which may be substituted by halogen(s), (2) a phenoxy group which may be substituted by halogen(s) or carbamoyl(s), (3) a halogen atom, (4) a $C_{1-6}$ alkyl group, (5) a $C_{1-4}$ alkyl group substituted by halogen(s), (6) $C_{3-8}$ cycloalkyl, (7) an amino group, (8) an amino group substituted by one or two members selected from the group consisting of carbamoyl, $C_{1-4}$ alkyl and $C_{1-4}$ alkyl-sulfonyl, (9) a carbamoyl group which may be substituted by $C_{1-6}$ alkyl(s), (10) formyl, (11) a $C_{2-6}$ alkanoyl group, (12) a $C_{6-14}$ aryl group, (13) a $C_{6-14}$ aryl-carbonyl group, (14) a $C_{7-13}$ aralkyl-carbonyl group, (15) a hydroxyl group, (16) a $C_{2-5}$ alkanoyl-oxy group, (17) a $C_{7-13}$ aralkyl-carbonyloxy group, (18) a nitro group, (19) a sulfamoyl group, (20) a N—$C_{1-4}$ alkyl-sulfamoyl group, (21) a phenyl-thio group, (22) a $C_{1-4}$ alkyl-phenylthio group, (23) —N=N-phenyl group, (24) a cyano group, (25) an oxo group, (26) an amidino group, (27) a carboxyl group, (28) a $C_{1-4}$ alkoxy-carbonyl group, (29) a $C_{1-6}$ alkyl-thio group, (30) a $C_{1-6}$ alkyl-sulfinyl group, (31) a $C_{1-6}$ alkyl-sulfonyl group, (32) a $C_{6-14}$ aryl-thio group, (33) a $C_{6-14}$ aryl-sulfinyl group, (34) a $C_{6-14}$ aryl-sulfonyl group and (35) a heterocyclic group selected from Group 6

Group 15 a $C_{1-6}$ alkyl group, a $C_{1-6}$ alkanoyl group, a $C_{7-13}$ aryl-carbonyl group, a $C_{1-6}$ alkyl-sulfonyl group, an aminosulfonyl group, a mono-$C_{1-6}$ alkyl-aminosulfonyl group, a di$C_{1-6}$ alkyl-aminosulfonyl group and a $C_{1-4}$ alkyl group substituted by halogen Group 16

(1) an aromatic heterocyclic group selected from Groups 24 and 26, and (2) a saturated or unsaturated non-aromatic heterocyclic group selected from Group 25, each of which contains at least one hetero atom selected from the group consisting of an oxygen atom, a sulfur atom and a nitrogen atom Group 17

(1) a $C_{1-6}$ alkyl group which may be substituted by halogen or a $C_{1-6}$ alkoxy, (2) a $C_{6-12}$ aryl group, (3) a $C_{6-12}$ aryl group substituted by $C_{1-4}$ alkyl(s), (4) a $C_{3-8}$ cycloalkyl group which may be substituted by halogen(s) or $C_{1-6}$ alkoxy(s), (5) a $C_{1-6}$ alkoxy group, (6) a $C_{1-6}$ alkanoyl, (7) a $C_{7-13}$ aryl-carbonyl group, (8) a $C_{7-13}$ aryl-carbonyl group substituted by $C_{1-4}$ alkyl(s), (9) a $C_{1-6}$ alkyl-sulfonyl group, (10) a $C_{6-14}$ aryl-sulfonyl group, (11) a aminosulfonyl group, (12) a mono- or di-substituted aminosulfonyl group substituted by $C_{1-4}$ alkyl(s) and (13) a $C_{1-6}$ alkoxy-carbonyl group which may be substituted by halogen(s)

Group 18

(1) a hydroxyl group, (2) an amino group, (3) a mono or di-substituted amino group which may be substituted by member(s) selected from Group 28, (4) a halogen atom, (5) a nitro group, (6) a cyano group, (7) a $C_{1-6}$ alkyl group which may be substituted by halogen(s) and (8) a $C_{1-6}$ alkoxy group which may be substituted by halogen(s)

Group 19 a $C_{1-6}$ alkyl group which may be substituted by member(s) selected from Group 18, a $C_{3-6}$ cycloalkyl group which may be substituted by member(s) selected from Group 18, a $C_{6-10}$ aryl group which may be substituted by member(s) selected from Group 18, a $C_{7-10}$ aralkyl group which may be substituted by member(s) selected from Group 18, a $C_{1-6}$ alkoxy group which may be substituted by member(s) selected from Group 18 and a heterocyclic group selected from Group 16 which may be substituted by member(s) selected from Group 18

Group 20 a $C_{1-6}$ alkyl group, a $C_{3-6}$ cycloalkyl group and a $C_{7-10}$ aralkyl group Group 21 a 1-azetidinyl-carbonyl group, a 1-pyrrolidinyl-carbonyl group, a 1-piperidinyl-carbonyl group, a 4-morpholinyl-carbonyl group and a 1-piperazinyl-carbonyl group which may be substituted by member(s) selected from Group 27

Group 22 a $C_{1-10}$ alkyl-sulfonyl group which may be substituted by member(s) selected from Group 18, a $C_{2-6}$ alkenyl-sulfonyl group which may be substituted by member(s) selected from Group 18, a $C_{2-6}$ alkynyl-sulfonyl group which may be substituted by member(s) selected from Group 18, a $C_{3-9}$ cycloalkyl-sulfonyl group which may be substituted by member(s) selected from Group 18, a $C_{3-9}$ cycloalkenyl-sulfonyl group which may be substituted by member(s) selected from Group 18, a $C_{6-14}$ aryl-sulfonyl group and a $C_{7-10}$ aralkyl-sulfonyl group which may be substituted by member(s) selected from Group 18

Group 23 a $C_{1-6}$ alkoxy group, a halogen atom, a $C_{1-6}$ alkyl group, an amino group, a hydroxyl group, a cyano group and an amidino group Group 24 furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl Group 25 oxylanyl, azetidinyl, oxetanyl, thietanyl, pyrrolidinyl, tetrahydro furyl, thiolanyl, piperidinyl, tetrahydro pyranyl, morpholinyl, thiomorpholinyl and piperazinyl Group 26 benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, benzodioxolyl, benzimidazolyl, 2,1,1-benzoxadiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenathrolinyl, indolizinyl, pyrrolo(1,2-b)pyridazinyl, pyrazolo(1,5-a)pyridyl, pyrazolo[3,4-b]pyridyl, imidazo(1,2-a)pyridyl, imidazo(1,5-a)pyridyl, imidazo(1,2-b)pyridazinyl, imidazo(1,2-a)pyrimidinyl, 1,2,4-triazolo(4,3-a)pyridyl and 1,2,4-triazolo(4,3-b)pyridazinyl Group 27 a $C_{1-6}$ alkyl group, a $C_{7-10}$ aralkyl group and a $C_{6-10}$ aryl group

Group 28 a $C_{1-6}$ alkyl group, a $C_{1-6}$ alkanoyl, a $C_{7-13}$ aryl-carbonyl group and a $C_{1-6}$ alkyl-sulfonyl group (3) A compound as shown in the above (2), wherein the 3- to 8-membered saturated or unsaturated nonaromatic heterocyclic group which may be substituted by member(s) selected from Group 1, represented by each of $R^1$ and $R^2$ is a 3- to 8-membered saturated or unsaturated nonaromatic heterocyclic group selected from Group 25 which may be substituted by member(s) selected from Group 1, and the heterocyclic group forming by combining $R^1$ and $R^2$ together with A, selected from Group 4 which may be substituted by member(s) selected from Group 3 is a cyclic-amino group selected from Group 29.

Group 29

1-azetidinyl, 1-pyrrolidinyl, 1-piperidinyl, 1-homopiperidinyl, heptamethylenimino, 1-piperazinyl, 1-homopiperazinyl, 4-morpholinyl, 4-thiomorpholinyl, 2-isoindolinyl, 1,2,3,4-tetrahydro-2-isoquinolyl, 1,2,4,5-tetrahydro-3H-3-benzazepin-3-yl and indene-1-spiro-4'-piperidine-1'-yl (4) A compound as shown in the above (2) wherein $R^1$ and $R^2$ combine each other together with A to form a 3- to 8-membered saturated or unsaturated non-aromatic heterocyclic group selected from Group 4, which may be substituted by member(s) selected from Group 3.

(5) A compound as shown in the above (2) wherein $R^1$ and $R^2$ combine each other together with A to form a 3- to 8-membered saturated or unsaturated non-aromatic heterocyclic group containing one or two heteroatoms which are nitrogen, which ring may be substituted by member(s) selected from Group 3.

(6) A compound as shown in the above (4), wherein the group represented by $-AR^1R^2$ is (1) a piperidinyl or (2) a piperazinyl group, each of which may be substituted by member(s) selected from Group 3.

(7) A compound as shown in the above (4), wherein the group represented by $-AR^1R^2$ is a group represented by the formula:

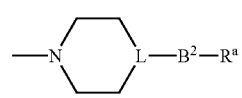

(1)

[wherein L is methine or a nitrogen atom, $B^2$ is a bond, $-CH_2-$, $-SO_2-$, $-SO-$, $-S-$, $-O-$, $-CO-$, $-NR^{b1}-SO_2-$ (wherein $R^{b1}$ is a hydrogen atom, a $C_{1-6}$ alkyl group, a $C_{2-6}$ alkenyl group, a $C_{2-6}$ alkynyl group, a $C_{3-6}$ cycloalkyl group), $-CH(OH)-$, $-NR^{b2}-$ (wherein $R^{b2}$ is a hydrogen atom or a $C_{2-4}$ alkanoyl group), $-NR^{b1}-CO-$ (wherein $R^{b1}$ has the meaning given above), $-NR^{b1}-CO-O-$ (wherein $R^{b1}$ has the meaning given above), $-CH_2SO_2-$ or $-CH_2S-$, $R^a$ is a hydrocarbon group selected from Group 2 which may be substituted by member(s) selected from Group 1 or a heterocyclic group selected from Group 6 which may be substituted by member(s) selected from Group 1].

(8) A compound as shown in the above (4), wherein the group represented by the formula $-AR^1R^2$ is a group represented by the formula:

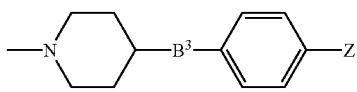

(wherein $B^3$ is —$CH_2$—, —$SO_2$—, —SO—, —S—, —O—, —CO—, —$NR^{b1}$—$SO_2$— (wherein $R^{b1}$ is a hydrogen atom, a $C_{1-6}$ alkyl group, a $C_{2-6}$ alkenyl group, a $C_{2-6}$ alkynyl group, a $C_{3-6}$ cycloalkyl group), —$NR^{b1}$—CO—, —$NR^{b1}$—CO—O— (wherein $NR^{b1}$ has the meaning given above), Z is a halogen, $SO_2NR^{b3}R^{b4}$ (wherein each of $R^{b3}$ and $R^{b4}$ is (1) a $C_{1-6}$ alkyl group which may be substituted by halogen(s), hydroxyl(s) or $C_{1-6}$ alkoxy(s), (2) a $C_{3-8}$ cycloalkyl group which may be substituted by halogen(s) or $C_{1-6}$ alkoxy(s), (3) a $C_{1-6}$ alkoxy group, (4) a hydrogen atom or, $R^{b3}$ and $R^{b4}$ are combine each other together with A to form a cyclic-amino group), $SO_2R^{b5}$, (wherein $R^{b5}$ is (1) a $C_{1-6}$ alkyl group which may be substituted by halogen(s), hydroxyl(s) or $C_{1-6}$ alkoxy(s), (2) a $C_{3-8}$ cycloalkyl group which may be substituted by halogen(s) or $C_{1-6}$ alkoxy(s)), a $CONR^{b3}R^{b4}$ (wherein each of $R^{b3}$ and $R^{b4}$ has the meaning given above) or —$NR^{b7}$—$SO_2R^{b6}$ (wherein $R^{b6}$ is (1) a $C_{1-6}$ alkyl group which may be substituted by halogen(s) or $C_{1-6}$ alkoxy(s), (2) a $C_{3-8}$ cycloalkyl group which may be substituted by halogen(s) or $C_{1-6}$ alkoxy(s), $R^{b7}$ is (1) a $C_{1-6}$ alkyl group which may be substituted by halogen(s) or $C_{1-6}$ alkoxy(s), (2) a $C_{3-8}$ cycloalkyl group which may be substituted by halogen(s) or $C_{1-6}$ alkoxy(s) or (3) a hydrogen atom), a $C_{1-6}$ alkoxy group, an amino group which may be substituted by $C_{2-4}$ alkanoyl(s), nitro(s), cyano(s), tetrazolyl(s) or morpholinyl(s)).

(9) A compound as shown in the above (2), wherein $R^3$ is a $C_{6-14}$ aryl group which may be substituted by member(s) selected from Group 1.

(10) A compound as shown in the above (2), wherein $R^3$ is a phenyl group which may be substituted by member(s) selected from Group 1.

(11) A compound as shown in the above (1), wherein E is —$CH_2CH_2$—, —$CH_2CH_2CH_2$—, —$CH_2CH_2CH_2CH_2$— or —$CH_2CH_2CH_2CH_2CH_2$—.

(12) A compound as shown in the above (1), wherein E is —$CH_2CH_2CH_2$—.

(13) A compound as shown in the above (1), wherein $G^2$ is CO, $SO_2$, CONH or OCO.

(14) A compound as shown in the above (1), wherein $G^2$ is CO or NHCO.

(15) A compound as shown in the above (1), wherein $G^2$ is CO.

(16) A compound as shown in the above (1), wherein J is methine.

(17) A compound as shown in the above (1), wherein $G^1$ is CO or $SO_2$.

(18) A compound as shown in the above (2), wherein $R^4$ is a hydrocarbon group selected from Group 2 which may be substituted by member(s) selected from Group 1, a heterocyclic group selected from Group 6 which may be substituted by member(s) selected from Group 1, a $C_{1-6}$ alkoxy group which may be substituted by member(s) selected from Group 7, or an amino group which may be substituted by member(s) selected from Group 9.

(19) A compound as shown in the above (1), wherein $R^4$ is a $C_{1-3}$ alkyl.

(209) A compound as shown in the above (1), wherein $R^4$ is methyl.

(21) A compound as shown in the above (1), wherein each of Q and R is —$CH_2CH_2$—.

(22) A compound as shown in the above (1), wherein n is zero.

(23) A compound represented by the formula:

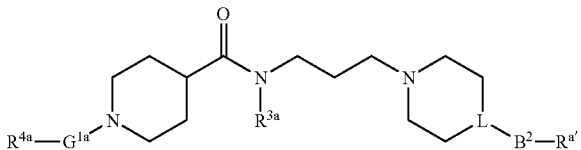

(I-a)

[wherein $R^{4a}$ is (1) a $C_{1-6}$ alkyl group which may be substituted by halogen(s), $C_{1-6}$ alkoxy(s), oxo(s), amino(s), phenyl(s), pyridyl(s) or tetrazolyl(s), (2) a $C_{2-6}$ alkenyl group, (3) a $C_{3-8}$ cycloalkyl group which may be substituted by halogen(s), $C_{1-6}$ alkyl(s) or $C_{1-6}$ alkoxy(s), (4) a phenyl group which may be substituted by halogen(s), $C_{1-6}$ alkyl(s), $C_{1-6}$ alkoxy(s), nitro(s), cyano(s), hydroxyl(s), $C_{1-4}$ alkanoyl-amino(s), carbamoyl(s) or sulfamoyl(s), (5) an amino group which may be substituted by $C_{1-6}$ alkyl(s), (6) a $C_{1-6}$ alkoxy group which may be substituted by phenyl(s), (7) a $C_{3-8}$ cycloalkyl-oxy group (8) a heterocyclic group which may be substituted by halogen(s), $C_{1-6}$ alkyl(s) or hydroxyl(s), $G^{1a}$ is CO or $SO_2$, $R^{3a}$ is a $C_{6-10}$ aryl group which may be substituted by (1)halogen(s), (2) $C_{1-6}$ alkyl(s) which may be substituted by halogen(s), (3) $C_{1-6}$ alkoxy(s) which may be substituted by halogen(s), (4) $C_{1-6}$ alkyl-thio(s), or (5) $C_{1-6}$ alkyl-sulfonyl(s), L is methine or a nitrogen atom, $B^2$ is a bond, —$CH_2$—, —$SO_2$—, —SO—, —S—, —O—, —CO—, —$NR^{b1}$—$SO_2$— (wherein R is a hydrogen atom, a $C_{1-6}$ alkyl group, a $C_{2-6}$ alkenyl group, a $C_{2-6}$ alkynyl group or a $C_{3-6}$ cycloalkyl group), —CH(OH)—, —$NR^{b2}$ (wherein $R^{b2}$ is a hydrogen atom or a $C_{2-4}$ alkanoyl group), —$NR^{b1}$—CO— (wherein $R^{b1}$ has the meaning given above), —$NR^{b1}$—CO—O— (wherein $R^{b1}$ has the meaning given above), —$CH_2SO_2$— or —$CH_2S$—, $R^{a'}$ is ① an aromatic hydrocarbon group which may be substituted by halogen(s), $SO_2NR^{b3}R^{b4}$ (wherein each of $R^{b3}$ and $R^{b4}$ is (1) a $C_{1-6}$ alkyl group which may be substituted by 1) halogen(s), 2) hydroxyl(s) or 3) $C_{1-6}$ alkoxy(s), (2) a $C_{3-8}$ cycloalkyl group which may be substituted by 1) halogen(s), 2) hydroxyl(s) or 3) $C_{1-6}$ alkoxy(s), (3) a $C_{1-6}$ alkoxy group or (4) a hydrogen atom, or $R^{b3}$ and $R^{b4}$ may combine each other together with a nitrogen atom to form a cyclic-amino group), $SO_2R^{b5}$ (wherein $R^{b5}$ is (1) a $C_{1-6}$ alkyl group which may be substituted by halogen(s), hydroxyl(s) or $C_{1-6}$ alkoxy(s), (2) a $C_{3-8}$ cycloalkyl group which may be substituted by halogen(s) or $C_{1-6}$ alkoxy(s)), $CONR^{b3}R^{b4}$ (wherein $R^{b3}$ and $R^{b4}$ have the meanings given above) or —$NR^{b7}$—$SO_2R^{b6}$ (wherein $R^{b6}$ is (1) a $C_{1-6}$ alkyl group which may be substituted by halogen(s) or $C_{1-6}$ alkoxy(s), (2) a $C_{3-8}$ cycloalkyl group which may be substituted by halogen(s) or $C_{1-6}$ alkoxy(s), $R^{b7}$ is (1) a $C_{1-6}$ alkyl group which may be substituted by halogen(s) or $C_{1-6}$ alkoxy(s), (2) a $C_{3-8}$ cycloalkyl group which may be substituted by halogen(s) or $C_{1-6}$ alkoxy(s) or (3) a hydrogen atom), a $C_{1-6}$ alkoxy group, an amino group which may be substituted by a $C_{2-4}$ alkanoyl(s), a nitro group, a cyano group, a tetrazolyl group or a morpholinyl group or ② an aromatic heterocyclic group which may be substituted by substituent(s) selected from the above mentioned substituents of aromatic hydrocarbon group] or a salt thereof.

(24) A compound as shown in the above (23), wherein $R^{3a}$ is a phenyl group which may be substituted by halogen(s), trifluoromethyl(s) or $C_{1-6}$ alkyl(s).

(25) A compound as shown in the above (23), wherein L is methine.

(26) A compound as shown in the above (23), wherein $B^2$ is —$CH_2$—, —$SO_2$—, —SO—, —S—, —O—, —CO—, —$NR^{b1}$—$SO_2$—, —$NR^{b1}$—CO— or $NR^{b1}$—CO—O— (wherein $R^{b1}$ is a hydrogen atom, a $C_{1-4}$ alkyl group, a $C_{2-6}$ alkenyl group, a $C_{2-6}$ alkynyl group or a $C_{3-6}$ cycloalkyl group).

(27) A compound as shown in the above (23), wherein $R^{a'}$ is a phenyl group which may be substituted by (1) halogen(s), (2) $SO_2R^e$ (wherein $R^e$ is a $C_{1-6}$ alkyl group or a $C_{3-8}$ cycloalkyl group), (3) $N(R^d)SO_2R^e$ (wherein $R^d$ is a hydrogen atom or a $C_{1-4}$ alkyl group, $R^e$ has the meaning given above), (4) $SO_2NR^fR^g$ (wherein each of $R^f$ and $R^g$ is a hydrogen atom or a $C_{1-6}$ alkyl group or $R^f$ and $R^g$ may combine each other together with a nitrogen atom to form a cyclic-amino group) or (5) $CONR^fR^g$ (wherein each of $R^f$ and $R^g$ is a hydrogen atom or a $C_{1-6}$ alkyl group or, $R^f$ and $R^g$ combine each other together with a nitrogen atom to form a cyclic-amino group).

(28) A compound as shown in the above (23), wherein $B^2$ is $SO_2$, $CH_2$ or $N(R^d)$—$SO_2$ (wherein $R^d$ is a hydrogen atom or a $C_{1-4}$ alkyl gruop); $R^{a'}$ is a phenyl group which may be substituted by (1) halogen(s), (2) $SO_2R^e$ (wherein $R^e$ is a $C_{1-6}$ alkyl group or a $C_{3-8}$ cycloalkyl group), (3) $N(R^d)SO_2R^e$ (wherein $R^d$ is a hydrogen atom or a $C_{1-4}$ alkyl gruop, and $R^e$ has the meaning given above), (4) $SO_2NR^fR^g$ (wherein each of $R^f$ and $R^g$ is a hydrogen atom or a $C_{1-6}$ alkyl group or $R^f$ and $R^g$ may combine each other with a nitrogen atom to form a cyclic-amino group) or (5) $CONR^fR^g$ (wherein each of $R^f$ and $R^g$ is a hydrogen atom or a $C_{1-6}$ alkyl group or $R^f$ and $R^g$ may combine each other together with a nitrogen atom to form a cyclic-amino group); $R^{3a'}$ is a phenyl group substituted by one or two members selected from the group of halogen atom and a $C_{1-4}$ alkyl.

(29) A compound as clamed in claim 23, wherein $G^{1a}$ is $SO_2$ or CO, L is methine, $B^2$ is $SO_2$ or $CH_2$, $R^{a'}$ is a group represented by the formula:

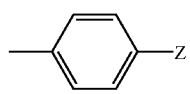

(3)

(wherein Z is a $C_{1-4}$ alkyl-sulfonyl group, a sulfamoyl group which may be substituted by a $C_{1-4}$ alkyl or a carbamoyl group); $R^{3a}$ is a phenyl group which may be substituted by one or two members selected from the group consisting of halogen(s) and $C_{1-4}$ alkyl(s); $R^{4a}$ is methyl.

(30) A compound as shown in the above (1), which is N-(3,4-Dichlorophenyl)-1-(methylsulfonyl)-N-{3-[4-((4-[(methylsulfonyl)amino]phenyl)sulfonyl)-1-piperidinyl]propyl]-4-piperidinecarboxamide or a salt thereof.

(31) A compound as shown in the above (1), which is N-(3-chlorophenyl)-1-(methylsulfonyl)-N-(3-{4-[4-(methylsulfonyl)benzyl]-1-piperidinyl}propyl)-4-piperidinecarboxamide or a salt thereof.

(32) A compound as shown in the above (1), which is N-(3-{4-[4-(Aminocarbonyl)benzyl]-1-piperidinyl}propyl)-N-(3,4-dichlorophenyl)-1-(methylsulfonyl)-4-piperidinecarboxamide or a salt thereof.

(33) A compound as shown in the above (1), which is 1-Acetyl-N-(3-{4-[4-(aminocarbonyl)benzyl]-1-piperidinyl}propyl)-N-(3-chloro-4-methylphenyl)-4-piperidinecarboxamide or a salt thereof.

(34) A compound as shown in the above (1), which is N-(3,4-Dichlorophenyl)-N-(3-{4-[4-(ethylsulfonyl)benzyl]-1-piperidinyl}propyl)-1-(methylsulfonyl)-4-piperidinecarboxamide or a salt thereof.

(35) A compound as shown in the above (1), which is N-(3,4-Dichlorophenyl)-N-(3-{4-[4-(isopropylsulfonyl)benzyl]-1-piperidinyl}propyl)-1-(methylsulfonyl)-4-piperidinecarboxamide or a salt thereof.

(36) A compound as shown in the above (1), which is N-(3-Chlorophenyl)-N-(3-{4-[4-(isopropylsulfonyl)benzyl]-1-piperidinyl}propyl)-1-(methylsulfonyl)-4-piperidinecarboxamide hydrochloride or a salt thereof.

(37) A compound as shown in the above (1), which is N-(3-Chlorophenyl)-N-(3-{4-[4-(ethylsulfonyl)benzyl]-1-piperidinyl}propyl)-1-(methylsulfonyl)-4-piperidinecarboxamide hydrochloride or a salt thereof.

(38) A compound as shown in the above (1), which is N-(3,4-Dichlorophenyl)-1-(methylsulfonyl)-N-(3-{4-[4-(methylsulfonyl)benzyl]-1-piperidinyl}propyl)-4-piperidinecarboxamide hydrochloride or a salt thereof.

(39) A compound as shown in the above (1), which is N-(3-{4-[4-(Aminocarbonyl)benzyl]-1-piperidinyl}propyl)-N-(3-chloro-4-methylphenyl)-1-(methylsulfonyl)-4-piperidinecarboxamide or a salt thereof.

(40) A prodrug of a compound of the formula (I) or a salt thereof.

(41) A pharmaceutical composition containing a compound represented by the formula (I), a salt thereof or a prodrug thereof.

(42) A pharmaceutical composition as shown in the above (41), which is a chemokine receptor antagonist.

(43) A pharmaceutical composition as shown in the above (41), which is a $CCR^5$ antagonist.

(44) A composition as shown in the above (41), which is for the treatment or prevention of infectious disease of HIV.

(45) A composition as shown in the above (41), which is for the treatment or prevention of AIDS.

(46) A composition as shown in the above (41), which is for the prevention of the progression of AIDS.

(47) A composition as shown in the above (44), which is used in combination with a protease inhibitor and/or a reverse transcriptase inhibitor.

(48) A composition as shown in the above (47), wherein the reverse transcriptase inhibitor is zidovudine, didanosine, zalcitabine, lamivudine, stavudine, abacavir, nevirapine, delavirdine or efavirenz.

(49) A composition as shown in the above (47), wherein the protease inhibitor is saquinavir, ritonavir, indinavir, amprenavir or nelfinavir.

(50) Use of a compound as shown in the above (1) or prodrug thereof for the manufacture of a medicament to treat a disease which can be prevented or treated by antagonism of a chemokine receptor.

(51) Use of a compound as shown in the above (1) or prodrug thereof for the manufacture of a medicament to treat a disease which can be prevented or treated by antagonism of a CCR5.

(52) Use of a compound as shown in the above (1) or prodrug thereof, for the manufacture of a medicament for the treatment or prevention of infectious disease of HIV.

(53) Use of a compound as shown in the above (1) or a prodrug thereof in combination with a protease inhibitor and/or a reverse transcrilptase inhibitor for the treatment or prevention of infectious disease of HIV.

(54) A method for antagonizing CCR5 which comprises administering to a mammal in need thereof an effective amount of the compound as shown in the above (1) or a prodrug thereof.

(55) A method for producing a compound of the formula (I) or a salt thereof, which comprises reacting a compound of the formula:

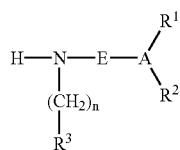
(II)

(wherein each symbol has the meaning given above) or a salt thereof with a compound of the formula:

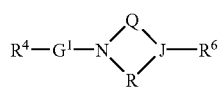
(III)

(wherein $R^6$ is a carboxyl group, or sulfonic acid group or a salt thereof or a reactive derivatives thereof, and the other symbols have the meanings given above) or a salt thereof.

(56) A method for producing a compound of the formula (I) or a salt thereof, which comprises reacting a compound of the formula:

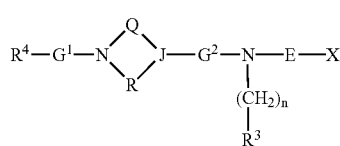
(IV)

(wherein x is a leaving group, and other symbols have the meanings given above) or a salt thereof with a compound of the formula:

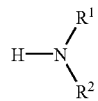
(V)

(wherein each symbol has the meaning given above) or a salt thereof or a compound of the formula:

(VI)

(wherein $R^5$ is a hydrocarbon group, and other symbols have the meanings given above).

(57) N-(3,4-Dichlorophenyl)-N-(3-halogeno-propyl)-1-(methylsulfonyl)-4-piperidinecarboxamide or a salt thereof.

(58) N-(3-Chloro-4-methylphenyl)-N-(3-halogeno-propyl)-1-(methylsulfonyl)-4-piperidinecarboxamide or a salt thereof.

Examples of the hydrocarbon group in the "optionally substituted hydrocarbon group" represented by $R^1$ include e.g. an aliphatic hydrocarbon group, an alicyclic hydrocarbon group and an aryl group, etc. Among them, an aliphatic hydrocarbon group and an alicyclic hydrocarbon group are preferable.

Examples of the "aliphatic hydrocarbon group" include e.g. a straight-chain or branched aliphatic hydrocarbon group such as an alkyl group, an alkenyl group, an alkynyl group, etc. Examples of the alkyl group include e.g. a $C_{1-10}$ alkyl group (preferably a $C_{1-6}$ alkyl, etc.) such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methyl-heptyl, nonyl, etc. Examples of the alkenyl group include e.g. a $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Examples of the alkynyl group include e.g. a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexyntl, 2-hexyntl, 3-hexyntl, 4-hexyntl, 5-hexyntl, etc.

Examples of the "alicyclic hydrocarbon group" include e.g. a saturated or unsaturated alicyclic hydrocarbon group such as a cycloalkyl group, a cycloalkenyl group, a cycloalkanedienyl group, etc. Examples of the "cycloalkyl group" include e.g. a $C_{3-9}$ cycloalkyl (preferably a $C_{3-8}$ cycloalkyl) such as cyclopropyl, cyclobutyl, cyclopentyl, cyclohexyl, cycloheptyl, cyclooctyl, cyclononyl, etc., and a fused ring such as 1-indanyl, 2-indanyl, etc. Examples of the "cycloalkenyl group" include e.g. a $C_{3-6}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc. Examples of the "cycloalkanedienyl group"

include e.g. a $C_{4-6}$ cycloalkanedienyl group such as 2,4-cyclopentadien-1-yl, 2,4-cyclohexadien-1-yl, 2,5-cyclohexadien-1-yl, etc.

Examples of the "aryl group" exemplified by the hydrocarbon group include e.g. a monocyclic or fused aromatic hydrocarbon group. Among others, a $C_{6-14}$ aryl group such as phenyl, naphthyl, anthryl, phenathryl, acenaphthylenyl, 4-indanyl, 5-indanyl, etc. are preferable. In particular, phenyl, 1-naphthyl, 2-naphthyl, etc. are preferable.

Examples of the "non-aromatic heterocyclic group" in the "optionally substituted non-aromatic heterocyclic group" represented by $R^1$ include a 3- to 8-membered (preferably 5- or 6-membered) saturated or unsaturated (preferably saturated) non-aromatic heterocyclic group (alicyclic heterocyclic group) such as oxiranyl, azetidinyl, oxetanyl, thiethanyl, pyrrolidinyl, tetrahydrofuryl, thiolanyl, piperidinyl, tetrahydropyranyl, morpholinyl, thiomorpholinyl, piperazinyl, etc.

Examples of the substituent of the "optionally substituted hydrocarbon group" and "optionally substituted non-aromatic heterocyclic group" represented by $R^1$ include an optionally substituted alkyl group, an optionally substituted alkenyl group, an optionally substituted alkynyl group, an optionally substituted aryl group, an optionally substituted cycloalkyl or cycloalkenyl group, an optionally substituted heterocyclic group, an optionally substituted amino group, an optionally substituted imidoyl group, an optionally substituted amidino group, an optionally substituted hydroxyl group, an optionally substituted thiol group, an optionally esterified carboxyl group, an optionally substituted carbamoyl group, an optionally substituted thiocarbamoyl group, an optionally substituted sulfamoyl group, a halogen atom (e.g. fluorine, chlorine, bromine, iodine, etc., preferably chlorine, bromine, etc.), a cyano group, a nitro group, an acyl group derived from a sulfonic acid, an acyl group derived from an carboxylic acid, an optionally substituted alkyl-sulfinyl group, an optionally substituted aryl-sulfinyl group, etc. The "optionally substituted hydrocarbon group" and "optionally substituted non-aromatic heterocyclic group" may have 1 to 5 substituents as described above. (preferably 1 to 3 substituents) at any possible position.

Examples of the aryl group in the "optionally substituted aryl group" as the substituent include a $C_{6-14}$ aryl group such as phenyl, naphthyl, anthryl, phenathryl, acenaphthylenyl, etc. Said aryl groups may have 1 or 2 substituents at any possible positions. Examples of the substituent include a lower alkoxy group (e.g. a $C_{1-6}$ alkoxy group such as methoxy, ethoxy, propoxy, etc., a $C_{1-4}$ alkoxy group substituted by halogen such as fluoromethoxy, difluoromethoxy, trifluoromethoxy, 1,1-difluoroethoxy, 2,2-difluoroethoxy, 3,3-difluoropropoxy, 2,2,3,3,3-pentafluoropropoxy, etc.), an aryloxy which may be substituted (e.g., phenoxy, 4-fluorophenoxy, 2-carbamoylphenoxy, etc.), a halogen atom (e.g., fluorine, chlorine, bromine, iodine, etc.), a lower alkyl group which may be substituted (an unsubstituted $C_{1-6}$ alkyl group such as methyl, ethyl, propyl, etc., a $C_{1-4}$ alkyl group substituted by halogen such as fluoromethyl, difluoromethyl, trifluoromethyl, 1,1-difluoroethyl, 2,2-difluoroethyl, 3,3-difluoropropyl, 2,2,3,3,3-pentafluoropropyl, etc.), a $C_{3-8}$ cycloalkyl (e.g., cyclopropyl, cyclobutyl, cyclopentyl, cyclohexyl, cycloheptyl, etc.), an amino group, a mono-substituted amino (e.g., carbamoylamino, methylsulfonylamino, methylamino, ethylaminopropylamino, etc.), di-substituted amino (e.g., dimethylamino, diethylamino, N-methyl-N-methylsulfonylamino, dimethylsulfonylamino, etc.), a carbamoyl group which may be substituted by a $C_{1-6}$ alkyl (e.g., butylcarbamoyl, etc.), formyl, a $C_{2-6}$ alkanoyl group (e.g., a $C_{2-6}$ alkanoyl such as acetyl, propionyl, butyryl, etc.), a $C_{6-14}$ aryl group (e.g., phenyl, naphthyl, etc.), a $C_{6-14}$ aryl carbonyl (e.g., benzoyl, naphthoyl, etc.), a $C_{7-13}$ aralkyl carbonyl (e.g., benzylcarbonyl, naphthylmethylcarbonyl, etc.), a hydroxyl group, an alkanoyloxy (a $C_{2-5}$ alkanoyloxy such as acetyloxy, propionyloxy, butyryloxy, etc.), a $C_{7-13}$ aralkyl-carbonyloxy (e.g., benzylcarbonyloxy, etc.), a nitro group, a sulfamoyl group which may be substituted (e.g., unsubstituted sulfamoyl group, N-methylsulfamoyl, etc.), an arylthio group which may be substituted (e.g., phenylthio, 4-methylphenylthio, etc.), —N=N-phenyl, a cyano group, an amidino group, a carboxyl group which may be esterified (free carboxyl group, and a $C_{1-4}$ alkoxy carbonyl such as methoxycarbonyl, ethoxycarbonyl, t-butoxycarbonyl, etc., etc.), a $C_{1-6}$ alkylthio, a $C_{1-6}$ alkylsulfinyl, a $C_{1-6}$ alkylsulfonyl, a $C_{6-14}$ arylthio, a $C_{6-14}$ arylsulfinyl, a $C_{6-14}$ arylsulfonyl, a heterocyclic group which may be substituted (e.g., pyridyl, thienyl, tetrazolyl, morpholinyl, oxazolyl, etc. and those as mentioned below for the definition of heterocyclic group which may be substituted shown as $R^3$), etc.

Examples of the cycloalkyl group in the "optionally substituted cycloalkyl group" as the substituent include a $C_{3-7}$ cycloalkyl group such as cyclopropyl, cyclobutyl, cyclopentyl, cyclohexyl, cycloheptyl, etc. Said cycloalkyl groups may have the same kind and number of substituents as those of the above described "optionally substituted aryl group".

Examples of the cycloalkenyl group in the "optionally substituted cycloalkenyl group" as the substituent include e.g. a $C_{3-6}$ cycloalkenyl group such as cyclopropenyl, cyclobutenyl, cyclopentenyl, cyclohexenyl, etc. Said cycloalkenyl groups may have the same kind and number of substituents as those of the above described "optionally substituted aryl group".

Examples of the alkyl group in the "optionally substituted alkyl group" as the substituent include e.g. a $C_{1-6}$ alkyl etc. such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, etc. Said alkyl groups may have the same kind and number of substituents as those of the above described "optionally substituted aryl group".

Examples of the alkenyl group in the "optionally substituted alkenyl group" as the substituent include e.g. a $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Said alkenyl groups may have the same kind and number of substituents as those of the above described "optionally substituted aryl group".

Examples of the alkynyl group in the "optionally substituted alkynyl group" as the substituent include e.g. a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexyntl, 2-hexyntl, 3-hexyntl, 4-hexyntl, 5-hexyntl, etc. Said alkynyl groups may have the same kind and number of substituents as those of the above described "optionally substituted aryl group".

Examples of the heterocyclic group in the "optionally substituted heterocyclic group" as the substituent include e.g. an aromatic heterocyclic group, saturated or unsaturated non-aromatic heterocyclic group (alicyclic heterocyclic group) etc., which contains, besides carbon atoms, at least one hetero-atom (preferably 1 to 4 hetero-atoms, more preferably 1 to 2 hetero-atoms) consisting of 1 to 3 kinds of hetero-atoms (preferably 1 to 2 kinds of hetero-atoms) selected from an oxygen atom, a sulfur atom, a nitrogen atom, etc.

Examples of the "aromatic heterocyclic group" include an aromatic monocyclic heterocyclic group such as a 5- to 6-membered aromatic monocyclic heterocyclic group (e.g. furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as a 8- to 12-membered aromatic fused heterocyclic group (e.g. benzofuranyl, isobenzofuranyl, benzothienyl, indolyl, isoindolyl, 1H-indazolyl, benzindazolyl, benzoxazolyl, 1,2-benzoisooxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc., preferably, a heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5-or 6-membered aromatic monocyclic heterocyclic group, etc.

Examples of the "non-aromatic heterocyclic group" include a 3- to 8-membered (preferably 5- or 6-membered) saturated or unsaturated (preferably saturated) non-aromatic heterocyclic group (alicyclic heterocyclic group) such as oxiranyl, azetidinyl, oxetanyl, thiethanyl, pyrrolidinyl, tetrahydrofuryl, thiolanyl, piperidinyl, tetrahydropyranyl, morpholinyl, thiomorpholinyl, piperazinyl, etc.

Examples of the substituent of the "optionally substituted heterocyclic group" as the substituent include a lower alkyl group (e.g. a $C_{1-6}$ alkyl group such as methyl, ethyl, propyl, etc.), an acyl group (e.g. a $C_{1-6}$ alkanoyl such as formyl, acetyl, propionyl, pivaloyl, etc., an $C_{6-14}$ aryl carbonyl such as benzoyl, etc., a $C_{1-6}$ alkylsulfonyl such as methylsulfonyl, ethylsulfonyl, etc., a substituted sulfonyl such as aminosulfonyl, methylaminosulfonyl, dimethylaminosulfonyl, etc.), a lower alkyl substituted by a halogen (e.g., trifluoromethyl, 1,1-difluoroethyl, etc.), etc.

Examples of the substituent in the "optionally substituted amino group", "optionally substituted imidoyl group", "optionally substituted amidino group", "optionally substituted hydroxyl group" and "optionally substituted thiol group" as the substituent include e.g. a lower alkyl group (e.g. a $C_{1-6}$ alkyl group such as methyl, ethyl, propyl, isopropyl, butyl, isobutyl, t-butyl, pentyl, hexyl, etc.), aryl group (e.g., phenyl, 4-methylphenyl, etc.), acyl group ($C_{1-6}$ alkanoyl (e.g., formyl, acetyl, propionyl, pivaloyl, etc.), aryl-carbonyl (e.g. benzoyl, etc.), $C_{1-6}$ alkylsulfonyl (e.g., methylsulfonyl, ethylsulfonyl, etc.), $C_{6-14}$ aryl-sulfonyl (e.g., para-toluenesulfonyl, etc.), etc., substituted-sulfonyl (e.g., aminosulfonyl, methylaminosulfonyl, dimethylaminosulfonyl, etc.), an optionally halogenated $C_{1-6}$ alkoxy-carbonyl (e.g. trifluoromethoxycarbonyl, 2,2,2-trifluoroethoxycarbonyl, trichloromethoxycarbonyl, 2,2,2-trichloroethoxycarbonyl, etc.), etc. In addition, the "amino group" in the "optionally substituted amino group" as the substituent may be substituted with an optionally substituted imidoyl group (e.g., a $C_{1-6}$ alkylimidoyl, formimidoyl, amidino, etc.), etc. and two substituents of the "amino group" may form a cyclic amino group together with a nitrogen atom. Examples of said cyclic amino group include e.g. 3- to 8-membered (preferably 5- to 6-membered) cyclic amino group such as 1-azetidinyl, 1-pyrrolidinyl, 1-piperidinyl, 4-morpholinyl, 1-piperazinyl and 1-piperazinyl which may have at the 4-position a lower alkyl group (e.g. a $C_{1-6}$ alkyl group such as methyl, ethyl, propyl, isopropyl, butyl, t-butyl, pentyl, hexyl, etc.), an aralkyl group (e.g. a $C_{7-10}$ aralkyl group such as benzyl, phenethyl, etc.), an aryl group (e.g. a $C_{6-10}$ aryl group such as phenyl, 1-naphthyl, 2-naphthyl, etc.), etc.

Examples of the "optionally substituted carbamoyl group" include unsubstituted carbamoyl, a N-mono-substituted carbamoyl group and a N,N-di-substituted carbamoyl group.

The "N-mono-substituted carbamoyl group" is a carbamoyl group having one substituent on the nitrogen atom and said substituent include e.g. a lower alkyl group (e.g. a $C_{1-6}$ alkyl group such as methyl, ethyl, propyl, isopropyl, butyl, isobutyl, t-butyl, pentyl, hexyl, etc.), a cycloalkyl group (e.g. a $C_{3-6}$ cycloalkyl group such as cyclopropyl, cyclobutyl, cyclopentyl, cyclohexyl, etc.), an aryl group (e.g. a $C_{6-10}$ aryl group such as phenyl, 1-naphthyl, 2-naphthyl, etc.), an aralkyl group (e.g. a $C_{7-10}$ aralkyl group, preferably a phenyl-$C_{1-4}$ alkyl group such as benzyl, phenethyl, etc.), a heterocyclic group (e.g. the above described "heterocyclic group" as the substituent of the "optionally substituted hydrocarbon group" represented by $R^1$, etc.), etc. Said the lower alkyl group, the cycloalkyl group, the aryl group, the aralkyl group and the heterocyclic group may have a substituent and examples of the substituent include e.g. a hydroxyl group, an optionally substituted amino group [said amino group may have 1 to 2 substituents (e.g. a lower alkyl group (e.g. a $C_{1-6}$ alkyl group such as methyl, ethyl, propyl, isopropyl, butyl, isobutyl, t-butyl, pentyl, hexyl, etc.), an acyl group (e.g. a $C_{1-6}$ alkanoyl such as formyl, acetyl, propionyl, pivaloyl, etc., a $C_{6-14}$ aryl-carbonyl such as benzoyl, etc., a $C_{1-6}$ alkylsulfonyl such as methylsulfonyl, ethylsulfonyl, etc.), etc.)], a halogen atom (e.g. fluorine, chlorine, bromine, iodine, etc.), a nitro group, a cyano group, a lower alkyl group optionally substituted with 1 to 5 halogen atoms (e.g. fluorine, chlorine, bromine, iodine, etc.), a lower alkoxy group optionally substituted with 1 to 5 halogen atoms (e.g. fluorine, chlorine, bromine, iodine, etc.), etc. Said lower alkyl group include e.g. a $C_{1-6}$ alkyl group such as methyl, ethyl, n-propyl, isopropyl, n-butyl, isobutyl, sec-butyl, tert-butyl, pentyl, hexyl, etc. and in particular methyl, ethyl, etc. are preferable. Said lower alkoxy group include e.g. a $C_{1-6}$ alkoxy group such as methoxy, ethoxy, n-propoxy, isopropoxy, n-butoxy, isobutoxy, sec-butoxy, tert-butoxy, etc. and in particular methoxy, ethoxy, etc. are preferable. The above described lower alkyl group, cycloalkyl group, aryl group, aralkyl group and heterocyclic group may have 1 or 2 to 3 (preferably 1 or 2) substituents. When these groups have 2 or 3 substituents, these substituents may be same or different.

The "N,N-di-substituted carbamoyl group" is a carbamoyl group having two substituents on the nitrogen atom. Examples of one of the substituents include the same as those of the above described "N-mono-substituted carbamoyl group" and examples of the other substituent include e.g. a lower alkyl group (e.g. a $C_{1-6}$ alkyl group such as methyl, ethyl, propyl, isopropyl, butyl, t-butyl, pentyl, hexyl, etc.), a $C_{3-6}$ cycloalkyl group (e.g. cyclopropyl, cyclobutyl, cyclopentyl, cyclohexyl, etc.), a $C_{7-10}$ aralkyl group (e.g. benzyl, phenethyl, etc., preferably phenyl-$C_{1-4}$ alkyl group, etc.), etc. In addition, two substituents of the "N,N-di-substituted carbamoyl group" may form a cyclic amino-carbamoyl group together with a nitrogen atom. Examples of said cyclic amino-carbamoyl group include e.g. 3- to 8-membered (preferably 5- to 6-membered) cyclic amino-carbamoyl group such as 1-azetidinylcarbonyl, 1-pyrrolidinylcarbonyl, 1-piperidinylcarbonyl, morpholinylcarbonyl, 1-piperazinylcarbonyl and 1-piperazinylcarbonyl which may have at the 4-position a lower alkyl group (e.g. a $C_{1-6}$ alkyl group such as methyl, ethyl, propyl, isopropyl, butyl, t-butyl, pentyl, hexyl, etc.), an aralkyl group (e.g. a $C_{7-10}$ aralkyl group such as benzyl, phenethyl, etc.), an aryl group (e.g. a $C_{6-10}$ aryl group such as phenyl, 1-naphthyl, 2-naphthyl, etc.), etc.

Examples of the substituent in the "optionally substituted thiocarbamoyl group" include the same substituent as those in the above described "optionally substituted carbamoyl group". Examples of the sulfamoyl group which may be substituted include an unsubstituted-sulfamoyl group, a N-mono-substituted sulfamoyl group and a N,N-di-substituted sulfamoyl group. The mono-substituted sulfamoyl group is a sulfamoyl group having one substituent at the nitrogen atom, and examples of the substituent include those mentioned as the substituent of N-mono-substituted carbamoyl group. The N,N-di-substituted sulfamoyl group is a sulfamoyl group having two substituents at the nitrogen atom, and examples of the substituent include those mentioned as the substituent of the N,N-di-substituted carbamoyl group.

Examples of the "optionally esterified carboxyl group" in the present specification include a free carboxyl group as well as a lower alkoxycarbonyl group, an aryloxycarbonyl group, an aralkyloxycarbonyl group, etc.

Examples of the "lower alkoxycarbonyl group" include e.g. a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, etc. Among others, a $C_{1-3}$ alkoxy-carbonyl group such as methoxycarbonyl, ethoxycarbonyl, propoxycarbonyl, etc. are preferable.

Examples of the "aryloxycarbonyl group" include e.g. a $C_{7-12}$ aryloxy-carbonyl group such as phenoxycarbonyl, 1-naphthoxycarbonyl, 2-naphthoxycarbonyl, etc.

Examples of the "aralkyloxycarbonyl group" include e.g. a $C_{7-10}$ aralkyloxy-carbonyl group, etc. (preferably, a $C_{6-10}$ aryl-$C_{1-4}$ alkoxy-carbonyl, etc.) such as benzyloxycarbonyl, phenethyloxycarbonyl, etc.

Said "aryloxycarbonyl group" and "aralkyloxycarbonyl group" may be substituted. Examples of the substituent include the same kind and number of the substituents of the aryl group and aralkyl group as the substituent for the above described N-mono-substituted carbamoyl group.

Examples of the "acyl group derived from a sulfonic acid" as the substituent include a sulfonyl group substituted by a hydrocarbon group, and preferably include an acyl group such as $C_{1-10}$ alkyl-sulfonyl, $C_{2-6}$ alkenyl-sulfonyl, $C_{2-6}$ alkynyl-sulfonyl, $C_{3-9}$ cyclo-alkyl-sulfonyl, $C_{3-9}$ cyclo-alkenyl-sulfonyl, $C_{6-14}$ aryl-sulfonyl, $C_{7-10}$ aralkyl-sulfonyl. Examples of the $C_{1-10}$ alkyl include, for example, methyl, ethyl, propyl, isopropyl, butyl, isobutyl, t-butyl, pentyl, hexyl, heptyl, octyl, etc. Examples of the $C_{2-6}$ alkenyl include, for example, vinyl, allyl, 1-propenyl, isopropenyl, 2-butenyl, 3-butenyl, 2-hexenyl, etc. Examples of $C_{2-6}$ alkynyl include, for example, ethynyl, 2-propynyl, 2-butynyl, 5-hexynyl, etc. Examples of the $C_{3-9}$ cyclo-alkyl include, for example, cyclopropyl, cyclobutyl, cyclopentyl, cyclohexyl, cyclooctyl, etc.

Examples of the $C_{3-9}$ cyclo-alkenyl include, for example, 1-cyclopenten-1-yl, 2-cyclopenten-1-yl, 3-cyclopenten-1-yl, 3-cyclohexen-1-yl, 3-cycloocten-1-yl, etc. Examples of the $C_{6-14}$ aryl include, for example, phenyl, 1-naphthyl, 2-naphthyl, etc. Examples of the $C_{7-10}$ aralkyl-sulfonyl include, for example, benzyl, phenethyl, etc.

The hydrocarbon group which is the substituent of the sulfonyl may be substituted. Examples of the substituent include, for example, hydroxyl, unsubstituted-amino, mono- or di-substituted-amino [(Examples of the substituent include $C_{1-6}$ alkyl (e.g., methyl, ethyl, propyl, isopropyl, butyl, isobutyl, t-butyl, pentyl, hexyl, etc.), an acyl group (e.g., $C_{1-6}$ alkanoyl such as formyl, acetyl, propionyl, pivaloyl, etc., aryl carbonyl such as benzoyl, etc., $C_{1-6}$ alkyl-sulfonyl such as methylsulfonyl, ethylsulfonyl, etc.)], halogen atom (for example, fluorine, chlorine, bromine, iodine, etc.), nitro, cyano, $C_{1-6}$ alkyl which may be substituted by 1 to 5 halogen atom (for example, fluorine, chlorine, bromine, iodine, etc.), $C_{1-6}$ alkoxy which may be substituted by 1 to 5 halogen atom (for example, fluorine, chlorine, bromine, iodine, etc.). Examples of the $C_{1-6}$ alkyl group include, for example, methyl, ethyl, n-propyl, isopropyl, n-butyl, isobutyl, sec-butyl, tert-butyl, pentyl, hexyl, etc., and preferably include methyl, ethyl, etc. Examples of the $C_{1-6}$ alkoxy group include, for example, methoxy, ethoxy, n-propoxy, isopropoxy, n-butoxy, isobutoxy, sec-butoxy, tert-butoxy, etc, and preferably include methoxy, ethoxy, etc. These substituents may be the same or different from each other, and one, two or three substituents, preferably one or two substituents may substitute.

Examples of the "acyl group derived from a carboxylic acid" as the substituent include a carbonyl group having a hydrogen atom or one substituent which the above described "N-mono-substituted carbamoyl group" have on the nitrogen atom, etc., preferably, a $C_{1-6}$ alkanoyl such as formyl, acetyl, trifluoroacetyl, propionyl, butyryl, isobutyryl, pivaloyl, etc., an $C_{1-6}$ aryl-carbonyl such as benzoyl. Examples of the alkyl group in "alkyl-sulfinyl which may be substituted" include, for example, $C_{1-6}$ alkyl such as methyl, ethyl, propyl, isopropyl, butyl, isobutyl, t-butyl, pentyl, hexyl, etc. Examples of the aryl group in "aryl-sulfinyl which may be substituted" include, for example, $C_{6-14}$ aryl such as phenyl, naphthyl, anthryl, phenanthryl, acenaphthylenyl, etc.

Examples of the substituent of the alkyl group or the aryl group include lower alkoxy ($C_{1-6}$ alkoxy such as methoxy, ethoxy, propoxy, etc.), halogen (e.g., fluorine, chlorine, bromine, iodine, etc.), lower alkyl ($C_{1-6}$ alkyl such as methyl, ethyl, propyl, etc.), amino, hydroxyl, cyano, amidino, etc. One or two of these substituents may substitute at any substitutable position.

Examples of each "hydrocarbon group which may be substituted" and "non-aromatic heterocyclic group which may be substituted" shown as $R^2$ include the same ones as those shown by $R^1$. Among them, a $C_{2-6}$ alkyl which may be substituted and a $C_{3-8}$ cycloalkyl which may be substituted are preferable.

When $R^1$ and $R^2$ are bind to each other together with the nitrogen atom to form a heterocyclic ring which may be substituted, the heterocyclic ring contains one nitrogen atom, and may further contain nitrogen atom, oxygen atom and sulfur atom. Examples of the ring include, for example, cyclic amino group such monocyclic ring as 1-azetidinyl, 1-pyrrolidinyl, 1-piperidinyl, 1-homopiperidinyl, heptamethyleneimino, 1-piperazinyl, 1-homopiperazinyl, 4-morpholinyl, 4-thiomorpholinyl, etc., such fused ring as 2-isoindolinyl, 1,2,3,4-tetrahydro-2-isoquinolyl, 1,2,4,5-tetrahydro-3H-3-benzoazepine-3-yl, etc., such spiro ring as inden-1-spiro-4'-piperidin-1'-yl, etc. The cyclic amino group may have 1 to 5 substituents, preferably 1 to 3 substituents at substitutable positions on the ring.

Examples of the substituent include a hydroxyl group, a cyano group, a nitro group, an amino group, an oxo group, a halogen atom and a group represented by the formula: —$YR^a$, wherein $R^a$ is a hydrocarbon group which may be substituted or a heterocyclic group which may be substituted, and Y is a bond (a single bond), —$CR^bR^c$—, —COO—, —CO—, —$CR^b(OH)$—, —CO—$NR^b$—, —CS—$NR^b$—, —CO—S—, —CS—S—, —CO—$NR^b$—CO—$NR^c$—, —C(=NH)—$NR^b$—, —$NR^b$—, —$NR^b$—CO—, —$NR^b$—CS—, —$NR^b$—CO—$NR^c$—, —$NR^b$—CS—$NR^c$—, —$NR^b$—CO—O—, —$NR^b$—CS—O—, —$NR^b$—CO—S—, —$NR^b$—CS—S—, —$NR^b$—C(=NH)—$NR^c$—, —$NR^b$—$SO_2$—, —$NR^b$—$NR^c$—, —O—, —O—CO—, —O—CS—, —O—CO—O, —O—CO—$NR^b$—, —O—C(=NH)—$NR^b$—, —S—, —SO—, $SO_2$—, —$CR^bR^c$—S—, $CR^bR^c$—$SO_2$—, —$SO_2$—$NR^b$—, —S—CO—, —S—CS—, —S—CO—$NR^b$—, —S—CS—$NR^b$—, —S—C(=NH)—$NR^b$— (wherein each of $R^b$ and $R^c$ is a hydrogen atom, an alkyl group which may be substituted, an alkenyl group which may be substituted, an alkynyl group which may be substituted, an aryl group which may be substituted, a cycloalkyl group which may be substituted, a cycloalkenyl group which may be substituted, a heterocyclic group which may be substituted, an acyl group derived from sulfonic acid, an acyl group derived from carboxylic acid, etc.

Examples of the hydrocarbon group in the "optionally substituted hydrocarbon group" represented by $R^a$ include e.g. an aliphatic hydrocarbon group, an alicyclic hydrocarbon group and an aryl group, etc. Examples of the aliphatic hydrocarbon group, the alicyclic hydrocarbon group and the aryl group include those described for $R^1$.

Examples of the substituent of the "hydrocarbon group optionally substituted" include the same substituent as, those in the above described "hydrocarbon group which may be substituted" represented by $R^1$.

Examples of the "heterocyclic group" in the "heterocyclic group which may be substituted" represented by $R^a$ include the same heterocyclic group as those of "heterocyclic group which may be substituted" represented by $R^3$ mentioned below. Examples of the "substituent" in the "heterocyclic group which may be substituted" include the same substituent as those of non-aromatic heterocyclic group which may be substituted represented by $R^1$.

Examples of the "alkyl group which may be substituted", "alkenyl group which may be substituted", "alkynyl group which may be substituted", "aryl group which may be substituted", "cyclo-alkyl group which may be substituted", "cyclo-alkenyl group which may be substituted", "heterocyclic group which may be substituted", "acyl group derived from sulfonic acid", and "acyl group derived from carboxylic acid", each of which is represented by $R^b$ and $R^c$, include those mentioned as the substituent in the "hydrocarbon which may be substituted" represented by $R^1$. $R^1$ and $R^2$ are preferable to bind to each other together with the nitrogen atom to form a heterocycle which may be substituted. More preferably, $NR^1R^2$ is a group represented by the formula:

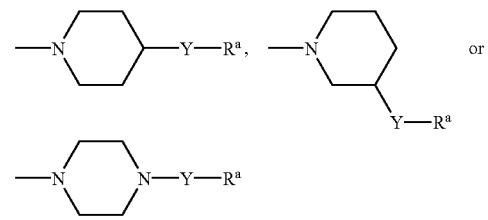

(wherein Y and $R^a$ have the meanings give above). In the above, while Y and $R^a$ have the meanings give above, $R^a$ is more preferably an aryl group which may be substituted or a heterocyclic group which may be substituted.

Examples of a cyclic hydrocarbon group in the "a cyclic hydrocarbon group which may be substituted" represented by $R^3$ include e.g. an alicyclic hydrocarbon group, an aryl group, etc.

Examples of the "alicyclic hydrocarbon group" include e.g. a saturated or unsaturated alicyclic hydrocarbon group such as a cycloalkyl group, a cycloalkenyl group, a cycloalkanedienyl group, etc., preferably a cycloalkyl group.

Examples of the "cycloalkyl group" include e.g. a $C_{3-9}$ cycloalkyl, (preferably a $C_{3-8}$ acycloalkyl, etc.) such as cyclopropyl, cyclobutyl, cyclopentyl, cyclohexyl, cycloheptyl, cyclooctyl, cyclononyl, etc., and a fused ring such as 1-indanyl, 2-indanyl, etc.

Examples of the "cycloalkenyl group" include e.g. a $C_{3-6}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc.

Examples of the "cycloalkanedienyl group" include e.g. a $C_{4-6}$ cycloalkanedienyl group such as 2,4-cyclopentadien-1-yl, 2,4-cyclohexadien-1-yl, 2,5-cyclohexadien-1-yl, etc.

Examples of the "aryl group" exemplified by the cyclic hydrocarbon group include e.g. a monocyclic or fused aromatic hydrocarbon group. Among them, a $C_{6-14}$ aryl group such as phenyl, naphthyl, anthryl, phenathryl, acenaphthyl, etc. is preferable. In particular, phenyl, 1-naphthyl, 2-naphthyl, etc. are preferable.

Examples of the substituent in the "a cyclic hydrocarbon group which may be substituted" represented by $R^3$ include the same substituent as those in the above described "hydrocarbon group which may be substituted" for $R^1$. The substituent is preferably, for example, a phenyl group, a phenyl group which may be substituted by a $C_{1-6}$ alkyl group such as tolyl, etc., a naphthyl group, etc., when the cyclic hydrocarbon group is alicyclic hydrocarbon group, and is preferably, for example a halogen atom (e.g., chlorine, fluorine, etc.), $C_{1-6}$ alkyl (methyl, ethyl, propyl, isopropyl, butyl, isobutyl, t-butyl, pentyl, hexyl, etc.), $C_{1-6}$ alkoxy (for example, methoxy, ethoxy, n-propoxy, isopropoxy, n-butoxy, etc.), $C_{3-6}$ cyclo-alkyl (for example, cyclopropyl, cyclobutyl, cyclopentyl, cyclohexyl, etc.), halogenated-$C_{1-6}$ alkyl (trifluoromethyl, etc.), halogenated-$C_{1-6}$ alkoxy (trifluoromethyloxy, etc.), $C_{1-6}$ alkyl-thio (methylthio, ethylthio, etc.), $C_{1-6}$ alkyl-sulfonyl (methylsulfonyl, ethylsulfonyl, etc.), cyano, nitro, when the cyclic hydrocarbon group is an aryl group.

Examples of the heterocyclic group in the "optionally substituted heterocyclic group" represented by $R^1$ include e.g. an aromatic heterocyclic group, a saturated or unsaturated non-aromatic heterocyclic group (an alicyclic heterocyclic group) etc., which contains, besides carbon atoms, at least one hetero-atom (preferably 1 to 4 hetero-atoms, more preferably 1 to 2 hetero-atoms) consisting of 1 to 3 kinds of hetero-atoms (preferably 1 to 2 kinds of hetero-atoms) selected from an oxygen atom, a sulfur atom, a nitrogen atom, etc.

Examples of the "aromatic heterocyclic group" include an aromatic monocyclic heterocyclic group such as a 5- to 6-membered aromatic monocyclic heterocyclic group, etc. (e.g. furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as a 8- to 12-membered aromatic fused heterocyclic group (e.g. benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1, 2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc., preferably, a heterocyclic group consisting of the above-mentioned 5- or 6-membered aromatic monocyclic heterocyclic group fused with a benzene ring or a heterocyclic group consisting of the above-mentioned 5- or 6-membered aromatic monocyclic heterocyclic group fused with the same or different above-mentioned 5- or 6-membered aromatic monocyclic heterocyclic group, etc.

Examples of the "non-aromatic heterocyclic group" include a 3- to 8-membered (preferably 5- or 6-membered) saturated or unsaturated (preferably saturated) non-aromatic heterocyclic group (alicyclic heterocyclic group) such as oxiranyl, azetidinyl, oxetanyl, thiethanyl, pyrrolidinyl, tetrahydrofuryl, thiolanyl, piperidinyl, tetrahydropyranyl, morpholinyl, thiomorpholinyl, piperazinyl, etc.

Examples of the substituent in the "heterocyclic group which may be substituted" represented by $R^3$ include the same substituent as those in the above described "non-aromatic heterocyclic group which may be substituted" represented by $R^1$. $R^3$ is preferably a phenyl group which may be substituted.

Examples of the "hydrocarbon group which may be substituted" represented by $R^4$ include the same "hydrocarbon group which may be substituted" represented by $R^1$. Examples of the "heterocyclic group which may be substituted" represented by $R^4$ include the same "heterocyclic group which may be substituted" represented by $R^3$.

Examples of the alkoxy group in "alkoxy group which may be substituted" represented by $R^4$ preferably include, for example, a $C_{1-6}$ alkoxy such as methoxy, ethoxy, n-propoxy, isopropoxy, n-butoxy, isobutoxy, sec-butoxy, tert-butoxy, etc. Examples of the substituent in "alkoxy group which may be substituted" include, for example, a cycloalkyl group (a $C_{3-6}$ cycloalkyl group such as cyclopropyl, cyclobutyl, cyclopentyl, cyclohexyl, etc.), an aryl group (a $C_{6-10}$ aryl group, etc., for example, phenyl, 1-naphthyl, 2-naphthyl, etc.), an aralkyl group (a $C_{7-10}$ aralkyl group, preferably a phenyl-$C_{1-4}$ alkyl group, etc., for example, benzyl, phenethyl, etc.), a heterocyclic group (e.g., a heterocyclic group mentioned as the substituent of the "hydrocarbon group which may be substituted" represented by $R^1$). Each of the lower alkyl group, the cycloalkyl group, the aryl group, the aralkyl group and the heterocyclic group may be substituted. Examples of the substituents include, for example, a hydroxyl group, an amino group which may be substituted [the amino group may have 1 to 5 substituents, for example, by a lower alkyl group (a $C_{1-6}$ alkyl group such as methyl, ethyl, propyl, isopropyl, butyl, isobutyl, t-butyl, pentyl, hexyl, etc.), an acyl group ($C_{1-6}$ alkanoyl such as formyl, acetyl, propionyl, pivaloyl, etc., benzoyl, etc.)], a halogen atom (e.g. fluorine, chlorine, bromine, iodine etc.), a nitro group, a cyano group, a lower alkyl group (which may have 1 to 5 halogen atoms (e.g. fluorine, chlorine, bromine, iodine etc.)), a lower alkoxy group (which may have 1 to 5 halogen atoms (e.g. fluorine, chlorine, bromine, iodine etc.)), etc. Examples of the lower alkyl group include a $C_{1-6}$ alkyl group such as methyl, ethyl, n-propyl, isopropyl, n-butyl, isobutyl, sec-butyl, tert-butyl, pentyl, hexyl, etc., and in particular methyl, ethyl, etc. are preferable. Examples of the lower alkoxy group include, for example, a $C_{1-6}$ alkoxy group such as methoxy, ethoxy, n-propoxy, isopropoxy, n-butoxy, isobutoxy, sec-butoxy, tert-butoxy, etc., and in, particular methoxy, ethoxy, etc. are preferable. The above described lower alkoxy group may have 1 or 2 to 3 (preferably 1 or 2) substituents. When the alkoxy group has 2 or 3 substituents, these substituents may be the same or different.

Examples of the aryl group in "aryloxy group which may be substituted" represented by $R^4$ preferably include, for example, a $C_{6-14}$ aryl group such as phenyl, naphthyl, anthryl, phenanthryl, acenaphthylenyl, etc. Examples of the substituent include, for example, a lower alkoxy group (for example a $C_{1-6}$ alkoxy group such as methoxy, ethoxy, propoxy, etc.), a halogen atom (e.g., fluorine, chlorine, bromine, iodine, etc.), a lower alkyl group (for example a $C_{1-6}$ alkyl group such as methyl, ethyl, propyl, etc.), an amino group, a hydroxyl group, a cyano group, an amidino group, etc. The aryloxy group may have 1 or 2 selected from these substituents at any possible position.

Examples of the substituent in "amino group which may be substituted" represented by $R^4$ preferably include, for example, a lower alkyl group (e.g., a $C_{1-6}$ alkyl group such as methyl, ethyl, propyl, isopropyl, butyl, isobutyl, t-butyl, pentyl, hexyl, etc.), an acyl group ($C_{1-6}$ alkanoyl (e.g., formyl, acetyl, propionyl, pivaloyl, etc.), benzoyl, etc.), a $C_{1-6}$ alkoxy-carbonyl which may be halogenated (e.g., trifluoromethoxycarbonyl, 2,2,2-trifluoroethoxycarbonyl, trichloromethoxy carbonyl, 2,2,2-trichloroethoxy carbonyl, etc.), etc. In addition, the "amino group" in the "optionally substituted amino group" as the substituent may be substituted with an optionally substituted imidoyl group (e.g., a $C_{1-6}$ alkylimidoyl, formimidoyl, amidino, etc.), etc. and two substituents of the "amino group" may form a cyclic amino group together with a nitrogen atom. Examples of said cyclic amino group include e.g. a 3- to 8-membered (preferably 5- to 6-membered) cyclic amino group such as 1-azetidinyl, 1-pyrrolidinyl, 1-piperidinyl, 4-morpholinyl, 1-piperazinyl and 1-piperazinyl which may have at the 4-position a lower alkyl group (e.g. a $C_1$-6 alkyl group such as methyl, ethyl, propyl, isopropyl, butyl, t-butyl, pentyl, hexyl, etc.), an aralkyl group (e.g. a $C_{7-10}$ aralkyl group such as benzyl, phenethyl, etc.), an aryl group (e.g. a $C_{6-10}$ aryl group such as phenyl, 1-naphthyl, 2-naphthyl, etc.), etc. $R^4$ is preferably a $C_{1-3}$ alkyl, a phenyl group which may be substituted, 3-pyridyl, 4-pyridyl, etc.

Examples of the hydrocarbon group represented by $R^5$ include the same substituent as those in the above described "hydrocarbon group which may be substituted" represented by $R^1$. The preferable examples of the hydrocarbon group include a lower alkyl group having 1 to 4 carbon atoms such as methyl, ethyl, n-propyl, isopropyl, butyl, n-butyl, isobutyl, tert-butyl, etc.

Examples of the counter anion represented by $Y^-$ include, for example, $Cl^-$, $Br^-$, $I^-$, $NO_3^-$, $SO_4^{2-}$, $PO4^{3-}$, $CH_3SO_{3-}$, etc.

Examples of the divalent aliphatic hydrocarbon group in divalent aliphatic hydrocarbon group which may be substituted by group other than an oxo group represented by E include, for example, a $C_{1-6}$ alkylene such as methylene, ethylene, etc., a $C_{2-6}$ alkynylene such as ethenylene, etc., and among them, a $C_{2-5}$ alkylene is more preferable and trimethylene is the most preferable.

The substituent of the divalent hydrocarbon group may be a substituent other than an oxo group, and examples of the substituents include, for example, an alkyl group which may be substituted, an aryl group which may be substituted, a cycloalkyl group which may be substituted, a cycloalkenyl group which may be substituted, a carboxyl group which may be esterified, a carbamoyl group which may be substituted, a thiocarbamoyl group which may be substituted, an amino group which may be substituted, a hydroxyl group which may be substituted, a thiol group (i.e. mercapto group) which may be substituted, an acyl group derived from carboxylic acid, an acyl group derived from sulfonic acid, a halogen (e.g., fluorine, chlorine, bromine, etc.), nitro, cyano, etc. The divalent hydrocarbon group may have 1 to 3 substituents. Each of these alkyl group which may be substituted, aryl group which may be substituted, cycloalkyl group which may be substituted, cycloalkenyl group which may be substituted, carboxyl group which may be esterified, carbamoyl group which may be substituted, thiocarbamoyl group which may be substituted, amino group which may be substituted, hydroxyl group which may be substituted, thiol group (i.e. mercapto group) which may be substituted, acyl group derived from carboxylic acid, acyl group derived from sulfonic acid include those mentioned as the substituent in "heterocyclic group which may be substituted" of $R^3$.

Examples of the $C_{1-3}$ aliphatic hydrocarbon group in "divalent $C_{1-3}$ aliphatic hydrocarbon group which may be substituted" represented by Q and R inclde a divalent aliphatic hydrocarbon group having 1 to 3 carbon atoms among the divalent aliphatic hydrocarbon group in divalent aliphatic hydrocarbon group which may be substituted by a group other than an oxo group represented by E.

Examples of the substituent in the "divalent $C_{1-3}$ aliphatic hydrocarbon group which may be substituted" represented by Q and R include those mentioned as the substituent in divalent aliphatic hydrocarbon group which may be substituted by a group other than an oxo group represented by E.

J is methine or a nitrogen atom, and methine is preferable.

$G^1$ is a bond, CO or $SO_2$, and CO or $SO_2$ is preferable.

$G^2$ is CO, $SO_2$, NHCO, CONH or OCO, and among them, CO,NHCO and OCO are preferable.

Examples of the salt at the carboxyl group or sulfonic acid group represented by $R^6$ include a salt with an alkali metal such as sodium, potassium, lithium, etc., a salt with alkaline earth metal such as calcium, magnesium, strontium, etc., a salt with ammonium, etc.

Examples of the reactive derivative of the carboxylic acid represented by $R^6$ include, for example, an acid halide, an acid azide, an acid anhydride, a mixed acid anhydride, an active amide, an active ester, an active thio ester, an isocyanate, etc. Examples of the acid halide include, for example, an acid chloride, an acid bromide, etc.; examples of the mixed acid anhydrides include a mono-$C_{1-6}$alkyl-carbonic acid mixed acid anhydride (e.g. a mixed acid anhydride of free acid and monomethylcarbonic acid, monoethylcarbonic acid, mono-isopropylcarbonic acid, mono-isobutylcarbonic acid, mono-tert-butylcarbonic acid, mono-benzylcarbonic acid, mono-(p-nitrobenzyl)carbonic acid, mono-allylcarbonic acid, etc.), a $C_{1-6}$ aliphatic carboxylic acid mixed acid anhydride (e.g. a mixed acid anhydride of free acid and acetic acid, trichloroacetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), a $C_{7-12}$ aromatic carboxylic acid mixed acid anhydride (e.g. a mixed acid anhydride of free acid and benzoic acid, p-toluic acid, p-chloro benzoic acid, etc.), an organic sulfonic acid mixed acid anhydride (e.g. mixed acid anhydride of free acid and methanesulfonic acid, ethane sulfonic acid, benzenesulfonic acid, p-toluenesulfonic acid, etc.) etc.; examples of the active amide include an amide with a nitrogen-containing heterocyclic compound (an acid amide of a free acid and, for example, pyrazole, imidazole, benzotriazole, etc., these nitrogen-containing heterocyclic compound may be substituted with a $C_{1-6}$alkyl group (e.g., methyl, ethyl, etc.), a $C_{1-6}$alkoxy group (e.g., methoxy, ethoxy, etc.), a halogen atom (e.g., fluorine, chlorine, bromine, etc.), an oxo group, a thioxo group, a $C_{1-6}$alkylthio group (e.g., methylthio, ethylthio, etc.), etc.), etc.

As an active ester, all the active esters used in the field of the synthesis of â-lactam and peptide may be used. Examples of the active ester include, for example, an organic phosphoric acid ester (e.g. diethoxyphosphoric acid ester, diphenoxyphosphoric acid ester, etc.), p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyridone ester, etc. Examples of the active thio ester include an ester of the acid with an aromatic heterocyclic thiol compound (e.g. 2-pyridylthiol ester, 2-benzothiazolylthiol ester, etc., which heterocyclics may be substituted with a $C_{1-6}$alkyl group (e.g. methyl, ethyl, etc.), a $C_{1-6}$alkoxy group (e.g., methoxy, ethoxy, etc.), a halogen atom (e.g., fluorine, chlorine, bromine, etc.), a $C_{1-6}$alkyl-thio group (e.g., methylthio, ethylthio, etc.), etc.).

Examples of the reactive derivative at the sulfonic acid group include, for example, sulfonyl halide (e.g., sulfonyl chloride, sulfonyl bromide, etc.), sulfonylazide, an acid anhydride thereof.

Examples of the leaving group represented by X include, for example, a halogen atom (e.g., a chlorine atom, a bromine atom, an iodine atom, etc.), an alkyl or arylsulfonyloxy group (e.g., methanesulfonyloxy, ethanesulfonyloxy, benzenesulfonyloxy, p-toluenesulfonyloxy, etc.), etc.

Examples of the salt of a compound of the formula (I) of the present invention include an acid addition salt such as a salt of an inorganic acid (e.g., hydrochloric acid salt, sulfuric acid salt, hydrobromic acid salt, phosphoric acid salt, etc.), a salt of an organic acid (e.g., acetic acid salt, trifluoroacetic acid salt, succinic acid salt, maleic acid salt, fumaric acid salt, propionic acid salt, citric acid salt, tartaric acid salt, lactic acid salt, oxalic acid salt, methanesulfonic acid salt, p-toluenesulfonic acid salt, etc.), etc., a salt with a base (e.g. an alkali metal salt such as potassium salt, sodium salt, lithium salt, etc., an alkaline earth metal salt such as calcium salt, magnesium salt, etc., ammonium salt, a salt with an organic base such as trimethylamine salt, triethylamine salt, tert-butyl dimethylamine salt, dibenzyl methylamine salt, benzyl, dimethylamine salt, N,N-dimethylaniline salt, pyridine salt, quinoline salt, etc.).

Also, the compound represented by the formula (I) or salt thereof may be hydrated. Hereinafter, the compound of the formula (I), its salt and its hydrate referred to as Compound (I).

The prodrug of the compound (I) of the present invention means a compound which is converted to Compound (I) having inhibitory activity of CCR5 by a reaction due to an enzyme, an gastric acid, etc. in vivo.

Examples of theprodrug of Compound (I) include a compound wherein an amino group of Compound (I) is substituted with acyl, alkyl, phosphoric acid (e.g. a compound wherein an amino group of Compound (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl, tert-butyl, etc.); a compound wherein an hydroxyl group of Compound (I) is substituted with an acyl, an alkyl, a phosphoric acid group, boric acid group (e.g. a compound wherein an hydroxyl group of Compound (I) is substituted with acetyl, palmitoyl, propanoyl, pivaloyl, succinyl, fumaryl, alanyl, dimethylaminomethylcarbonyl, etc.); a compound wherein a carboxyl group of Compound (I) is modified to ester, amide (e.g. a compound wherein a carboxyl group of Compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester, methyl amide, etc.); etc. These prodrug can be produced by per se known method from Compound (I).

The prodrug of Compound (I) may be a compound which is converted into Compound (I) under the physiological conditions as described in "Pharmaceutical Research and Development", Vol. 7 (Drug Design), pages 163-198 published in 1990 by Hirokawa Publishing Co. (Tokyo, Japan).

The prodrug of Compound (I) may be distinct entity or in the form of any possible pharmaceutically acceptable salts thereof. Examples of said salt include a salt with an inorganic base (e.g., an alkaline metal such as sodium, potassium, etc.; an alkaline earth metal such as calcium, magnesium, etc.; transition metal such as zinc, iron, copper, etc.; etc.); an organic base (e.g., an organic amine such as trimethylamine, triethylamine, pyridine, picoline, ethanolamine, diethanolamine, triethanolamine, dicyclohexylamine, N,N'-dibenzylethylenediamine, etc.; a basic amino acid such as arginine, lysine, ornithine, etc.; etc.); etc., when said compound has an acidic group such as a carboxyl group, etc.

Examples of said salt also include a salt with an inorganic acid or an organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.); an acidic amino acid such as aspartic acid, glutamic acid, etc.; etc., when said compound has a basic group such as an amino group, etc.

The prodrug of the compound (I) may be hydrated or unhydrated.

Compound (I) may have one or more asymmetric carbons in the molecule. The compound of the present invention may have R-configuration or S-configuration as to the asymmetric carbons.

The "lower" in "a lower alkyl group", "a lower alkoxy group", etc., throughout the present specification means a straight, branched or cyclic ones having 1 to 6 carbon otherwise mentioned.

Among the compound of the formulas (II) to (VI), the compound having a basic group or acidic group may form an acid addition salt or a salt with a base, respectively. Examples of the salt include those mentioned as the salt of the compound of the formula (I). Hereinafter compound of each formula and a salt thereof are referred to as Compound (symbol of the formula). For example, the compound of the formula (II) and salt thereof are simply referred to as Compound (II).

Compound (I) can, for example, be prepared by the following methods:

Production 1

As shown in the following formula, Compound (II) can be reacted with Compound (III) to give Compound (I).

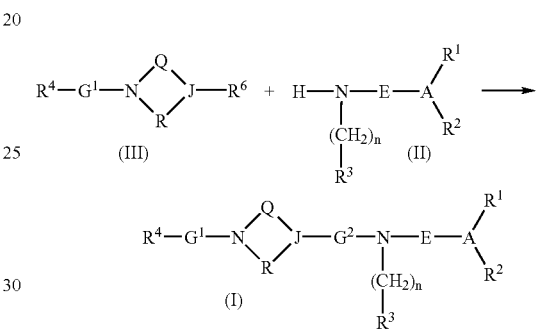

(wherein each symbol has the same meaning as defined above)

The reaction is usually carried out in a solvent inert to the reaction. Examples of the solvent include an ether (e.g., ethyl ether, diisoprpyl ether, dimethoxy ethane, tetrahydrofuran, dioxane, etc.), a halogenated hydrocarbon (e.g., dichloromethane, dicholoroethane, chloroform, etc.), an aromatic solvent (e.g., toluene, chlorobenzene, xylene, etc.), acetonitrile, N,N-dimethylformamide (DMF), acetone, methylethyl ketone, dimethylsulfoxide (DMSO), water, etc., or a mixed solvent thereof.

Among them, acetonitrile, dichloromethane, chloroform, etc. are preferable. The reaction is usually carried out by using 1 to 5 equivalent, preferably 1 to 3 equivalents of Compound (III) relative to 1 equivalent of Compound (II). The reaction temperature ranges from −20° C. to 50° C., preferably 0° C. to room temperature, and reaction time is usually 5 minutes to 100 hours. The reaction may smoothly proceed by using a base. As the base, an inorganic base and an organic base can be used effectively. Examples of the inorganic base include a hydroxide, a hydride, a carbonate, a bicarbonate of alkaline metal or alkaline earth metal. Among them, potassium carbonate, sodium carbonate, sodium hydroxide, potassium hydroxide, sodium hydrogencarbonate, potassium hydrogencarbonate are preferable. Examples of the organic base preferably include a tertiary amine such as triethylamine. Examples of the reactive derivative include an acid anhydride, an acid halide (e.g., acid chloride, acid bromide), an active ester, an isocyanate, etc. Among them, an acid halide is preferable. The used amount of the base is usually 1 to 10 equivalents, preferably 1 to 3 equivalents relative to 1 equivalent of Compound (II).

The acylation reaction in which a carboxylic acid is used is carried out in an inert Solvent (e.g., a halogenated hydrocarbon, acetonitrile) by reacting one equivalent of Compound (II) with 1 to 1.5 equivalent of carboxylic acid in the presence of 1 to 1.5 equivalent of dehydrating condensation agent such as dicyclohexyl carbodiimide (DCC), etc. The reaction is usually carried out at room temperature, and the, reaction time is 0.5 to 24 hours.

Compound (II) wherein the divalent aliphatic hydrocarbon group which may be substituted by a group other than an oxo group represented by E is a group of the formula:

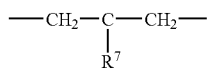

(wherein $R^7$ is a group other than an oxo group) can be produced, for example, by a method described in Synthetic Comm., 1991, 20, 3167-3180. That is, the above compound can be produced by the following method by applying an addition reaction of amines or amides to unsaturated bond.

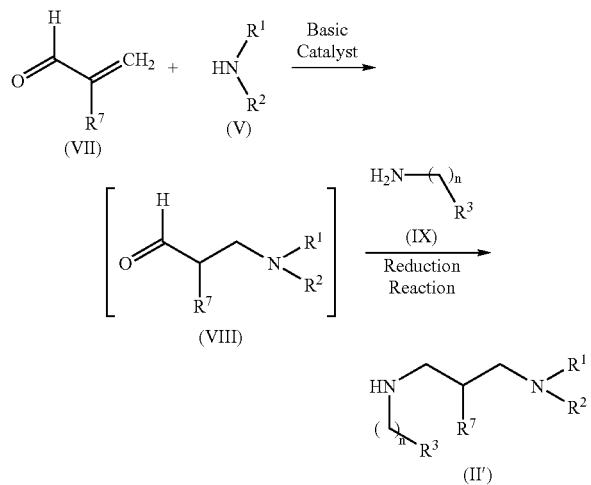

(wherein each symbol has the same meaning as defined above)

The substituent other than an oxo group represented by $R^7$ means those in the divalent aliphatic hydrocarbon group which may be substituted by a group other than an oxo group represented by E.

The compound can be produced by reacting acrolein derivatives (VII) with Compound (V), followed by reacting the resulting compound with Compound (IX) under a condition of reduction. The reaction of Compound (VII) with Compound (V) is usually carried out in a solvent inert to the reaction in the presence of a base. Examples of the base include 1) a strong base such as hydride of alkali metal or alkaline earth metal (e.g., lithium hydride, sodium hydride, potassium hydride, calcium hydride, etc.), an amide of an alkali metal or an alkaline earth metal (e.g., lithium amide, sodium amide, lithium diisopropylamide, lithium dicyclohexylamide, lithium hexamethyldisilazide, sodium hexamethyldisilazide, potassium hexamethyldisilazide, etc.), a lower alkoxide of alkali metal or alkaline earth metal (e.g., sodium methoxide, sodium ethoxide, potassium t-butoxide, etc.), etc., 2) an inorganic base such as a hydroxide of an alkali metal or an alkaline earth metal (e.g., sodium hydroxide, potassium hydroxide, lithium hydroxide, barium hydroxide, etc.), a carbonate of an alkali metal or an alkaline earth metal (e.g., sodium carbonate, potassium carbonate, cesium carbonate, etc.), a bicarbonate of alkali metal or alkaline earth metal (e.g., sodium hydrogencarbonate, potassium hydrogencarbonate, etc.), etc., 3) an organic base, etc., such an amine as triethylamine, diisopropylethylamine, N-methylmorpholine, dimethylaminopyridine, DBU(1,8-diazabicyclo[5.4.0]-7-undecene), DBN(1,5-diazabicyclo[4.3.0]non-5-ene), etc., and such basic heterocyclic Compound, etc., as pyridine, imidazole, 2,6-lutidine, etc. Examples of the solvent include those mentioned in the reaction of Compound (II) with Compound (III). These solvent can be used solely or in combination. Compound (VIII) can be obtained in the reaction.

Examples of the reducing agent for the reaction of Compound (VIII) with Compound (IX) include sodium borohydride, lithium borohydride, sodium cyanoborohydride, sodium triacetoxyborohydride, etc. The used amount of the reducing agent is usually in the range of 1 to 10 equivalents, preferably in the range of 1 to 4 equivalents relative to 1 equivalent of Compound (VIII). The reaction temperature ranges –20 to 50° C., preferably 0° C., to room temperature, and reaction time is 0.5 to 24 hours.

Catalytic reduction reaction is carried out in the presence of a catalytic amount of a metal catalyst such as Raney nickel, platinum oxide, metallic palladium, palladium-carbon, etc., in an inert solvent (e.g., an alcohol such as methanol, ethanol, isopropanol, t-butanol, etc.), at room temperature to 100° C., under a hydrogen pressure of 1 to 100 atm for 1 to 48 hours.

Compound (II) used in this method can be produced by a manner similar to that described in Chem. Pharm. Bull. 47(1) 28-36 (1999), Japanese unexamined patent publication No. 56-53654, etc. Compound (III) used in this method can be produced by a manner similar to that described in J. Am. Chem. Soc., 1950, 72, 1415., J. Am. Chem. Soc., 1952, 74,4549, J. Org. Chem., 1956, 21, 1087., etc.

Production 2

Compound (I) can be produced by reacting Compound (IV) with Compound (V) or Compound (VI) as shown below.

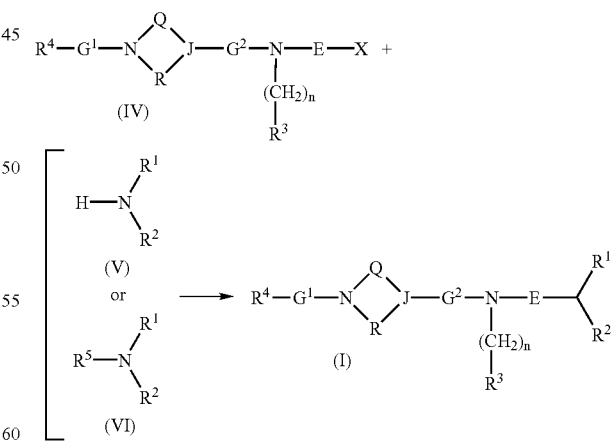

(wherein each symbol has the same meaning as defined above)

The reaction can be carried out by a manner similar to that described in Organic Functional Group Preparations 2nd ed., (Academic Press, Inc.).

The reaction is usually carried out in a solvent inert to the reaction. Examples of the solvent include an alcohol, an ether, a halogenated hydrocarbon, an aromatic solvent, acetonitrile, N,N-dimethylformamide (DMF), acetone, methylethyl ketone, dimethylsulfoxide (DMSO), etc. These solvent can be used solely or in combination. Among them, acetonitrile, dimethylformamide, acetone, ethanol, etc., are preferable. The reaction temperature ranges usually from room temperature to 100° C., preferably from room temperature to 50° C., and the reaction time is usually 0.5 to 1 day. In this reaction, a base is usually added in an amount of 1 to 3 equivalents relative to 1 equivalent of Compound (IV), but it is not essential. Examples of the base include those mentioned in the reaction of Compound (II) with Compound(III).

Compound (IV) used as the starting compound in the reaction can be produced from Compound (III) by a known conventional manner.

Production 3

Compound (I) wherein E is a group of the formula:

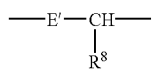

(wherein E' is a group obtainable by reducing one carbon from E, $R^8$ is hydrogen atom or hydrocarbon group) can be produced by reacting a compound represented by the formula(X) with a compound represented by the formula (V) under a reduction condition as shown below.

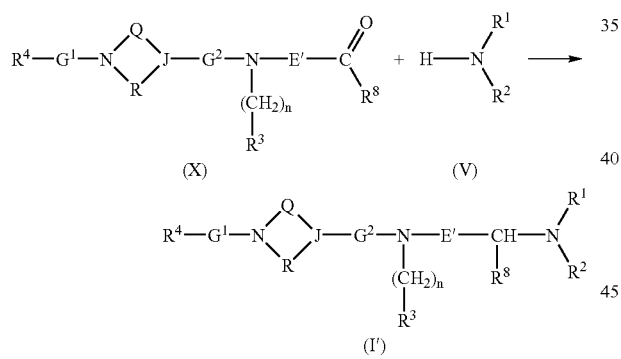

(wherein each symbol has the same meaning as defined above)

A group obtainable by reducing one carbon from E represented by E' is a divalent aliphatic hydrocarbon group which may be substituted by a group other than an oxo group and a group obtainable by reducing one carbon from E. The hydrocarbon group represented by $R^8$ is the unsubstituted alkyl group, the unsubstituted aryl group, the unsubstituted cycloalkyl group, the unsubstituted cycloalkenyl group among the alkyl group which may be substituted, the aryl group which may be substituted, the cycloalkyl group which may be substituted, the cycloalkenyl group which may be substituted, each of which is mentioned as the substituent of the divalent aliphatic hydrocarbon group which may be substituted by a group other than an oxo group represented by E.

The reaction is carried out by reacting Compound (X) with Compound (V) in an appropriate solvent (e.g., water, an alcohol, an ether, a halogenated hydrocarbon, acetonitrile, or a mixed solvent of two or more of these solvent, etc.), if necessary, by the addition of acidic substance such as acetic acid, trifluoroacetic acid, etc., in the presence of 1 to 5 equivalents, preferably 1 to 1.5 equivalent of a reducing agent. The reducing agent and the reaction condition mentioned in Production 1 can be applied for this reaction.

Compound (X) used as starting materials in the reaction can be produced from Compound (III) by a known conventional method.

Production 4

A compound represented by the formula (I) wherein E is a group of the formula:

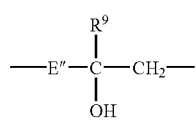

(wherein E" is a group obtainable by reducing two carbons from E, and $R^9$ is a hydrocarbon group.) can be produced by reacting a compound of the formula (XI) with a compound represented by the formula (V).

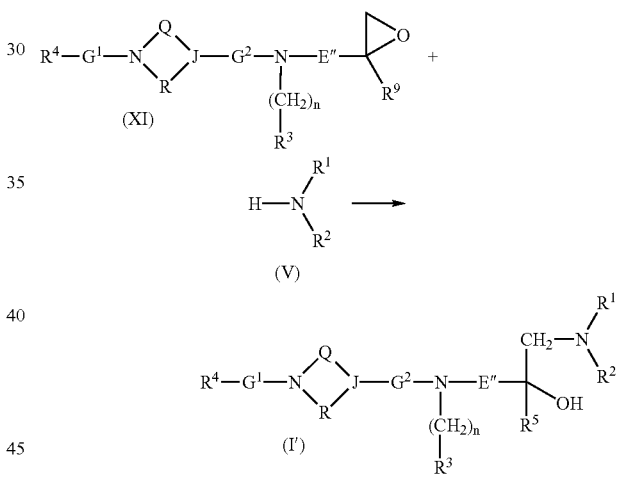

(wherein each symbol has the same meaning as defined above)

The group obtainable by reducing two carbons from E represented by E" is a divalent aliphatic hydrocarbon group which may be substituted by a group other than an oxo group and a group obtainable by reducing two carbons from E. Examples of the hydrocarbon group represented by $R^9$ include those mentioned as a hydrocarbon group represented by $R^8$.

The reaction is carried out in the absence or presence of a solvent. Examples of the solvent include those mentioned for the reaction of Compound (II) and Compound (III). In this reaction, Lewis acid such as anhydrous zinc chloride, anhydrous aluminum chloride, anhydrous iron (II) chloride, titanium (IV) chloride, tin (IV) chloride, cobalt chloride, copper (II) chloride, trifluoroboron etherate, etc., or the base mentioned above is used as a catalyst so as to accelerate the reaction. The reaction temperature is usually in the range of from −40° C. to 180° C.

Compound (XI) used as the starting compound in the reaction can be produced from Compound (III) by a known conventional method.

Production 5

Compound (I) can be produced by reacting Compound (XII) with Compound (XIII).

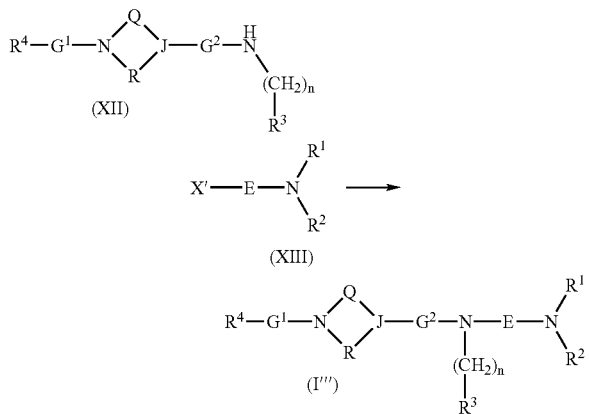

wherein X' is a leaving group, and the other symbols have the meanings give above)

Examples of the leaving group represented by X' include those mentioned as the leaving group represented by X.

The reaction is carried out by a manner similar to that for Production 2.

Compound (XIII) used as the starting compound in the reaction can be produced from Compound (V) by a known conventional method.

Compound (XII) used as the starting compound in the reaction can be produced by reacting Compound (III) with Compound represented by the formula: $H_2N(CH_2)_n—R^3$ (wherein each symbol has the meaning given above) by a manner similar to that for Production 1.

Production 6

Compound (I) can be produced by reacting Compound (XIV) with Compound (XV).

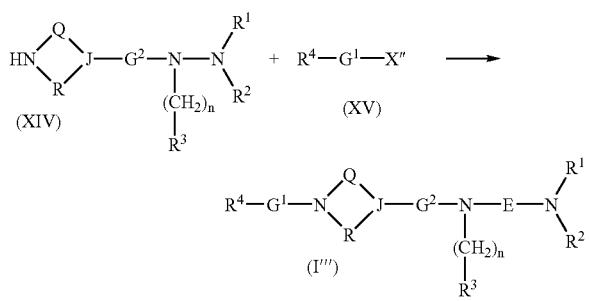

(wherein X" means a leaving group or a $G^1$-X" means a carboxylic group, sulfonic acid group or a reactive derivative thereof, and the other symbols have the meanings given above)

Examples of the reactive derivative of the carboxyl group or sulfonic acid group represented by the formula: $G^1$-X" include those mentioned for $R^6$.

The reaction is carried out by a manner similar to that for Production 2. Examples of the leaving group include that mentioned as the leaving group represented by X.

The compound (I) of the present invention may be used in combination with other drug for the treatment or prevention of infectious disease of HIV (in particular, a pharmaceutical composition for the treatment or prevention of AIDS). In this case, these drugs can be formulated by mixing individually or simultaneously with pharmaceutically acceptable carriers, excipients, binders, diluents or the like, which can be administered orally or non-orally as a pharmaceutical composition for the treatment or prevention of infectious disease of HIV. In the case of formulating these effective components individually, while the individually formulated agents can be administered in the form of their mixture prepared by using e.g. a diluent when administered, the individually formulated agents can also be administered separately or simultaneously or with time intervals to the one and same subject. A kit for administering the individually formulated effective components in the form of their mixture prepared by using e.g. a diluent when administered (e.g. a kit for injection which comprises two or more ampoules each comprising a powdery component and a diluent for mixing and dissolving two or more components when administered, etc.), a kit for administering the individually formulated agents simultaneously or with time intervals to the one and the same subject (e.g. a kit for tablets to be administered simultaneously or with time intervals, characterized by having two or more tablets each comprising an agent and said tablets being put in one or separate bags and, if necessary, a column to describe time to be administered each agent, etc.), etc. are also included by the pharmaceutical composition of the present invention.

Example of the other pharmaceutical agent for the treatment or prevention of infectious disease of HIV to be used in combination with the compound (I) of the present invention include nucleoside reverse transcriptase inhibitor such as zidovudine, didanosine, zalcitabine, lamivudine, stavudine, abacavir, adefovir, adefovir dipivoxil, fozivudine tidoxil, etc.; non-nucleoside reverse transcriptase inhibitor (including an agent having anti-oxidative activity such as immunocal, oltipraz, etc.) such as nevirapine, delavirdine, efavirenz, loviride, immunocal, oltipraz, etc.; protease inhibitors such as saquinavir, ritonavir, indinavir, nelfinavir, amprenavir, palinavir, lasinavir, etc.; etc.

As the nucleoside reverse transcriptase inhibitor, zidovudine, didanosine, zalcitabine, lamivudine, stavudine, etc. are preferable; as the non-nucleoside reverse transcriptase inhibitor, nevirapine, delavirdine, etc. are preferable; and as the protease inhibitor, saquinavir, ritonavir, indinavir, nelfinavir, etc. are preferable.

The compound (I) of the present invention may be used in combination with, for example, CXCR4 antagonist (CXCR4 being a second receptor of T cell-tropic HIV-1) such as AMD-3100, etc., antibody against HIV-1 surface antigen, HIV-1 vaccine, etc., in addition to the above-mentioned protease inhibitor, reverse transcriptase inhibitor, etc.

The compound (I) of the present, invention has potent CCR antagonistic activity (in particular, potent CCR5antagonistic activity) and therefore can be used for the treatment or prevention of various infectious diseases of HIV, for example, AIDS in human. The compound (I) of the present invention is low toxic and safely used as CCR5 antagonist for the treatment or prevention of AIDS and also for the prevention of the progression of AIDS.

The dose per day of the compound (I) varies depending on the condition and body weight of a patient, administration route, etc. Typical daily dose per adult patient (body weight: 50 Kg) for oral administration is about 5 to 1000 mg, preferably about 10 to 600 mg, more preferably about 10 to 300 mg, and in particular about 15 to 150 mg, as active ingredient [the compound (I)] and the compound (I) is administered once or 2 to 3 times par day.

When the compound (I) is used in combination with a reverse transcriptase inhibitor and/or a protease inhibitor, the dose of the reverse transcriptase inhibitor or the protease inhibitor ranges, for example, from about 1/200 to 1/2 or more of usual dose to about 2 to 3 times or less of usual dose. In case that two or more drugs are used in combination, each dose of the drugs is appropriately adjusted if one drug affects metabolism of the other drug, while each dose of the drugs when they are used in combination is generally the same as the dose when they are used alone.

Typical daily dose of the reverse transcriptase inhibitor and the protease inhibitor is as follows:

| | |
|---|---|
| zidovudine | 100 mg |
| didanosine | 125 to 200 mg |
| zalcitabine | 0.75 mg |
| lamivudine | 150 mg |
| stavudine | 30 to 40 mg |
| saquinavir | 600 mg |
| ritonavi | 600 mg |
| indinavir | 800 mg |
| nelfinavir | 750 mg |

In case of combination use of the compound (I) with a reverse transcriptase inhibitor and/or a protease inhibitor preferred embodiments are shown below.

① A drug containing about 10 to 300 mg of the compound (I) and a drug containing about 50 to 200 mg of zidovudine to one adult patient (body weight: 50 Kg) are administered. Each of the drugs may be administered to the one and the same subject simultaneously or with time intervals of 12 hours or less.

② A drug containing about 10 to 300 mg of the compound (I) and a drug containing about 300 to 1200 mg of saquinavir to one adult patient (body weight: 50 Kg) are administered. Each of the drugs may be administered to the one and the same subject simultaneously or with time intervals of 12 hours or less.

N-(3,4-Dichlorophenyl)-N-(3-halogeno-propyl)-1-(methylsulfonyl)-4-piperidinecarboxamide, N-(3-chloro-4-methylphenyl)-N-(3-halogeno-propyl)-1-(methylsulfonyl)-4-piperidinecarboxamide and a salt thereof are useful as intermediate compounds for producing the compound of present invention.

BEST MODE FOR CARRYING OUT THE INVENTION

The present invention is hereinafter described in more detail by means of the following Example, Reference Example, Test Example and Formulation Example, which are mere examples of the, present invention and are not construed as limitative to the present invention.

The following gene manipulation is carried out in accordance with methods described in textbook (Maniatis et al., Molecular Cloning, Cold Spring Harbor Laboratory, 1989) or protocol attached to reagents.

In the following Reference Examples and Examples, silica gel 60 (Merck, 70 to 230 or 230 to 400 mesh) or alumina (ICN, basic, activity III), was used as packing for column chromatography. Melting point was measured by using Yanaco MP-J3.

$^1$H NMR spectra were measured using tetramethylsilane (CDCl$_3$, DMSO-d$_6$, CD$_3$OD) or 3-(trimethylsilyl) propionic acid, sodium salt-2,2,3,3-d$_4$ (D$_2$O) as an internal standard with a Gemini 200 spectrometer (Varian, 200 MHz). Mass spectrum (APCI-MS)was measured by using PlatformII (Micromass).

In Examples 32 to 48, 68 to 88, 91 to 170, 431 to 456, and 469, preparative HPLC was conducted under the following condition.
Instrument: combinatorial chromatography system (Gilson)
Column: YMC CombiPrep ODS-A, 50×20 mm, S-5 μm
Eluent: A) 0.1% solution of trifluoroacetic acid in water, B) 0.1% solution of trifluoroacetic acid in acetonitrile 0.00 min(A/B=90/10), 1.20 min(A/B=90/10), 4.40 min(A/B=0/100), 5.60 min(A/B=0/100)
Amount Injected: 500 μl
Flow Rate: 25 ml/min
Detection: UV 220 nm In Examples 32 to 48, 68, to 88, 91 to 161, 431 to 456, and 469, HPLC analysis was conducted under the following condition.
Instrument: LC-10Avp system (Shimadzu)
Column: CAPCELL PAK C$_{18}$ UG120, 50×2.0 mm, S-3 μm
Eluent: A) 0.1% solution of trifluoroacetic acid in water, B) 0.1% solution of trifluoroacetic acid in acetonitrile 0.00 min(A/B=90/10), 4.00 min(A/B=5/95), 5.50 min(A/B=5/95), 5.51 min(A/B=90/10), 8.00 min(A/B=90/10)
Flow Rate: 0.5 ml/min
Detection: UV 220 nm In Examples 52 to 64, and 264 to 278, preparative HPLC was conducted under the following condition.
Instrument: combinatorial chromatography system (Gilson)
Column: YMC CombiPrep ODS-A, 50×20 mm, S-5 μm
Eluent: A) 0.1% solution of trifluoroacetic acid in water, B) 0.1% solution of trifluoroacetic acid in acetonitrile 0.00 min(A/B=90/10), 1.00 min(A/B=90/10), 4.00 min(A/B=10/90), 7.00 min(A/B=10/90)
Amount Injected: 1000 μl×2
Flow Rate: 25 ml/min
Detection: UV 220 nm In Examples 52 to 64, 264 to 321, and 459, HPLC analysis was conducted under the following condition.
Instrument: LCSS-905 system (JASCO)
Column: YMC-Pack ODS-A, 250×4.6 mm, S-5 μm
Eluent: A) 0.2% solution of acetic acid in water, B) 0.2% solution of acetic acid in acetonitrile 0.00 min(A/B=30/70), 20.00 min(A/B=30/70)
Flow Rate: 0.5 ml/min
Detection: UV 220 nm

REFERENCE EXAMPLE 1

N-[3-(4-benzyl-1-piperidinyl)propyl]aniline 2 hydrochloride

To a solution of 4-benzylpiperidine (52.58 g, 300 mmol), DBU (0.449 ml, 3.0 mmol) in THF (600 ml) was added dropwise a solution of acrolein (90%, 18.69 g, 300 mmol) in THF (60 ml) over a period of 10 minutes at −20° C. under stirring. While a temperature of the solution was elevated from −20° C. to −10° C., the solution was stirred 1 hour. To the solution were added at −10° C. aniline (27.94 g, 300 mmol) and sodium triacetoxyborohydride (127.16 g, 600 mmol), successively, and the mixture was stirred for 19 hours while the temperature of the mixture was elevated to room temperature. To the mixture was added an aqueous solution of 2N-sodium hydroxide (900 ml) under ice cooling, and the mixture was stirred for 30 minutes and extracted with diethyl ether (400 ml, 200 ml×2). The organic layer was dried over magnesium sulfate and concentrated under reduced pressure. The concentrate was dissolved in 2-propanol (400 ml), and to the solution was added 4N-hydrogen chloride in ethyl acetate (200 ml) with stirring. The resulting precipitates were collected by filtration. The precipitates were washed with 2-propanol (100 ml×3), and dried under reduced pressure to give the titled compound (75.66 g, 198 mmol, Yield 66%) as white crystals. mp 217° C. (dec.)

$^1$H NMR (DMSO-$d_6$) δ 1.4-1.9 (5H, m), 2.0-2.25 (2H, m), 2.45-2.6 (2H, m), 2.83 (2H, br t, J=11.4 Hz), 3.12 (2H, br t, J=7.2 Hz), 3.29 (2H, br t, J=6.9 Hz), 3.41 (2H, br d, J=12.6 Hz), 7.05-7.5 (10H, m)

Anal. Calcd for $C_{21}H_{28}N_2 \cdot 2HCl \cdot 0.55H_2O$: C, 64.61; H, 8.00; N, 7.18. Found: C, 64.71; H, 7.92; N, 7.32.

Free base (N-[3-(4-benzyl-1-piperidinyl)propyl]aniline)

$^1$H NMR (CDCl$_3$) δ 1.05-1.85 (9H, m), 2.34 (2H, t, J=6.8 Hz), 2.46 (2H, d, J=6.6 Hz), 2.83 (2H, br d, J=11.8 Hz), 3.06 (2H, t, J=6.4 Hz), 6.45-6.65 (3H, m), 7.0-7.25 (7H, m)

REFERENCE EXAMPLE 2

N-(3-(4-Benzyl-1-piperidinyl)propyl]-3,4-dichloroaniline 2 hydrochloride

By a similar manner to Reference Example 1, the titled compound was synthesized by using 3,4-dichloroaniline. Yield 53%.

mp 203° C. (dec.)

$^1$H NMR (DMSO-$d_6$) δ 1.49-1.76 (5H, m), 1.91-1.96 (2H, m), 2.50-2.55 (2H, m), 2.79-3.17 (6H, m), 3.38-3.44 (2H, m), 6.68 (1H, dd, J=2.8, 8.8 Hz), 6.75 (1H, d, J=2.6 Hz), 7.17-7.30 (6H, m)

Anal. Calcd for $C_{21}H_{26}Cl_2N_2 \cdot 2HCl \cdot 0.5H_2O$: C, 54.92; H, 6.36; N, 6.10. Found: C, 55.11; H, 6.64; N, 6.37.

REFERENCE EXAMPLE 3-1

4-(4-Fluorobenzyl)piperidine hydrochloride 4-fluorobenzyl bromide (100 g) and triethyl phosphite (120 ml) were mixed, and the mixture was stirred at 150° C. for 22 hours. The obtained reaction mixture was distilled under reduced pressure (bp 115-120° C./1.5 mmHg) to give diethyl 4-fluorobenzylphosphonate (125 g). To a solution of 4-fluorobenzylphosphonate (60.8 g), 15-Crown-5 (4 ml) in THF (400 ml) was added 60% sodium hydride in mineral oil (9.75 g) under ice cooling with stirring, and the mixture was stirred at the same temperature for 30 minutes. To the mixture was added dropwise a solution of 1-tert-butoxycarbonyl-4-piperidone (42.0 g) in THF (150 ml) under ice cooling, and the mixture was stirred at room temperature for 22 hours. After the addition of water under ice cooling, the mixture was extracted with ethyl acetate;, and the organic layer was washed with saturated aqueous solution of sodium hydrogencarbonate, saturated aqueous solution of sodium chloride, successively. The organic layer was dried over magnesium sulfate and concentrated under reduced pressure. The concentrate was subjected to column chromatography (silica gel 650 g, hexane/ethyl acetate=30/1 to 10/1), and the desired fraction was concentrated under reduced pressure to give 1-tert-butoxycarbonyl-4-(4-fluorobenzylidene)piperidine (47.0 g).

$^1$H NMR (CDCl$_3$) δ 1.48 (9H, s), 2.32-2.44 (4H, m), 3.37-3.53 (4H, m), 6.31 (1H, s), 7.00-7.19 (4H, m)

1-tert-Butoxycarbonyl-4-(4-fluorobenzylidene)piperidine (47.0 g) was dissolved in methanol (450 ml). To the solution was added 10% palladium carbon (water content: 50%, 4.7 g), and the mixture was subjected to catalytic hydrogenation reaction for 5 hours. The catalyst was filtered off, and the filtrate was concentrated under reduced pressure to give 1-tert-butoxycarbonyl-4-(4-fluorobenzyl)piperidine (39.9 g).

$^1$H NMR (CDCl$_3$) δ 1.08-1.64 (14H, m), 2.49-2.69 (4H, m), 4.04-4.10 (2H, m), 6.92-7.12 (4H, m)

To 1-tert-butoxycarbonyl-4-(4-fluorobenzyl)piperidine (39.9 g) was added 4N-hydrogen chloride in ethyl acetate (100 ml), and the solution was stirred at room temperature for 1 hour. The reaction mixture was concentrated under reduced pressure, and to the concentrate was added diethyl ether. The resulting precipitates were collected by filtration, washed with diethyl ether, and dried under reduced pressure to give the titled compound (30.1 g).

$^1$H NMR (CDCl$_3$) δ 1.70-1.81 (5H, m), 2.52-2.59 (2H, m), 2.71-2.89 (2H, m), 3.42-3.59 (2H, m), 6.93-7.07 (4H, m)

REFERENCE EXAMPLE 3-2

4-(4-Fluorobenzyl)piperidine

To the compound obtained in Reference Example 3-1 (5.05 g) was added aqueous solution of 1N-sodium hydroxide (66 ml), and the mixture was extracted with diethyl ether. The organic layer was dried over anhydrous sodium sulfate and concentrated under reduced pressure to give the titled compound (4.20 g).

$^1$H NMR (CDCl$_3$) δ 1.0-1.35 (2H, m), 1.35-1.7 (3H, m), 2.45-2.65 (2H, m), 2.49 (2H, d, J=6.6 Hz), 2.95-3.1 (2H, m), 6.95 (2H, t, J=8.8 Hz), 7.0-7.15 (2H, m)

REFERENCE EXAMPLE 3-3

3,4-Dichloro-N-{3-[4-(4-fluorobenzyl)-1-piperidinyl]propyl}aniline 2 hydrochloride By a similar manner to Reference Example 1, the titled compound was synthesized by using the compound obtained in Reference Example 3-2 and 3,4-dichloroaniline. Yield 48%.

mp 203-209° C. (dec.)

$^1$H NMR (DMSO-$d_6$) δ 1.35-2.05 (7H, m), 2.45-2.6 (2H, m), 2.6-3.3 (6H, m), 3.41 (2H, br d, J=10.6 Hz), 6.57 (1H, dd, J-J2.7, 8.8 Hz), 6.75 (1H, d, J=2.7 Hz), 7.05-7.3 (5H, m)

Anal. Calcd for $C_{21}H_{25}Cl_2FN_2 \cdot 2HCl \cdot 0.5H_2O$: C, 52.85; H. 5.91; N, 5.87. Found: C, 52.90; H, 6.12; N, 5.94.

REFERENCE EXAMPLE 4

3-Chloro-N-(3-[4-(4-fluorobenzyl)-1-piperidinyl]propyl}aniline 2 hydrochloride

By a similar manner to Reference Example 1, the titled compound was synthesized by using the compound obtained in Reference Example 3-2 and 3-chloroaniline. Yield 59%.

mp 202-208° C. (dec.)

$^1$H NMR(DMSO-$d_6$) δ 1.35-2.05 (7 H,m), 2.45-2.6 (2 H,m), 2.6-2.95 (2H, m), 2.95-3.3 (2H, m), 3.09 (2H, t, J=6.6 Hz), 3.41 (2H, br d, J=12.0 Hz), 6.5-6.7 (3H, m), 7.0-7.3 (5H, m)

Anal. Calcd for $C_{21}H_{26}ClFN_2 \cdot 2HCl \cdot 0.9H_2O$: C, 56.05; H, 6.67; N, 6.22. Found: C, 56.09; H. 6.62;, N, 6.27.

REFERENCE EXAMPLE 5-1

4-(3-Fluorobenzyl)piperidine hydrochloride

By a similar manner to Reference Example 3-1, the titled compound was synthesized by using 3-fluorobenzyl bromide.

$^1$H NMR (CDCl$_3$) δ 1.67-1.87 (5H, m), 2.61 (2H, s), 2.80-2.89 (2H, m), 3.45-3.57 (2H, m), 6.82-6.96 (2H, m), 7.23-7.29 (2H, m)

REFERENCE EXAMPLE 5-2

3-Chloro-N-{3-[4-(3-fluorobenzyl)-1-piperidinyl]propyl}aniline 2 hydrochloride

By a similar manner to Reference Example 3-2, the 4-(3-fluorobenzyl)piperidine was synthesized by using the compound obtained in Reference Example 5-1.

By a similar manner to Reference Example 1, the titled compound was synthesized by using 4-(3-fluorobenzyl)piperidine and 3-chloroaniline. Yield 58%.

mp 192-194° C. (dec.)

$^1$H NMR (DMSO-d$_6$) δ 1.39-2.08 (7H, m), 2.45-2.60 (2H, m), 2.65-2.96 (2H, m), 2.99-3.30 (4H, m), 3.41 (2H, br d, J=12 Hz), 6.70-6.81 (3H, m), 7.00-7.41 (5H, m)

REFERENCE EXAMPLE 6-1

4-(2-Fluorobenzyl)piperidine hydrochloride

By a similar manner to Reference Example 3-1, the titled compound was synthesized by using the 2-fluorobenzyl bromide.

$^1$H NMR (CDCl$_3$) δ 1.67-2.08 (5H, m), 2.64-2.66 (2H, m), 2.79-2.90 (2H, m), 3.44-3.58 (2H, m), 6.98-7.26 (4H, m)

REFERENCE EXAMPLE 6-2

3-Chloro-N-{3-[4-(2-fluorobenzyl)-1-piperidinyl]propyl}aniline 2 hydrochloride

By a similar manner to Reference Example 3-2, the 4-(2-fluorobenzyl)piperidine was synthesized by using the compound obtained in Reference Example 6-1.

By a similar manner to Reference Example 1, the titled compound was synthesized by using 4-(2-fluorobenzyl)piperidine and 3-chloroaniline. Yield 45%.

mp 180-182° C. (dec.);

$^1$H NMR (DMSO-d$_6$) δ 1.49-2.10 (7H, m), 2.47-2.61 (2H, m), 2.70-2.96 (2H, m), 3.02-3.29 (4H, m), 3.43 (2H, br d, J=12 Hz), 6.70-6.81 (3H, m), 7.11-7.31 (5H, m)

REFERENCE EXAMPLE 7-1

4-(2,4-Difluorobenzyl)piperidine hydrochloride

By a similar manner to Reference Example 3-1, the titled compound was synthesized by using 2,4-difluorobenzyl bromide.

$^1$H NMR (CDCl$_3$) δ 1.64-1.88 (5H, m), 2.62 (2H, s), 2.72-2.85 (2H, m), 3.45-3.52 (2H, m), 6.73-6.86 (2H, m), 7.02-7.14 (1H, m)

REFERENCE EXAMPLE 7-2

3-Chloro-N-{3-[4-(2,4-difluorobenzyl)-1-piperidinyl]propyl}aniline 2 hydrochloride By a similar manner to Reference Example 3-2,4-(2,4-difluorobenzyl)piperidine was synthesized by using the compound obtained in Reference Example 7-1.

By the similar manner to Reference Example 1, the titled compound was synthesized by using 4-(2,4-difluorobenzyl)piperidine and 3-chloroaniline Yield 54%.

mp 203-205° C. (dec.)

$^1$H NMR (DMSO-d$_6$) δ 1.47-2.11 (7H, m), 2.51-2.62 (2H, m), 2.72-2.92 (2H, m), 3.00-3.20 (4H, m), 3.41 (2H, br d, J=12 Hz), 6.71-6.91 (3H, m), 6.99-7.42 (4H, m)

REFERENCE EXAMPLE 8

N-[3-(4-Benzyl-1-piperidinyl)propyl]-4-methylaniline 2 hydrochloride

By a similar manner to Reference Example 1, the titled compound was synthesized by using p-toluidine. Yield 57%.

mp 182-192° C. (dec.)

$^1$H NMR (DMSO-d$_6$) δ 1.4-1.9 (5H, m), 2.0-2.25 (2H, m), 2.31 (3H, s), 2.45-2.6 (2H, m), 2.7-2.95 (2H, m), 2.95-3.55 (6H, m), 7.1-7.45 (9H, m)

Anal. Calcd for $C_{22}H_{30}N_2 \cdot 2HCl \cdot 0.5H_2O$: C, 65.34; H, 8.22; Cl, 17.53; N, 6.93. Found: C, 65.24; H, 8.38; Cl, 17.37; N, 6.98.

REFERENCE EXAMPLE 9

N-[3-(4-Benzyl-1-piperidinyl)propyl]-3-chloro-4-methylaniline 2 hydrochloride

By a similar manner to Reference Example 1, the titled compound was synthesized by using 3-chloro-4-methylaniline. Yield70%.

mp 195-200° C. (dec.)

$^1$H NMR(DMSO-d$_6$) δ 1.4-2.15 (7H, m), 2.21 (3H, s), 2.45-2.6 (2H, m), 2.6-2.95 (2H, m), 2.95-3.3 (2H, m), 3.15 (2H, t, J=7.0 Hz), 3.41 (2H, br d, J=11.0 Hz), 6.77 (1H, d, J=7.6 Hz), 6.93 (1H, s), 7.1-7.4 (6H, m)

REFERENCE EXAMPLE 10

N-[3-(4-Benzyl-1-piperidinyl)propyl]-3-(trifluoromethyl)aniline 2 hydrochloride

By a similar manner to Reference Example 1, the titled compound was synthesized by using 3-(trifluoromethyl)aniline. Yield 56%.

mp 167-173° C. (dec.)

$^1$H NMR (DMSO-d$_6$) δ 1.4-2.1 (7H, m), 2.45-2.6 (2H, m), 2.6-2.95 (2H, m), 2.95-3.3 (2H, m), 3.13 (2H, t, J=6.6 Hz), 3.41 (2H, br d, J=11.6 Hz), 6.75-6.95 (3H, m), 7.1-7.4 (6H, m)

REFERENCE EXAMPLE 11-1

3-Chloro-N-(3-chloropropyl)-4-methylaniline

A mixture of 3-chloro-4-methylaniline (7.79 g, 55 mmol), 1-chloro-3-iodopropane (5.91 ml, 55 mmol), cesium carbonate (35.84 g, 110 mmol) and DMF (15 ml) was stirred at room temperature for 19 hours. To the mixture was added water (75 ml), and the mixture was extracted with hexane (60 ml, 30 ml×2). The organic layer was washed with water (10 ml), dried over magnesium sulfate and concentrated under reduced pressure. The concentrate was subjected to column chromatography (silica gel 200 g, hexane/ethyl acetate=1/0 to 19/1), and the desired fraction was concentrated under reduced pressure to give the titled compound (7.30 g, 33 mmol, Yield 61%) as a pale brown oily substance.

$^1$H NMR (CDCl$_3$) δ 2.05 (2H, quint, J=6.4 Hz), 2.24 (3H, s), 3.30 (2H, t, J=6.4 Hz), 3.5-3.8 (1H, m), 3.64 (2H, t, J=6.4 Hz), 6.44 (1H, dd, J=2.4, 8.3 Hz), 6.63 (1H, d, J=2.4 Hz), 7.00 (1H, d, J=8.3 Hz)

REFERENCE EXAMPLE 11-2

1-Acetyl-N-(3-chloro-4-methylphenyl)-N-(3-chloropropyl)-4-piperidinecarboxamide

The compound obtained in Reference Example 11-1 (6.54 g, 30 mmol) was dissolved in dichloromethane (200 ml), and under ice cooling, to the solution were added triethylamine (10.0 ml, 72 mmol) and 1-acetyl-4-piperidinecarbonyl chloride (11.38 g, 60 mmol), successively. The mixture was stirred at the same temperature for 3 hours.

Under ice cooling, a saturated aqueous solution of sodium hydrogencarbonate (150 ml) was added, and the organic layer was distilled off under reduced pressure.

The aqueous layer was extracted with ethyl acetate (100 ml, 50 ml×2). The organic layer was washed with a saturated aqueous solution of sodium hydrogencarbonate (30 ml×3), 1N-hydrochloric acid (30 ml×3), saturated sodium chloride solution (30 ml), successively, dried over magnesium sulfate and concentrated under reduced pressure.

The concentrate was subjected to column chromatography (silica gel 150 g, ethyl acetate/methanol=1/0 to 95/5), and the desired fraction was concentrated under reduced pressure to give the titled compound (10.41 g, 28 mmol, Yield 94%) as a pale brown oily substance.

$^1$H NMR (CDCl$_3$) δ 1.5-2.1 (6H, m), 2.05 (3H, s), 2.25.-2.5 (2H, m), 2.43 (3H, s), 2.75-2.95 (1H, m), 3.53 (2H, t, J=6.6 Hz), 3.65-3.85 (1H, m), 3.77 (2H, t, J=7.1 Hz), 4.51 (1H, br d, 12.8 Hz), 6.98 (1H, dd, J=2.2, 7.7 Hz), 7.18 (1H, d, J=2.2 Hz), 7.31 (1H, d, J=7.7 Hz)

REFERENCE EXAMPLE 12-1

3-Chloro-N-(3-chloropropyl)aniline

By a similar manner to Reference Example 11-1, the titled compound was synthesized by using 3-chloroaniline. Yield 72%.

$^1$H NMR (CDCl$_3$) δ 2.00-2.13 (2H, m), 3.23-3.37 (2H, m), 3.65 (2H, t, J=6.6 Hz), 3.80 (1H, br), 6.48 (1H, dd, J=2.4, 8.4 Hz), 6.59 (1H, t, J=2.4 Hz), 6.64-6.69 (1H, m), 7.08 (1H, t, J=8.4 Hz)

REFERENCE EXAMPLE 12-2

1-Acetyl-N-(3-chlorophenyl)-N-(3-chloropropyl)-4-piperidinecarboxamide

By a similar manner to Reference Example 11-2, the titled compound was synthesized by using the compound obtained in Reference Example 12-1. Yield 74%.

$^1$H NMR (CDCl$_3$) δ 1.5-1.9 (4H, m), 1.94-2.14 (5H, m), 2.15-2.50 (2H, m), 2.75-3.0 (1H, m), 3.54 (2H, t, J=6.6 Hz), 3.7-4.0 (3H, m), 4.40-4.65 (1H, m), 7.05-7.10 (1H, m), 7.19 (1H, s), 7.39-7.42 (2H, m)

REFERENCE EXAMPLE 13-1

Ethyl 1-(methylsulfonyl)-4-piperidinecarboxylate

Ethyl isonipecotate (31.44 g, 200 mmol) and triethylamine (50.2 ml, 360 mmol) were dissolved in THF (500 ml), and under ice cooling, to the solution was added dropwise methanesulfonyl chloride (23.2 ml, 300 mmol). The mixture was stirred at the same temperature for 1 hour. Under ice cooling, water (200 ml) was added, and the organic layer was distilled off under reduced pressure. The aqueous layer was extracted with ethyl acetate (200 ml, 100 ml×2). The organic layer was washed with a saturated aqueous solution of sodium hydrogencarbonate (50 ml×2), 1N-hydrochloric acid (50 ml×3), saturated sodium chloride solution (50 ml), successively, dried over magnesium sulfate and concentrated under reduced pressure. To the concentrate was added diisopropyl ether (100 ml), and the resulting precipitates were collected by filtration. The precipitates were washed with diisopropyl ether (50 ml×3), and dried under reduced pressure to give the titled compound (43.20 g, 184 mmol, Yield 92%) as white crystals.

$^1$H NMR (CDCl$_3$) δ 1.27 (3H, t, J=7.2 Hz), 1.75-2.1 (4H, m), 2.35-2.55 (1H, m), 2.78 (3H, s), 2.8-2.95 (2H, m), 3.6-3.75 (2H, m), 4.16 (2H, q, J=7.2 Hz)

REFERENCE EXAMPLE 13-2

1-(Methylsulfonyl)-4-piperidine carboxylic acid

The compound obtained in Reference Example 13-1 (2.35 g, 10 mmol) was suspended in methanol (20 ml), and to the suspension was added aqueous solution of 8N-sodium hydroxide (2.5 ml). The mixture was stirred at room temperature for 15 hours. To the reaction mixture was added 1N-hydrochloric acid (22 ml), and the mixture was concentrated under reduced pressure. To the concentrate was added toluene, and the mixture was concentrated under reduced pressure. These procedure was repeated twice. To the concentrates were added THF and anhydrous magnesium sulfate, and the mixture was stirred at room temperature for 2 hours. The insolubles were filtered off, and the filtrate was concentrated under reduced pressure. To the concentrate was added diethyl ether, and the resulting precipitates were collected by filtration. The precipitates were washed with diethyl ether, and dried under reduced pressure to give the titled compound (1.95 g, 9.4 mmol, Yield 94%) as white crystals.

$^1$H NMR (D$_2$O) δ 1.6-1.85 (2H, m), 1.95-2.15 (2H, m), 2.45-2.65 (1H, m), 2.8-3.0 (2H, m), 2.98 (3H, s), 3.55-3.75 (2H, m)

REFERENCE EXAMPLE 14-1

Ethyl 1-(N,N-dimethylcarbamoyl)-4-piperidinecarboxylate

Ethyl isonipecotate (31.44 g, 200 mmol) and triethylamine (50.2 ml, 360 mmol) were dissolved in dichloromethane (200 ml), and under ice cooling, to the solution was added dropwise N,N-dimethylcarbamoyl chloride (27.6 ml, 300 mmol). The mixture was stirred for 18 hours while the temperature was elevating to room temperature. To the reaction mixture was added water (100 ml) under ice cooling, and the organic layer was taken by separatory funnel. The aqueous layer was extracted with dichloromethane (50 ml×2) and the extracts were mixed with the organic layer. The combined organic layer was washed with 1N-hydrochloric acid (100 ml×3), dried over anhydrous magnesium sulfate and concentrated under reduced pressure to give the titled compound (51.30 g, It was proved that N,N-dimethyl carbamoyl chloride is contained about 10 wt % by $^1$H NMR.) as a pale brown oily substance.

$^1$H NMR (CDCl$_3$) δ 1.26 (3H, t, J=7.1 Hz), 1.55-2.0 (4H, m), 2.35-2.55 (1H, m), 2.7-2.9 (2H, m), 2.82 (6H, s), 3.55-3.7 (2H, m), 4.14 (2H, q, J=7.1 Hz)

REFERENCE EXAMPLE 14-2

1-(N,N'-Dimethyl carbamoyl)-4-piperidine carboxylic acid

To a solution of the compound obtained in Reference Example 14-1 (6.85 g) in methanol (30 ml) was added aqueous solution of 8N-sodium hydroxide (7.5 ml), and the mixture was stirred at room temperature for 4 hours. To the reaction mixture was added concentrated hydrochloric acid (5.5 ml), and the mixture was concentrated under reduced pressure. To the concentrate was added toluene, and the mixture was concentrated under reduced pressure. These procedure was repeated twice. To the concentrates were added THF and anhydrous magnesium sulfate, and the mixture was stirred at room temperature for 2 hours. The insolubles were filtered off, and the filtrate was concentrated under reduced pressure. To the concentrate was added ethyl acetate and resulting precipitates were collected by filtration. The precipitates were washed with ethyl acetate, and dried under reduced pressure to give the titled compound (3.22 g, 16 mmol) as white crystals.

$^1$H NMR (D$_2$O) δ 1.5-1.75 (2H, m), 1.85-2.0 (2H, m), 2.5-2.7 (1H, m), 2.8-3.0 (2H, m), 2.83 (6H, s), 3.55-3.75 (2H, m)

REFERENCE EXAMPLE 15

N-[3-(4-Benzyl-1-piperidinyl)propyl]benzylamine

To a solution of 4-benzylpiperidine (10.0 g, 57 mmol) and DBU (85 μl, 0.57 mmol) in THF (10 ml) was dropwise added a solution of acrolein (90%, 3.2 g, 57 mmol) in THF (2 ml) at −20° C. with stirring over a period of 10 minutes. The mixture was stirred for 1 hour while the temperature of the mixture was elevating from −20° C. to −10° C. To the mixture were added benzylamine (6.1 g, 57 mmol), sodium triacetoxyborohydride (24.2 g, 114 mmol), successively, at −10° C., and the mixture was stirred 19 hours while the temperature was elevated to room temperature. To the mixture was added aqueous solution of 2N-sodium hydroxide (100 ml) under ice cooling, and the mixture was stirred for 30 minutes and extracted with diethyl ether (100 ml, 80 ml×2). The organic layer was dried over magnesium sulfate and concentrated under reduced pressure. The concentrate was dissolved in 2-propanol (50 ml). To the solution was added 4N-hydrogen chloride in ethyl acetate (50 ml) with stirring, and the resulting precipitates were collected by filtration. The precipitates were washed with 2-propanol (20 ml×3), and dried under reduced pressure to give the titled compound as white crystals (6.5 g). To the white crystaline (2.0 g) obtained was added aqueous solution of 1N-sodium hydroxide (10 ml), and the resulting solution was extracted by ethyl acetate (10 ml, 8 ml×2). The organic layer was dried over magnesium sulfate and concentrated under reduced pressure to give the titled compound (1.6 g) as a colorless oily substance.

$^1$H NMR (CDCl$_3$) δ 1.30 (2H, dt, J=11.8 Hz, 2.4 Hz), 1.49 (1H, m), 1.59-1.89 (6H, m), 2.35 (2H, t, J=7.8 Hz), 2.52 (2H, d, J=6.8 Hz), 2.66 (2H, t, J=6.8 Hz), 2.90 (2H, d, J=11.8 Hz), 3.78 (2H, s), 7.12-7.33 (10H, m)

MS (APCI$^+$) 323 (M+1)

REFERENCE EXAMPLE 16

N-[3-(4-Benzyl-1-piperidinyl)propyl]-4-fluorobenzylamine

By a similar manner to Reference Example 15, the titled compound was synthesized by using 4-fluorobenzylamine.

$^1$H NMR (CDCl$_3$) δ 1.26 (2H, dt, J=12.0 Hz, 2.6 Hz), 1.51 (1H, m), 1.59-1.92 (6H, m), 2.39 (2H, t, J=7.0 Hz), 2.49 (2H, d, J=6.8 Hz), 2.66 (2H, t, J=7.0 Hz), 2.91 (2H, d, J=11.8 Hz), 3.74 (2H, s), 6.94-7.32 (9H, m)

MS (APCI$^+$) 341 (M+1)

REFERENCE EXAMPLE 17

N-[3-(4-Benzyl-1-piperidinyl)propyl]-3-chlorobenzylamine

By a similar manner to Reference Example 15, the titled compound was synthesized by using 3-chlorobenzylamine.

$^1$H NMR (CDCl$_3$) δ 1.29 (2H, dt, J=12.0 Hz, 3.6 Hz), 1.41-1.91 (7H, m), 2.38 (2H, t, J=7.6 Hz), 2.51 (2H, d, J=6.6 Hz), 2.67 (2H, t, J=6.6 Hz), 2.92 (2H, d, J=11.6 Hz), 3.76 (2H, s), 7.11-7.33 (9H, m)

MS (APCI$^+$) 357 (M+1)

REFERENCE EXAMPLE 18

N-[3-(4-Benzyl-1-piperidinyl)propyl]-3,4-dichlorobenzylamine

By a similar manner to Reference Example 15, the titled compound was synthesized by using 3,4-dichlorobenzylamine.

$^1$H NMR (CDCl$_3$) δ 1.29 (2H, dt, J=12.0 Hz, 2.6 Hz), 1.52 (1H, m), 1.60-1.92 (6H, m), 2.39 (2H, t, J=7.4 Hz), 2.51 (2H, d, J=6.8 Hz), 2.65 (2H, t, J=7.4 Hz), 2.92 (2H, d, J=11.8 Hz), 3.73 (2H, s), 7.10-7.43 (8H, m)

MS (APCI$^+$) 391 (M+1)

REFERENCE EXAMPLE 19

N-[3-(4-Benzyl-1-piperidinyl)propyl](3-pyridylmethyl)amine

By a similar manner to Reference Example 15, the titled compound was synthesized by using 3-(aminomethyl)pyridine.

$^1$H NMR (CDCl$_3$) δ 1.30 (2H, dt, J=11.8 Hz, 2.4 Hz), 1.49 (1H, m), 1.51-1.95 (6H, m), 2.39 (2H, t, J=7.8 Hz), 2.54 (2H, d, J=7.2 Hz), 2.69 (2H, t, J=7.0 Hz), 2.92 (2H, d, J=12.2 Hz), 3.79 (2H, 5s), 7.1,5-7.19 (7H, m), 8.25 (1H, d, J=2.0 Hz), 8.54 (1H, d, J=1.8 Hz),

MS (APCI$^+$) 324 (M+1)

REFERENCE EXAMPLE 20

N-[3-(4-Benzyl-1-piperidinyl)propyl](cyclohexylmethyl)amine

By a similar manner to Reference Example 15, the titled compound was synthesized by using (cyclohexylmethyl)amine.
$^1$H NMR (CDCl$_3$) δ 0.90 (2H, t, J=10.4 Hz), 1.17-1.30 (7H, m), 1.53-1.94 (11H, m), 2.35 (2H, t, J=7.8 Hz), 2.50-2.53 (4H, m), 2.66 (2H, t, J=6.8 Hz), 2.90 (2H, d, J=11.8 Hz), 7.09-7.21 (5H, m)
MS (APCI$^+$) 329 (M+1)

REFERENCE EXAMPLE 21

N-[3-(4-Benzyl-1-piperidinyl)propyl]-4-methoxybenzylamine

By a similar manner to Reference Example 15, the titled compound was synthesized by using 4-methoxybenzylamine.
$^1$H NMR (CDCl$_3$) δ 1.33 (2H, dt, J=12.2 Hz, 2.6 Hz), 1.52 (1H, m), 1.56-1.91 (6H, m), 2.39 (2H, t, J=7.8 Hz), 2.48 (2H, d, J=6.8 Hz), 2.69 (2H, t, J=6.8 Hz), 2.91 (2H, d, J=11.8 Hz), 3.80 (2H, s), 3.94 (3H, s), 7.12-7.47 (9H, m)
MS (APCI$^+$) 353 (M+1)

REFERENCE EXAMPLE 22

N-[3-(4-Benzyl-1-piperidinyl)propyl]-4-methylbenzylamine

By a similar manner to Reference Example 15, the titled compound was synthesized by using 4-methylbenzylamine.
$^1$H NMR (CDCl$_3$) δ 1.33 (2H, dt, J=12.2 Hz, 2.6 Hz), 1.52 (1H, m), 1.56-1.84 (6H, m), 2.25 (3H, s); 2.39 (2H, t, J=7.6 Hz), 2.52 (2H, d, J=6.8 Hz), 2.70 (2H, t, J=7.0 Hz), 2.90 (2H, d, J=11.8 Hz), 3.78 (2H, s), 7.15-7.35 (9H, m)
MS (APCI$^+$) 337 (M+1)

REFERENCE EXAMPLE 23

N-[3-(4-Benzyl-1-piperidinyl)propyl]-4-chlorobenzylamine

By a similar manner to Reference Example 15, the titled compound was synthesized by using 4-chlorobenzylamine.
$^1$H NMR (CDCl$_3$) δ 1.26 (2H, dt, J=12.0 Hz, 2.8 Hz), 1.51 (1H, m), 1.59-1.90 (6H, m), 2.39 (2H, t, J=7.0 Hz), 2.51 (2H, d, J=6.8 Hz), 2.66 (2H, t, J=7.0 Hz), 2.93 (2H, d, J=11.8 Hz), 3.72 (2H, s), 6.95-7.33 (9H, m)
MS (APCI$^+$) 357 (M+1)

REFERENCE EXAMPLE 24

N-[3-(4-Benzyl-1-piperidinyl)propyl]-2,6-difluorobenzylamine

By a similar manner to Reference Example 15, the titled compound was synthesized by using 2,6-difluorobenzylamine.
$^1$H NMR (CDCl$_3$) δ 1.24 (2H, dt, J=12.0 Hz, 2.6 Hz), 1.52 (1H, m), 1.55-1.90 (6H, m), 2.42 (2H, t, J=7.0 Hz), 2.52 (2H, d, J=6.8 Hz), 2.69 (2H, t, J=7.0 Hz), 2.94 (2H, d, J=11.8 Hz), 3.76 (2H, s), 6.91-7.38 (8H, m)
MS (APCI$^+$) 359 (M+1)

REFERENCE EXAMPLE 25

N-[3-(4-Benzyl-1-piperidinyl)propyl]-2-chlorobenzylamine

By a similar manner to Reference Example 15, the titled compound was synthesized by using 2-chlorobenzylamine.
$^1$H NMR (CDCl$_3$) δ 1.23 (2H, dt, J=11.8 Hz, 2.6 Hz), 1.52 (1H, m), 1.57-1.89 (6H, m), 2.37 (2H, t, J=7.0 Hz), 2.48 (2H, d, J=6.8 Hz), 2.63 (2H, t, J=7.0 Hz), 2.91 (2H, d, J=11.8 Hz), 3.72 (2H, s), 6.95-7.40 (9H, m)
MS (APCI$^+$) 357 (M+1)

REFERENCE EXAMPLE 26

N-[3-(4-Benzyl-1-piperidinyl)propyl]-1,3-thiazol-2-amine

To a solution of 4-benzylpiperidine (3.51 g, 20.0 mmol) and DBU (0.030 ml, 0.220 mmol) in THF (40 ml) was dropwise added a solution of acrolein (90%, 1.485 ml, 20.0 mmol) in THF (10 ml) at −20° C. with stirring over a period of 10 minutes. The mixture was stirred for 1 hour while the temperature of the mixture is elevated from −20° C. to −10° C. To the mixture were added 2-amino-1,3-thiazole (2.00 g, 20.0 mmol) and sodium triacetoxyborohydride (8.48 g, 40.0 mmol), successively, at −10° C., and the mixture was stirred for 15 hours while the temperature of the mixture is elevated to room temperature. Under ice cooling, aqueous solution of 1N-sodium hydroxide (120 ml) was added, and the mixture was stirred for 30 minutes and extracted with diethyl ether (60 ml×4). The organic layer was dried over magnesium sulfate and concentrated under reduced pressure. The concentrate was subjected to column chromatography (silica gel 100 g, ethyl acetate/methanol=1/0 to 85/15), and the desired fraction was concentrated under reduced pressure to give the titled compound (680 mg, 2.16 mmol) as white crystals. Yield 11%.
$^1$H NMR (CDCl$_3$) δ 1.22-1.92 (9H, m), 2.47 (2H, t, J=6.2 Hz), 2.56 (2H, d, J=6.6 Hz), 2.94 (2H, br d, J=11.6 Hz), 3.38 (2H, t, J=6.2 Hz), 6.45 (1H, d, J=3.8 Hz), 6.83 (1H, brs), 7.11-7.33 (6H, m)

REFERENCE EXAMPLE 27

N-[3-(4-Benzyl-1-piperidinyl)propyl]-5-methyl-3-isoxazoleamine

To a solution of 4-benzylpiperidine (3.51 g, 20.0 mmol) and DBU (0.030 ml, 0.20 mmol) in THF (40 ml) was dropwise added a solution of acrolein (90%, 1.485 ml, 20.0 mmol) in THF (10 ml) at −20° C. with stirring over a period of 10 minutes. The mixture was stirred for 1 hour while the temperature of the mixture is elevated from −20° C. to −10° C. To the mixture were added 3-amino-5-methyl isoxazole (1.96 g, 20.0 mmol) and sodium triacetoxyborohydride (8.48 g, 40.0 mmol), successively, at −10° C. The mixture was stirred for 15 hours while the temperature of the mixture is elevated to −10° C. To the mixture was added aqueous solution of 1N-sodium hydroxide (120 ml) under ice cooling, and the mixture was stirred for 30 minutes and extracted with diethyl ether (60 ml×3). The organic layer was dried over magnesium sulfate and concentrated under reduced pressure. The concentrate was subjected to column chromatography (silica gel 100 g, ethyl acetate/methanol=1/0 to 75/25), and the desired fraction was concentrated under reduced pressure to give the titled compound (2.30 g, 7.34 mmol) as white crystals. Yield 37%.

$^1$H NMR (CDCl$_3$) δ 1.22-1.90 (9H, m), 2.27 (3H, d, J=0.8 Hz), 2.42 (2H, t, J=6.6 Hz), 2.54 (2H, d, J=6.6 Hz), 2.91 (2H, br d, J=11.8 Hz), 3.24 (2H, t, J=6.2 Hz), 5.09 (1H, br s), 5.41 (1H, d, J=1.0 Hz), 7.12-7.31 (5H, m)

REFERENCE EXAMPLE 28

4-[4-(Trifluoromethyl)benzyl]piperidine hydrochloride

By a similar manner to Reference Example 3-1, the titled compound was synthesized by using 4-(trifluoromethyl)benzyl bromide.

$^1$H NMR (CDCl$_3$) δ 1.65-1.88 (5H, m), 2.68 (2H, s), 2.78-2.89 (2H, m), 3.45-3.51 (2H, m), 7.25 (2H, d, J=8.0 Hz), 7.56 (2H, d, J=8.0 Hz)

REFERENCE EXAMPLE 29

1-tert-Butoxycarbonyl-4-(1H-1,2,4-triazol-1-ylmethyl)piperidine

To a solution of 1-tert-butoxycarbonyl-piperidin-4-methanol (1.08 g, 5.0 mmol) and diisopropylethylamine (2.6 mL, 15 mmol) in dry dichloromethane (30 mL) was added anhydrous trifluoromethanesulfonic acid (1.0 mL, 6.0 mmol) at −78° C., and the mixture was stirred for 1 minute under iced cooling. The mixture was cooled to −78° C. To the reaction mixture were added 1H-1,2,4-triazole (1.04 g, 15 mmol) and THF (20 mL), and the mixture was stirred at room temperature for 6 hours. To the reaction mixture was added a saturated aqueous solution of sodium hydrogencarbonate, and the mixture was extracted with ethyl acetate. The extract was washed with saturated aqueous solution of sodium chloride and dried over anhydrous sodium sulfate. The solvent was distilled off under reduced pressure. The residue was subjected to silica gel column chromatography (50 g, ethyl acetate/ethanol=1/0 to 20/1), and recrystallization to give the titled compound as pale yellow crystals (473 mg, 36%).

IR (KBr) 2978, 2934, 2854, 1682 cm$^{-1}$; $^1$H-NMR (CDCl$_3$) δ 1.1-1.3 (2H, m), 1.45 (9H, s), 1.5-1.7 (2H, m), 2.0-2.2 (1H, m), 2.68 (2H, t, J=12.0 Hz), 4.04 (2H, d, J=7.4 Hz), 4.0-4.2 (2H, m), 7.95 (1H, s), 8.02 (1H, s).

REFERENCE EXAMPLE 30

1-tert-Butoxycarbonyl-4-(imidazol-1-ylmethyl)piperidine

By a similar manner to Reference Example 29, 1-tert-butoxycarbonyl-piperidin-4-methanol (1.08 g, 5.0 mmol) was reacted with imidazole (1.02 g, 15 mmol) to give the titled compound as an amorphous-like substance 239 mg, 18%).

IR (KBr) 2978, 2934, 1682 cm$^{-1}$; $^1$H-NMR (CDCl$_3$) δ 1.1-1.4 (2H, m), 1.45 (9H, s), 1.5-2.0 (3H, m), 2.65 (2H, t, J=11.5 Hz), 3.82 (2H, d, J=7.0 Hz), 4.0-4.2 (2H, m), 6.88 (1H, s), 7.07 (1H, s), 7.46 (1H, s)

REFERENCE EXAMPLE 31

1-tert-Butoxycarbonyl-4-(pyrazol-1-ylmethyl)piperidine

By a similar manner to Reference Example 29, 1-tert-butoxycarbonyl-piperidin-4-methanol (1.08 g, 5.0 mmol) was reacted with pyrazole (1.02 g, 15 mmol) to give the titled compound as pale yellow oily substance (980 mg, 74%).

IR (KBr) 2976, 2932, 1694 cm$^{-1}$; $^1$H-NMR (CDCl$_3$) δ 1.1-1.4 (3H, m), 1.45 (9H, s), 1.5-1.7 (2H, m), 2.0-2.2 (1H, m), 2.5-2.8 (2H, m), 3.99 (2H, d, J=7.2 Hz), 4.0-4.2 (2H, m), 6.24 (1H, dd, J=1.8 and 2.6 Hz), 7.34 (1H, d, J=2.6 Hz), 7.51 (1H, d, J=1.8 Hz)

REFERENCE EXAMPLE 32

1-tert-Butoxycarbonyl-4-(2H-tetrazol-2-ylmethyl)piperidine 1-tert-Butoxycarbonyl-4-(1H-tetrazol-1-ylmethyl)piperidine By a similar manner to Reference Example 29, 1-tert-butoxycarbonyl-piperidin-4-methanol (2.15 g, 10.0 mmol) was reacted with 1H-tetrazole (2.10 g, 30 mmol) to give 1tert-butoxycarbonyl-4-(2H-tetrazol-2-ylmethyl)piperidine as pale yellow oily substance (1.35 g, 50%) and 1-tert-1butoxycarbonyl-4-(1H-tetrazol-1-ylmethyl)piperidine as pale yellow solid substance (1.23 g, 46%).

1-tert-Butoxycarbonyl-4-(2H-tetrazol-2-ylmethyl)piperidine: IR (KBr) 2976, 2934, 2858, 1694 cm$^{-1}$; $^1$H-NMR (CDCl$_3$) δ 1.2-1.4 (2H, m), 1.45 (9H, s), 1.5-1.6 (2H, m), 2.1-2.3 (1H, m), 2.6-2.8 (2H, m), 4.0-4.2 (2H, m), 4.55 (2H, d, J=7.0 Hz), 8.52 (1H, s)

1-tert-Butoxycarbonyl-4-(1H-tetrazol-1-ylmethyl)piperidine: IR (KBr) 2976, 2934, 2854, 1686 cm$^{-1}$; $^1$H-NMR (CDCl$_3$) δ 1.1-1.3 (2H, m), 1.45 (9H, s), 1.5-1.7 (2H, m), 2.0-2.2 (1H, m), 2.6-2.8 (2H, dt, J=2.6 and 12.9 Hz), 4.16 (2H, d, 13.2 Hz), 4.33 (2H, d, J=7.4 Hz), 8.59 (1H, s)

REFERENCE EXAMPLE 33

1-tert-Butoxycarbonyl-4-(2H-1,2,3-triazol-2-ylmethyl)piperidine 1-tert-Butoxycarbonyl-4-(1H-1,2,3-triazol-1-ylmethyl)piperidine By a similar manner to Reference Example 29, 1-tert-butoxycarbonyl-piperidin-4-methanol (1.08 g, 5.0 mmol) was reacted with 1H-1,2,3-triazole (1.04 g, 15 mmol) to give 1-tert-butoxycarbonyl-4-(2H-1,2,3-triazol-2-ylmethyl)piperidine as pale yellow solid substance (168 mg, 13%) and 1-tert-butoxycarbonyl-4-(1H-1,2,3-triazol-1-ylmethyl)piperidine as pale yellow solid substance (1.04 g, 78%).

1-tert-Butoxycarbonyl-4-(2H-1,2,3-triazol-2-ylmethyl) piperidine: IR (KBr) 2976, 2932, 2853, 1694 cm$^{-1}$; $^1$H-NMR (CDCl$_3$) δ 1.1-1.4 (2H, m), 1.45 (9H, s), 1.52 (2H, d, J=8.4 Hz), 2.1-2.3 (1H, m), 2.68 (2H, dt, J=2.6 and 12.8 Hz), 4.11 (2H, d, J=14.2 Hz), 4.33 (2H, d, J=7.4 Hz), 7.60 (2H, s)

1-tert-Butoxycarbonyl-4-(1H-1,2,3-triazol-1-ylmethyl) piperidine: IR (KBr) 2976, 2934, 2856, 1693 cm$^{-1}$; $^1$H-NMR (CDCl$_3$) δ 1.1-1.3 (2H, m), 1.45 (9H, s), 1.58. (2H, d, J=12.2 Hz), 2.0-2.2 (1H, m), 2.67 (2H, dt, J=2.6 and 12.9 Hz), 4.0-4.2 (2H, m), 4.28 (2H, d, J=7.0 Hz), 7.52 (1H, s), 7.72 (1H, s)

REFERENCE EXAMPLE 34

1-tert-Butoxycarbonyl-4-(2-pyridinylthio)piperidine

To a solution of 1-tert-butoxycarbonyl-4-hydroxypiperidine (1.01 g, 5.0 mmol)and diisopropylethylamine(2.6 mL, 15 mmol) in dry dichloromethane (30 mL) was added anhydrous trifluoromethanesulfonic acid (1.0 mL, 6.0 mmol) at −78° C. The mixture was stirred for 1 minute under ice cooling, and cooled to −78° C. To the reaction mixture was added 2-mercaptopyridine (1.67 g, 15 mmol), and the mixture was stirred at room temperature for 20 hours. To the reaction mixture was added a saturated aqueous solution of sodium hydrogencarbonate, and the mixture was extracted with ethyl acetate. The extract was washed with saturated aqueous solution of sodium hydrogen carbonate and saturated aqueous solution of sodium chloride, successively, and dried over anhydrous sodium sulfate. The solvent was distilled off under reduced pressure, and the residue was purified by silica gel column chromatography (50 ethyl acetate-hexane 1:5) to give the titled compound as pale yellow oily substance (937 mg, 64%).

IR (KBr) 2976, 2928, 2851, 1694 cm$^{-1}$; $^1$H-NMR (CDCl$_3$) δ 1.47 (9H, s), 1.5-1.7 (2H, m), 2.0-2.2 (2H, m), 3.09 (2H, ddd, J=3.4, 10.6, and 13.6 Hz), 3.9-4.1 (3H, m), 6.98 (1H, ddd, J=1.0, 5.0, and 7.2 Hz), 7.16 (1H, d, J=8.0 Hz), 7.48 (1H, ddd, J=1.8, 7.2, and 8.0 Hz), 8.42 (1H, ddd, J=1.0, 1.8, and 5.0 Hz)

REFERENCE EXAMPLE 35

1-tert-Butoxycarbonyl-4-(1-methyl-1H-tetrazol-5-ylthio)piperidine

To a solution of 1-tert-butoxycarbonyl-4-hydroxypiperidine (1.01 g, 5.0 mmol) in dry THF (30 mL) were added triphenylphosphine (2.0 g, 7.5 mmol) and 5-mercapto-1-methyl-1H-tetrazole (0.70 g, 6.0 mmol). To the mixture was added diisopropyl azodicarboxylate (1.2 mL, 6.0 mmol) under ice cooling, and the mixture was stirred at the same temperature for 1 hour. The reaction mixture was diluted with ethyl acetate (100 mL), which was washed with water, saturated aqueous solution of sodium hydrogen carbonate and saturated aqueous solution of sodium chloride, successively. The solvent was dried over anhydrous sodium sulfate. The solvent was distilled off under reduced pressure. The residue was purified by silica gel column chromatography (50 g, diethyl ether-hexane 1:1) to give the titled compound as a colorless oily substance. (1.11 g, 74%).

IR (KBr) 2976, 2932, 2865, 1694 cm$^{-1}$; $^1$H-NMR (CDCl$_3$) δ 1.47 (9H, s), 1.6-1.8 (2H, m), 2.1-2.3 (2H, m), 3.05 (2H, ddd, J=3.0, 10.6, and 13.6 Hz), 3.92 (3H, s), 3.9-4.1 (2H, m)

REFERENCE EXAMPLE 36

1-tert-Butoxycarbonyl-4-(2-thiazolylthio)piperidine

By a similar manner to Reference Example 35, 1-tert-butoxycarbonyl-4-hydroxypiperidine (1.01 g, 5.0 mmol) was reacted with 2-mercaptothiazole (0.70 g, 6.0 mmol) to give the titled compound as pale yellow oily substance (1.33 g, 89%).

IR (KBr) 2976, 2930, 2854, 1694 cm$^{-1}$; $^1$H-NMR (CDCl$_3$) δ 1.46 (9H, s), 1.5-1.8 (2H, m), 2.0-2.2 (2H, m), 3.03 (2H, ddd, J=2.8, 10.2, and 13.4 Hz), 3.78 (1H, tt, J=4.0 and 10.2 Hz), 3.9-4.1 (2H, m), 7.26 (1H, d, J=3.4 Hz), 7.71 (1H, d, J=3.4 Hz)

REFERENCE EXAMPLE 37

1-tert-Butoxycarbonyl-4-(4-pyridinylthio)piperidine

By a similar manner to Reference Example 35, 1-tert-butoxycarbonyl-4-hydroxypiperidine (1.01 g, 5.0 mmol) was reacted with 4-mercaptopyridine (0.67 g, 6.0 mmol) to give the titled compound as pale yellow oily substance (1.33 g, 90%)

IR (KBr) 2976, 2930, 2865, 1694 cm$^{-1}$; $^1$H-NMR (CDCl$_3$) δ 1.46 (9H, s), 1.6-2.1 (4H, m), 3.0-3.2 (2H, m), 3.51 (1H, tt, J=4.0 and 9.8 Hz), 3.8-4.0 (2H, m), 7.1-7.2 (2H, m), 8.4-8.5 (2H, m)

REFERENCE EXAMPLE 38

1-tert-Butoxycarbonyl-4-(2-pyrazinylthio)piperidine

By a similar manner to Reference Example 35, 1-tert-butoxycarbonyl-4-hydroxypiperidine (1.01 g, 5.0 mmol) was reacted with mercaptopyridine (0.67 g, 6.0 mmol) to give the titled compound as pale yellow oily substance (1.26 g, 85%).

IR (KBr) 2976, 2932, 1694 cm$^{-1}$; $^1$H-NMR (CDCl$_3$) δ 1.47 (9H, s), 1.5-1.8 (2H, m), 2.0-2.1 (2H, m), 3.09 (2H, ddd, J=3.2, 10.6, and 13.4 Hz), 3.8-4.0 (3H, m), 8.21 (1H, d, J=2.6 Hz), 8.35 (1H, dd, J=1.8 and 2.6 Hz), 8.42 (1H, d, J=1.8 Hz)

REFERENCE EXAMPLE 39

1-tert-Butoxycarbonyl-4-(2-benzothiazolylthio)piperidine

By a similar manner to Reference Example 35, 1-tert-butoxycarbonyl-4-hydroxypiperidine (1.01 g, 5.0 mmol) was reacted with 2-mercaptobenzothiazole (1.00 g, 6.0 mmol) to give the titled compound as a colorless oily substance (1.54 g, 88%).

IR (KBr) 2975, 1694 cm$^{-1}$; $^1$H-NMR (CDCl$_3$) δ 1.47 (9H, s), 1.6-1.9 (2H, m), 2.1-2.3 (2H, m), 3.12 (2H, ddd,J=3.0, 10.4, and 13.6 Hz), 3.9-4.1 (2H, m), 4.10 (2H, tt, J=3.6 and 9.8 Hz), 7.3-7.5 (2H, m), 7.76 (1H, d, J=7.2 Hz), 7.88 (1H, d, J=7.2 Hz)

REFERENCE EXAMPLE 40

1-tert-Butoxycarbonyl-4-(2-thienylthio)piperidine

By a similar manner to Reference Example 35, 1-tert-butoxycarbonyl-4-hydroxypiperidine (1.01 g, 5.0 mmol) was reacted with 2-mercaptothiophene (0.70 g, 6.0 mmol) to give the titled compound as pale yellow oily substance (987 mg, 66%).

IR (KBr) 2975, 2941, 1694 cm$^{-1}$; $^1$H-NMR (CDCl$_3$) δ 1.44 (9H, s), 1.5-1.7 (2H, m), 1.8-2.0 (2H, m), 2.85 (ddd, J=3.0, 11.0, and 13.6 Hz), 2.9-3.1 (1H, m), 3.9-4.1 (1H, m), 7.00 (1H, dd, J=3.4 and 5.2 Hz), 7.13 (1H, dd, J=1.4 and 3.4 Hz), 7.38 (1H, dd, J=1.4 and 5.2 Hz)

REFERENCE EXAMPLE 41

1-tert-Butoxycarbonyl-4-(1-methylimidazol-2-ylthio)piperidine

By a similar manner to Reference Example 35, 1-tert-butoxycarbonyl-4-hydroxypiperidine (1.01 g, 5.0 mmol) was reacted with 2-mercapto-1-methylimidazole (0.68 g, 6.0 mmol) to give the titled compound as pale yellow oily substance (1.04 g, 70%).

IR (KBr) 2975, 2938, 2865, 1694 cm$^{-1}$; $^1$H-NMR (CDCl$_3$) δ 1.45 (9H, s), 1.5-1.7 (2H, m)), 1.9-2.0 (2H, m), 2.93 (2H, ddd, J=2.8, 11.0, and 13.4 Hz), 3.49 (1H, tt, J=4.0 and 10.6 Hz), 3.66 (3H, s), 3.9-4.1 (2H, m), 6.96 (1H, d, J=1.4 Hz), 7.09 (1H, d, J=1.4 Hz)

REFERENCE EXAMPLE 42

1-tert-Butoxycarbonyl-4-[7-trifluoromethyl-4-quinolynylthio]piperidine

By a similar manner to Reference Example 35, 1-tert-butoxycarbonyl-4-hydroxypiperidine (1.01 g, 5.0 mmol) was reacted with 7-trifluoromethyl-4-quinolinethiol (1.38 g, 6.0 mmol) to give the titled compound as pale yellow solid substance (1.53 g, 74%).

IR (KBr) 2978, 2934, 2859, 1694 cm$^{-1}$; $^1$H-NMR (CDCl$_3$) δ 1.47 (9H, s), 1.7-1.8 (2H m), 2.0-2.2 (2H, m), 3.11 (2H, ddd, J=3.4, 10.2, and 13.6 Hz), 3.63 (1H, dt, J=4.0 and 9.8 Hz), 3.9-4.1 (2H, m), 7.38 (1H, d, J=4.8 Hz). 7.73 (1H, dd, J=1.8 and 8.8 Hz), 8.32 (1H, d, J=8.8 Hz), 8.38 (1H, d, J=1.8 Hz), 8.82 (1H, d, J=4.8 Hz)

REFERENCE EXAMPLE 43

1-tert-Butoxycarbonyl-4-(4-pyridinyloxy)piperidine

By a similar manner to Reference Example 35, 1-tert-butoxycarbonyl-4-hydroxypiperidine (1.01 g, 5.0 mmol) was reacted with 4-hydroxypyridine (0.57 g, 6.0 mmol) to give the titled compound as pale yellow solid substance (1.05 g, 75%).

IR (KBr) 2975, 2870, 1694 cm$^{-1}$; $^1$H-NMR (CDCl$_3$) δ 1.47 (9H, s), 1.7-2.0 (4H, m), 3.37 (2H, ddd, J=3.6, 7.2, and 13.4 Hz), 3.69 (2H, ddd, J=4.0, 7.6, and 13.4 Hz), 4.58 (1H, tt, J=3.6 and 7.0 Hz), 6.8-6.9 (2H, m), 8.4-8.5 (2H, m)

REFERENCE EXAMPLE 44

1-tert-Butoxycarbonyl-4-(2-pyridinyloxy)piperidine

60% sodium hydride (0.26 g, 6.5 mmol) was washed with hexane, and suspended in dry DMSO (10 mL). To the suspension was added a solution of 1-tert-butoxycarbonyl-4-hydroxypiperidine (1.01 g, 5.0 mmol) in dry DMSO (10 mL). The mixture was stirred at room temperature for 1 hour and at 60° C. for 1 hour, and cooled to room temperature. To the reaction mixture was added 2-bromopyridine (0.62 mL, 6.5 mmol), and the mixture was stirred at room temperature for 24 hours. To the reaction mixture was added water (50 mL), and the mixture was extracted with diethyl ether. The extract was washed with water and saturated aqueous solution of sodium hydrogen carbonate, successively, and dried over anhydrous sodium sulfate. The solvent was distilled off under reduced pressure, and the residue was purified by silica gel column chromatography (50 g, ethyl acetate-hexane 1:5) to give the titled compound as colorless crystals (928 mg, 67%).

IR (KBr) 2975, 2865, 1694 cm$^{-1}$; $^1$H-NMR (CDCl$_3$) δ 1.47 (9H, s), 1.6-1.8 (2H, m), 1.9-2.1 (2H, m), 3.29 (2H, ddd, J=3.6, 8.8, and 12.8 Hz), 3.7-3.9 (2H, m), 5.22 (1H, tt, J=4.2 and 8.2 Hz), 6.71 (1H, d, J=8.4 Hz), 6.84 (1H, dd, J=5.0 and 7.0 Hz), 7.56 (1H, ddd, J=2.0, 7.0, and 8.4 Hz), 8.12 (1H, dd, J=2.0 and 5.0 Hz)

REFERENCE EXAMPLE 45

1-tert-Butoxycarbonyl-4-(2-thiazolyloxy)piperidine

By a similar manner to Reference Example 44, 1-tert-butoxycarbonyl-4-hydroxypiperidine (1.01 g, 5.0 mmol) was reacted with 2-bromothiazole (0.59 mL, 6.5 mmol) to give the titled compound as pale yellow oily substance (189 mg, 13%)

IR (KBr) 2974, 2866, 1696 cm$^{-1}$; $^1$H-NMR (CDCl$_3$) δ 1.47 (9H, s), 1.7-2.1 (4H, m), 3.32 (2H, ddd, J=3.6, 8.0, and 13.6 Hz), 3.6-3.8 (2H, m), 5.0-5.2 (1H, m), 6.67 (1H, d, J=3.8 Hz), 7.11 (1H, d, J=3.8 Hz)

REFERENCE EXAMPLE 46

4-(5-Methyl-1,3,4-thiadiazol-2-ylthio)piperidine trifluoroacetate

To a solution of 1-tert-butoxycarbonyl-4-hydroxypiperidine (1.01 g, 5.0 mmol) in dry THF (30 mL) were added triphenylphosphine (2.0 g, 7.5 mmol) and 5-methyl-1,3,4-thiadiazol-2-thiol (0.79 g, 6.0 mmol). To the mixture was added diisopropyl azodicarboxylate (1.2 mL, 6.0 mmol) under ice cooling, and the mixture was stirred at the same temperature for 1 hour. The reaction mixture was diluted with ethylacetate (100 mL), which was washed with saturated aqueous solution of sodium hydrogen carbonate, aqueous solution of 1N-sodium hydroxide and saturated aqueous solution of sodium chloride. The solvent was dried over anhydrous sodium sulfate and distilled off under reduced pressure. The residue was subjected to silica gel column chromatography (50 g, ethyl acetate-hexane 1:2) to give a crude product (1.63 g). The crude product (0.82 g) was dissolved in dichloromethane (5 mL). To the solution was added trifluoroacetic acid (5 mL), and the mixture was stirred at room temperature for 30 minutes. The reaction mixture was concentrated under reduced pressure, and the concentrate was dissolved in water (20 mL) and washed twice with diethyl ether (20 mL). The solvent was distilled off under reduced pressure, and the residue was subjected to toluene azeotrope, and the resulting residue was vacuum-dried to give the titled compound as white solid substance (535 mg, 65%).

IR (KBr) 2488, 2214, 1674 cm$^{-1}$; $^1$H-NMR (CD$_3$OD) δ 1.8-2.1 (2H, m), 2.3-2.5 (2H, m), 2.74 (3H, s), 3.1-3.3 (2H, m), 3.45 (2H, dt, J=13.6 and 3.6 Hz), 4.02 (1H, tt, J=4.0 and 10.6 Hz)

REFERENCE EXAMPLE 47

4-(1H-Benzotriazol-1-yloxy)piperidine trifluoroacetate

By a similar manner to Reference Example 46, 1-tert-butoxycarbonyl-4-hydroxypiperidine (1.01 g, 5.0 mmol) was reacted with 1-hydroxybenzotriazole (0.81 g, 6.0 mmol) to give the titled compound as white solid substance (800 mg, 96%).

IR (KBr) 2476, 2074, 1676 cm$^{-1}$; $^1$H-NMR (CD$_3$OD) δ 2.2-2.3 (4H, m), 3.2-3.3 (2H, m), 3.60 (2H, ddd, J=4.8, 7.4, and 12.8 Hz), 4.9-5.1 (1H, m), 7.4-8.0 (4H, m)

REFERENCE EXAMPLE 48-1

1-tert-Butoxycarbonyl-4-[hydroxy(2-pyridyl)methyl]piperidine

To a solution of 2-bromopyridine (488 μL, 5 mmol) in ether (10 mL) was added dropwise butyl lithium (1.6M hexane solution, 3.125 mL, 5 mmol) at −78° C., and the mixture was stirred for 30 minutes. To the mixture was added dropwise a solution of 1-tert-butoxycarbonyl-4-formylpiperidine (1066 mg, 5 mmol) in ether (10 mL) at −78° C. The mixture was stirred for 18 hours while the temperature is elevated to room temperature. The reaction mixture was washed with saturated aqueous solution of sodium hydrogencarbonate and saturated aqueous solution of sodium chloride, and dried over magnesium sulfate. The solvent was distilled off under reduced pressure, and the residue was purified by column chromatography (ethyl acetate:hexane=1:2) to give the titled compound as yellowish oily substance (913 mg). Yield 62%.

$^1$H NMR (CDCl$_3$) δ 1.20-1.49 (3H, m), 1.44 (9H, s), 1.66-1.93 (2H, m), 2.44-2.85 (2H, m), 4.01-4.23 (2H, m), 4.53 (1H, d, J=5.2 Hz), 7.18-7.25 (2H, m), 7.69 (1H, dt, J=1.8, 7.2 Hz), 8.55 (1H, dd, J=1.8, 5.4 Hz)

IR (KBr) 3418, 3024, 2922, 2854, 1732, 1694 cm$^{-1}$

REFERENCE EXAMPLE 48-2

1-tert-Butoxycarbonyl-4-[(methylsulfonyloxy)(2-pyridyl)methyl]piperidine

To a solution of the compound obtained in Reference Example 48-1 (407 mg, 1.39 mmol) in dichloromethane (10 mL) was added dropwise triethylamine (0.385 mL, 2.78 mmol) at room temperature. To the mixture was added dropwise methanesulfonyl chloride (0.129 mL, 1.67 mmol), and the mixture was stirred for 4 hours. After the reaction has been completed, the reaction mixture was washed with aqueous solution of 5% potassium hydrogensulfate (10 mL), saturated aqueous solution of sodium hydrogencarbonate (10 mL×2) and saturated sodium chloride solution (10 mL×2), and dried over magnesium sulfate. The solvent was distilled off whereby the titled compound was obtained as yellowish oily substance (484 mg). Yield 94%.

$^1$H NMR (CDCl$_3$) δ 1.27-1.39 (2H, m), 1.44 (9H, s), 1.71-1.96 (3H, m), 2.09-2.36 (2H, m), 2.53-2.78 (2H, m), 2.83 (3H, s), 5.39 (1H, d, J=7.2 Hz), 7.29-7.33 (1H, m), 7.41 (1H, d, J=7.6 Hz), 7.77 (1H, dd, J=1.8, 7.6 Hz), 8.62-8.65 (1H, dd, J=1.8, 4.8 Hz)

IR (KBr) 3366, 2857, 2363, 2338, 1694 cm$^{-1}$

REFERENCE EXAMPLE 48-3

1-tert-Butoxycarbonyl-4-(2-pyridylmethyl)piperidine

To the solution of the compound obtained in Reference Example 48-2 (450 mg, 1.21 mmol) in methanol (15 mL) was added 10% palladium carbon (48% wet)(450 mg), and the mixture was subjected to catalytic hydrogenation reaction at room temperature for 13 hours. The catalyst was filtered off, and the filtrate was concentrated under reduced pressure to give the titled compound (308 mg) as a colorless oily substance. Yield 92%.

$^1$H NMR (CDCl$_3$) δ 1.05-1.39 (2H, m), 1.45 (9H, s), 1.41-1.73 (3H, m), 1.80-2.08 (2H, m), 2.71 (2H, d, J=7.0 Hz), 3.93-4.22 (2H, m), 7.03-7.20 (2H, m), 7.60 (1H, dt, J=1.8, 7.6 Hz), 8.55 (1H, d, J=4.4 Hz)

IR (KBr) 2976, 2932, 2853, 2249, 1682 cm$^{-1}$

REFERENCE EXAMPLE 49-1

1-tert-Butoxycarbonyl-4-[hydroxy(3-pyridyl)methyl]piperidine

By using 3-bromopyridine, the reaction and the purification procedure were carried out by a similar manner to Example 48-1 to give the titled compound as yellowish oily substance (373 mg). Yield 26%.

$^1$H NMR (CDCl$_3$) δ 1.10-1.37 (2H, m), 1.45 (9H, s), 1.61-2.00 (3H, m), 2.47-2.75 (2H, m), 3.96-4.22 (2H, m), 4.45 (1H, d, J=7.0 Hz), 7.29 (1H, dd, J=4.6, 8.0 Hz), 7.67 (1H, dt, J=1.8, 8.0 Hz), 8.45-8.57 (2H, m)

IR (KBr) 3430, 2924, 2855, 2342, 1674, 1653 cm$^{-1}$

REFERENCE EXAMPLE 49-2

1-tert-Butoxycarbonyl-4-[(methylsulfonyloxy)(3-pyridyl)methyl]piperidine

By using the compound obtained in Reference Example 49-1, the reaction and the purification procedure were carried out by a similar manner to Reference Example 48-2 to give the titled compound as yellowish oily substance (299 mg). Yield 95%.

$^1$H NMR (CDCl$_3$) δ 1.10-1.31 (3H, m), 1.44 (9H, s), 1.86-2.04 (2H, m), 2.49-2.74 (2H, m), 2.78 (3H, s), 3.99-4.29 (2H, m), 5.29 (1H, d, J=8.0 Hz), 7.37 (1H, dd, J=4.6, 8.0 Hz), 7.69 (1H, dt, J=2.2, 8.0 Hz), 8.60-8.66 (2H, m)

IR (KBr) 3416, 2976, 2932, 2862, 1694, 1682 cm$^{-1}$

REFERENCE EXAMPLE 49-3

1-tert-Butoxycarbonyl-4-(3-pyridylmethyl)piperidine

By using the compound obtained in Reference Example 49-2, the reaction and the purification procedure were carried out by a similar manner to Reference Example 48-3 to give the titled compound as yellowish oily substance (190 mg). Yield 8.5%.

$^1$H NMR (CDCl$_3$) δ 0.97-1.32 (2H, m), 1.45 (9H, s), 1.52-1.81 (3H, m), 2.54 (2H, d, J=7.0 Hz), 2.60-2.74 (2H, m), 3.96-4.20, (2H, m), 7.22 (1H, dd, J=4.6, 8.0 Hz), 7.46 (1H, dt, J=1.8, 8.0 Hz), 8.41 (1H, d, J=2.2 Hz), 8.45 (1H, dd, J=1.8, 4.6 Hz),

IR (KBr) 3544, 2974, 2928, 2856, 1682 cm$^{-1}$

REFERENCE EXAMPLE 50-1

1-tert-Butoxycarbonyl-4-[hydroxy(4-pyridyl)methyl]piperidine

By using 4-bromopyridine, the reaction and the purification procedure were carried out by a similar manner to Reference Example 48-1 to give the titled compound as yellowish oily substance (510 mg). Yield 35%.

$^1$H NMR (CDCl$_3$) δ 1.10-1.48 (2H, m), 1.43 (9H, s), 1.63-1.87 (3H, m), 2.47-2.73 (2H, m), 4.00-4.22 (2H, m), 4.45 (1H, d, J=6.0 Hz), 7.24 (2H, d, J=5.4 Hz), 8.52 (2H, d, J=5.4 Hz)

IR (KBr) 3246, 2922, 2858, 2247, 1941, 1695, 1674, 1603 cm$^{-1}$

REFERENCE EXAMPLE 50-2

1-tert-Butoxycarbonyl-4-[(methylsulfonyloxy)(4-pyridyl)methyl]piperidine

By using the compound obtained in Reference Example 50-1, the reaction and the purification procedure were carried out by a similar manner to Reference Example 48-2 to give the titled compound as yellowish oily substance (446 mg). Yield 85%.

$^1$H NMR (CDCl$_3$) δ 1.07-1.40 (2H, m), 1.45 (9H, s), 1.69-1.95 (3H, m), 2.53-2.75 (2H, m), 2.86 (3H, s), 4.01-4.20 (2H, m), 7.67 (2H, d, J=6.6 Hz), 8.81 (2H, d, J=6.6 Hz)

IR (KBr) 3501, 2975, 2928, 2853, 1694, 1682 cm$^{-1}$

REFERENCE EXAMPLE 50-3

1-tert-Butoxycarbonyl-4-(4-pyridylmethyl)piperidine

By using the compound obtained in Reference Example 50-2, the reaction and the purification procedure were carried out by a similar manner to Reference Example 48-3 to give the titled compound as yellowish oily substance (69 mg). Yield 93%.

$^1$H NMR (CDCl$_3$) δ 1.08-1.25 (2H, m), 1.45 (9H, s), 1.50-1.80 (3H, m), 2.54 (2H, d, J=7.2 Hz), 3.97-4.21 (2H, m), 7.17 (2H, dd, J=1.6, 4.4 Hz), 8.49 (2H, dd, J=1.6, 4.4 Hz)

IR (KBr) 2975, 2928, 2851, 1682 cm$^{-1}$

REFERENCE EXAMPLE 51-1

1-tert-Butoxycarbonyl-4-[hydroxy(2-thiazolyl)methyl]piperidine

By using 2-bromothiazole, the reaction and the purification procedure were carried out by a similar manner to Reference Example 48-1 to give the titled compound as yellowish oily substance (1.13 g). Yield 76%.

$^1$H NMR (CDCl$_3$) δ 1.22-1.41 (2H, m), 1.44 (9H, s), 1.47-1.72 (2H, m), 1.89-2.12 (1H, m), 2.56-2.88 (2H, m), 4.01-4.24 (2H, m), 4.85 (1H, d, J=5.6 Hz), 7.33 (1H, d, J=2.6 Hz), 7.51 (1H, d, J=2.6 Hz)

IR (KBr) 3485, 2976, 2934, 2857, 1684 cm$^{-1}$

REFERENCE EXAMPLE 51-2

1-tert-Butoxycarbonyl-4-[(methylsulfonyloxy)(2-thiazolyl)methyl]piperidine

By using the compound obtained in Reference Example 51-1, the reaction and the purification procedure were carried out by a similarlmanner to Reference Example 48-2 to give the titled compound as yellowish oily substance (560 mg). Yield 45%.

$^1$H NMR (CDCl$_3$) δ 1.19-1.41 (2H, m), 1.44 (9H, s), 1.49-1.77 (2H, m), 1.80-2.13 (2H, m), 2.56-2.78 (2H, m), 2.91 (3H, s), 4.03-4.24 (2H, m), 4.84 (1H, d, J=5.4 Hz), 7.33 (1H, d, J=3.4 Hz), 7.75 (1H, d, J=3.4 Hz)

IR (KBr) 3171, 2975, 2926, 2859, 1669 cm$^{-1}$

REFERENCE EXAMPLE 51-3

1-tert-Butoxycarbonyl-4-(2-thiazolylmethyl)piperidine

By using the compound obtained in Reference Example 51-2, the reaction and the purification procedure were carried out by a similar manner to Reference Example 48-3 to give the titled compound as yellowish oily substance (71 mg). Yield 93%.

$^1$H NMR (CDCl$_3$) δ 1.08-1.29 (2H, m), 1.45 (9H, s), 1.61-1.79 (2H, m), 1.85-2.09 (1H, m), 2.54-2.78 (2H, m), 2.96 (2H, d, J=7.0 Hz), 4.00-4.20 (2H, m), 7.21 (1H, d, J=3.2 Hz), 7.70 (1H, d, J=3.2 Hz)

IR (KBr) 3081, 2975, 2928, 2853, 1694 cm$^{-1}$

REFERENCE EXAMPLE 52

1-tert-Butoxycarbonyl-4-(3-pyridyloxy)piperidine

By using 3-hydroxypyridine, the reaction and the purification procedure were carried out by a similar manner to Reference Example 35 to give to give the titled compound as yellowish oily substance (1.08 g). Yield 78%.

$^1$H NMR (CDCl$_3$) δ 1.47 (9H, s), 1.65-1.84 (2H, m), 1.85-2.05 (2H, m), 3.28-3.37 (2H, m), 3.65-3.78 (2H, m), 4.47-4.54 (1H, m), 7.20-7.23 (2H, m), 8.21-8.24 (1H, m), 8.31-8.33 (2H, m)

IR (KBr) 2971, 2870, 1684 cm$^{-1}$

REFERENCE EXAMPLE 53

1-tert-Butoxycarbonyl-4-(4-phenyl-2-thiazolylthio)piperidine

By using 2-mercapto-4-phenylthiazole, the reaction and the purification procedure were carried out by a similar manner to Reference Example 35 to give to give the titled compound as yellowish oily substance (0.71 g). Yield 38%.

$^1$H NMR (CDCl$_3$) δ 1.46 (9H, s), 1.49-1.77 (2H, m), 2.11-2.21 (2H, m), 3.00-3.13 (2H, m), 3.80-4.10 (3H, m), 7.29-7.46 (4H, m), 7.84-7.87 (1H, m), 7.88-7.90 (2H, m)

IR (KBr) 3094, 2976, 2938, 2865, 1684 cm$^{-1}$

REFERENCE EXAMPLE 54

3-Chloro-N-{3-[4-(4-fluorobenzyl)-1-piperidinyl]propyl}-4-methylaniline 2 hydrochloride By a similar manner to Reference Example 1, the titled compound was synthesized by using 4-(4-fluorobenzyl)piperidine and 3-chloro-4-methylaniline. Yield 63%.

$^1$H NMR (DMSO-d$_6$) δ 1.4-2.15 (7H, m), 2.22 (3H, s), 2.45-2.6 (2H, m), 2.82 (2H, m), 3,08 (2H, m), 3.16 (2H, t, J=7.0 Hz), 3.41 (2H, br d, J=12.2 Hz), 6.75-7.35 (7H, m)

REFERENCE EXAMPLE 55

N-{3-[4-(4-Fluorobenzyl)-1-piperidinyl]propyl}-4-methylaniline 2 hydrochloride

By a similar manner to Reference Example 1, the titled compound was synthesized by using 4-(4-fluorobenzyl)piperidine and p-toluidine. Yield 61%.

$^1$H NMR (DMSO-d$_6$) δ 1.4-1.9 (5H, m), 2.0-2.25 (2H, m), 2.30 (3H, s), 2.45-2.6 (2H, m), 2.83 (2H, m), 3.12 (2H, m)), 3.29 (2H, m), 3.41 (2H, m), 7.05-7.4 (8H, m)

REFERENCE EXAMPLE 56-1

3,4-Dichloro-N-(3-chloropropyl)-N-formylaniline

To the mixture of 3,4-dichloro-N-formylaniline (133.0 g, 700 mmol), 1-bromo-3-chloropropane (132.3 g, 840 mmol) and acetone (700 mL) was added cesium carbonate (273.7 g, 840 mmol), and the mixture was stirred for under reflux. The reaction mixture was concentrated under reduced pressure, and to the concentrate was added ethyl acetate (500 mL). The organic layer was washed with water (300 mL) and saturated sodium chloride solution (100 mL×3), successively, dried over magnesium sulfate and concentrated under reduced pressure. The concentrate was subjected to column chromatography (silica gel 500 g×2, hexane/ethyl acetate=1/0 to 9/1 to 4/1), and the desired fraction was concentrated under reduced pressure to give the titled compound (143.5 g, 538 mmol, Yield 77%) as pale yellow oily substance.

$^1$H NMR (CDCl$_3$) δ 1.9-2.2 (2H, m), 3.5-3.6 (2H, m), 3.85-4.0 (2H, m), 7.06 (⅞×1H, dd, J=2.7, 8.7 Hz), 7.22 (⅛×1H, dd, J=2.4, 8.7 Hz), 7.31 (⅞×1H, d, J=2.7 Hz), 7.50 (⅛×1H, d, J=2.4 Hz), 7.50 (⅛×1H, d, J=8.7 Hz), 7.51 (⅞×1H, d, J=8.7 Hz), 8.37 (⅛×1H, s), 8.40 (⅞×1H, s)

REFERENCE EXAMPLE 56-2

3,4-Dichloro-N-(3-chloropropyl)aniline hydrochloride

The compound obtained in Reference Example 56-1 (142.5 g, 534 mmol) was dissolved in 2-propanol (500 mL). To the solution was added concentrated hydrochloric acid (100 mL), and the mixture was stirred at 60° C. for 3 hours. The reaction mixture was cooled to room temperature, and the resulting precipitates were collected by filtration. The precipitates were washed with 2-propanol (100 mL×3), and dried under reduced pressure to give the titled compound (133.0 g, 484 mmol, Yield 90%) as white crystaline.

$^1$H NMR (CD$_3$OD) δ 2.20 (2H, m), 3.51 (2H, m), 3.71 (2H, t, J=6.2 Hz), 7.33 (1H, dd, J=2.9, 8.7 Hz), 7.59 (1H, d, J=2.9 Hz), 7.66 (1H, d, J=8.7 Hz)

REFERENCE EXAMPLE 56-3

1-Acetyl-N-(3-chloropropyl)-N-(3,4-dichlorophenyl)-4-piperidinecarboxamide

By a similar manner to Reference Example 11-2, the titled compound was synthesized by using the compound obtained in Reference Example 56-2. Yield 84%.

$^1$H NMR (CDCl$_3$) δ 1.62-1.87 (4H, m), 1.94-2.06 (2H, m), 2.06 (3H, s), 2.34-2.44 (2H, m), 2.81-2.94 (1H, m), 3.54 (2H, t, J=6.6 Hz), 3.75-3.82 (3H, m), 4.50-4.56 (1H; m), 7.05 (1H, dd, J=8.4, 2.4 Hz), 7.31 (1H, d, J=2.4 Hz), 7.55 (1H, d, J=8.4 Hz)

REFERENCE EXAMPLE 57

N-(3-Chloropropyl)-N-(3,4-dichlorophenyl)-1-(methylsulfonyl)-4-piperidinecarboxamide To a suspension of the compound obtained in Reference Example 13-2 (22.6 g, 109 mmol) and DMF (0.084 mL, 1.1 mmol) in dichloromethane (200 mL) was added dropwise oxalyl chloride (14 mL, 164 mmol), and the mixture was stirred for 1.5 hour. The solvent was distilled off to give the acid chloride. On the other hand, To a suspension of the compound obtained in Reference Example 56-2 (10.0 g, 36.4 mmol) in dichloromethane (200 mL) was added dropwise triethylamine (28 mL) under ice cooling, and the mixture was stirred for 10 minutes. To the mixture was added dropwise the solution of above acid chloride in dichloromethane (100 mL) The mixture was stirred for 14 hours while the temperature was gradually elevated to room temperature. To the mixture was added an aqueous solution of saturated sodium hydrogencarbonate (300 mL), and the organic soluvent was distilled off under reduced pressure. The aqueous layer was extracted with ethyl acetate. The extract was washed with saturated sodium chloride solution and dried over anhydrous magnesium sulfate, and concentrated under reduced pressure. The concentrate was subjected to silica gel column chromatography (dichloromethane/ethyl acetate=2/1), and the desired fraction was concentrated under reduced pressure to give the titled compound (14.5 g, 33.9 mmol, Yield 93%) as colorless solid substance.

$^1$H NMR (CDCl$_3$) δ 1.60-2.01 (6H, m), 2.05-2.37 (1H, m), 2.39-2.68 (2H, m), 2.74 (3H, s), 3.55 (2H, t, J=6.4 Hz), 3.65-3.83 (4H, m), 7.05 (1H, dd, J=2.2, 8.4 Hz), 7.31 (1H, d, J=2.2 Hz), 7.55 (1H, d, J=8.4 Hz)

REFERENCE EXAMPLE 58-1

1-tert-Butoxycarbonyl-4-methylsulfonyloxypiperidine

To the solution of 1-tert-butoxycarbonyl-4-hydroxypiperidine (20.13 g, 10 mmol) and triethylamine (16.7 mL, 120 mmol) in THF (200 mL) was added dropwise methanesulfonyl chloride (9.3 mL, 120 mmol) under ice cooling, and the mixture was stirred at the same temperature for 3 hours. To the mixture was added water (200 mL), and the mixture was extracted with ethyl acetate (200 mL, 100 mL×2). The organic layer was washed with 1N-hydrochloric acid (50 mL×2), a saturated aqueous solution of sodium hydrogencarbonate (50 mL×2), saturated sodium chloride solution (50 mL), successively, dried over magnesium sulfate and concentrated under reduced pressure. To the concentrate were added diisopropyl ether (100 ml) and hexane (100 mL), and the resulting precipitates were collected by filtration. The precipitates were washed with diisopropyl ether/hexane (1/1) mixed solvent (100 mL), and dried under reduced pressure to give the titled compound (25.65 g, 92 mmol, Yield 92%) as white crystals.

$^1$H NMR (CDCl$_3$) δ 1.46 (9H, s), 1.7-2.1 (4H, m), 3.04 (3H, s), 3.30 (2H, ddd, J=4.2, 7.9, 13.7 Hz), 3.71 (2H, ddd, J=4.1, 6.7, 13.7 Hz), 4.89 (1H, tt, J=3.8, 7.7 Hz)

REFERENCE EXAMPLE 58-2

1-tert-Butoxycarbonyl-4-(6-imidazo[1,2-b]pyridazinylthio)piperidine

A mixture of the compound obtained in Reference Example 58-1 (2.24 g, 8.0 mmol), sodium 6-imidazo[1,2-b]pyridazinethiolate (1.80 g) and DMF (8 mL) was stirred at 70° C. for 7 hours. The reaction mixture was diluted with water (40 mL), and extracted with ethyl acetate (40 mL, 20 mL×2). The organic layer was washed with aqueous solution of 0.5N-sodium hydroxide (10 mL×3), saturated sodium chloride solution (10 mL), successively, dried over magnesium sulfate and concentrated under reduced pressure. The concentrate was subjected to column chromatography (silica gel 70 g, hexane/ethyl acetate=1/1 to 0/1), and the desired fraction was concentrated under reduced pressure. To the concentrate was added diisopropyl ether and the precipitates were collected by filtration. The precipitates were washed with diisopropyl ether, and dried under reduced pressure to give the titled compound (2.14 g, 6.4 mmol, Yield 80%) as pale yellow solid.

$^1$H NMR (CDCl$_3$) δ 1.47 (9H, s), 1.70 (2H, m), 2.14 (2H, m), 3.13 (2H, ddd, J=3.4, 10.3, 13.6 Hz), 3.85-4.1 (3H, m), 6.82 (1H, d, J=9.5 Hz), 7.66 (1H, d, J=0.9 Hz), 7.74 (1H, d, J=9.5 Hz), 7.85 (1H, d, J=0.9 Hz)

REFERENCE EXAMPLE 58-3

4-(6-Imidazo[1,2-b]pyridazinylthio)piperidine 2 hydrochloride

By a similar manner to Reference Example 61-2, the titled compound was synthesized by using the compound obtained in Reference Example 58-2. Yield 98%.

$^1$H NMR (D$_2$O) δ 2.05 (2H, m), 2.47 (2H, m), 3.27 (2H, m), 3.52 (2H, m), 4.25 (1H, m), 7.58 (1H, d, J=9.6 Hz), 7.95 (1H, s), 8.13 (1H, d, J=9.6 Hz), 8.22 (1H, s)

REFERENCE EXAMPLE 59-1

1-tert-Butoxycarbonyl-4-(5-imidazo[1,2-a]pyridylthio)piperidine 5-imidazo[1,2-a]pyridinethiol (1.95 g, 13.0 mmol) was dissolved in DMF (10 mL), and under ice cooling, to the solution were added sodium hydride (60%, 800 mg, 20 mmol). The mixture was stirred at the same temperature for 1 hour. To the mixture was added the compound obtained in Reference Example 58-1 (2.79 g, 10.0 mmol), and the mixture was stirred at 70° C. for 7 hours. The reaction mixture was concentrated under reduced pressure, and to the concentrate was added ethyl acetate (70 mL). The organic layer was washed with water (10 mL), aqueous solution of 0.5N-sodium hydroxide (10 mL×3), saturated sodium chloride solution (10 mL), successively, dried over magnesium sulfate and concentrated under reduced pressure. The concentrate was subjected to column chromatography (silica gel 70 g, hexane/ethyl acetate=1/1 to 0/1), and the desired fraction was concentrated under reduced pressure to give the titled compound (2.55 g, 7.6 mmol, Yield 76%) as pale yellow oily substance.

$^1$H NMR (CDCl$_3$) δ 1.45 (9H, s), 1.60 (2H, m), 1.90 (2H, m), 2.90 (2H, ddd, J=3.0, 10.6, 13.7 Hz), 3.35 (1H, tt, J=4.0, 10.4 Hz), 3.99 (2H, br d, J=12.8 Hz), 7.02 (1H, dd, J=1.1, 7.1 Hz), 7.15 (1H, dd, J=7.1, 8.9 Hz), 7.64 (1H, d, J=8.9 Hz), 7.70 (1H, d, J=1.1 Hz), 7.96 (1H, s)

REFERENCE EXAMPLE 59-2

4-(5-Imidazo[1,2-a]pyridylthio)piperidine 2 hydrochloride

By a similar manner to Reference Example 61-2, the titled compound was synthesized by using the compound obtained in Reference Example 59-1. Yield 94%.

$^1$H NMR (CD$_3$OD) δ 1.96 (2H, dtd, J=3.8, 10.9, 14.5 Hz), 2.31 (2H, m), 3.14 (2H, m), 3.46 (2H, td, J=4.0, 13.5 Hz), 3.86 (1H, tt, J=4.0, 10.7 Hz), 7.80 (1H, m), 7.9-8.05 (2H, m), 8.17 (1H, d, J=2.4 Hz), 8.51 (1H, d, J2.4 Hz)

REFERENCE EXAMPLE 60-1

4-(2-Benzoimidazolylthio)-1-tert-butoxycarbonylpiperidine

By a similar manner to Reference Example 61-1, the titled compound was synthesized by using 2-benzoimidazolethiol. Yield 50%.

$^1$H NMR (DMSO-d$_6$) δ 1.40 (9H, s), 1.55 (2H, m), 2.07 (2H, m), 3.03 (2H, m), 3.83 (2H, m), 3.96 (1H, tt, J=3.9, 10.3 Hz), 7.12 (2H, m), 7.44 (2H, m)

REFERENCE EXAMPLE 60-2

4-(2-Benzoimidazolylthio)piperidine 2 hydrochloride

By a similar manner to Reference Example 61-2, the titled compound was synthesized by using the compound obtained in Reference Example 60-1. Yield 89%.

$^1$H NMR (CD$_3$OD) δ 2.02 (2H, dto J=3.9, 11.0, 14.8 Hz), 2.42 (2H, m), 3.24 (2H, m), 3.50 (2H, ta, J=4.0, 13.5 Hz), 4.17 (1H, tt, J=4.0, 10.8 Hz), 7.5-7.65 (2H, m), 7.7-7.85 (2H, m)

REFERENCE EXAMPLE 61-1

1-tert-Butoxycarbonyl-4-(4-fluorophenylthio)piperidine

A mixture of the compound obtained in Reference Example 58-1 (4.19 g, 15.0 mmol), 4-fluorobenzenethiol (2.08 mL, 19.5 mmol), potassium carbonate (2.70 g, 19.5 mmol) and DMF (150 mL) was stirred at 70° C. for 7 hours. The reaction mixture was concentrated under reduced pressure, and to the concentrate was added ethyl acetate (80 mL). The organic layer was washed with water (20 mL), aqueous solution of 0.5N-sodium hydroxide (10 mL×3), saturated sodium chloride solution (10 mL), successively, dried over magnesium sulfate and concentrated under reduced pressure. The concentrate was subjected to column chromatography (silica gel 100 g, hexane/ethyl acetate=19/1 to 9/1), and the desired fraction was concentrated under reduced pressure to give the titled compound (4.04 g, 13.0 mmol, Yield 86%) as a colorless oily substance.

$^1$H NMR (CDCl$_3$) δ 1.44 (9H, s), 1.49 (2H, m), 1.88 (2H, m), 2.88 (2H, ddd, J=3.0, 10.6, 13.6 Hz), 3.09 (1H, tt, J=4.0, 10.3 Hz), 3.97 (2H, m), 7.01 (2H, m), 7.43 (2H, m)

REFERENCE EXAMPLE 61-2

4-(4-Fluorophenylthio)piperidine hydrochloride

The compound obtained in Reference Example 61-1 (1.87 g, 6.0 mmol) was dissolved in methanol (10 mL). To the solution was added 4N-hydrogen chloride in ethyl acetate (20 mL), and the mixture was stirred at room temperature for 18 hours. The reaction mixture was concentrated under reduced pressure, and to the concentrate was added ethyl acetate. The resulting precipitates were collected by filtration. The precipitates were washed with ethyl acetate, and dried under reduced pressure to give the titled compound (1.35 g, 5.5 mmol, Yield 91%) as white crystals.

$^1$H NMR (CD$_3$OD) δ 1.73 (2H, dtd, J=4.0, 10.6, 14.5 Hz), 2.16 (2H, m), 3.05 (2H, m), 3.25-3.5 (3H, m), 7.11 (2H, m), 7.53 (2H, m)

REFERENCE EXAMPLE 62-1

1-tert-Butoxycarbonyl-4-(4-fluorophenylsulfinyl)piperidine

To a solution of the compound obtained in Reference Example 61-1 (1.87 g, 16.0 mmol) in dichloromethane (30 mL) was added dropwise a solution of m-chloroperbenzoic acid (70%, 1.48 g, 6.0 mmol) in dichloromethane (30 mL) under ice cooling, and the mixture was stirred at the same temperature for 1 hour. The insolubles were filtered off, and the filtrate was washed with a saturated aqueous solution of sodium hydrogencarbonate (30 mL×3), dried over magnesium sulfate and concentrated under reduced pressure. The concentrate was subjected to column chromatography (silica gel 100 g, hexane/ethyl acetate=1/1 to 1/2), and the desired fraction was concentrated under reduced pressure to give the titled compound (1.39 g, 4.2 mmol, Yield 71%) as a colorless oily substance.

$^1$H NMR (CDCl$_3$) δ 1.4-1.85 (4H, m), 1.44 (9H, s), 2.55-2.8 (3H, m), 4.20 (2H, m), 7.24 (2H, m), 7.60 (2H, m)

REFERENCE EXAMPLE 62-2

4-(4-Fluorophenylsulfinyl)piperidine trifluoroacetate

To a solution of the compound obtained in Reference Example 62-1 (1.08 g, 3.3 mmol) in dichloromethane (21 mL) was added trifluoroacetic acid (7 mL) under ice cooling, and the mixture was stirred at the same temperature for 1 hour. The reaction mixture was concentrated under reduced pressure, and to the concentrate was added diisopropyl ether. The resulting precipitates were collected by filtration, washed with diisopropyl ether, and dried under reduced pressure to give the titled compound (1.11 g, 3.3 mmol, Yield 99%) as white crystals.

$^1$H NMR (CD$_3$OD) δ 1.65-2.05 (3H, m), 2.19 (1H, m), 2.9-3.2 (3H, m), 3.50 (2H, m), 7.40 (2H, m), 7.73 (2H, m)

REFERENCE EXAMPLE 63-1

1-tert-Butoxycarbonyl-4-(4-fluorophenylsulfonyl)piperidine

To a solution of the compound obtained in Reference Example 61-1 (1.87 g, 6.0 mmol) in dichloromethane (30 mL) was added m-chloroperbenzoic acid (70%, 3.25 g, 13 mmol) under ice cooling with stirring, and the mixture was stirred at the same temperature for 1 hour. The insolubles were filtered off, and the filtrate was washed with aqueous solution of 5% sodium thiosulfate (10 mL×2), a saturated aqueous solution of sodium hydrogencarbonate (10 mL×3), successively, dried over magnesium sulfate and concentrated under reduced pressure. To the concentrate was added diethyl ether, and the resulting precipitates were collected by filtration. The precipitates were washed with diethyl ether, and dried under reduced pressure to give the titled compound (1.85 g, 5.4 mmol, Yield 90%) as white crystals.

$^1$H NMR (CDCl$_3$) δ 1.43 (9H, s), 1.59 (2H, m), 1.98 (2H, br d, J=11.8 Hz), 2.66 (2H, br t, J=12.6 Hz), 3.03 (1H, tt, J=3.8, 12.0 Hz), 4.23 (2H, br d, J=13.2 Hz), 7.26 (2H, m), 7.89 (2H, m)

REFERENCE EXAMPLE 63-2

4-(4-Fluorophenylsulfonyl)piperidine hydrochloride 1-tert-Butoxycarbonyl-4-(4-fluorophenylsulfonyl)piperidine (1.76 g, 5.1 mmol) was suspended in methanol (10 mL). To the suspension was added 4N-hydrogen chloride in ethyl acetate (20 mL), and the mixture was stirred at room temperature for 18 hours. The reaction mixture was concentrated under reduced pressure, and to the concentrate was added ethyl acetate. The precipitates were collected by filtration, washed with ethyl acetate, and dried under reduced pressure to give the titled compound (1.39 g, 5.0 mmol, Yield 97%) as white crystals.

$^1$H NMR (CD$_3$OD) δ 1.90 (2H, m), 2.20 (2H, m), 3.01 (2H, dt, J=3.3, 12.9 Hz), 3.4-3.65 (3H, m), 7.43 (2H, m), 7.99 (2H, m)

REFERENCE EXAMPLE 64-1

1-tert-Butoxycarbonyl-4-(2-Naphthylthio)piperidine

By a similar manner to Reference Example 61-1, the titled compound was synthesized by using 2-naphthalenethiol. Yield 82%.

$^1$H NMR (CDCl$_3$) δ 1.44 (9H, s), 1.57 (2H, m), 1.96 (2H, m), 2.94 (2H, ddd, J=2.9, 10.6, 13.5 Hz), 3.33 (1H, tt, J=4.0, 10.3 Hz), 3.98 (2H, br d, J=12.8 Hz), 7.4-7.55 (3H, m), 7.7-7.95 (4H, m)

REFERENCE EXAMPLE 64-2

4-(2-Naphthylthio)piperidine hydrochloride

By a similar manner to Reference Example 61-2, the titled compound was synthesized by using the compound obtained in Reference Example 64-1. Yield 95%.

$^1$H NMR (CD$_3$OD) δ 1.80 (2H, dtd, J=4.0, 10.5, 14.7 Hz), 2.23 (2H, m), 3.09 (2H, ddd, J=3.1, 10.9, 13.2 Hz), 3.42 (2H, td, J=4.1, 13.2 Hz), 3.58 (1H, tt, J=3.9, 10.1 Hz), 7.45-7.6 (3H, m), 7.8-7.9 (3H, m), 7.99 (1H, d, J=1.8 Hz)

REFERENCE EXAMPLE 65-1

1-tert-Butoxycarbonyl-4-(4-fluorophenylsulfonyl)piperazine

To the solution of 1-tert-butoxycarbonylpiperazine (1.86 g, 10.0 mmol) and triethylamine (1.67 mL, 12.0 mmol) in dichloromethane (30 mL) was added 4-fluorobenzenesulfonyl chloride (2.34 g, 12.0 mmol), and the mixture was stirred at room temperature for 24 hours. To the mixture was added water(30 mL), and the mixture was concentrated under reduced pressure. To the concentrate was added ethyl acetate (70 mL). The organic layer was washed with water (30 mL), 1N-hydrochloric acid (10 mL×3), a saturated aqueous solution of sodium hydrogencarbonate (10 mL×3), saturated sodium chloride solution (10 mL), successively, dried over magnesium sulfate and concentrated under reduced pressure. To the concentrate was added diisopropyl ether, and the resulting precipitates were collected by filtration. The precipitates were washed with diisopropyl ether, and dried under reduced pressure to give the titled compound (1.94 g, 5.6 mmol, Yield 56%) as white crystals.

$^1$H NMR (CDCl$_3$) δ 1.41 (9H, s), 2.97 (4H, t, J=5.1 Hz), 3.52 (4H, t, J=5.1 Hz), 7.24 (2H, m), 7.77 (2H, m)

REFERENCE EXAMPLE 65-2

1-(4-Fluorophenylsulfonyl)piperazine hydrochloride

By a similar manner to Reference Example 61-2, the titled compound was synthesized by using the compound obtained in Reference Example 65-1. Yield 87%.
$^1$H NMR (CD$_3$OD) δ 3.15-3.45 (8H, m), 7.41 (2H, m), 7.91 (2H, m)

REFERENCE EXAMPLE 66

4-Chloro-N-[3-(4-benzyl-1-piperidinyl)propyl]-3-(trifluoromethyl)aniline 2 hydrochloride By a similar manner to Reference Example 1, the titled compound was synthesized by using 4-chloro-3-(trifluoromethyl)aniline. Yield 40%.
$^1$H NMR (CD$_3$OD) δ 1.35-1.65 (2H, m), 1.65-2.15 (5H, m), 2.61 (2H, d, J=6.2 Hz), 2.91 (2H, m), 3.18 (2H, m), 3.25 (2H, t, J=6.5 Hz), 3.56 (2H, br d, J=12.8 Hz), 6.85 (1H, dd, J=3.1, 8:6 Hz), 7.01 (1H, d, J=3.1 Hz), 7.1-7.4 (6H, m)

REFERENCE EXAMPLE 67

3-Chloro-N-{3-[4-(4-fluorobenzyl)-1-piperidinyl]propyl}-4-methoxyaniline 2 hydrochloride By a similar manner to Reference Example 1, the titled compound was synthesized by using 4-(4-fluorobenzyl)piperidine and 3-chloro-4-methoxyaniline. Yield 65%.
$^1$H NMR (CD$_3$OD) δ 1.4-2.0 (5H, m), 2.22 (2H, m), 2.60 (2H, d, J=6.6 Hz), 2.95 (2H, dt, J=2.2, 12.7 Hz), 3.21 (2H, m), 3.47 (2H, m), 3.58 (2H, br d, J=12.2 Hz), 3.93 (3H, s), 7.01 (2H, m), 7.20 (2H, m), 7.25 (1H, d, J=8.9 Hz), 7.49 (1H, dd, J=2.7, 8.9 Hz), 7.63 (1H, d, J=2.7 Hz)

REFERENCE EXAMPLE 68

3-Chloro-4-ethoxy-N-{3-[4-(4-fluorobenzyl)-1-piperidinyl]propyl}aniline 2 hydrochloride By a similar manner to Reference Example 1, the titled compound was synthesized by using 4-(4-fluorobenzyl)piperidine and 3-chloro-4-ethoxyaniline. Yield 64%.
$^1$H NMR (CD$_3$OD) δ 1.4-2.0 (5H, m), 1.44 (3H, t, J=6.9 Hz), 2.20 (2H, m), 2.61 (2H, d, J=6.6 Hz), 2.94 (2H, m), 3.20 (2H, m), 3.46 (2H, t, J=7.8 Hz), 3.57 (2H, br d, J=11.4 Hz), 4.16 (2H, q, J=6.9 Hz), 7.01 (2H, m), 7.20 (2H, m), 7.21 (1H, d, J=9.0 Hz), 7.42 (1H, dd, J=2.8, 9.0 Hz), 7.58 (1H, d, J=2.8 Hz)

REFERENCE EXAMPLE 69

3-Bromo-N-{3-[4-(4-fluorobenzyl)-1-piperidinyl]propyl}-4-(trifluoromethoxy)aniline 2 hydrochloride By a similar manner to Reference Example 1, the titled compound was synthesized by using 4-(4-fluorobenzyl)piperidine and 3-bromo-4-(trifluoromethoxy)aniline. Yield 56%.
$^1$H NMR (CD$_3$OD) δ 1.4-2.0 (5H, m), 2.12 (2H, m), 2.60 (2H, d, J=6.6 Hz), 2.94 (2H, m), 3.20 (2H, m), 3.34 (2H, t, J=7.0 Hz), 3.57 (2H, br d, J=12.4 Hz), 7.01 (2H, m), 7.07 (1H, dd, J=2.6, 9.2 Hz), 7.20 (2H, m), 7.3-7.4 (1H, m), 7.36 (1H, d, J=2.6 Hz)

REFERENCE EXAMPLE 70-1

2-Chloro-N-(3,4-dichlorophenyl)acetamide 3,4-Dichloroaniline (8.10 g, 50.0 mmol) was dissolved in THF (50 mL). To the solution was added anhydrous chloroacetic acid (9.40 g, 55.0 mmol), and the mixture was stirred at room temperature for 3 hours. The reaction mixture was concentrated under reduced pressure, and to the concentrate was added ethyl acetate (100 mL). The organic layer was washed with a saturated aqueous solution of sodium hydrogencarbonate (50 mL, 20 mL×2), saturated sodium chloride solution (20 mL), successively, dried over magnesium sulfate and concentrated under reduced pressure. To the concentrate was added diisopropyl ether (30 mL), and the resulting precipitates were collected by filtration. The precipitates were washed with diisopropyl ether (10 mL×3), and dried under reduced pressure to give the titled compound (8.08 g) as white crystals. The filtrate was concentrated under reduced pressure. To the concentrate was added diisopropyl ether/hexane (1/1) mixed solvent (30 mL), and the precipitates was collected by filtration. The precipitates were washed with diisopropyl ether/hexane (1/1). mixed solvent (10 mL×3), and dried under reduced pressure to-give the titled compound (3.01 g) as white crystals. Yield (11.09 g, 93%, 46.5 mmol).
$^1$H NMR (CDCl$_3$) δ 4.20 (2H, s), 7.38 (1H, dd, J=1.9, 8.8 Hz), 7.43 (1H, dd, J=0.8, 8.8 Hz), 7.80 (1H, dd, J=0.8, 1.9 Hz), 8.22 (1H, br s)

REFERENCE EXAMPLE 70-2

2-[4-(4-Fluorobenzyl)-1-piperidinyl]-N-(3,4-dichlorophenyl)acetamide

To a solution of 4-(4-fluorobenzyl)piperidine (4.25 g, 22.0 mmol) in DMF (50 mL) were added 2-chloro-N-(3,4-dichlorophenyl)acetamide (Reference Example 70-1, 4.77 g, 20.0 mmol) and potassium carbonate (3.04 g, 22.0 mmol), successively, and the mixture was stirred at room temperature for 12 hours. The reaction mixture was concentrated under reduced pressure, and to the concentrate was added ethyl acetate (70 mL). The organic layer was washed with water (20 mL, 10 mL×2), saturated sodium chloride solution (10 mL), successively, dried over magnesium sulfate and concentrated under reduced pressure. To the concentrate was added a mixed solvent of diisopropyl ether/diethyl ether (2/1)(30 mL), and the resulting precipitates were collected by filtration. The precipitates were washed with diisopropyl ether (15 mL×4), and dried under reduced pressure to give the titled compound (5.90 g) as white crystals. The filtrate was concentrated. To the concentrate was added a mixed solvent of diisopropyl ether/diethyl ether (2/1)(15 mL), and the resulting precipitates were collected by filtration. The precipitates were washed with diisopropyl ether (5 mL×4), and dried under reduced pressure to give the titled compound (1.20 g) as white crystals. Yield: 7.10 g, 90%, 7.10 g, 18.0 mmol.
$^1$H NMR (CDCl$_3$) δ 1.2-1.8 (5H, m), 2.21 (2H, dt, J=2.1, 11.6 Hz), 2.55 (2H, d, J=7.0 Hz), 2.86 (2H, br d, J=11.8 Hz), 3.08 (2H, s), 6.97 (2H, m), 7.10 (2H, m), 7.37 (1H, d, J=8.5 Hz), 7.45 (1H, dd, J=2.5, 8.5 Hz), 7.77 (1H, d, J=2.5 Hz), 9.26 (1H, br s)

REFERENCE EXAMPLE 70-3

3,4-Dichloro-N-{2-[4-(4-fluorobenzyl)-1-piperidinyl]ethyl}aniline 2 hydrochloride To a solution of 2-[4-(4-fluorobenzyl)-1-piperidinyl]-N-(3,4-dichlorophenyl)acetamide (Reference Example 70-2, 3.95 g, 10.0 mmol) in THF (30 mL) was added dropwise borane dimethyl sulfide (3.0 mL) at room temperature with stirring. The mixture was stirred for 3 hours under reflux. To the mixture was added dropwise methanol (10 mL) at room temperature, and the mixture was stirred at the same temperature for 18 hours. To the mixture was added a solution of 1N-hydrogen chloride in diethyl ether (30 mL), and the mixture was concentrated under reduced pressure. To the mixture was added methanol (30 mL), and the mixture was concentrated under reduced pressure. To the concentrate was added ethyl acetate and resulting precipitates were collected by filtration. The precipitates were washed with ethyl acetate, and dried under reduced pressure to give the titled compound (4.07 g, 9.0 mmol, 90%) as white crystals.

$^1$H NMR (CD$_3$OD) δ 1.4-2.0 (5H, m), 2.60 (2H, d, J=6.2 Hz), 2.98 (2H, m), 3.28 (2H, t, J=6.4 Hz), 3.53 (2H, t, J=6.4 Hz), 3.61 (2H, br d, J=12.4 Hz), 6.64 (1H, dd, J=2.6, 8.8 Hz), 6.85 (1H, d, J=2.8 Hz), 7.01 (2H, m), 7.20 (2H, m), 7.24 (1H, d, J=8.8 Hz)

REFERENCE EXAMPLE 71-1

3,4-Dichloro-N-(4-chlorobutyl)aniline hydrochloride

By a similar manner to Reference Examples 56-1 and 56-2, the titled compound was synthesized by using 1-bromo-4-chlorobutane.

$^1$H NMR (CD$_3$OD) δ 1.75-2.05 (4H, m), 3.43 (2H, m), 3.64 (2H, m), 7.44 (1H, dd, J=2.8, 8.8 Hz), 7.72 (1H, d, J=2.8 Hz), 7.72 (1H; d, J=8.8 Hz)

REFERENCE EXAMPLE 71-2

1-Acetyl-N-(4-chlorobutyl)-N-(3,4-dichlorophenyl)-4-piperidinecarboxamide

By a similar manner to Reference Example 56-3, the titled compound was synthesized by using the compound obtained in Reference Example 71-1.

$^1$H NMR (CDCl$_3$) δ 1.45-1.9 (8H, m), 2.06 (3H, s), 2.2-2.5 (2H, m), 2.87 (1H, m), 3.55 (2H, t, J=6.0 Hz), 3.68 (2H, t, J=7.0 Hz), 3.78 (1H, br d, J=12.8 Hz), 4.54 (1H, br d, J=12.8 Hz), 7.05 (1H, dd, J=2.6, 8.4 Hz), 7.31 (1H, d, J=2.6 Hz), 7.55 (1H, d, J=8.4 Hz)

REFERENCE EXAMPLE 72-1 tert-Butyl 4-[4-(1H-tetrazol-1-yl)anilino]-1-piperidinecarboxylate

To a solution of 4-(1H-tetrazol-1-yl)aniline (2 g, 12.4 mmol) and 1-tert-butoxycarbonyl-4-piperidone (3.71 g, 18.6 mmol) in THF (15 ml) were added acetic acid (1.42 ml, 24.8 mmol) and sodium triacetoxyborohydride (4 g, 18.6 mmol), successively, under ice cooling, and the mixture was stirred for 20 hours. To the mixture was added sodium triacetoxyborohydride (4 g, 18.6 mmol), and the mixture was stirred at room temperature for 20 hours. To the mixture was added saturated aqueous solution of sodium hydrogencarbonate (100 ml), and the mixture was stirred at room temperature for 1 hour. The mixture was extracted with ethyl acetate (100 ml), and the organic layer was washed with saturated sodium chloride solution (50 ml), dried over anhydrous sodium sulfate and concentrated under reduced pressure. To the concentrate was added diisopropyl ether (20 ml), and the resulting precipitates were collected by filtration to give the titled compound (4.2 g).

$^1$H NMR (CDCl$_3$) δ 1.22-1.67 (2H, m), 1.48 (9H, s), 2.00-2.14 (2H, m), 2.88-3.02 (2H, m), 3.40-3.60 (1H, m), 3.80-4.14 (3H, m), 6.70 (2H, d, J=9.2 Hz), 7.43 (2H, d, J=9.2 Hz), 8.83 (1H, s)

REFERENCE EXAMPLE 72-2

N-[4-(1H-Tetrazol-1-yl)phenyl]-4-piperidineamine 2 hydrochloride

To a solution of the compound obtained in Reference Example 72-1 (1 g, 2.9 mmol) in methanol (5 ml) was added a solution of 4N-hydrogen chloride in ethyl acetate (10 ml), and the mixture was stirred at room temperature for 2 hours. The reaction mixture was concentrated under reduced pressure, and to the concentrate was added diisopropyl ether (20 ml). The resulting precipitates were collected by filtration, washed with diisopropyl ether, and dried under reduced pressure to give the titled compound (1 g) as white powders.

$^1$H NMR (DMSO-d$_6$) δ 1.60-2.10 (4H, m), 2.80-3.08 (2H, m), 3.28-3.34 (1H, m), 3.57-3.64 (2H, m), 6.24 (2H, brs), 6.88 (2H, d, J=8.8 Hz), 7.59 (2H, d, J=8.8 Hz), 9.13 (2H, br s), 9.89 (1H, s)

REFERENCE EXAMPLE 73-1 tert-Butyl 4-(4-cyanoanilino)-1-piperidinecarboxylate

By a similar manner to Reference Example 72-1, the titled compound was synthesized by using 4-cyanoaniline. Yield 73%.

$^1$H NMR (CDCl$_3$) δ 1.27-1.47 (2H, m), 1.47 (9H, s), 2.00-2.05 (2H, m), 2.87-3.00 (2H, m), 3.40-3.49 (1H, m), 4.04-4.11 (3H, m), 6.55 (2H, d, J=8.8 Hz), 7.42 (2H, d, J=8.8 Hz)

REFERENCE EXAMPLE 73-2

4-(4-Piperidinylamino)benzonitrile 2 hydrochloride

By a similar manner to Reference Example 72-2, the titled compound was synthesized by using the compound obtained in Reference Example 73-1. Yield 100%.

$^1$H NMR (DMSO-d$_6$) δ 1.80-2.00 (2H, m), 2.14-2.19 (2H, m), 3.03-3.08 (2H, m), 3.31-3.50 (2H, m), 3.60-3.80 (1H, m), 6.47 (2H, br s), 6.72 (2H, d, J=8.8 Hz), 7.38 (2H, d, J=8.8 Hz), 9.40-9.60 (2H, m)

REFERENCE EXAMPLE 74-1 tert-Butyl 4-(1,4,7b-triazacyclopenta[cd]inden-2-ylsulfanyl)-1-piperidinecarboxylate To a solution of tert-butyl 4-[(methylsulfonyl)oxy]-1-piperidinecarboxylate (3.5 g, 12.5 mmol) in DMF (60 ml) were added 1,4,7b-triazacyclopenta[cd]inden-2-thiol (3.7 g, 21.3 mmol) and DBU (3.7 ml, 25 mmol), and the mixture was stirred at 80° C. for 11 hours. The reaction mixture was concentrated under reduced pressure, and to the concentrate was added water (200 ml) The mixture was extracted with a mixed solution of THF and ethyl acetate (3/2, 500 ml). The organic layer was washed with saturated aqueous solution of sodium chloride (200 ml), successively, and dried over anhydrous sodium sulfate, concentrated under reduced pressure. The concentrate was subjected to flash column chromatography (silica gel 30 g, ethyl acetate/hexane=1/2 to 1/0), and the desired fraction was concentrated under reduced pressure. To the concentrate was added disopropyl ether and the precipitates were collected by filtration to give the titled compound (2.5 g, 7 mmol) as yellowish powdery crystals.

$^1$H NMR (CDCl$_3$) δ 1.49 (9H, s), 1.75-1.94 (2H, m), 2.26-2.35 (2H, m), 3.15-3.29 (2H, m), 3.98-4.05 (2H, m), 4.25-4.40 (1H, m), 7.78 (1H, d, J=8.0 Hz), 7.93 (1H, d, J=8.0 Hz), 8.04 (1H, t, J=8.0 Hz), 8.49 (1H, s)

REFERENCE EXAMPLE 74-2

2-(4-Piperidinylsulfanyl)-1,4,7b-triazacyclopenta[cd]inden hydrochloride

By a similar manner to Reference Example 72-2, the titled compound was synthesized by using the compound obtained in Reference Example 74-1. Yield 100%.

$^1$H NMR (DMSO-d$_6$) δ 2.07-2.27 (2H, m), 2.45-2.55 (2H, m), 2.80-3.50 (4H, m), 4.42-4.53 (1H, m), 7.30 (1H, br s), 8.11 (1H, d, J=7.6 Hz), 8.22 (1H, d, J=7.6 Hz), 8.37 (1H, t, J=7.6 Hz), 9.30 (1H, s), 9.50 (1H, br s)

REFERENCE EXAMPLE 75-1 tert-Butyl 4-[(2,2,3,3,3-pentafluoropropoxy)anilino]-1-piperidinecarboxylate

By a similar manner to Reference Example 72-1, the titled compound was synthesized by using 4-(2,2,3,3,3-pentafluoropropoxy)aniline. Yield 56%.

$^1$H NMR (CDCl$_3$) δ 1.14-1.56 (2H, m), 1.46 (9H, s), 1.97-2.04 (2H, m), 2.84-2.97 (2H, m), 3.30-3.40 (2H, m), 4.01-4.26 (2H, m), 4.26-4.40 (2H, m), 6.56 (2H, d, J=8.8 Hz), 6.82 (2H, d, J=8.8 Hz)

REFERENCE EXAMPLE 75-2

N-[4-(2,2,3,3,3-Pentafluoropropoxy)phenyl]-4-piperidineamine 2 hydrochloride

By a similar manner to Reference Example 72-2, the titled compound was synthesized by using the compound obtained in Reference Example 75-1. Yield 100%.

$^1$H NMR (DMSO-d$_6$) δ 1.88-2.13 (4H, m), 2.81-3.00 (2H, m), 3.33-3.39 (2H, m), 3.57-3.74 (1H, m), 3.80 (2H, br s), 4.87 (2H, t, J=13.2 Hz), 7.22 (2H, d, J=8.6 Hz), 7.51 (2H, d, J=8.6 Hz), 8.93-8.98 (1H, m), 9.20-9.40 (1H, m)

REFERENCE EXAMPLE 76-1 tert-Butyl 4-[acetyl-4-(2,2,3,3,3-pentafluoropropoxy)anilino]-1-piperidinecarboxylate To a solution of the compound obtained in Reference Example 75-1 (1 g, 2.4 mmol) in THF (10 ml) was added triethylamine (1.5 ml, 10.5 mol) and acetyl bromide (0.63 ml, 8.4 mmol) under ice cooling, and the mixture was stirred for 2 hours under ice cooling. To the reaction mixture was added aqueous solution of 0.05N-hydrochloric acid (100 ml), and the mixture was extracted with ethyl acetate(100 ml). The organic layer was washed with saturated aqueous solution of sodium chloride (100 ml), successively, and dried over anhydrous sodium sulfate, concentrated under reduced pressure. The concentrate was subjected to flash column chromatography (silica gel 20 g, ethyl acetate/hexane=1/2 to 1/1), and the desired fraction was concentrated under reduced pressure. To the concentrate was added diisopropyl ether (10 ml) and the precipitates were collected by filtration to give the titled compound (339 mg, 0.85 mmol) as white powdery crystals.

$^1$H NMR (CDCl$_3$) δ 1.90-1.30 (2H, m), 1.39 (9H, s), 1.70-1.80 (2H, m), 1.75 (3H, s), 2.73-2.86 (2H, m), 4.08-4.15 (2H, m), 4.45 (2H, t, J=12.0 Hz), 4.69-4.81 (1H, m), 6.97 (2H, d, J=9.2 Hz), 7.04 (2H, d, J=9.2 Hz)

REFERENCE EXAMPLE 76-2

N-[4-(2,2,3,3,3-Pentafluoropropoxy)phenyl]-N-(4-piperidinyl)acetamide hydrochloride By a similar manner to Reference Example 72-2, the titled compound was synthesized by using the compound obtained in Reference Example 76-1. Yield 71%.

$^1$H NMR (DMSO-d$_6$) δ 1.35-1.52 (2H, m), 1.64 (3H, s), 1.84-1.95 (2H, m), 2.92-3.05 (2H, m), 3.21-3.27 (2H, m), 4.62-4.74 (1H, m), 4.88 (2H, t, J=Hz), 7.16 (2H, d, J=Hz), 7.23 (2H, d, J=Hz), 8.63 (2H, br s)

REFERENCE EXAMPLE 77-1 tert-Butyl 4-(4-nitroanilino)-1-piperidinecarboxylate.

By a similar manner to Reference Example 72-1, the titled compound was synthesized by using 4-nitroaniline. Yield 28%.

$^1$H NMR (CDCl$_3$) δ 1.31-1.47 (2H, m), 1.47 (9H, s), 2.03-2.07 (2H, m), 2.89-3.00 (2H, m), 3.47-3.61 (1H, m), 4.07-4.13 (2H, m), 4.38–4.14 (1H, m), 6.53,(2H, d, J=9.0 Hz), 8.09 (2H, d, J=9.0 Hz)

REFERENCE EXAMPLE 77-2

N-(4-Nitrophenyl)-4-piperidineamine 2 hydrochloride

By a similar manner to Reference Example 72-2, the titled compound was synthesized by using the compound obtained in Reference Example 77-1. Yield 100%.

$^1$H NMR (DMSO-d$_6$-CDCl$_3$) δ 1.85-2.02 (2H, m), 2.15-2.20 (2H, m), 3.00-3.20 (2H, m), 3.93–3.50 (2H, m), 3.70-3.79 (1H, m), 5.96 (2H, br s), 6.69 (2H, d, J=9.2 Hz), 7.99 (2H, d, J=9.2 Hz), 9.20-9.60 (2H, m)

REFERENCE EXAMPLE 78-1 tert-Butyl 4-[acetyl-4-(1H-tetrazol-1-yl)anilino]-1-piperidinecarboxylate

To a solution of the compound obtained in Reference Example 72-1 (1 g, 2.9 mmol) in DMF (10 ml) were added pyridine (0.48 ml, 7.255 mmol) and acetyl chroride (0.25 ml, 3.5 mmol), successively, under ice cooling and the mixture was stirred at room temperature for 24 hours. The reaction mixture was concentrated under reduced pressure, and to the concentrate was added aqueous solution of 0.05N-hydrochloric acid (20 ml). The mixture was extracted with ethyl acetate (20 ml). The organic layer was washed with saturated aqueous solution of sodium chloride (20 ml) and dried over anhydrous sodium sulfate, concentrated under reduced pressure. The concentrate was subjected to column chromatography (silica gel 15 g, ethyl acetate/hexane=1/1 to 1/0), and the desired fraction was concentrated under reduced pressure. To the concentrate was added diisopropyl ether (10 ml) and the precipitates were collected by filtration to give the titled compound (589 mg, 1.52 mmol) as white powdery crystals.
$^1$H NMR (CDCl$_3$) δ 1.07-1.32 (2H, m), 1.39 (9H, s), 1.80-1.90 (2H, m), 1.81 (3H, s), 2.75-2.88 (2H, m), 4.10-4.18 (2H, m), 4.76-4.88 (1H, m), 7.35 (2H, d, J=8.81 Hz), 7.84 (2H, d, J=8.8 Hz), 9.08 (1H, s)

REFERENCE EXAMPLE 78-2

N-(4-Piperidinyl)-N-[4-(1H-tetrazol-1-yl)phenyl]acetamide hydrochloride

By a similar manner to Reference Example 72-2, the titled compound was synthesized by using the compound obtained in Reference Example 78-1. Yield 96%.
$^1$H NMR (DMSO-d$_6$) δ 1.02-1.60 (2H, m), 1.71 (3H, s), 1.91-1.98 (2H, m), 2.92-3.10 (2H, m), 3.17-3.29 (2H, m), 4.60-4.90 (1H, m), 7.58 (2H, d, J=8.4 Hz), 8.07 (2H, d, J=8.4 Hz), 8.50-8.60 (1H, m), 8.92-9.20 (1H, m), 10.22 (1H, s)

REFERENCE EXAMPLE 79-1 tert-Butyl 4-[(6-ethoxy-1,3-benzothiazol-2-yl)sulfanyl]-1-piperidinecarboxylate

To the mixture of tert-butyl 4-hydroxy-1-piperidinecarboxylate (2 g, 10 mmol), 6-ethoxy-1,3-benzothiazol-2-thiol (2.54 g, 12 mmol), triphenylphosphine (3.9 g, 15 mmol) and THF (60 ml) was dropwise added a solution of 40% diethyl azodicarboxylate in toluene (5.23 g, 15 mmol) under ice cooling over a period of 10minutes. The mixture was stirred at room tmperature for 20 hours. The reaction mixture was concentrated under reduced pressure, and the concentrate was dissolved in ethyl acetate (50 ml). The organic layer was washed with aqueous solution of 0.5N-sodium hydroxide (30 ml),and saturated aqueous solution of sodium chloride (30 ml), successively, dried-over anhydrous sodium sulfate, and concentrated under reduced pressure. The concentrate was subjected to flash column chromatography (silica gel 50 g, ethyl acetate/hexane=1/20 to 1/5), and the desired fraction was concentrated under reduced pressure. To the concentrate was added hexane (10 ml) and the precipitates were collected by filtration to give the titled compound (2.6 g, 6.5 mmol) as white powdery crystals.
$^1$H NMR (CDCl$_3$) δ 1.44 (3H, t, J=7.0 Hz), 1.46 (9H, s), 1.62-1.81 (2H, m), 2.12-2.20 (2H, m), 3.02-3.16 (2H, m), 3.92-4.02 (3H, m), 4.07 (2H, q, J=7.0 Hz), 7.01 (1H, dd, J=8.8, 2.4 Hz), 7.22 (1H, d, J=2.4 Hz), 7.76 (1H, d, J=8.8 Hz)

REFERENCE EXAMPLE 79-2

6-Ethoxy-2-(4-piperidinylsulfanyl)-1,3-benzothiazole hydrochloride

By a similar manner to Reference Example 72-2, the titled compound was synthesized by using the compound obtained in Reference Example 79-1. Yield 100%.
$^1$H NMR (DMSO-d$_6$) δ 1.37 (3H, t, J=7.0 Hz), 1.87-2.07 (2H, m), 2.26-2.35 (2H, m), 3.00-3.33 (4H, m), 4.03-4.13 (1H, m), 4.08 (2H, q, J=7.0 Hz), 7.05 (1H, dd, J=8.8, 2.2 Hz), 7.57 (1H, d, J=2.2 Hz), 7.76 (1H, d, J=8.8 Hz), 9.23 (2H, br s)

REFERENCE EXAMPLE 80-1 tert-Butyl 4-[(5-chloro-1,3-benzothiazol-2-yl)sulfanyl]-1-piperidinecarboxylate

By a similar manner to Reference Example 79-1, the titled compound was synthesized by using 5-chloro-1,3-benzothiazol-2-thiol. Yield 40%.
$^1$H NMR (CDCl$_3$) δ 1.47 (9H, s), 1.64-1.81 (2H, m), 2.16-2.21 (2H, m), 3.07-3.17 (2H, m), 3.93-4.16 (3H, m), 7.28 (1H, dd, J=8.8, 2.0 Hz), 7.66 (1H, d, J=8.8 Hz), 7.86 (1H, d, J=2.0 Hz)

REFERENCE EXAMPLE 80-2

5-Chloro-2-(4-piperidinylsulfanyl)-1,3-benzothiazole hydrochloride

By a similar manner to Reference Example 72-2, the titled compound was synthesized by using the compound obtained in Reference Example 80-1. Yield 100%.
$^1$H NMR (DMSO-d$_6$) δ 1.89-2.09 (2H, m), 2.29-2.38 (2H, m), 3.00-3.34 (4H, m), 4.11-4.25 (1H, m), 7.44 (1H, dd, J=8.4, 2.2 Hz), 7.93 (1H, d, J=2.2 Hz), 8.07 (1H, d, J=8.4 Hz), 9.23 (2H, br s)

REFERENCE EXAMPLE 81

Methyl 4-(4-piperidinylmethyl)benzoate hydrochloride

By a similar manner to Reference Example 3-1, the titled compound was synthesized by using methyl 4-(bromomethyl)benzoate.
$^1$H NMR (DMSO-d$_6$) δ 1.28-1.84 (5H, m), 2.62 (2H, d, J=7.0 Hz), 2.70-2.83 (2H, m), 3.18-3.24 (2H, m), 3.84 (3H, s), 7.34 (2H, d, J=8.2 Hz), 7.90 (2H, d, J=8.2 Hz), 8.95 (2H, br s)

REFERENCE EXAMPLE 82-1 tert-Butyl 4-(1,3-benzothiazol-2-ylsulfonyl)-1-piperidinecarboxylate

To a solution of the compound obtained in Reference Example 39 (340 mg, 1 mmol) in dichloromethane (10 ml) was added m-chloroperbenzoic acid (445 mg, 2.6 mmol) under ice cooling, and the mixture was stirred at room temperature for 3 hours. To the reaction mixture was added saturated sodium hydrogencarbonate (20 ml), and the mixture was extracted with ethyl acetate (30 ml×2). The organic layer was washed with saturated aqueous solution of sodium chloride (40 ml), dried over anhydrous sodium sulfate and concentrated under reduced pressure. The concentrate was subjected to flash column chromatography (silica gel 20 g, ethyl acetate/hexane=1/10 to 1/5), and the desired fraction was concentrated under reduced pressure to give the titled compound (294 mg, 0.77 mmol) as white crystals.
$^1$H NMR (CDCl$_3$) δ 1.44 (9H, s), 1.75-1.96 (2H, m), 2.10-2.16 (2H, m), 2.70-2.82 (2H, m), 3.55-3.71 (1H, m), 4.25-4.31 (2H, m), 7.58-7.71 (2H, m), 7.99-8.06 (1H, m), 8.02-8.27 (1H, m)

REFERENCE EXAMPLE 82-2

2-(4-Piperidinylsulfonyl)-1,3-benzothiazole hydrochloride

By a similar manner to Reference Example 72-2, the titled compound was synthesized by using the compound obtained in Reference Example 82-1. Yield 85%.

$^1$H NMR (DMSO-d$_6$) δ 1.87-2.08 (2H, m), 2.19-2.25 (2H, m), 2.88-2.99 (2H, m), 3.35-3.41 (2H, m), 4.03-4.15 (1H, m), 7.68-7.81 (2H, m), 8.25-8.43 (2H, m), 9.02 (2H, br s)

REFERENCE EXAMPLE 83-1

4-[(1-Acetyl-4-piperidinyl)methyl]benzenesulfonamide

To chlorosulfonic acid (3.1 mL) was added dropwise a solution of 1-acetyl-4-benzylpiperidine (2.0 g) in chloroform (5 mL) under ice cooling, and the mixture was stirred at the same temperature for 1 hour and at room temperature for 30 minutes. The reaction mixture was poured into ice-water, and the mixture was extracted with chloroform. The organic layer was dried over magnesium sulfate and concentrated under reduced pressure to give chlorosulfone derivatives (1.87 g). A solution of the above chlorosulfone derivatives (1.04 g), 10% ammonia water (12 mL) and triethylamine (0.92 mL) in THF (20 mL) was heated for 1.5 hour under reflux. The organic solvent was distilled off, and the residue was extracted with ethyl acetate. The organic layer was washed with saturated sodium chloride solution, dried over magnesium sulfate and concentrated under reduced pressure The concentrate was subjected to silica gel column, chromatography (ethyl acetate/methanol=8/1), and the desired fraction was concentrated under reduced pressure to give the titled compound (0.755 g, 2.55 mmol, Yield 78%) as a colorless oily substance.

$^1$H NMR (CDCl$_3$) δ 1.03-1.32 (2H, m), 1.58-1.90 (3H, m), 2.08 (3H, s), 2.48 (1H, dt, J=2.8, 13.2 Hz), 2.98 (1H, dt, J=2.2, 12.4 Hz), 3.70-3.87 (1H, m), 4.53-4.67 (1H, m), 4.90-5.05 (2H, m), 7.29 (2H, d, J=8.4 Hz), 7.86 (2H, d, J=8.4 Hz)

REFERENCE EXAMPLE 83-2

4-(4-Piperidinylmethyl)benzenesulfonamide hydrochloride

To the compound obtained in Reference Example 83-1 (755 mg) was added concentrated hydrochloric acid (10 mL), and the mixture was heated under reflux for 4.5 hours. The organic solvent was distilled off to give the desired product (708 mg, 2.43 mmol, Yield 95%).

$^1$H NMR (CDCl$_3$) δ 1.32-1.58 (2H, m), 1.78-2.05 (3H, m), 2.71 (2H, d, J=6.8 Hz), 2.83-3.02 (2H, m), 3.28-3.43 (2H, m), 7.38 (2H, d, H=8.4 Hz), 7.83 (2H, d, J=8.4 Hz)

REFERENCE EXAMPLE 84-1

N-Methyl-4-[(1-acetyl-4-piperidinyl)methyl]benzenesulfonamide

By a similar manner to Reference Example 83-1, the titled compound was synthesized by using aqueous solution of 40% methylamine. Yield 46%.

$^1$H NMR (CDCl$_3$) δ 1.05-1.30 (2H, m), 1.60-1.93 (3H, m), 2.08 (3H, s), 2.40-2.60 (2H, m), 2.63 (2H, dd, J=2.2, 7.0 Hz), 2.72 (6H, s), 2.90-3.07 (1H, m), 3.72-3.88 (1H, m), 4.56-4.70 (1H, m), 7.31 (2H, d, J=8.4 Hz), 7.71 (2H, d, J=8.4 Hz)

REFERENCE EXAMPLE 84-2

N-Methyl-4-(4-piperidinylmethyl)benzenesulfonamide hydrochloride

By a similar manner to Reference Example 83-2, the titled compound was synthesized by using the compound obtained in Reference Example 84-1. Yield 90%.

$^1$H NMR (CDCl$_3$) δ 1.30-1.60 (2H, m), 1.78-2.05 (3H, m), 2.71 (2H, d, J=7.0 Hz), 2.83-3.04 (2H, m), 3.30-3.45 (2H, m), 7.42 (2H, d, J=8.4 Hz), 7.77 (2H, d, J=8.4 Hz)

REFERENCE EXAMPLE 85-1

N,N-Dimethyl-4-[(1-acetyl-4-piperidinyl)methyl]benzenesulfonamide

By a similar manner to Reference Example 83-1, the titled compound was synthesized by using aqueous solution of 50% dimethylamine. Yield 56%.

$^1$H NMR (CDCl$_3$) δ 1.05-1.30 (2H, m), 1.60-1.91 (3H, m), 2.08 (3H, s), 2.49 (1H, dt, J=2.6, 12.8 Hz), 2.63 (1H, d, J=8.4 Hz), 2.67 (3H, d, J=6.2 Hz), 2.99 (1H, dt, J=2.6, 12.8 Hz), 3.73-3.86 (1H, m), 4.53-4.80 (2H, m), 7.29 (2H, d, J=8.4 Hz), 7.79 (2H, d, J=8.4 Hz)

REFERENCE EXAMPLE 85-2

N,N-Dimethyl-4-(4-piperidinylmethyl)benzenesulfonamide hydrochloride

By a similar manner to Reference Example 83-2, the titled compound was synthesized by using the compound obtained in Reference Example 85-1. Yield 95%.

$^1$H NMR (CDCl$_3$) δ 1.30-1.55 (2H, m), 1.78-2.02 (3H, m), 2.69 (2H, d, J=7.0 Hz), 2.73 (6H, s), 2.81-3.03 (2H, m), 3.33-3.48 (2H, m), 7.38 (2H, d, J=8.4 Hz), 7.74 (2H, d, J=8.4 Hz)

REFERENCE EXAMPLE 86-1

1-Acetyl-4-[4-(methylsulfonyl)benzyl]piperidine

N-acetyl-4-benzylpiperidine (508 mg) was added to chlorosulfonic acid (1.66 mL) under ice cooling, and the mixture was stirred at the same temperature for 20 minutes and: at room temperature for 20 minutes. The reaction mixture was poured into ice, and the mixture was stirred for 10 minutes and extracted with dichloromethane. The extract was dried over anhydrous magnesium sulfate and concentrated under reduced pressure to give chlorosulfone derivatives. To a mixture of sodium sulfite (627 mg) and sodium hydrogencarbonate (1.25 g) was added water (5 mL), and the temperature of the mixture was adjusted to 75° C. To the mixture was added dropwise the above chlorosulfone derivatives, and the mixture was heated for 1 hour. To the mixture were added chloroacetic acid (706 mg) and an aqueous solution of 50% sodium hydroxide (0.6 mL), and the mixture was heated for 24 hours under reflux. The mixture was cooled, to room temperature, and adjusted to pH 5 by adding 1N-hydrochloric acid and extracted with ethyl acetate. The extract was washed with saturated sodium chloride solution, dried over anhydrous magnesium sulfate and concentrated under reduced pressure. The concentrate was subjected to silica gel column chromatography (ethyl acetate/methanol=5/1), and the desired fraction was concentrated under reduced pressure to give the titled compound (347 mg, 1.18 mmol, Yield 50%) as a colorless oily substance.

$^1$H NMR (CDCl$_3$) δ 1.05-1.30 (2H, m), 1.60-1.94 (3H, m), 2.08 (3H, s), 2.49 (1H, dt, J=2.6, 13.2 Hz), 2.65 (2H, d, J=7.2 Hz), 2.99 (1H, dt, J=2.6, 13.2 Hz), 3.06 (3H, s), 3.73-3.87 (1H, m), 4.55-4.69 (1H, m), 7.34 (2H, d, J=8.2 Hz), 7.87 (2H, d, J=8.2 Hz)

REFERENCE EXAMPLE 86-2

4-[4-(Methylsulfonyl)benzyl]piperidine hydrochloride

By a similar manner to Reference Example 83-2, the titled compound was synthesized by using the compound obtained in Reference Example 86-1. Yield 96%., $^1$H NMR (CD$_3$OD) δ 1.32-1.58 (2H, m), 1.79-2.10 (3H, m), 2.73 (2H, d, J=7.0 Hz), 2.84-3.04 (2H, m), 3.10 (3H, s), 3.29-3.44 (2H, m), 7.48 (2H, d, J=8.4 Hz), 7.89 (2H, d, J=8.4 Hz)

REFERENCE EXAMPLE 87-1

4-(4-Methoxybenzyl)piperidine hydrochloride

By a similar manner to Reference Example 3-1, the titled compound was synthesized by using 4-methoxybenzyl chloride.

$^1$H NMR (CD$_3$OD) δ 128-1.55 (2H, m), 1.73-1.95 (3H, m), 2.55 (2H, d, J=6.8 Hz). 2.92 (2H, dt, J=3.0, 13.0 Hz), 3.29-3.43 (2H, m), 3.75 (3H, s), 6.84 (2H, d, J=8.4 Hz), 7.09 (2H, d, J=8.4 Hz)

REFERENCE EXAMPLE 87-2

1-Acetyl-4-(4-methoxybenzyl)piperidine

To a suspension of the compound obtained in Reference Example 87-1 (2.13 g) in THF (50 mL) was added triethylamine (4.6 mL), and the mixture was stirred for 30 minutes. To the reaction mixture was added dropwise acetyl chroride (1.05 mL) under ice cooling, and the mixture was stirred for 25 hours while the temperature of the mixture was gradually elevated to room temperature. The reaction mixture was partitioned between water and ethyl acetate, and the organic layer was washed with saturated sodium chloride solution, dried over anhydrous magnesium sulfate and concentrated under reduced pressure. The concentrate was subjected to silica gel column chromatography (ethyl acetate), and the desired fraction was concentrated under reduced pressure to give the titled compound (2.08 g, 8.42 mmol:, Yield 96%) as a colorless oily substance.

$^1$H NMR (CDCl$_3$) δ 1.02-1.25 (2H, m), 1.60-1.78 (3H, m), 2.07 (3H, s), 2.39-2.55 (3H, m), 2.96 (1H, dt, J=2.2, 13.2 Hz), 3.79 (3H, s), 3.70-3.85 (1H, m), 4.52-4.67 (1H, m), 6.83 (2H, d, J=8.4 Hz), 7.05 (2H, d, J=8.4 Hz)

REFERENCE EXAMPLE 87-3

5-[(1-Acetyl-4-piperidinyl)methyl]-2-methoxybenzenesulfonamide

By a similar manner to Reference Example 83-1, the titled compound was synthesized by using the compound obtained in Reference Example 87-2. Yield 24%.

$^1$H NMR (CDCl$_3$) δ 1.00-1.25 (2H, m), 1.60-1.83 (3H, m), 2.07 (3H, s), 2.54 (2H, d, J=7.0 Hz), 2.38-2.56 (1H, m), 2.87-3.05 (1H, m), 3.72-3.85 (1H, m), 4.01 (3H, s), 4.52-4.68 (1H, m), 5.08 (2H, br s), 6.98 (1H, d, J=6.4 Hz), 7.29 (1H, dd, J=2.2, 6.4 Hz), 7.71 (1H, d, J=2.2 Hz)

REFERENCE EXAMPLE 87-4

2-Methoxy-5-(4-piperidinylmethyl)benzenesulfonamide hydrochloride

By a similar manner to Reference Example 83-2, the titled compound was synthesized by using the compound obtained in Reference Example 87-3. Yield 100%.

$^1$H NMR (CD$_3$OD) δ 1.30-1.55 (2H, m), 1.78-1.95 (3H, m), 2.62 (2H, d, J=6.6 Hz), 2.85-3.02 (2H, m), 3.28-3.44 (2H, m), 3.96 (3H, s), 7.14 (1H, d, J=8.4 Hz), 7.41 (1H, dd, J=2.2, 8.4 Hz), 7.66 (1H, d, J=2.2 Hz)

REFERENCE EXAMPLE 88-1 tert-Butyl 4-[(4-nitrophenyl)sulfanyl]-1-piperidinecarboxylate

A suspension of the compound obtained in Reference Example 58-1 (4.45 g), 4-nitrothiophenol (2.97 g) and potassium carbonate (2.85 g) in DMF (150 mL) was stirred at 70° C. for 23 hours. The solvent was distilled off, and to the residue was added water. The mixture was extracted with ethyl acetate. The extract was washed with aqueous solution of 0.5N-sodium hydroxide two times and saturated sodium chloride solution, successively, dried over anhydrous magnesium sulfate and concentrated under reduced pressure. The concentrate was subjected to silica gel column chromatography (ethyl acetate/hexane=1/6), and the desired fraction was concentrated under reduced pressure to give the titled compound (2.20 g, 6.51 mmol, Yield 41%) as pale yellow solid substance.

$^1$H NMR (CDCl$_3$) δ 1.46 (9H, s), 1.51-1.72 (2H, m), 1.93-2.10 (2H, m), 3.50 (1H, tt, J=4.0, 10.0 Hz), 3.90-4.06 (2H, m), 7.31 (2H, d, J=9.2 Hz), 8.15 (2H, d, J=9.2 Hz)

REFERENCE EXAMPLE 88-2 tert-Butyl 4-[(4-aminophenyl)sulfanyl]-1-piperidinecarboxylate

To a suspension of the compound obtained in Reference Example 88-1 (2.2 g), hydrazine monohydrate (1.3 mL) and activated carbon (0.42 g) in THF (30 mL) was added iron chloride (III)(0.105 g), and the mixture was heated for 26 hours under reflux. The precipitates were filtered with Celite and washed with ethyl acetate. The filtrate was concentrated under reduced pressure. The concentrate was subjected to silica gel column chromatography (ethyl acetate/hexane=2/3), and the desired fraction was concentrated under reduced pressure to give the titled compound (1.99 g, 6.46 mmol, Yield 100%) as a colorless oily substance.

$^1$H NMR (CDCl$_3$) δ 1.32-1.57 (2H, m), 1.44 (9H, s), 1.78-1.93 (2H, m), 2.73-3.01 (3H, m), 3.70-3.85 (2H, m), 3.90-4.05 (2H, m), 6.62 (2H, d, J=8.8 Hz), 7.26 (2H, d, J=8.8 Hz)

REFERENCE EXAMPLE 88-3 tert-Butyl 4-({4-[(methylsulfonyl)amino]phenyl}sulfanyl)-1-piperidinecarboxylate To a solution of the compound obtained in Reference Example 88-2 (1.99 g) and triethylamine (1.36 mL) in THF (50 mL) was added dropwise methanesulfonyl chloride (0.65 mL) at 0° C., and the mixture was stirred for 50 minutes. The reaction mixture was partitioned between water and ethyl acetate. The organic layer was washed with saturated sodium chloride solution, dried over anhydrous magnesium sulfate and concentrated under reduced pressure. The concentrate was subjected to silica gel column chromatography (ethyl acetate/hexane=2/3), and the desired fraction was concentrated under reduced pressure to give the titled compound (0.514 g, 1.33 mmol, Yield 21%) as a colorless oily substance.

$^1$H NMR (CDCl$_3$) δ 1.40-1.62 (2H, m), 1.45 (9H, s), 1.83-1.98 (2H, m), 2.82-3.00 (2H, m), 3.03 (3H, s), 3.15 (1H, tt, J=4.0, 10.4 Hz), 3.90-4.05 (2H, m), 7.20 (2H, d, J=8.8 Hz), 7.29 (1H, brs), 7.41 (2H, d, J=8.8 Hz)

REFERENCE EXAMPLE 88-4 tert-Butyl 4-({4-[(methylsulfonyl)amino]phenyl}sulfonyl)-1-piperidinecarboxylate By a similar manner to Reference Example 63-1, the titled compound was synthesized by using the compound obtained in Reference Example 88-3. Yield 83%.

$^1$H NMR (CDCl$_3$) δ 1.44 (9H, s), 1.45-1.70 (2H, m), 1.90-2.05 (2H, m), 2.55-2.75 (2H, m), 2.92-3.10 (1H, m), 3.15 (3H, s), 4.15-4.30 (2H, m), 7.00-7.10 (1H, m), 7.35 (2H, d, J=8.8 Hz), 7.84 (2H, d, J=8.8 Hz)

REFERENCE EXAMPLE 88-5

N-[4-(4-Piperidinylsulfonyl)phenyl]methanesulfonamide hydrochloride

By a similar manner to Reference Example 63-2, the titled compound was synthesized by using the compound obtained in Reference Example 88-4. Yield 93%.

$^1$H NMR (CD$_3$OD) δ 1.75-2.03 (2H, m), 2.10-2.30 (2H, m), 2.90-3.15 (2H, m), 3.11 (3H, s), 3.40-3.60 (3H, m), 7.47 (2H, d, J=8.4 Hz), 7.86 (2H, d, J=8.4 Hz)

REFERENCE EXAMPLE 89-1 tert-Butyl 4-[(4-hydroxyphenyl)sulfanyl]-1-piperidinecarboxylate

By a similar manner to Reference Example 88-1, the titled compound was synthesized by using 4-hydroxythiophenol. Yield 56%.

$^1$H NMR (CDCl$_3$) δ 1.41-1.53 (2H, m), 1.44 (9H, s), 1.79-1.95 (2H, m), 2.77-3.08 (3H, m), 3.87-4.05 (2H, m), 5.34 (1H, s), 6.78 (2H, d, J=8.4 Hz), 7.34 (2H, d, J=8.4 Hz)

REFERENCE EXAMPLE 89-2 tert-Butyl 4-[(4-hydroxyphenyl)sulfonyl]-1-piperidinecarboxylate

By a similar manner to Reference Example 63-1, the titled compound was synthesized by using the compound obtained in Reference Example 89-1. Yield 87%.

$^1$H NMR (CDCl$_3$) δ 1.45 (9H, s), 1.45-1.63 (2H, m), 1.90-2.10 (2H, m), 2.53-2.77 (2H, m), 3.01 (1H, t, J=3.6, 12.0 Hz), 4.15-4.30 (2H, m), 6.96 (2H, d, J=8.8 Hz), 7.11 (1H, s), 7.70 (2H, d, J=8.8 Hz):

REFERENCE EXAMPLE 89-3 tert-Butyl 4-{[4-(2-butoxyethoxy)phenyl]sulfonyl}-1-piperidinecarboxylate

A suspension of the compound obtained in Reference Example 89-2 (0.99 g), butyl chloroethyl ether (0.50 mL), potassium iodide (0.58 g) and potassium carbonate (0.60 g) in DMF (20 mL) was stirred at 80° C. for 5 hours. The solvent was distilled off, and to the residue was added water. The mixture was extracted with ethyl acetate. The extract was washed with saturated sodium chloride solution, dried over anhydrous magnesium sulfate, and evaporated under reduced pressure. The residue was subjected to silica gel column chromatography (ethyl acetate/hexane=2/3), and the desired fraction was concentrated under reduced pressure to give the titled compound (0.87 g, 1.96 mmol, Yield 68%) as colorless solid substance.

$^1$H NMR (CDCl$_3$) δ 0.93 (3H, t, J=7.0 Hz), 1.28-1.48 (4H, m), 1.43 (9H, s), 1.50-1.68 (2H, m), 1.90-2.05 (2H, m), 2.55-2.75 (2H, m), 2.90-3.08 (1H, m), 3.54 (2H, t, J=6.4 Hz), 3.81 (2H, t, J=4.6 Hz), 4.15-4.30 (2H, m), 4.20 (2H, t, J=4.6 Hz), 7.06 (2H, d, J=8.8 Hz), 7.77 (2H, d, J=8.8 Hz)

REFERENCE EXAMPLE 89-4

4-{[4-(2-Butoxyethoxy)phenyl]sulfonyl}piperidine hydrochloride

By a similar manner to Reference Example 63-2, the titled compound was synthesized by using the compound obtained in Reference Example 89-3. Yield 98%.

$^1$H NMR (CD$_3$OD) δ 0.93 (3H, t; J=7.0 Hz), 1.30-1.68 (4H, m), 1.73-2.00 (2H, m), 2.12-2.30 (2H, m), 2.90-3.10 (2H, m), 3.40-3.62 (5H, m), 3.78-3.88 (2H, m), 4.20-4.30 (2H, m), 7.20 (2H, d, J=9.0 Hz), 7.83 (2H, d, J=9.0 Hz)

REFERENCE EXAMPLE 90-1 tert-Butyl 4-[(4-methoxyphenyl)sulfanyl]-1-piperidinecarboxylate

By a similar manner to Reference Example 88-1, the titled compound was synthesized by using 4-methoxythiophenol. Yield 89%.

$^1$H NMR (CDCl$_3$) δ 1.44 (9H, s), 1.44-1.60 (2H, s), 1.78-1.95 (2H, m), 2.77-2.93 (2H, m), 3.00 (1H, tt, J=4.0, 10.6 Hz), 3.81 (3H, s), 3.88-4.02 (2H, m), 6.85 (2H, d, J=8.8 Hz), 7.40 (2H, d, J=8.8 Hz)

REFERENCE EXAMPLE 90-2 tert-Butyl 4-[(4-methoxyphenyl)sulfonyl]-1-piperidinecarboxylate

By a similar manner to Reference Example 63-1, the titled compound was synthesized by using the compound obtained in Reference Example 90-1. Yield 61%.

$^1$H NMR (CDCl$_3$) δ 1.43 (9H, s), 1.44-1.69 (2H, m), 1.90-2.05 (2H, m), 2.55-2.85 (2H, m), 3.00 (1H, tt, J=4.4, 12.2 Hz), 3.90 (3H, s), 4.13-4.30 (2H, m), 7.03 (2H, d, J=9.0 Hz), 7.79 (2H, d, J=9.0 Hz)

REFERENCE EXAMPLE 90-3

4-[(4-Methoxyphenyl)sulfonyl]piperidine hydrochloride

By a similar manner to Reference Example 63-2, the titled compound was synthesized by using the compound obtained in Reference Example 90-1. Yield 100%.

$^1$H NMR (CD$_3$OD) δ 1.75-2.03 (2H, m), 2.10-2.30 (2H, m), 2.90-3.12 (2H, m), 3.32-3.60 (3H, m), 3.91 (3H, s), 7.18 (2H, d, J=8.8 Hz), 7.84 (2H, d, J=8.8 Hz)

REFERENCE EXAMPLE 91-1 t-Butyl 4-methylsulfonyloxymethyl-1-piperidinecarboxylate t-butyl 4-hydroxymethyl-1-piperidinecarboxylate (5.00 g, 23.2 mmol) was dissolved in tetrahydrofuran (75 ml). To the solution were added triethylamine (2.83 g) and methanesulfonyl chloride (3.19 g) under ice cooling, and the mixture was stirred at 0° C. for 5 hours. To the reaction mixture was added water, and the mixture was extracted with ethyl acetate twice. The organic layer was washed with 1N-hydrochloric acid and a saturated aqueous solution of sodium hydrogencarbonate, dried over anhydrous magnesium sulfate and concentrated under reduced pressure. The resulting solid materials were washed with hexane to give the titled compound (6.55 g, 22.3 mmol, Yield 96%).

REFERENCE EXAMPLE 91-2 t-Butyl 4-(1H-benzimidazol-1-ylmethyl)-1-piperidinecarboxylate t-Butyl 4-methylsulfonyloxymethyl-1-piperidinecarboxylate (0.50 g, 1.7 mmol) was dissolved in dimethylformamide (8 ml). To the solution were added potassium iodide (0.37 g), benzimidazole (0.26 g) and 60% sodium hydride in mineral oil (0.088 g), successively, and the mixture was stirred at 60° C. for 2 hours. To the reaction mixture was added water, and the mixture was extracted with ethyl acetate twice. The organic layer was washed with water three times, dried over magnesium sulfate and concentrated under reduced pressure. The resulting solid materials were recrystallized from ethyl acetate/hexane to give the titled compound (0.45 g, 1.4 mmol, Yield 82%).

$^1$H NMR (CDCl$_3$) δ 1.12-1.37 (2H, m), 1.45 (9H, s), 1.50-1.70 (2H, m), 1.92-2.15 (1H, m), 2.63 (2H, t, J=12 Hz), 4.06 (2H, d, J=7.2 Hz), 4.10-4.23 (2H, m), 7.26-7.42 (3H, m), 7.78-7.88 (2H, m)

REFERENCE EXAMPLE 92 t-Butyl 4-(1H-indol-1-ylmethyl)-1-piperidinecarboxylate t-butyl 4-methylsulfonyloxy methyl-1-piperidinecarboxylate (0.200 g, 0.68 mmol) was dissolved in dimethylformamide (8 ml). To the solution were added potassium iodide (0.148 g), indol (0.104 g) and 60% sodium hydride in mineral oil (0.036 g), successively, and the mixture was heated at 60° C. for 2 hours. To the reaction mixture was added water, and the mixture was extracted with ethyl acetate twice. The organic layer was washed with water three times, dried over magnesium sulfate and concentrated under reduced pressure. The concentrate was subjected to column chromatography (silica gel, ethyl acetate/hexane=1:4), and the desired fraction was concentrated under reduced pressure to give the titled compound (0.194 g, 0.62 mmol, Yield 91%) as colorless oily substance.

$^1$H NMR (CDCl$_3$) δ 1.10-1.38 (2H, m), 1.45 (9H, s), 1.50-1.63 (2H, m), 1.90-2.12 (1H, m), 2.60 (2H, t, J=12 Hz), 4.00 (2H, d, J=7.4 Hz), 4.00-4.20 (2H, m), 6.49 (1H, dd, J=3.4, 0.8 Hz), 7.03-7.37 (4H, m), 7.64 (1H, d, J=7.6 Hz)

REFERENCE EXAMPLE 93

4-(4-Cyanobenzyl)piperidine hydrochloride

By a similar manner to Reference Example 3-1, the titled compound was synthesized by using 4-cyanobenzyl bromide.

$^1$H NMR(CDCl$_3$) δ 1.69-1.89 (5H, m), 2.54-2.69 (2H, m), 2.75-2.90 (2H, m), 3.41-3.59 (2H, m), 7.25 (2H, d, J=8.0 Hz), 7.60 (2H, d, J=8.0 Hz), 9.42 (1H, brs), 9.61 (1H, brs)

REFERENCE EXAMPLE 94

4-Piperonylpiperidine hydrochloride

By a similar manner to Reference Example 3-1, the titled compound was synthesized by using piperonylchloride (produced by reacting piperonyl alcohol with thionyl chloride).

$^1$H NMR(CDCl$_3$) δ 1.61-1.90 (5H, m), 2.51-2.68 (2H, m), 2.73-2.91 (2H, m), 3.44-3.59 (2H, m), 5.93 (2H, s), 6.54-6.75 (3H, m), 9.47 (1H, brs), 9.61 (1H, brs)

REFERENCE EXAMPLE 95-1

1-tert-Butoxycarbonyl-4-(4-nitrobenzyl)piperidine 4-(4-nitrobenzyl)-1-(trifluoroacetyl)piperidine (8 g, 25.2 mmol) was dissolved in ethanol (90 mL). To the solution was added a aqueous solution of 10% sodium hydroxide (40 mL), and the mixture was stirred at room temperature for 1 hour. To the reaction mixture was added water (200 mL), and the mixture was extracted with ethyl acetate. The extract was washed with saturated sodium chloride solution, dried over anhydrous magnesium sulfate and concentrated under reduced pressure, and the concentrate was dissolved in tetrahydrofuran (50 mL). To the solution was added di-tert-butyldicarbonate (5.5 g, 25 mmol) under ice cooling, and the mixture was stirred at room temperature for 2 hours. The reaction mixture was poured into water (200 mL), and the mixture was extracted with ethyl acetate. The extract was washed with water and saturated sodium chloride solution, dried over anhydrous magnesium sulfate and concentrated under reduced pressure, and the concentrate was purified by silica gel column chromatography (hexane/ethyl acetate=5/1) to give the titled compound (6 g) as pale yellow oily substance.

REFERENCE EXAMPLE 95-2

1-tert-Butoxycarbonyl-4-(4-aminobenzyl)piperidine

To the solution of 1-tert-butoxycarbonyl-4-(4-nitrobenzyl)piperidine (4.53 g, 14.2 mmol) in methanol-tetrahydrofuran (1:1, 100 mL) were added activated carbon (2 g) and anhydrous ferric chloride (250 mg). To the mixture was added hydrazine monohydrate (5.64 mL), and the mixture was heated for 26 hours under ref lux. The reaction mixture was cooled to room temperature, the activated carbon was filtered off. The activated carbon was washed with methanol. The filtrate and washings were combined, and concentrated under reduced pressure. The concentrate was purified by silica gel column chromatography (hexane/ethyl acetate=2/3) to give the titled compound (4 g) as colorless powdery crystals.

$^1$H NMR (CDCl$_3$) δ 1.07-1.23 (2H, m), 1.45 (9H, s), 1.57-1.72 (3H, m), 2.42 (2H, d, J=6.0 Hz), 2.56 (2H, d, J=13 Hz), 3.57 (2H, br s), 4.06 (2H, d, J=13 Hz), 6.61 (2H, d, J=8.4 Hz), 6.92 (2H, d, J=8.4 Hz)

REFERENCE EXAMPLE 95-3

4-[4-(1H-Tetrazol-1-yl)benzyl]piperidine hydrochloride

To a solution of 1-tert-butoxycarbonyl-4-(4-aminobenzyl)piperidine (1 g, 3.46 mmol) in acetic acid (14 mL) were added orthoethyl formate (2.4 mL, 20.7 mmol) and sodium azide (0.27 g, 4.13 mmol), and the mixture was stirred at room temperature for 30 minutes and at 80° C. for 2 hours. The mixture was cooled to room temperature. To the mixture were added water (20 mL) and a solution of sodium nitrite (4.3 g) in water (20 mL), and the mixture was stirred at room temperature for 10 minutes and extracted with ethyl acetate. The extract was washed with aqueous solution of sodium hydrogencarbonate and saturated sodium chloride solution, dried over anhydrous magnesium sulfate and concentrated under reduced pressure, and the concentrate was purified by silica gel column chromatography (hexane/ethyl acetate=2/3) to give 1-tert-butoxycarbonyl-4-[4-(1H-tetrazol-1-yl)benzyl]piperidine (950 mg) as colorless powdery crystals. This compound (950 mg, 2.78 mmol) was dissolved in ethyl acetate (10 mL). To the solution was added 4N-hydrogen chloride in ethyl acetate (10 mL), and the mixture was stirred at room temperature for 2 hours. The resulting crystals were collected by filtration, washed with ethyl acetate (5 mL) and dried to give the titled compound (697 mg) as colorless powdery crystals.

$^1$H NMR (DMSO-d$_6$) δ 1.37-1.92 (5H, m), 2.53-2.90 (4H, m), 3.23-3.29 (2H, m), 7.46 (2H, d, J=8.4 Hz), 7.86 (2H, d, J=8.4 Hz), 9.02 (1H, br s), 9.21 (1H, br s), 10.12 (1H, s)

REFERENCE EXAMPLE 96

4-[2-(1H-Tetrazol-1-yl)benzyl]piperidine hydrochloride

By a similar manner to the production of 4-[4-(1H-tetrazol-1-yl)benzyl]piperidine hydrochloride (Reference Example 95), the titled compound was synthesized by using 4-(2-nitrobenzyl)-1-(trifluoroacetyl)piperidine as a starting compound.

$^1$H NMR (DMSO-d$_6$) δ 1.25-1.85 (5H, m), 2.40-2.89 (4H, m), 3.16-3.21 (2H, m), 7.50-7.57 (4H, m), 8.81 (1H, br s), 9.12 (1H, br s), 9.83 (1H, s)

REFERENCE EXAMPLE 97

4-(4-Morpholinobenzyl)piperidine hydrochloride 1-tert-Butoxycarbonyl-4-(4-aminobenzyl)piperidine (1 g, 3.45 mmol) was dissolved in 1-butanol (20 mL). To the solution were added bis(2-chloroethyl) ether (490 mg, 3.45 mmol) and potassium carbonate (1 g, 7.23 mmol), and the mixture was heated for 30 hours under reflux. The reaction mixture was poured into water (50 mL), and the mixture was extracted with ethyl acetate. The extract was washed with saturated sodium chloride solution, dried over anhydrous magnesium sulfate and concentrated under reduced pressure, and the concentrate was purified by silica gel column chromatography (hexane/ethyl acetate=3/1) to give 1-tert-butoxycarbonyl-4-(4-morpholinobenzyl)piperidine (869 mg) as a colorless oily substance. This compound (859 mg, 2.39 mmol) was dissolved in ethyl acetate (10 mL). To the solution was added 4N-hydrogen chloride in ethyl acetate (5 mL), and the mixture was stirred at room temperature for 2 hours. The solvent was distilled off under reduced pressure to give the titled compound (562 mg) as colorless powders.

$^1$H NMR (DMSO-d$_6$) δ 1.36-1.88 (5H, m), 2.52-2.80 (4H, m), 3.17-3.22 (2H, m), 3.42 (4H, m), 4.00 (4H, m), 7.25-7.30 (2H, m), 7.53-7.60 (2H, m), 8.89 (1H, m), 9.12 (1H, m)

REFERENCE EXAMPLE 98-1

1-tert-Butoxycarbonyl-4-[4-(methylsulfonyl)aminobenzyl]piperidine 1-tert-Butoxycarbonyl-4-(4-aminobenzyl)piperidine (1.2 g, 4.15 mmol) was dissolved in tetrahydrofuran (20 mL). To the solution was added triethylamine (0.64 mL, 4.57 mmol). To the mixture was added dropwise methanesulfonyl chloride (0.39 mL, 4.95 mmol) under ice cooling, and the mixture was stirred under ice cooling for 30 minutes and at room temperature for 30 minutes. The reaction mixture was poured into ice-water (20 mL), and the mixture was extracted with ethyl acetate. The extract was washed with water and saturated sodium chloride solution, dried over anhydrous magnesium sulfate and concentrated under reduced pressure, and the concentrate was purified by silica gel column chromatography (hexane/ethyl acetate=1/1) to give the titled compound (1.43 g) as colorless powdery crystals.

$^1$H NMR (CDCl$_3$) δ 1.19-1.63 (5H, m), 1.45 (9H, s), 2.50-2.81 (4H, m), 3.00 (3H, s), 4.02-4.15 (2H, m), 7.07-7.21 (5H, m)

REFERENCE EXAMPLE 98-2

1-tert-Butoxycarbonyl-4-{4-[methyl(methylsulfonyl)amino]benzyl}piperidine 1-tert-Butoxycarbonyl-4-[4-(methylsulfonyl)aminobenzyl]piperidine (1.4 g, 3.81 mmol) was dissolved in N,N-dimethylformamide (10 mL). To the solution was added 72% sodium hydride in mineral oil (143 mg, 4.29 mmol) under ice cooling, and the mixture was stirred for 10 minutes. To the mixture was added methyl iodide (0.25 mL, 4 mmol), and the mixture was stirred at room temperature for 1 hour. After cooling, the reaction mixture was poured into ice-water (20 mL) and the mixture was extracted with ethyl acetate. The extract was washed with water and saturated sodium chloride solution, dried over anhydrous magnesium sulfate and concentrated under reduced pressure, and the concentrate was purified by silica gel column chromatography (hexane/ethyl acetate=3/2) to give the titled compound (1.20 g) as colorless powdery crystals.

$^1$H NMR (CDCl$_3$) δ 1.22-1.67 (5H, m), 1.45 (9H, s), 2.52-2.72 (4H, m), 2.84 (3H, s), 3.31 (3H, s), 4.02-4.14 (2H, m), 7.15 (2H, d, J=8.2 Hz), 7.29 (2H, d, J=8.2 Hz)

REFERENCE EXAMPLE 98-3

4-{4-[Methyl(methylsulfonyl)amino]benzyl}piperidine hydrochloride 1-tert-Butoxycarbonyl-4-{4-[methyl(methylsulfonyl)amino]benzyl}piperidine (1.2 g, 3.15 mmol) was dissolved in ethyl acetate (5 mL). To the solution was added 4N-hydrogen chloride in ethyl acetate (10 mL), and the mixture was stirred at room temperature for 2 hours. The resulting crystals were collected by filtration, washed with ethyl acetate (5 mL) and dried to give the titled compound (851 mg) as colorless powdery crystals.

$^1$H NMR (CDCl$_3$) δ 1.63-1.90 (5H, m), 2.52-2.67 (2H, m), 2.73-2.90. (2H, m), 2.85 (3H, s), 3.11 (3H, s), 3.42-3.58 (2H, m), 7.15 (2H, d, J=8.4 Hz), 7.30 (2H, d, J=8.4 Hz), 9.35 (1H, br s), 9.56 (1H, br s)

REFERENCE EXAMPLE 99-1

1-tert-Butoxycarbonyl-4-[(4-ethoxyphenyl)sulfanyl]piperidine

A mixture of 1-tert-Butoxycarbonyl-4-[(4-hydroxyphenyl)sulfanyl]piperidine (3.09 g, 10.0 mmol), ethyl iodide, (1.04 mL, 13.0 mmol), and potassium carbonate (1.80 g, 13.0 mmol) in DMF (15 mL) was stirred at 60° C. for 20 hours. The reaction mixture was evaporated under reduced pressure. The residue was diluted with ethyl acetate (40 mL), washed with water (10 mL), 0.5 N sodium hydroxide solution (10 mL×3), brine (10 mL) The organic layer was dried over anhydrous magnesium sulfate, filtered and evaporated under reduced pressure. The residue was purified by column chromatography on silica gel, using ethyl acetate/hexane (1/19 to 1/9) as eluent to afford the title compound (3.21 g, 9.52 mmol, 95%) as a colorless oil.

$^1$H NMR (CDCl$_3$) δ 1.3-1.6 (2H, m), 1.42 (3H, t, J=7.0 Hz), 1.44 (9H, s), 1.75-1.95 (2H, m), 2.75-3.1 (3H, m), 3.85-4.1 (2H, m), 4.02 (2H, q, J=7.0 Hz), 6.84 (2H, d, J=9.0 Hz), 7.38 (2H, d, J=9.0 Hz)

REFERENCE EXAMPLE 99-2

1-tert-Butoxycarbonyl-4-[(4-ethoxyphenyl)sulfonyl]piperidine

The title compound was prepared using a similar procedure to that described for reference example 63-1 from the title compound of reference example 99-1 (yield 80%).

$^1$H NMR (CDCl$_3$) δ 1.4-1.7 (2H, m), 1.46 (3H, t, J=7.0 Hz), 1.43 (9H, s), 1.9-2.05 (2H, m), 2.5-2.75 (2H, m), 2.9-3.1 (1H, m), 4.1-4.35 (2H, m), 4.11 (2H, q, J=7.0 Hz), 7.01 (2H, d, J=9.0 Hz), 7.77 (2H, d, J=9.0 Hz)

REFERENCE EXAMPLE 99-3

4-[(4-Ethoxyphenyl)sulfonyl]piperidine hydrochloride

The title compound was prepared using a similar procedure to that described for reference example 63-2 from the title compound of reference example 99-2 (yield 98%).

$^1$H NMR (CD$_3$OD) δ 1.43 (3H, t, J=7.0 Hz), 1.75-2.0 (2H, m), 2.1-2.3 (2H, m), 2.9-3.1 (2H, m), 3.35-3.6 (3H, m), 4.16 (2H, q, J=7.0 Hz), 7.16 (2H, d, J=9.2 Hz), 7.82 (2H, d, J=9.2 Hz)

REFERENCE EXAMPLE 100-1

1-tert-Butoxycarbonyl-4-{[4-(trifluoromethyl)phenyl]sulfanyl}piperidine

The title compound was prepared using a similar procedure to that described for reference example 61-1 from 4-(trifluoromethyl)benzenethiol (yield 79%).

$^1$H NMR (CDCl$_3$) δ 1.4-1.7 (2H, m), 1.45 (9H, s), 1.85-2.05 (2H, m), 2.85-3.1 (2H, m), 3.25-3.45 (1H, m), 3.8-4.1 (2H, m), 7.45 (2H, d, J=8.6 Hz), 7.54 (2H, d, J=8.6 Hz)

REFERENCE EXAMPLE 100-2

1-tert-Butoxycarbonyl-4-{[4-(trifluoromethyl)phenyl]sulfonyl}piperidine

The title compound was prepared using a similar procedure to that described for reference example 63-1 from the title compound of reference example 100-1 (yield 72%).

$^1$H NMR (CDCl$_3$) δ 1.43 (9H, s), 1.45-1.75 (2H, m), 1.9-2.05 (2H, m), 2.5-2.8 (2H, m), 2.95-3.2 (1H, m), 4.1-4.35 (2H, m), 7.86 (2H, d, J=8.2 Hz), 8.02 (2H, d, J=8.2 Hz)

REFERENCE EXAMPLE 100-3

4-{[4-(trifluoromethyl)phenyl]sulfonyl}piperidine hydrochloride

The title compound was prepared using a similar procedure to that described for reference example 63-2 from the title compound of reference example 100-2 (yield 95%).

$^1$H NMR (CD$_3$OD) δ 1.8-2.05 (2H, m), 2.1-2.3 (2H, m), 2.9-3.15 (2H, m), 3.4-3.75 (3H, m), 8.02 (2H, d, J=8.8 Hz), 8.15 (2H, d, J=8.8 Hz)

REFERENCE EXAMPLE 101-1

1-tert-Butoxycarbonyl-4-[(4-isopropoxyphenyl)sulfanyl]piperidine

The title compound was prepared using a similar procedure to that described for reference example 99-1 from isopropyl iodide (yield 98%).

$^1$H NMR (CDCl$_3$) δ 1.3-1.6 (2H, m), 1.34 (6H, d, J=6.1 Hz), 1.44 (9H, s), 1.75-1.95.(2H, m), 2.75-3.1 (3H, m), 3.85-4.1 (2H, m), 4.54 (1H, sept, J=6.1 Hz), 6.82 (2H, d, J=8.8 Hz), 7.37 (2H, d, J=8.8 Hz)

REFERENCE EXAMPLE 101-2

1-tert-Butoxycarbonyl-4-[(4-isopropoxyphenyl)sulfonyl]piperidine

The title compound was prepared using a similar procedure to that described for reference example 63-1 from the title compound of reference example 101-1 (yield 87%).

$^1$H NMR (CDCl$_3$) δ 1.38 (6H, d, J=6.1 Hz), 1.4-1.7 (2H, m), 1.43 (9H, s), 1.9-2.1 (2H, m), 2.55-2.75 (2H, m), 2.85-3.1 (1H, m), 4.1-4.35 (2H, m), 4.65 (1H, sept, J=6.1 Hz), 6.99 (2H, d, J=9.0 Hz),.7.75 (2H, d, J=9.0 Hz)

REFERENCE EXAMPLE 101-3

4-[(4-isopropoxyphenyl)sulfonyl]piperidine hydrochloride

The title compound was prepared using a similar procedure to that described for reference example 63-2 from the title compound of reference example 101-2 (yield 92%).

$^1$H NMR(CD$_3$OD) δ 1.35 (6H, d, J=5.9 Hz), 1.7-2.0 (2H, m), 2.1-2.3 (2H, m), 2.9-3.15 (2H, m), 3.3-3.6 (3H, m), 4.76 (1H, sept, J=5.9 Hz), 7.14 (2H, d, J=9.0 Hz), 7.81 (2H, d, J=9.0 Hz)

REFERENCE EXAMPLE 102-1

1-tert-Butoxycarbonyl-4-[(4-tert-butylphenyl)sulfanyl]piperidine

The title compound was prepared using a similar procedure to that described for reference example 61-1 from 4-tert-butylbenzenethiol (yield 73%).

$^1$H NMR (CDCl$_3$) δ 1.31 (9H, s), 1.35-1.65 (2H, m), 1.44 (9H, s), 1.8-2.0 (2H, m), 2.8-3.0 (2H, m), 3.05-3.25 (1H, m), 3.8-4.1 (2H, m), 7.25-7.4 (4H, m)

REFERENCE EXAMPLE 102-2

1-tert-Butoxycarbonyl-4-[(4-tert-butylphenyl)sulfonyl]piperidine

The title compound was prepared using a similar procedure to that described for reference example 63-1 from the title compound of reference example 102-1 (yield 61%).

$^1$H NMR (CDCl$_3$) δ 1.36 (9H, s), 1.43 (9H, s), 1.45-1.75 (2H, m), 1.9-2.1 (2H, m), 2.5-2.8 (2H, m), 2.9-3.15 (1H, m), 4.1-4.35 (2H, m), 7.58 (2H, d, J=8.4 Hz), 7.78 (2H, d, J=8.4 Hz)

REFERENCE EXAMPLE 102-3

4-[(4-tert-butylphenyl)sulfonyl]piperidine hydrochloride

The title compound was prepared using a similar procedure to that described for reference example 63-2 from the title compound of reference example 102-2 (yield 97%).

$^1$H NMR (CD$_3$OD) δ 1.37 (9H, s), 1.75-2.0 (2H, m), 2.1-2.3 (2H, m), 2.9-3.1 (2H, m), 3.4-3.6 (3H, m), 7.73 (2H, d, J=8.8 Hz), 7.85 (22H, d, J=8.8 Hz)

REFERENCE EXAMPLE 103-1

1-tert-Butoxycarbonyl-4-{[4-(trifluoromethoxy)phenyl]sulfanyl}piperidine

The title compound was prepared using a similar procedure to that described for reference example 61-1 from 4-(trifluoromethoxy)benzenethiol (yield 71%).

$^1$H NMR (CDCl$_3$) δ 1.35-1.65 (2H, m), 1.45 (9H, s), 1.8-2.0 (2H, m), 2.8-3.0 (2H, m), 3.05-3.3 (1H, m), 3.8-4.1 (2H, m), 7.16 (2H, d, J=8.3 Hz), 7.44 (2H, d, J=8.3 Hz)

REFERENCE EXAMPLE 103-2

1-tert-Butoxycarbonyl-4-{[4-(trifluoromethoxy)phenyl]sulfonyl}piperidine

The title compound was prepared using a similar procedure to that described for reference example 63-1 from the title compound of reference example 103-1 (yield 85%).

$^1$H NMR (CDCl$_3$) δ 1.43 (9H, s), 1.45-1.75 (2H, m), 1.9-2.1 (2H, m), 2.5-2.8 (2H, m), 2.95-3.15 (1H, m), 4.1-4.35 (2H, m), 7.41 (2H, dd, J=0.6 Hz, 8.8 Hz), 7.93 (2H, d, J=8.8 Hz)

REFERENCE EXAMPLE 103-3

4-{[4-(trifluoromethoxy)phenyl]sulfonyl}piperidine hydrochloride

The title compound was prepared using a similar procedure to that described for reference example 63-2 from the title compound of reference example 103-2 (yield 64%).

$^1$H NMR (CD$_3$OD) δ 1.75-2.05 (2H, m), 2.1-2.3 (2H, m), 2.9-3.15 (2H, m), 3.4-3.7 (3H, m), 7.60 (2H, dd, J=0.8 Hz, 8.8 Hz), 8.06 (2H, d, J=8.8 Hz)

REFERENCE EXAMPLE 104-1

1-tert-Butoxycarbonyl-4-{[4-(methylsulfanyl)phenyl]sulfanyl}piperidine

The title compound was prepared using a similar procedure to that described for reference example 61-1 from 4-(methylsulfanyl)benzenethiol (yield 33%).

$^1$H NMR (CDCl$_3$) δ 1.3-1.65 (2H, m), 1.44 (9H, s), 1.8-2.0 (2H, m), 2.48 (3H, s), 2.75-3.0 (2H, m), 3.0-3.15 (1H, m), 3.85-4.05 (2H, m), 7.18 (2H, d, J=8.4 Hz), 7.35 (2H, d, J=8.4 Hz)

REFERENCE EXAMPLE 104-2

1-tert-Butoxycarbonyl-4-{[4-(methylsulfonyl)phenyl]sulfonyl}piperidine

To a stirred solution of the title compound of reference example 104-1 (700 mg, 2.06 mmol) in dichloromethane (40 mL) was added m-chloroperoxybenzoic acid (70%, 2.24 g, 9.07 mmol) at 0° C., and the reaction mixture was stirred at room temperature for 18 hours. The reaction mixture was quenched with 5% aqueous sodium thiosulfate solution (30 mL), saturated aqueous sodium bicarbonate solution (30 mL) and stirred for 30 minutes. The organic layer was separated and the aqueous layer was extracted with dichloromethane (2×20 mL). The combined organic layers were washed with saturated aqueous sodium bicarbonate solution (3×15 mL), brine (15 mL), dried over anhydrous magnesium sulfate, filtered, and evaporated under reduced pressure. Diisopropyl ether was added to the residue, the resulting precipitate was collected by filtration, washed with diisopropyl ether, and dried under reduced pressure to afford the title compound (766 mg, 1.90 mmol, 92%) as a white solid.
$^1$H NMR (CDCl$_3$) δ 1.44 (9H, s), 1.5-1.75 (2H, m), 1.9-2.05 (2H, m), 2.55-2.8 (2H, m), 3.0-3.2 (1H, m), 3.13 (3H, s), 4.15-4.35 (2H, m), 8.09 (2H, d, J=8.6 Hz), 8.18 (2H, d, J=8.6 Hz)

REFERENCE EXAMPLE 104-3

4-{[4-(methylsulfonyl)phenyl]sulfonyl}piperidine hydrochloride

The title compound was prepared using a similar procedure to that described for reference example 63-2 from the title compound of reference example 104-2 (yield 99%).
$^1$H NMR (CD$_3$OD/DMSO-d$_6$=1/1) δ 1.7-1.95 (2H, m), 2.0-2.2 (2H, m), 2.8-3.05 (2H, m), 3.28 (3H, s), 3.3-3.5 (2H, m)D 3.55-3.8 (1H, m), 8.16 (2H, d, J=8.8 Hz), 8.28 (2H, d, J=8.8 Hz)

REFERENCE EXAMPLE 105-1

4-(4-isobutyrylbenzyl)-1-(trifluoroacetyl)piperidine

To a stirred solution of 4-benzyl-1-(trifluoroacetyl)piperidine (4.34 g, 16.0 mmol) and isobutyryl chloride (2.18 mL, 20.8 mmol) in dichloromethane (50 mL) was added aluminum chloride (5.33 g, 40.0 mmol) at 0° C., and the reaction mixture was stirred at room temperature for 3 hours. The reaction mixture was poured into ice water (50 g), the organic layer was separated and the aqueous layer was extracted with dichloromethane (30 mL) The combined organic layers were washed with saturated aqueous sodium bicarbonate solution (3×15 mL), brine (15 mL), dried over anhydrous magnesium sulfate, filtered, and evaporated under reduced pressure. The residue was purified by column chromatography on silica gel, using ethyl acetate/hexane (1/19 to 1/9) as eluent to afford the title compound (3.60 g, 10.5 mmol, 66%) as a colorless oil.
$^1$H NMR (CDCl$_3$) δ 1.1-1.4 (2H, m), 1.22 (6H, d, J=6.9 Hz), 1.7-2.0 (3H, m), 2.6-2.8 (1H, m). 2.63 (2H, d, J=6.8 Hz), 2.95-3.15 (1H, m), 3.54 (1H, sept, J=6.9 Hz), 3.9-4.1 (1H, m), 4.45-4.6 (1H, m), 7.23 (2H, d, J=8.5 Hz), 7.90 (2H, d, J=8.5 Hz)

REFERENCE EXAMPLE 105-2

4-(4-isobutyrylbenzyl)piperidine

To a solution of the title compound of reference example 105-1 (3.55 g, 10.4 mmol) and in methanol (60 mL) was added a solution of potassium carbonate (4.31 g, 31.2 mmol) in water (30 mL), and the reaction mixture was stirred at room temperature for 19 hours. The reaction mixture was evaporated under reduced pressure, water (40 mL) was added, and the aqueous layer was extracted with dichloromethane (40 mL, 2×20 mL). The combined organic layers were dried over anhydrous sodium sulfate, filtered and evaporated under reduced pressure to afford the title compound (2.59 g) as a pale yellow oil.
$^1$H NMR (CDCl$_3$) δ 1.05-1.35 (2H, m) 1.21 (6H, d, J=6.8 Hz), 1.55-1.8 (3H, m), 2.45-2.65 (2H, m), 2.59 (2H, d, J=7.0 Hz), 3.0-3.15 (2H, m), 3.54 (1H, sept, J=6.8 Hz), 7.24 (2H, d, J=8.3 Hz), 7.88 (2H, d, J=8.3 Hz)

REFERENCE EXAMPLE 106-1

1-Acetyl-4-[4-(methylsulfanyl)benzoyl]piperidine

To a stirred suspension of aluminum chloride (16.66 g, 125 mmol) in dichloromethane (100 mL) was added 1-acetyl-4-piperidinecarbonyl chloride (12.33 g, 65.0 mmol) at −10° C. Thioanisole (6.21 g, 50.0 mmol) was added dropwise at −10° C., the reaction mixture was stirred at room temperature for 1.5 hours. The reaction mixture was poured into ice water (80 g), the organic layer was separated and the aqueous layer was extracted with dichloromethane (40 mL) The combined organic layers were washed with 1N aqueous sodium hydroxide (2×40 mL), brine (40 mL), dried over anhydrous magnesium sulfate, filtered, and evaporated under reduced pressure. Ethyl acetate and diethyl ether was added to the residue, the resulting precipitate was collected by filtration, washed with diethyl ether, and dried under reduced pressure to afford the title compound (11.43 g, 41.2 mmol, 82%) as a white solid.
$^1$H NMR (CDCl$_3$) δ 1.5-2.0 (4H, m), 2.12 (3H, s), 2.53 (3H, s), 2.7-2.95 (1H, m), 3.1-3.3 (1H, m), 3.35-3.55 (1H, m), 3.8-4.0 (1H, m), 4.5-4.65 (1H, m), 7.29 (2H, d, J=8.6 Hz), 7.86 (2H, d, J=8.6 Hz)

REFERENCE EXAMPLE 106-2

1-Acetyl-4-[4-(methylsulfonyl)benzoyl]piperidine

To a stirred solution of the title compound of reference example 106-1 (2.77 g, 10.0 mmol) in dichloromethane (50 mL) was added m-chloroperoxybenzoic acid (70%, 5.42 g, 22 mmol) at 0° C., and the reaction mixture was stirred at room temperature for 18 hours. The reaction mixture was quenched with 5% aqueous sodium thiosulfate solution (30 mL), saturated aqueous sodium bicarbonate solution (60 mL) and stirred for 30 minutes. The organic layer was separated and the aqueous layer was extracted with dichloromethane (2×20 mL). The combined organic layers were washed with saturated aqueous sodium bicarbonate solution (3×20 mL), brine (20 mL), dried over anhydrous magnesium sulfate, filtered, and evaporated under reduced pressure. Ethyl acetate and diisopropyl) ether was added to the residue, the resulting precipitate was collected by filtration, washed with diisopropyl ether, and dried under reduced pressure to afford the title compound (2.91 g, 9.41 mmol, 94%) as a white solid.
$^1$H NMR (CDCl$_3$) δ 1.5-2.05 (4H, m), 2.13 (3H, s), 2.75-2.95 (1H, m), 3.10 (3H, s), 3.15-3.35 (1H, m), 3.4-3.6 (1H, m), 3.85-4.0 (1H, m), 4.5-4.65 (1H, m), 8.0-8.2 (4H, m)

REFERENCE EXAMPLE 106-3

4-[4-(Methylsulfonyl)benzoyl]piperidine hydrochloride

A suspension of the title compound of reference example 106-2 (2.82 g, 9.12 mmol) in concentrated hydrochloric acid (30 mL) was stirred under reflux for 3 hours. The reaction mixture was diluted with 2-propanol (60 mL) and stirred for 1 hour. The resulting precipitate was collected by filtration, washed with 2-propanol, and dried under reduced pressure to afford the title compound (2.55 g, 8.39 mmol, 92%) as a white solid.
$^1$H NMR (DMSO-d$_6$) δ 1.6-2.1 (4H, m), 2.9-3.15 (2H, m), 3.2-3.4 (2H, m), 3.31 (3H, s), 3.7-3.95 (1H, m), 8.10 (2H, d, J=8.6 Hz), 8.24 (2H, d, J=8.6 Hz)

REFERENCE EXAMPLE 107-1

1-tert-Butoxycarbonyl-4-(ethylamino)piperidine

To a stirred solution of 1-tert-butoxycarbonyl-4-piperidone (3.99 g, 20 mmol) in THF (40 mL) were added ethylamine (20 mL of a 2.0 M solution in THF, 40 mmol), acetic acid (1.15 mL, 20 mmol) and sodium triacetoxyborohydride (8.48 g, 40 mmol) at 0° C., and the reaction mixture was stirred at room temperature for 3 hours. The reaction mixture was quenched with 1 N aqueous sodium hydroxide (120 mL) at 0° C. and stirred at room temperature for 30 minutes. The organic solvent was evaporated under reduced pressure, and the remaining aqueous layer was extracted with ethyl acetate (40 mL, 2×20 mL). The combined organic layers were washed with brine (2×20 mL), dried over anhydrous sodium sulfate, filtered, and evaporated under reduced pressure to afford the title compound (4.54 g, 19.9 mmol, 99%) as a pale yellow oil.

$^1$H NMR (CDCl$_3$) δ 1.05-1.4 (2H, m), 1.11 (3H, t, J=7.2 Hz), 1.45 (9H, s), 1.7-1.95 (2H, m), 2.5-2.9 (3H, m), 2.68 (2H, q, J=7.2 Hz), 3.9-4.2 (2H, m)

REFERENCE EXAMPLE 107-2

1-tert-Butoxycarbonyl-4-{ethyl[4-(methylsulfanyl) phenylsulfonyl]amino}piperidine To a stirred solution of the title compound of reference example 107-1 (4.54 g, 19.9 mmol) in THF (50 mL) were added triethylamine (3.05 mL, 21.9 mmol) and 4-(methylsulfanyl)benzenesulfonyl chloride (4.42 g, 19.9 mmol) at 0° C., and the reaction mixture was stirred at room temperature for 20 hours. The reaction mixture was quenched with water (50 mL), extracted with ethyl acetate (50 mL, 25 mL). The combined organic layers were washed with 1N hydrochloric acid (3×10 mL), saturated aqueous sodium bicarbonate solution (2×10 mL), brine (10 mL), dried over anhydrous magnesium sulfate, filtered, and evaporated under reduced pressure. Diethyl ether was added to the residue, the resulting precipitate was collected by filtration, washed with diethyl ether, and dried under reduced pressure to afford the title compound (6.83 g, 16.5 mmol, 83%) as a white solid.

$^1$H NMR (CDCl$_3$) δ 1.23 (3H, t, J=7.1 Hz), 1.3-1.7 (4H, m), 1.44 (9H, s), 2.52 (3H, s), 2.5-2.8 (2H, m), 3.21 (2H, q, J=7.1 Hz), 3.65-3.9 (1H, m), 4.0-4.25 (2H, m), 7.28 (2H, d, J=8.4 Hz), 7.72 (2H, d, J=8.4 Hz)

REFERENCE EXAMPLE 107-3

4-{Ethyl[4-(methylsulfanyl)phenylsulfonyl] amino}piperidine hydrochloride

To a suspension of the title compound of reference example 107-2 (2.07 g, 5.00 mmol) in methanol (15 mL) was sdded hydrogen chloride (4N solution in ethyl acetate, 20 mL), and the reaction mixture was stirred at room temperature for 3 days. The reaction mixture was evaporated under reduced pressure, ethyl acetate was added to the residue, the resulting precipitate was collected by filtration, washed with ethyl acetate, and dried under reduced pressure to afford the title compound (1.74 g, 4.97 mmol, 99%) as a white solid.

$^1$H NMR (CD$_3$OD) δ 1.23 (3H, t, J=7.2 Hz), 1.7-2.15 (4H, m), 2.54 (3H, s), 2.95-3.15 (2H, m), 3.27 (2H, q, J=7.2 Hz), 3.3-3.5 (2H, m), 3.85-4.1 (1H, m), 7.40 (2H, d, J=8.6 Hz), 7.77 (2H, d, J=8.6 Hz)

REFERENCE EXAMPLE 108

3-Chloro-4-methyl-N-(3-{4-[4-(methylsulfonyl)benzyl]-1-piperidinyl}propyl)aniline dihydrochloride The title compound was prepared using a similar procedure to that described for reference example 1 from 4-[4-(methylsulfonyl)benzyl]piperidine and 3-chloro-4-methylaniline, yield 54%.

$^1$H NMR (CD$_3$OD) δ 1.45-2.35 (7H, m), 2.39 (3H, s), 2.75 (2H, d, J=7.0 Hz), 2.8-3.7 (8H, m), 3.10 (3H, s), 7.31 (1H, dd, J=2.3 Hz, 8.1 Hz), 7.45 (1H, d, J=8.1 Hz), 7.48 (2H, d, J=8.4 Hz), 7.52 (1H, d, J=2.3 Hz), 7.89 (2H, d, J=8.4 Hz)

REFERENCE EXAMPLE 109

3-(Methylsulfanyl)-N-(3-{4-[4-(methylsulfonyl) benzyl]-1-piperidinyl}propyl)aniline dihydrochloride The title compound was prepared using a similar procedure to that described for reference example 1 from 4-[4-(methylsulfonyl)benzyl]piperidine and 3-(methylsulfanyl)aniline, yield 55%.

$^1$H NMR (CD$_3$OD) δ 1.45-2.35 (7H, m), 2.54 (3H, s), 2.75 (2H, d, J=7.0 Hz), 2.8-3.7 (8H, m), 3.10 (3H, s), 7.15-7.55 (4H, m), 7.48 (2H, d, J=8.4 Hz), 7.89 (2H, d, J=8.4 Hz)

REFERENCE EXAMPLE 110

4-(Methylsulfanyl)-N-(3-{4-[4-(methylsulfonyl) benzyl]-1-piperidinyl}propyl)aniline dihydrochloride The title compound was prepared using a similar procedure to that described for reference example 1 from 4-[4-(methylsulfonyl)benzyl]piperidine and 4-(methylsulfanyl)aniline, yield 61%.

$^1$H NMR (CD$_3$OD) δ 1.45-2.35 (7H, m), 2.50 (3H, s), 2.75 (2H, d, J=7.0 Hz), 2.8-3.7 (8H, m), 3.10 (3H, s), 7.3-7.55 (4H, m), 7.49 (2H, d, J=8.3 Hz), 7.89 (2H, d, J=8.3 Hz)

REFERENCE EXAMPLE 111

3-Chloro-4-fluoro-N-(3-{4-[4-(methylsulfonyl)benzyl]-1-piperidinyl}propyl)aniline dihydrochloride The title compound was prepared using a similar procedure to that described for reference example 1 from 4-[4-(methylsulfonyl)benzyl]piperidine and 3-chloro-4-fluoroaniline, yield 50%.

$^1$H NMR (CD$_3$OD) δ 1.45-2.3 (7H, m), 2.75 (2H, d, J=6.6 Hz), 2.8-3.7 (8H, m), 3.10 (3H, s), 7.2-7.6 (3H, m), 7.49 (2H, d, J=8.3 Hz), 7.89 (2H, d, J=8.3 Hz)

REFERENCE EXAMPLE 112

3,4-Difluoro-N-(3-{4-[4-(methylsulfonyl)benzyl]-1-piperidinyl}propyl)aniline dihydrochloride The title compound was prepared using a similar procedure to that described for reference example 1 from 4-[4-(methylsulfonyl)benzyl]piperidine and 3,4-difluoroaniline, yield 52%.

¹H NMR (CD₃OD) δ 1.45-2.3 (7H, m), 2.75 (2H, d, J=7.0 Hz), 2.8-3.7 (8H, m), 3.10 (3H, s), 7.1-7.25 (1H, m), 7.25-7.55 (2H, m), 7.49 (2H, d, J=8.4 Hz), 7.89 (2H, d, J=8.4 Hz)

REFERENCE EXAMPLE 113

N-(3-{4-[4-(methylsulfonyl)benzyl]-1-piperidinyl}propyl)-5-indanamine dihydrochloride The title compound was prepared using a similar procedure to that described for reference example 1 from 4-[4-(methylsulfonyl)benzyl]piperidine and 5-aminoindan, yield 63%.

¹H NMR (CD₃OD) δ 1.45-2.35 (7H, m), 2.12 (2H, quint, J=7.4 Hz), 2.75 (2H, d, J=7.0 Hz), 2.8-3.7 (8H, m), 2.93 (2H, t, J=7.4 Hz), 2.97 (2H, t, J=7.4 Hz), 3.10 (3H, s), 7.2-7.3 (1H, m), 7.3-7.45 (2H, m), 7.49 (2H, d, J=8.4 Hz), 7.89 (2H, d, J=8.4 Hz)

REFERENCE EXAMPLE 114

3,4-Dimethyl-N-(3-{4-[4-(methylsulfonyl)benzyl]-1-piperidinyl}propyl)aniline dihydrochloride The title compound was prepared using a similar procedure to that described for reference example 1 from 4-[4-(methylsulfonyl)benzyl]piperidine and 3,4-dimethylaniline, yield 52%.

¹H NMR (CD₃OD) δ 1.45-2.35 (7H, m), 2.30 (3H, s), 2.33 (3H, s), 2.75 (2H, d, J=7.0 Hz), 2.8-3.7 (8H, m), 3.10 (3H, s), 7.2-7.4 (3H, m), 7.48 (2H, d, J=8.4 Hz), 7.89 (2H, d, J=8.4 Hz)

REFERENCE EXAMPLE 115

3-Chloro-N-{3-[4-(4-fluorobenzyl)-1-piperidinyl]propyl}-4-isopropylaniline dihydrochloride The title compound was prepared using a similar procedure to that described for reference example 1 from the title compound of reference example 3-2 and 3-chloro-4-isopropylaniline in 66% yield.

¹H NMR (CD₃OD) δ 1.25 (6H, d, J=7.0 Hz), 1.50-1.65 (2H, m), 1.86-2.02 (3H, m), 2.12-2.28 (2H, m), 2.60 (2H, d, J=6.6 Hz), 2.88-3.00 (2H, m), 3.16-3.24 (2H, m), 3.38-3.50 (3H, m), 3.54-3.61 (2H, m), 6.97-7.05 (2H, m), 7.16-7.23 (2H, m), 7.34-7.39 (1H, m), 7.48-7.54 (2H, m)

REFERENCE EXAMPLE 116-1

4-[(1-Acetyl-4-piperidinyl)methyl]-N-propylbenzenesulfonamide

1-Propylamine (0.586 ml, 7.13 mmol) and triethylamine (0.993 ml, 7.13 mmol) were added to a solution of 4-(1-acetylpiperidin-4-ylmethyl)benzenesulfonylchloride (1.5 g, 4.75 mmol) in THF (20 ml) and this mixture was refluxed for 5 h. After having been cooled, 1N hydrochloric acid (20 ml) was added. The resulting mixture was extracted with ethyl acetate (20 ml×2). The combined organic layers were washed with saturated sodium chloride solution (40 ml), and then dried over anhydrous sodium sulfate. The solvent was removed under reduced pressure and the residue was purified by flash column chromatography (silica gel 25 g, ethyl acetate to ethyl acetate/methanol=10/1) to give the title compound (1.15 g, 71%) as pale yellow oil.

¹H NMR (CDCl₃) δ 0.87 (3H, t, J=6.8 Hz), 1.08-1.30 (2H, m), 1.50 (2H, qt. J=6.8 Hz, 6.8 Hz), 1.64-1.85 (3H, m), 2.08 (3H, s), 2.42-2.56 (1H, m), 2.62 (2H, d, J=6.6 Hz), 2.92 (2H, q, J=6.8 Hz), 2.90-3.06 (1H, m), 3.76-3.83 (1H, m), 4.57-4.65 (1H, m), 4.76 (1H, t, J=6.8 Hz), 7.28 (2H, d, J=8.4 Hz), 7.79 (2H, d, J=8.4 Hz)

REFERENCE EXAMPLE 116-2

4-(4-Piperidinylmethyl)-N-propylbenzenesulfonamide hydrochloride

The title compound was prepared using a similar procedure to that described for reference example 83-2 from the title compound of reference example 116-1. Yield 98%.

¹H NMR (CDCl₃) δ 0.88 (3H, t, J=7.0 Hz), 1.50 (2H, qt, J=7.0 Hz, 7.0 Hz), 1.66-2.24 (5H, m), 2.63 (1H, d, J=7.0 Hz), 2.67-2.97 (5H, m), 3.47-3.53 (1H, m), 4.00-4.40 (1H, br), 7.19 (1H, t, J=7.0 Hz), 7.28 (2H, d, J=8.0 Hz), 7.81 (2H, d, J=8.0 Hz), 9.10-9.60 (2H, br)

REFERENCE EXAMPLE 117-1

4-[(1-Acetyl-4-piperidinyl)methyl]-N-cyclohexylbenzenesulfonamide

The title compound was prepared using a similar method to that described for reference example 116-1 from cyclohexylamine. Yield 87%.

¹H NMR (CDCl₃) δ 1.07-1.33 (7H, m), 1.50-1.94 (8H, m), 2.09 (3H, s), 2.44-2.57 (1H, m), 2.64 (2H, d, J=7.4 Hz), 2.92-3.20 (2H, m), 3.77-3.84 (1H, m), 4.59-4.67 (1H, m), 4.71 (1H, d, J=7.2 Hz), 7.28 (2H, d, J=8.4 Hz), 7.82 (2H, d, J=8.4 Hz)

REFERENCE EXAMPLE 117-2

N-Cyclohexyl-4-(4-piperidinylmethyl)benzenesulfonamide hydrochloride

The title compound was prepared from the title compound of reference example 117-1 using a similar method to that described for reference example 83-2. Yield 89%.

¹H NMR (CD₃OD) δ 1.00-2.02 (15H, m), 2.71 (2H, d, J=7.0 Hz), 2.89-3.00 (3H, m), 3.34-3.40 (2H, m), 7.40 (2H, d, J=8.4 Hz), 7.79 (2H, d, J=8.4 Hz)

REFERENCE EXAMPLE 118-1

4-{[1-(Trifluoroacetyl)-4-piperidinyl]methyl}benzenesulfonylchloride

A mixture of 1-(trifluoroacetyl)-4-benzylpiperidine (29.2 g, 108 mmol) and dichloromethane (10 ml) was added dropwise to chlorosulfonic acid (36 ml, 539 mmol) over period of 1 h at −10° C. The mixture was stirred at 0° C. for 1 h and then at room temperature for 1 h. The whole was poured into ice-water (500 ml). The mixture was extracted with dichloromethane (200 ml×2). The extracts were washed with 5% aqueous sodium bicarbonate (500 ml), saturated sodium chloride solution (500 ml) successively. The organic layer was dried over anhydrous magnesium sulfate and concentrated in vacuo. The residue was purified by flash column chromatography (silica gel 100 g, ethyl acetate/hexane=1/20 to 1/5) to obtain the title compound (16.5 g, 41%) as a colorless crystalline powder.

$^1$H NMR (CDCl$_3$) δ 1.26-1.39 (2H, m), 1.75-2.05 (3H, m), 2.66-2.78 (1H, m), 2.48 (2H, d, J=7.0 Hz), 3.01-3.15 (1H, m), 3.98-4.10 (1H, m), 4.50-4.61 (1H, m), 7.40 (2H, d, J=8.4 Hz), 7.98 (2H, d, J=8.4 Hz)

REFERENCE EXAMPLE 118-2

4-[(4-{[1-(Trifluoroacetyl)-4-piperidinyl]methyl}phenyl)sulfonyl]morpholine

Morpholine (0.88 ml, 10.1 mmol) was added to a solution of the title compound of reference example 118-1 (1.5 g, 4.1 mmol) in THF (10 ml) at 0° C. The mixture was stirred at room temperature for 1 h. The resulting mixture was diluted with 1N hydrochloric acid (50 ml). The whole was extracted with ethyl acetate (50 ml). The organic layer was washed with saturated sodium chloride solution (50 ml) and dried over anhydrous sodium sulfate. The solvent was removed in vacuo. The residue was purified by flash column chromatography (silica gel 20 g, ethyl-acetate/hexane=1/5 to 1/1) to give the title compound (1.37 g, 80%) as pale yellow oil.

$^1$H NMR (CDCl$_3$) δ 1.17-1.38 (2H, m), 1.73-1.94 (3H, m), 2.66 (2H, d, J=7.0 Hz), 2.68-2.78 (1H, m), 3.00 (4H, t, J=4.8 Hz), 3.01-3.15 (1H, m), 3.76 (4H, t, J=4.8 Hz), 3.98-4.10 (1H, m), 4.53-4.60 (1H, m), 7.33 (2H, d, J=8.4 Hz), 7.69 (2H, d, J=8.4 Hz)

REFERENCE EXAMPLE 118-3

4-{[4-(4-Piperidinylmethyl)phenyl]sulfonyl}morpholine

A mixture of the title compound of reference example 118-2 (1.3 g, 3 mmol), 1M aqueous potassium carbonate (10 ml) and methanol (20 ml) was stirred at room temperature for 5 h. The mixture was diluted with saturated sodium chloride solution (20 ml) and extracted with dichloromethane (20 ml×2) and diethyl ether (20 ml) successively. The extracts were dried over anhydrous magnesium sulfate and concentrated in vacuo to give the title compound (937 mg, 48%) as colorless crystalline powder.

$^1$H NMR (CDCl$_3$) δ 1.21-1.82 (5H, m)), 2.60-2.71 (4H, m), 3.00 (4H, t, J=4.8 Hz), 3.19-3.26 (2H, m), 3.75 (4H, t, J=4.8 Hz), 5.08 (1H, brs), 7.32 (2H, d, J=8.4 Hz), 7.67 (2H, d, J=8.4 Hz)

REFERENCE EXAMPLE 119-1

4-{[1-(Trifluoroacetyl)-4-piperidinyl]methyl}benzonitrile

To a solution of the title compound of reference example 93 (2 g, 8.5 mmol) in water (10 ml) was added dropwise 1N aqueous sodium hydroxide solution (12.7 ml) at 0° C. The resulting mixture was extracted with ethyl acetate (100 ml). The extract was washed with saturated sodium chloride solution (500 ml), dried over sodium sulfate and concentrated in vacuo to give 4-(4-cyanobenzyl)piperidine (1.7 g, 100%). Trifluoroacetic anhydride (20 ml) was added to a solution of 4-(4-cyanobenzyl)piperidine (1.7 g, 8.5 mmol) prepared above in dichloromethane (5 ml). The mixture was stirred at room temperature for 7 h. The whole was concentrated in vacuo and the resulting residue was purified by flash column chromatography (silica gel 25 g, ethyl acetate/hexane=1/5 to 1/2) to give the title compound (2.3 g, 100%) as pale yellow oil.

$^1$H NMR (CDCl$_3$) δ 1.16-1.36 (2H, m), 1.73-2.00 (3H, m), 2.64 (2H, d, J=7.0 Hz), 2.66-2.77 (1H, m), 3.00-3.14 (1H, m), 3.97-4.05 (1H, m), 4.50-4.59 (1H, m), 7.26 (2H, d, J=8.2 Hz), 7.60 (2H, d, J=8.2 Hz)

REFERENCE EXAMPLE 119-2

4-[4-(2H-Tetrazol-5-yl)benzyl]-1-(trifluoroacetyl)piperidine

A mixture of the title compound of reference example 119-1 (2.1 g, 7.64 mmol), trimethylsilyl azide (2.01 ml, 15.3 mmol), dibutyltin oxide (46 mg, 3.7 mmol) and toluene (20 ml) was stirred at 100° C. for 20 h. After having been cooled, 1N hydrochloric acid (20 ml) was added and the mixture was stirred at room temperature for 0.5 h. The resulting solution was extracted with ethyl acetate (20 ml×2). The extracts were washed with saturated sodium chloride solution (50 ml), dried over anhydrous sodium sulfate and concentrated in vacuo. The residue was crystallized from diisopropyl ether to give the title compound (1.6 g, 60%) as a colorless powder.

$^1$H NMR (CDCl$_3$) δ 1.20-1.40 (2H, m), 1.70-2.00 (3H, m), 2.56-2.81 (3H, m), 3.06-3.18 (1H, m), 4.00-4.06 (1H, m), 4.52-4.5 (1H, m) 9, 7.31 (2H, d, J=8.4 Hz), 8.10 (2H, d, J=8.4 Hz)

REFERENCE EXAMPLE 119-3

1-(Trifluoroacetyl)-4-[4-(2-trityl-2H-tetrazol-5-yl)benzyl]piperidine

A mixture of the title compound of reference example 119-2, sodium hydride (60% in oil, 201.2 mg, 5.03 mmol) and DMF (15 ml) was stirred at room temperature for 1 h. Tritylchloride (1.27 g, 4.57 mmol) was to the resulting solution. Then, the mixture was stirred at room temperature for 2 h. Ethyl acetate (20 ml) was added to the mixture and the whole was washed with water (50 ml×2), saturated sodium chloride solution (50 ml) successively. The organic layer was dried over anhydrous sodium sulfate and concentrated in vacuo. The residue was crystallized from diisopropyl ether (20 ml) to give the title compound (2.3 g, 85%) as a colorless powder.

$^1$H NMR (CDCl$_3$) δ 1.15-1.34 (2H, m), 1.63-2.00 (3H, m), 2.61 (2H, d, J=6.6 Hz), 2.63-2.76 (1H, m), 2.99-3.10 (1H, m), 3.95-4.02 (1H, m), 4.49-4.56 (1H, m), 7.14-7.41 (17H, m), 8.08 (2H, d, J=8.0 Hz)

REFERENCE EXAMPLE 119-4

4-[4-(2-Trityl-2H-tetrazol-5-yl)benzyl]piperidine 1N aqueous sodium hydroxide (34.4 ml) was added dropwise to a solution of the title compound of reference example 119-3 (1 g, 1.7 mmol) in ethanol/dichloromethane (4/1, 50 ml). The resulting solution was stirred at room temperature for 2 h. The whole was poured into water (100 ml) and the mixture was extracted with ethyl acetate (100 ml×2). The resulting extracts were washed with saturated sodium chloride solution (100 ml), dried over anhydrous magnesium sulfate and concentrated in vacuo. The residue was crystallized from diisopropyl ether (20 ml) to give the title compound (374 mg, 45%) as a colorless crystalline powder.

$^1$H NMR (CDCl$_3$) δ 1.40-1.78 (5H, m), 2.61 (2H, d, J=5.8 Hz), 2.63-2.74 (2H, m), 3.26-3.31 (2H, m), 4.20-4.60 (1H, m), 7.14-7.36 (17H, m), 8.06 (2H, d, J=8.0 Hz)

REFERENCE EXAMPLE 120-1

N,N-Diethyl-4-{[1-(trifluoroacetyl)-4-piperidinyl]methyl}benzenesulfonamide

The title compound was prepared from diethylamine using a similar method to that described for reference example 118-2. Yield 75%.

$^1$H NMR (CDCl$_3$) δ 1.17 (6H, t, J=7.0 Hz), 1.21-1.36 (2H, m), 1.64-1.93 (3H, m), 2.63 (2H, d, J=7.0 Hz), 2.65-2.77 (1H, m), 2.99-3.13 (1H, m), 3.24 (4H, q, J=7.0 Hz), 3.96-4.03 (1H, m), 4.49-4.58 (1H, m), 7.26 (2H, d, J=8.4 Hz), 7.74 (2H, d, J=8.4 Hz)

REFERENCE EXAMPLE 120-2

N,N-Diethyl-4-(4-piperidinylmethyl)benzenesulfonamide

The title compound was prepared from the title compound of reference example 120-1 using a similar method to that described for reference example 118-3. Yield 78%.

$^1$H NMR (CDCl$_3$) δ 1.13 (6H, t, J=7.0 Hz), 1.66-1.30 (2H, m), 1.59-1.72 (3H, m), 2.48-2.63 (5H, m), 3.06-3.12 (2H, m), 3.24 (4H, q, J=7.0 Hz), 7.25 (2H, d, J=8.4 Hz), 7.71 (2H, d, J=8.4 Hz)

REFERENCE EXAMPLE 121-1

4-[4-(1-Piperidinylsulfonyl)benzyl]-1-(trifluoroacetyl)piperidine

The title compound was prepared from piperidine using a similar method to that described for reference example 118-2. Yield 95%.

$^1$H NMR (CDCl$_3$) δ 1.16-2.09 (11H, m), 2.65 (2H, d, J=7.4 Hz), 2.67-2.78 (1H, m), 2.90-3.14 (5H, m), 3.97-4.04 (1H, m), 4.50-4.59 (1H, m), 7.29 (2H, d, J=8.8 Hz), 7.69 (2H, d, J=8.8 Hz)

REFERENCE EXAMPLE 121-2

1-{[4-(4-Piperidinylmethyl)phenyl]sulfonyl}piperidine

The title compound was prepared from the title compound of reference example 121-1 using a similar method to that described for reference example 118-3. Yield 71%.

$^1$H NMR (CDCl$_3$) δ 1.10-1.74 (10H, m), 2.21 (2H, s), 2.50-2.62 (4H, m), 2.89-3.11 (6H, m), 7.29 (2H, d, J=8.4 Hz), 7.66 (2H, d, J=8.4 Hz)

REFERENCE EXAMPLE 122-1

4-[4-(1-Pyrrolidinylsulfonyl)benzyl]-1-(trifluoroacetyl)piperidine

The title compound was prepared from pyrrolidine using a similar method to that described for reference example 118-2. Yield 89%.

$^1$H NMR (CDCl$_3$) δ 1.16-1.37 (2H, m), 1.73-2.00 (7H, m), 2.65 (2H, d, J=7.0 Hz), 2.71-2.77 (1H, m), 3.00-3.14 (1H, m), 3.22-3.29 (4H, m), 3.97-4.04 (1H, m), 4.50-4.59 (1H, m), 7.29 (2H, d, J=8.2 Hz), 7.77 (2H, d, J=8.2 Hz)

REFERENCE EXAMPLE 122-2

4-[4-(1-Pyrrolidinylsulfonyl)benzyl]piperidine

The title compound was prepared from the title compound of reference example 122-1 using a similar method to that described for reference example 118-3. Yield 88%.

$^1$H NMR (CDCl$_3$) δ 1.19-1.38 (2H, m), 1.54-1.87 (8H, m), 2.54-2.76 (4H, m), 3.12-3.25 (6H, m), 7.29 (2H, d, J=8.4 Hz), 7.74 (2H, d, J=8.4 Hz)

REFERENCE EXAMPLE 123-1 tert-Butyl 4-(4-methoxycarbonylbenzyl)piperidine-1-carboxylate

A mixture of methyl 4-(bromomethyl)benzoate (25 g, 109 mmol) and triethyl phosphate (24.3 ml, 142 mmol) was stirred at 150° C. for 24 h. The resulting mixture was purified by distillation (165-172° C., 1 mmHg) to obtain diethyl 4-(methoxycarbonyl)benzylphosphonate (21.5 g, 69%).

To a mixture of diethyl 4-(methoxycarbonyl)benzylphosphonate (20.5 g, 71.5 mmol), 15-crown-5 (1.4 ml, 7.1 mmol) and THF (120 ml) was added sodium hydride (60% in oil, 2.9 g, 71.5 mmol) at 0° C. The mixture was stirred at 0° C. for 0.5 h. A solution of tert-butyl 4-oxo-1-piperidinecarboxylate (11.9 g, 59.6 mmol) in THF (45 ml) was added dropwise to the resulting mixture over period of 10 min at 0° C. The mixture was stirred at room temperature for 20 h. The resulting mixture was poured into ice-water (200 ml) and the whole was extracted with ethyl acetate (100 ml×2). The extracts were washed with 5% aqueous sodium bicarbonate (100 ml), saturated sodium chloride solution (100 ml) successively. The organic layer was dried over anhydrous sodium sulfate and concentrated in vacuo. The residue was purified by flash column chromatography (silica gel 200 g, ethyl acetate/hexane=1/10) followed by recrystallization from hexane to give tert-butyl 4-(4-methoxycarbonylbenzylidene)piperidine-1-carboxylate (6.9 g, 35%) as a colorless crystalline powder. A mixture of tert-butyl 4-(4-methoxycarbonylbenzylidene)piperidine-1-carboxylate (6 g, 18 mmol) in methanol (150 ml) was hydrogenated over 10% palladium carbon (50% wet, 1 g) for 5 h at room temperature. The catalyst was, removed by filtration and the filtrate was concentrated in vacuo. The residue was purified by flash column chromatography (silica gel 90 g, ethyl acetate/hexane=1/10) to obtain the title compound (6.1 g, 100%) as pale yellow oil.

$^1$H NMR (CDCl$_3$) δ 1.05-1.42 (2H, m), 1.45 (9H, s), 1.55-1.77 (3H, m), 2.59 (2H, d, J=7.0 Hz), 2.57-2.69 (2H, m), 3.91 (3H, s), 4.04-4.18 (2H, m), 7.21 (2H, d, J=8.0 Hz), 7.96 (2H, d, J=8.0 Hz).

REFERENCE EXAMPLE 123-2

4-{[1-(tert-butoxycarbonyl)-4-piperidinyl]methyl}benzoic acid

A mixture of the title compound of reference example 123-1 (3 g, 9 mmol), ethanol (30 ml) and 1N aqueous sodium hydroxide (14 ml) was stirred at 80° C. for 5 h and the resulting mixture was concentrated in vacuo. The residue was purified by flash column chromatography (silica gel 100 g, ethyl acetate/methanol=10/1) to give the title compound (2.9 g, 99%) as a colorless crystalline powder.

¹H NMR (CDCl₃) δ 1.08-1.26 (2H, m), 1.45 (9H, s), 1.57-1.77 (3H, m), 1.26-2.70 (2H, m), 2.61 (2H, d, J=7.4 Hz), 4.05-4.11 (2H, m), 7.24 (2H, d, J=8.0 Hz), 8.03 (2H, d, J=8.0 Hz)

REFERENCE EXAMPLE 123-3 tert-Butyl 4-[4-(aminocarbonyl)benzyl]-1-piperidinecarboxylate

1-Hydroxy-1H-benzotriazole (3.6 g, 27 mmol), ammonium chloride (1.9 g, 35.1 mmol), triethylamine (4.9 ml, 35.1 ml) and 1-ethyl-3-(3-dimethylaminopropyl)carbodimide hydrochloride (6.7 g, 35.1 mmol) were added to a solution of the title compound of reference example 123-2 (8.6 g, 22.7 mmol) in DMF (160 ml) at 0° C. and the resulting mixture was stirred at room temperature for 20 h. The whole was concentrated in vacuo. To the residue was added water (200 ml) and this mixture was extracted with ethyl acetate (200 ml×2). The extracts were washed with 0.5 M hydrochloric acid (200 ml), 5% aqueous sodium bicarbonate (200 ml) and saturated sodium chloride solution (100 ml) successively. The organic layer was dried over anhydrous sodium sulfate and concentrated in vacuo. The residue was purified by flash column chromatography (silica gel 200 g, ethyl acetate/hexane=1/1 to 3/1) followed by recrystallization from hexane to give the title compound (8.1 g, 94%) as a colorless crystalline powder.

¹H NMR (CDCl₃) δ 1.05-1.25 (2H, m), 1.45 (9H, s), 1.56-1.76 (3H, m), 2.59 (2H, d, J=2.0 Hz), 2.57-2.69 (2H, m), 4.04-4.10 (2H, m), 5.50-6.20 (2H, br), 7.22 (2H, d, J=8.4 Hz), 7.74 (2H, d, J=8.4 Hz)

REFERENCE EXAMPLE 123-4

4-(4-Piperidinylmethyl)benzamide hydrochloride

A solution of 4N hydrogen chloride in ethyl acetate (120 ml) was added to a solution of the title compound of reference example 123-3 (8.1 g, 25.4 mmol) in methanol (120 ml) and the mixture was stirred at room temperature for 3 h. The resulting solution was concentrated in vacuo. The residue was crystallized from isopropanol-ethyl acetate (1/1, 20 ml) to give the title compound (5.97 g, 73%) as a colorless crystalline powder.

¹H NMR (CD₃OD) δ 1.25-1.56 (2H, m), 1.82-2.01 (3H, m), 2.68 (2H, d, J=6.8 Hz), 2.88-3.01 (2H, m), 3.30-3.40 (2H, m), 7.31 (2H, d, J=8.4 Hz), 7.82 (2H, d, J=8.4 Hz)

REFERENCE EXAMPLE 124-1 tert-Butyl 4-(4-[(dimethylamino)carbonyl]benzyl)-1-piperidinecarboxylate

The title compound was prepared from dimethylamine hydrochloride using a similar method to that described for reference example 123-3. Yield 98%.

¹H NMR (CDCl₃) δ 1.10-1.30 (2H, m), 1.45 (9H, s), 1.58-1.70 (3H, m), 2.55 (2H, d, J=7.0 Hz), 2.63-2.69 (2H, m), 3.00 (3H, brs), 3.10 (3H, brs), 4.04-4.18 (2H, m), 7.16 (2H, d, J=8.2 Hz), 7.35 (2H, d, J=8.2 Hz)

REFERENCE EXAMPLE 124-2

N,N-Dimethyl-4-(4-piperidinylmethyl)benzamide

A solution of 4N hydrogen chloride in ethyl acetate (20 ml) was added to a solution of the title compound of reference example 124-1(367 mg, 1.06 mmol) in methanol (10 ml) and the mixture was stirred at room temperature for 3 h. The resulting solution was concentrated in vacuo. To a solution of this residue in water (20 ml) was added 1N aqueous sodium hydroxide (5 ml) at 0° C. The resulting solution was diluted with saturated sodium chloride solution (20 ml). The whole was extracted with dichloromethane (20 ml×3). The organic layers were dried over potassium carbonate and concentrated in vacuo to obtain the title compound (88.4 mg, 34%) as pale yellow amorphous powder.

¹H NMR (CDCl₃) δ 1.09-1.26 (2H, m), 1.59-1.65 (3H, m), 1.80-2.00 (1H, m), 2.49-2.60 (4H, m). 3.01-3.09 (8H, m), 7.16 (2H, d, J=8.0 Hz), 7.34 (2H, d, J=8.0 Hz)

REFERENCE EXAMPLE 125-1

N-Isopropyl-N-methyl-4-{[1-(trifluoroacetyl)-4-piperidinyl]methyl}benzenesulfonamide The title compound was prepared from isopropylmethylamine using a similar method to that described for reference example 118-2. Yield 99%.

¹H NMR (CDCl₃) δ 0.98 (6H, d, J=7.0 Hz) 1.09-1.36 (2H, m), 1.71-1.93 (3H, m), 2.64 (2H, d, J=7.4 Hz), 2.68-2.77 (1H, m), 2.72 (3H, s), 2.99-3.14 (1H, m), 3.96-4.03 (1H, m), 4.22 (1H, septet, J=7.0 Hz), 4.48-4.58 (1H, m), 7.27 (2H, d, J=8.0 Hz), 7.74 (2H, d, J=8.0 Hz)

REFERENCE EXAMPLE 125-2

N-Isopropyl-N-methyl-4-(4-piperidinylmethyl)benzenesulfonamide

The title compound was prepared from the title compound of reference example 125-1 using a similar method to that described for reference example 118-3. Yield 30%.

¹H NMR (CDCl₃) δ 0.99 (6H, d, J=7.0 Hz), 1.60-1.90 (6H, m), 2.67 (2H, d, J=5.0 Hz), 2.71 (3H, s), 2.73-2.85 (2H, m), 3.42-3.49 (2H, m), 4.22 (1H, septet, J=7.0 Hz), 7.25 (2H, d, J=8.4 Hz), 7.74 (2H, d, J=8.4 Hz)

REFERENCE EXAMPLE 126-1

4-[(1-Acetyl-4-piperidinyl)methyl]-N-isopropylbenzenesulfonamide

The title compound was prepared from isopropylamine using a similar method to that described for reference example 116-1. Yield 88%.

¹H NMR (CDCl₃) δ 1.09 (6H, d, J=6.6 Hz), 1.10-1.30 (2H, m), 1.64-1.94 (3H, m), 2.08 (3H, s), 2.40-2.56 (1H, m), 2.62 (2H, dd, J=7.0 Hz, 2.2 Hz), 2.89-3.06 (1H, m), 3.39-3.52 (1H, m), 3.70-3.85 (1H, m), 4.50-4.70 (1H, m), 4.61 (1H, d, J=7.6 Hz), 7.27 (2H, d, J=8.4 Hz), 7.81 (2H, d, J=8.4 Hz)

REFERENCE EXAMPLE 126-2

N-Isopropyl-4-(4-piperidinylmethyl)benzenesulfonamide hydrochloride

The title compound was prepared from the title compound of reference example 126-1 using a similar procedure to that described for reference example 83-2. Yield 62%.

¹H NMR (CD₃OD) δ 1.01 (6H, d, J=6.6 Hz), 1.42-1.56 (2H, m), 1.82-2.01 (3H, m), 2.72 (2H, d, J=7.0 Hz), 2.89-3.04 (2H, m), 3.27-3.40 (3H, m), 7.40 (2H, d, J=8.0 Hz), 7.79 (2H, d, J=8.0 Hz)

REFERENCE EXAMPLE 127-1

4-[(1-Acetyl-4-piperidinyl)methyl]-N-(4-fluorophenyl)benzenesulfonamide

The title compound was prepared from 4-fluoroaniline using a similar method to that described for reference example 116-1.

Yield 81%. ¹H NMR (CDCl₃) δ 1.03-1.30 (2H, m), 1.58-1.81 (3H, m), 2.09 (3H, s), 2.41-2.54 (1H, m), 2.58 (2H, d, J=6.8 Hz), 2.90-3.05 (1H, m), 3.75-3.82 (1H, m), 4.56-4.64 (1H, m), 6.89-7.11 (4H, m), 7.10 (2H, d, J=8.0 Hz), 7.30 (1H, brs), 7.66 (2H, d, J=8.0 Hz)

REFERENCE EXAMPLE 127-2

N-(4-Fluorophenyl)-4-(4-piperidinylmethyl)benzenesulfonamide hydrochloride

The title compound was prepared from the title compound of reference example 127-1 using a similar procedure to that described for reference example 83-2. Yield 100%.

¹H NMR (CD₃OD) 1.21-1.50 (2H, m), 1.76-1.99 (3H, m), 2.65 (2H, d, J=7.0 Hz), 2.86-2.97 (2H, m), 3.30-3.38 (2H, m), 6.89-7.09 (2H, m), 7.23-7.34 (3H, m), 7.40-7.49 (1H, m), 7.60-7.77 (2H, m)

REFERENCE EXAMPLE 128-1

N-Methoxy-N-methyl-4-{[1-(trifluoroacetyl)-4-piperidinyl]methyl}benzenesulfonamide The title compound was prepared from O,N-dimethylhydroxyamine using a similar method to that described for reference example 118-2. Yield 97%.

¹H NMR (CDCl₃) δ 1.17-1.43 (2H, m), 1.73-1.95 (3H, m), 2.67 (2H, d, J=7.4 Hz), 2.72-2.77 (1H, m), 2.79 (3H, s), 2.97-3.14 (1H, m), 3.82 (3H, s), 3.97-4.04 (1H, m), 4.51-4.59 (1H, m), 7.34 (2H, d, J=8.4 Hz), 7.81 (2H, d, J=8.4 Hz)

REFERENCE EXAMPLE 128-2

N-Methoxy-N-methyl-4-(4-piperidinylmethyl)benzenesulfonamide

The title compound was prepared from the title compound of reference example 128-1 using a similar method to that described for reference example 118-3. Yield 99%.

¹H NMR (CDCl₃) δ 1.10-1.30 (2H, m), 1.50-1.96 (4H, m), 2.50-2.63 (2H, m), 2.62 (2H, d, J=7.0 Hz), 2.78 (3H, s), 3.05-3.11 (2H, m), 3.82 (3H, s), 7.33 (2H, d, J=8.4 Hz), 7.79 (2H, d, J=8.4 Hz)

REFERENCE EXAMPLE 129-1 tert-Butyl 4-{4-[(methylamino)carbonyl]benzyl}-1-piperidinecarboxylate

The title compound was prepared from methylamine hydrochloride using a similar method described for reference example 123-3. Yield 86%.

¹H NMR (CDCl₃) δ 1.04-1.25 (2H, m), 1.45 (9H, s), 1.56-1.79 (3H, m), 2.57 (2H, d, J=6.6 Hz), 2.63-2.69 (2H, m), 3.01 (3H, d, J=4.8 Hz), 4.04-4.10 (2H, m), 6.14 (1H, brs), 7.19 (2H, d, J=8.0 Hz), 7.68 (2H, d, J=8.0 Hz)

REFERENCE EXAMPLE 129-2

N-Methyl-4-(4-piperidinylmethyl)benzamide hydrochloride

The title compound was prepared from the title compound of reference example 129-1 using a similar method to that described for reference example 123-4. Yield 100%.

¹H NMR (CD₃OD) δ 1.30-1.60 (2H, m), 1.82-2.00 (3H, m), 2.68 (2H, d, J=7.0 Hz), 2.88-2.99 (2H, m), 2.91 (3H, s), 3.29-3.39 (2H, m), 7.30 (2H, d, J=8.4 Hz), 7.76 (2H, d, J=8.4 Hz)

REFERENCE EXAMPLE 130-1 tert-Butyl 4-{4-[(tert-butylamino)carbonyl]benzyl}-1-piperidinecarboxylate

1-Hydroxy-1H-benzotriazole (169 mg, 1.25 mmol), tert-butylamine (0.171 ml, 1.63 mmol) and 1-ethyl-3-(3-dimethylaminopropyl)carbodimide hydrochloride (312 mg, 1.63 mmol) were added to a solution of the title compound of reference example 123-2 (400 mg, 1.25 mmol) in DMF (6 ml) at 0° C. and the resulting mixture was stirred at room temperature for 15 h. The resulting mixture was poured into water (20 ml) and the whole was extracted with ethyl acetate (20 ml×2). The extracts were washed with 0.5N hydrochloric acid (20 ml), 5% aqueous sodium bicarbonate (20 ml) and saturated sodium chloride solution (20 ml) successively. The organic layer was dried over anhydrous sodium sulfate and concentrated in vacuo to give the title compound (419 mg, 89%) as a colorless crystalline powder.

¹H NMR (CDCl₃) δ 1.05-1.26 (2H, m), 1.45 (9H, s), 1.47 (9H, s), 1.55-1.80 (3H, m), 2.57 (2H, d, J=7.0 Hz), 2.62-2.69 (2H, m), 4.04-4.11 (2H, m), 5.91 (1H, brs), 7.18 (2H, d, J=8.0 Hz), 7.64 (2H, d, J=8.0 Hz)

REFERENCE EXAMPLE 130-2

N-(tert-Butyl)-4-(4-piperidinylmethyl)benzamide hydrochloride

The title compound was prepared from the title compound of reference example 130-1 using a similar method to that described for reference example 123-4. Yield 100%.

¹H NMR(CD₃OD) δ 1.32-1.45 (2H, m), 1.45 (9H, s), 1.82-2.00 (3H, m), 2.67 (2H, d, J=7.0 Hz), 2.86-3.00 (2H, m), 3.29-3.39 (2H, m), 7.27 (2H, d, J=8.0 Hz), 7.69 (2H, d, J=8.0 Hz)

REFERENCE EXAMPLE 131-1 tert-Butyl 4-[4-(4-morpholinylcarbonyl)benzyl]-1-piperidinecarboxylate

The title compound was prepared from morpholine using a similar method to that described for reference example 130-1. Yield 87%.

¹H NMR(CDCl₃) δ 1.04-1.25 (2H, m), 1.45 (9H, s), 1.57-1.76 (3H, m), 2.56 (2H, d, J=6.6 Hz), 2.89-2.9 (2H, m) 3.40-3.80 (8H, m), 4.04-4.10 (2H, m), 7.18 (2H, d, J=8.0 Hz), 7.36 (2H, d, J=8.0 Hz)

REFERENCE EXAMPLE 131-2

4-[4-(4Piperidinylmethyl)benzoyl]morpholine hydrochloride

The title compound was prepared from the title compound of reference example 131-1 using a similar method to that described for reference example 123-4. Yield 100%.

$^1$H NMR (CD$_3$OD) δ 1.37-1.54 (2H, m), 1.83-2.01 (3H, m), 2.67 (2H, d, J=7.0 Hz) 2.87-3.01 (2H, m), 3.32-3.89 (10H, m), 7.31 (2H, d, J=8.0 Hz), 7.38 (2H, d, J=8.0 Hz)

REFERENCE EXAMPLE 132-1 tert-Butyl 4-[4-(1-pyrrolidinylcarbonyl)benzyl]-1-piperidinecarboxylate

The title compound was prepared from pyrrolidine using a similar method to that described for reference example 130-1. Yield 88%.

$^1$H NMR (CDCl$_3$) δ 1.03-1.25 (2H, m), 1.45 (9H, s), 1.57-1.76 (3H, m), 1.84-2.05 (4H, m), 2.55 (2H, d, J=7.0 Hz), 2.63-2.69 (2H, m), 3.45 (2H, t, J=6.2 Hz), 3.64 (2H, t, J=6.2 Hz), 4.04-4.10 (2H, m), 7.14 (2H, d, J=8.0 Hz), 7.45 (2H, d, J=8.0 Hz)

REFERENCE EXAMPLE 132-2

4-[4-(1-Pyrrolidinylcarbonyl)benzyl]piperidine hydrochloride

The title compound was prepared from the title compound of reference example 132-1 using a similar method to that described for reference example 123-4. Yield 100%.

$^1$H NMR (CD$_3$OD) δ 1.34-1.54 (2H, m), 1.84-2.04 (7H, m), 2.68 (2H, d, J=7.0 Hz), 2.87-3.00 (2H, m), 3.31-3.40 (2H, m), 3.48 (2H, t, J=6.2 Hz), 3.61 (2H, t, J=6.2 Hz), 7.31 (2H, d, J=8.0 Hz), 7.49 (2H, d, J=8.0 Hz)

REFERENCE EXAMPLE 133-1

4-[(1-Acetyl-4-piperidinyl)methyl]-N-(5-methyl-3-isoxazolyl)benzenesulfonamide 2-amino-5-methyl-3-isoxazole (623 mg, 6.35 mmol) and pyridine (0.77 ml, 9.52 mmol) were added to a solution of 4-(1-acetylpiperidin-4-ylmethyl)benzenesulfonylchloride (1 g, 3.17 mmol) in THF (6 ml). The mixture was stirred at room temperature for 15 h. To the resulting mixture was added water (20 ml). The whole was extracted with dichloromethane (20 ml×2). The combined organic layers were washed with 0.5N hydrochloric acid (20 ml) and saturated sodium chloride solution (20 ml), dried over anhydrous sodium sulfate and concentrated in vacuo. The residue was purified by flash column chromatography (silica gel 25 g, ethyl acetate/hexane=3/1 to ethyl acetate) followed by crystallization from diisopropyl ether to give the title compound (815 mg, 68%) as a colorless powder.

$^1$H NMR (CDCl$_3$) δ 1.05-1.30 (2H, m), 1.62-1.78(3H, m), 2.08 (3H, s), 2.37 (3H, s), 2.42-2.62 (3H, m), 2.90-3.04 (1H, m), 3.75-3.82 (1H, m), 4.58-4.63 (1H, m), 6.25 (1H, s), 7.25 (2H, d, J=8.4 Hz), 7.77 (2H, d, J=8.4 Hz), 8.37 (1H, br)

REFERENCE EXAMPLE 133-2

N-(5-Methyl-3-isoxazolyl)-4-(4-piperidinylmethyl)benzenesulfonamide hydrochloride The title compound was prepared from the title compound of reference example 133-1 using a similar procedure to that described for reference example 83-2. Yield 88%.

$^1$H NMR (CD$_3$OD) δ 1.30-1.54 (2H, m), 1.80-2.01 (3H, m), 2.31 (3H, s), 2.69 (2H, d, J=7.0 Hz), 2.87-3.03 (2H, m), 3.31-3.38 (2H, m), 6.14 (1H, s), 7.40 (2H, d, J=8.4 Hz), 7.83 (2H, d, J=8.4 Hz)

REFERENCE EXAMPLE 134-1 tert-Butyl 4-[4-(methylsulfanyl)phenoxy]-1-piperidinecarboxylate

A solution of diethyl azodicarboxylate in toluene (6.76 ml, 14.9 mmol) was added dropwise to a mixture of tert-butyl 4-hydroxypiperidine-1-carboxylate (2 g, 9.94 mmol), 4-(Methylsulfanyl)phenol (2,8 g, 20 mmol), triphenylphosphine (3.9 g, 15 mmol) and THF (20 ml) over the period of 0.5 h at 0° C. The resulting solution was stirred at room temperature for 3 d. The mixture was diluted in ethyl acetate (20 ml) and the whole was washed with 1N aqueous sodium hydroxide (20 ml), 0.5N hydrochloric acid (20 ml) and saturated sodium chloride solution (20 ml). The organic layer was dried over anhydrous sodium sulfate and concentrated in vacuo. The residue was purified by flash column chromatography (silica gel 25 g, ethyl acetate/hexane=1/20 to 1/10) to give the title compound (1.8 g, 52%) as a colorless powder.

$^1$H NMR (CDCl$_3$) δ 1.47 (9H, s), 1.65-1.97 (4H, m), 2.44 (3H, s), 3.26-3.39 (2H, m), 3.63-3.79 (2H, m), 4.35-4.50 (1H, m), 6.85 (2H, d, J=8.8 Hz), 7.25 (2H, d, J=8.8 Hz)

REFERENCE EXAMPLE 134-2

4-[4-(Methylsulfanyl)phenoxy]piperidine hydrochloride

The title compound was prepared from the title compound of reference example 134-1 using a similar method to that described for reference example 123-4. Yield 91%.

$^1$H NMR (CDCl$_3$) δ 2.05-2.36 (4H, m), 2.45 (3H, s), 3.26-3.45 (4H, m), 4.58-4.70 (1H, m), 6.85 (2H, d, J=8.8 Hz), 7.26 (2H, d, J=8.8 Hz), 9.40-9.90 (2H, br)

REFERENCE EXAMPLE 135-1 tert-Butyl 4-[4-(methylsulfonyl)phenoxy]-1-piperidinecarboxylate m-Chloroperoxybenzoic acid (65%, 2.19 g, 8.25 mmol) was added to a solution of the title compound of reference example 134-1 (1.4 g, 3.93 mmol) in dichloromethane (10 ml) at 0° C. and the mixture was stirred at room temperature for 15 h. The resulting mixture was diluted in 5% aqueous sodium bicarbonate (20 ml) and the whole was extracted with dichloromethane (20 ml). The extract was washed with 5% aqueous sodium bicarbonate (20 ml) and saturated sodium chloride (20 ml), dried over anhydrous sodium sulfate and concentrated in vacuo. The residue was purified by flash column chromatography (silica gel 25 g, ethyl acetate/hexane=1/5 to 1/1) to give the title compound (1.3 g, 95%) as a colorless powder.

¹H NMR (CDCl₃) δ 1.47 (9H, s), 1.67-2.05 (4H, m), 3.04 (3H, s), 3.32-3.44 (2H, m), 3.63-3.76 (2H, m), 4.54-4.65 (1H, m), 7.03 (2H, d, J=8.8 Hz), 7.87 (2H, d, J=8.8 Hz)

REFERENCE EXAMPLE 135-2

4-[4-(Methylsulfonyl)phenoxy]piperidine hydrochloride

The title compound was prepared from the title compound of reference example 135-1 using a similar method to that described for reference example 123-4. Yield 95%.

¹H NMR (CD₃OD) δ 1.97-2.31 (4H, m), 3.09 (3H, s), 3.19-3.48 (5H, m), 7.22 (2H, d, J=9.0 Hz), 7.90 (2H, d, J=9.0 Hz)

REFERENCE EXAMPLE 136-1

N-(tert-Butyl)-4-{[1-(trifluoroacetyl)-4-piperidinyl]methyl}benzenesulfonamide

The title compound was prepared from tert-butylamine using a similar method to that described for reference example 118-2. Yield 100%.

¹H NMR (CDCl₃) δ 1.14-1.34 (2H, m), 1.23 (9H, s), 1.72-1.90 (3H, m), 2.63 (2H, d, J=6.6 Hz), 2.71-2.77 (1H, m), 2.93-3.12 (1H, m), 3.96-4.07 (1H, m), 4.42-4.58 (2H, m), 7.25 (2H, d, J=8.4 Hz), 7.82 (2H, d, J=8.4 Hz)

REFERENCE EXAMPLE 136-2

N-(tert-Butyl)-4-(4-piperidinylmethyl)benzenesulfonamide hydrochloride

A mixture of the title compound of reference example 136-1 (1 g, 2.5 mmol), 1M aqueous potassium carbonate (10 ml) and methanol (15 ml) was stirred at room temperature for 24 h. The resulting mixture was concentrated in vacuo. To the residue was added dichloromethane (20 ml) and potassium carbonate (2 g) and the mixture was stirred at 1 h. The precipitate was removed by filtration and the filtrate was concentrated in vacuo. A solution of 4N hydrogen chloride in ethyl acetate (20 ml) was added to a solution of the residue in methanol (15 ml) and the whole was concentrated in vacuo to obtain the title compound (880 mg, 100%) as pale yellow oil.

¹H NMR (CD₃OD) δ 1.17 (9H, s), 1.36-1.53 (2H, m), 1.82-1.99 (3H, m), 2.71 (2H, d, J=7.0 Hz), 2.88-3.08 (2H, m), 3.31-3.40 (2H, m), 7.38 (2H, d, J=8.4 Hz), 7.81 (2H, d, J=8.4 Hz)

REFERENCE EXAMPLE 137-1

1-Acetyl-4-[4-(ethylsulfonyl)benzyl]piperidine

The title compound was prepared using a similar procedure to that described in reference example 86-1 from 2-bromopropionic acid. Yield 61%.

¹H NMR (CDCl₃) δ 1.05-1.30 (2H, m), 1.29 (3H, t, J=7.2 Hz), 1.60-1.92 (3H, m), 2.09 (3H, s), 2.40-2.60 (1H, m), 2.65 (2H, dd, J=2.0, 7.4 Hz), 2.90-3.05 (1H, m), 3.12 (2H, q, J=7.2 Hz), 3.72-3.88 (1H, m), 4.55-4.70 (1H, m), 7.34 (2H, d, J=8.4 Hz), 7.83 (2H, d, J=8.4 Hz).

REFERENCE EXAMPLE 137-2

4-[4-(Ethylsulfonyl)benzyl]piperidine

The title compound was prepared using a similar procedure to that described in reference example 143-2 from the title compound of reference example 137-1. Yield 69%.

¹H NMR (CDCl₃) δ 1.05-1.30 (2H, m), 1.28 (3H, t, J=5.4 Hz), 1.55-1.78 (3H, m), 2.45-2.65 (4H, m), 3.00-3.15 (2H, m), 3.11 (2H, q, J=5.4 Hz), 7.34 (2H, d, J=8.4 Hz), 7.81 (2H, d, J=8.4 Hz).

REFERENCE EXAMPLE 138-1

1-Acetyl-4-[4-(propylsulfonyl)benzyl]piperidine

The title compound was prepared using a similar procedure to that described in reference example 86-1 from 2-bromobutyric acid. Yield 41%.

¹H NMR (CDCl₃) δ 1.01 (3H, t, J=7.2 Hz), 1.10-1.30 (2H, m), 1.60-1.90 (5H, m), 2.08 (3H, s), 2.40-2.60 (1H, m), 2.62-2.70 (2H, dd, J=2.2, 6.8 Hz), 2.90-3.15 (3H, m), 3.75-3.95 (1H, m), 4.57-4.70 (1H, m), 7.33 (2H, d, J=8.4 Hz), 7.83 (2H, d, J=8.4 Hz).

REFERENCE EXAMPLE 138-2

4-[4-(Propylsulfonyl)benzyl]piperidine

The title compound was prepared using a similar procedure to that described in reference example 143-2 from the title compound of reference example 138-1. Yield 93%.

¹H NMR (CDCl₃) δ 1.00 (3H, t, J=7.6 Hz), 1.60-1.90 (7H, m), 2.65-2.85 (4H, m), 3.00-3.13 (2H, m), 3.37-3.50 (2H, m), 7.33 (2H, d, J=8.4 Hz), 7.84 (2H, d, J=8.4 Hz).

REFERENCE EXAMPLE 139-1

1-Acetyl-4-[4-(butylsulfonyl)benzyl]piperidine

The title compound was prepared using a similar procedure to that described in reference example 86-1 from 2-bromovaleric acid. Yield 25%.

¹H NMR (CDCl₃) δ 0.90 (3H, t, J=7.4 Hz), 1.05-1.50 (4H, m), 1.60-1.93 (5H, m), 2.08 (3H, s), 2.39-2.58 (1H, m), 2.60-2.68 (2H, m), 2.90-3.14 (3H, m), 3.72-3.87 (1H, m), 4.55-4.69 (1H, m), 7.33 (2H, d, J=8.2 Hz), 7.83 (2H, d, J=8.2 Hz).

REFERENCE EXAMPLE 139-2

4-[4-(Butylsulfonyl)benzyl]piperidine

The title compound was prepared using a similar procedure to that described in reference example 143-2 from the title compound of reference example 139-1. Yield 74%.

¹H NMR (CDCl₃) δ 0.90 (3H, t, J=7.4 Hz), 1.05-1.47 (4H, m), 1.52-1.80 (5H, m), 2.45-2.65 (4H, m), 2.98-3.05 (4H, m), 7.33 (2H, d=J=8.4 Hz), 7.81 (2H, d, J=8.4 Hz).

REFERENCE EXAMPLE 140-1

1-Acetyl-4-(4-mercaptobenzyl)piperidine

To chlorosulfonic acid (3.1 mL) was added a solution of 1-acetyl-4-benzylpiperidine (2.0 g) in chloroform (5 mL) at 0° C. The mixture was stirred at same temperature for 1 hour and at room temperature for 30 min. The mixture poured into ice-water and extracted with chloroform. The extract was dried (MgSO$_4$) and concentrated to give 1-acetyl-4-(4-chlorosulfonyl)benzylpiperidine (1.87 g).

To a solution of conc.sulfonic acid (6.6 mL) in water (36 mL) was added slowly above compound (3 g) at 0° C. Powdered Zn (6.33 g) was added to the mixture in portions at room temperature. The whole was heated at 60° C. for 6 hours. After cooling to room temperature, water (40 mL) and dichloromethane (80 mL) was added to the mixture and the precipitate was filtered. The separated aqueous layer was extracted with dichloromethane (50 mL). Combined extracts were dried over MgSO$_4$ and concentrated to give the title compound (2.22 g, 8.92 mmol, 94%) as a colorless oil.

$^1$H NMR (CDCl$_3$) δ 1.00-1.25 (2H, m), 1.60-2.00 (3H, m), 2.07 (3H, s), 2.38-2.57 (3H, m), 2.88-3.03 (1H, m), 3.41 (1H, m), 3.72-3.83 (1H, m), 4.55-4.65 (1H, m), 7.01 (2H, d, J=8.4 Hz), 7.22 (2H, d, J=8.4 Hz).

REFERENCE EXAMPLE 140-2

1-Acetyl-4-[4-(isopropylsulfanyl)benzyl]piperidine

The title compound was prepared using a similar procedure to that described in reference example 143-1 from isopropyl iodide. Yield 77%.

$^1$H NMR (CDCl$_3$) δ 1.02-1.30 (2H, m), 1.29 (6H, d, J=6.6 Hz), 1.60-1.82 (3H, m), 2.07 (3H, s), 2.40-2.58 (3H, m), 2.90-3.05 (1H, m), 3.25-3.42 (1H, m), 3.70-3.85 (1H, m), 4.55-4.65 (1H, m), 7.06 (2H, d, J=8.0 Hz), 7.33 (2H, d, J=8.0 Hz).

REFERENCE EXAMPLE 140-3

1-Acetyl-4-[4-(isopropylsulfonyl)benzyl]piperidine

To a stirred solution of the title compound of reference example 140-2 (1.06 g) in dichloromethane (30 mL) was added m-chloroperoxybenzoic acid (1.89 g) at 0° C. After being stirred at room temperature for 3 hours, the mixture was diluted with dichloromethane (30 mL). The organic layer was washed with 5% sodium thiosulfate/sat.sodium bicarbonate (20 mL/20 mL twice), sat.sodium bicarbonate and brine (each 20 mL). Dried over MgSO$_4$, the solvent was removed in vacuo to give crude, which was chromatographed. Elution with ethyl acetate/methanol=10/1 afforded the title compound (1.12 g, 3.47 mmol, 95%) as a colorless oil.

$^1$H NMR (CDCl$_3$) δ 1.03-1.40 (2H, m), 1.29 (6H, d, J=6.8 Hz), 1.53-2.00 (3H, m), 2.07 (3H, s), 2.40-2.70 (3H, m), 2.82-3.05 (1H, m), 3.10-3.25 (1H, m), 3.70-3.85 (1H, m), 4.55-4.70 (1H, m), 7.32 (2H, d, J=8.2 Hz), 7.80 (2H, d, J=8.2 Hz).

REFERENCE EXAMPLE 140-4

4-[4-(Isopropylsulfonyl)benzyl]piperidine

The title compound was prepared using a similar procedure to that described in reference example 143-2 from the title compound of reference example 140-3. Yield 86%.

$^1$H NMR (CDCl$_3$) δ 1.07-1.25 (2H, m), 1.30 (6H, d, J=7.0 Hz), 1.55-1.78 (3H, m), 2.55 (2H, ddd, J=2.6, 12.0, 12.0 Hz), 2.62 (2H, d, J=6.8 Hz), 3.00-3.30 (3H, m), 7.33 (2H, d, J=8.4 Hz), 7.78 (2H, d, J=8.4 Hz).

REFERENCE EXAMPLE 141-1

1-Acetyl-4-[4-(cyclopentylsulfanyl)benzyl]piperidine

The title compound was prepared using a similar procedure to that described in reference example 143-1 from is cyclopentyl bromide. Yield 62%.

$^1$H NMR (CDCl$_3$) δ 1.00-1.25 (2H, m), 1.50-1.88 (9H, m), 1.92-2.10 (2H, m), 2.07 (3H, s), 2.40-2.58 (3H, m), 2.88-3.05 (1H, m), 3.48-3.63 (1H, m), 3.70-3.83 (1H, m), 4.55-4.65 (1H, m), 7.04 (2H, d, J=8.4 Hz), 7.29 (2H, d, J=8.4 Hz).

REFERENCE EXAMPLE 141-2

1-Acetyl-4-[4-(cyclopentylsulfonyl)benzyl]piperidine

The title compound was prepared using a similar procedure to that described in reference example 140-3 from the title compound of reference example 141-1. Yield 95%.

$^1$H NMR (CDCl$_3$) δ 1.05-1.30 (2H, m), 1.53-2.18 (12H, m), 2.08 (3H, s), 2.39-2.56 (1H, m), 2.64 (1H, dd, J=2.8, 7.2 Hz), 2.90-3.05 (1H, m), 3.40-3.58 (1H, m), 3.70-3.85 (1H, m), 4.55-4.68 (1H, m), 7.32 (2H, d, J=8.2 Hz), 7.82 (2H, d, J=8.2 Hz).

REFERENCE EXAMPLE 141-3

4-[4-(Cyclopentylsulfonyl)benzyl]piperidine

The title compound-was prepared using a similar procedure to that described in reference example 143-2 from the title compound of reference example 141-2. Yield 86%.

$^1$H NMR (CDCl$_3$) δ 1.05-1.19 (2H, m), 1.43-2.18 (11H, m), 2.45-2.63 (2H, m), 2.62 (2H, d, J=6.6 Hz), 2.99-3.11 (2H, m), 3.39-3.58 (1H, m), 7.32 (2H, d, J=8.2 Hz), 7.81 (2H, d, J=8.2 Hz).

REFERENCE EXAMPLE 142-1

1-Acetyl-4-[4-(isobutylsulfanyl)benzyl]piperidine

The title compound was prepared using a similar procedure to that described in reference example 143-1 from isobutyl iodide. Yield 80%.

$^1$H NMR (CDCl$_3$) δ 1.03 (6H, d, J=6.6 Hz), 1.05-1.25 (2H, m), 1.40-2.00 (4H, m), 2.07 (3H, s), 2.38-2.58 (3H, m), 2.79 (2H, d, J=6.6 Hz), 2.88-3.05 (1H, m), 3.70-3.85 (1H, m), 4.55-4.65 (1H, m), 7.04 (2H, d, J=8.0 Hz), 7.25 (2H, d, J=8.0 Hz).

REFERENCE EXAMPLE 142-2

1-Acetyl-4-[4-(isobutylsulfonyl)benzyl]piperidine

The title compound was prepared using a similar procedure to that described in reference example 140-3 from the title compound of reference example 142-1. Yield 96%.

$^1$H NMR (CDCl$_3$) δ 1.07 (6H, d, J=6.6 Hz), 1.10-1.30 (2H, m), 1.60-1.90 (3H, m), 2.08 (3H, s), 2.15-2.37 (1H, m), 2.40-2.58 (1H, m), 2.65 (2H, d, J=2.2, 7.0 Hz), 2.90-3.05 (1H, m), 2.99 (2H, d, J=6.2 Hz), 3.74-3.85 (1H, m), 4.55-4.69 (1H, 7.33 (2H, d, J=8.4 Hz), 7.83 (2H, d, J=8.4 Hz).

REFERENCE EXAMPLE 142-3

4-[4-(Isobutylsulfonyl)benzyl]piperidine

The title compound was prepared using a similar procedure to that described in reference example 143-2 from the title compound of reference example 142-2. Yield 85%.

$^1$H NMR (CDCl$_3$) δ 1.06 (6H, d, J=7.0 Hz), 1.08-1.32 (2H, m), 1.55-1.75 (3H, m), 2.03 (1H, brs), 2.15-2.35 (1H, m), 2.47-2.64 (2H, m), 2.62 (1H, d, J=6.6 Hz), 2.99 (2H, d, J=6.6 Hz), 3.00-3.14 (2H, m), 7.33 (2H, d, J=8.2 Hz), 7.81 (2H, d, J=8.2 Hz).

REFERENCE EXAMPLE 143-1

1-Acetyl-4-[4-(methylsulfanyl)benzyl]piperidine

To a stirred solution of the title compound of reference example 140-1 (2.22 g) in N,N-dimethylformamide (50 mL) was added methyliodide (0.72 mL), followed by potassium carbonate (2.4 g). After 15 hours, water (50 mL) was added and the mixture was extracted with ethyl acetate. The extract was washed with brine, dried over MgSO$_4$ and concentrated to give crude. Chromatography on silica gel (elution; ethyl acetate) afforded the title compound (2.03 g, 7.72 mmol, 87%) as a colorless oil.

$^1$H NMR (CDCl$_3$) δ 1.00-1.25 (2H, m), 1.60-1.75 (3H, m), 2.07 (3H, s), 2.40-2.57 (3H, m), 2.47 (3H, s), 2.88-3.03 (1H, m), 3.71-3.84 (1H, m), 4.54-4.65 (1H, m), 7.06 (2H, d, J=8.4 Hz), 7.21 (2H, d, J=8.4 Hz).

REFERENCE EXAMPLE 143-2

4-[4-(Methylsulfanyl)benzyl]piperidine

A mixture of the title compound of reference example 143-1 (1.98 g) in concentrated hydrochloric acid (10 mL) was heated under reflux for 6 hours. After cooling 0° C., 8N sodium hydroxide (20 mL) was added and the mixture was extracted with dichloromethane (40 mL, twice). Combined extracts were dried over potassium carbonate. The solvent was removed in vacuo to give the title compound (1.21 g, 5.48 mmol, 73%) as a colorless needle.

$^1$H NMR (CDCl$_3$) δ 1.08-1.34 (2H, m), 1.52-1.72 (3H, m), 2.47 (3H, s), 2.47-2.67 (4H, m), 3.02-3.15 (2H, m), 7.06 (2H, d, J=8.5 Hz), 7.19 (2H, d, J=8.5 Hz).

REFERENCE EXAMPLE 144-1 tert-Butyl 4-(4-phenylsulfanyl)-1-piperidinecarboxylate

A mixture of the title compound of reference example 58-1 (20.6 g), thiophenol (9 mL) and potassium carbonate (13.3 g) in N,N-dimethylformamide (300 mL) was heated at 45° C. for 15 hours. The solvent was removed in vacuo and the residue was partitioned between ethyl acetate and water (each 200 mL). The separated aqueous layer was extracted with ethyl acetate (150 mL) and combined organic layers were washed with 0.5N sodium hydroxide(100 mL, twice) and brine (100 mL). Dried over MgSO$_4$, the solvent was removed in vacuo to give crude, which was chromatographed. Elution with ethyl acetate/hexane=1/5 afforded the title compound (21.9 g, 74.7 mmol, 100%) as a pale yellow oil.

$^1$H NMR (CDCl$_3$) δ 1.45 (9H, s), 1.48-1.63 (2H, m), 1.84-2.00 (2H, m), 2.83-3.00 (2H, m), 3.21 (1H, tt, J=4.0, 8.2 Hz), 3.85-4.04 (2H, m), 7.24-7.36 (3H, m), 7.38-7.45 (2H, m).

REFERENCE EXAMPLE 144-2

4-(Phenylsulfanyl)piperidine hydrochloride

To a stirred solution of the title compound of reference example 144-1 (21.9 g) in methanol (100 mL) was added dropwise 4N hydrogen chloride in ethyl acetate (55 mL). After 2 hours, ethyl acetate (100 mL) was added and the organic solvent was removed in vacuo to give a colorless powder, which was washed with ethyl acetate to afford the title compound (12.3 g, 53.5 mmol, 72%).

$^1$H NMR (CD$_3$OD) δ 1.70-1.87 (2H, m), 2.03-2.27 (2H, m), 2.97-3.15 (2H, m), 3.25-3.53 (3H, m), 7.25-7.53 (5H, m).

REFERENCE EXAMPLE 144-3

4-(Phenylsulfanyl)-1-(trifluoroacetyl)piperidine

To a stirred solution of the title compound of reference example 144-2 (6.55 g) in water (15 mL) was added dropwise 8N sodium hydroxide and the mixture was stirred for 5 min. The mixture was extracted with dichloromethane (80 mL) and the extract was dried over potassium carbonate and concentrated to give a amine (5.62 g,) as a colorless oil.

To a stirred solution of above amine (5.62 g) and triethylamine (8.1 mL) in dichloromethane (80 mL) was added dropwise trifluoroacetic anhydride (6.2 mL) at 0° C. The mixture was stirred at 0° C. for 30 min and room temperature for 1 hour. Water was added to the mixture and the whole was extracted with dichloromethane. The extract was dried over MgSO$_4$ and concentrated to give crude. Chromatography on silica gel eluting with hexane/ethyl acetate=3/1 afforded the title compound (8.39 g, 28.9 mmol, 100%) as a colorless oil.

$^1$H NMR (CDCl$_3$) δ 1.53-1.75 (2H, m), 1.97-2.12 (2H, m), 3.10-3.42 (3H, m), 3.85-4.01 (1H, m), 4.15-4.30 (1H, m), 7.25-7.47 (5H, m).

REFERENCE EXAMPLE 144-4

4-[4-(Chlorosulfonyl)phenylsulfanyl]-1-(trifluoroacetyl)piperidine

To chlorosulfonic acid (9.7 mL) was added dropwise a solution of reference example 144-3 (8.39 g) in dichloromethane: (150 mL) at 0° C. After 1 hour, the mixture was warmed to room temperature and stirred for 1 hour. The reaction mixture was poured into crushed ice water (200 mL) and the whole was stirred for 20 min. the separated aqueous layer was extracted with dichloromethane. Combined organic layers were washed with sat.sodium bicarbonate (twice) and brine. Dried over MgSO$_4$, the solvent was removed in vacuo to give crude, which was chromatographed. Elution with ethyl acetate/hexane=1/3 afforded the title compound (7.73 g, 19.9 mmol, 69%) as a colorless powder.

$^1$H NMR (CDCl$_3$) δ 1.65-1.87 (2H, m), 2.10-2.25 (2H, m), 3.25-3.43 (2H, m), 3.60-3.77 (1H, m), 3.89-4.04 (1H, m), 4.15-4.31 (1H, m), 7.49 (2H, d, J=8.8 Hz), 7.95 (2H, d, J=8.8 Hz).

REFERENCE EXAMPLE 144-5

N,N-Dimethyl-4-{[1-(trifluoroacetyl)-4-piperidinyl]sulfanyl}benzensulfonamide

To a stirred solution of the title compound of reference example 144-4 (2.02 g) in tetrahydrofuran (40 mL) was added 50% dimethylamine (1.18 mL). After 10 min, 1N hydrochloric acid (10 mL) was added and the mixture was extracted with ethyl acetate. The extract was washed with brine, dried over MgSO$_4$ and concentrated to give crude. Chromatography on silica gel eluting with ethyl acetate/hexane=1/1 afforded the title compound (1.98 g, 5.00 mmol, 96%) as a colorless oil.

$^1$H NMR (CDCl$_3$) δ 1.62-1.82 (2H, m), 2.05-2.21 (2H, m), 2.72 (6H, s), 3.21-3.48 (2H, m), 3.52-3.65 (1H, m), 3.88-4.03 (1H, m), 4.15-4.30 (1H, m), 7.59 (2H, d, J=8.6 Hz), 7.71 (2H, d, J=8.6 Hz).

REFERENCE EXAMPLE 144-6

N,N-Dimethyl-4-{[1-(trifluoroacetyl)-4-piperidinyl]sulfonyl}benzensulfonamide

To a stirred solution of the title compound of reference example 144-5 (1.98 g) in N,N-dimethylformamide (15 mL) and acetonitrile (15 mL) was added m-chloroperoxybenzoic acid (2.16 g) and the mixture was stirred for 3 hours. 5% sodium thiosulfate and sat.sodium bicarbonate (each 15 mL) was added and the mixture was extracted with dichloromethane (30 mL). The extract was washed with 5% sodium thiosulfate and sat.sodium bicarbonate (15 mL+15 mL), sat.sodium bicarbonate (20 mL) and brine (30 mL). Dried over MgSO$_4$, the solvent was removed in vacuo to give a colorless powder, which was washed with diethyl ether to give the title compound (1.17 g, 2.73 mmol, 55%).

$^1$H NMR (DMSO) δ 1.40-1.65 (2H, m), 1.90-2.10 (2H, m), 2.68 (6H, s), 2.80-3.00 (1H, m), 3.10-3.30 (1H, m), 3.70-4.05 (2H, m), 4.30-4.45 (1H, m), 8.04 (2H, d, J=8.6 Hz), 8.12 (2H, d, J=8.6 Hz).

REFERENCE EXAMPLE 144-7

N,N-Dimethyl-4-(4-piperidinylsulfonyl)benzensulfonamide

To a stirred suspension of the title compound of reference example 144-6 (1.17 g) in methanol (16 mL) was added 1M potassium carbonate (8 mL). After 4 hours, the organic solvent was removed in vacuo and brine (30 mL) was added. The mixture was extracted with dichloromethane (30 mL, twice). The combined extracts were dried over potassium carbonate and evaporated under reduced pressure to give the title compound (0.683 g, 2.06 mmol, 75%) as a colorless powder.

$^1$H NMR (CDCl$_3$) δ 1.40-2.20 (4H, m) 2.50-2.70 (2H, m), 2.79 (6H, s), 3.00-3.35 (3H, m), 7.93-8.10 (4H, m).

REFERENCE EXAMPLE 145-1

N-Methoxy-N-methyl-4-{[1-(trifluoroacetyl)-4-piperidinyl]sulfanyl}benzensulfonamide To a stirred solution of N,O-dimethylhydroxyamine (0.835 g) and triethylamine (1.3 mL) in tetrahydrofuran (10 mL) was added a solution of the title compound of reference example 144-4 (1.66 g) in tetrahydrofuran (10 mL). After 2 hours, N,O-dimethylhydroxyamine (0.4 g) and diisopropylethylamine (0.82 mL) was added. After 14 hours, the mixture was diluted with water and extracted with ethyl acetate. The extract was washed with brine, dried over MgSO$_4$ and concentrated to give crude, which was chromatographed. Elution with hexane/chloroform/ethyl acetate=2/2/1 afforded the title compound (1.65 g, 4.00 mmol, 94%) as a colorless powder.

$^1$H NMR (CDCl$_3$) δ 1.62-1.85 (2H, m), 2.05-2.22 (2H, m), 2.79 (3H, s), 3.22-3.50 (2H, m), 3.54-3.70 (1H, m), 3.82 (3H, s), 3.85-4.05 (1H, m), 4.15-4.30 (1H, m), 7.48 (2H, d, J=8.4 Hz), 7.79 (2H, d, J=8.4 Hz).

REFERENCE EXAMPLE 145-2

N-Methoxy-N-methyl-4-{[1-(trifluoroacetyl)-4-piperidinyl]sulfonyl}benzensulfonamide The title compound was prepared using a similar procedure to that described in reference example 144-6 from the title compound of reference example 145-1. Yield 90%.

$^1$H NMR (CDCl$_3$) δ 1.70-1.95 (2H, m), 2.02-2.21 (2H, m), 2.73-2.90 (1H, m), 2.83(3H, s), 3.08-3.35(2H, m), 3.85(3H, s), 4.09-4.23 (1H, m), 4.58-4.73 (1H, m), 8.03-8.15 (4H, m).

REFERENCE EXAMPLE 145-3

N-Methoxy-N-methyl-4-(4-piperidinylsulfonyl)benzensulfonamide

The title compound was prepared using a similar procedure to that described in reference example 144-7 from the title compound of reference example 145-2. Yield 100%.

$^1$H NMR (CDCl$_3$) δ 1.63 (2H, ddd, J=4.0, 12.2, 12.2 Hz), 1.82-2.05 (2H, m), 2.58 (2H, ddd, J=2.4, 12.7, 12.7 Hz), 2.82 (3H, s), 3.00-3.28 (3H, m), 3.85 (3H, s), 8.07 (4H, s).

REFERENCE EXAMPLE 146-1

N,N-Diethyl-4-{[1-(trifluoroacetyl)-4-piperidinyl]sulfanyl}benzensulfonamide

The title compound was prepared using a similar procedure to that described in reference example 144-5 from diethylamine. Yield 100%.

$^1$H NMR (CDCl$_3$) δ 1.14 (6H, t, J=6.8 Hz), 1.60-1.80 (2H, m), 2.05-2.20 (2H, m), 3.25 (4H, q, J=6.8 Hz), 3.25-3.65 (3H, m), 3.87-4.03 (1H, m), 4.14-4.30 (1H, m), 7.45 (2H, d, J=8.6 Hz), 7.74 (2H, d, J=8.6 Hz).

REFERENCE EXAMPLE 146-2

N,N-Diethyl-4-{[1-(trifluoroacetyl)-4-piperidinyl]sulfonyl}benzensulfonamide

The title compound was prepared using a similar procedure to that described in reference example 144-6 from the title compound of reference example 146-1. Yield 87%.

$^1$H NMR (CDCl$_3$) δ 1.56 (6H, t, J=7.2 Hz), 1.65-1.90 (2H, m), 2.05-2.20 (2H, m), 2.71-2.90 (1H, m), 3.07-3.25 (2H, m), 3.30 (4H, q, J=7.2 Hz), 4.07-4.23 (1H, m), 4.57-4.72 (1H, m), 797-8.08 (4H, m).

REFERENCE EXAMPLE 146-3

N,N-Diethyl-4-(4-piperidinylsulfonyl)benzensulfonamide

The title compound was prepared using a similar procedure to that described in reference example 144-7 from the title compound of reference example 146-2. Yield 100%.

$^1$H NMR (CDCl$_3$) δ 1.16 (6H, t, J=7.4 Hz), 1.50-1.70 (2H, m), 1.90-2.05 (2H, m), 2.57 (2H, ddd, J=2.2, 12.4, 12.4 Hz), 2.97-3.25 (3H, m), 3.29 (4H, q, J=7.4 Hz), 8.01, (4H, s).

REFERENCE EXAMPLE 147-1

4-{[4-(1-Pyrrolidinylsulfonyl)phenyl]sulfanyl}-1-(trifluoroacetyl)piperidine

The title compound was prepared using a similar procedure to that described in reference example 144-5 from pyrrolidine. Yield 100%.

$^1$H NMR (CDCl$_3$) δ 1.60-1083 (6H, m), 2.04-2.20 (2H, m), 3.19-3.48 (6H, m), 3.50-3.64 (1H, m), 3.88-4.02 (1H, m), 4.17-4.30 (1H, m), 7.47 (2H, d, J=8.6 Hz), 7.76 (2H, d, J=8.6 Hz).

REFERENCE EXAMPLE 147-2

4-{[4-(1-Pyrrolidinylsulfonyl)phenyl]sulfonyl}-1-(trifluoroacetyl)piperidine

The title compound was prepared using a similar procedure to that described in reference example 144-6 from the title compound of reference example 147-1. Yield 91%.

$^1$H NMR(CDCl$_3$) δ 1.75-1.92(6H, m), 2.05-2.21 (2H, m), 2.72-2.90 (1H, m), 3.06-3.35 (6H, m), 4.07-4.23 (1H, m), 4.58-4.72 (1H, m), 8.05 (4H, s).

REFERENCE EXAMPLE 147-3

4-{[4-(1-Pyrrolidinylsulfonyl)phenyl]sulfonyl}piperidine

A mixture of the title compound of reference example 147-2 (1.07 g) and 1M potassium carbonate (10 mL) in N,N-dimethylformamide (20 mL) was heated at 50° C. for 1.5 hours. After cooling to room temperature, brine (20 ml) was added and the mixture was extracted with dichloromethane (60 mL, twice). Combined organic extracts were dried over potassium carbonate and concentrated to give the title compound (0.937 g, 2.62 mmol, 100%) as a colorless powder.

$^1$H NMR (CDCl$_3$) δ 1.53-1.70 (2H, m), 1.80-1.88 (4H, m), 1.94-2.17 (2H, m), 2.58 (2H, ddd, J=2.2, 12.6, 12.6 Hz), 3.00-3.35 (7H, m), 8.03 (4H, s).

REFERENCE EXAMPLE 148-1 tert-Butyl 4-[(4-nitrophenyl)sulfanyl]-1-piperidinecarboxylate

The title compound was prepared using a similar procedure to that described in reference example 144-1 from 4-nitrothiophenol. Yield 55%.

$^1$H NMR (CDCl$_3$) δ 1.46 (9H, s), 1.50-1.73 (2H, m), 1.96-2.10 (2H, m), 3.05 (2H, dd, J=3.2, 10.7, 13.6 Hz), 3.42-3.57 (1H, m), 3.90-4.10 (2H, m), 7.41 (2H, d, J=9.2 Hz), 8.15 (2H, d, J=9.2 Hz).

REFERENCE EXAMPLE 148-2 tert-Butyl 4-[(4-aminophenyl)sulfanyl]-1-piperidinecarboxylate

A mixture of the title compound of reference example 148-1 (13.9 g), hydrazine monohydrate (8 mL), activated carbon (2.65 g) and iron trichloride hexahydrate (1.11 g) in tetrahydrofuran (200 mL) was heated under reflux for 24 hours. After cooling to room temperature, the precipitate was filtered off and the filtrate was concentrated to give crude, which was chromatographed. Elution with hexane/ethyl acetate=3/2 afforded the title compound (11 g, 35.7 mmol, 87%) as a pale yellow powder.

$^1$H NMR (CDCl$_3$) δ 1.34-1.65 (2H, m), 1.44 (9H, s), 1.78-1.93 (2H, m), 2.73-3.01 (3H, m), 3.75 (2H, brs), 3.90-4.05 (2H, m), 6.62 (2H, d, J=8.6 Hz), 7.27 (2H, d, J=8.6 Hz).

REFERENCE EXAMPLE 148-3 tert-Butyl 4-{[4-(methylsulfonylamino)phenyl]sulfanyl}-1-piperidinecarboxylate

To a stirred solution of the title compound of reference example 148-2 (3.46 g) and methanesulfonyl chloride (0.92 ml) in tetrahydrofuran was added triethylamine (1.7 mL) at 0° C. The mixture was stirred at room temperature for 30 min. Water (30 mL) was added and the mixture was extracted with ethyl acetate. The extract was washed with 0.1N hydrochloric acid and brine (each 20 mL). The solvent was dried over MgSO$_4$ and concentrated to give crude. Chromatography on silica gel eluting with hexane/ethyl acetate=3/1 afforded the title compound (4.61 g, 11.9 mmol, 100%) as a colorless oil.

$^1$H NMR (CDCl$_3$) δ 1.40-1.65 (2H, m), 1.45(9H, s), 1.82-1.98 (2H, m), 2.91 (2H, ddd, J=2.8, 10.8, 13.6 Hz), 3.04 (3H, s), 3.15 (1H, tt, J=3.6, 10.8 Hz), 3.90-4.05 (2H, m), 6.71 (1H, brs), 7.17 (2H, d, J=8.8 Hz), 7.42 (2H, d, J=8.8 Hz).

REFERENCE EXAMPLE 148-4 tert-Butyl 4-{[4-(methylsulfonylamino)phenyl]sulfonyl}-1-piperidinecarboxylate

The title compound was prepared using a similar procedure to that described in reference example 140-3 from the title compound of reference example 148-3. Yield 90%.

$^1$H NMR (CDCl$_3$) δ 1.44(9H, s), 1.50-1.70(2H, m), 1.93-2.07 (2H, m), 2.57-2.76 (2H, m), 3.04 (1H, tt, J=3.8, 12.6 Hz), 3.15 (3H, s), 4.14-4.33 (2H, m), 7.37 (2H, d, J=8.8 Hz), 7.45 (1H, brs), 7.83 (2H, d, J=8.8 Hz).

REFERENCE EXAMPLE 148-5 tert-Butyl 4-({4-[methyl(methylsulfonyl)amino]phenyl}sulfonyl)-1-piperidinecarboxylate To a stirred solution of the title compound of reference example 148-3 (1.22 g) and methyl iodide (0.22 mL) in N,N-dimethylformamide (20 mL) was added potassium carbonate (0.602 g). After 17 hours, the mixture was partitioned between ethyl acetate and water. The separated organic layer was washed with brine, dried over MgSO$_4$ and concentrated to give a colorless powder, which was washed with diisopropyl ether to afford the title compound (1.03 g, 2.38 mmol, 82%).

¹H NMR (CDCl₃) δ 1.44 (9H, s), 1.49-1.77 (2H, m), 1.94-2.02 (2H, m), 2.56-2.76 (2H, m), 2.92 (3H, s), 2.95-3.15 (1H, m), 3.41 (3H, s), 4.17-4.37 (2H, m), 7.59 (2H, d, J=7.0 Hz), 7.88 (2H, d, J=7.0 Hz).

REFERENCE EXAMPLE 148-6

4-({4-[Methyl(methylsulfonyl)amino]phenyl}sulfanyl)piperidine hydrochloride

The title compound was prepared using a similar procedure to that described in reference example 144-2 from the title compound of reference example 148-5. Yield 69%.

¹H NMR (CD₃OD) δ 1.77-2.01 (2H, m), 2.13-2.48 (2H, m), 2.92-3.08 (2H, m), 2.99 (3H, s), 3.39 (3H, s), 3.43-3.61 (3H, m), 7.73 (2H, d, J=8.8 Hz), 7.93 (2H, d, J=8.8 Hz).

REFERENCE EXAMPLE 149-1 tert-Butyl 4-{[(4-fluorophenyl)sulfanyl]methyl}-1-piperidinecarboxylate

To a stirred solution of the title compound of reference example, 91-1 (2.57 g) and 4-fluorothiophenol (1.12 mL) in N,N-dimethylformamide (30 mL) was added potassium carbonate 1.57 g). After 26 hours, water (50 mL) was added and the mixture was extracted with ethyl acetate (50 mL+100 mL). Combined extracts were washed with brine and dried over MgSO₄. After removal of the solvent, the residue was purified by column chromatography on silica gel. Elution with ethyl acetate/hexane=1/5 afforded the title compound (2.63 g, 8.09 mmol, 92%) as a colorless powder.

¹H NMR (CDCl₃) δ 1.05-1.30 (3H, m), 1.45 (9H, s), 1.75-1.90 (2H, m), 2.55-2.75 (2H, m), 2.80 (2H, d, J=6.6 Hz), 4.02-4.20 (2H, m), 6.94-7.05 (2H, m), 7.26-7.38 (2H, m).

REFERENCE EXAMPLE 149-2

4-{[(4-Fluorophenyl)sulfanyl]methyl}-1-piperidinecarboxylate hydrochloride

The title compound was prepared using a similar procedure to that described in reference example 144-2 from the title compound of reference example 149-1. Yield 75%.

¹H NMR(CD₃OD) δ 1.32-1.58(2H, m), 1.63-1.90 (1H, m), 2.02-2.18 (2H, m), 2.85-3.02 (2H, m), 2.91 (2H, d, J=6.6 Hz), 3.30-3.43 (2H, m), 7.00-7.13 (2H, m), 7.38-7.48 (2H, m).

REFERENCE EXAMPLE 150-1 tert-Butyl 4-{[(4-fluorophenyl)sulfonyl]methyl}-1-piperidinecarboxylate

The title compound was prepared using a similar procedure to that described in reference example 144-6 from the title compound of reference example 149-1. Yield 78%.

¹H NMR (CDCl₃) δ 1.20-1.38 (2H, m), 1.45 (9H, s), 1.80-1.95 (2H, m), 2.05-2.24 (1H, m), 2.65-2.83 (2H, m), 3.01 (2H, d, J=6.2 Hz), 4.00-4.17 (2H, m), 7.21-7.32 (2H, m), 7.90-7.98 (2H, m).

REFERENCE EXAMPLE 150-2

4-{[(4-Fluorophenyl)sulfonyl]methyl}-1-piperidinecarboxylate hydrochloride

The title compound was prepared using a similar procedure to that described in reference example 144-2 from the title compound of reference example 150-1. Yield 75%.

¹H NMR (CD₃OD) δ 1.47-1.71 (2H, m), 2.06-2.40 (3H, m), 3.02 (2H, ddd, J=3.0, 12.8, 12.8 Hz), 3.23-3.43 (4H, m), 7.34-7.45 (2H, m), 7.95-8.05 (2H, m).

REFERENCE EXAMPLE 151

4-Fluoro-N-(3-{4-[4-(methylsulfonyl)benzyl]-1-piperidinyl}propyl)aniline

The title compound was prepared using a similar procedure to that described in reference example 1 from 4-[4-(methylsulfonyl)benzyl]piperidine and 4-fluoroaniline. Yield 79%.

¹H NMR (CDCl₃) δ 1.20-1.95 (9H, m), 2.44 (2H, t, J=6.8 Hz), 2.66 (2H, d, J=6.6 Hz), 2.89-3.00 (2H, m), 3.06 (3H, s), 3.12 (2H, t, J=6.4 Hz), 6.47-6.55 (2H, m), 6.81-6.95 (2H, m), 7.35 (2H, d, J=8.4 Hz), 7.86 (2H, d, J=8.4 Hz).

REFERENCE EXAMPLE 152

3-Ethyl-N-(3-{4-[4-(methylsulfonyl)benzyl]-1-piperidinyl}propyl)aniline

The title compound was prepared using a similar procedure to that described in reference example 1 from 4-[4-(methylsulfonyl)benzyl]piperidine and 3-ethylaniline. Yield 81%.

¹H NMR (CDCl₃) δ 1.22 (3H, t, J=6.6 Hz), 1.25-1.95 (9H, m), 2.44 (2H, t, J=6.88 Hz), 2.57 (2H, q, J=6.6 Hz), 2.65 (2H, d, J=6.2 Hz), 2.85-3.00 (2H, m), 3.06 (3H, s), 3.16 (2H, t, J=6.4 Hz), 6.37-6.45 (2H, m), 6.50-6.57 (1H, m), 7.03-7.18 (1H, m), 7.35 (2H, d, J=8.4 Hz), 7.85 (2H, d, J=8.4 Hz).

REFERENCE EXAMPLE 153

4-Ethyl-N-(3-{4-[4-(methylsulfonyl)benzyl]-1-piperidinyl}propyl)aniline

The title compound was prepared using a similar procedure to that described in reference example 1 from 4-[4-(methylsulfonyl)benzyl]piperidine and 4-ethylaniline. Yield 85%.

¹H NMR (CDCl₃) δ 1.19 (3H, t, J=7.6 Hz), 1.22-1.94 (9H, m), 2.43 (2H, t, J=6.8 Hz), 2.54 (2H, q, J=7.6 Hz), 2.65 (2H, d, J=6.6 Hz), 2.88-2.99 (2H, m), 3.06 (3H, s), 3.14 (2H, t, J=6.6 Hz), 6.54 (2H, d, J=8.8 Hz), 7.01 (2H, d, J=8.8 Hz), 7.35 (2H, d, J=8.4 Hz), 7.86 (2H, d, J=8.4 Hz).

REFERENCE EXAMPLE 154

4-Propyl-N-(3-{4-[4-(methylsulfonyl)benzyl]-1-piperidinyl}propyl)aniline

The title compound was prepared using a similar procedure to that described in reference example 1 from 4-[4-(methylsulfonyl)benzyl]piperidine and 4-propylaniline. Yield 54%.

¹H NMR (CDCl₃) δ 0.92 (3H, t, J=7.2 Hz), 1.20-1.95 (11H, m), 2.43 (2H, t, J=6.6 Hz), 2.47 (2H, t, J=7.4 Hz). 2.65

(2H, d, J=6.2 Hz), 2.87-3.00 (2H, m), 3.05 (3H, s), 3.14 (2H, t, J=6.6 Hz), 6.53 (2H, d, J=8.4 Hz), 6.99 (2H, d, J=8.4 Hz), 7.35 (2H, d, J=8.4 Hz), 7.86 (2H, d, J=8.4 Hz).

REFERENCE EXAMPLE 155

4-Butyl-N-(3-{4-[4-(methylsulfonyl)benzyl]-1-piperidinyl}propyl)aniline

The title compound was prepared using a similar procedure to that described in reference example 1 from 4-[4-(methylsulfonyl)benzyl]piperidine and 4-butylaniline. Yield 79%.

$^1$H NMR (CDCl$_3$) δ 0.91 (3H, t, J=7.2 Hz), 1.22-1.94 (13H, m), 2.43 (2H, t, J=6.6 Hz), 2.49 (2H, t, J=7.2 Hz), 2.65 (2H, d, J=6.2 Hz), 2.88-3.00 (2H, m), 3.05 (3H, s), 3.14 (2H, t, J=6.4 Hz), 6.53 (2H, d, J=8.4 Hz), 6.99 (2H, d, J=8.4 Hz), 7.35 (2H, d, J=8.4 Hz), 7.86 (2H, d, J=8.4 Hz).

REFERENCE EXAMPLE 156

4-tert-Butyl-N-(3-{4-[4-(methylsulfonyl)benzyl]-1-piperidinyl}propyl)aniline The title compound was prepared using a similar procedure to that described in reference example 1 from 4-[4-(methylsulfonyl)benzyl]piperidine and 4-tert-butylaniline. Yield 70%.

$^1$H NMR (CDCl$_3$) δ 1.22-1.93 (9H, m), 1.28 (9H, s), 2.43 (2H, t, J=6.6 Hz), 2.65 (2H, d, J=6.6 Hz), 2.83-3.00 (2H, m), 3.06 (3H, s), 3.14 (2H, t, J=6.4 Hz), 6.55 (2H, d, J=8.8 Hz), 7.21 (2H, d, J=8.8 Hz), 7.35 (2H, d, J=8.6 Hz), 7.86 (2H, d, J=8.6 Hz).

REFERENCE EXAMPLE 157

4-Cyclohexyl-N-(3-{4-[4-(methylsulfonyl)benzyl]-1-piperidinyl}propyl)aniline The title compound was prepared using a similar procedure to that described in reference example 1 from 4-[4-(methylsulfonyl)benzyl]piperidine and 4-cyclohexylaniline. Yield 61%.

$^1$H NMR (CDCl$_3$) δ 1.20-1.94 (19H, m), 2.30-2.45 (1H, m), 2.43 (2H, t, J=6.66 Hz), 2.65 (2H, d, J=6.2 Hz), 2.88-2.99 (2H, m), 3.05 (3H, s), 3.14 (2H, t, J=6.6 Hz), 6.53 (2H, d, J=8.4 Hz), 7.02 (2H, d, J=8.4 Hz), 7.35 (2H, d, J=8.1 Hz), 7.86 (2H, d, J=8.1 Hz).

REFERENCE EXAMPLE 158

1-(Methylsulfonyl)-4-piperidinecarbonylchloride

To a stirred suspension of the title compound of reference example 13-2 (51.81 g, 250 mmol) and DMF (0.194 mL, 2.50 mmol) in dichloromethane (250 mL) was added dropwise oxalyl chloride (32.0 mL, 375 mmol) at room temperature, and the reaction mixture was stirred at room temperature for 3 hours. The reaction mixture was evaporated under reduced pressure, petroleum ether (300 mL) was added, and the mixture was evaporated under reduced pressure. Petroleum ether (200 mL) was added to the residue. The resulting precipitate was collected by filtration, washed with petroleum ether (5×100 mL), and dried under reduced pressure to afford the title compound (54.54 g, 242 mmol, yield 97%).

REFERENCE EXAMPLE 159

N-(3-Chloropropyl)-1-(methylsulfonyl)-N-phenyl-4-piperidinecarboxamide

To a mixture of phenylformamide (49.6 g, 410 mmol), 1-bromo-3-chloropropane (75.4 g, 490 mmol) in acetone (400 mL) was added CsCO$_3$ (156.4 g, 480 mmol) and the resulting mixture was stirred at reflux temperature for 14 hours. The reaction mixture was filtered and the filtrate was concentrated under reduced pressure. Ethyl acetate (400 mL) and water (150 mL) were added to the residue and the organic layer was washed with brine (150 nL), dried over MgSO$_4$, and concentrated under reduced pressure. The residue was purified by silica gel column chromatography (n-hexane-ethyl acetate, 1/0 to 10/3, v/v) to give 3-chloropropyl(phenyl)formamide (69.1 g, 350 mmol) as pale yellow oil. Yield: 85%. To a solution of this pale yellow oil (36.2 g, 180 mmol) in 2-propanol (140 mL) was added conc. HCl (25 mL) and the mixture was stirred at 70° C. for 3 hours. The reaction mixture was cooled to r.t. and diisopropyl ether (140 mL), was added. The resulting mixture was allowed to stand at r.t. for 12 hours, that led precipitation of crystals. The crystals were collected by filtration and washed with diisopropyl ether (10 mL×2) to give N-(3-chloropropyl) aniline hydrochloride (13.7 g, 57 mmol) as colorless needles. The combined filtrates were concentrated under reduced pressure and recrystallized from diisopropyl ether-2-propanol (1/2, v/v) to give N-(3-chloropropyl) aniline hydrochloride (19.5 g, 81 mmol). Yield: 76%. From N-(3-chloropropyl)aniline hydrochloride (5.0 g, 21 mmol), using a similar procedure to that described for reference example 57, the title compound (7.0 g, 19 mmol) was obtained as colorless crystals. Yield: 90%.

$^1$H NMR (CDCl$_3$) δ 1.65-1.95 (4H, m), 2.03 (2H, qin, J=7.0 Hz), 2.20-2.40 (1H, m), 2.53 (2H, dt, J=3.0, 11.8 Hz), 2.73 (3H, s), 3.55 (2H, t, J=7.0 Hz), 3.71 (2H, dt, J=4.0, 12.4 Hz), 3.82 (2H, t, J=7.0 Hz), 7.10-7.25 (2H, m), 7.40-7.55 (3H, m).

REFERENCE EXAMPLE 160

3-Fluoro-N-(3-{4-[4-(methylsulfonyl)benzyl]-1-piperidinyl}propyl)aniline dihydrochloride Reference Example of the title compound from 4-[4-(methylsulfonyl)benzyl]piperidine and 3-fluoroaniline was carried out according to the procedure of reference example 1. Yield: 39%.

$^1$H NMR (CD$_3$OD) δ 1.40-1.70(2H, m), 1.80-2.30 (5H, m), 2.75 (2H, d, J=6.6 Hz), 2.80-3.05 (2H, m), 3.10 (3H, s), 3.15-3.25 (2H, m), 3.43 (2H, t, J=7.5 Hz), 3.58 (2H, d, J=12.6 Hz), 6.90-7.15 (3H, m), 7.40-7.55 (3H, m), 7.85-7.95 (2H, m) IR (KBr): 3275, 2925. 2635, 2485, 1610, 1595, 1495, 1455, 1410, 1300, 1255, 1145, 1090, 965, 945, 855, 770, 675, 555, 525 cm$^{-1}$.

REFERENCE EXAMPLE 161

N-(3-{4-[4-(Methylsulfonyl)benzyl]-1-piperidinyl}propyl)-4-(trifluoromethyl)aniline dihydrochloride Reference Example of the title compound from 4-[4-(methylsulfonyl)benzyl]piperidine and 4-(trifluoromethyl) aniline was carried out according to the procedure of reference example 1. Yield: 47%.

mp 130-134° C. ¹H NMR (CD₃OD) δ 1.40-1.70 (2H, m), 1.80-2.15 (5H, m), 2.75 (2H, d, J=7.0 Hz), 2.80-3.00 (2H, m), 3.10 (3H, s), 3.15-3.35 (4H, m), 3.56 (2H, d, J=11.8 Hz), 6.60-7.00 (2H, m), 7.35-7.50 (4H, m), 7.80-7.95 (4H, m) IR (KBr): 2940, 2635, 2470, 2410, 1615, 1595, 1455, 1435, 1410, 1330, 1300, 1145, 1125, 1065, 950, 850, 755, 545, 530 cm⁻¹.

REFERENCE EXAMPLE 162

3-Isopropyl-N-(3-{4-[4-(methylsulfonyl)benzyl]-1-piperidinyl}propyl)aniline dihydrochloride Reference Example of the title compound from 4-[4-(methylsulfonyl)benzyl]piperidine and 3-isopropylaniline was carried out according to the procedure of reference example 1. Yield: 61%.

mp 181-185° C. ¹H NMR (CD₃OD) δ 1.28 (6H, d, J=6.8 Hz), 1.55-1.75 (2H, m), 1.80-2.05 (3H, m), 2.15-2.35 (2H, m), 2.75 (2H, d, J=6.2 Hz). 2.85-3.05 (3H, m), 3.10 (3H, s), 3.21 (2H, t, J=8.1 Hz), 3.40-3.65 (4H, m), 7.30-7.55 (6H, m), 7.85-7.90 (2H, m) IR (KBr): 3385, 2920, 2680, 2425, 1590, 1460, 1410, 1310, 1300, 1150, 1090, 960, 795, 760, 700, 530 cm⁻¹.

REFERENCE EXAMPLE 163

4-Methyl-N-(3-{4-[4-(methylsulfonyl)benzyl]-1-piperidinyl}propyl)aniline dihydrochloride Reference Example of the title compound from 4-[4-(methylsulfonyl)benzyl]piperidine and p-toluidine was carried out according to the procedure of reference example 1. Yield: 60%.

mp 129-135° C. ¹H NMR (CD₃OD) δ 1.55-1.75 (2H, m), 1.85-2.10 (3H, m), 2.15-2.35 (2H, m), 2.40 (3H, s), 2.75 (2H, d, J=6.4 Hz), 2.85-3.05 (2H, m), 3.10 (3H, s), 3.15-3.20 (2H, m), 3.40-3.65 (4H, m), 7.35-7.55 (6H, m), 7.85-7.95 (2H, m) IR (KBr): 3310, 2925, 2665, 1595, 1510, 1435, 1300, 1140, 1090, 960, 800, 770, 560, 550, 520 cm⁻¹.

REFERENCE EXAMPLE 164-1

1-(4-{4-[(2-Ethoxyethyl)sulfanyl]benzyl}-1-piperidinyl)-1-ethanone

Alkylation of the compound of reference example 140-1 using 2-bromoethyl ethyl ether was carried out according to the procedure of reference example 143-1 to give the title compound. Yield: 81%.

¹H NMR (CDCl₃)) δ 1.00-1.25 (2H, m). 1.20 (3H, t, J=7.0 Hz), 1.60-1.85 (5H, m), 2.07 (3H, s), 2.40-2.60 (2H, m), 3.09 (2H, t, J=7.0 Hz), 3.51 (2H, q, J=7.0 Hz), 3.61 (2H, t, J=7.0 Hz), 3.70-3.85 (1H, m), 4.50-4.65 (1H, m), 7.00-7.10 (2H, m), 7.25-7.35 (2H, m)

REFERENCE EXAMPLE 164-2

1-(4-{4-[(2-Ethoxyethyl)sulfonyl]benzyl}-1-piperidinyl)-1-ethanone

Oxidation of the compound of reference example 164-1 was carried out according to the procedure of reference example 140-3 to give the title compound. Yield: 99%.

¹H NMR (CDCl₃) δ 1.15-1.30 (2H, m), 1.20 (3H, t, J=7.0 Hz), 1.60-1.90 (3H, m), 2.08 (3H, s), 2.40-2.60 (1H, m), 2.64 (2H, d, J=6.6 Hz), 2.90-3.10 (1H, m), 3.30-3.45 (2H, m), 3.37 (2H, q, J=7.0 Hz), 3.70-3.90 (1H, m)), 3.79 (2H, t, J=6.2 Hz), 4.50-4.70 (1H, m), 7.25-7.40 (2H, m), 7.80-7.90 (2H, m).

REFERENCE EXAMPLE 164-3

4-{4-[(2-Ethoxyethyl)sulfonyl]benzyl}piperidine

Reference Example of the title compound from the compound of reference example 164-2 was carried out according to the procedure of reference example 143-2. Yield: 76%.

¹H NMR (CDCl₃) δ 1.03 (3H, t, J=7.0 Hz), 1.05-1.30 (2H, m), 1.55-2.00 (3H, m), 2.45-2.70 (4H, m), 3.06 (2H, d, J=12.0 Hz), 3.37 (2H, q, J=7.0 Hz), 3.39 (2H, t, J=6.2 Hz), 3.78 (2H, t, J=6.2 Hz), 7.25-7.40 (2H, m), 7.75-7.90 (2H, m).

REFERENCE EXAMPLE 165-1

3-Chloro-N-formylaniline

Acetic anhydride (189 ml, 2.0 mol) was mixed with formic acid (91 ml, 2.4 mol) at 0° C. and the mixture was stirred at 60° C. for 1 h and then cooled to 0° C. To the solution was added dropwise 3-chloroaniline (105.7 ml, 1.0 mol) and the mixture was stirred at room temperature for 18 h. After removal of solvent in vacuo, the residue was extracted with EtOAc-H₂O. The organic layer was washed with 5% aqueous citric acid, saturated aqueous NaHCO₃ and brine, dried over Na₂SO₄ and then concentrated. The residue was crystallized from iPr₂O to give the title compound (115 g, 0.739 mol, 74%) as a colorless solid.

¹H NMR (CDCl₃) δ 6.90-7.30 (4H, m), 7.67 (1H, s), 8.38 (½×1H, s), 8.69 (½×1H, s)

REFERENCE EXAMPLE 165-2

3-Chloro-N-(3-chloropropyl)-N-formylaniline

A mixture of the compound obtained at reference example 165-1 (50.0 g, 10.321 mol), 1-bromo-3-chloropropane (61.0 ml, 0.385 mol), K₂CO₃ (53 g, 0.385 mol) and acetone (250 ml) was refluxed for 18 h. After filtration, the filtrate was evaporated in vacuo. The residue was purified by silica gel column chromatography with hexane/EtOAc(3/1) as an eluent. The fractions containing the target compound were combined and evaporated to give the title compound (57.1 g, 0.232 mol, 72%) as a pale yellow syrup.

¹H NMR(CDCl₃) δ 1.90-2.20 (2H, m), 3.55 (2H, t, J=6.2 Hz), 3.97 (2H, t, J=7.4 Hz), 7.05-7.45 (4H, m), 8.41 (1H, s)

REFERENCE EXAMPLE 165-3

3-Chloro-N-(3-chloropropyl)aniline hydrochloride

To a solution of the compound obtained at reference example 165-2 (57.0 g, 0.232 mol) in 2-propanol (150 ml) was added concentrated hydrochloric acid (35 ml). After being stirred at 60° C. for 3 h, the reaction mixture was cooled to room temperature. iPr₂O was added to the mixture and the resulting precipitates were collected by filtration. The solid was washed with 2-propanol and dried under reduced pressure to give the title compound (52.5 g, 0.218 mol, 97%) as a colorless solid.

¹H NMR (CD₃OD) δ 2.10-2.30 (2H, m), 3.54 (2H, t, J=7.6 Hz), 3.70 (2H, t, J=6.4 Hz). 7.30-7.60 (4H, m)

REFERENCE EXAMPLE 165-4

N-(3-Chlorophenyl)-N-(3-chloropropyl)-1-(methylsulfonyl)-4-piperidinecarboxamide From the title compound of reference example 165-3 (5.0 g, 20.8 mmol), using a similar procedure to that described for reference example 57, the title compound (5.90 g, 15.0 mol, 72%) was obtained as a colorless solid.

$^1$H NMR (CDCl$_3$) δ 1.60-2.10 (6H, m), 2.20-2.40 (1H, m), 2.45-2.70 (2H, m), 2.74 (3H, s), 3.55 (2H, t, J=6.6 Hz), 3.65-3.90 (4H, m), 7.00-7.15 (1H, m), 7.20 (1H, s), 7.30-7.50 (2H, m)

REFERENCE EXAMPLE 166-1

1-{4-[4-(Ethylsulfanyl)benzyl]-1-piperidinyl}-1-ethanone

A mixture of the compound obtained at reference example 140-1 (3.70 g, 14.8 mmol), ethyl bromide (1.93 g, 17.8 mmol), K$_2$CO$_3$ (2.46 g, 17.8 mmol) and DMF (30 ml) was stirred at room temperature for 18 h. The reaction mixture was filtered and the filtrate was evaporated in vacuo. The residue was extracted with EtOAc-H$_2$O. The organic layer was washed with brine, dried over Na$_2$SO$_4$ and then concentrated. The residue was purified by silica gel column chromatography with hexane/EtOAc (1/1) as an eluent. The fractions containing the target compound were combined and evaporated to give the title compound (3.22 g, 11.6 mol, 79%) as colorless syrup.

$^1$H NMR (CDCl$_3$) δ 1.00-1.40 (3H, m), 1.30 (3H, t, J=7.4 Hz), 1.60-1.80 (2H, m), 2.07 (3H, s), 2.40-2.60 (3H, m), 2.92 (2H, q, J=7.4 Hz), 2.90-3.05 (1H, m), 3.70-3.90 (1H, m), 4.50-4.70 (1H, m), 7.05 (2H, d, J=8.0 Hz), 7.27 (2H, d, J=8.0 Hz)

REFERENCE EXAMPLE 166-2

1-{4-[4-(Ethylsulfonyl)benzyl]-1-piperidinyl}-1-ethanone

To a solution of the compound obtained at reference example 166-1 (3.20 g, 11.6 mmol) in CH$_2$Cl$_2$ (70 ml) was added m-chloroperoxybenzoic acid (6.0 g, 34.8 mmol) at 0° C. After being stirred at room temperature for 1.5 h, water was added to the mixture. The organic layer was separated and washed with 5% aqueous Na$_2$S$_2$O$_3$, saturated aqueous NaHCO$_3$ and brine, dried over Na$_2$SO$_4$, concentrated. The residue was purified by silica gel column chromatography with EtOAc/MeOH (10/1) as an eluent. The fractions containing the target compound were combined and evaporated to give the title compound (3.28 g, 10.6 mol, 92%) as colorless syrup.

$^1$H NMR (CDCl$_3$) δ 1.00-1.15 (3H, m); 1.29 (3H, t, J=7.8 Hz), 1.60-1.90 (2H, m), 2.08 (3H, s), 2.40-2.70 (3H, m), 2.90-3.10 (1H, m), 3.12(2H, q, J=7.8 Hz), 3.70-3.90(1H, m) 4.50-4.70 (1H, m), 7.34 (2H, d, J=8.0 Hz), 7.83 (2H, d, J=8.0 Hz)

REFERENCE EXAMPLE 166-3

4-[4-(Ethylsulfonyl)benzyl]-1-piperidine hydrochloride

The compound obtained at reference example 166-2 (3.20 g, 10.4 mmol) was suspended in concentrated hydrochloric acid (30 ml.) and refluxed for 2 h. After being cooled to room temperature, the reaction mixture was evaporated to give the title compound (3.00 g, 9.87 mmol, 95%) as a colorless solid.

$^1$H NMR (CD$_3$OD) δ 1.22 (3H, t, J=7.4 Hz), 1.30-1.60 (2H, m), 1.80-2.10 (3H, m), 2.75 (2H, d, J=6.8 Hz), 2.80-3.10 (2H, m), 3.19 (2H, q, J=7.4 Hz), 3.30-3.50 (2H, m), 7.48 (2H, d, J=8.4 Hz), 7.85 (2H, d, J=8.4 Hz)

REFERENCE EXAMPLE 167

N-(3-{4-[4-(Methylsulfonyl)benzyl]-1-piperidinyl}propyl)-3-(trifluoromethyl)aniline dihydrochloride The title compound was prepared by a similar procedure that employed for reference example 1 using 4-[4-(methylsulfonyl)benzyl]piperidine and 3-(trifluoromethyl)aniline in 25% yield.

$^1$H NMR (CD$_3$OD) δ 1.40-1.75 (2H, m), 1.80-2.05 (3H, m), 2.10-2.30 (2H, m), 2.75 (2H, d, J=7.0 Hz), 2.80-3.05 (2H, m), 3.10 (3H, s), 3.15-3.30 (2H, m), 3.35-3.70 (4H, m), 7.15-7.60 (6H, m), 7.89 (2H, d, J=8.2 Hz)

REFERENCE EXAMPLE 168

4-Isopropyl-N-(3-{4-[4-(methylsulfonyl)benzyl]-1-piperidinyl}propyl)aniline dihydrochloride The title compound was prepared by a similar procedure that employed for reference example 1 using 4-[4-(methylsulfonyl)benzyl]piperidine and 4-isopropylaniline in 41% yield.

$^1$H NMR (CD$_3$OD) δ 1.26 (6H, d, J=7.0 Hz), 1.50-1.80 (2H, m), 1.80-2.05 (3H, m), 2.10-2.40 (2H, m), 2.75 (2H, d, J=7.0 Hz), 2.80-3.10 (3H, m), 3.11 (3H, s), 3.15-3.30 (2H, m), 3.40-3.70 (4H, m), 7.40-7.60 (6H, m), 7.89 (2H, d, J=8.0 Hz)

REFERENCE EXAMPLE 169

4-Chloro-N-(3-{4-[4-(methylsulfonyl)benzyl]-1-piperidinyl}propyl)aniline dihydrochloride The title compound was, prepared by a similar procedure that employed for reference example 1 using 4-[4-(methylsulfonyl)benzyl]piperidine and 4-chloroaniline in 53% yield.

$^1$H NMR (CD$_3$OD) δ 1.50-1.75(2H, m), 1.80-2.05 (3H, m), 2.10-2.30 (2H, m), 2.75 (2H, d, J=7.0 Hz), 2.80-3.05 (2H, m), 3.11 (3H, s), 3.15-3.30 (2H, m), 3.35-3.65 (4H, m), 7.28 (2H, d, J=8.8 Hz), 7.46 (2H, d, J=8.8 Hz), 7.47 (2H, d, J=8.4 Hz), 7.89 (2H, d, J=8.4 Hz)

REFERENCE EXAMPLE 170

3-Methyl-N-(3-{4-[4-(methylsulfonyl)benzyl]-1-piperidinyl}propyl)aniline dihydrochloride The title compound was prepared by a similar procedure that employed for reference example 1 using 4-[4-(methylsulfonyl)benzyl]piperidine and 3-methylaniline in 39% yield.

$^1$H NMR (CD$_3$OD) δ 1.50-1.75(2H, m), 1.85-2.05 (3H, m), 2.10-2.30 (2H, m), 2.41 (3H, s), 2.75 (2H, d, J=7.0 Hz), 2.85-3.10 (2H, m), 3.10 (3H, s), 3.15-3.30 (2H, m), 3.40-3.70 (4H, m), 7.20-7.30 (3H, m), 7.35-7.55 (3H, m), 7.89 (2H, d, J=8.0 Hz)

REFERENCE EXAMPLE 171

N-(3-{4-[4-(4-Morpholinylsulfonyl)benzyl]-1-piperidinyl}propyl)aniline dihydrochloride A solution of 4-{[4-(4-piperidinylmethyl)phenyl]sulfonyl}morpholine (2.6 g, 7.89 mmol) in THF (10 ml) containing DBU (12.0 mg, 0.0789 mmol) was cooled to −15° C. To the stirred solution was added acrolein (90%, 0.586 ml, 7.89 mmol) dropwise. The mixture was stirred for a further 30 minutes. Then aniline (719 ml, 7.89 mmol) and sodium triacetoxyborohydride (3.34 g, 15.78 mmol) was added at −15° C. and the reaction mixture was stirred, being allowed to warm to room temperature, for 15 hours. After quenching with 1N sodium hydroxide solution in water (100 ml) at 0° C. and the reaction mixture being stirred for another 30 minutes, the resulting solution was extracted with diethyl ether (100 ml×3). The organic layer was dried over magnesium sulfate and the solvent was removed in vacuo. The yellow oily residue was chromatographed on silica gel (100 g) with 4:1 ethyl acetate/methanol to give 1.37 g of colorless oil.

$^1$H-NMR(CDCl$_3$) δ 1.23-2.10 (9H, m), 2.47 (2H, t, J=6.4 Hz), 2.64 (2H, t, J=6.4 Hz), 2.89-3.06 (6H, m), 3.17 (2H, t, J=6.4 Hz), 3.68-3.80 (4H, m), 6.57-6.72 (3H, m), 7.14-7.22 (2H, m), 7.33 (2H, d, J=8.2 Hz), 7.67 (2H, d, J=8.2 Hz)

To the solution of the colorless oil obtained here in 2-propanol (5 ml) was added 4N hydrogen chloride solution in ethyl acetate (3 ml) dropwise under stirring. The white precipitate was filtered, and washed with 2-propanol (5 ml×3). The title compound was obtained as white crystals (1.26 g, yield 30%) after drying in vacuo.

REFERENCE EXAMPLE 172

3-Chloro-N-(3-{4-[4-(4-morpholinylsulfonyl)benzyl]-1-piperidinyl}propyl)aniline dihydrochloride The title compound was obtained by a similar procedure employed for reference example 171 from 4-{[4-(4-piperidinylmethyl)phenyl]sulfonyl}morpholine and 3-chloroaniline, yield 54%.

Free base: $^1$H-NMR(CDCl$_3$) δ 1.22-2.00 (9H, m), 2.45 (2H, t, J=6.4 Hz,), 2.65 (2H, d, J=6.4 Hz), 2.92-3.06 (6H, m), 3.15 (2H, t, J=6.4 Hz), 3.70-3.80 (4H, m), 6.42-6.45 (3H, m), 7.06 (1H, t, J=8.0 Hz), 7.33 (2H, d, J=8.4 Hz), 7.67 (2H, d, J=8.4 Hz)

REFERENCE EXAMPLE 173

N-(3-{4-[4-(4-Methylsulfonyl)benzyl]-1-piperidinyl}propyl)aniline dihydrochloride The title compound was obtained by a similar procedure employed for reference example 171 from 4-[4-(methylsulfonyl)benzyl]piperidine and aniline, yield 30%.

$^1$H-NMR(CD$_3$OD) δ 1.59-2.35 (7H, m), 2.75 (2H, d, J=64 Hz), 2.86-3.05 (2H, m), 3.13 (3H, s), 3.22 (2H, t, J=7.4 Hz), 3.48 (2H, t, J=8.0 Hz), 3.59-3.68 (2H, m), 6.63-6.75 (3H, m), 7.10-7.25 (2H, m), 7.50 (2H, d, J=8.2 Hz), 7.90 (2H, d, J=8.2 Hz)

REFERENCE EXAMPLE 174

3-Chloro-N-(3-{4-[4-(4-methylsulfonyl)benzyl]-1-piperidinyl}propyl)aniline dihydrochloride The title compound was obtained by a similar procedure employed for reference example 171 from 4-[4-(methylsulfonyl)benzyl]piperidine and 3-chloroaniline, yield 30%.

$^1$H-NMR (CD$_3$OD) δ 1.50-2.30 (7H, m), 2.75 (2H, d, J=6.6 Hz), 2.86-3.02 (2H, m), 3.11 (3H, s), 3.22 (2H, m), 3.43 (2H, t, J=7.2 Hz), 3.55-3.64 (2H, m), 7.20-7.30 (2H, m), 7.34-7.39 (2H, m), 7.48 (2H, d, J=8.0 Hz), 7.89 (2H, d, J=8.0 Hz)

REFERENCE EXAMPLE 175-1 tert-Butyl 4-{4-[(isopropylamino)carbonyl]benzyl}-1-piperidinecarboxylate

The title compound (3078 mg, yield 91%) was obtained by a similar procedure employed for reference example 130-1 from isopropylamine (721 mg).

$^1$H-NMR(CDCl$_3$) δ 1.04-1.18 (2H, m), 1.26 (6H, d, J=6.6 Hz), 1.45 (9H, s), 1.53-1.78 (3H, m), 2.58 (2H, d, J=7.0 Hz), 2.56-2.69 (2H, m), 4.00-4.14 (2H, m), 4.20-4.34 (1H, m), 5.87-5.91 (1H, br), 7.19 (2H, d, J=8.2 Hz), 7.68 (2H, d, J=8.2 Hz)

REFERENCE EXAMPLE 175-2

N-Isopropyl-4-(4-piperidinylmethyl)benzamide hydrochloride

The title compound (2.44 g, yield 99%) was obtained by a similar procedure employed for reference example 123-4 from the title compound of reference example 175-1 (3.0 g).

$^1$H-NMR(CD$_3$OD) δ 1.24 (6H, d, J=6.6 Hz), 1.38-1.59 (2H, m), 1.82-1.99 (3H, m), 2.68 (2H, d, J=7.0 Hz), 2.82-3.01 (2H, m), 3.29-3.39 (2H, m), 4.20 (1H, septet, J=6.6 Hz), 7.29 (2H, d, J=8.4 Hz), 7.75 (2H, d, J=8.4 Hz)

REFERENCE EXAMPLE 176-1 tert-Butyl 4-(4-{[(2-hydroxyethyl)amino]carbonyl}benzyl)-1-piperidinecarboxylate The title compound (1603 mg, yield 97%) was obtained by a similar procedure employed for reference example 130-1 from 2-aminoethanol (373 mg).

$^1$H-NMR (CDCl$_3$) δ 1.00-1.27 (2H, m), 1.45 (9H, s), 1.52-1.80 (3H, m), 2.58 (2H, d, J=7.0 Hz). 2.56-2.73 (3H, m), 3.59-3.67 (2H, m), 3.80-3.87 (2H, m), 3.98-4.16 (2H, m), 6.57-6.70 (1H, br), 7.20 (2H, d, J=8.2 Hz), 7.71 (2H, d, J=8.2 Hz)

REFERENCE EXAMPLE 176-2

N-(2-Hydroxyethyl)-4-(4-piperidinylmethyl)benzamide hydrochloride

The title compound (1.3 g, yield 99%) was obtained by a similar procedure employed for reference example 123-4 from the title compound of reference example 176-1 (1.6 g).

$^1$H-NMR(CD$_3$OD) δ 1.33-1.58 (2H, m), 1.82-2.05 (3H, m), 2.68 (2H, d, J=6.6 Hz), 2.82-3.03 (2H, m), 3.30-3.37 (2H, m), 3.50 (2H, t, J=5.6 Hz), 3.71 (2H, t, J=5.6 Hz), 7.30 (2H, d, J=8.4 Hz), 7.79 (2H, d, J=8.4 Hz)

REFERENCE EXAMPLE 177

N-[3-(4-Benzyl-1-piperidinyl)propyl]-3-pyridinamine

To a solution of 4-benzylpiperidine (3.51 g) in 40 ml of tetrahyfrofuran, 1,8-diazabicyclo[5.4.0]-7-undecene (0.03 ml) was added and the mixture was cooled at −20° C. Acrolein (1.485 ml) was added dropwise for 10 min and the mixture was stirred for 1 h at −20° C. 3-Aminopyridine (1.88 g) and sodium triacetoxyborohydride (8.48 g) were added and the mixture was stirred at room temperature for 15 h. 1N NaOH (120 ml) was added and stirred for 1 h. The reaction mixture was extracted with ethyl ether (60 ml) 3 times. The combined organic layer was washed with brine (50 ml), dried over anhydrous $MgSO_4$. After concentration, the residue was purified on silica gel column chromatography (AcOEt-methanol 3:1) to give the title compound (2.34 g, yield 37.8%).

$^1$H NMR (CDCl$_3$) δ 1.17-1.93 (9H, m), 2.45 (2H, t, J=6.6 Hz), 2.50 (2H, d, J=6.6 Hz), 2.93 (2H, m), 3.17 (2H, t, J=6.2 Hz), 5.20 (1H, bs), 6.81 (1H, m), 7.03-7.33 (6H, m), 7.91 (1H, dd, J=1.2 Hz and 4.8 Hz), 7.99 (1H, d, J=2.6 Hz).

REFERENCE EXAMPLE 178

N-[3-(4-Benzyl-1-piperidinyl)propyl]-2-pyridinamine

The title compound (0.81 g, yield 12.9%) was obtained by a similar procedure employed for reference example 177 from 2-aminopyridine (1.88 g).

$^1$H NMR (CDCl$_3$) δ 1.22-1.93 (9H, m), 2.44 (2H, t, J=6.6 Hz), 2.55 (2H, d, J=6.6 Hz), 2.93 (2H, m), 3.33 (2H, t, J=6.4 Hz), 5.37 (1H, bs), 6.34 (1H, d, J=8.4 Hz), 6.52 (1H, m), 7.13-7.43 (6H, m), 8.06 (1H, m).

REFERENCE EXAMPLE 179

N-[3-(4-Benzyl-1-piperidinyl)propyl]-1H-indazol-6-amine

The title compound (3.96 g, yield 56.8%) was obtained by a similar procedure employed for reference example 177 from 6-aminoindazole (2.66 g).

$^1$H NMR (CDCl$_3$) δ 1.35 (2H, dt, J=3.6 Hz and 12.0 Hz), 1.49-2.05 (7H, m), 2.47 (2H, t, J=6.6 Hz), 2.58 (2H, d, J=6.6 Hz); 2.96 (2H, m), 3.19 (2H, t, J=6.2 Hz), 5.29 (1H, bs), 6.41 (1H, s), 6.47 (1H, dd, J=1.8 Hz and 8.4 Hz), 7.14-7.34 (5H, m), 7.46 (1H, d, J=8.8 Hz), 7.87 (1H, s), 9.79 (1H, bs).

REFERENCE EXAMPLE 180

3-(4-Benzyl-1-piperidinyl)-N-(1-phenylethyl)-1-propanamine

The title compound (3.70 g, yield 55.0%) was obtained by a similar procedure employed for reference example 177 from 1-phenylethylamine (2.43 g).

$^1$H NMR (CDCl$_3$) δ 1.22-1.84 (9H, m), 1.34 (3H, d, J=6.6 Hz), 2.30 (2H, m), 2.36-2.57 (2H, m), 2.51 (2H, d, J=6.6 Hz), 2.87 (2H, m), 3.73 (1H, q, J=6.6 Hz), 7.13-7.43 (10H, m).

REFERENCE EXAMPLE 181-1

4-(4-Piperidinylmethyl)benzamide

The title compound of reference example 123-4 (10 g, 39.3 mmol) was added to 1N aqueous sodium hydroxide solution (86 ml) at 0° C. and the mixture was stirred at room temperature for 1 h. The precipitate was collected by filtration to give the title compound (5.96 g, 70%) as colorless crystalline powder.

$^1$H NMR (CDCl$_3$) δ 1.07-1.30 (2H, m), 1.58-1.75 (4H, m), 2.48-2.60 (4H, m), 3.01-3.07 (2H, m), 5.70-6.40 (2H, br), 7.23 (2H, d, J=7.4 Hz), 7.74 (2H, d, J=7.4 Hz)

REFERENCE EXAMPLE 181-2

4-({1-[3-(3-Chloro-4-methylanilino)propyl]-4-piperidinyl}methyl)benzamide dihydrochloride The title compound was prepared from the title compound of reference example 181-1 and 3-chloro-4-methylaniline using a similar procedure to that described for reference example 1. Yield 32%

$^1$H NMR (CD$_3$OD) δ 1.50-1.68 (2H, m), 1.80-1.99 (3H, m), 2.10-2.31 (2H, m), 2.39 (3H, s), 2.69 (2H, d, J=6.6 Hz), 2.79-3.01 (2H, m), 3.17-3.25 (2H, m), 3.42-3.61 (4H, m), 7.31 (2H, d, J=8.4 Hz), 7.32 (1H, dd, J=8.6 Hz, 2.6 Hz), 7.46 (1H, d, J=8.6 Hz), 7.53 (1H, d, J=2.6 Hz), 7.82 (2H, d, J=8.4 Hz)

REFERENCE EXAMPLE 182-1 tert-Butyl 4-({4-[ethyl(methylsulfonyl)amino]phenyl}sulfonyl)-1-piperidinecarboxylate The title compound was prepared using a similar procedure to that described in reference example 148-5 from iodoethane. Yield 94%.

$^1$H NMR (CDCl$_3$) δ 1.20 (3H, t, J=7.2 Hz), 1.44 (9H, s), 1.50-1.77 (2H, m), 1.93-2.07 (2H, m), 2.58-2.76 (2H, m), 2.95 (3H, s), 3.06 (1H, tt, J=3.4, 12.2 Hz), 3.85 (2H, q, J=7.2 Hz), 4.15-4.32 (2H, m), 7.56 (2H, d, J=8.4 Hz), 7.91 (2H, d, J=8.4 Hz).

REFERENCE EXAMPLE 182-2

N-Ethyl-N-[4-(4-piperidinylsulfonyl)phenyl]methanesulfonamide hydrochloride 4-({4-[ethyl(methylsulfonyl)amino]phenyl)sulfonyl)-1-piperidinecarboxylate The title compound was prepared using a similar procedure to that described in reference example 144-2 from the title compound of reference example 182-1. Yield 96%.

$^1$H NMR (CD$_3$OD) δ 1.15 (3H, t, J=6.8 Hz), 1.79-2.04 (2H, m), 2.16-2.30 (2H, m), 2.93-3.10 (2H, m), 3.00 (3H, s), 3.45-3.64 (3H, m), 3.87 (2H, q, J=6.8 Hz), 7.70 (2H, d, J=8.8 Hz), 7.97 (2H, d, J=8.8 Hz).

REFERENCE EXAMPLE 183

4-[4-(Methylsulfonyl)benzyl]piperidine

To a solution of the title compound of reference example 86-2 (1000 mg) in water (10 mL) was added 1N aqueous sodium hydroxide (5 mL) at 0° C. and the aqueous layer was extracted with dichloromethane (3×10 mL). The combined organic layers were dried over potassium carbonate, filtered and evaporated under reduced pressure. Diisopropyl ether (10 mL) was added to the residue, the resulting precipitate was collected by filtration, washed with diisopropyl ether and dried under reduced pressure to afford the title compound (712 mg) as a white solid.

$^1$H NMR(CDCl$_3$) δ 1.07-1.27 (2H, m), 1.50-1.73 (3H, m), 2.48-2.61 (2H, m), 2.62 (2H, d, J=6.6 Hz), 3.03-3.08 (2H, m), 3.05 (3H, s), 7.34 (2H, d, J=8.4 Hz), 7.85 (2H, d, J=8.4 Hz)

EXAMPLE 1

1-(Benzyloxycarbonyl)-N-[3-(4-benzyl-1-piperidinyl)propyl]-N-phenyl-4-piperidinecarboxamide To a solution of 1-(benzyloxycarbonyl)-4-piperidine carboxylic acid (2.37 g, 9.0 mmol) and DMF (0.007 ml) in dichloromethane (15 ml) was added oxalyl chloride (1.00 ml) at room temperature with stirring, and the mixture was stirred at the same temperature for 1 hour. The reaction mixture was concentrated under reduced pressure, and to the concentrate was added toluene (10 ml). The mixture was concentrated again under reduced pressure, and the concentrate was dissolved in dichloromethane (5 ml). The solution was added dropwise to the solution of the compound obtained in Reference Example 1 (1.91 g, 5.0 mmol) and triethylamine (3.97 ml) in dichloromethane (45 ml) with stirring at −20° C. The mixture was stirred for 1 hour while the temperature of the mixture was elevating room temperature. To the mixture was added a saturated aqueous solution of sodium hydrogencarbonate (45 ml), and the organic solvent was distilled off under reduced pressure. The aqueous layer was extracted with ethyl acetate (40 ml, 20 ml×2). The organic layer was washed with a saturated aqueous solution of sodium hydrogencarbonate (10 ml×3), saturated sodium chloride solution (10 ml), successively, dried over magnesium sulfate and concentrated under reduced pressure. The concentrate was subjected to column chromatography (silica gel 100 g, ethyl acetate/methanol=1/0 to 9/1), and the desired fraction was concentrated under reduced pressure to give the titled compound (2.54 g, 4.6 mmol, Yield 92%) as a colorless oily substance.

$^1$H NMR (CDCl$_3$) δ 1.1-1.9 (13H, m), 2.15-2.35 (1H, m), 2.27 (2H, t, J=7.3 Hz), 2.4-2.65 (2H, m), 2.50 (2H, d, J=6.6 Hz), 2.82 (2H, br d, J=11.8 Hz), 3.67 (2H, t, J=7.7 Hz), 4.0-4.2 (2H, m), 5.09 (2H, s), 7.05-7.5 (15H, m)

EXAMPLE 2

N-[3-(4-Benzyl-1-piperidinyl)propyl]-N-phenyl-4-piperidinecarboxamide

The compound obtained in Example 1 (2.32 g, 4.2 mmol) was dissolved in methanol (30 ml). To the solution was added 10% palladium carbon (water content:50%, 0.93 g), and the mixture was subjected to catalytic hydrogenation reaction at room temperature for 16 hours. The catalyst was filtered off, and the filtrate was concentrated under reduced pressure to give the titled compound (1.70 g, 4.1 mmol, Yield 97%).

$^1$H NMR (CDCl$_3$) δ 1.1-1.95 (13H, m), 2.05-2.45 (5H, m), 2.51 (2H, d, J=6.6 Hz), 2.84(2H, br d, J=11.8 Hz), 3.01(2H, br d, J=12.8 Hz), 3.67 (2H, t, J=7.7 Hz), 7.05-7.5 (10H, m)

EXAMPLE 3

1-Acetyl-N-[3-(4-benzyl-1-piperidinyl)propyl]-N-phenyl-4-piperidinecarboxamide

The compound obtained in Example 2 (252 mg, 0.60 mmol), triethylamine (0.201 ml) were dissolved in THF (5 ml), and under ice cooling, to the solution was added acetyl chloride (0.085 ml). The mixture was stirred at the same temperature for 30 minutes. To the mixture was added a saturated aqueous solution of sodium hydrogencarbonate (15 ml) under ice cooling, and the mixture was extracted with ethyl acetate (15 ml×3). The organic layer was dried over magnesium sulfate and concentrated under reduced pressure. The concentrate was subjected to column chromatography (silica gel 10 g, ethyl acetate/methanol=1/0 to 9/1 to 4/1), and the desired fraction was concentrated under reduced pressure. To the concentrate was added ethyl acetate and the insolubles were filtered off. The filtrate was concentrated under reduced pressure to give the titled compound (237 mg, 0.51 mmol, Yield 85%) as colorless oily substance.

$^1$H NMR (CDCl$_3$) δ 1.1-1.9 (13H, m), 2.03 (3H, s), 2.2-2.45 (2H, m), 2.28 (2H, t, J=7.5 Hz), 2.50 (2H, d, J=6.6 Hz), 2.7-2.9 (1H, m), 2.83 (2H, br d, J=11.6 Hz), 3.68 (2H, t, J=7.7 Hz), 3.74 (1H, br d, J=12.8 Hz), 4.50 (1H, br d, J=12.8 Hz), 7.05-7.5 (10H, m)

EXAMPLE 4

1-Benzoyl-N-[3-(4-benzyl-1-piperidinyl)propyl]-N-phenyl-4-piperidinecarboxamide

By a similar manner to Example 3, the titled compound was synthesized by using benzoyl chloride. Yield 88%.

$^1$H NMR (CDCl$_3$) δ 1.1-1.95 (13H, m), 2.2-2.9 (3H, m), 2.29 (2H, t, J=7.7 Hz), 2.50 (2H, d, J=6.2 Hz), 2.83 (2H, br d, J=11.8 Hz), 3.45-3.9 (1H, m), 3.69 (2H, t, J=7.7 Hz), 4.4-4.85 (1H, m), 7.05-7.5 (15H, m)

EXAMPLE 5

N-[3-(4-Benzyl-1-piperidinyl)propyl]-1-(methylsulfonyl)-N-phenyl-4-piperidinecarboxamide The compound obtained in Example 2 (252 mg, 0.60 mmol) and triethylamine (0.201 ml) were dissolved in THF (5 ml), and under ice cooling, to the solution was added methanesulfonyl chloride (0.093 ml). The mixture was stirred at the same temperature for 1 hour. The compound obtained in Example 2 (252 mg, 0.60 mmol) and triethylamine (0.201 ml) were dissolved in THF (5 ml). To the solution was added methanesulfonyl chloride (0.093 ml) under ice cooling with stirring, and the mixture was stirred at the same temperature for 1 hour. To the mixture was added a saturated aqueous solution of sodium hydrogencarbonate (15 ml) under ice cooling, and the mixture was extracted with ethyl acetate (15 ml×3). The organic layer was dried over magnesium sulfate and concentrated under reduced pressure. The concentrate was subjected to column chromatography (silica gel 10 g, ethyl acetate/methanol=1/0 to 9/1), and the desired fraction was concentrated under reduced pressure. To the concentrate was added diisopropyl ether (100 ml), and the resulting precipitates were collected by filtration. The precipitates were washed with diisopropyl ether, and dried under reduced pressure to give the titled compound (110 mg, 0.22 mmol, Yield 37%) as white crystals.

mp 116-118° C.

$^1$H NMR (CDCl$_3$) δ 1.1-2.0 (13H, m), 2.15-2.4 (3H, m), 2.4-2.6 (2H, m), 2.51 (2H, d, J=6.2 Hz), 2.72 (3H, s), 2.75-2.95 (2H, m), 3.6-3.8 (4H, m), 7.05-7.5 (10H, m)

EXAMPLE 6

N-[3-(4-Benzyl-1-piperidinyl)propyl]-1-isobutyryl-N-phenyl-4-piperidinecarboxamide By a similar manner to Example 3, the titled compound was synthesized by using isobutyryl chloride. Yield 62%.

$^1$H NMR (CDCl$_3$) δ 0.95-2.0 (19H, m), 2.15-2.6 (2H, m), 2.32 (2H, t, J=7.7 Hz), 2.51 (2H, d, J=6.6 Hz), 2.6-2.95 (2H, m), 2.87 (2H, br d, J=11.8 Hz), 3.68 (2H, t, J=7.5 Hz), 3.87(1H, br d, J=14.1 Hz), 4.54 (1H, br d, J=14.1 Hz), 7.05-7.5 (10H, m)

EXAMPLE 7

N-[3-(4-Benzyl-1-piperidinyl)propyl]-1-(tert-butoxycarbonyl)-N-phenyl-4-piperidinecarboxamide To the solution of 1-(tert-butoxycarbonyl)-4-piperidine carboxylic acid (1.72 g, 7.5 mmol) and DMF (0.058 ml) in dichloromethane (30 ml) was added oxalyl chloride (0.77 ml) under ice cooling, and the mixture was stirred at room temperature for 1 hour. The obtained reaction mixture was added dropwise to a solution of the compound obtained in Reference Example 1 (1.91 g, 5.0 mmol) and triethylamine (4.18 ml) in dichloromethane (45 ml) at −30° C. with stirring. The mixture was stirred for 2 hours while the temperature of the mixture was elevating room temperature. To the mixture was added a saturated aqueous solution of sodium hydrogencarbonate (45 ml), and the organic solvent was distilled off under reduced pressure. The aqueous layer was extracted with ethyl acetate (40 ml, 20 ml×2). The organic layer was washed with a saturated aqueous solution of sodium hydrogencarbonate (10 ml×3), saturated sodium chloride solution (10 ml), successively, dried over magnesium sulfate and concentrated under reduced pressure. The concentrate was subjected to column chromatography (silica gel 70 g, ethyl acetate/methanol=1/0 to 9/1), and the desired fraction was concentrated under reduced pressure to give the titled compound (1.47 g, 2.8 mmol, Yield 56%) as colorless oily substance.

$^1$H NMR (CDCl$_3$) δ 1.1-1.9 (13H, m), 1.42 (9H, s), 2.1-2.55 (3H, m), 2.28 (2H, t, J=7.5 Hz), 2.50 (2H, d, J=6.6 Hz), 2.82 (2H, br d, J=11.0 Hz), 3.68 (2H, t, J=7.7 Hz), 3.9-4.15 (2H, m), 7.05-7.5 (10H, m)

EXAMPLE 8

1-(Benzyloxycarbonyl)-N-[3-(4-benzyl-1-piperidinyl)propyl]-N-phenyl-3-piperidine carboxamide By a similar manner to Example 1, the titled compound was synthesized by using 1-(benzyloxycarbonyl)-3-piperidine carboxylic acid. Yield 71%.

$^1$H NMR (CDCl$_3$) δ 1.0-1.9 (13H, m), 2.15-2.35 (1H, m), 2.26 (2H, t, J=7.7 Hz), 2.50 (2H, d, J=6.6 Hz), 2.55-3.05 (2H, m), 2.81 (2H, br d, J=11.8 Hz), 3.55-3.8 (2H, m), 3.95-4.2 (2H, m), 5.03 (2H, br s), 7.0-7.5 (15H, m)

EXAMPLE 9

N-[3-(4-Benzyl-1-piperidinyl)propyl]-N-phenyl-3-piperidine carboxamide

By a similar manner to Example 2, the titled compound was synthesized by using the compound obtained in Example 8. Yield 95%.

$^1$H NMR (CDCl$_3$) δ 1.0-2.05 (13H, m), 2.15-2.4 (1H, m), 2.26 (2H, t, J=7.5 Hz), 2.45-2.7 (1H, m), 2.51 (2H, d, J=6.6 Hz), 2.7-3.0 (5H, m), 3.66 (2H, t, J=7.5 Hz), 7.05-7.5 (10H, m)

EXAMPLE 10

1-Acetyl-N-[3-(4-benzyl-1-piperidinyl)propyl]-N-phenyl-3-piperidine carboxamide

By a similar manner to Example 3, the titled compound was synthesized by using the compound obtained in Example 9. Yield 85%.

$^1$H NMR (CDCl$_3$) δ 1.0-2.0 (16H, m), 2.1-2.55 (1H, m), 2.29 (2H, t, J=7.5 Hz), 2.51 (2H, d, J=6.6 Hz), 2.65-3.4 (2H, m), 2.83 (2H, br d, J=2.83 Hz), 3.5-3.85 (3H, m), 4.4-4.65 (1H, m), 7.05-7.5 (10H, m)

EXAMPLE 11

N-[3-(4-Benzyl-1-piperidinyl)propyl]-1-(methylsulfonyl)-N-phenyl-3-piperidine carboxamide By a similar manner to Example 5, the titled compound was synthesized by using the compound obtained in Example 9. Yield 41%.

$^1$H NMR (CDCl$_3$) δ 1.1-2.0 (13H, m), 2.2-2.65 (2H, m), 2.28 (2H, t, J=7.5 Hz), 2.51 (2H, d, J=6.66 Hz), 2.68 (3H, s), 2.75-2.95 (3H, m), 3.5-3.85 (4H, m), 7.05-7.5 (10H, m)

EXAMPLE 12

N'-[1-(Benzyloxycarbonyl)-4-piperidinyl]-N-[3-(4-benzyl-1-piperidinyl)propyl]-N-phenylurea To a solution of 1-(benzyloxycarbonyl)-4-piperidine carboxylic acid (7.90 g, 30 mmol) and DMF (0.023 ml) in dichloromethane (100 ml) was added oxalyl chloride (3.84 ml) at room temperature with stirring, and the mixture was stirred at the same temperature for 1 hour. The reaction mixture was concentrated under reduced pressure. To the concentrate was added toluene (50 ml) and the mixture was concentrated under reduced pressure. The procedure was repeated. A solution of the concentrate in acetone (10 ml) was added dropwise to a solution of sodium azide (4.88 g, 75 mmol) in water (25 ml)-acetone (25 ml) under ice cooling, and the mixture was stirred at the same temperature for 2 hours. To the mixture was added water (100 ml), ant the mixture was extracted with toluene (100 ml×2). The organic layer was washed with saturated sodium chloride solution (20 ml×2), dried over anhydrous sodium sulfate and concentrated under reduced pressure the volume becomes to about 100 ml. The solution was stirred at 90° C. for 1 hour. The reaction mixture was concentrated under reduced pressure to give 1-(benzyloxycarbonyl)-4-piperidinylisocyanate (7.99 g). To a solution of the compound obtained in Reference Example 1 (3.81 g, 10 mmol) and triethylamine (3.49 ml) in dichloromethane (100 ml) was, added 1-(benzyloxycarbonyl)-4-piperidinylisocyanate (3.90 g) with stirring at room temperature. The mixture was stirred at the same temperature for 3 days. The reaction mixture was concentrated under reduced pressure, and to the concentrate was added a saturated aqueous solution of sodium hydrogencarbonate (50 ml) under ice cooling, and the mixture was extracted with ethyl acetate (50 ml×3). The organic layer was dried over magnesium sulfate and concentrated under reduced pressure. The concentrate was subjected to column chromatography (silica gel 100 g, ethyl acetate/methanol=1/0 to 9/1), and the desired fraction was concentrated under reduced pressure to give the titled compound (5.54 g, 9.7 mmol, Yield 97%) as colorless oily substance.

$^1$H NMR (CDCl$_3$) δ 1.0-1.95 (13H, m), 2.30 (2H, t, J=7.5 Hz), 2.50 (2H, d, J=6.66 Hz), 2.75-3.0 (4H, m), 3.6-4.1 (3H, m), 3.67 (2H, t, J=7.5 Hz), 4.17 (1H, d, J=7.8 Hz), 5.08(2H, s), 7.05-7.45(15H, m)

EXAMPLE 13

N-[3-(4-Benzyl-1-piperidinyl)propyl]-N-phenyl-N'-(4-piperidinyl)urea

The compound obtained in Example 12 (5.50 g, 9.7 mmol) was dissolved in methanol (60 ml). To the solution was added 10% palladium carbon (water content:50%, 2.2 g), and the mixture was subjected to catalytic hydrogenation reaction at room temperature for 16 hours. The catalyst was filtered off, and the filtrate was concentrated under reduced pressure to give the titled compound (4.11 g, 9.5 mmol, Yield 98%).

mp 85-87° C.

$^1$H NMR (CDCl$_3$) δ 1.0-1.95 (13H, m), 2.32 (2H, t, J=7.3 Hz), 2.51 (2H, d, J=6.2 Hz), 2.55-2.75 (2H, m), 2.86 (2H, br d, J=11.8 Hz), 2.9-3.05 (2H, m), 3.55-3.85 (1H, m), 3.68 (2H, t, J=7.3 Hz), 4.16 (1H, d, J=8.0 Hz), 7.05-7.5 (10H, m)

EXAMPLE 14

N'-(1-Acetyl-4-piperidinyl)-N-[3-(4-benzyl-1-piperidinyl)propyl]-N-phenylurea

The compound obtained in Example 13 (435 mg, 1.00 mmol), triethylamine (0.335 ml) were dissolved in THF (10 ml), and under ice cooling, to the solution was added acetyl chloride (0.142 ml). The mixture was stirred at the same temperature for 1 hour. To the reaction mixture was added a saturated aqueous solution of sodium hydrogencarbonate (15 ml) under ice cooling, and the mixture was extracted with ethyl acetate (15 ml×3). The organic layer was dried over anhydrous sodium sulfate and concentrated under reduced pressure. The concentrate was subjected to column chromatography (silica gel 10 g, ethyl acetate/methanol=1/0 to 9/1 to 4/1), and the desired fraction was concentrated under reduced pressure. To the concentrate was added ethyl acetate and resulting precipitates were collected by filtration. The filtrate was concentrated under reduced pressure. To the concentrate was added diethyl ether, and the resulting precipitates were collected by filtration. The precipitates were washed with diethyl ether, and dried under reduced pressure to give the titled compound (331 mg, 0.69 mmol, Yield 69%) as white crystals.

mp 132-135° C.

$^1$H NMR (CDCl$_3$) δ 1.0-2.1 (13H, m), 2.04 (3H, 2.30 (2H, t, J=7.5 Hz), 2.50 (2H, d, J=6.2 Hz), 2.6-2.8 (1H, m), 2.83 (2H, br d, J=10.6 Hz), 3.0-3.2 (1H, m), 3.6-3.95 (2H, m), 3.68 (2H, t, J=7.3 Hz), 4.19 (1H, d, J=7.2 Hz), 4.40 (1H, br d, J=12.8 Hz), 7.05-7.5 (10H, m)

EXAMPLE 15

N-[3-(4-Benzyl-1-piperidinyl)propyl]-N'-[1-(methylsulfonyl)-4-piperidinyl]-N-phenylurea The compound obtained in Example 13 (435 mg, 1.00 mmol) and triethylamine (0.335 ml) were dissolved in THF (10 ml). To the solution was added methanesulfonyl chloride (0.155 ml) under ice cooling with stirring, and the mixture was stirred at the same temperature for 1 hour. To the reaction mixture was added a saturated aqueous solution of sodium hydrogencarbonate (15 ml) under ice cooling, and the mixture was extracted with ethyl acetate (15 ml×3). The organic layer was dried over anhydrous sodium sulfate and concentrated under reduced pressure. The concentrate was subjected to column chromatography (silica gel, 10 g, ethyl acetate/methanol=1/0 to 9/1 to 4/1), and the desired fraction was concentrated under reduced pressure. To the concentrate was added ethyl acetate and resulting precipitates were filtered off. The filtrate was concentrated under reduced pressure. To the concentrate was added diethyl ether and resulting precipitates were collected by filtration. The precipitates were washed with diethyl ether, and dried under reduced pressure to give the titled compound (310 mg, 0.60 mmol, Yield 60%) as white solid.

mp 158-160° C.

$^1$H NMR (CDCl$_3$) δ 1.1-2.05 (13H, m), 2.30 (2H, t, J=7.3 Hz), 2.51 (2H, d, J=6.6 Hz), 2.65-2.9 (4H, m), 2.75 (3H, s), 3.6-3.85 (5H, m), 4.23 (1H, d, J=7.6 Hz), 7.05-7.5 (10H, m)

EXAMPLE 16

1-Acetyl-N-[3-(4-benzyl-1-piperidinyl)propyl]-N-(3,4-dichlorophenyl)-4-piperidinecarboxamide To a solution of the compound obtained in Reference Example 2 (450 mg, 1.0 mmol) and triethylamine (0.836 ml) in dichloromethane (10 ml) was added 1-acetyl-4-piperidinecarbonyl chloride (569 mg, 3.0 mmol) under ice cooling with stirring, and the mixture was stirred at the same temperature for 1 hour. Under ice cooling, a saturated aqueous solution of sodium hydrogencarbonate (15 ml) was added, and the organic layer was distilled off under reduced pressure. The aqueous layer was extracted with ethyl acetate (15 ml×3). The organic layer was washed with a saturated aqueous solution of sodium hydrogencarbonate (5 ml×3), saturated sodium chloride solution (5 ml), successively, dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure to give the titled compound (522 mg, 0.98 mmol, Yield 98%) as colorless oily substance.

$^1$H NMR (CDCl$_3$) δ 1.1-1.9 (13H, m), 2.04 (3H, s), 2.2-2.55 (2H, m), 2.27 (2H, t, J=7.4 Hz), 2.51 (2H, d, J=6.2 Hz), 2.75-2.95 (1H, m), 2.82 (2H, br d, J=11.2 Hz), 3.65 (2H, t, J=7.5 Hz), 3.77 (1H, br d J=13.4 Hz), 4.52 (1H, br d, J=13.4 Hz), 7.0-7.35 (5H, m), 7.04 (1H, dd, J=2.4, 8.4 Hz), 7.32 (1H, d, J=2.4 Hz), 7.52 (1H, d, J=8.4 Hz)

EXAMPLE 17

1-Acetyl-N-(3,4-dichlorophenyl)-N-{3-[4-(4-fluorobenzyl)-1-piperidinyl]propyl}-4-piperidinecarboxamide By a similar manner to Example 16, the titled compound was synthesized by using the compound obtained in Reference Example 3-3. Yield 99%.

$^1$H NMR (CDCl$_3$) δ 1.1-1.9 (13H, m), 2.05 (3H, s), 2.2-2.55 (2H, m), 2.27 (2H, t, J=7.5 Hz), 2.48 (2H, d, J=6.6 Hz), 2.7-3.0 (1H, m), 2.81 (2H, br d, J=11.8 Hz), 3.65 (2H, t, J=7.5 Hz), 3.78 (1H, br d, J=13.0 Hz), 4.52 (1H, br d, J=13.0 Hz), 6.94 (2H, t, J=8.6 Hz), 6.95-7.15 (3H, m), 7.32 (1H, d, J=2.2 Hz), 7.52 (1H, d, J=8.4 Hz)

EXAMPLE 18

1-Acetyl-N-(3-chlorophenyl)-N-{3-[4-(4-fluorobenzyl)-1-piperidinyl]propyl}-4-piperidinecarboxamide By a similar manner to Example 16, the titled compound was synthesized by using the compound obtained in Reference Example 4. Yield 83%.

$^1$H NMR (CDCl$_3$) δ 1.1-1.9 (13H, m), 2.05 (3H, s), 2.2-2.55 (2H, m), 2.27 (2H, t, J=7.5 Hz), 2.48 (2H, d, J=6.6 Hz), 2.7-2.95 (1H, m), 2.82 (2H, br d, J=11.6 Hz), 3.67 (2H, t, J=7.7 Hz), 3.77 (1H, br d, J=13.1 Hz), 4.52 (1H, br d, J=13.1 Hz), 6.94 (2H, t, J=8.8 Hz), 7.0-7.15 (3H, m), 7.20 (1H, s), 7.38 (2H, d, J=5.0 Hz)

EXAMPLE 19

1-Acetyl-N-(3-chlorophenyl)-N-{3-[4-(3-fluorobenzyl)-1-piperidinyl]propyl}-4-piperidinecarboxamide By a similar manner to Example 16, the titled compound was synthesized by using the compound obtained in Reference Example 5-2. Yield 68%.

$^1$H NMR (CDCl$_3$) δ 1.15-1.90 (13H, m), 2.05 (3H, s), 2.22-2.57 (2H, m), 2.27 (2H, t, J=7.5 Hz), 2.51 (2H, d, J=6.4 Hz), 2.69-3.00 (1H, m), 2.81 (2H, br d, J=11 Hz), 3.66 (2H, t, J=7.5 Hz), 3.76 (1H, br d, J=13 Hz), 4.51 (1H, br d, J=13 Hz), 6.80-7.23 (6H, m), 7.38 (2H, d, J=5 Hz)

EXAMPLE 20

1-Acetyl-N-(3-chlorophenyl)-N-{3-[4-(2-fluorobenzyl)-1-piperidinyl]propyl}-4-piperidinecarboxamide By a similar manner to Example 16, the titled compound was synthesized by using the compound obtained in Reference Example 6-2. Yield 82%.

$^1$H NMR (CDCl$_3$) δ 1.10-1.89 (13H, m), 2.05 (3H, s), 2.23-2.57 (2H, m), 2.27 (2H, t, J=7.5 Hz), 2.57 (2H, d, J=6.6 Hz), 2.70-3.00 (1H, m), 2.82 (2H, br d, J=11 Hz), 3.67 (2H, t, J=7.5 Hz), 3.76 (1H, br d, J=13 Hz), 4.52 (1H, br d, J=13 Hz), 6.94-7.20 (6H, m), 7.38 (2H, d, J=5 Hz)

EXAMPLE 21

1-Acetyl-N-(3-chlorophenyl)-N-{3-[4-(2,4-difluorobenzyl)-1-piperidinyl]propyl}-4-piperidinecarboxamide By a similar manner to Example 16, the titled compound was synthesized by using the compound obtained in Reference Example 7-2. Yield 70%.

$^1$H NMR (CDCl$_3$) δ 1.09-1.89 (13H, m), 2.05 (3H, s), 2.21-2.56 (2H, m), 2.28 (2H, t, J=7.5 Hz), 2.52 (2H, d, J=6.4 Hz), 2.65-2.99 (1H, m), 2.82 (2H, br d, J=11 Hz), 3.66 (2H, t, J=7.5 Hz), 3.75 (1H, br d, J=13 Hz), 4.52 (1H, br d, J=13 Hz), 6.71-7.20 (5H, m), 7.38 (2H, d, J=5 Hz)

EXAMPLE 22

1-Acetyl-N-[3-(4-benzyl-1-piperidinyl)propyl]-N-(4-methylphenyl)-4-piperidinecarboxamide By a similar manner to Example 16, the titled compound was synthesized by using the compound obtained in Reference Example 8. Yield 83%.

$^1$H NMR (CDCl$_3$) δ 1.1-1.9 (13H, m), 2.03 (3H, s), 2.2-2.45 (2H, m), 2.28 (2H, t, J=7.5 Hz), 2.39 (3H, s), 2.50 (2H, d, J=6.6 Hz), 2.7-2.9 (1H, m), 2.83 (2H, br d, J=11.0 Hz), 3.65 (2H, t, J=7.6 Hz), 3.74 (1H, br d, J=13.2 Hz), 4.50 (1H, br d, J=13.2 Hz), 7.02 (2H, d, J=8.2 Hz), 7.05-7.35 (7H, m)

EXAMPLE 23

1-Acetyl-N-[3-(4-benzyl-1-piperidinyl)propyl]-N-(3-chloro-4-methylphenyl)-4-piperidinecarboxamide By a similar manner to Example 16, the titled compound was synthesized by using the compound obtained in Reference Example 9. Yield 54%.

mp 96-99° C.

$^1$H NMR (CDCl$_3$) δ 1.1-1.9 (13H, m), 2.04 (3H, s), 2.2-2.45 (2H, m), 2.27 (2H, t, J=7.5 Hz), 2.42 (3H, s), 2.51 (2H, d, J=6.6 Hz), 2.7-2.95 (1H, m), 2.82 (2H, br d, J=11.4 Hz), 3.64 (2H, t, J=7.7 Hz), 3.76 (1H, br d, J=13.9 Hz), 4.51 (1H, br d, J=13.9 Hz), 6.96 (1H, dd, J=2.2, 8.0 Hz), 7.05-7.35 (7H, m)

EXAMPLE 24

1-Acetyl-N-[3-(4-benzyl-1-piperidinyl)propyl]-N-[3-(trifluoromethyl)phenyl]-4-piperidinecarboxamide By a similar manner to Example 16, the titled compound was synthesized by using the compound obtained in Reference Example 10. Yield 97%.

$^1$H NMR (CDCl$_3$) δ 1.1-2.0 (13H, m), 2.04 (3H, s), 2.15-2.45 (2H, m), 2.29 (2H, t, J=7.5 Hz), 2.51 (2H, d, J=6.6 Hz), 2.7-2.9 (1H, m), 2.82 (2H, br d, J=11.0 Hz), 3.65-4.85 (1H, m), 3.72 (2H, t, J=7.3 Hz), 4.51 (1H, br d, J=13.2 Hz), 7.05-7.7 (9H, m)

EXAMPLE 25

N-(3,4-Dichlorophenyl)-N-{3-[4-(4-fluorobenzyl)-1-piperidinyl]propyl}-1-(methylsulfonyl)-4-piperidinecarboxamide To a suspension of the compound obtained in Reference Example 13-2 (518 mg, 2.5 mmol) and DMF (0.023 ml) in dichloromethane (10 ml) was added oxalyl chloride (0.320 ml) under ice cooling, and the mixture was stirred for 1 hour while the temperature was elevating to room temperature. The reaction mixture was concentrated under reduced pressure, and to the concentrate was added toluene(10 ml). The mixture was concentrated again under reduced pressure. A solution of the concentrate in dichloromethane (5 ml) was added dropwise to a solution of the compound obtained in Reference Example 3-3 (468 mg, 1.0 mmol) and triethylamine (0.836 ml) in dichloromethane (10 ml) under ice cooling, and the mixture was stirred at the same temperature for 3 hours. To the mixture was added a saturated aqueous solution of sodium hydrogencarbonate (15 ml) under ice cooling, and the mixture was extracted with dichloromethane. The organic layer was washed with a saturated aqueous solution of sodium hydrogencarbonate, saturated sodium chloride solution, successively, dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure. To the mixture was added diethyl ether, and the resulting precipitates were collected by filtration. The precipitates were washed with diethyl ether, and dried under reduced pressure to give the titled compound (485 mg, 0.83 mmol, Yield 83%) as white crystals.

mp 148-150° C.

$^1$H NMR (CDCl$_3$) δ 1.05-2.05 (13H, m), 2.1-2.35 (1H, m), 2.27 (2H, t, J=7.5 Hz), 2.4-2.7 (2H, m), 2.48 (2H, d, J=6.6 Hz), 2.74 (3H, s), 2.81 (2H, br d, J=11.8 Hz), 3.55-3.8 (4H, m), 6.85-7.15 (5H, m), 7.31 (1H, d, J=2.6 Hz), 7.52 (1H, d, J=8.4 Hz)

EXAMPLE 26

N-(3-Chlorophenyl)-N-(3-[4-(4-fluorobenzyl)-1-piperidinyl]propyl}-1-(methylsulfonyl)-4-piperidinecarboxamide By a similar manner to Example 25, the titled compound was synthesized by using the compound obtained in Reference Example 4. Yield 47%.

$^1$H NMR (CDCl$_3$) δ 1.1-2.0 (13H, m), 2.1-2.35 (1H, m), 2.27 (2H, t, J=7.4 Hz), 2.4-2.65 (2H, m), 2.48 (2H, d, J=6.6 Hz), 2.73 (3H, s), 2.82 (2H, br d, J=11.0 Hz), 3.6-3.8 (4H, m), 6.94 (2H, t, J=8.8 Hz), 7.0-7.15 (3H, m), 7.20 (1H, s), 7.38 (2H, d, J=5.22 Hz)

EXAMPLE 27

N-[3-(4-Benzyl-1-piperidinyl)propyl]-N-(3,4-dichlorophenyl)-1-(N,N-dimethyl carbamoyl)-4-piperidinecarboxamide To a suspension of the compound obtained in Reference Example 14-2 (501 mg, 2.5 mmol) and DMF (0.023 ml) in dichloromethane (10 ml) was added oxalyl chloride (0.320 ml), and the mixture was stirred for 1 hour while the temperature was elevating to room temperature. The reaction mixture was concentrated under reduced pressure, and to the concentrate was added toluene (10 ml). The mixture was concentrated again under reduced pressure. A solution of the concentrate in dichloromethane (5 ml) was added dropwise to a solution of the compound obtained in Reference Example 2 (450 mg, 1.0 mmol) and triethylamine (0.836 ml) in dichloromethane (10 ml) under ice cooling, and the mixture was stirred at the same temperature for 3 hours. Under ice cooling, a saturated aqueous solution of sodium hydrogencarbonate (15 ml) was added, and the organic layer was distilled off under reduced pressure. The aqueous layer was extracted with ethyl acetate (15 ml×3). The organic layer was washed with a saturated aqueous solution of sodium hydrogencarbonate (5 ml×3), saturated sodium chloride solution (5 ml), successively, dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure. To the mixture was added diethyl ether, and the resulting precipitates were collected by filtration. The precipitates were washed with diethyl ether, and dried under reduced pressure to give the titled compound (243 mg, 0.43 mmol, Yield 43%) as white crystals.

mp 109-112° C.

$^1$H NMR (CDCl$_3$) δ 1.1-1.95 (13H, m), 2.1-2.35 (1H, m), 2.27 (2H, t, J=7.5 Hz), 2.35-2.65 (2H, m), 2.51 (2H, d, J=6.6 Hz,), 2.7-2.9 (2H, m), 2.79 (6H, s), 3.5-3.75 (4H, m), 7.02 (1H, dd, J=2.1, 8.5 Hz), 7.05-7.35 (5H, m), 7.31 (1H, d, J=2.1 Hz), 7.51 (1H, d, J=8.5 Hz)

EXAMPLE 28

1-Acetyl-N-(3-chloro-4-methylphenyl)-N-{3-[4-(4-fluorobenzoyl)-1-piperidinyl]propyl}-4-piperidinecarboxamide A mixture of the compound obtained in Reference Example 11-2 (743 mg, 2.0 mmol), 4-(4-fluorobenzoyl) piperidine hydrochloride (487 mg, 2.0 mmol), potassium iodide (332 mg, 2.0 mmol), potassium carbonate (829 mg, 6.0 mmol) and acetonitrile (40 ml) was stirred at 80° C. for 18 hours. The reaction mixture was concentrated under reduced pressure, and to the concentrate was added water (15 ml). The mixture was extracted with ethyl acetate (15 ml×3). The organic layer was dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure to give the titled compound (742 mg, 1.4 mmol, Yield 68%) as pale yellow oily substance.

$^1$H NMR (CDCl$_3$) δ 1.5-2.15 (12H, m), 2.05 (3H, s), 2.25-2.5 (2H, m), 2.36 (2H, t, J=7.5 Hz), 2.42 (3H, s), 2.7-3.3 (2H, m), 2.94 (2H, br d, J=11.4 Hz), 3.67 (2H, t, J=7.7 Hz), 3.77 (1H, br d, J=13.4 Hz), 4.52 (1H, br d, J=13.4 Hz), 6.99 (1H, dd, J=2.1, 7.9 Hz), 7.13 (2H, t, J=8.8 Hz), 7.20 (1H, d, J=2.1 Hz), 7.30 (1H, d, J=7.9 Hz), 7.96 (2H, dd, J=5.4, 8.8 Hz)

EXAMPLE 29

1-Acetyl-N-(3-chloro-4-methylphenyl)-N-{3-[4-(2-oxo-1,3-dihydro-2H-benzoimidazol-1-yl)-1-piperidinyl]propyl}-4-piperidinecarboxamide By a similar manner to Example 28, the titled compound was synthesized by using 4-(2-oxo-1,3-dihydro-2H-benzoimidazol-1-yl)piperidine. Yield 37%.

$^1$H NMR (CDCl$_3$) δ 1.5-2.6 (16H, m), 2.05 (3H, s), 2.43 (3H, s), 2.75-3.15 (3H, m), 3.6-3.9 (3H, m), 4.2-4.5 (1H, m), 4.53 (1H, br d, J=13.0 Hz), 6.9-7.4 (7H, m), 10.0 (1H, s)

EXAMPLE 30

1-Acetyl-N-{3-[4-(1H-1,2,3-benzotriazol-1-yl)-1-piperidinyl]propyl}-N-(3-chloro-4-methylphenyl)-4-piperidinecarboxamide By a similar manner to Example 28, the titled compound was synthesized by using 4-(1H-1,2,3-benzotriazol-1-yl)piperidine hydrochloride. Yield 45%.

$^1$H NMR (CDCl$_3$) δ 1.5-1.9 (6H, m), 2.0-2.6 (10H, m), 2.05 (3H, s), 2.43 (3H, s), 2.75-2.95 (1H, m), 2.95-3.15 (2H, m), 3.72 (2H, t, J=7.5 Hz), 3.78 (1H, br d, J=13.2 Hz), 4.52 (1H, br d, J=13.2 Hz), 4.6-4.8 (1H, m), 7.01 (1H, dd, J=2.2, 8.9 Hz), 7.22 (1H, d, J=2.2 Hz), 7.25-7.55 (3H, m), 7.60 (1H, d, J=8.2 Hz), 8.05 (1H, d, J=8.0 Hz)

EXAMPLE 31

1-Acetyl-N-(3-chlorophenyl)-N-{3-[4-(4-fluorobenzyl)-4-hydroxy-1-piperidinyl]propyl}-4-piperidinecarboxamide A mixture of the compound obtained in Reference Example 12-2 (357 mg, 1.0 mmol), 4-(4-fluorobenzyl)-4-hydroxypiperidine (230 mg, 1.1 mmol), potassium iodide (166 mg, 1.0 mmol), potassium carbonate (207 mg, 1.5 mmol) and acetonitrile (20 ml) was stirred at 80° C. for 20 hours. The reaction mixture was concentrated under reduced pressure, and to the concentrate was added water (15 ml). The mixture was extracted with ethylacetate (15 ml×3). The organic layer was dried over anhydrous sodium sulfate and concentrated under reduced pressure. The concentrate was subjected to column chromatography (silica gel 10 g, ethyl acetate/methanol=1/0 to 9/1 to 4/1), and the desired fraction was concentrated under reduced pressure. To the concentrate was added ethyl acetate and resulting precipitates were collected by filtration. The filtrate was concentrated under reduced pressure to give the titled compound (379 mg, 0.71 mmol, Yield 72%) as pale yellow amorphous substance. $^1$H NMR (CDCl$_3$) δ 1.4-1.9 (10H, m), 2.05 (3H, s), 2.15-2.45 (6H, m), 2.55-2.95 (3H, m), 2.71 (2H, s), 3.68 (2H, t, J=7.7 Hz), 3.77 (1H, br d, J=13.6 Hz), 4.52 (1H, br d, J=13.6 Hz), 6.9-7.25 (6H, m), 7.39 (2H, d, J=5.0 Hz)

EXAMPLE 32

1-Acetyl-N-[3-(4-benzyl-1-piperidinyl)propyl]-N-(3-chlorobenzyl)-4-piperidinecarboxamide trifluoroacetate To the reaction vessel containing carbodiimide resine (Argonaut company Ltd., 1.15 mmol/g, 87 mg, 100 μmol) was added a solution of 1-acetyl-4-piperidine carboxylic acid (12.8 mg, 75 μmol) in dichloromethane (0.3 ml) at room temperature, and the mixture was kept standing for 30 minutes. To the mixture was added a solution of the compound obtained in Reference Example 17 (16.1 mg, 50 μmol) in dichloromethane (0.3 ml) at room temperature, and the mixture was stirred for24 hours. The resin was filtered off, and the filtrate was concentrated under reduced pressure and purified by preparative HPLC. The desired fraction was concentrated to give the titled compound (17.3 mg) as a colorless oily substance.

HPLC analysis (220 nm): Purity 93% (Retention time 3.041 minutes): MS (APCI$^+$) 510 (M+1)

$^1$H NMR (CDCl$_3$) δ 1.23-1.90 (8H, m), 2.10 (3H, s), 2.19 (2H, br), 2.41-2.79 (5H, m), 2.89 (2H, br), 3.39-3.71 (7H, m), 3.83 (2H, s), 4.40-4.82 (2H, br), 7.11-7.33 (9H, m)

EXAMPLE 33

1-Acetyl-N-benzyl-N-[3-(4-benzyl-1-piperidinyl)propyl]-4-piperidinecarboxamide trifluoroacetate By a similar manner to Example 32, the titled compound was synthesized by using the compound obtained in Reference Example 15.

HPLC analysis (220 nm) Purity 93% (Retention time 2.813 minutes) MS (APCI$^+$) 476 (M+1)

EXAMPLE 34

1-Acetyl-N-[3-(4-benzyl-1-piperidinyl)propyl]-N-(4-fluorobenzyl)-4-piperidinecarboxamide trifluoroacetate By a similar manner to Example 32, the titled compound was synthesized by using the compound obtained in Reference Example 16.

HPLC analysis (220 nm): Purity 96% (Retention time 2.964 minutes) MS (APCI$^+$) 494 (M+1)

EXAMPLE 35

1-Acetyl-N-[3-(4-benzyl-1-piperidinyl)propyl]-N-(3,4-dichlorobenzyl)-4-piperidinecarboxamide trifluoroacetate By a similar manner to Example 32, the titled compound was synthesized by using the compound obtained in Reference Example 18.

HPLC analysis (220 nm): Purity 99% (Retention time 3.216 minutes) MS (APCI$^+$) 544 (M+1)

EXAMPLE 36

1-Acetyl-N-[3-(4-benzyl-1-piperidinyl)propyl]-N-(3-pyridylmethyl)-4-piperidinecarboxamide trifluoroacetate By a similar manner to Example 32, the titled compound was synthesized by using the compound obtained in Reference Example 19.

HPLC analysis (220 nm): Purity 95% (Retention time 2.371 minutes) MS (APCI$^+$) 477 (M+1)

EXAMPLE 37

1-Acetyl-N-[3-(4-benzyl-1-piperidinyl)propyl]-N-(cyclohexylmethyl)-4-piperidinecarboxamide trifluoroacetate By a similar manner to Example 32, the titled compound was synthesized by using the compound obtained in Reference Example 20.

HPLC analysis (220 nm): Purity 93% (Retention time 3.589 minutes) MS (APCI$^+$) 482 (M+1)

EXAMPLE 38

1-Acetyl-N-[3-(4-benzyl-1-piperidinyl)propyl]-N-(4-methoxybenzyl)-4-piperidinecarboxamide trifluoroacetate By a similar manner to Example 32, the titled compound was synthesized by using the compound obtained in Reference Example 21.

HPLC analysis (220 nm): Purity 93% (Retention time 3.004 minutes) MS (APCI$^+$) 506 (M+1)

EXAMPLE 39

1-Acetyl-N-[3-(4-benzyl-1-piperidinyl)propyl]-N-(4-methyl benzyl)-4-piperidinecarboxamide trifluoroacetate By a similar manner to Example 32, the titled compound was synthesized by using the compound obtained in Reference Example 22.

HPLC analysis (220 nm) Purity 98% (Retention time 3.314 minutes) MS (APCI$^+$) 490 (M+1)

EXAMPLE 40

1-Acetyl-N-[3-(4-benzyl-1-piperidinyl)propyl]-N-(4-chlorobenzyl)-4-piperidinecarboxamide trifluoroacetate By a similar manner to Example 32, the titled compound was synthesized by using the compound obtained in Reference Example 23.

HPLC analysis (220 nm): Purity 99% (Retention time 3.031 minutes) MS (APCI$^+$) 510 (M+1)

EXAMPLE 41

1-Acetyl-N-[3-(4-benzyl-1-piperidinyl)propyl]-N-(2,6-difluorobenzyl)-4-piperidinecarboxamide trifluoroacetate By a similar manner to Example 32, the titled compound was synthesized by using the compound obtained in Reference Example 24.

HPLC analysis (220 nm): Purity 95% (Retention time 3.219 minutes) MS (APCI$^+$) 512 (M+1)

EXAMPLE 42

1-Acetyl-N-[3-(4-benzyl-1-piperidinyl)propyl]-N-(2-chlorobenzyl)-4-piperidinecarboxamide trifluoroacetate By a similar manner to Example 32, the titled compound was synthesized by using the compound obtained in Reference Example 25.

HPLC analysis (220 nm): Purity 100% (Retention time 2.999 minutes) MS (APCI$^+$) 510 (M+1)

EXAMPLE 43

N-Benzyl-N-[3-(4-benzyl-1-piperidinyl)propyl]-1-(tert-butoxycarbonyl)-4-piperidinecarboxamide trifluoroacetate By a similar manner to Example 32, the titled compound was synthesized by using 1-(tert-butoxycarbonyl)-4-piperidine carboxylic acid and the compound obtained in Reference Example 15.

HPLC analysis (220 nm): Purity 97% (Retention time 3.549 minutes) MS (APCI$^+$) 534 (M+1)

EXAMPLE 44

N-Benzyl-N-[3-(4-benzyl-1-piperidinyl)propyl]-4-piperidinecarboxamide trifluoroacetate To the reaction vessel containing carbodimide resine (Argonaut company Ltd., 1.15 mmol/g, 87 mg, 100 µmol) was added a solution of 1-(tert-butoxycarbonyl)-4-piperidine carboxylic acid (17.2 mg, 75 µmol) in dichloromethane (0.3 ml) at room temperature, and the mixture was kept standing for 30 minutes. To the mixture was added a solution of the compound obtained in Reference Example 15 (16.1 mg, 50 µmol) in dichloromethane (0.3 ml) at room temperature, and the mixture was stirred for 24 hours. The resin was filtered off, and the filtrate was concentrated under reduced pressure. To the concentrate was added trifluoroacetic acid (0.5 ml). The mixture was concentrated under reduced pressure and purified by preparative HPLC. The desired fraction was concentrated to give the titled compound (8.3 mg) as a colorless oily substance.

HPLC analysis (220 nm): Purity 94% (Retention time 2.596 minutes) MS (APCI$^+$) 434 (M+1)

EXAMPLE 45

(2S)-N-Benzyl-N-[3-(4-benzyl-1-piperidinyl)propyl]-1-(tert-butoxycarbonyl)-2-pyrrolidine carboxamide trifluoroacetate By a similar manner to Example 32, the titled compound was synthesized by using 1-(tert-butoxycarbonyl)-L-proline and the compound obtained in Reference Example 15.

HPLC analysis (220 nm): Purity 99% (Retention time 3.490 minutes) MS (APCI$^+$) 520 (M+1)

EXAMPLE 46

(2S)-N-Benzyl-N-[3-(4-benzyl-1-piperidinyl)propyl]-2-pyrrolidine carboxamide trifluoroacetate By a similar manner to Example 44, the titled compound was synthesized by using 1-(tert-butoxycarbonyl)-L-proline.

HPLC analysis (220 nm) Purity 97% (Retention time 2.617 minutes) MS (APCI$^+$) 420 (M+1)

EXAMPLE 47

(2S, 4R)-N-Benzyl-N-[3-(4-benzyl-1-piperidinyl)propyl]-1-(tert-butoxycarbonyl)-4-hydroxy-2-pyrrolidine carboxamide trifluoroacetate By a similar manner to Example 32, the titled compound was synthesized by using trans-1-(tert-butoxycarbonyl)-4-hydroxy-L-proline and the compound obtained in Reference Example 15.

HPLC analysis (220 nm): Purity 100% (Retention time 3.152 minutes) MS (APCI$^+$) 536 (M+1)

EXAMPLE 48

(2S, 4R)-N-Benzyl-N-[3-(4-benzyl-1-piperidinyl) propyl]-4-hydroxy-2-pyrrolidine carboxamide trifluoroacetate By a similar manner to Example 44, the titled compound was synthesized by using trans-1-(tert-butoxycarbonyl)-4-hydroxy-L-proline.

HPLC analysis (220 nm): Purity 99% (Retention time 2.549 minutes) MS (APCI$^+$) 436 (M+1)

EXAMPLE 49

1-{3-[N-(1-acetyl-4-piperidinylcarbonyl)-3-chloroanilino]propyl)-4-(4-fluorobenzyl)-1-methyl piperidinium iodide A mixture of the compound obtained in Example 18 (310 mg, 0.60 mmol), methyl iodide (0.75 ml) and acetonitrile (10 ml) was stirred at room temperature for 14 hours. The reaction mixture was concentrated under reduced pressure. To the concentrate was added diethyl ether, and the resulting precipitates were collected by filtration. The precipitates were washed with diethyl ether, and dried under reduced pressure to give the titled compound (344 mg, 0.52 mmol, Yield 87%) as white amorphous substance.

$^1$H NMR (CDCl$_3$) δ 1.4-2.55 (13H, m), 2.02 (3H, s), 2.64 (2H, d, J=7.0 Hz), 2.7-2.95 (1H, m), 3.23 (0.7×3H, s), 3.42 (0.3×3H, s), 3.55-4.1 (9H, m), 4.4-4.6 (1H, m), 6.9-7.65 (8H, m)

EXAMPLE 50

1-Acetyl-N-[3-(4-benzyl-1-piperidinyl)propyl]-N-(1,3-thiazol-2-yl)-4-piperidinecarboxamide To a solution of the compound obtained in Reference Example 26 (330 mg, 1.05 mmol) and triethylamine (0.585 ml) in dichloromethane (5 ml) was added 1-acetyl-4-piperidinecarbonyl chloride (597 mg, 3.15 mmol) at 0° C., and the mixture was stirred at 0° C. for 2 hours. To the mixture were added triethylamine (0.439 ml) and 1-acetyl-4-piperidinecarbonyl chloride,(597 mg, 3.1.5 mmol), and the mixture was stirred at 0° C. for 1 hour. To the mixture were added triethylamine (0.300 ml) and 1-acetyl-4-piperidinecarbonyl chloride (300 mg, 1.58 mmol), and the mixture was stirred 1 hour. To the mixture was added a saturated aqueous solution of sodium hydrogencarbonate (15 ml), and the organic solvent was distilled off under reduced pressure. The concentrate was extracted with ethyl acetate (20 ml×3). The organic layer was washed with a saturated aqueous solution of sodium hydrogencarbonate (10 ml×3), saturated sodium chloride solution (10 ml), successively, dried over magnesium sulfate and concentrated under reduced pressure. The concentrate was subjected to column chromatography (alumina 70 g, hexane/ethyl acetate=10/1 to 1/1), and the desired fraction was concentrated under reduced pressure to give the titled compound (283 mg, 0.60 mmol, Yield 58%) as a colorless oily substance.

$^1$H NMR (CDCl$_3$) δ 1.2-1.99 (13H, m), 2.13 (3H, s), 2.36 (2H, t, J=6.6 Hz), 2.55 (2H, d, J=6.2 Hz), 2.70 (1H, m), 2.87 (2H, br d, J=10.6 Hz), 3.12 (2H, m), 3.92 (1H, br d, J=13.0 Hz), 4.23 (2H, m), 4.64 (1H, br d, J=14.0 Hz), 7.01-7.32 (6H, m), 7.51 (1H, d, J=3.2 Hz)

EXAMPLE 51

1-Acetyl-N-[3-(4-benzyl-1-piperidinyl)propyl]-N-(5-methyl-3-isoxazolyl)-4-piperidinecarboxamide To a solution of the compound obtained in Reference Example 27 (500 mg, 1.60 mmol) and triethylamine (0.892 ml) in THF (6 ml) was added 1-acetyl-4-piperidinecarbonyl chloride (908 mg, 4.79 mmol) at 0° C. with stirring, and the mixture was stirred at 0° C. for 3 hours. To the mixture was added a saturated aqueous, solution of sodium hydrogencarbonate (15 ml), and the organic solvent was distilled off under reduced pressure. The concentrate was extracted with ethyl acetate (20 ml×3). The organic layer was washed with a saturated aqueous solution of sodium hydrogencarbonate (10 ml×3), saturated sodium chloride solution (10 ml), successively, dried over magnesium sulfate and concentrated under reduced pressure. The concentrate was subjected to column chromatography (alumina 70 g, hexane/ethyl acetate=10/1 to 1/2), and the desired fraction was concentrated under reduced pressure to give the titled compound (380 mg, 0.81 mmol, Yield 51%) as a colorless oily substance.

$^1$H NMR (CDCl$_3$) δ 1.2-1.88 (13H, m), 2.08 (3H, s), 2.29 (2H, t, J=7.6 Hz), 2.45 (3H, s), 2.52 (2H, d, J=6.6 Hz), 2.50-2.70 (1H, m), 2.82 (2H, br d, J=11.8 Hz), 3.00 (2H, m), 3.60-3.90 (3H, m), 4.56 (1H, br d, J=13.2 Hz), 6.03 (1H, br s), 7.11-7.32 (5H, m)

EXAMPLE 52

1-Acetyl-N-(3-chlorophenyl)-N-{3-[4-(2-pyrimidinyl)-1-piperazinyl]propyl}-4-piperidinecarboxamide trifluoroacetate A mixture of the compound obtained in Reference Example 12-2 (50 mg, 0.140 mmol), 1-(2-pyrimidinyl) piperazine 2 hydrochloride (45.0 mg, 0.182 mmol), potassium iodide (23.2 mg, 0.140 mmol), potassium carbonate (77.4 mg, 0.560 mmol) and acetonitrile (1.5 ml) was stirred at 80° C. for 7 hours. To the reaction mixture was added water (2 ml), and the mixture was extracted with dichloromethane (3 ml). The organic layer was concentrated under reduced pressure and the concentrate was purified by preparative HPLC. The desired fraction was concentrated to give the titled compound (24.6 mg) as a colorless oily substance.

HPLC analysis (220 nm): Purity 99% (Retention time 4.211 minutes) MS (APCI$^+$) 485 (M+1) $^1$H NMR (CDCl$_3$) δ 1.5-1.9 (4H, m), 1.9-2.2 (5H, m), 2.2-2.4 (2H, m), 2.6-3.2 (5H, m), 3.3-3.9 (9H, m), 4.5-4.6 (1H, m), 4.6-5.2 (2H, br), 6.63 (1H, t, J=4.7 Hz), 7.1-7.2 (2H, m), 7.42 (2H, d, J=5.2 Hz), 8.35 (2H, d, J=4.7 Hz)

EXAMPLE 53

1-Acetyl-N-(3-chlorophenyl)-N-{3-[N-(3-phenyl propyl)amino]propyl}-4-piperidinecarboxamide trifluoroacetate By a similar manner to Example 52, the titled compound was synthesized by using 3-phenyl propylamine.

HPLC analysis (220 nm): Purity 92% (Retention time 4.781 minutes)

MS (APCI⁺) 456 (M+1) ¹H NMR (CDCl₃) δ 1.5-1.8 (4H, m), 1.8-2.2 (9H, m), 2.2-2.5 (2H, m), 2.77 (2H, t, J=7.7 Hz), 2.8-3.1 (4H, m), 3.6-3.9 (3H, m), 4.4-4.6 (1H, m), 7.11-7.45 (9H, m), 9.20 (1H, br)

EXAMPLE 54

1-Acetyl-N-(3-chlorophenyl)-N-{3-[4-(2-pyridyl)-1-piperazinyl]propyl}-4-piperidinecarboxamide trifluoroacetate By a similar manner to Example 52, the titled compound was synthesized by using 1-(2-pyridyl)piperazine.

HPLC analysis (220 nm): Purity 95% (Retention time 4.458 minutes) MS (APCI⁺) 484 (M+1)

EXAMPLE 55

1-Acetyl-N-[3-(4-benzyl-1-piperazinyl)propyl]-N-(3-chlorophenyl)-4-piperidinecarboxamide trifluoroacetate By a similar manner to Example 52, the titled compound was synthesized by using 1-benzylpiperazine.

HPLC analysis (220 nm): Purity 96% (Retention time 4.676 minutes) MS (APCI⁺) 497 (M+1)

EXAMPLE 56

1-Acetyl-N-(3-chlorophenyl)-N-[3-(4-phenyl-1-piperazinyl)propyl]-4-piperidinecarboxamide trifluoroacetate By a similar manner to Example 52, the titled compound was synthesized by using 1-phenylpiperazine.

HPLC analysis (220 nm): Purity 100% (Retention time 4.383 minutes) MS (APCI⁺) 483 (M+1)

EXAMPLE 57

1-Acetyl-N-(3-chlorophenyl)-N-[3-(4-piperonyl-1-piperazinyl)propyl]-4-piperidinecarboxamide trifluoroacetate By a similar manner to Example 52, the titled compound was synthesized by using 1-piperonylpiperazine.

HPLC analysis (220 nm): Purity 95% (Retention time 4.361 minutes) MS (APCI⁺) 541 (M+1)

EXAMPLE 58

1-Acetyl-N-(3-chlorophenyl)-N-[3-(cis-2,6-dimethylmorpholino)propyl]-4-piperidinecarboxamide trifluoroacetate By a similar manner to Example 52, the titled compound was synthesized by using cis-2,6-dimethylmorpholine.

HPLC analysis (220 nm): Purity 92% (Retention time 4.520 minutes) MS (APCI⁺) 436 (M+1)

EXAMPLE 59

1-Acetyl-N-(3-chlorophenyl)-N-[3-(6,7-dimethoxy-1,2,3,4-tetrahydro-2-isoquinolyl)propyl]-4-piperidinecarboxamide trifluoroacetate By a similar manner to Example 52, the titled compound was synthesized by using 6,7-dimethoxy-1,2,3,4-tetrahydroisoquinoline hydrochloride.

HPLC analysis (220 nm): Purity 95% (Retention time 4.030 minutes) MS (APCI⁺) 514 (M+1)

EXAMPLE 60

1-Acetyl-N-(3-chlorophenyl)-N-(3-{4-[4-(trifluoromethyl)benzyl]-1-piperidinyl}propyl)-4-piperidinecarboxamide trifluoroacetate By a similar manner to Example 52, the titled compound was synthesized by using the compound obtained in Reference Example 28.

HPLC analysis (220 nm): Purity 91% (Retention time 5.275 minutes) MS (APCI⁺) 564 (M+1)

EXAMPLE 61

1-Acetyl-N-(3-chlorophenyl)-N-{3-[4-(4-fluorobenzoyl)-1-piperidinyl]propyl}-4-piperidinecarboxamide trifluoroacetate By a similar manner to Example 52, the titled compound was synthesized by using 4-(4-fluorobenzoyl)piperidine hydrochloride.

HPLC analysis (220 nm): Purity 92% (Retention time 4.776 minutes) MS (APCI⁺) 528 (M+1)

EXAMPLE 62

1-Acetyl-N-(3-chlorophenyl)-N-{3-[4-(4-chlorophenyl)-4-hydroxy-1-piperidinyl]propyl}-4-piperidinecarboxamide trifluoroacetate By a similar manner to Example 52, the titled compound was synthesized by using 4-(4-chlorophenyl)-4-hydroxypiperidine.

HPLC analysis (220 nm): Purity 94% (Retention time 4.464 minutes) MS (APCI⁺) 532 (M+1)

EXAMPLE 63

1-Acetyl-N-(3-chlorophenyl)-N-{3-[N-(4-phenyl butyl)amino]propyl}-4-piperidinecarboxamide trifluoroacetate By a similar manner to Example 52, the titled compound was synthesized by using 4-phenylbutylamine.

HPLC analysis (220 nm): Purity 95% (Retention time 5.252 minutes) MS (APCI⁺) 470 (M+1)

EXAMPLE 64

1-Acetyl-N-{3-[N-(4-tert-butylcyclohexyl)amino] propyl}-N-(3-chlorophenyl)-4-piperidinecarboxamidepiperidinecarboxamide trifluoroacetate By a similar manner to Example 52, the titled compound was synthesized by using 4-tert-butylcyclohexylamine.

HPLC analysis (220 nm): Purity 85% (Retention time 5.325 minutes) MS (APCI+) 476 (M+1)

EXAMPLE 65

1-(Benzyloxycarbonyl)-N-[3-(4-benzyl-1-piperidinyl)propyl]-N-3,4-dichlorophenyl)-4-piperidinecarboxamide By a similar manner to Example 1, the titled compound was synthesized by using the compound obtained in Reference Example 2. Yield 90%.

$^1$H NMR (CDCl$_3$) δ 1.1-1.9 (13H, m), 2.15-2.35 (1H, m), 2.26 (2H, t, J=7.3 Hz), 2.45-2.7 (2H, m), 2.51 (2H, d, J=6.6 Hz), 2.81 (2H, br d, J=11.4 Hz), 3.65 (2H, t, J=7.7 Hz), 4.0-4.25 (2H, m), 5.10 (2H, s), 7.02 (1H, dd, J=2.6, 8.6 Hz), 7.05-7.4 (11H, m), 7.50 (1H, d, J=8.6 Hz)

EXAMPLE 66

N-[3-(4-Benzyl-1-piperidinyl)propyl]-N-(3,4-dichlorophenyl)-4-piperidinecarboxamide The compound obtained in Example 65 (4.89 g, 7.85 mmol) was dissolved in acetic acid (5 ml). To the solution was added 30% solution of hydrogen bromide in acetic acid (15 ml), and the mixture was stirred at room temperature for 30 minutes. To the reaction mixture was added diethylether (60 ml), and supernatant solution was removed by decantation. To the residue was added diethylether (60 ml), and supernatant solution was removed by decantation. These procedure was repeated further three times. To the residue was added aqueous solution of 1N-sodium hydroxide (50 ml) and the mixture was extracted with dichloromethane (80 ml, 30 ml×2). The organic layer was dried over anhydrous sodium sulfate and concentrated under reduced pressure. The concentrate was subjected to column chromatography (alumina 200 g, ethyl acetate/methanol=1/0 to 4/1 to 1/1), and the desired fraction was concentrated under reduced pressure to give the titled compound (3.18 g, 6.51 mmol, Yield 83%) as pale brown oily substance.

$^1$H NMR (CDCl$_3$) δ 1.1-1.9 (13H, m), 2.15-2.6 (3H, m), 2.26 (2H, t, J=7.6 Hz), 2.51 (2H, d, J=6.6 Hz), 2.81 (2H, br d, J=11.8 Hz), 3.03 (2H, br d, J=12.0 Hz), 3.65 (2H, t, J=7.5 Hz), 7.01 (1H, dd, J=2.3, 8.5 Hz), 7.05-7.35 (5H, m), 7.30 (1H, d, J=2.3 Hz), 7.49 (1H, d, J=8.5 Hz)

EXAMPLE 67

N-[3-(4-Benzyl-1-piperidinyl)propyl]-1-carbamoyl-N-(3,4-dichlorophenyl)-4-piperidinecarboxamide To a solution of the compound obtained in Example 66 (488 mg, 1.00 mmol) in dichloromethane (10 ml) was added trimethylsilylisocyanate (2.00 ml), and the mixture was stirred at room temperature for 3 days. To the mixture was added a saturated aqueous solution of sodium hydrogen carbonate (20 ml), and the mixture was stirred for 30 minutes. The mixture was extracted with ethyl acetate (20 ml×3). The organic layer was dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure. To the mixture was added diethyl ether, and the resulting precipitates were collected by filtration. The precipitates were washed with diethyl ether, and dried under reduced pressure to give the titled compound (353 mg, 0.66 mmol, Yield 66%) as white crystals.

$^1$H NMR (CDCl$_3$) δ 1.1-2.75 (20H, m), 2.9-3.2 (2H, m), 3.67 (2H, t, J=7.3 Hz), 3.89 (2H, br d, J=13.6 Hz), 4.39 (2H, s), 7.05-7.4 (6H, m), 7.36 (1H, d, J=2.2 Hz), 7.55 (1H, d, J=8.4 Hz)

EXAMPLE 68

1-Acetyl-N-(3-chlorophenyl)-N-[3-[4-(1H-1,2,4-triazol-1-ylmethyl)-1-piperidinyl]propyl]-4-piperidinecarboxamide trifluoroacetate To a solution of 1-tert-butoxycarbonyl-4-(1H-1,2,4-triazol-1-ylmethyl)piperidine (48 mg, 0.18 mmol) in dry dichloromethane (1.5 mL) was added trifluoroacetic acid (1.5 mL), and the mixture was stirred at room temperature for 30 minutes. The solvent was distilled of under reduced pressure, and the residue was dissolved in methanol (1 mL). The solvent was distilled off under reduced pressure, and the residue was dissolved in dry acetonitrile (1.5 mL). To the solution were added 1-acetyl-N-(3-chlorophenyl)-N-(3-chloropropyl)-4-piperidinecarboxamide (50 mg, 0.14 mmol), potassium carbonate (77 mg, 0.56 mmol) and potassium iodide (23 mg, 0.14 mmol), and the mixture was stirred at 80° C. for 5 hours. The mixture was cooled to room temperature, and to the mixture was added water. The mixture was saturated with sodium chloride, and extracted three times with ethyl acetate (2 mL). The extracts were combined and concentrated under reduced pressure. The concentrate was purified by using HPLC to give the titled compound as a colorless oily substance (49.1 mg, 58%).

IR (KBr) 3426, 2955, 1682, 1645 cm$^{-1}$; $^1$H-NMR (CDCl$_3$) δ 1.6-2.5 (18H, m), 2.05 (3H, s), 2.5-3.1 (3H, m), 3.6-3.8 (5H, m), 4.10 (2H, d, J=6.8 Hz), 4.53 (1H, d, J=13.6 Hz), 7.1-7.2 (1H, m), 7.4-7.5 (1H, m), 7.98 (1H, s), 8.09 (1H, s) HPLC (220 nm): Purity 97% (Retention time 2.236 minutes) MS (APCI+) 487 (M+1), 489 (M+3)

EXAMPLE 69

1-Acetyl-N-(3-chlorophenyl)-N-[3-[4-(imidazol-1-ylmethyl)-1-piperidinyl]propyl]-4-piperidinecarboxamide trifluoroacetate By a similar manner to Example 68, reaction was carried out by using 1-tert-butoxycarbonyl-4-(imidazol-1-ylmethyl)piperidine (48 mg, 0.18 mmol) to give the titled compound as pale yellow amorphous-like substance (40.1 mg, 40%).

IR (KBr) 3420, 2955, 1682, 1633 cm$^{-1}$; $^1$H-NMR (CDCl$_3$) δ 1.5-2.0 (11H, m), 2.04 (3H, s), 2.2-2.4 (3H, m), 2.7-3.1 (5H, m), 3.5-3.8 (5H, m), 4.19 (2H, brs), 4.49 (1H, d, J=13.4 Hz), 7.1-7.2 (3H, m), 7.4-7.5 (3H, m), 9.05 (1H, brs) HPLC (220 nm): Purity 97% (Retention time 1.995 minutes) MS (APCI+) 486 (M+1), 488 (M+3)

EXAMPLE 70

1-Acetyl-N-(3-chlorophenyl)-N-[3-[4-(pyrazol-1-ylmethyl)-1-piperidinyl]propyl]-4-piperidinecarboxamide trifluoroacetate By a similar manner to Example 68, the reaction was carried out by using 1-tert-butoxycarbonyl-4-(pyrazol-1-ylmethyl)piperidine (48 mg, 0.18 mmol) to give the titled compound as a colorless oily substance (49.1 mg, 58%).

IR (KBr) 2942, 1678, 1644 cm$^{-1}$; $^1$H-NMR (CDCl$_3$) δ 1.5-2.0 (11H, m), 2.05 (3H, s), 2.2-2.5 (5H, m), 2.8-3.2 (3H, m), 3.6-3.8 (5H, m), 4.03 (2H, d, J=7.0 Hz), 4.53 (1H, d, J=13.2 Hz), 6.24 (1H, dd, J=1.4 and 1.8 Hz), 7.1-7.2 (2H, m), 7.36 (1H, d, J=1.4 Hz), 7.4-7.5(2H, m), 7.54 (1H, d, J=1.8 Hz) HPLC (220 nm): Purity 99% (Retention time 2.468 minutes) MS (APCI+) 486 (M+1), 488 (M+3)

EXAMPLE 71

1-Acetyl-N-(3-chlorophenyl)-N-[3-[4-(2H-tetrazol-2-ylmethyl)-1-piperidine]propyl]-4-piperidinecarboxamide trifluoroacetate By a similar manner to Example 68, the reaction was carried out by using 1-tert-butoxycarbonyl-4-(2H-tetrazol-2-ylmethyl)piperidine (48 mg, 0.18 mmol) to give the titled compound as pale yellow oily substance (59.4 mg, 55%).

IR (KBr) 2953, 1676, 1647 cm$^{-1}$; $^1$H-NMR (CDCl$_3$) δ 1.6-2.0 (6H, m), 2.06 (3H, s), 2.2-2.4 (6H, m), 2.5-3.1 (6H, m), 3.6-3.9 (6H, m), 4.53 (2H, d, J=12.8 Hz), 4.62 (2H, d, J=7.0 Hz), 7.1-7.2 (2H, m), 7.3-7.4 (2H, m), 8.53 (1H, s) HPLC (220 nm): Purity 99% (Retention time 2.356 minutes) MS (APCI+) 488 (M+1), 490 (M+3)

EXAMPLE 72

1-Acetyl-N-(3-chlorophenyl)-N-[3-[4-(1H-tetrazol-1-ylmethyl)-1-piperidinyl]propyl]-4-piperidinecarboxamide trifluoroacetate By a similar manner to Example 68, the reaction was carried out by using 1-tert-butoxycarbonyl-4-(1H-tetrazol-1-ylmethyl)piperidine (48 mg, 0.18 mmol) to give the titled compound as pale yellow oily substance (62.2 mg, 57%).

IR (KBr) 2950, 1678, 1647 cm$^{-1}$; $^1$H-NMR (CDCl$_3$) δ 1.6-2.4 (12H, m), 2.06 (3H, s), 2.6-3.1 (6H, m), 3.6-3.9 (6H, m), 4.40 (2H, d, J=7.0 Hz), 4.52 (2H, d, J=13.6 Hz), 7.1-7.2 (2H, m), 7.4-7.5 (2H, m), 8.73 (1H, s)

HPLC (220 nm): Purity 99% (Retention time 2.288 minutes) MS (APCI+) 488 (M+1), 490 (M+3)

EXAMPLE 73

1-Acetyl-N-(3-chlorophenyl)-N-[3-[4-(2H-1,2,3-triazol-2-ylmethyl)-1-piperidinyl]propyl]-4-piperidinecarboxamide trifluoroacetate By a similar manner to Example 68, the reaction was carried out by using 1-tert-butoxycarbonyl-4-(2H-1,2,3-triazol-2-ylmethyl)piperidine (48 mg, 0.18 mmol) to give the titled compound as pale yellow oily substance (59.9 mg 55%).

IR (KBr) 2951, 1674, 1645 cm$^{-1}$; $^1$H-NMR (CDCl$_3$) δ 1.6-22.0 (6H, m), 2.06 (3H, s), 2.1-2.4 (6H, m), 2.5-3.1 (6H, m), 3.6-3.8 (6H, m), 4.39 (2H, d, J=6.8 Hz), 4.53 (1H, d, J=13.4 Hz), 7.1-7.2 (2H, m), 7.4-7.5 (2H, m), 7.61 (2H, s) HPLC (220 nm): Purity 99% (Retention time 2.409 minutes) MS (APCI+) 487 (M+1), 489 (M+3)

EXAMPLE 74

1-Acetyl-N-(3-chlorophenyl)-N-[3-[4-(1H-1,2,3-triazol-1-ylmethyl)-1-piperidinyl]propyl]-4-piperidinecarboxamide trifluoroacetate By a similar manner to Example 68, the reaction was carried out by using 1-tert-butoxycarbonyl-4-(1H-1,2,3-triazol-1-ylmethyl)piperidine (48 mg, 0.18 mmol) to give the titled compound as pale yellow oily substance (41.9 mg, 39%).

IR (KBr) 2955, 1678, 1644 cm$^{-1}$; $^1$H-NMR (CDCl$_3$) δ 1.6-2.0 (6H, m), 2.06 (3H, s), 2.2-2.4 (6H, m), 2.6-3.1 (6H, m), 3.6-3.8 (6H, m), 4.31 (2 h, d, J=7.2 Hz), 4.53 (1H, d, J=13.2 Hz), 7.1-7.2 (2H, m), 7.4-7.5 (2H, m), 7.57 (1H, s), 7.72 (1H, s) HPLC (220 nm): Purity 98% (Retention time 2.286 minutes) MS (APCI+) 487 (M+1), 489 (M+3)

EXAMPLE 75

1-Acetyl-N-(3-chlorophenyl)-N-[3-[4-(2-pyridinylthio)-1-piperidinyl]propyl]-4-piperidinecarboxamide trifluoroacetate By a similar manner to Example 68, the reaction was carried out by using 1-tert-butoxycarbonyl-4-(2-pyridinylthio)piperidine (53 mg, 0.18 mmol) to give the titled compound as a colorless oily substance (47.1 mg, 35%).

IR (KBr) 2953, 1651 cm$^{-1}$; $^1$H-NMR (CDCl$_3$) δ 1.6-1.8 (4H, m), 2.05 (3H, s), 2.0-2.5 (7H, m), 2.7-3.1 (6H, m), 3.5-3.9 (7H, m), 4.54 (1H, d, J=13.6 Hz), 7.0-7.2 (4H, m), 7.4-7.6 (3H, m), 8.3-8.5 (1H, m) HPLC (220 nm): Purity 100% (Retention time 2.559 minutes) MS (APCI+) 515 (M+1), 517 (M+3)

EXAMPLE 76

1-Acetyl-N-(3-chlorophenyl)-N-[3-[4-(1-methyl-1H-tetrazol-5-ylthio)-1-piperidinyl]propyl]-4-piperidinecarboxamide trifluorqacetate By a similar manner to Example 68, the reaction was carried out by using 1-tert-butoxycarbonyl-4-(1-methyl-1H-tetrazol-5-ylthio)piperidine (54 mg, 0.18 mmol) to give the titled compound as a colorless oily substance (40.3 mg, 45%).

IR (KBr) 2951, 1674, 1642, 1590 cm$^{-1}$; $^1$H-NMR (CDCl$_3$) δ 1.6-2.1 (11H, m) 2.06 (3H, s), 2.2-2.5 (5H, m) 2.7-3.1 (4H, m), 3.6-3.8 (4H, m), 3.93 (3H, s), 4.54 (1H, d, J=12.8 Hz), 7.1-7.2 (2H, m), 7.4-7.5 (2H, m) HPLC (220 nm): Purity 991 (Retention time 2.390 minutes) MS (APCI+) 520 (M+1), 522 (M+3)

EXAMPLE 77

1-Acetyl-N-(3-chlorophenyl)-N-[3-[4-(2-thiazolylthio)-1-piperidinyl]propyl]-4-piperidinecarboxamide trifluoroacetate By a similar manner to Example 68, the reaction was carried out by using 1-tert-butoxycarbonyl-4-(2-thiazolylthio)piperidine (54 mg, 0.18 mmol) to give the titled compound as a colorless oily substance (54.5 mg, 61%).

IR (KBr) 2951, 1680, 1645, 1590 cm$^{-1}$; $^1$H-NMR (CDCl$_3$) δ 1.6-2.2 (10H, m), 2.05 (3H, s), 2.3-3.2 (9H, m), 3.6-3.9 (5H, m), 4.53 (1H, d. J=14.0 Hz), 7.1-7.2 (2H, m), 7.31 (1H, brs), 7.4-7.5 (2H, m), 7.71 (1H, brs) HPLC (220 nm): Purity 99% (Retention time 2.686 minutes) MS (APCI+) 521 (M+1), 523 (M+3)

EXAMPLE 78

1-Acetyl-N-(3-chlorophenyl)-N-[3-[4-(4-pyridinylthio)-1-piperidinyl]propyl]-4-piperidinecarboxamide trifluoroacetate By a similar manner to Example 68, the reaction was carried out by using 1-tert-butoxycarbonyl-4-(4-pyridinylthio)piperidine (79 mg, 0.27 mmol) to give the titled compound as a colorless oily substance (72.3 mg, 46%).

IR (KBr) 2950, 1678, 1628 cm$^{-1}$; $^1$H-NMR (CDCl$_3$) δ 1.6-2.4 (10H, m), 2.05 (3H, s), 2.5-3.2 (8H, m), 3.4-3.8 (5H, m), 4.52 (1H, d, J=13.6 Hz), 7.1-7.2 (2H, m), 7.2-7.3 (3H, m), 8.56 (1H, brs) HPLC (220 nm): Purity 97% (Retention time 2.181 minutes) MS (APCI+) 515 (M+1), 517 (M+3)

EXAMPLE 79

1-Acetyl-N-(3-chlorophenyl)-N-[3-[4-(2-pyrazinylthio)-1-piperidinyl]propyl]-4-piperidinecarboxamide trifluoroacetate By a similar manner to Example 68, the reaction was carried out by using 1-tert-butoxycarbonyl-4-(2-pyrazinylthio)piperidine (53 mg, 0.18 mmol) to give the titled compound as pale yellow oily substance (51.3 mg, 45%).

IR (KBr) 2953, 1682, 1644 cm$^{-1}$; $^1$H-NMR (CDCl$_3$) δ 1.6-2.0 (6H, m), 2.05 (3H, s), 2.1-2.4 (5H, m), 2.7-3.2 (6H, m), 3.5-3.9 (7H, m), 4.54 (1H, d, J=13.2 Hz), 7.1-7.2 (2H, m), 7.4-7.5 (2H, m), 8.27 (1H, brs), 8.34 (1H, brs), 8.45 (1H, brs) HPLC (220 nm): Purity 99% (Retention time 2.581 minutes) MS (APCI+) 516 (M+1), 518 (M+3)

EXAMPLE 80

1-Acetyl-N-(3-chlorophenyl)-N-[3-[4-(2-benzothiazolylthio)-1-piperidinyl]propyl]1-4-piperidinecarboxamide trifluoroacetate By a similar manner to Example 68, the reaction was carried out by using 1-tert-butoxycarbonyl-4-(2-benzothiazolylthio)piperidine (63 mg, 0.18 mmol) to give the titled compound as a colorless oily substance (43.3 mg, 35%).

IR (KBr) 2951, 1674, 1645 cm$^{-1}$; $^1$H-NMR (CDCl$_3$) δ 1.6-2.10 (10H, m), 2.05 (3H, s), 2.2-3.2 (9H, m), 3.5-3.8 (5H, m), 4.54 ((1H, d, J=13.2 Hz), 7.1-7.2 (2H, m), 7.3-7.5 (4H, m), 7.78 (11H, d, J=8.6 Hz), 7.8-8.9 (1H, m) HPLC (220 nm): Purity 99% (Retention time 3.091 minutes) MS (APCI+) 571 (M+1), 573 (M+3)

EXAMPLE 81

1-Acetyl-N-(3-chlorophenyl)-N-[3-[4-(2-thienylthio)-1-piperidinyl]propyl]-4-piperidinecarboxamide trifluoroacetate By a similar manner to Example 68, the reaction was carried out by using 1-tert-butoxycarbonyl-4-(2-thienylthio)piperidine (54 mg, 0.18 mmol) to give the titled compound as a colorless oily substance (52.4 mg, 46%).

IR (KBr) 2953, 1680, 1645, cm$^{-1}$; $^1$H-NMR (CDCl$_3$) δ 1.6-2.1 (10H, m), 2.05 (3H, s), 2.2-3.2 (9H, m), 3.4-3.8 (5H, m), 3.54 (1H, d, J=13.0 Hz), 7.03 (1H, dd, J=3.6 and 5.4 Hz), 7.1-7.2 (3H, m), 7.4-7.5 (3H, m) HPLC (220, nm): Purity 96% (Retention time 3.017 minutes) MS (APCI+) 520 (M+1), 522 (M+3)

EXAMPLE 82

1-Acetyl-N-(3-chlorophenyl)-N-[3-[4-(1-methylimidazol-2-ylthio)-1-piperidinyl]propyl]-4-piperidinecarboxamide trifluoroacetate By a similar manner to Example 68, the reaction was carried out by using 1-tert-butoxycarbonyl-4-(1-methylimidazol-2-ylthio)piperidine (54 mg, 0.18 mmol) to give the titled compound as a colorless oily substance (59.4 mg, 44%).

IR (KBr) 2951, 1682, 1651 cm$^{-1}$; $^1$H-NMR (CDCl$_3$) δ 1.5-1.7 (4H, m), 1.9-2.0 (2H, m), 2.05 (3H, s), 2.1-2.4 (5H, m), 2.8-3.1 (6H, m), 3.5-3.8 (7H, m), 3.78 (3H, s), 4.52 (1H, d, J=12.8. Hz), 7.1-7.2 (3H, m), 7.4-7.5 (3H, m) HPLC (220, nm): Purity 99% (Retention time 2.113 minutes) MS (APCI+) 518 (M+1), 520 (M+3)

EXAMPLE 83

1-Acetyl-N-(3-chlorophenyl)-N-[3-[4-(7-trifluoromethyl-4-quinolynylthio)-1-piperidinyl]propyl]-4-piperidinecarboxamide trifluoroacetate By a similar manner to Example 68, the reaction was carried out by using 1-tert-butoxycarbonyl-4-(7-trifluoromethyl-4-quinolynylthio)piperidine (74 mg, 0.18 mmol) to give the titled compound as a colorless oily substance (50.3 mg, 32%).

IR (KBr) 2951, 2867, 1651 cm$^{-1}$; $^1$H-NMR (CDCl$_3$) δ 1.6-1.8 (4H, m), 1.9-2.9 (11H, m), 2.05 (3H, s), 3.0-3.2 (3H, m), 3.5-3.9 (9H, m), 4.54 (1H, d, J=13.2 Hz), 7.1-7.2 (2H, m), 7.3-7.5 (3H, m), 7.80 (1H, d, J=9.2 Hz), 8.32 (1H, d, J=8.8 Hz), 8.44 (1H, s), 8.8-9.0 (1H, m) HPLC (220 nm): Purity 97% (Retention time 2.856 minutes) MS (APCI+) 633 (M+1), 635 (M+3)

EXAMPLE 84

1-Acetyl-N-(3-chlorophenyl)-N-[3-[4-(4-pyridinyloxy)-1-piperidinyl]propyl]-4-piperidinecarboxamide trifluoroacetate By a similar manner to Example 68, the reaction was carried out by using 1-tert-butoxycarbonyl-4-(4-pyridinyloxy) piperidine (50 mg, 0.18 mmol) to give the titled compound as a colorless oily substance (34.4 mg, 26%).

IR (KBr) 2953, 1692, 1644 cm$^{-1}$; $^1$H-NMR (CDCl$_3$) δ 1.6-1.8 (4H, m), 2.05 (3H, s), 2.0-2.6 (7H, m), 2.8-4.2 (12H, m), 4.53 (1H, d, J=13.6 Hz), 4.99 (1H, brs), 7.1-7.5 (6H, m), 8.6-8.8 (2H, m) HPLC (220 nm): Purity 99% (Retention time 2.126 minutes) MS (APCI+) 499 (M+1), 501 (M+3)

EXAMPLE 85

1-Acetyl-N-(3-chlorophenyl)-N-[3-[4-(2-pyridinyloxy)-1-piperidinyl]propyl]-4-piperidinecarboxamide trifluoroacetate By a similar manner to Example 68, the reaction was carried out by using 1-tert-butoxycarbonyl-4-(2-pyridinyloxy)piperidine (50 mg, 0.18 mmol) to give the titled compound as a colorless oily substance (19.7 mg, 15%).

IR (KBr) 2955, 1645 cm$^{-1}$; $^1$H-NMR (CDCl$_3$) δ 1.6-1.8 (4H, m), 1.9-2.4 (7H, m), 2.06 (3H, s), 2.6-3.1 (7H, m), 3.5-3.9 (5H, m), 4.54 (1H, d, J=13.2 Hz), 5.4-5.5 (1H, m), 6.73 (1H, d, J=8.0 Hz), 6.91 (1H, dd, J=5.2 and 7.2 Hz), 7.1-7.2 (2H, m), 7.4-7.5 (2H, m), 7.6-7.7 (1H, m), 8.1-8.2 (1H, m) HPLC (220 nm): Purity 99% (Retention time 2.527 minutes) MS (APCI+) 499 (M+1), 501 (M+3)

EXAMPLE 86

1-Acetyl-N-(3-chlorophenyl)-N-[3-[4-(2-thiazolyloxy)-1-piperidinyl]propyl]-4-piperidinecarboxamide trifluoroacetate By a similar manner to Example 68, the reaction was carried out by using 1-tert-butoxycarbonyl-4-(2-thiazolyloxy)piperidine (51 mg, 0.18 mmol) to give the titled compound as a colorless oily substance (33.6 mg, 25%).

IR (KBr) 2953, 2864, 1645 cm$^{-1}$; $^1$H-NMR (CDCl$_3$) δ 1.6-1.8 (4H, m), 2.0-2.4 (7H, m), 2.05 (2H, s), 2.8-3.1 (6H, m), 3.5-3.8 (6H, m), 4.53 (1H, d, J=13.6 Hz), 5.31 (1H, brs), 6.73 (1H, d, J=4.0 Hz), 7.1-7.2 (3H, m), 7.4-7.5 (2H, m) HPLC (220 nm): Purity 99% (Retention time 2.647 minutes) MS (APCI+) 505 (M+1), 507 (M+3)

EXAMPLE 87

1-Acetyl-N-(3-chlorophenyl)-N-[3-[4-(5-methyl-1,3,4-thiadiazol-2-ylthio)-1-piperidinyl]propyl]-4-piperidinecarboxamide trifluoroacetate 4-(5-Methyl-1,3,4-thiadiazol-2-ylthio)piperidine trifluoroacetate (59 mg, 0.18 mmol) was dissolved in dry acetonitrile (1.5 mL). To the solution were added 1-acetyl-N-(3-chlorophenyl)-N-(3-chloropropyl)-4-piperidinecarboxamide (50 mg, 0.14 mmol), potassium carbonate (77 mg, 0.56 mmol) and potassium iodide (23 mg, 0.14 mmol), and the mixture was stirred at 80° C. for 5 hours. The mixture was cooled to room temperature, and to the mixture was added saturated sodium chloride solution (3 mL). The mixture was extracted three times with ethyl acetate (2 mL). The extracts were combined and concentrated under reduced pressure. The concentrate; was purified by using HPLC to give the titled compound as a colorless oily substance (32.2 mg, 28%).

IR (KBr) 2951, 1674, 1645 cm$^{-1}$; $^1$H-NMR (CDCl$_3$) δ 1.6-2.5 (11H, m), 2.05 (3H, s), 2.74 (3H, s), 2.8-3.1 (4H, m), 3.6-3.9 (9H, m), 4.54 (1H, d, J=14.6 Hz), 7.1-7.2 (2H, m), 7.4-7.5 (2H, m) HPLC (220 nm): Purity 99% (Retention time 2.576 minutes) MS (APCI+) 536 (M+1), 538 (M+3)

EXAMPLE 88

1-Acetyl-N-(3-chlorophenyl)-N-[3-[4-(1H-benzotriazol-1-yloxy)-1-piperidinyl]propyl]-4-piperidinecarboxamide trifluoroacetate By a similar manner to Example 87, the reaction was carried out by using 4-(1H-benzotriazol-1-yloxy)piperidine trifluoroacetate (60 mg, 0.18 mmol) to give the titled compound as a colorless oily substance (52.9 mg, 45%).

IR (KBr) 2951, 1645 cm$^{-1}$; $^1$H-NMR (CDCl$_3$) δ 1.6-2.4 (11H, m), 2.06 (3H, s), 2.8-3.8 (12H, m), 4.55 (1H, d, J=13.2 Hz), 4.87 (1H, brs), 7.2-7.3 (2H, m), 7.4-7.6 (5H, m), 8.06 (1H, d, J=8.4 Hz) HPLC (220 nm): Purity 98% (Retention time 2.772 minutes) MS (APCI+) 539 (M+1), 541 (M+3)

EXAMPLE 89

1-(Benzyloxycarbonyl)-N-(3,4-dichlorophenyl)-N-(3-[4-(4-fluorobenzyl)-1-piperidinyl]propyl)-4-piperidinecarboxamide By a similar manner to Example 1, the titled compound was synthesized by using the compound obtained in Reference Example 3-3. Yield 82%.

$^1$H NMR (CDCl$_3$) δ 1.12-1.85 (14H, m), 1.90-2.04 (2H, m), 2.04-2.28 (1H, br), 2.30-2.60 (4H, br), 2.64-2.89 (1H, br), 2.90-3.10 (1H, d, J=11.8 Hz), 3.54 (1H, t, J=7.0 Hz), 3.83-4.14 (2H, br), 5.00 (2H, s), 6.81-7.00 (5H, m), 7.17-7.23 (6H, m), 7.40 (1H, d, J=8.4 Hz) IR (KBr) 2926, 2857, 1698, 1659 cm$^{-1}$

EXAMPLE 90

N-(3,4-Dichlorophenyl)-N-{3-[4-(4-fluorobenzyl)-1-piperidinyl]propyl}-4-piperidinecarboxamide By a similar manner to Example 66, the titled compound was synthesized by using the compound obtained in Example 89. Yield 83%.

$^1$H NMR (CDCl$_3$) δ 1.27 (2H, dt, J=3.0, 11.4 Hz), 1.38-2.05 (12H, m), 2.30 (2H, t, J=7.6 Hz), 2.40-2.58 (4H, m), 2.85 (2H, d, J=11.4 Hz), 3.12 (2H, d, J=12.0 Hz), 3.61 (2H, t, J=7.6 Hz), 3.89 (1H, br), 6.90-7.11 (5H, m), 7.30 (1H, d, J=2.2 Hz), 7.51 (1H, d, J=8.4 Hz) IR (KBr) 2934, 1661, 1586 cm$^{-1}$

EXAMPLE 91

N-(3,4-Dichlorophenyl)-N-{3-[4-(4-fluorobenzyl)-1-piperidinyl]propyl}-1-(methylsulfonyl)-4-piperidinecarboxamide trifluoroacetate To a solution of the compound obtained in Example 90 (25.3 mg, 50 µmol) in dichloromethane (0.3 mL) was added triethylamine (14 µL, 100 µmol) at room temperature. To the mixture was added a solution of methanesulfonyl chloride (5.8 µL, 75 µmol) in dichloromethane (0.4 mL) at room temperature, and the mixture was stirred for 24 hours. The reaction mixture was concentrated under reduced pressure, and the concentrate was dissolved in dichloromethane (0.5 mL). To the solution was added PS-trisamine resine (3.62 mmol/g, 50 mg, 0.18 mmol), and the mixture was stirred at room temperature for 1 hour. The resin was filtered off, and the filtrate was concentrated under reduced pressure. The concentrate was dissolved in dichloromethane (0.5 mL). To the solution was added MP-sodium iodide resine (2.64 mmol/g, 45 mg, 0.12 mmol), and the mixture was stirred at room temperature for 30 minutes. The resin was filtered off, and the filtrate was concentrated under reduced pressure and purified by preparative HPLC. The desired fraction was concentrated to give the titled compound as a colorless oily substance (5.3 mg).

HPLC (220 nm): Purity 96% (Retention time 3.607 minutes) Mass (APCI+) 584 (M+1) $^1$H NMR (CDCl$_3$) δ 1.62-2.08 (11H, m), 2.15-2.49 (6H, m), 2.62 (2H, br), 2.78-3.27 (2H, m), 2.90 (3H s), 3.58-3.87 (4H, m), 4.59 (1H, br), 6.98-7.30 (5H, m), 7.39 (1H, d, J=2.2 Hz), 7.58 (1H, d, J=8.2 Hz)

EXAMPLE 92

N-(3,4-Dichlorophenyl)-N-{3-[4-(4-fluorobenzyl)-1-piperidinyl]propyl}-1-(isopropylsulfonyl)-4-piperidinecarboxamide trifluoroacetate By using isopropylsulfonyl chloride, the reaction and the purification procedure were carried out by a similar manner to Example 91 to give to give the titled compound.

HPLC (220 nm): Purity 90% (Retention time 3.764 minutes) Mass (APCI+) 612 (M+1)

EXAMPLE 93

N-(3,4-Dichlorophenyl)-N-{3-[4-(4-fluorobenzyl)-1-piperidinyl]propyl}-1-(octylsulfonyl)-4-piperidinecarboxamide trifluoroacetate By using 1-octanesulfonyl chloride, the reaction and the purification procedure were carried out by a similar manner to Example 91 to give to give the titled compound.

HPLC (220 nm): Purity 98% (Retention time 4.423 minutes) Mass (APCI+) 682 (M+1)

EXAMPLE 94

N-(3,4-Dichlorophenyl)-N-{3-[4-(4-fluorobenzyl)-1-piperidinyl]propyl}-1-(4-methoxyphenylsulfonyl)-4-piperidinecarboxamide trifluoroacetate By using 4-methoxybenzenesulfonyl chloride, the reaction and the purification procedure were carried out by a similar manner to Example 91 to give the titled compound.

HPLC (220 nm): Purity 100% (Retention time 3.945 minutes) Mass (APCI+) 677 (M+1)

EXAMPLE 95

N-(3,4-Dichlorophenyl)-N-{3-[4-(4-fluorobenzyl)-1-piperidinyl]propyl}-1-(4-fluorophenylsulfonyl)-4-piperidinecarboxamide trifluoroacetate By using 4-fluorobenzenesulfonyl chloride, the reaction and the purification procedure were carried out by a similar manner to Example 91 to give the titled compound.

HPLC (220 nm): Purity 99% (Retention time 3.980 minutes) Mass (APCI+) 665 (M+1)

EXAMPLE 96

N-(3,4-Dichlorophenyl)-N-{3-[4-(4-fluorobenzyl)-1-piperidinyl]propyl}-1-(2,3,4,5,6-pentafluorophenylsulfonyl)-4-piperidinecarboxamide trifluoroacetate By using pentafluorobenzenesulfonyl chloride, the reaction and the purification procedure were carried out by a similar manner to Example 91 to give the titled compound.

HPLC (220 nm): Purity 99% (Retention time 4.168 minutes) Mass (APCI+) 737 (M+1)

EXAMPLE 97

N-(3,4-Dichlorophenyl)-N-{3-[4-(4-fluorobenzyl)-1-piperidinyl]propyl}-1-(3-nitrophenylsulfonyl)-4-piperidinecarboxamide trifluoroacetate By using m-nitrobenzenesulfonyl chloride, the reaction and the purification procedure were carried out by a similar manner to Example 91 to give the titled compound.

HPLC (220 nm): Purity 98% (Retention time 3.974 minutes) Mass (APCI+) 692 (M+1)

EXAMPLE 98

1-(4-Acetylaminophenylsulfonyl)-N-(3,4-dichlorophenyl)-N-{3-[4-(4-fluorobenzyl)-1-piperidinyl]propyl}-4-piperidinecarboxamide trifluoroacetate By using 4-acetylaminobenzenesulfonyl chloride, the reaction and the purification procedure were carried out by a similar manner to Example 91 to give the titled compound.

HPLC (220 nm): Purity 93% (Retention time 3.695 minutes) Mass (APCI+) 704 (M+1)

EXAMPLE 99

4-({4-[(3,4-Dichloro{3-[4-(4-fluorobenzyl)-1-piperidinyl]propyl}anilino)carbonyl]-1-piperidinyl}sulfonyl)benzoic acid trifluoroacetate By using 4-(chlorosulfonyl)benzoic acid, the reaction and the purification procedure were carried out by a similar manner to Example 91 to give the titled compound.

HPLC (220 nm): Purity 94% (Retention time 3.717 minutes) Mass (APCI+) 691 (M+1)

EXAMPLE 100

1-(Benzylsulfonyl)-N-(3,4-dichlorophenyl)-N-{3-[4-(4-fluorbenzyl)-1-piperidinyl]propyl}-4-piperidinecarboxamide trifluoroacetate By using benzylsulfonyl chloride, the reaction and the purification procedure were carried out by a similar manner to Example 91 to give the titled compound.

HPLC (220 nm): Purity 90% (Retention time 3.961 minutes) Mass (APCI+) 661 (M+1)

EXAMPLE 101

N-(3,4-Dichlorophenyl)-N-{3-[4-(4-fluorobenzyl)-1-piperidinyl]propyl}-1-[3-(trifluoromethyl)phenylsulfonyl]-4-piperidinecarboxamide trifluoroacetate By using 3-(trifluoromethyl)benzenesulfonyl chloride, the reaction and the purification procedure were carried out by a similar manner to Example 91 to give the titled compound.

HPLC (220 nm): Purity 93% (Retention time 4.149 minutes) Mass (APCI+) 715 (M+1)

EXAMPLE 102

N-(3,4-Dichlorophenyl)-N-{3-[4-(4-fluorobenzyl)-1-piperidinyl]propyl}-1-(2-thienylsulfonyl)-4-piperidinecarboxamide trifluoroacetate By using 2-thiophenesulfonyl chloride, the reaction land the purification procedure were carried out by a similar manner to Example 91 to give the titled compound.
HPLC (220 nm): Purity 98% (Retention time 3.930 minutes) Mass (APCI+) 653 (M+1)

EXAMPLE 103

N-(3,4-Dichlorophenyl)-N-{3-[4-(4-fluorobenzyl)-1-piperidinyl]propyl}-1-{5-[5-(trifluoromethyl)-3-isoxazolyl]-2-thienylsulfonyl}-4-piperidinecarboxamide trifluoroacetate By using 5-[5-(trifluoromethyl)-3-isoxazolyl]-2-thiophenesulfonyl chloride, the reaction and the purification procedure were carried out by a similar manner to Example 91 to give the titled compound.
HPLC (220 nm): Purity 97% (Retention time 4.348 minutes) Mass (APCI+) 788 (M+1)

EXAMPLE 104

N-(3,4-Dichlorophenyl)-N-{3-[4-(4-fluorobenzyl)-1-piperidinyl]propyl}-1-{5-[1-methyl-5-(trifluoromethyl)-3-pyrazolyl]-2-thienylsulfonyl}-4-piperidinecarboxamide 2 trifluoroacetate By using 5-[1-methyl-5-(trifluoromethyl)-3-pyrazolyl]-2-thiophenesulfonyl chloride, the reaction and the purification procedure were carried out by a similar manner to Example 91 to give the titled compound.
HPLC (220 nm): Purity 98% (Retention time 4.234 minutes) Mass (APCI+) 801 (M+1)

EXAMPLE 105

N-(3,4-Dichlorophenyl)-N-{3-[4-(4-fluorobenzyl)-1-piperidinyl]propyl)-1-[5-(2-methyl-4-thiazolyl)-2-thienylsulfonyl]-4-piperidinecarboxamide trifluoroacetate By using 5-(2-methyl-4-thiazolyl)-2-thiophenesulfonyl chloride, the reaction and the purification procedure were carried out by a similar manner to Example 91 to give the titled compound.
HPLC (220 nm): Purity 97% (Retention time 4.119 minutes) Mass (APCI+) 750 (M+1)

EXAMPLE 106

1-(4-Benzofurazanylsulfonyl)-N-(3,4-dichlorophenyl)-N-(3-[4-(4-fluorobenzyl)-1-piperidinyl]propyl}-4-piperidinecarboxamide trifluoroacetate By using 4-benzofurazanesulfonyl chloride, the reaction and the purification procedure were carried out by a similar manner to Example 91 to give the titled compound.
HPLC (220 nm): Purity 94% (Retention time 3.968 minutes) Mass (APCI+) 689 (M+1)

EXAMPLE 107

N-(3,4-Dichlorophenyl)-N-{3-[4-(4-fluorobenzyl)-1-piperidinyl]propyl}-1-(8-quinolynylsulfonyl)-4-piperidinecarboxamide 2 trifluoroacetate By using 8-quinolinesulfonyl chloride, the reaction and the purification procedure were carried out by a similar manner to Example 91 to give the titled compound.
HPLC (220 nm): Purity 96% (Retention time 3.864 minutes) Mass (APCI+) 698 (M+1)

EXAMPLE 108

1-(2-Acetylamino-4-methyl-5-thiazolylsulfonyl)-N-(3,4-dichlorophenyl)-N-{3-[4-(4-fluorobenzyl)-1-piperidinyl]propyl}-4-piperidinecarboxamide trifluoroacetate By using 2-acetylamino-4-methyl-5-thiazolesulfonyl chloride, the reaction and the purification procedure were carried out by a similar manner to Example 91 to give the titled compound.
HPLC (220 nm): Purity 95% (Retention time 3.745 minutes) Mass (APCI+) 725 (M+1)

EXAMPLE 109

N-(3,4-Dichlorophenyl)-N-{3-[4-(4-fluorobenzyl)-1-piperidinyl]propyl}-1-{5-[1-methyl-3-(trifluoromethyl)-5-pyrazolyl]-2-thienylsulfonyl)-4-piperidinecarboxamide 2 trifluoroacetate By using 5-[1-methyl-3-(trifluoromethyl)-5-pyrazolyl]-2-thiophenesulfonyl chloride, the reaction and the purification procedure were carried out by a similar manner to Example 91 to give the titled compound.
HPLC (220 nm): Purity 97% (Retention time 4.306 minutes) Mass (APCI+) 801 (M+1)

EXAMPLE 110

N-(3,4-Dichlorophenyl)-N-{3-[4-(4-fluorobenzyl)-1-piperidinyl]propyl}-1-[4-(trifluoromethoxy)phenylsulfonyl]-4-piperidinecarboxamide trifluoroacetate By using 4-(trifluoromethoxy)benzenesulfonyl chloride, the reaction and the purification procedure were carried out by a similar manner to Example 91 to give the titled compound.
HPLC (220 nm): Purity 99% (Retention time 4.192 minutes) Mass (APCI+) 731 (M+1)

EXAMPLE 111

1-Benzoyl-N-(3,4-dichlorophenyl)-N-{3-[4-(4-fluorobenzyl)-1-piperidinyl]propyl}-4-piperidinecarboxamide trifluoroacetate By using benzoyl chloride, the reaction and the purification procedure were carried out by a similar manner to Example 91 to give the titled compound.
HPLC (220 nm): Purity 96% (Retention time 5.425 minutes) Mass (APCI+) 610 (M+1)

EXAMPLE 112

N-(3,4-Dichlorophenyl)-N-{3-[4-(4-fluorobenzyl)-1-piperidinyl]propyl}-1-(4-methoxyphenylacetyl)-4-piperidinecarboxamide trifluoroacetate By using 4-methoxyphenylacetyl chloride, the reaction and the purification procedure were carried out by a similar manner to Example 91 to give the titled compound.

HPLC (220 nm): Purity 97% (Retention time 5.163 minutes) Mass (APCI+) 654 (M+1)

EXAMPLE 113

N-(3,4-Dichlorophenyl)-N-{3-[4-(4-fluorobenzyl)-1-piperidinyl]propyl}-1-(2,3,4,5,6-pentafluorobenzoyl)-4-piperidinecarboxamide trifluoroacetate By using pentafluorobenzoyl chloride, the reaction and the purification procedure were carried out by a similar manner to Example 91 to give the titled compound.

HPLC (220 nm): Purity 91% (Retention time 5.403 minutes) Mass (APCI+) 700 (M+1)

EXAMPLE 114

N-(3,4-Dichlorophenyl)-N-{3-[4-(4-fluorobenzyl)-1-piperidinyl]propyl}-1-(2-furoyl)-4-piperidinecarboxamide trifluoroacetate By using 2-furoyl chloride, the reaction and the purification procedure were carried out by a similar manner to Example 91 to give the titled compound.

HPLC (220 nm): Purity 93% (Retention time 5.153 minutes) Mass (APCI+) 600 (M+1)

EXAMPLE 115

N-(3,4-Dichlorophenyl)-N-{3-[4-(4-fluorobenzyl)-1-piperidinyl]propyl}-1-(5-nitro-2-furoyl)-4-piperidinecarboxamide trifluoroacetate By using 5-nitro-2-furoyl chloride, the reaction and the purification procedure were carried out by a similar manner to Example 91 to give the titled compound.

HPLC (220 nm): Purity 89% (Retention time 5.435 minutes) Mass (APCI+) 645 (M+1)

EXAMPLE 116

N-(3,4-Dichlorophenyl)-N-{3-[4-(4-fluorobenzyl)-1-piperidinyl]propyl}-1-(2-quinoxalinylcarbonyl)-4-piperidinecarboxamide 3 trifluoroacetate By using 2-quinoxalinecarbonyl chloride, the reaction and the purification procedure were carried out by a similar manner to Example 91 to give the titled compound.

HPLC (220 nm): Purity 84% (Retention time 5.291 minutes) Mass (APCI+) 662 (M+1)

EXAMPLE 117

N-(3,4-Dichlorophenyl)-N-{3-[4-(4-fluorobenzyl)-1-piperidinyl]propyl}-1-(2-nitrobenzoyl)-4-piperidinecarboxamide trifluoroacetate By using 2-nitrobenzoyl chloride, the reaction and the purification procedure were carried out by a similar manner to Example 91 to give the titled compound.

HPLC (220 nm): Purity 83% (Retention time 5.401 minutes) Mass (APCI+) 655 (M+1)

EXAMPLE 118

N-(3,4-Dichlorophenyl)-N-{3-[4-(4-fluorobenzyl)-1-piperidinyl]propyl}-1-(3-nitrobenzoyl)-4-piperidinecarboxamide trifluoroacetate By using 3-nitrobenzoyl chloride, the reaction and the purification procedure were carried out by a similar manner to Example 91 to give the titled compound.

HPLC (220 nm): Purity 90% (Retention time 5.288 minutes) Mass (APCI+) 655 (M+1)

EXAMPLE 119

N-(3,4-Dichlorophenyl)-N-{3-[4-(4-fluorobenzyl)-1-piperidinyl]propyl}-1-(4-nitrobenzoyl)-4-piperidinecarboxamide trifluoroacetate By using 4-nitrobenzoyl chloride, the reaction and the purification procedure were carried out by a similar manner to Example 91 to give the titled compound.

HPLC (220 nm): Purity 88% (Retention time 4.141 minutes) Mass (APCI+) 655 (M+1)

EXAMPLE 120

N-(3,4-Dichlorophenyl)-N-{3-[4-(4-fluorobenzyl)-1-piperidinyl]propyl}-1-(2-pyridylcarbonyl)-4-piperidinecarboxamide 2 trifluoroacetate By using picolinoyl chloride hydrochloride, the reaction and the purification procedure were carried out by a similar manner to Example 91 to give the titled compound.

HPLC (220 nm): Purity 84% (Retention time 3.289 minutes) Mass (APCI+) 611 (M+1)

EXAMPLE 121

1-[(6-Chloro-3-pyridyl)carbonyl]-N-(3,4-dichlorophenyl)-N-{3-[4-(4-fluorobenzyl)-1-piperidinyl]propyl}-4-piperidinecarboxamide 2 trifluoroacetate By using 6-chloronicotinoyl chloride, the reaction and the purification procedure were carried out by a similar manner to Example 91 to give the titled compound.

HPLC (220 nm): Purity 92% (Retention time 3.490 minutes) Mass (APCI+) 645 (M+1)

EXAMPLE 122

N-(3,4-Dichlorophenyl)-N-{3-[4-(4-fluorobenzyl)-1-piperidinyl]propyl}-1-[2-(3-indolyl)-2-oxo acetyl]-4-piperidinecarboxamide 2 trifluoroacetate By using 2-(3-indolyl)-2-oxo acetyl chloride, the reaction and the purification procedure were carried out by a similar manner to Example 91 to give the titled compound.

HPLC (220 nm): Purity 84% (Retention time 3.562 minutes) Mass (APCI+) 677 (M+1)

EXAMPLE 123

N-(3,4-Dichlorophenyl)-N-{3-[4-(4-fluorobenzyl)-1-piperidinyl]propyl}-1-[2-(4-methylphenylthio)-3-pyridylcarbonyl]-4-piperidinecarboxaniide 2 trifluoroacetate By using 2-(4-methylphenylthio)-3-pyridinecarbonyl chloride, the reaction and the purification procedure were carried out by a similar manner to Example 91 to give the titled compound.

HPLC (220 nm): Purity 88% (Retention time 3.790 minutes) Mass (APCI+) 733 (M+1)

EXAMPLE 124

N-(3,4-Dichlorophenyl)-N-{3-[4-(4-fluorobenzyl)y-1-piperidinyl]propyl}-1-(2-thenoyl)-4-piperidinecarboxamide trifluoroacetate By using 2-thenoyl chloride, the reaction and the purification procedure were carried out by a similar manner to Example 91 to give the titled compound.

HPLC (220 nm): Purity 89% (Retention time 3.540 minutes) Mass (APCI+) 616 (M+1)

EXAMPLE 125

N-(3,4-Dichlorophenyl)-N-{3-[4-(4-fluorobenzyl)-1-piperidinyl]propyl}-1-[2-thienylacetyl]-4-piperidinecarboxamide trifluoroacetate By using 2-thiopheneacetyl chloride, the reaction and the purification procedure were carried out by a similar manner to Example 91 to give the titled compound.

HPLC (220 nm): Purity 95% (Retention time 3.571 minutes) Mass (APCI+) 630 (M+1)

EXAMPLE 126

1-[(3-Chlorobenzo[b]thiophene-2-yl)carbonyl]-N-(3,4-dichlorophenyl)-N-{3-[4-(4-fluorobenzyl)-1-piperidinyl]propyl}-4-piperidinecarboxamide trifluoroacetate By using 3-chlorobenzo[b]thiophene-2-carbonyl chloride, the reaction and the purification procedure were carried out by a similar manner to Example 91 to give the titled compound.

HPLC (220 nm): Purity 92% (Retention time 3.928 minutes) Mass (APCI+) 700 (M+1)

EXAMPLE 127

1-(4-Cyanobenzoyl)-N-(3,4-dichlorophenyl)-N-(3-[4-(4-fluorobenzyl)-1-piperidinyl]propyl}-4-piperidinecarboxamide trifluoroacetate By using 4-cyanobenzoyl chloride, the reaction and the purification procedure were carried out by a similar manner to Example 91 to give the titled compound.

HPLC (220 nm): Purity 98% (Retention time 3.544 minutes) Mass (APCI+) 635 (M+1)

EXAMPLE 128

1-(3-Cyanobenzoyl)-N-(3,4-dichlorophenyl)-N-{3-[4-(4-fluorobenzyl)-1-piperidinyl]propyl}-4-piperidinecarboxamide trifluoroacetate By using 3-cyanobenzoyl chloride, the reaction and the purification procedure were carried out by a similar manner to Example 91 to give, the titled compound.

HPLC (220 nm): Purity. 99% (Retention time 3.536 minutes) Mass (APCI+) 635 (M+1)

EXAMPLE 129

N-(3,4-Dichlorophenyl)-N-{3-[4-(4-fluorobenzyl)-1-piperidinyl]propyl}-1-[(5-methyl-2-phenyl-2H-1,2,3-triazol-4-yl)carbonyl]-4-piperidinecarboxamide 3 trifluoroacetate By using 5-methyl-2-phenyl-1,2,3-triazol-4-carbonyl chloride, the reaction and the purification procedure were carried out by a similar manner to Example 91 to give the titled compound.

HPLC (220 nm): Purity 100% (Retention time 3.862 minutes) Mass (APCI+) 691 (M+1)

EXAMPLE 130

N-(3,4-Dichlorophenyl)-N-{3-[4-(4-fluorobenzyl)-1-piperidinyl]propyl}-1-{[1-phenyl-5-(trifluoromethyl)-4-pyrazolyl]carbonyl}-4-piperidinecarboxamide 2 trifluoroacetate By using 1-phenyl-5-(trifluoromethyl)-4-pyrazolecarbonyl chloride, the reaction and the purification procedure were carried out by a similar manner to Example 91 to give the titled compound.

HPLC (220 nm): Purity 99% (Retention time 3.791 minutes) Mass (APCI+) 744 (M+1)

EXAMPLE 131

1-[(4-Chloro-1,3-dimethyl-1H-pyrazolo[3,4-b]pyridine-5-yl)carbonyl]-N-(3,4-dichlorophenyl)-N-{3-[4-(4-fluorobenzyl)-1-piperidinyl]propyl}-4-piperidinecarboxamide 3 trifluoroacetate By using 4-chloro-1,3-dimethyl-1H-pyrazolo[3,4-b]pyridine-5-carbonyl chloride, the reaction and the purification procedure were carried out by a similar manner to Example 91 to give the titled compound.

HPLC (220 nm): Purity 99% (Retention time 3.546 minutes) Mass (APCI+) 713 (M+1)

EXAMPLE 132

N-(3,4-Dichlorophenyl)-N-{3-[4-(4-fluorobenzyl)-1-piperidinyl]propyl}-1-[(5-methyl-3-isoxazolyl)carbonyl]-4-piperidinecarboxamide trifluoroacetate By using 5-methylisoxazol-3-carbonyl chloride, the reaction and the purification procedure were carried out by a similar manner to Example 91 to give the titled compound.

HPLC (220 nm): Purity 89% (Retention time 3.500 minutes) Mass (APCI+) 615 (M+1)

EXAMPLE 133

N-(3,4-Dichlorophenyl)-N-{3-[4-(4-fluorobenzyl)-1-piperidinyl]propyl}-1-[4-(phenylazo)benzoyl]-4-piperidinecarboxamide trifluoroacetate By using 4-(phenylazo)benzoyl chloride, the reaction and the purification procedure were carried out by a similar manner to Example 91 to give the titled compound.

HPLC (220 nm): Purity 99% (Retention time 4.012 minutes) Mass (APCI+) 714 (M+1)

EXAMPLE 134

N-(3,4-Dichlorophenyl)-N-{3-[4-(4-fluorobenzyl)-1-piperidinyl]propyl}-1-[trans-4-(trifluoromethyl)cinnamoyl]-4-piperidinecarboxamide trifluoroacetate By using trans-4-(trifluoromethyl)cinnamoyl chloride, the reaction and the purification procedure were carried out by a similar manner to Example 91 to give the titled compound.

HPLC (220 nm): Purity 99% (Retention time 3.911 minutes) Mass (APCI+) 704 (M+1)

EXAMPLE 135

1-(2-Anthraquinonylcarbonyl)-N-(3,4-dichlorophenyl)-N-{3-[4-(4-fluorobenzyl)-1-piperidinyl]propyl)-4-piperidinecarboxamide trifluoroacetate By using anthraquinon-2-carbonyl chloride, the reaction and the purification procedure were carried out by a similar manner to Example 91 to give the titled compound.

HPLC (220 nm): Purity 90% (Retention time 3.826 minutes) Mass (APCI+) 740 (M+1)

EXAMPLE 136

N-(3,4-Dichlorophenyl)-N-{3-[4-(4-fluorobenzyl)-1-piperidinyl]propyl}-1-(3,4-methylenedioxybenzoyl)-4-piperidinecarboxamide trifluoroacetate By using 3,4-methylenedioxybenzoyl chloride, the reaction and the purification procedure were carried out by a similar manner to Example 91 to give the titled compound.

HPLC (220 nm): Purity 89% (Retention time 3.568 minutes) Mass (APCI+) 654 (M+1)

EXAMPLE 137

1-Acetyl-N-(3,4-dichlorophenyl)-N-}3-[4-(4-fluorobenzyl)-1-piperidinyl]propyl}-4-piperidinecarboxamide trifluoroacetate By using acetyl chloride, the reaction and the purification procedure were carried out by a similar manner to Example 91 to give the titled compound.

HPLC (220 nm): Purity 99% (Retention time 3.266 minutes) Mass (APCI+) 548 (M+1)
$^1$H NMR (CDCl$_3$) δ 1.62-2.08 (11H, m), 2.15-2.49 (6H, m), 2.62 (2H, br), 2.78-3.27 (2H, m), 2.90 (3H, s), 3.58-3.87 (4H, m), 4.59 (1H, br), 6.98-7.30 (5H, m), 7.39 (1H, d, J=2.2 Hz), 7.58 (1H, d, J=8.2 Hz)

EXAMPLE 138

N-(3,4-Dichlorophenyl)-N-{3-[4-(4-fluorobenzyl)-1-piperidinyl]propyl}-1-isobutyryl-4-piperidinecarboxamide trifluoroacetate By using isobutyryl chloride, the reaction and the purification procedure were carried out by a similar manner to Example 91 to give the titled compound.

HPLC (220 nm): Purity 96% (Retention time 2.910 minutes) Mass (APCI+) 576 (M+1)
$^1$H NMR (CDCl$_3$) δ 1.05 (6H, s), 1.53-2.07 (11H, m), 2.13-2.49 (7H, m), 2.59 (2H, br), 2.81-3.19 (2H, m), 3.62-3.89 (4H, m), 4.55 (1H, d, J=12.0 Hz), 6.93-7.25 (5H, m), 7.38 (1H, d, J=2.0 Hz), 7.58 (1H, d, J=8.6 Hz)

EXAMPLE 139

1-Acryloyl-N-(3,4-dichlorophenyl)-N-{3-[4-(4-fluorobenzyl)-1-piperidinyl]propyl}-4-piperidinecarboxamide trifluoroacetate By using acryloyl chloride, the reaction and the purification procedure were carried out by a similar manner to Example 91 to give the titled compound.

HPLC (220 nm): Purity 96% (Retention time 3.358 minutes) Mass (APCI+) 560 (M+1)

EXAMPLE 140

1-(Cyclohexylcarbonyl)-N-(3,4-dichlorophenyl)-N-{3-[4-(4-fluorobenzyl)-1-piperidinyl]propyl}-4-piperidinecarboxamide trifluoroacetate By using cyclohexanecarbonyl chloride, the reaction and the purification procedure were carried out by a similar manner to Example 91 to give the titled compound.

HPLC (220 nm): Purity 98% (Retention time 3.707 minutes) Mass (APCI+) 616 (M+1)

EXAMPLE 141

N-(3,4-Dichlorophenyl)-N-{3-[4-(4-fluorobenzyl)-1-piperidinyl]propyl}-1-{[(2S)-1-(2,2,2-trifluoroacetyl)-2-pyrrolidinyl]carbonyl}-4-piperidinecarboxamide trifluoroacetate By using (S)-(–)-N-(trifluoroacetyl)prolyl chloride (0.1M solution in dichloromethane), the reaction and the purification procedure were carried out by a similar manner to Example 91 to give the titled compound.

HPLC (220 nm): Purity 97% (Retention time 3.567 minutes) Mass (APCI+) 699 (M+1)

EXAMPLE 142

N-(3,4-Dichlorophenyl)-N-{3-[4-(4-fluorobenzyl)-1-piperidinyl]propyl}-1-(2-methoxyacetyl)-4-piperidinecarboxamide trifluoroacetate By using methoxyacetyl chloride, the reaction and the purification procedure were carried out by a similar manner to Example 91 to give the titled compound.

HPLC (220 nm): Purity 98% (Retention time 3.263 minutes) Mass (APCI+) 578 (M+1)

EXAMPLE 143

N-(3,4-Dichlorophenyl)-N-{3-[4-(4-fluorobenzyl)-1-piperidinyl]propyl}-1-(2-acetoxy-2-methylpropanoyl)-4-piperidinecarboxamide trifluoroacetate By using 2-acetoxyisobutyryl chloride, the reaction and the purification procedure were carried out by a similar manner to Example 91 to give the titled compound.

HPLC (220 nm): Purity 97% (Retention time 3.352 minutes) Mass (APCI+) 634 (M+1)

EXAMPLE 144

N-(3,4-Dichlorophenyl)-N-{3-[4-(4-fluorobenzyl)-1-piperidinyl]propyl}-1-(morpholinocarbonyl)-4-piperidinecarboxamide trifluoroacetate By using morpholinocarbonyl chloride, the reaction and the purification procedure were carried out by a similar manner to Example 91 to give the titled compound.

HPLC (220 nm): Purity 97% (Retention time 3.346 minutes) Mass (APCI+) 619 (M+1)

EXAMPLE 145

N-(3,4-Dichlorophenyl)-N-{3-[4-(4-fluorobenzyl)-1-piperidinyl]propyl}-1-(4-pyridylcarbonyl)-4-piperidinecarboxamide 2 trifluoroacetate To the reaction vessel containing carbodiimide resine (Argonaut, 1.15 mmol/g, 87 mg, 100 μmol) was added a solution of isonicotinic acid(9.2 mg, 75 μmol) in dichloromethane (0.3 mL) at room temperature, and the mixture was kept standing for 30 minutes. To the mixture was added a solution of N-(3,4-dichlorophenyl)-N-{3-[4-(4-fluorobenzyl)-1-piperidinyl]propyl}-4-piperidinecarboxamide (Example 90)(16.1 mg, 50 μmol) in dichloromethane (0.3 mL) at room temperature, and the mixture was stirred for 24 hours. The resin was filtered off, and the filtrate was concentrated under reduced pressure and purified by preparative HPLC. The desired fraction was concentrated to give the desired product as a colorless oily substance (24.6 mg).

HPLC (220 nm): Purity 97% (Retention time 2.980 minutes) Mass (APCI+) 611 (M+1)

EXAMPLE 146

N-(3,4-Dichlorophenyl)-N-{3-[4-(4-fluorobenzyl)-1-piperidinyl]propyl}-1-(3-pyridylcarbonyl)-4-piperidinecarboxamide 2 trifluoroacetate By using nicotinic acid, the reaction and the purification procedure were carried out by a similar manner to Example 145 to give the titled compound.

HPLC (220 nm): Purity 98% (Retention time 3.010 minutes) Mass (APCI+) 611 (M+1)

EXAMPLE 147

N-(3,4-Dichlorophenyl)-N-{3-[4-(4-fluorobenzyl)-1-piperidinyl]propyl}-1-[2-(4-pyridyl)acetyl]-4-piperidinecarboxamide 2 trifluoroacetate By using 4-pyridyl acetic acid, the reaction and the purification procedure were carried out by a similar manner to Example 145 to give the titled compound.

HPLC (220 nm): Purity 98% (Retention time 2.960 minutes) Mass (APCI+) 625 (M+1)

EXAMPLE 148

N-(3,4-Dichlorophenyl)-N-{3-[4-(4-fluorobenzyl)-1-piperidinyl]propyl}-1-(2-pyrazinylcarbonyl)-4-piperidinecarboxamide trifluoroacetate By using 2-pyrazine carboxylic acid, the reaction and the purification procedure were carried out by a similar manner to Example 145 to give the titled compound.

HPLC (220 nm): Purity 98% (Retention time 3.268 minutes) Mass (APCI+) 612 (M+1)

EXAMPLE 149

N-(3,4-Dichlorophenyl)-1-[2-(dimethylamino)acetyl]-N-{3-[4-(4-fluorobenzyl)-1-piperidinyl]propyl}-4-piperidinecarboxamide 2 trifluoroacetate By using N,N-dimethyl glycine, the reaction and the purification procedure were carried out by a similar manner to Example 145 to give the titled compound.

HPLC (220 nm): Purity 96% (Retention time 2.850 minutes) Mass (APCI+) 591 (M+1) $^1$H NMR (CDCl$_3$) δ 1.64-2.09 (11H, m), 2.14-2.40 (6H, m), 2.20 (6H, s), 2.58 (2H, br), 2.62 (2H, s), 2.82-3.25 (2H, m), 3.55-3.88 (4H, m), 4.51 (1H, br), 6.99-7.26 (5H, m), 7.34 (1H, d, J=2.0 Hz), 7.56 (1H, d, J=8.2 Hz)

EXAMPLE 150

N-(3,4-Dichlorophenyl)-N-{3-[4-(4-fluorobenzyl)-1-piperidinyl]propyl}-1-oxamoyl-4-piperidinecarboxamide trifluoroacetate By using oxamic acid, the reaction and the purification procedure were carried out by a similar manner to Example 145 to give the titled compound.

HPLC (220 nm): Purity 96% (Retention time 3.121 minutes) Mass (APCI+) 577 (M+1)

EXAMPLE 151

1-(2-Aminoacetyl)-N-(3,4-dichlorophenyl)-N-{3-[4-(4-fluorobenxyl)-1-piperidinyl]propyl}-4-piperidinecarboxamide 2 trifluoroacetate To the reaction vessel containing carbodiumide resine (Argonaut, 1.15 mmol/g, 87 mg, 100 μmol) was added a solution of N-Boc-glycine (13.1 mg, 75 μmol) in dichloromethane (0.3 mL) at room temperature, and the mixture was kept standing for 30 minutes. To the mixture was added a solution of N-(3,4-dichlorophenyl)-N-{3-[4-(4-fluorobenzyl)-1-piperidinyl]propyl}-4-piperidinecarboxamide (Example 90)(16.1 mg, 50 μmol) in dichloromethane (0.3 mL) at room temperature, and the mixture was stirred for 24 hours. The resin was filtered off, and the filtrate was concentrated under reduced pressure. To the concentrate was added a mixed solution of trifluoroacetic acid and dichloromethane (trifluoracetic acid:dichloromethane=1:1), and the mixture was concentrated under reduced pressure. The concentrate was purified by preparative HPLC. The desired fraction was concentrated to give the desired product as a colorless oily substance (29.6 mg).

HPLC (220 nm): Purity 93% (Retention time 3.506 minutes) Mass (APCI+) 563 (M+1)

EXAMPLE 152

N-(3,4-Dichlorophenyl)-N-{3-[4-(4-fluorobenzyl)-1-piperidinyl]propyl}-1-{[(2S,4R)-4-hydroxy-2-pyrrolidinyl]carbonyl}-4-piperidinecarboxamide 2 trifluoroacetate By using trans-1-(tert-butoxycarbonyl)-4-hydroxy-L-proline, the reaction and the purification procedure were carried out by a similar manner to Example 151 to give the titled compound.

HPLC (220 nm): Purity 94% (Retention time 3.321 minutes) Mass (APCI+) 619 (M+1)

EXAMPLE 153

N-(3,4-Dichlorophenyl)-N-{3-[4-(4-fluorobenzyl)-1-piperidinyl]propyl}-1-[(1-hydroxycyclopropyl)carbonyl]-4-piperidinecarboxamide trifluoroacetate By using 1-hydroxy-1-cyclopropanecarboxylic acid, the reaction, and, the purification procedure were carried out by a similar, manner to Example 145 to give the titled compound.

HPLC (2 nm): Purity 89% (Retention time 3.255 minutes) Mass (APCI+) 590 (M+1)

EXAMPLE 154

N-(3,4-Dichlorophenyl)-N-{3-[4-(4-fluorobenzyl)-1-piperidinyl]propyl}-1-[(4-methoxycyclohexyl)carbonyl]-4-piperidinecarboxamide trifluoroacetate By using 4-methoxycyclohexane carboxylic acid, the reaction and the purification procedure were carried out by a similar manner to Example 145 to give the titled compound.

HPLC (220 nm): Purity 93% (Retention time 3.470 minutes) Mass (APCI+) 646 (M+1)

EXAMPLE 155

1-[2-(2-Carbamoylphenoxy)acetyl]-N-(3,4-dichlorophenyl)-N-{3-[4-(4-fluorobenzyl)-1-piperidinyl]propyl}-4-piperidinecarboxamide trifluoroacetate By using (2-carbamoyl phenoxy)acetic acid, the reaction and the purification procedure were carried out by a similar manner to Example 145 to give the titled compound.

HPLC (220 nm): Purity 98% (Retention time 3.394 minutes) Mass (APCI+) 683 (M+1)

EXAMPLE 156

N-(3,4-Dichlorophenyl)-N-{3-[4-(4-fluorobenzyl)-1-piperidinyl]propyl}-1-(4-sulfamoylbenzoyl)-4-piperidinecarboxamide trifluoroacetate By using 4-carboxybenzenesulfonamide, the reaction and the purification procedure were carried out by a similar manner to Example 145 to give the titled compound.

HPLC (220 nm): Purity 100% (Retention time 3.307 minutes); Mass (APCI+) 689 (M+1)

EXAMPLE 157

N-(3,4-Dichlorophenyl)-N-{3-[4-(4-fluorobenzyl)-1-piperidinyl]propyl}-1-(4-hydroxybenzoyl)-4-piperidinecarboxamide trifluoroacetate By using 4-hydroxybenzoic acid, the reaction and the purification procedure were carried out by a similar manner to Example 145 to give the titled compound.

HPLC (220 nm): Purity 88% (Retention time 3.355 minutes) Mass (APCI+) 626 (M+1)

EXAMPLE 158

1-[4-(Acetylamino)benzoyl]-N-(3,4-dichlorophenyl)-N-{3-[4-(4-fluorobenzyl)-1-piperidinyl]propyl}-4-piperidinecarboxamide trifluoroacetate By using 3-acetamide benzoic acid, the reaction and the purification procedure were carried out by a similar manner to Example 145 to give the titled compound.

HPLC (220 nm): Purity 97% (Retention time 3.349 minutes) Mass (APCI+) 667 (M+1)

EXAMPLE 159

N-(3,4-Dichlorophenyl)-N-{3-[4-(4-fluorobenzyl)-1-piperidinyl]propyl}-1-(4-piperidinylcarbonyl)-4-piperidinecarboxamide 2 trifluoroacetate By using N-Boc-isonipetic acid, the reaction and the purification procedure were carried out by a similar manner to Example 151 to give the titled compound.

HPLC (220 nm): Purity 93% (Retention time 3.657 minutes) Mass (APCI+) 617 (M+1)

EXAMPLE 160

N-(3,4-Dichlorophenyl)-N-{3-[4-(4-fluorobenzyl)-1-piperidinyl]propyl}-1-(1,2,3-thiadiazol-4-ylcarbonyl)-4-piperidinecarboxamide trifluoroacetate By using 1,2,3-thiadiazol-4-carboxylic acid, the reaction and the purification procedure were carried out by a similar manner to Example 145 to give the titled compound.

HPLC (220 nm): Purity 86% (Retention time 3.430 minutes) Mass (APCI+) 618 (M+1)

EXAMPLE 161

N-(3,4-Dichlorophenyl)-N-{3-[4-(4-fluorobenzyl)-1-piperidinyl]propyl}-1-[2-(1H-tetrazol-1-yl)acetyl]-4-piperidinecarboxamide trifluoroacetate By using (1H-tetrazol-1-yl)acetic acid, the reaction and the purification procedure were carried out by a similar manner to Example 145 to give the titled compound as HPLC (220 nm): Purity 100%. (Retention time 3.225 minutes) Mass (APCI+) 616 (M+1)

EXAMPLE 162

1-Acetyl-N-(3-chlorophenyl)-N-(3-{4-[hydroxy(2-pyridyl)methyl]-1-piperidinyl}propyl)-4-piperidinecarboxamide ditrifluoroacetate To the compound obtained in Reference Example 48-1 (53 mg, 0.14 mmol) was added a solution of trifluoroacetic acid and dichloromethane (1:1) (2 mL), and the mixture was stirred for 1 hour. The solvent was distilled off under reduced pressure, and acetonitrile (1 mL) was added. To the mixture were added the compound obtained in Reference Example 12(50 mg, 0.14 mmol), potassium carbonate (77.4 mg, 0.56 mmol) and potassium iodide (23.2 mg, 0.14 mmol), and the mixture was stirred at 80° C. for 6 hours. To the reaction mixture was added ethyl acetate (1 mL), and the mixture was washed with saturated aqueous solution of sodium hydrogen carbonate and saturated aqueous solution of sodiumchloride, successively, and dried over magnesium sulfate. The solvent was distilled off, and the residue was dissolved in a mixed solution of DMSO and methanol (DMSO:methanol=1:1, 400 mL) and purified by preparative HPLC. The solvent was distilled of to give the titled compound as yellow oily substance (77.9 mg). Yield 79%.

$^1$H NMR (CDCl$_3$) δ 1.52-2.48 (14H, m), 2.05 (3H, s), 2.55-2.78 (2H, m), 2.93-3.09 (2H, m), 3.22-3.96 (6H; m), 4.42-4.58 (1H, m), 4.80-4.92 (1H, m), 7.15-7.20 (2H, m), 7.41 (2H, d, J=5.2 Hz), 7.55-7.82 (2H, m), 8.04-8.22 (1H, m), 8.70 (1H, d, J=4.8 Hz) IR (KBr) 3401, 2934, 1682, 1645, 1590 cm$^{-1}$

EXAMPLE 163

1-Acetyl-N-(3-chlorophenyl)-N-{3-[4-(2-pyridylmethyl)-1-piperidinyl]propyl}-4-piperidinecarboxamide ditrifluoroacetate By using the compound obtained in Reference Example 48-3, the reaction and the purification procedure were carried out by a similar manner to Example 162 to give the titled compound as yellowish oily substance (54.2 mg). Yield 56%.

$^1$H NMR (CDCl$_3$) δ 1.50-2.06 (12H, m), 2.05 (3H, s), 2.20-2.45 (2H, m), 2.50-2.92 (4H, m), 3.04 (2H, d, J=7.0 Hz), 3.48-3.89 (4H, m), 4.07-4.18 (1H, m), 4.42-4.61 (1H, m), 7.10-7.22 (2H, m), 7.41 (2H, d, J=5.6 Hz), 7.52 (1H, d, J=7.6 Hz), 7.59-7.70 (1H, m), 8.09-8.18 (1H, m), 8.74-8.79 (1H, m) IR (KBr) 3410, 2942, 1682, 1645, 1589 cm$^{-1}$

EXAMPLE 164

1-Acetyl-N-(3-chlorophenyl)-N-{3-[4-(3-pyridylmethyl)-1-piperidinyl]propyl}-4-piperidinecarboxamide ditrifluoroacetate By using the compound obtained in Reference Example 49-3, the reaction and the purification procedure were carried out by a similar manner to Example 162 to give the titled compound as a yellowish oily substance (26.6 mg). Yield 28%.

$^1$H NMR (CDCl$_3$) δ 1.55-2.11 (12H, m), 2.05 (3H, s), 2.25-2.48 (2H, m), 2.50-2.70 (2H, m), 2.74-2.90 (2H, m), 2.93-3.17 (2H, m), 3.55-3.91 (4H, m), 4.03-4.20 (1H, m), 4.44-4.61 (1H, m), 7.10-7.23 (3H, m), 7.28-7.34 (1H, br), 7.41-7.43 (2H, d, J=5.0 Hz), 7.60-7.81 (1H, m), 7.98 (1H, d, J=7.2 Hz) IR (KBr) 3416, 2945, 1682, 1653, 1590 cm$^{-1}$

EXAMPLE 165

1-Acetyl-N-(3-chlorophenyl)-N-(3-{4-[hydroxy(4-pyridyl)methyl]-1-piperidinyl}propyl)-4-piperidinecarboxamide ditrifluoroacetate By using the compound obtained in Reference Example 50-1, the reaction and the purification procedure were carried out by a similar manner to Example 162 to give the titled compound as a yellowish oily substance (31.5 mg). Yield 32%.

$^1$H NMR (CDCl$_3$) δ 1.53-2.48 (14H, m), 2.07 (3H, s), 2.74-2.93 (2H, m), 2.97-3.15 (2H, m), 3.53-3.90 (5H, m), 4.43-4.59 (1H, m), 4.73-4.83 (1H, m), 7.13-7.26 (2H, m), 7.44 (2H, d, J=5.6 Hz), 7.67-7.82 (2H, m), 8.65-8.80 (2H, m) IR (KBr) 3400, 2256, 1682, 1645, 1590 cm$^{-1}$

EXAMPLE 166

1-Acetyl-N-(3-chlorophenyl)-N-{3-[4-(4-pyridylmethyl)-1-piperidinyl]propyl}-4-piperidinecarboxamide ditrifluoroacetate By using the compound obtained in Reference Example 50-3, the reaction and the purification procedure were carried out by a similar manner to Example 162 to give the titled compound as a yellowish oily substance (34.8 mg). Yield 36%.

$^1$H NMR (CDCl$_3$) δ 1.55-2.49 (14H, m), 2.05 (3H, s), 2.52-3.17 (6H, m), 3.55-3.88 (4H, m), 4.01-4.19 (1H, m), 4.23-4.40 (1H, m), 7.11-7.25 (2H, m), 7.42 (2H, d, J=5.2 Hz), 7.61 (2H, br), 8.75 (2H, br) IR (KBr) 3419, 2932, 1682, 1645, 1590 cm$^{-1}$

EXAMPLE 167

1-Acetyl-N-(3-chlorophenyl)-N-(3-{4-[hydroxy(2-thiazolyl)methyl]-1-piperidinyl}propyl)-4-piperidinecarboxamide ditrifluoroacetate By using the compound obtained in Reference Example 51-1, the reaction and the purification procedure were carried out by a similar manner to Example 162 to give the titled compound as a yellowish oily substance (41.8 mg). Yield 40%.

$^1$H NMR (CDCl$_3$) δ 1.44-2.53 (14H, m), 2.09 (3H, s), 2.60-3.25 (6H, m), 3.52-3.82 (3H, m), 4.39-4.60 (2H, m), 5.17-6.50 (1H, br), 7.07-7.33 (4H, m), 7.35-7.50 (2H, m) IR (KBr) 3280, 2941, 2351, 1682, 1668, 1634 cm$^{-1}$

EXAMPLE 168

1-Acetyl-N-(3-chlorophenyl)-N-{3-[4-(2-thiazolylmethyl)-1-piperidinyl]propyl}-4-piperidinecarboxamide ditrifluoroacetate By using the compound obtained in Reference Example 51-3, the reaction and the purification procedure were carried out by a similar manner to Example 162 to give the titled compound as a yellowish oily substance (41.2 mg). Yield 40%.

$^1$H NMR (CDCl$_3$) δ 1.55-2.51 (14H, m), 2.11 (3H, s), 2.57-3.20 (6H, m), 3.56-3.83 (4H, m), 4.43-4.60 (2H, m), 7.05-7.48 (5H, m), 7.76-7.90 (1H, m) IR (KBr) 3421, 2934, 1682, 1651, 1634 cm$^{-1}$

EXAMPLE 169

1-Acetyl-N-(3-chlorophenyl)-N-{3-[4-(3-pyridyloxy)-1-piperidinyl]propyl}-4-piperidinecarboxamide ditrifluoroacetate By using the compound obtained in Reference Example 52, the reaction and the purification procedure were carried out by a similar manner to Example 162 to give the titled compound as a yellowish oily Substance (8.4 mg). Yield 8%.

$^1$H NMR (CDCl$_3$) δ 1.56-2.62 (14H, m), 2.09 (3H, s), 2.75-3.28 (4H, m), 3.33-3.95 (4H, m), 4.40-4.62 (1H, m), 4.80-4.96 (1H, m), 7.09-7.24 (2H, m), 7.43 (2H, d, J=5.4 Hz), 7.64-7.86 (2H, m), 8.30-8.48 (1H, m), 8.55-8.79 (1H, m) IR (KBr) 3483, 2948, 2357, 1682, 1651, 1634, cm$^{-1}$

EXAMPLE 170

1-Acetyl-N-(3-chlorophenyl)-N-{3-[4-(4-phenyl-2-thiazolylthio)-1-piperidinyl]propyl}-4-piperidinecarboxamide ditrifluoroacetate By using the compound obtained in Reference Example 53, the reaction and the purification procedure were carried out by a similar manner to Example 162 to give the titled compound as a yellowish oily substance (32.7 mg). Yield 28%.

$^1$H NMR (CDCl$_3$) δ 1.56-2.60 (14H, m), 2.10 (3H, s), 2.61-3.24 (4H, m), 3.45-3.95 (4H, m), 4.27-4.64 (2H, m), 7.05-7.24 (2H, m), 7.33-7.51 (6H, m), 7.84 (2H, d, J=7.8 Hz) IR (KBr) 2948, 2351, 2245, 1651, 1634, 1590 cm$^{-1}$

EXAMPLE 171

1-Acetyl-N-(3-chloro-4-methylphenyl)-N-{3-[4-(4-fluorobenzyl)-1-piperidinyl]propyl}-4-piperidinecarboxamide By a similar manner to Example 16, the titled compound was synthesized by using the compound obtained in Reference Example 54. Yield 96%.

$^1$H NMR (CDCl$_3$) δ 1.1-1.9 (13H, m), 2.04 (3H, s), 2.2-2.55 (2H, m), 2.28 (2H, t, J=7.5 Hz), 2.42 (3H, s), 2.48 (2H, d, J=6.6 Hz), 2.7-2.95 (1H, m), 2.83 (2H, br d, J=11.0 Hz), 3.65 (2H, t, J=7.7 Hz), 3.76 (1H, br d, J=12.8 Hz), 4.51 (1H, br d, J=12.8 Hz), 6.85-7.15 (5H, m), 7.19 (1H, d, J=2.2 Hz), 7.29 (1H, d, J=8.0 Hz)

EXAMPLE 172

1-Acetyl-N-{3-[4-(4-fluorobenzyl)-1-piperidinyl]propyl}-N-(4-methylphenyl)-4-piperidinecarboxamide By a similar manner to Example 16, the titled compound was synthesized by using the compound obtained in Reference Example 55. Yield 96%.

$^1$H NMR (CDCl$_3$) δ 1.1-1.9 (13H, m), 2.03 (3H, s), 2.2-2.55 (2H, m), 2.29 (2H, t, J=7.7 Hz), 2.40 (3H, s), 2.48 (2H, d, J=6.6 Hz), 2.7-2.95 (1H, m), 2.84 (2H, br d, J=11.2 Hz), 3.65 (2H, t, J=7.6 Hz), 3.74 (1H, br d, J=13.2 Hz), 4.50 (1H, br d, J=13.2 Hz), 6.85-7.15 (6H, m), 7.22 (2H, d, J=7.6 Hz)

EXAMPLE 173

N-(3-Chloro-4-methylphenyl)-N-{3-[4-(4-fluorobenzyl)-1-piperidinyl]propyl}-1-(methylsulfonyl)-4-piperidinecarboxamide By a similar manner to Example 25, the titled compound was synthesized by using the compound obtained in Reference Example 54. Yield 75%.

$^1$H NMR (CDCl$_3$) δ 1.1-2.0 (13H, m), 2.15-2.4 (1H, m), 2.28 (2H, t, J=7.6 Hz), 2.41 (3H, s), 2.48 (2H, d, J=6.4 Hz), 2.55 (2H, dt, J=2.8, 11.4 Hz), 2.72 (3H, s), 2.84 (2H, br d, J=11.6 Hz), 3.64 (2H, t, J=7.5 Hz), 3.71 (2H, m), 6.85-7.15 (5H, m), 7.18 (1H, d, J=2.2 Hz), 7.28 (1H, d, J=8.0 Hz)

EXAMPLE 174

N-{3-[4-(4-Fluorobenzyl)-1-piperidinyl]propyl}-1-(methylsulfonyl)-N-(4-methylphenyl)-4-piperidinecarboxamide By a similar manner to Example 25, the titled compound was synthesized by using the compound obtained in Reference Example 55. Yield 47%.

$^1$H NMR (CDCl$_3$) δ 1.1-2.05 (13H, m), 2.15-2.6 (5H, m), 2.40 (3H, s), 2.48 (2H, d, J=6.6 Hz), 2.71 (3H, s), 2.91 (2H, br d, J=11.8 Hz), 3.65 (2H, t, J=7.5 Hz), 3.70 (2H, m), 6.94 (2H, m), 7.02 (2H, d, J=8.0 Hz), 7.07 (2H, m), 7.22 (2H; d, J=8.0 Hz)

EXAMPLE 175

N-[3-(4-Benzyl-1-piperidinyl)propyl]-N-(3,4-dichlorophenyl)-1-sulfamoyl-4-piperidinecarboxamide A mixture of the compound obtained in Example 66 (391 mg, 0.80 mmol), sulfamide (1.54 g, 16.0 mmol), 2-propanol (20 mL) and distilled water (10 mL) was stirred under reflux for 4 days. The reaction mixture was concentrated under reduced pressure, and to the concentrate was added a saturated aqueous solution of sodium hydrogen carbonate. The mixture was extracted with, dichloromethane. The organic layer was dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure. To the concentrate were added diethyl ether and ethyl acetate, and the resulting precipitates were collected by filtration. The precipitates were washed with diethyl ether, and dried under reduced pressure to give the titled compound (230 mg, 0.41 mmol, Yield 51%) as white crystals.

$^1$H NMR (CDCl$_3$) δ 1.1-2.05 (13H, m), 2.1-2.35 (3H, m), 2.4-2.6 (2H, m), 2.51 (2H, d, J=6.2 Hz), 2.82 (2H, br d, J=11.8 Hz), 3.55-3.75 (2H, m), 3.65 (2H, t, J=7.4 Hz), 4.28 (2H, br s), 7.03 (1H, dd, J=2.5, 8.5 Hz), 7.05-7.35 (5H, m), 7.31 (1H, d, J=2.5 Hz), 7.51 (1H, d, J=8.5 Hz)

EXAMPLE 176

N-[3-(4-Benzyl-1-piperidinyl)propyl]-1-carbamoylmethyl-N-(3,4-dichlorophenyl)-4-piperidinecarboxamide A mixture of the compound obtained in Example 66 (391 mg, 0.80 mmol), 2-bromoacetamide (132 mg, 0.96 mmol), potassium carbonate (265 mg, 1.92 mmol) and DMF (5mL) was stirred at room temperature for 2 days. To the reaction mixture was added water (15 mL), and the mixture was extracted with ethyl acetate (15 mL×3). The organic layer was washed with water (5 mL×3), saturated sodium chloride solution (5 mL), successively, dried over, anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure to give the titled compound (357 mg, 0.65 mmol, Yield 82%) as a colorless oily substance.

$^1$H NMR (CDCl$_3$) δ 1.1-2.2 (16H, m), 2.28 (2H, t, J=7.5 Hz), 2.51 (2H, d, J=6.6 Hz), 2.7-3.0 (4H, m), 2.89 (2H; s), 3.65 (2H, t, J=7.6 Hz), 6.00 (1H, br d, J=4.4 Hz), 6.95-7.35 (6H, m), 7.02 (1H, dd, J=2.4, 8.5 Hz), 7.30 (1H, d, J=2.4 Hz), 7.50 (1H, d, J=8.5 Hz)

EXAMPLE 177

N-[3-(4-Benzyl-1-piperidinyl)propyl]-N-(3,4-dichlorophenyl)-1-(2-pyridylcarbonyl)-4-piperidinecarboxamide To the solution of the compound obtained in Example 66 (391 mg, 0.80 mmol), picolinic acid (108 mg, 0.88 mmol) and 1-hydroxbenzotriazole (119 mg, 0.88 mmol) in DMF (8 mL) was added 1-[3-(dimethylamino)propyl]-3-ethylcarbodiimide hydrochloride (307 mg, 1.60 mmol), and the mixture was stirred at room temperature for 20 hours. The reaction mixture was concentrated under reduced pressure, and to the concentrate were added a saturated aqueous solution of sodium hydrogen carbonate (15 mL) and water (5 mL). The mixture was extracted with ethyl acetate (15 mL×5). The organic layer was washed with a saturated aqueous solution of sodium hydrogen carbonate (5 mL×3), saturated sodium chloride solution (5 mL), successively, dried over anhydrous sodium sulfate, and concentrated under reduced pressure. The concentrate was subjected to column chromatography (silica gel 10 g, ethyl acetate/methanol=1/0 to 9/1), and the desired fraction was concentrated under reduced pressure to give the titled compound (433 mg, 0.73 mmol, Yield 91%).

$^1$H NMR (CDCl$_3$) δ 1.1-2.0 (13H, m), 2.2-3.2 (3H, m), 2.27 (2H, t, J=7.5 Hz), 2.51 (2H, d, J=6.2 Hz), 2.82 (2H, br d, J=11.4 Hz), 3.65 (2H, t, J=7.5 Hz), 3.93 (1H, br d, J=13.6 Hz), 4.66 (1H, br d, J=13.6 Hz), 7.04 (1H, dd, J=2.6, 8.4 Hz), 7.05-7.35 (7H, m), 7.51 (1H, d, J=8.4 Hz), 7.58 (1H, d, J=7.9 Hz), 7.77 (1H, dt, J=1.5, 7.9 Hz), 8.55 (1H, d, J=4.8 Hz)

EXAMPLE 178

N-[3-(4-Benzyl-1-piperidinyl)propyl]-N-(3,4-dichlorophenyl)-1-(4-pyridylcarbonyl)-4-piperidinecarboxamide By a similar manner to Example 177, the titled compound was synthesized by using isonicotinic acid. Yield 84%.

$^1$H NMR (CDCl$_3$) δ 1.1-2.0 (13H, m), 2.2-3.0 (3H, m), 2.29 (2H, t, J=7.5 Hz), 2.51 (2H, d, J=6.2 Hz), 2.83 (2H, br d, J=11.4 Hz), 3.59 (1H, br d, J=12.4 Hz), 3.66 (2H, t, J=7.5 Hz), 4.62 (1H, br d, J=12.4 Hz), 7.04 (1H, dd, J=2.5, 8.6 Hz), 7.05-7.35 (7H, m), 7.32 (1H, d, J=2.5 Hz), 7.52 (1H, d, J=8.6 Hz), 8.67 (2H, m)

EXAMPLE 179

1-Acetyl-N-(3,4-dichlorophenyl)-N-{3-[4-(4-fluorobenzoyl)-1-piperidinyl]propyl}-4-piperidinecarboxamide A mixture of the compound obtained in Reference Example 56-3 (470 mg, 1.2 mmol), 4-(4-fluorobenzoyl)piperidine hydrochloride (292 mg, 1.2 mmol), potassium iodide (199 mg, 1.2 mmol), potassium carbonate (498 mg, 3.6 mmol) and acetonitrile (24 mL) was stirred at 80° C. for 24 hours. The reaction mixture was concentrated under reduced pressure, and to the concentrate was added water (15 mL). The mixture was extracted with ethyl acetate (15 mL×3). The organic layer was dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure to give the titled compound (378 mg, 0.67 mmol, Yield 56%) as a colorless oily substance.

$^1$H NMR (CDCl$_3$) δ 1.5-2.2 (12H, m), 2.06 (3H, s), 2.2-2.5 (2H, m), 2.35 (2H, t, J=7.4 Hz), 2.75-3.0 (1H, m), 2.93 (2H, br d, J=11.4 Hz), 3.19 (1H, m), 3.69 (2H, t, J=7.7 Hz), 3.79 (1H, br d, J=13.7 Hz), 4.53 (1H, br d, J=13.7 Hz), 7.07 (1H, dd, J=2.6, 8.4 Hz), 7.14 (2H, m), 7.34 (1H, d, J=2.6 Hz), 7.54 (1H, d, J=8.4 Hz), 7.96 (2H, m)

EXAMPLE 180

1-Acetyl-N-(3,4-dichlorophenyl)-N-{3-[4-(4-fluorobenzyl)-4-hydroxy-1-piperidinyl]propyl}-4-piperidinecarboxamide By a similar manner to Example 179, the titled compound was synthesized by using 4-(4-fluorobenzyl)-4-hydroxypiperidine. Yield 168%.

$^1$H NMR (CDCl$_3$) δ 1.4-1.9 (10H, m), 2.05 (3H, s), 2.1-2.5 (4H, m), 2.33 (2H, t, J=7.5 Hz), 2.60 (2H, m), 2.71 (2H, s), 2.87 (1H, m), 3.67 (2H, t, J=7.5 Hz), 3.78 (1H, br d, J=14.0 Hz), 4.53 (1H, br d, J=14.0 Hz), 6.99 (2H, m), 7.04 (1H, dd, J=2.4, 8.5 Hz), 7.15 (2H, m), 7.32 (1H, d, J=2.4 Hz), 7.52 (1H, d, J=8.5 Hz)

EXAMPLE 181

1-Acetyl-N-{3-[4-(1H-1,2,3-benzotriazol-1-yl)-1-piperidinyl]propyl}-N-(3,4-dichiorophenyl)-4-piperidinecarboxamide By a similar manner to Example 179, the titled compound was synthesized by using 4-(1H-1,2,3-benzotriazol-1-yl)piperidine hydrochloride. Yield 41%.

¹H NMR (CDCl₃) δ 1.5-1.95 (6H, m), 2.0-2.6 (8H, m) 2.06 (3H, s), 2.43 (2H, t, J=7.2 Hz), 2.89 (1H, m), 3.08 (2H, m), 3.73 (2H, t, J=7.5 Hz), 3.79 (1H, br d, J=13.6 Hz), 4.54 (1H, br d, J=13.6 Hz), 4.70 (1H, tt, J=4.0, 11.4 Hz), 7.09 (1H, dd, J=2.3, 8.5 Hz), 7.3-7.65 (3H, m), 7.36 (1H, d, J=2.3 Hz), 7.56 (1H, d, J=8.5 Hz), 8.06 (1H, m)

EXAMPLE 182

1-Acetyl-N-{3-[4-(1-benzoimidazolyl)-1-piperidinyl]propyl}-N-(3,4-dichlorophenyl)-4-piperidinecarboxamide By a similar manner to Example 179, the titled compound was synthesized by using 4-(1-benzoimidazolyl)piperidine 2 hydrochloride. Yield 40%.
¹H NMR (CDCl₃) δ 1.5-1.9 (6H, m), 2.0-2.5 (8H, m), 2.06 (3H, s), 2.43 (2H, t, J=7.1 Hz), 2.88 (1H, m), 3.08 (2H, m), 3.72 (2H, t, J=7.5 Hz), 3.79 (1H, br d, J=12.8 Hz), 4.20 (1H, m), 4.54 (1H, br d, J=12.8 Hz), 7.07 (1H, dd, J=2.4, 8.4 Hz), 7.2-7.5 (3H, m), 7.35 (1H, d, J=2.4 Hz), 7.56 (1H, d, J=8.4 Hz), 7.75-7.85 (1H, m), 7.99 (1H, s)

EXAMPLE 183

1-Acetyl-N-(3,4-dichlorophenyl)-N-{3-[4-(3-indolyl)-1-piperidinyl]propyl}-4-piperidinecarboxamide By a similar manner to Example 179, the titled compound was synthesized by using 4-(3-indolyl)piperidine. Yield 57%.
¹H NMR (CDCl₃) δ 1.5-2.2 (12H, m), 2.06 (3H, s), 2.2-2.5 (2H, m), 2.39 (2H, t, J=7.3 Hz), 2.7-3.05 (2H, m), 2.99 (2H, br d, J=11.4 Hz), 3.70 (2H, t, J=7.5 Hz), 3.78 (1H, br d, J=12.8 Hz), 4.54 (1H, br d, J=12.8 Hz), 6.95 (1H, d, J=2.2 Hz), 7.06 (1H, dd, J=2.3, 8.4 Hz), 7.09 (1H, dt, J=1.8, 7.6 Hz), 7.18 (11H, dt, J=1.3, 7.5 Hz), 7.35 (1H, d, J=2.3 Hz), 7.35 (1H, d, J=7.4 Hz), 7.53 (1H, d, J=8.4 Hz), 7.63 (1H, d, J=7.2 Hz), 8.09 (1H, br s)

EXAMPLE 184

1-Acetyl-N-(3,4-dichlorophenyl)-N-{3-[4-(6-imidazo[1,2-b]pyridazinylthio)-1-piperidinyl]propyl}-4-piperidinecarboxamide By a similar manner to Example 179, the titled compound was synthesized by using the compound obtained in Reference Example 58-3. Yield 44%.
¹H NMR (CDCl₃) δ 1.5-1.9 (8H, m), 2.0-2.5 (6H, m), 2.06 (3H, s), 2.35 (2H, t, J=7.1 Hz), 2.7-3.0 (3H, m), 3.6-3.95 (2H, m), 3.68 (2H, t, J=7.9 Hz), 4.54 (1H, br d, J=13.0 Hz), 6.81 (1H, d, J=9.6 Hz), 7.05 (1H, dd, J=2.4, 8.4 Hz), 7.33 (1H, d, J=2.4 Hz), 7.54 (1H, d, J=8.4 Hz), 7.65 (1H, d, J=1.2 Hz), 7.72 (1H, d, J=9.6 Hz), 7.84 (1H, s)

EXAMPLE 185

1-Acetyl-N-(3,4-dichlorophenyl)-N-{3-[4-(5-imidazo[1,2-a]pyridylthio)-1-piperidinyl]propyl}-4-piperidinecarboxamide By a similar manner to Example 179, the titled compound was synthesized by using the compound obtained in Reference Example 59-2. Yield 50%.
¹H NMR (CDCl₃) δ 1.5-2.1 (12H, m), 2.05 (3H, s), 2.2-2.5 (2H, m), 2.30 (2H, t, J=7.3 Hz), 2.7-3.0 (3H, m), 3.20 (1H, m), 3.65 (2H, t, J=7.5 Hz), 3.78 (1H, br d, J=13.4 Hz), 4.53 (1H, br d, J=13.4 Hz), 7.00 (1H, dd, J=1.2, 7.0 Hz), 7.03 (1H, dd, J=2.3, 8.5 Hz), 7.14 (1H, dd, J=7.0, 9.0 Hz), 7.31 (1H, d, J=2.3 Hz), 7.53 (1H, d, J=8.5 Hz), 7.61 (1H, d, J=9.0 Hz), 7.68 (1H, d, J=1.0 Hz), 7.95 (1H, s)

EXAMPLE 186

1-Acetyl-N-{3-[4-(2-benzoimidazolylthio)-1-piperidinyl]propyl}-N-(3,4-dichlorophenyl)-4-piperidinecarboxamide By a similar manner to Example 179, the titled compound was synthesized by using the compound obtained in Reference Example 60-2. Yield 32%.
¹H NMR (CDCl₃) δ 1.5-2.5 (14H, m), 2.06 (3H, s), 2.32 (2H, t, J=7.3 Hz), 2.77 (2H, m), 2.87 (1H, m), 3.6-3.95 (2H, m), 3.66 (2H, t, J=7.5 Hz), 4.54 (1H, br d, J=13.6 Hz), 4.65 (1H, br d, J=7.8 Hz), 7.02 (1H, dd, J=2.6, 8.4 Hz), 7.15-7.8 (4H, m), 7.31 (1H, d, J=2.6 Hz), 7.51 (1H, d, J=8.4 Hz), 9.68 (1H, br s, NH)

EXAMPLE 187

1-Acetyl-N-(3,4-dichlorophenyl)-N-{3-[4-(4-fluorophenylthio)-1-piperidinyl]propyl}-4-piperidinecarboxamide By a similar manner to Example 179, the titled compound was synthesized by using the compound obtained in Reference Example 61-2. Yield 74%.
¹H NMR (CDCl₃) δ 1.45-2.1 (12H, m), 2.05 (3H, s), 2.2-2.5 (2H, m), 2.29 (2H, t, J=7.1 Hz), 2.7-3.05 (4H, m), 3.65 (2H, t, J=7.7 Hz), 3.78 (1H, br d, J=13.2 Hz), 4.52 (1H, br d, J=13.2 Hz), 6.99 (2H, m), 7.04 (1H, dd, J=2.4, 8.4 Hz), 7.32 (1H, d, J=2.4 Hz), 7.40 (2H, m), 7.53 (1H, d, J=8.4 Hz)

EXAMPLE 188

1-Acetyl-N-(3,4-dichlorophenyl)-N-{3-[4-(4-fluorophenylsulfinyl)-1-piperidinyl]propyl}-4-piperidinecarboxamide By a similar manner to Example 179, the titled compound was synthesized by using the compound obtained in Reference Example 62-2. Yield 70%.
¹H NMR (CDCl₃) δ 1.4-2.1 (12H, m), 2.05 (3H, s), 2.2-2.65 (3H, m), 2.28 (2H, t, J=7.2 Hz), 2.75-3.0 (3H, m), 3.63 (2H, m), 3.78 (1H, br d, J=13.1 Hz), 4.53 (1H, br d, J=13.1 Hz), 7.02 (1H, dd, J=2.4, 8.6 Hz), 7.22 (2H, m), 7.29 (1H, d, J=2.4 Hz), 7.52 (1H, d, J=8.6 Hz), 7.60 (2H, m)

EXAMPLE 189

1-Acetyl-N-(3,4-dichlorophenyl)-N-{3-[4-(4-fluorophenylsulfonyl)-1-piperidinyl]propyl}-4-piperidinecarboxamide By a similar manner to Example 179, the titled compound was synthesized by using the compound obtained in Reference Example 63-2. Yield 49%.
¹H NMR (CDCl₃) δ 1.5-2.1 (12H, m), 2.05 (3H, s), 2.2-2.5 (2H, m), 2.28 (2H, t, J=7.2 Hz), 2.75-3.0 (4H, m), 3.62 (2H, t, J=7.5 Hz), 3.78 (1H, br d, J=13.2 Hz), 4.52 (1H, br d, J=13.2 Hz), 7.02 (1H, dd, J=2.2, 8.4 Hz), 7.25 (2H, m), 7.29 (1H, d, J=2.2 Hz), 7.53 (1H, d, J=8.4 Hz), 7.87 (2H, m)

EXAMPLE 190

N-(3,4 Dichlorophenyl)-N-{3-[4-(4-fluorophenylsulfonyl)-1-piperidinyl]propyl}-1-(methylsulfonyl)-4-piperidinecarboxamide A mixture of the compound obtained in Reference Example 57 (513 mg, 1.2 mmol) and the compound obtained in Reference Example 63-2 (280 mg, 1.0 mmol), potassium iodide (199 mg, 1.2 mmol), potassium carbonate (498 mg, 3.6 mmol) and acetonitrile (12 mL) was stirred at 80° C. for 20 hours. The reaction mixture was concentrated under reduced pressure, and to the concentrate was added ethyl acetate (40 mL). The organic layer was washed with water (10 mL, 5 mL×2), saturated sodium chloride solution (5 mL), successively, dried over magnesium sulfate and concentrated under reduced pressure. The concentrate was subjected to column chromatography (silica gel 10 g, ethyl acetate), and the desired fraction was concentrated under reduced pressure. To the concentrate were added ethyl acetate (3 mL) and diethyl ether (3 mL), and the resulting precipitates were collected by filtration. The precipitates were washed with ethyl acetate/diethyl ether (1/2), and dried under reduced pressure to give the titled compound (356 mg, 0.56 mmol, Yield 56%) as white crystals.

$^1$H NMR (CDCl$_3$) δ 1.5-2.05 (12H, m), 2.1-2.35 (1H, m), 2.28 (2H, t, J=7.3 Hz), 2.55 (2H, m), 2.7-3.0 (3H, m), 2.74 (3H, s), 3.62 (2H, t, J=7.7 Hz). 3.73 (2H, m), 7.01 (1H, dd, J=2.6, 8.4 Hz), 7.25 (2H, m), 7.28 (1H, d, J=2.6 Hz), 7.52 (1H, d, J=8.4 Hz), 7.87 (2H, m)

EXAMPLE 191

1-Acetyl-N-(3,4-dichlorophenyl)-N-{3-[4-(2-Naphthylthio)-1-piperidinyl]propyl}-4-piperidinecarboxamide By a similar manner to Example 179, the titled compound was synthesized by using the compound obtained in Reference Example 64-2. Yield 62%.

$^1$H NMR (CDCl$_3$) δ 1.45-2.1 (12H, m), 2.04 (3H, s), 2.2-2.5 (2H, m), 2.29 (2H, t, J=7.3 Hz), 2.7-2.95 (3H, m), 3.17 (1H, m), 3.64 (2H, t, J=7.7 Hz), 3.76 (1H, br d, J=13.4 Hz), 4.52 (1H, br d, J=13.4 Hz), 7.02 (1H, dd, J=2.3, 8.4 Hz), 7.31 (1H, d, J=2.3 Hz), 7.35-7.6 (4H, m), 7.7-7.9 (4H, m)

EXAMPLE 192

1-Acetyl-N-(3,4-dichlorophenyl)-N-{3-[4-(4-fluorophenylsulfonyl)-1-piperazinyl]propyl}-4-piperidinecarboxamide By a similar manner to Example 179, the titled compound was synthesized by using the compound obtained in Reference Example 65-2. Yield 61%.

$^1$H NMR (CDCl$_3$) δ 1.45-1.9 (6H, m), 2.05 (3H, s), 2.2-2.55 (2H, m), 2.32 (2H, t, J=7.0 Hz), 2.47 (4H, t, J=4.9 Hz), 2.85 (1H, m), 3.00 (4H, m), 3.61 (2H, t, J=7.7 Hz), 3.77 (1H, br d, J=13.0 Hz), 4.52 (1H, br d, J=13.0 Hz), 6.98 (1H, dd, J=2.5, 8.5 Hz), 7.22 (2H, m), 7.26 (1H, d, J=2.5 Hz), 7.51 (1H, d, J=8.5 Hz), 7.76 (2H, m)

EXAMPLE 193

1-Acetyl-N-[3-(4-tert-butoxycarbonylamino-1-piperidinyl)propyl]-N-(3,4-dichlorophenyl)-4-piperidinecarboxamide By a similar manner to Example 179, the titled compound was synthesized by using 4-tert-butoxycarbonylaminopiperidine. Yield 77%.

$^1$H NMR (CDCl$_3$) δ 1.2-2.1 (12H, m), 1.44 (9H, s), 2.06 (3H, s), 2.2-2.45 (2H, m), 2.29 (2H, t, J=7.3 Hz), 2.76 (2H, br d, J=12.4 Hz), 2.87 (1H, m), 3.3-3.55 (1H, m), 3.65 (2H, t, J=7.5 Hz), 3.78 (1H, br d, J=14.0 Hz), 4.40 (1H, br d, J=6.6 Hz, NH), 4.53 (1H, br d, J=14.0 Hz), 7.03 (1H, dd, J=2.4, 8.4 Hz), 7.31 (1H, d, J=2.4 Hz), 7.53 (1H, d, J=8.4 Hz)

EXAMPLE 194

1-Acetyl-N-[3-(4-amino-1-piperidinyl)propyl]-N-(3,4-dichlorophenyl)-4-piperidinecarboxamide 2 hydrochloride The compound obtained in Example 193 (4.08 g, 7.34 mmol) was dissolved in methanol (20 mL). To the solution was added a solution of 4N-hydrogen chloride in ethyl acetate (40 mL), and the mixture was stirred at room temperature for 2 hours. The reaction mixture was concentrated under reduced pressure, and to the concentrate was added diethyl ether. The resulting precipitates were collected by filtration, washed with diethyl ether, and dried under reduced pressure to give the titled compound (4.07 g) as white amorphous substance.

$^1$H NMR (CD$_3$OD) δ 1.4-2.65 (12H, m), 2.09 (3H, s), 2.85-3.35 (5H, m), 3.4-4.0 (6H, m), 4.43 (1H, br d, J=12.6 Hz), 7.42 (1H, br d, J=8.6 Hz), 7.70 (1H, d, J=8.6 Hz), 7.74 (1H, br s)

EXAMPLE 195

1-Acetyl-N-(3,4-dichlorophenyl)-N-{3-[4-(4-fluorophenylsulfonylamino)-1-piperidinyl]propyl}-4-piperidinecarboxamide To the mixture of the compound obtained in Example 194 (528 mg, 1.00 mmol), triethylamine (0.502 mL, 3.60 mmol), THF (10 mL) and dichloromethane (10 mL) was added 4-fluorobenzenesulfonyl chloride (234 mg, 1.20 mmol), and the mixture was stirred at room temperature for 16 hours. To the mixture was added a saturated aqueous solution of sodium hydrogen carbonate (15 ml), and the organic solvent was distilled off under reduced pressure. The aqueous layer was extracted with ethyl acetate (15 mL×3). The organic layer was washed with a saturated aqueous solution of sodium hydrogen carbonate (5 mL×3), saturated sodium chloride solution (5 mL), successively, dried over magnesium sulfate and concentrated under reduced pressure. The concentrate was subjected to column chromatography (silica gel log, ethyl acetate/methanol=1/0 to 9/1), and the desired fraction was concentrated under reduced pressure. To the concentrate was added ethyl acetate and resulting precipitates were filtered off. The filtrate was concentrated under reduced pressure to give the titled compound (516 mg, 0.84 mmol, Yield 84%) as colorless foam like substance.

$^1$H NMR (CDCl$_3$) δ 1.3-2.45 (14H, m), 2.05 (3H, s), 2.26 (2H, t, J=7.3 Hz), 2.68 (2H, m), 2.86 (1H, m), 3.15 (1H, m), 3.63 (2H, t, J=7.5 Hz), 3.77 (1H, br d, J=13.4 Hz), 4.53 (1H, br d, J=13.4 Hz), 4.65 (1H, br d, J=7.8 Hz), 7.01 (1H, dd, J=2.6, 8.5 Hz), 7.19 (2H, m), 7.29 (1H, d, J=2.6 Hz), 7.52 (1H, d, J=8.5 Hz), 7.89 (2H, m)

EXAMPLE 196

1-Acetyl-N-(3,4-dichlorophenyl)-N-{3-[4-(methylamino)-1-piperidinyl]propyl}-4-piperidinecarboxamide To a solution of the compound obtained in Example 208, (454 mg, 1.00 mmol) in 1,2-dicholoroethane (10 mL) were added a solution of 2.0M-methylamine in THF (2.0 mL, 4.0 mmol), acetic acid (0.057 mL, 1.0 mmol), sodium triacetoxyborohydridesodium triacetoxyborohydride (424 mg, 2.00 mmol), successively, and, the mixture was stirred at room temperature for 1.5 hours. To the mixture was added aqueous solution of 1N-sodium hydroxide (15 mL), and the mixture was stirred at room temperature for 30 minutes and extracted with dichloromethane (15 mL, 10 mL×2). The organic layer was dried over anhydrous sodium sulfate and concentrated under reduced pressure to give the titled compound. (466 mg, 0.99 mmol, Yield 99%) as a colorless oily substance.

$^1$H NMR (CDCl$_3$) δ 1.15-2.15 (12H, m), 2.06 (3H, s), 2.2-2.5 (3H, m), 2.30 (2H, t, J=7.3 Hz), 2.42 (3H, s), 2.7-3.0 (3H, m), 3.66 (2H, t, J=7.7 Hz), 3.78 (1H, br d, J=12.8 Hz), 4.53 (1H, br d, J=12.8 Hz), 7.06 (1H, dd, J=2.4, 8.4 Hz), 7.33 (1H, d, J=2.4 Hz), 7.53 (1H, d, J=8.4 Hz)

EXAMPLE 197

1-Acetyl-N-(3,4-dichlorophenyl)-N-{3-[4-(N-4-fluorophenylsulfonyl-N-methylamino)-1-piperidinyl]propyl}-4-piperidinecarboxamide By a similar manner to Example 195, the titled compound was synthesized by using the compound obtained in Example 196.

Yield 90%. $^1$H NMR (CDCl$_3$) δ 1.3-2.1 (12H, m), 2.05 (3H, s), 2.2-2.5 (2H, m), 2.27 (2H, t, J=7.3 Hz), 2.74 (3H, s), 2.75-2.95 (3H, m), 3.55-3.85 (2H, m), 3.63 (2H, t, J=7.7 Hz), 4.53 (1H, br d, J=12.8 Hz), 7.01 (1H, dd, J=2.2, 8.4 Hz), 7.18 (2H, m), 7.29 (1H, d, J=2.2 Hz), 7.52 (1H, d, J=8.4 Hz), 7.81 (2H, m)

EXAMPLE 198

N-[3-(4-tert-Butoxycarbonylamino-1-piperidinyl) propyl]-N-(3,4-dichlorophenyl)-1-(methylsulfonyl)-4-piperidinecarboxamide By a similar manner to Example 190, the titled compound was synthesized by using 4-tert-butoxycarbonylaminopiperidine.

Yield 78%. $^1$H NMR (CDCl$_3$) δ 1.2-2.1 (12H, m), 1.44 (9H, s), 2.1-2.35 (1H, m), 2.29 (2H, t, J=7.3 Hz), 2.45-2.85 (4H, m), 2.74 (3H, s), 3.3-3.55 (1H, m), 3.6-3.8 (4H, m), 4.25-4.5 (1H, br), 7.02 (1H, dd, J=2.4, 8.4 Hz), 7.31 (1H, d, J=2.4 Hz); 7.52 (1H, d, J=8.4 Hz)

EXAMPLE 199

N-[3-(4-amino-1-piperidinyl)propyl]-N-(3,4-dichlorophenyl) -1-(methylsulfonyl)-4-piperidinecarboxamide 2 hydrochloride By a similar manner to Example 194, the titled compound was synthesized by using the compound obtained in Example 198.

Yield 95%. $^1$H NMR (CD$_3$OD) δ 1.6-2.65 (13H, m), 2.73 (3H, s), 3.0-3.3 (4H, m), 3.4-3.85 (5H, m), 3.80(2H, t, J=6.8 Hz), 7.41 (1H, dd, J=2.3, 8.5 Hz), 7.70 (1H, d, J=8.5 Hz), 7.73 (1H, d, J=2.3 Hz)

EXAMPLE 200

N-(3,4-Dichlorophenyl)-N-{3-[4-(4-fluorophenylsulfonylamino)-1-piperidinyl]propyl}-1-(methylsulfonyl)-4-piperidinecarboxamide By a similar manner to Example 195, the titled compound was synthesized by using the compound obtained in Example 199.

Yield 94%. $^1$H NMR (CDCl$_3$) δ 1.25-2.05 (12H, m), 2.1-2.35 (1H, m), 2.25 (2H, t, J=7.4 Hz), 2.45-2.8 (4H, m), 2.74 (3H, s), 3.14 (1H, m), 3.63 (2H, t, J=7.7 Hz), 3.73 (2H, m), 4.62 (1H, br d, J=8.0 Hz), 7.01 (1H, dd, J=2.4, 8.5 Hz), 7.19 (2H, m), 7.29 (1H, d, J=2.4 Hz), 7.52 (1H, d, J=8.5 Hz), 7.89 (2H, m)

EXAMPLE 201

1-Acetyl-N-[3-(4-benzyl-1-piperidinyl)propyl]-N-[4-chloro-3-(trifluoromethyl)phenyl]-4-piperidinecarboxamide By a similar manner to Example 16, the titled compound was synthesized by using the compound obtained in Reference Example 66.

$^1$H NMR (CDCl$_3$) δ 1.05-1.95 (13H, m), 2.05 (3H, s), 2.15-2.55 (2H, m), 2.28 (2H, t, J=7.3 Hz), 2.51 (2H, d, J=6.2 Hz), 2.7-2.95 (1H, m), 2.81 (2H, br d, J=11.4 Hz), 3.69 (2H, t, J=7.5 Hz), 3.78 (1H, br d, J=13.6 Hz), 4.53 (1H, br d, J=13.6 z), 7.05-7.35 (6H, m), 7.50 (1H, d, J=2.2 Hz), 7.59 (1H, d, J=8.6 Hz)

EXAMPLE 202

1-Acetyl-N-[3-chloro-4-methoxyphenyl]-N-(3-[4-(4-fluorobenzyl)-1-piperidinyl]propyl}-4-piperidinecarboxamide By a similar manner to Example 16, the titled compound was synthesized by using the compound obtained in Reference Example 67. Yield 87%.

$^1$H NMR (CDCl$_3$) δ 1.1-1.95 (13H, m), 2.04 (3H, s), 2.2-2.55 (2H, m), 2.29 (2H, t, J=7.5 Hz), 2.48 (2H, d, J=6.6 Hz), 2.75-2.95 (3H, m), 3.63 (2H, t, J=7.5 Hz), 3.76 (1H, br d, J=13.4 Hz), 3.95 (3H, s), 4.52 (1H, br d, J=13.4 Hz), 6.85-7.15 (6H, m), 7.21 (1H, d, J=2.6 Hz)

EXAMPLE 203

1-Acetyl-N-[3-chloro-4-ethoxyphenyl]-N-{3-[4-(4-fluorobenzyl)-1-piperidinyl]propyl}-4-piperidinecarboxamide By a similar manner to Example 16, the titled compound was synthesized by using the compound obtained in Reference Example 68. Yield 93%.

$^1$H NMR (CDCl$_3$) δ 1.1-1.95 (13H, m), 1.51 (3H, t, J=7.0 Hz), 2.04 (3H, s), 2.2-2.55 (2H, m), 2.28(2H, t, J=7.5 Hz), 2.48 (2H, d, J=6.6 Hz), 2.7-2.95 (3H, m), 3.63 (2H, t, J=7.5 Hz), 3.76 (1H, br d, J=13.2 Hz), 4.15 (2H, q, J=7.0 Hz), 4.52 (1H, br d, J=13.2 Hz), 6.85-7.15 (6H, m), 7.21 (1H, d, J=2.2 Hz)

EXAMPLE 204

1-Acetyl-N-[3-bromo-4-(trifluoromethoxy)phenyl]-N-{3-[4-(4-fluorobenzyl)-1-piperidinyl]propyl}-4-piperidinecarboxamide By a similar manner to Example 16, the titled compound was synthesized by using the compound obtained in Reference Example 69. Yield 92%.

$^1$H NMR (CDCl$_3$) δ 1.1-1.95 (13H, m), 2.06 (3H, s), 2.2-2.55 (2H, m), 2.28 (2H, t, J=7.5 Hz), 2.48 (2H, d, J=6.6 Hz), 2.75-3.0 (1H, m), 2.83 (2H, br d, J=11.8 Hz), 3.67 (2H, t, J=7.6 Hz), 3.79 (1H, br d, J=13.6 Hz), 4.53 (1H, br d, J=13.6 Hz), 6.94 (2H, m), 7.07 (2H, m), 7.17 (1H, dd, J=2.3, 8.6 Hz), 7.39 (1H, m), 7.52 (1H, d, J=2.3 Hz)

EXAMPLE 205

1-Acetyl-N-(3,4-dichlorophenyl)-N-{2-[4-(4-fluorobenzyl)-1-piperidinyl]ethyl}-4-piperidinecarboxamide To a solution of the compound obtained in Reference Example 70-3 (454 mg, 1.00 mmol) and triethylamine (0.836 mL) in dichloromethane (10 mL) was added 1-acetyl-4-piperidinecarbonyl chloride (569 mg, 3.00 mmol) under ice cooling with stirring, and the mixture was stirred at the same temperature for 1 hour. To the mixture was added a saturated aqueous solution of sodium hydrogen carbonate (15 ml), and the organic solvent was removed under reduced pressure.

To the residue was added ethyl acetate (40 mL). The organic layer was washed with water (15 mL), a saturated aqueous solution of sodium hydrogen carbonate (5 mL×3), saturated sodium chloride solution (5 mL), successively, dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure to give. To the residue was added ethyl acetate and resulting precipitates were filtered off. The filtrate was concentrated under reduced pressure to give the titled compound (527 mg, 0.99 mmol, Yield 99%) as a colorless oily substance.

$^1$H NMR (CDCl$_3$) δ 1.05-2.0 (11H, m), 2.06 (3H, s), 2.25-2.55 (2H, m), 2.40 (2H, t, J=6.4 Hz), 2.49 (2H, d, J=7.0 Hz), 2.7-3.0 (3H, m), 3.6-3.9 (3H, m), 4.53 (1H, br d, J=13.2 Hz), 6.95 (2H, m), 7.08 (2H, m), 7.10 (1H, dd, J=2.9, 8.5 Hz), 7.50 (1H, d, J=8.5 Hz), 7.51 (1H, d, J=2.9 Hz)

EXAMPLE 206

1-Acetyl-N-(3,4-dichlorophenyl)-N-{4-[4-(4-fluorobenzyl)-1-piperidinyl]butyl}-4-piperidinecarboxamide A mixture of the compound obtained in Reference Example 71-2 (487 mg, 1.20 mmol), 4-(4-fluorobenzyl)piperidine hydrochloride (276 mg, 1.20 mmol), potassium iodide (199 mg, 1.20 mmol), potassium carbonate (498 mg, 3.60 mmol) and acetonitrile (24 mL) was stirred at 80° C. for 20 hours. The reaction mixture was concentrated under reduced pressure, and to the concentrate was added water (15 mL.). The mixture was extracted with ethyl acetate (15 mL×3). The organic layer was dried over anhydrous sodium sulfate and concentrated under reduced pressure. The concentrate was subjected to column chromatography (silica gel 10 g, ethyl acetate/methanol=1/0 to 9/1), and the desired fraction was concentrated under reduced pressure. To the concentrate was added ethyl acetate and resulting precipitates were filtered off. The filtrate was concentrated under reduced pressure to give the titled compound (391 mg, 0.70 mmol, Yield 58%).

$^1$H NMR (CDCl$_3$) δ 1.1-1.9 (15H, m), 2.06 (3H, s), 2.2-2.55 (4H, m), 2.49 (2H, d, J=6.6 Hz), 2.75-3.0 (1H, m), 2.85 (2H, br d, J=11.6 Hz), 3.64 (2H, m), 3.78 (1H, br d, J=13.7 Hz), 4.53 (1H, br d, J=13.7 Hz), 6.95 (2H, m), 7.03 (1H, dd, J=2.6, 8.5 Hz), 7.08 (2H, m), 7.30 (1H, d, J=2.6 Hz), 7.53 (1H, d, J=8.5 Hz)

EXAMPLE 207

1-Acetyl-N-(3,4-dichlorophenyl)-N-(3-{4-[4-(1H-tetrazol-1-yl)anilino]-1-piperidinyl]propyl}-4-piperidinecarboxamide A mixture of the compound obtained in Reference Example 56-3 (470 mg, 1.2 mmol), the compound obtained in Reference Example 72-2 (495 mg, 1.56 mmol), potassium iodide (259 mg, 1.56 mmol), potassium carbonate (663 mg, 4.8 mmol) and acetonitrile (24 mL) was stirred at 80° C. for 16 hours. The reaction mixture was concentrated under reduced pressure, and to the concentrate was added water (50 mL). The mixture was extracted with ethyl acetate (50 mL). The organic layer was washed with saturated aqueous solution of sodium chloride (50 ml), dried over anhydrous sodiumsulfate and concentrated under reduced pressure. The concentrate was subjected to flash column chromatography (silica gel 20 g, ethyl acetate/methanol=1/0 to 5/1), and the desired fraction was concentrated under reduced pressure to give the titled compound (279 mg, 0.47 mmol, Yield 39%) as pale yellow amorphous substance.

$^1$H NMR (CDCl$_3$) δ 1.40-1.75 (8H, m), 2.01-2.18 (4H, m), 2.06 (3H, s), 2.33-2.40 (4H, m), 2.82-2.88 (3H, m), 3.20-3.40 (1H, m), 3.65-3.94 (4H, m), 4.50-4.57 (1H, m), 6.67 (2H, d, J=9.2 Hz), 7.05 (1H, dd, J=8.4, 2.2 Hz), 7.33 (1H, d, J=2.2 Hz), 7.42 (2H, d, J=9.2 Hz), 7.54 (1H, d, J=8.4 Hz), 8.83 (1H, s)

EXAMPLE 208

1-Acetyl-N-(3,4-dichlorophenyl)-N-[3-(4-oxo-1-piperidinyl)propyl]-4-piperidinecarboxamide By a similar manner to Example 207, the titled compound was synthesized by using 4-piperidone monohydrate hydrochloride.

Yield 54%. $^1$H NMR (CDCl$_3$) δ 1.62-1.82 (6H, m), 2.06 (3H, s), 2.30-2.49 (8H, m), 2.71 (4H, q, J=5.8 Hz), 2.81-2.94

(1H, m), 3.69-3.82 (3H, m), 4.51-4.57 (1H, m), 7.06 (1H, dd, J=8.4, 2.6 Hz), 7.33 (1H, d, J=2.6 Hz), 7.55 (1H, d, J=8.4 Hz)

EXAMPLE 209

1-Acetyl-N-(3,4-dichlorophenyl)-N-{3-[4-(4-fluoroanilino)-1-piperidinyl]propyl}-4-piperidinecarboxamide To a solution of the compound obtained in Example 208 (1000 mg, 2.2 mmol) and 4-fluoroaniline (269 mg, 2.4 mmol) in THF (3 mL) were added acetic acid (0.126 mL, 2.2 mmol) and sodium triacetoxyborohydride (699 mg, 3.3 mmol) under ice cooling, and the mixture was stirred at room temperature for 20 hours. To the reaction mixture was added saturated aqueous solution of sodium hydrogen carbonate (100 mL). The mixture was stirred at room temperature for 2 hours and extracted with ethyl acetate (100 mL×2). The organic layer was washed with saturated sodium chloride solution (100 mL), dried over anhydrous sodium sulfate and concentrated under reduced pressure. The concentrate was subjected to flash column chromatography (silica gel 20 g, ethyl acetate/methanol=1/0 to 9/1 to 4/1), and the desired fraction was concentrated under reduced pressure to give the titled compound (695 mg, 1.3 mmol, Yield 58%) as a pale purple amorphous substance.

$^1$H NMR (CDCl$_3$) δ 1.30-1.50 (2H, m), 1.50-1.87 (6H, m), 2.00-2.13 (4H, m), 2.06 (3H, s), 2.30-2.37 (4H, m), 2.78-2.93 (3H, m), 3.10-3.30 (1H, m), 3.63-3.81 (4H, m), 4.50-4.57 (1H, m), 6.52 (2H, dd, J=8.8, 4.4 Hz), 6.87 (2H, t, J=8.8 Hz), 7.09 (1H, dd, J=8.4, 2.2 Hz), 7.32 (1H, d, J=2.2 Hz), 7.53 (1H, d, J=8.4 Hz)

EXAMPLE 210

Methyl 4-{[1-(3-{[(1-acetyl-4-piperidinyl)carbonyl]-3,4-dichloroanilino}propyl)-4-piperidinyl]amino}benzoate By a similar manner to Example 209, the titled compound was synthesized by using methyl 4-aminobenzoate. Yield 36%.

$^1$H NMR (CDCl$_3$) δ 1.38-1.90 (8H, m), 2.01-2.15 (4H, m), 2.06 (3H, s), 2.30-2.42 (4H, m), 2.79-2.93 (3H, m), 3.20-3.40 (1H, m), 3.58-3.74 (3H, m), 3.84 (3H, s), 3.98-4.02 (1H, m), 4.51-4.57 (1H, m), 6.52 (2H, d, J=8.8 Hz), 7.04 (1H, dd, J=8.4, 2.6 Hz), 7.33 (1H, d, J=2.6 Hz), 7.53 (1H, d, J=8.4 Hz), 7.84 (2H, d, J=8.8 Hz)

EXAMPLE 211

1-Acetyl-N-{3-[4-(4-cyanoanilino)-1-piperidinyl]propyl}) N-(3,4-dichlorophenyl)-4-piperidinecarboxamide A mixture of the compound obtained in Reference Example 56-3 (391 mg, 1 mmol), the compound obtained in Reference Example 73-2 (356 mg, 1.3 mmol), potassium iodide (166 mg, 1 mmol), potassium carbonate (691 mg, 5 mmol) and acetonitrile (6 mL) was stirred at 80° C. for 7 hours. The reaction mixture was concentrated under reduced pressure, and to the concentrate was added water (5 mL). The mixture was extracted with dichloromethane (5 mL). The organic layer was concentrated under reduced pressure. The concentrate was subjected to flash column chromatography (silica gel 20 g, ethyl acetate/methanol=1/0 to 5/1), and the desired fraction was concentrated under reduced pressure to give the titled compound (428 mg, 0.77 mmol, Yield 77%) as pale yellow amorphous substance.

$^1$H NMR (CDCl$_3$) δ 1.38-2.16 (12H, m), 2.06, (3H, s), 2.32-2.39 (4H, m), 2.80-2.93 (3H, m), 3.30-3.34 (1H, m), 3.64-3.82 (3H, m), 4.07-4.14 (1H, m), 4.50-4.56 (1H, m), 6.53 (2H, d, J=8.6 Hz), 7.05 (1H, dd, J=8.4, 2.6 Hz), 7.33 (1H, d, J=2.6 Hz), 7.40 (2H, d, J=8.16 Hz), 7.54 (1H, d, J=8.4 Hz)

EXAMPLE 212

1-Acetyl-N-{3-[4-(1,4,7b-triazacyclopenta[cd]inden-2-ylsulfanyl)-1-piperidinyl]propyl}-N-(3,4-dichlorophenyl)-4-piperidinecarboxamide By a similar manner to Example 211, the titled compound was synthesized by using the compound obtained in Reference Example 74-2. Yield 52%.

$^1$H NMR (CDCl$_3$) δ 1.50-2.06 (9H, m), 2.06 (3H, s), 2.20-2.42 (7H, m), 2.82-2.93 (3H, m), 3.66-3.82 (3H, m), 4.07-4.18 (1H, m), 4.51-4.57 (1H, m), 7.06 (1H, dd, J=8.4, 2.2 Hz), 7.34 (1H, d, J=2.2 Hz), 7.54 (1H, d, J=8.4 Hz), 7.76 (1H, d, J=7.6 Hz), 7.92 (1H, d, J=7.6 Hz), 8.03 (1H, t, J=7.6 Hz), 8.47 (1H, s)

EXAMPLE 213

1-Acetyl-N-(3,4-dichlorophenyl)-N-(3-{4-[4-(2,2,3,3,3-pentafluoropropoxy)anilino]-1-piperidinyl}propyl)-4-piperidinecarboxamide By a similar manner to Example 211, the titled compound was synthesized by using the compound obtained in Reference Example 75-2. Yield 72%.

$^1$H NMR (CDCl$_3$) δ 1.30-1.80 (8H, m), 2.00-2.14 (5H, m), 2.06 (3H, s), 2.31-2.38 (4H, m), 2.79-2.93 (3H, m), 3.16-3.21 (1H, m), 3.63-3.81 (3H, m), 4.33 (2H, t, J=12.4 Hz), 4.50-4.57 (1H, m), 6.54 (2H, d, J=8.8 Hz), 6.81 (2H, d, J=8.8 Hz), 7.05 (1H, dd, J=8.4, 2.4 Hz), 7.33 (1H, d, J=2.4 Hz), 7.53 (1H, d, J=8.4 Hz)

EXAMPLE 214

1-Acetyl-N-(3-{4-[acetyl-4-(2,2,3,3,3-pentafluoropropoxy)anilino]-1-piperidinyl}propyl)-N-(3,4-dichlorophenyl)-4-piperidinecarboxamide By a similar manner to Example 211, the titled compound was synthesized by using the compound obtained in Reference Example 76-2. Yield 50%.

$^1$H NMR (CDCl$_3$) δ 1.23-1.39 (2H, m), 1.57-1.80 (8H, m), 1.74 (3H, s), 1.97-2.08 (2H, m), 2.05 (3H, s), 2.22-2.40 (4H, m), 2.81-2.96 (3H, m), 3.56-3.63 (2H, m), 3.74-3.80 (1H, m), 4.44 (2H, t, J=12.0 Hz), 4.38-4.66 (2H, m), 6.93-7.06 (5H, m), 7.27 (1H, d, J=2.2 Hz), 7.49 (1H, d, J=8.4 Hz)

EXAMPLE 215

N-{3-[4-(4-Cyanoanilino)-1-piperidinyl]propyl}-N-(3,4-dichlorophenyl)-1-(methylsulfonyl)-4-piperidinecarboxamide A mixture of the compound obtained in Reference Example 57 (428 mg, 1 mmol), the compound obtained in Reference Example 73-2 (356 mg, 1.3 mmol), potassium iodide,(166 mg, 1 mmol), potassium carbonate (691 mg, 5 mmol) and acetonitrile (6 mL) was stirred at 80° C. for 7 hours. The reaction mixture was concentrated under reduced pressure, and to the concentrate was added water (5 mL). The mixture was extracted with dichloromethane (5 mL). The organic layer was concentrated under reduced pressure. The concentrate was subjected to flash column chromatography (silica gel 20 g, ethyl acetate/methanol=1/0 to 5/1), and the desired fraction was concentrated under reduced pressure to give the titled compound (430 mg, 0.73 mmol, Yield 73%) as pale yellow amorphous substance.

$^1$H NMR (CDCl$_3$) δ 1.40-2.41 (16H, m), 2.53-2.64 (2H, m), 2.76 (3H, s), 2.82-2.88 (2H, m), 3.32-3.36 (1H, m), 3.66-3.78 (3H, m), 4.09-4.12 (1H, m), 6.55 (2H, d, J=8.8 Hz), 7.06 (1H, dd, J=8.8, 2.2 Hz), 7.34 (1H, d, J=2.2 Hz), 7.42 (2H, d, J=8.8 Hz), 7.55 (1H, d, J=8.8 Hz)

EXAMPLE 216

N-{3-[4-(1,4,7b-Triazacyclopenta[cd]inden-2-ylsulfanyl)-1-piperidinyl]propyl}-N-(3,4-dichlorophenyl)-1-(methylsulfonyl)-4-piperidinecarboxamide By a similar manner to Example 215, the titled compound was synthesized by using the compound obtained in Reference Example 74-2. Yield 64%.

$^1$H NMR (CDCl$_3$) δ 1.60-2.00 (9H, m), 2.20-2.42 (6H, m), 2.53-2.63 (2H, m), 2.74 (3H, s), 2.82-2.87 (2H, m), 3.66-3.77 (4H, m), 4.07-4.18 (1H, m), 7.05 (1H, dd, J=8.4, 2.2 Hz), 7.35 (1H, d, J=2.2 Hz), 7.54 (1H, d, J=8.4 Hz), 7.76 (1H, d, J=8.0 Hz), 7.93 (1H, d, J=8.0 Hz), 8.03 (1H, t, J=8.0 Hz), 8.47 (1H, s)

EXAMPLE 217

N-(3,4-Dichlorophenyl)-1-(methylsulfonyl)-N-(3-{4-[4-(2,2,3,3,3-pentafluoropropoxy)anilino]-1-piperidinyl}propyl)-4-piperidinecarboxamide By a similar manner to Example 215, the titled compound was synthesized by using the compound obtained in Reference Example 75-2. Yield 66%.

$^1$H NMR (CDCl$_3$) δ 1.32-2.37 (16H, m), 2.51-2.63 (2H, m), 2.74 (3H, s), 2.74-2.84 (2H, m), 3.15-3.26 (1H, m), 3.63-3.76 (4H, m), 4.33 (2H, t, J=12.8 Hz), 6.54 (2H, d, J=8.8 Hz), 6.80 (2H, d, J=8.8 Hz), 7.04 (1H, dd, J=8.4, 2.2 Hz), 7.32 (1H, d, J=2.2 Hz), 7.53 (1H, d, J=8.41 Hz)

EXAMPLE 218

N-(3-{4-[Acetyl-4-(2,2,3,3,3-pentafluoropropoxy)anilino]-1-piperidinyl}propyl)-N-(3,4-dichlorophenyl)-1-(methylsulfonyl)-4-piperidinecarboxamide By a similar manner to Example 215, the titled compound was synthesized by using the compound obtained in Reference Example 76-2. Yield 56%.

$^1$H NMR (CDCl$_3$) δ 1.23-1.39 (2H, m), 1.50-2.08 (10H, m), 1.74 (3H, s), 2.22-2.29 (3H, m), 2.50-2.60 (2H, m), 2.73 (3H, s), 2.80-2.86 (2H, m), 3.56-3.74 (4H, m), 4.44 (2H, t, J=12.2 Hz), 4.44-4.66 (1H, m), 6.93-7.06 (5H, m), 7.27 (1H, d, J=2.2 Hz), 7.49 (1H, d, J=8.4 Hz)

EXAMPLE 219

1-Acetyl-N-(3,4-dichlorophenyl)-N-{3-[4-(4-nitroanilino)-1-piperidinyl]propyl}-4-piperidinecarboxamide By a similar manner to Example 211, the titled compound was synthesized by using the compound obtained in Reference Example 77-2. Yield 74%.

$^1$H NMR (CDCl$_3$) δ 1.49-2.18 (12H, m), 2.06 (3H, s), 2.32-2.40 (4H, m), 2.82-2.88 (3H, m), 3.37-3.46 (1H, m), 3.65-3.82 (3H, m), 4.41-4.58 (2H, m), 6.51 (2H, d, J=9.4 Hz), 7.05 (1H, dd, J=8.4, 2.6 Hz), 7.33 (1H, d, J=2.6 Hz), 7.55 (1H, d, J=8.4 Hz), 8.08 (2H, d, J=9.4 Hz)

EXAMPLE 220

N-(3,4-Dichlorophenyl)-1-(methylsulfonyl)-N-{3-[4-(4-nitroanilino)-1-piperidinyl]propyl}-4-piperidinecarboxamide By a similar manner to Example 215, the titled compound was synthesized by using the compound obtained in Reference Example 77-2. Yield 77%.

$^1$H NMR (CDCl$_3$) δ 1.42-2.39 (16H, m), 2.51-2.62 (2H, m), 2.74 (3H, s), 2.80-2.92 (1H, m), 3.31-3.45 (1H, m), 3.64-3.77 (4H, m), 4.37-4.41 (1H, m), 6.51 (2H, d, J=9.0 Hz), 7.04 (1H, dd, J=8.4, 2.6 Hz), 7.32 (1H, d, J=2.6 Hz), 7.54 (1H, d, J=8.4 Hz), 8.07 (2H, d, J=9.0 Hz)

EXAMPLE 221

1-Acetyl-N-{3-[4-(4-aminoanilino)-1-piperidinyl]propyl}-N-(3,4-dichlorophenyl)-4-piperidinecarboxamide To a solution of the compound obtained in Example 219 (162 mg, 0.26 mmol) in methanol/THF (1/1, 10 mL) were added nickel bromide (II)(5.7 mg) and sodium borohydride (40 mg, 1.1 mmol), and the mixture was stirred at room temperature for 10 minutes. To the reaction mixture were added ethyl acetate (20 mL) and water (20 mL), and the insolubles were filtered off with Celite. The organic layer was washed with saturated aqueous solution of sodium chloride (10 ml), dried with anhydrous sodium sulfate and concentrated under reduced pressure. The concentrate was subjected to flash column chromatography (alumina 2 g, ethyl acetate/methanol=1/0 to 10/1), and the desired fraction was concentrated under reduced pressure to give the titled compound (99 mg, 0.17 mmol, Yield 64%) as pale yellow amorphous substance.

$^1$H NMR (CDCl$_3$) δ 1.26-1.43 (2H, m), 1.60-1.80 (7H, m), 1.99-2.06 (5H, m), 2.06 (3H, s), 2.27-2.36 (5H, m), 2.70-2.90 (3H, m), 3.00-3.20 (1H, m), 3.63-3.80 (3H, m), 4.51-4.57 (1H, m), 6.50 (2H, d, J=8.8 Hz), 6.60 (2H, d, J=8.8 Hz), 7.04 (1H, dd, J=8.4, 2.2 Hz), 7.33 (1H, d, J=2.2 Hz), 7.53 (1H, d, J=8.4 Hz)

EXAMPLE 222

4-{[1-(3-{[(1-Acetyl-4-piperidinyl)carbonyl]-3,4-dichloroanilino}propyl)-4-piperidinyl]amino}benzoic acid To a solution of the compound obtained in Example 210 (51.8 mg, 0.09 mmol) in ethanol (2 mL) was added aqueous solution of 1N-sodium hydroxide (0.53 mL, 0.53 mmol), and the mixture was stirred at 90° C. for 5 hours. To the mixture was added dropwise aqueous solution of 1N-hydrochloric acid (0.53 mL, 0.53 mmol) under ice cooling, and the mixture was concentrated under reduced pressure. The concentrate was subjected to flash column chromatography (silica gel 5 g, ethyl acetate/methanol=1/0 to 1/1), and the desired fraction was concentrated under reduced pressure to give the titled compound (28 mg, 0.05 mmol, Yield 55%) as white amorphous substance.

$^1$H NMR (CDCl$_3$) δ 1.26-1.78 (9H, m), 1.90-2.17 (3H, m), 2.04 (3H, s), 2.17-2.52 (5H, m), 2.78-2.91 (1H, m), 2.91-3.20 (2H, m), 3.30-3.47 (1H, m), 3.60-3.78 (3H, m), 4.20-4.55 (2H, m), 6.51 (2H, d, J=8.0 Hz), 7.60 (1H, dd, J=8.4, 1.8 Hz), 7.32 (1H, d, J=1.8 Hz), 7.41 (1H, d, J=8.4 Hz), 7.83 (2H, d, J=8.0 Hz)

EXAMPLE 223

1-Acetyl-N-(3-{4-[acetyl-4-(1H-tetrazol-1-yl)anilino]-1-piperidinyl}propyl)-N-(3,4-dichlorophenyl)-4-piperidinecarboxamide By a similar manner to Example 211, the titled compound was synthesized by using the compound obtained in Reference Example 78-2. Yield 44%.

$^1$H NMR (CDCl$_3$) δ 1.23-1.42 (2H, m), 1.57-1.90 (9H, m), 1.80 (3H, s), 1.95-2.11 (1H, m), 2.05 (3H, s), 2.23-2.39 (4H, m), 2.80-2.89 (3H, m), 3.49-3.65 (2H, m), 3.73-3.80 (1H, m), 4.46-4.53 (1H, m), 4.60-4.80 (1H, m), 6.98 (1H, dd, J=8.4, 2.6 Hz), 7.26 (1H, d, J=2.6 Hz), 7.34 (2H, d, J=8.8 Hz), 7.49 (1H, d, J=8.4 Hz), 7.81 (2H, d, J=8.8 Hz), 9.07 (1H, s)

EXAMPLE 224

1-Acetyl-N-{3-[4-(1,3-benzothiazol-2-ylsulfanyl)-1-piperidinyl]propyl}-N-(3,4-dichlorophenyl)-4-piperidinecarbxamide By a similar manner to Reference Example 72-2, 2-(4-piperidinylsulfanyl)-1,3-benzothiazole hydrochloride was synthesized by using the compound obtained in Reference Example 39. By a similar manner to Example 211, the titled compound was synthesized by using the obtained 2-(4-piperidinylsulfanyl)-1,3-benzothiazole hydrochloride.

Yield 66%. $^1$H NMR (CDCl$_3$) δ 1.50-1.90 (10H, m), 2.06 (3H, s), 2.17-2.38 (6H, m), 2.76-2.93 (3H, m), 3.64-3.97 (4H, m), 4.50-4.57 (1H, m), 7.45 (1H, dd, J=8.4, 2.2 Hz), 7.27-7.32 (1H, m), 7.33 (1H, d, J=2.2 Hz), 7.37-7.51 (1H, m), 7.53 (1H, d, J=8.4 Hz), 7.73-7.78 (1H, m), 7.85-7.89 (1H, m)

EXAMPLE 225

1-Acetyl-N-(3,4-dichlorophenyl)-N-(3-{4-[(6-ethoxy-1,3-benzothiazol-2-yl)sulfanyl]-1-piperidinyl}propyl)-4-piperidinecarboxamide By a similar manner to Example 211, the titled compound was synthesized by using the compound obtained in Reference Example 79-2. Yield 71%.

$^1$H NMR (CDCl$_3$) δ 1.44 (3H, t, J=7.0 Hz), 1.50-1.90 (9H, m), 2.06 (3H, s), 2.15-2.37 (7H, m), 2.76-2.92 (3H, m), 3.63-3.82 (4H, m), 4.07 (2H, q, J=7.0 Hz), 4.50-4.57 (1H, m), 7.00 (1H, dd, J=8.8, 2.2 Hz), 7.05 (1H, dd, J=8.8, 2.2 Hz), 7.22 (1H, d, J=2.2 Hz), 7.32 (1H, d, J=2.2 Hz), 7.53 (1H, d, J=8.8 Hz), 7.75 (1H, d, J=8.8 Hz)

EXAMPLE 226

1-Acetyl-N-(3-{4-[(5-chloro-1,3-benzothiazol-2-yl)sulfanyl]-1-piperidinyl}propyl)-N-(3,4-dichlorophenyl)-4-piperidinecarboxamide By a similar manner to Example 211, the titled compound was synthesized by using the compound obtained in Reference Example 80-2. Yield 65%.

$^1$H NMR (CDCl$_3$) δ 1.62-1.90 (9H, m), 2.06 (3H, s), 2.17-2.38 (7H, m), 2.76-2.93 (3H, m), 3.64-3.99 (4H, m), 4.50-4.57 (1H, m), 7.04 (1H, dd, J=8.4, 2.2 Hz), 7.27 (1H, dd, J=8.4, 2.2 Hz), 7.33 (1H, d, J=2.2 Hz), 7.53 (1H, d, J=8.4 Hz), 6.65 (1H, d, J=8.4 Hz), 7.84 (1H, d, J=2.2 Hz)

EXAMPLE 227

1-Acetyl-N-(3,4-dichlorophenyl)-N-{3-[4-(1,3-thiazol-2-ylsulfanyl)-1-piperidinyl]propyl}-4-piperidinecarboxamide By a similar manner to Reference Example 72-2, 2-(4-piperidinylsulfanyl)-1,3-thiazole hydrochloride was synthesized by using the compound obtained in Reference Example 36.

By using the obtained 2-(4-piperidinylsulfanyl)-1,3-thiazole hydrochloride, the titled compound was synthesized by a similar manner to Example 211. Yield 82%.

$^1$H NMR (CDCl$_3$) δ 1.61-1.83 (8H, m), 2.06 (3H, s), 2.06-2.17 (4H, m), 2.28-2.35 (4H, m), 2.75-2.93 (3H, m), 3.55-3.81 (4H, m), 4.50-4.56 (1H, m), 7.04 (1H, dd, J=8.4, 2.2 Hz), 7.24 (1H, d, J=3.2 Hz), 7.32 (1H, d, J=2.2 Hz), 7.53 (1H, d, J=8.4 Hz), 7.70 (1H, d, J=3.2 Hz)

EXAMPLE 228

N-(3-{4-[Acetyl-4-(1H-tetrazol-1-yl)anilino]-1-piperidinyl}propyl)-N-(3,4-dichlorophenyl)-1-(methylsulfonyl)-4-piperidinecarboxamide By a similar manner to Example 215, the titled compound was synthesized by using the compound obtained in Reference Example 78-2. Yield 69%.

$^1$H NMR (CDCl$_3$) δ 1.23-1.4 (2H, m), 1.50-2.30 (13H, m), 1.80 (3H, s), 2.48-2.58 (2H, m), 2.72 (3H, s), 2.84-2.89 (2H, m), 3.56-3.73 (4H, m), 4.60-4.80 (1H, m), 7.98 (1H, dd, J=8.4, 2.2 Hz), 7.26 (1H, d, J=2.2 Hz), 7.34 (2H, d, J=8.8 Hz), 7.49 (1H, d, J=8.4 Hz), 7.80 (2H, d, J=8.8 Hz), 9.05 (1H, s)

EXAMPLE 229

N-{3-[4-(1,3-Benzothiazol-2-ylsulfanyl)-1-piperidinyl]propyl}-N-(3,4-dichlorophenyl)-1-(methylsulfonyl)-4-piperidinecarboxamide By a similar manner to Reference Example 72-2, 2-(4-piperidinylsulfanyl)-1,3-benzothiazole hydrochloride was synthesized by using the compound obtained in Reference Example 39.

By using the obtained 2-(4-piperidinylsulfanyl)-1,3-benzothiazole hydrochloride, the titled compound was synthesized by a similar manner to Example 215. Yield 61%.

$^1$H NMR (CDCl$_3$) δ 1.63-2.05 (10H, m), 2.17-2.38 (6H, m), 2.53-2.63 (2H, m), 2.74 (3H, s), 2.74-2.82 (1H, m), 3.64-3.76 (4H, m), 3.80-4.00 (1H, m), 7.04 (1H, dd, J=8.4, 2.2 Hz), 7.29-7.34 (1H, m), 7.32 (1H, d, J=2.2 Hz), 7.37-7.46 (1H, m), 7.53 (1H, d, J=8.4 Hz), 7.73-7.78 (1H, m), 7.85-7.89 (1H, m)

EXAMPLE 230

N-(3,4-Dichlorophenyl)-N-(3-{4-[(6-ethoxy-1,3-benzothiazol-2-yl)sulfanyl]-1-piperidinyl}propyl)-1-(methylsulfonyl)-4-piperidinecarboxamide By a similar manner to Example 215, the titled compound was synthesized by using the compound obtained in Reference Example 79-2. Yield 61%.

$^1$H NMR (CDCl$_3$) δ 1.44 (3H, t, J=7.0 Hz), 1.64-1.98 (10H, m), 2.05-2.37 (6H, m), 2.52-2.64 (2H, m), 2.74 (3H, s), 2.74-2.81 (1H, m), 3.63-3.81 (5H, m), 4.07 (2H, q, J=7.0 Hz), 7.00 (1H, dd, J=8.8, 2.2 Hz), 7.04 (1H, dd, J=8.8, 2.2 Hz), 7.22 (1H, d, J=2.2 Hz), 7.32 (1H, d, J=2.2 Hz), 7.53 (1H, d, J=8.8 Hz), 7.75 (1H, d, J=8.8 Hz)

EXAMPLE 231

N-(3-{4-[(5-Chloro-1,3-benzothiazol-2-yl)sulfanyl]-1-piperidinyl}propyl)-N-(3,4-dichlorophenyl)-1-(methylsulfonyl)-4-piperidinecarboxamide By a similar manner to Example 215, the titled compound was synthesized by using the compound obtained in Reference Example 80-2. Yield 49%.

$^1$H NMR (CDCl$_3$) δ 1.63-2.05 (10H, m), 2.17-2.38 (6H, m), 2.53-2.64 (2H, m), 2.74 (3H, s), 2.74-2.81 (1H, m), 3.58-3.82 (4H, m), 3.82-3.98 (1H, m), 7.04 (1H, dd, J=8.4, 2.2 Hz), 7.27 (1H, dd, J=8.4, 2.2 Hz), 7.32 (1H, d, J=2.2 Hz), 7.53 (1H, d, J=8.4 Hz), 7.65 (1H, d, J=8.4 Hz) 7.84 (1H, d, J=2.2 Hz)

EXAMPLE 232

N-(3,4-Dichlorophenyl)-1-(methylsulfonyl)-N-{3-4-(1,3-thiazol-2-ylsulfanyl)-1-piperidinyl]propyl}-4-piperidinecarboxamide By a similar manner to Reference Example 72-2, 2-(4-piperidinylsulfanyl)-1,3-thiazole hydrochloride was synthesized by using the compound obtained in Reference Example 36.

By a similar manner to Example 215, the titled compound was synthesized by using the obtained 2-(4-piperidinylsulfanyl)-1,3-thiazole hydrochloride. Yield 84%.

$^1$H NMR (CDCl$_3$) δ 1.64-2.35 (16H, m), 2.52-2.63 (2H, m), 2.74 (3H, s), 2.63-2.74 (1H, m), 3.55-3.76 (5H, m), 7.03 (1H, dd, J=8.4, 2.2 Hz), 7.24 (1H, d, J=3.6 Hz), 7.31 (1H, d, J=2.4 Hz), 7.53 (1H, d, J=8.4 Hz), 7.70 (1H, d, J=3.6 Hz)

EXAMPLE 233

Methyl 4-{[1-(3-{[(1-acetyl-4-piperidinyl)carbonyl]-3,4-dichloroanilino}propyl)-4-piperidinyl]methyl}benzoate By a similar manner to Example 211, the titled compound was synthesized by using the compound obtained in Reference Example 81. Yield 83%.

$^1$H NMR (CDCl$_3$) δ 1.24-1.90 (14H, m), 2.05 (3H, s), 2.29 (2H, t, J=7.2 Hz), 2.25-2.36 (1H, m), 2.57 (2H, d, J=6.2 Hz), 2.81-2.92 (3H, m), 3.65 (2H, t, J=7.2 Hz), 3.74-3.80 (1H, m), 3.90 (3H, s), 4.50-4.56 (1H, m), 7.04 (1H, dd, J=8.8, 2.2 Hz), 7.12 (2H, d, J=8.4 Hz), 7.32 (1H, d, J=2.2 Hz), 7.52 (1H, d, J=8.8 Hz), 7.94 (2H, d, J=8.4 Hz)

EXAMPLE 234

1-Acetyl-N-{3-[4-(1,3-benzothiazol-2-ylsulfonyl)-1-piperidinyl]propyl}-N-(3,4-dichlorophenyl)-4-piperidinecarboxamide By a similar manner to Example 211, the titled compound was synthesized by using the compound obtained in Reference Example 82-2. Yield 61%.

$^1$H NMR (CDCl$_3$) δ 1.40-1.81 (7H, m), 1.87-1.96 (3H, m), 2.00-2.20 (1H, m), 2.05 (3H, s), 2.27-2.34 (3H, m), 2.80-3.00 (3H, m), 3.30-3.50 (3H, m), 3.60-3.67 (2H, m), 3.74-3.82 (1H, m), 4.49-4.56 (1H, m), 7.02 (1H, dd, J=8.6, 2.2 Hz), 7.29 (1H, d, J=2.2 Hz), 7.52 (1H, d, J=8.4 Hz), 7.57-7.69 (2H, m), 8.01-8.05 (1H, m), 8.22-8.25 (1H, m)

EXAMPLE 235

1-Acetyl-N-(3,4-dichlorophenyl)-N-{3-[4-(2-thienylsulfanyl)-1-piperidinyl]propyl}-4-piperidinecarboxamide By a similar manner to Reference Example 72-2, 2-(4-piperidinylsulfanyl)thiophene hydrochloride was synthesized by using the compound obtained in Reference Example 40.

By using the above obtained 2-(4-piperidinylsulfanyl) thiophene hydrochloride, the titled compound was synthesized by a similar manner to Example 211.

Yield 77%. $^1$H NMR (CDCl$_3$) δ 1.50-1.96 (12H, m), 1.96 (3H, s), 2.28 (2H, t, J=7.2 Hz), 2.28-2.42 (2H, m), 2.75-2.92 (4H, m), 3.64 (2H, t, J=7.2 Hz), 3.74-3.81 (1H, m), 4.49-4.56 (1H, m), 6.99 (1H, dd, J=5.2, 3.6 Hz), 7.11 (1H, dd, J=3.6, 1.0 Hz), 7.24 (1H, dd, J=8.4, 2.2 Hz), 7.30 (1H, d, J=2.2 Hz), 7.36 (1H, dd, J=5.2, 1.0 Hz), 7.52 (1H, d, J=8.4 Hz)

EXAMPLE 236

Methyl 4-({1-[3-(3,4-dichloro{[1-(methylsulfonyl)-4-piperidinyl]carbonyl}anilino)propyl]-4-piperidinyl}methyl)benzoate By a similar manner to Example 215, the titled compound was synthesized by using the compound obtained in Reference Example 81.

yield 62%. $^1$H NMR (CDCl$_3$) δ 1.23-1.42 (13H, m), 2.20-2.40 (3H, m), 2.52-2.59 (4H, m), 2.74 (3H, s), 2.80-2.89 (2H, m), 3.62-3.76 (4H, m), 3.90 (3H, s), 7.06 (1H, dd, J=8.4, 2.6 Hz), 7.19 (2H, d, J=8.4 Hz), 7.32 (1H, d, J=2.6 Hz), 7.52 (1H, d, J=8.4 Hz), 7.94 (2H, d, J=8.4 Hz)

EXAMPLE 237

N-{3-[4-(1,3-Benzothiazol-2-ylsulfonyl)-1-piperidinyl]propyl}-N-(3,4-dichlorophenyl)-1-(methylsulfonyl)-4-piperidinecarboxamide By a similar manner to Example 215, the titled compound was synthesized by using the compound obtained in Reference Example 82-2.

yield 33%. $^1$H NMR (CDCl$_3$) δ 1.58-2.34 (15H, m), 2.51-2.62 (2H, m), 2.73 (3H, s), 2.95-2.98 (2H, m), 3.30-3.50 (1H, m), 3.60-3.75 (4H, m), 7.01 (1H, dd, J=8.4, 2.4

Hz), 7.28 (1H, d, J=2.4 Hz), 7.52 (1H, d, J=8.4 Hz), 7.57-7.70 (2H, m), 8.01-8.05 (1H, m), 8.21-8.26 (1H, m)

EXAMPLE 238

N-(3,4-Dichlorophenyl)-1-(methylsulfonyl)-N-{3-[4-(2-thienyl sulfanyl)-1-piperidinyl]propyl}-4-piperidinecarboxamide By a similar manner to Reference Example 72-2, 2-(4-piperidinylsulfanyl)thiophene hydrochloride was synthesized by using the compound obtained in Reference Example 40. By using the obtained 2-(4-piperidinylsulfanyl) thiophene hydrochloride, the titled compound was synthesized by a similar manner to Example 215. Yield 65%.

$^1$H NMR (CDCl$_3$) δ 1.51-1.69 (6H, m), 1.79-2.05 (6H, m), 2.20-2.31 (3H, m), 2.51-2.62 (2H, m), 2.74 (3H, s), 2.74-2.83 (3H, m), 3.60-3.76 (4H, m), 6.99 (1H, dd, J=5.4, 3.6 Hz), 7.02 (1H, dd, J=8.4, 2.2 Hz), 7.11 (1H, dd, J=3.6, 1.0 Hz), 7.30, (1H, d, J=2.2 Hz), 7.37 (1H, dd, J=5.4, 1.0 Hz), 7.52 (1H, d, J=8.4 Hz)

EXAMPLE 239

4-{[1-(3-{[(1-Acetyl-4-piperidinyl)carbonyl]-3,4-dichloroanilino}propyl)-4-piperidinyl]methyl}benzoic acid To a solution of the compound obtained in Example 233 (200 mg, 0.37 mmol) in ethanol (2 mL) was added aqueous solution of 1N-sodium hydroxide (0.56 mL, 0.56 mmol), and the mixture was stirred at 80° C. for 3 hours. To the mixture was added, dropwise aqueous solution of 1N-hydrochloric acid (0.56 mL, 0.56 mmol) under ice cooling, and the mixture was concentrated under reduced pressure. The concentrate was subjected to flash column chromatography (silica gel 20 g, dichloromethane/methanol=20/1 to 2/1), and the desired fraction was concentrated under reduced pressure. To the concentrate was added diisoprpyl ether, and the resulting precipitates were collected by filtration to give the titled compound (120 mg, 0.21 mmol, Yield 56%) as white amorphous substance.

$^1$H NMR (CD$_3$OD) δ 1.53-2.09 (11H, m), 2.05 (3H, s), 2.38-2.49 (2H, m), 2.69 (2H, d, J=7.0 Hz), 2.87-2.99 (3H, m), 3.06-3.14 (2H, m), 3.49-3.55 (2H, m), 3.73-3.89 (3H, m), 4.39-4.45 (1H, m), 7.26 (2H, d, J=8.4 Hz), 7.38 (1H, dd, J=8.4, 2.2 Hz), 7.68 (1H, d, J=8.4 Hz), 7.70 (1H, d, J=2.2 Hz), 7.94 (2H, d, J=8.4 Hz)

EXAMPLE 240

4-({1-[3-(3,4-Dichloro{[1-(methylsulfonyl)-4-piperidinyl]carbonyl}anilino)propyl]-4-piperidinyl}methyl)benzoic acid By a similar manner to Example 239, the titled compound was synthesized by using the compound obtained in Example 236.

Yield 97%. $^1$H NMR (CD$_3$OD) δ 1.51-1.95 (11H, m), 2.20-2.40 (1H, m), 2.40-2.60 (2H, m), 2.67 (2H, d, J=6.6 Hz), 2.73 (3H, s), 2.80-3.10 (4H, m), 3.46-4.89 (6H, m), 7.23 (2H, d, J=8.0 Hz), 7.36 (1H, dd, J=8.4, 2.2 Hz), 7.68 (1H, d, J=8.4 Hz), 7.70 (1H, d, J=2.2 Hz), 7.91 (2H, d, J=8.0 Hz)

EXAMPLE 241

N-{3-[4-(1H-1,2,3-Benzotriazol-1-yl)-1-piperidinyl]propyl}-N-(3,4-dichlorophenyl)-1-(methylsulfonyl)-4-piperidinecarboxamide By a similar manner to Example 190, the titled compound was synthesized by using 4-(1H-1,2,3-benzotriazol-1-yl)piperidine hydrochloride. Yield 67%.

$^1$H NMR (CDCl$_3$) δ 1.62-2.70 (17H, m), 2.74 (3H, s), 2.99-3.12 (2H, m), 3.63-3.81 (4H, m), 4.60-4.78 (1H, m), 7.09 (1H, dd, J=2.6, 8.4 Hz), 7.29-7.62 (5H, m), 8.05 (1H, br d, J=8.0 Hz)

EXAMPLE 242

1-Acetyl-(3,4-dichlorophenyl)-N-{3-[4-(3-pyridylamino)-1-piperidinyl]propyl}-4-piperidinecarboxamide By a similar manner to Example 209, the titled compound was synthesized by using 3-aminopyridine. Yield 34%.

$^1$H NMR (CDCl$_3$) δ 1.40-1.95 (9H, m), 2.06 (3H, s), 1.98-2.19 (3H, m), 2.23-2.50 (4H, m), 2.75-2.97 (3H, m), 3.18-3.40 (1H, br s), 3.55-3.85 (4H, m), 4.47-4.60 (1H, m), 6.84 (1H, ddd, J=1.0, 2.6, 8.0 Hz), 7.00-7.10 (2H, m), 7.33 (1H, d, J=2.6 Hz), 7.54 (1H, d, J=8.4 Hz), 7.93 (1H, dd, J=1.4, 4.6 Hz), 8.00 (1H, d, J=2.6 Hz)

EXAMPLE 243

1-Acetyl-N-(3-{4-[4-(aminosulfonyl)benzyl]-1-piperidinyl}propyl)-N-(3,4-dichlorophenyl)-4-piperidinecarboxamide By a similar manner to Example 179, the titled compound was synthesized by using the compound obtained in Reference Example 83-2. Yield 64%.

$^1$H NMR (CDCl$_3$) δ 1.30-1.40 (2H, m), 1.20-1.95 (1H, m), 2.05 (3H, s), 2.20-2.45 (4H, m), 2.59 (2H, d, J=6.2 Hz), 2.78-2.95 (3H, m), 3.60-3.85 (3H, m), 4.45-4.60 (1H, m,), 7.03 (1H, dd, J=2.4, 8.4 Hz), 7.22-7.35 (3H, m), 7.52 (1H, d, J=8.4), 7.83 (2H, d, H=8.4)

EXAMPLE 244

N-(3-{4-(4-(Aminosulfonyl)benzyl]-1-piperidinyl}propyl)-N-(3,4-dichlorophenyl)-1-(methylsulfonyl)-4-piperidinecarboxamide By a similar manner to Example 190, the titled compound was synthesized by using the compound obtained in Reference Example 83-2. Yield 66%.

$^1$H NMR (CDCl$_3$) δ 1.20-1.40 (2H, m), 1.45-2.00 (11H, m ), 2.10-2.40 (3H, m), 2.45-2.65 (4H, m), 2.74 (3H, s), 2,70-2.98 (2H, m), 3.60-3.80 (4H, m), 7.04 (1H, dd, J=2.6, 8.4 Hz), 7.26-7.34 (3H, m), 7.53 (1H, d, J=8.4 Hz), 7.84 (2H, d, J=8.4 Hz)

EXAMPLE 245

1-Acetyl-N-(3,4-dichlorophenyl)-N-[3-(4-{4-[(methylamino)sulfonyl]benzyl}-1-piperidinyl)propyl]-4-piperidinecarboxamide By a similar manner to Example 179, the titled compound was synthesized by using the compound obtained in Reference Example 84-2. Yield 58%.

¹H NMR (CDCl₃) δ 1.20-1.40 (2H, m), 1.45-2.00. (10H, m), 2.06 (3H, s), 2.21-2.47 (3H, m), 2.59 (2H, d, J=6.2 Hz), 2.67 (3H, d, J=5.4 Hz), 2.75-2.98 (3H, m), 3.60-3.88 (3H, m), 4.22-4.40 (1H, m), 4.46-4.60 (1H, m), 7.03 (1H, dd, J=2.4, 7.4 Hz), 7.26-7.37 (3H, m), 7.52 (1H, d, J=8.4 Hz), 7.76 (2H, d, J=8.4 Hz)

EXAMPLE 246

N-(3,4-Dichlorophenyl)-N-[3-(4-{4-[(methylamino) sulfonyl]benzyl}-1-piperidinyl)propyl]-1-(methylsulfonyl)-4-piperidinecarboxamide By a similar manner to Example 190, the titled compound was synthesized by using the compound obtained in Reference Example 84-2. Yield 60%.

¹H NMR (CDCl₃) δ 1.20-1.40 (2H, m), 1.50-2.00 (10H, m), 2.13-2.35 (3H, m), 2.46-2.66 (4H, m), 2.67 (3H, d, J=6.4 Hz), 2.74 (3H, s), 2.78-2.90 (2H, m), 3.58-3.80 (4H, m), 4.21-4.35 (1H, m), 7.03 (2H, dd, J=2.2, 8.4 Hz), 7.27-7.35 (3H, m), 7.52 (1H, d, J=8.4 Hz), 7.76 (2H, d, J=8.4 Hz)

EXAMPLE 247

1-Acetyl-N-(3,4-dichlorophenyl)-N-(3-(4-{4-[(dimethylamino)sulfonyl]benzyl}-1-piperidinyl)propyl]-4-piperidinecarboxamide By a similar manner to Example 211, the titled compound was synthesized by using the compound obtained in Reference Example 85-2. Yield 20%.

¹H NMR (CDCl₃) δ 1.20-1.43 (2H, m), 1.45-1.98 (12H, m), 2.05 (3H, s), 2.15-2.50 (3H, m), 2.60 (2H, d, J=6.2 Hz), 2.70 (6H, s), 2.75-2.98 (3H, m), 3.59-3.86 (3H, m), 4.47-4.60 (1H, m), 7.05 (1H, d, J=2.6, 8.4 Hz), 7.29 (1H, d, J=8.4 Hz), 7.32 (1H, d, J=2.4 Hz), 7.53 (1H, d, J=8.4 Hz), 7.68 (1H, d, J=8.4 Hz)

EXAMPLE 248

N-(3,4-Dichlorophenyl)-N-[3-(4-{4-[(dimethylamino)sulfonyl]benzyl}-1-piperidinyl)propyl]-1-(methylsulfonyl)-4-piperidinecarboxamide By a similar manner to Example 215, the titled compound was synthesized by using the compound obtained in Reference Example 85-2. Yield 19%.

¹H NMR (CDCl₃) δ 1.20-1.45 (2H, m), 1.47-2.02 (11H, m), 2.15-2.40 (3H, m), 2.45-2.67 (4H, m), 2.70 (6H, s), 2.73 (3H, s), 2.80-2.95 (2H, m), 3.60-3.80 (4H, m), 7.06 (1H, d, J=2.4, 8.6 Hz), 7.29 (2H, d, J=8.2 Hz), 7.32 (1H, d, J=2.4 Hz), 7.52 (1H, d, J=8.6 Hz), 7.78 (1H, d, J=8.2 Hz)

EXAMPLE 249

1-Acetyl-N-(3,4-dichlorophenyl)-N-{3-[4-(4-methoxybenzyl)-1-piperidinyl]propyl}-4-piperidinecarboxamide By a similar manner to Example 179, the titled compound was synthesized by using the compound obtained in Reference Example 87-1. Yield 81%.

¹H NMR (CDCl₃) δ 1.15-1.35 (3H, m), 1.54-1.90 (13H, m), 2.06 (3H, s), 2.21-2.41 (3H, m), 2.45 (2H, d, J=6.6 Hz), 2.75-2.90 (3H, m), 3.60-3.70 (2H, m), 3.78 (3H, s), 4.46-4.60 (1H, m), 6.81 (2H, d, J=8.8 Hz), 7.00-7.06 (3H, m), 7.31 (1H, d, J=2.4 Hz), 7.52 (1H, d, J=8.4 Hz)

EXAMPLE 250

N-(3,4-Dichlorophenyl)-N-{3-[4-(4-methoxybenzyl)-1-piperidinyl]propyl}-1-(methylsulfonyl)-4-piperidinecarboxamide By a similar manner to Example 190, the titled compound was synthesized by using the compound obtained in Reference Example 87-1. Yield 73%.

¹H NMR (CDCl₃) δ 1.15-1.35 (2H, m), 1.55-2.00 (11H, m), 2.10-2.35 (3H, m), 2.46 (2H, d, J=6.6 Hz), 2.45-2.65 (2H, m), 2.74 (3H, s), 2.74-2.90 (2H, m), 3.58-3.77 (4H, m), 3.79 (3H, s), 6.81 (2H, d, J=8.4 Hz), 7.00-7.08 (3H, m), 7.31 (1H, d, J=2.6 Hz), 7.52 (1H, d, J=8.6 Hz)

EXAMPLE 251

1-Acetyl-N-(3-{4-[3-(aminosulfonyl)-4-methoxybenzyl]-1-piperidinyl}propyl)-N-(3,4-dichlorophenyl)-4-piperidinecarboxamide By a similar manner to Example 179, the titled compound was synthesized by using the compound obtained in Reference Example 87-4. Yield 54%.

¹H NMR (CDCl₃) δ 1.10-1.35 (2H, m), 1.50-1.92 (11H, m), 2.06 (3H, s), 2.21-2.43 (4H, m), 2.51 (2H, d, J=6.6 Hz), 2.76-2.98 (3H, m), 3.60-3.88 (3H, m), 3.99 (3H, s), 4.47-4.60 (1H, m), 5.02-5.11 (2H, m), 6.94 (1H, d, J=8.4 Hz), 7.03 (1H, dd, J=2.2, 8.4 Hz), 7.28-7.34 (2H, m), 7.53 (1H, d, J=8.4 Hz), 7.68 (1H, d, J=2.2 Hz)

EXAMPLE 252

N-(3-{4-[3-(Aminosulfonyl)-4-methoxybenzyl)-1-piperidinyl}propyl)-N-(3,4-dichlorophenyl)-1-(methylsulfonyl)-4-piperidinecarboxamide By a similar manner to Example 190, the titled compound was synthesized by using the compound obtained in Reference Example 87-4. Yield 73%.

¹H NMR (CDCl₃) δ 1.17-1.38 (2H, m), 1.50-2.02 (11H, m), 2.20-2.34 (3H, m), 2.45-2.66 (4H, m), 2.74 (3H, s), 2.68-2.92 (2H, m), 3.99 (3H, s), 5.00-5.17 (2H, m), 6.96 (1H, d, J=8.4 Hz), 7.02 (1H, dd, J=2.2, 8.4 Hz), 7.27-7.33 (2H, m), 7.53 (1H, d, J=8.4 Hz), 7.68 (1H, d, J=2.2 Hz)

EXAMPLE 253

N-(3,4-Dichlorophenyl)-1-(methylsulfonyl)-N-(3-{4-[4-(methylsulfonyl)benzyl]-1-piperidinyl}propyl)-4-piperidinecarboxamide By a similar manner to Example 190, the titled compound was synthesized by using the compound obtained in Reference Example 86-2. Yield 66%.

¹H NMR (CDCl₃) δ 1.20-1.40 (2H, m), 1.43-1.98 (12H, m), 2.18-2.36 (2H, m), 2.45-2.68 (4H, m), 2.63 (3H, s), 2.78-2.91 (2H, m), 3.05 (3H, s), 3.60-3.81 (4H, m), 7.03 (2H, dd, J=2.8, 8.4 Hz), 7.30-7.35 (3H, m), 7.52 (2H, d, J=8.4 Hz), 7.85 (2H, d, J=8.4 Hz)

EXAMPLE 254

1-Acetyl-N-(3,4-dichlorophenyl)-N-{3-[4-({4-[(methylsulfonyl)amino]phenyl}sulfonyl)-1-piperidinyl]propyl}-4-piperidinecarboxamide By a similar manner to Example 211, the titled compound was synthesized by using the compound obtained in Reference Example 88-5. Yield 21%.

$^1$H NMR (CD$_3$OD) δ 1.50-1.80 (8H, m), 1.88-2.05 (3H, m), 2.05 (3H, s), 2.08-2.50 (4H, m), 2.90-3.05 (3H, m), 3.09 (3H, s), 3.55-3.92 (5H, m), 4.38-4.50 (2H, m), 7.22-7.34 (1H, m), 7.43 (2H, d, J=8.8 Hz), 7.60-7.70 (2H, m), 7.81 (2H, dd, J=8.8 Hz)

EXAMPLE 255

N-(3,4-Dichlorophenyl)-1-(methylsulfonyl)-N-{3-[4-({4-[(methylsulfonyl)amino]phenyl}sulfonyl)-1-piperidinyl]propyl}-4-piperidinecarboxamide By a similar manner to Example 215, the titled compound was synthesized by using the compound obtained in Reference Example 88-5. Yield 21%.

$^1$H NMR (CDCl$_3$) δ 1.40-2.08 (2H, m), 2.10-2.35 (3H, m), 2.40-2.65 (2H, m), 2.74 (3H, s), 2.75-3.00 (3H, m), 3.15 (3H, s), 3.57-3.85 (4H, m), 7.01 (1H, dd, J=2.4, 8.6 Hz), 7.27-7.39 (3H, m), 7.52 (1H, d, J=8.6 Hz), 7.83 (2H, d, J=8.4 Hz)

EXAMPLE 256

1-Acetyl-N-(3,4-dichlorophenyl)-N-(3-{4-[(4-methoxyphenyl) sulfonyl]-1-piperidinyl}propyl)-4-piperidinecarboxamide By a similar manner to Example 211, the titled compound was synthesized by using the compound obtained in Reference Example 90-3. Yield 52%.

$^1$H NMR (CDCl$_3$) δ 1.50-2.06 (12H, m), 2.05 (3H, s), 2.20-2.48 (4H, m), 2.75-3.00 (4H, m), 3.55-3.68 (2H, m), 3.70-3.85 (2H, m), 3.89 (3H, s), 4.45-4.60 (1H, m), 6.95-7.08 (3H, m), 7.29 (1H, d, J=2.2 Hz), 7.52 (2H, d, J=8.4 Hz), 7.77 (2H, d, J=8.8 Hz)

EXAMPLE 257

N-(3,4-Dichlorophenyl)-N-(3-{4-[(4-methoxyphenyl)sulfonyl]-1-piperidinyl}propyl)-1-(methylsulfonyl)-4-piperidinecarboxamide By a similar manner to Example 215, the titled compound was synthesized by using the compound obtained in Reference Example 90-3. Yield 66%.

$^1$H NMR (CDCl$_3$) δ 1.55-2.10 (12H, m), 2.13-2.33 (3H, m), 2.47-2.63 (2H, m), 2.73 (3H, s), 2.73-2.97 (3H, m), 3.56-3.81 (4H, m), 3.89 (3H, s), 6.98-7.06 (3H, m), 7.28 (1H, d, J=3.0 Hz), 7.52 (2H, d, J=8.4 Hz), 7.77 (2H, d, J=9.2 Hz)

EXAMPLE 258

1-Acetyl-N-[3-(4-{[4-(2-butoxyethoxy)phenyl]sulfonyl}-1-piperidinyl)propyl]-N-(3,4-dichlorophenyl)-4-piperidinecarboxamide By a similar manner to Example 211, the titled compound, was synthesized by using the compound obtained in Reference Example 89-4. Yield 49%.

$^1$H NMR (CDCl$_3$) δ 0.93 (2H, t, J=7.2 Hz), 1.28-2.05 (16H, m), 2.05 (3H, s), 2.20-2.50 (4H, m), 2.72-3.00 (4H, m), 3.54 (2H, t, J=7.6 Hz), 3.56-3.64 (2H, m), 3.65-3.86 (3H, m), 4.19 (2H, t, J=4.8 Hz), 4.47-4.62 (1H, m), 7.01 (1H, dd, J=2.4, 8.0 Hz), 7.04 (2H, d, J=9.0 Hz), 7.29 (1H, d, J2.4 Hz), 7.52 (1H, d, J=8.0 Hz), 7.76 (2H, d, J=9.0 Hz)

EXAMPLE 259

N-[3-(4-{[4-(2-Butoxyethoxy)phenyl]sulfonyl}-1-piperidinyl)propyl]-N-(3,4-dichlorophenyl)-1-(methylsulfonyl)-4-piperidinecarboxamide By a similar manner to Example 215, the titled compound was synthesized by using the compound obtained in Reference Example 89-4. Yield 51%.

$^1$H NMR (CDCl$_3$) δ 0.93 (3H, t, J=7.2 Hz), 1.20-2.05 (15H, m), 2.10-2.33 (3H, m), 2.45-2.65 (2H, m), 2.73 (3H, s), 2.73-2.98 (4H, m), 3.54 (2H, t, J=6.6 Hz), 3.54-3.85 (6H, m), 4.19 (2H, t, J=4.8 Hz), 7.01 (1H, dd, J=2.2, 8.4 Hz), 7.04 (2H, d, J=9.2 Hz), 7.28 (1H, d, J=2.2 Hz), 7.52 (1H, d, J=8.4 Hz), 7.74 (2H, d, J=9.2 Hz)

EXAMPLE 260

1-Acetyl-N-{3-[4-(1H-benzimidazol-1-ylmethyl)-1-piperidinyl]propyl}-N-(3,4-dichlorophenyl)-4-piperidinecarboxamide By a similar manner to Reference Example 61-2, t-butyl 4-(1H-benzimidazol-1-ylmethyl)-1-piperidine carboxylate was converted to 4-(1H-benzimidazol-1-ylmethyl)piperidine, and by a similar manner to Example 179, the titled compound was obtained. Yield 85% (2 steps)

$^1$H NMR (CDCl$_3$) δ 1.20-2.00 (15H, m), 2.05 (3H, s), 2.20-2.45 (3H, m), 2.75-2.95 (2H, m), 3.65 (2H, t, J=7.4 Hz), 3.78 (1H, br d, J=14 Hz), 4.04 (2H, d, J=3.6 Hz), 4.53 (1H, br d, J=14 Hz), 7.02 (1H, m), 7.24-7.40 (4H, m), 7.52 (1H, d, J=8.4 Hz), 7.80-7.85 (2H, m)

EXAMPLE 261

N-{3-[4-(1H-Benzimidazol-1-ylmethyl)-1-piperidinyl]propyl}-N-(3,4-dichlorophenyl)-1-methylsulfonyl-4-piperidinecarboxamide By a similar manner to Reference Example 61-2, t-butyl 4-(1H-benzimidazol-1-ylmethyl)-1-piperidine carboxylate was converted to 4-(1H-benzimidazol-1-ylmethyl)piperidine, and the titled compound was obtained by a similar manner to Example 190. Yield 82% (2 steps)

$^1$H NMR (CDCl$_3$) δ 1.30-2.05 (13H, m), 2.15-2.40 (3H, m), 2.45-2.67 (2H, m), 2.74 (3H, s), 2.83-2.95 (2H, m), 3.60-3.80 (4H, m), 4.04 (2H, d, J=7.0 Hz), 7.04 (1H, m), 7.13-7.42 (4H, m), 7.52 (1H, d, J=8.4 Hz), 7.75-7.85 (2H, m)

EXAMPLE 262

1-Acetyl-N-(3,4-dichlorophenyl)-N-{3-[4-(1H-indol-1-ylmethyl)-1-piperidinyl]propyl}-4-piperidinecarboxamide By a similar manner to Reference Example 61-2, t-butyl 4-(1H-indol-1-ylmethyl)-1-piperidine carboxylate was converted to 4-(1H-indol-1-ylmethyl)piperidine, and the titled compound was obtained by a similar manner to Example 179. Yield 62% (2 steps)
$^1$H NMR (CDCl$_3$) δ 1.20-1.95 (15H, m), 2.05 (3H, s), 2.20-2.45 (3H, m), 2.78-2.95 (2H, m), 3.65 (2H, t, J=7.4 Hz), 3.77 (1H, br d, J=13 Hz), 3.98 (2H, d, J=7.0 Hz), 4.53 (1H, br d, J=13 Hz), 6.48 (1H, m), 7.00-7.35 (6H, m), 7.52 (1H, d, J=8.4 Hz), 7.62 (1H, d, J=7.6 Hz)

EXAMPLE 263

N-(3,4-Dichlorophenyl)-N-{3-[4-(1H-indol-1-ylmethyl)-1-piperidinyl]propyl}-1-methylsulfonyl-4-piperidinecarboxamide By a similar manner to Reference Example 61-2, t-butyl 4-(1H-indol-1-ylmethyl)-1-piperidine carboxylate was converted to 4-(1H-indol-1-ylmethyl)piperidine, the titled compound was obtained by a similar manner to Example 190. Yield 40% (2 steps)
$^1$H NMR (CDCl$_3$) δ 1.30-2.00 (13H, m), 2.10-2.43 (3H, m), 2.47-2.67 (2H, m), 2.73 (3H, s), 2.80-2.98 (2H, m), 3.58-3.80 (4H, m), 3.99 (2H, d, J=7.4 Hz), 6.48 (1H, d, J=3.0 Hz), 7.00-7.35 (6H, m), 7.52 (1H, d, J=8.4 Hz), 7.63 (1H, d, J=7.2 Hz)

EXAMPLE 264

1-Acetyl-N-[3-(4-benzyl-3-oxo-1-piperazinyl)propyl]-N-(3-chlorophenyl)-4-piperidinecarboxamide trifluoroacetate By a similar manner to Example 52, the titled compound was synthesized by using 1-benzyl-2-oxopiperazine hydrochloride. HPLC analysis (220 nm): Purity 96% (Retention time 9.519 minutes) MS (APCI$^+$) 511 (M+1)

EXAMPLE 265

1-Acetyl-N-(3-chlorophenyl)-N-{3-[4-(4-fluorobenzyl)-3-oxo-1-piperazinyl]propyl}-4-piperidinecarboxamide trifluoroacetate By a similar manner to Example 52, the titled compound was synthesized by using 1-(4-fluorobenzyl)-2-oxopiperazine hydrochloride.
HPLC analysis (220 nm): Purity 89% (Retention time 10.108 minutes). MS (APCI$^+$) 529 (M+1)

EXAMPLE 266

1-Acetyl-N-(3-chlorophenyl)-N-{3-[4-(4-methyl benzyl)-1-piperazinyl]propyl}-4-piperidine carboxamide 2 trifluoroacetate By a similar manner to Example 52, the titled compound was synthesized by using 1-(4-methyl benzyl)piperazine 2 hydrochloride.

HPLC analysis (220 nm): Purity 99% (Retention time 4.984 minutes) MS (APCI$^+$) 511 (M+1)

EXAMPLE 267

1-Acetyl-N-(3-chlorophenyl)-N-{3-[4-(4-methoxybenzyl)-1-piperazinyl]propyl}-4-piperidinecarboxamide 2 trifluoroacetate By a similar manner to Example 52, the titled compound was synthesized by using 1-(4-methoxybenzyl)piperazine 2 hydrochloride.
HPLC analysis (220 nm): Purity 96% (Retention time 4.493 minutes) MS (APCI$^+$) 527 (M+1)

EXAMPLE 268

1-Acetyl-N-(3-chlorophenyl)-N-{3-[4-(2-pyridylmethyl)-1-piperazinyl]propyl}-4-piperidinecarboxamide 3 trifluoroacetate By a similar manner to Example 52, the titled compound was synthesized by using 1-(2-pyridylmethyl)piperazine 3 hydrochloride.
HPLC analysis (220 nm): Purity 95% (Retention time 4.194 minutes) MS (APCI$^+$) 498 (M+1)

EXAMPLE 269

1-Acetyl-N-(3-chlorophenyl)-N-{3-[4-(3-pyridylmethyl)-1-piperazinyl]propyl}-4-piperidinecarboxamide 3 trifluoroacetate By a similar manner to Example 52, the titled compound was synthesized by using 1-(3-pyridylmethyl)piperazine 3 hydrochloride.
HPLC analysis (220 nm): Purity 97% (Retention time 4.383 minutes) MS (APCI$^+$) 498 (M+1)

EXAMPLE 270

1-Acetyl-N-(3-chlorophenyl)-N-{3-[4-(4-pyridylmethyl)-1-piperazinyl]propyl}-4-piperidinecarboxamide 3 trifluoroacetate By a similar manner to Example 52, the titled compound was synthesized by using 1-(4-pyridylmethyl)piperazine 3 hydrochloride.
HPLC analysis (220 nm): Purity 97% (Retention time 4.131 minutes) MS (APCI$^+$) 498 (M+1)

EXAMPLE 271

1-Acetyl-N-(3-chlorophenyl)-N-{3-[4-(2-tetrahydrofuranylmethyl)-1-piperazinyl]propyl}-4-piperidinecarboxamide 2 trifluoroacetate By a similar manner to Example 52, the titled compound was synthesized by using 1-(2-tetrahydrofuranylmethyl)piperazine 2 hydrochloride.
HPLC analysis (220 nm): Purity 94% (Retention time 4.357 minutes) MS (APCI$^+$) 491 (M+1)

EXAMPLE 272

1-Acetyl-N-(3-chlorophenyl)-N-(3-{4-[(3,5-dimethyl isoxazol-4-yl)methyl]-1-piperazinyl}propyl)-4-piperidinecarboxamide 2 trifluoroacetate By a similar manner to Example 52, the titled compound was synthesized by using 1-[(3,5-dimethylisoxazol-4-yl)methyl]piperazine 2 hydrochloride.

HPLC analysis (220 nm): Purity 98% (Retention time 4.275 minutes) MS (APCI$^+$) 516 (M+1)

EXAMPLE 273

1-Acetyl-N-(3-chlorophenyl)-N-(3-{4-[(2,6-dioxo-1,2,3,6-tetrahydro pyrimidine-4-yl)methyl]-1-piperazinyl}propyl)-4-piperidinecarboxamide 2 trifluoroacetate By a similar manner to Example 52, the titled compound was synthesized by using 1-[(2,6-dioxo-1,2,3,6-tetrahydro pyrimidine-4-yl)methyl]piperazine 2 hydrochloride.

HPLC analysis (220 nm): Purity 91% (Retention time 4.084 minutes) MS (APCI$^+$) 531 (M+1)

EXAMPLE 274

1-Acetyl-N-(3-chlorophenyl)-N-(3-{4-[(1H-tetrazol-1-yl)benzyl]-1-piperazinyl}propyl)-4-piperidinecarboxamide 2 trifluoroacetate By a similar manner to Example 52, the titled compound was synthesized by using 1-[(1H-tetrazol-1-yl)benzyl]piperazine 2 hydrochloride.

HPLC analysis (220 nm): Purity 96% (Retention time 4.289 minutes)

EXAMPLE 275

1-Acetyl-N-{3-[(1-benzyl-4-piperidinyl)amino]propyl}-N-(3-chlorophenyl)-4-piperidinecarboxamide 2 trifluoroacetate By a similar manner to Example 52, the titled compound was synthesized by using (1-benzyl-4-piperidinyl)amine.

HPLC analysis (220 nm): Purity 91% (Retention time 4.080 minutes) MS (APCI$^+$) 511 (M+1)

EXAMPLE 276

1-Acetyl-N-(3-chlorophenyl)-N-[3-(indane-2-ylaminno)propyl]-4-piperidinecarboxamide trifluoroacetate By a similar manner to Example 52, the titled compound was synthesized by using 2-aminoindane.

HPLC analysis (220 nm): Purity 97% (Retention time 4.661 minutes) MS (APCI$^+$) 454 (M+1)

EXAMPLE 277

1-Acetyl-N-(3-chlorophenyl)-N-(3-{[2-(indol-3-yl)ethyl]amino}propyl)-4-piperidinecarboxamide trifluoroacetate By a similar manner to Example 52, the titled compound was synthesized by using tryptamine.

HPLC analysis (220 nm): Purity 96% (Retention time 4.447 minutes) MS (APCI$^+$) 481 (M+1)

EXAMPLE 278

1-Acetyl-N-(3-chlorophenyl)-N-{3-[2-(2-pyridyl)ethylamino]propyl}-4-piperidinecarboxamide 2 trifluoroacetate By a similar manner to Example 52, the titled compound was synthesized by using 2-(2-pyridyl)ethylamine.

HPLC analysis (220 nm): Purity 90% (Retention time 4.446 minutes) MS (APCI$^+$) 443 (M+1)

EXAMPLE 279

1-Acetyl-N-(3-chlorophenyl)-N-{3-[4-(4-cyanobenzyl)-1-piperazinyl]propyl}-4-piperidinecarboxamide By a similar manner to Example 211, the titled compound was synthesized by using the compound obtained in Reference Example 12-2 and 1-(4-cyanobenzyl)piperazine 2 hydrochloride.

HPLC analysis (220 nm): Purity 97% (Retention time 4.266 minutes) MS (APCI$^+$) 522 (M+1)

EXAMPLE 280

1-Acetyl-N-[3-(2-benzylmorpholino)propyl]-N-(3-chlorophenyl)-4-piperidinecarboxamide By a similar manner to Example 211, the titled compound was synthesized by using the compound obtained in Reference Example 12-2 and 2-benzylmorpholine hydrochloride.

HPLC analysis (220 nm): Purity 96% (Retention time 4.353 minutes) MS (APCI$^+$) 498 (M+1)

EXAMPLE 281

1-Acetyl-N-[3-(4-benzyloxy-1-piperidinyl)propyl]-N-(3-chlorophenyl)-4-piperidinecarboxamide By a similar manner to Example 211, the titled compound was synthesized by using the compound obtained in Reference Example 12-2 and 4-benzyloxypiperidine hydrochloride.

HPLC analysis (220 nm): Purity 97% (Retention time 4.845 minutes) MS (APCI$^+$) 512 (M+1)
$^1$H NMR (CDCl$_3$) δ 1.5-1.8 (8H, m), 1.8-2.0 (2H, m), 2.05 (3H, s), 2.1-2.2 (2H, m), 2.3-2.5 (2H, m), 2.33 (2H, t, J=7.2 Hz), 2.6-3.0 (3H, m), 3.4-3.5 (1H, m), 3.68 (2H, t, J=7.5 Hz), 3.75 (1H, br d, J=12.8 Hz), 4.5-4.6 (1H, m), 4.53 (2H, s), 7.0-7.1 (1H, m), 7.20 (1H, s), 7.3-7.4 (7H, m)

EXAMPLE 282

1-Acetyl-N-[3-(4-acetylamino-4-phenyl-1-piperidinyl)propyl]-N-(3-chlorophenyl)-4-piperidinecarboxamide By a similar manner to Example 211, the titled compound was synthesized by using the compound obtained in Reference Example 12-2 and 4-acetylamino-4-phenylpiperidine hydrochloride.

HPLC analysis (220 nm): Purity 98% (Retention time 4.294 minutes) MS (APCI$^+$) 539 (M+1) $^1$H NMR (CDCl$_3$) δ 1.5-1.9 (8H, m), 2.01 (3H, s), 2.05 (3H, s), 2.1-2.5 (8H, m), 2.7-2.9 (3H, m), 3.70 (2H, t, J=7.5 Hz), 3.78 (1H, br d, J=13.4 Hz), 4.53 (1H, br d, J=13.4 Hz), 5.50 (1H, s), 7.05-7.15 (1H, m), 7.21-7.5 (8H, m)

EXAMPLE 283

1-Acetyl-N-[3-(4-benzylidene-1-piperidinyl)propyl]-N-(3-chlorophenyl)-4-piperidinecarboxamide By a similar manner to Example 211, the titled compound was synthesized by using the compound obtained in Reference Example 12-2 and 4-benzylidenepiperidine hydrochloride.

HPLC analysis (220 nm): Purity 97% (Retention time 4.861 minutes) MS (APCI$^+$) 494 (M+1) $^1$H NMR (CDCl$_3$) δ 1.5-1.8 (8H, m), 2.05 (3H, s), 2.2-2.6 (10H, m), 2.75-2.9 (1H, m), 3.70 (2H, t, J=7.6 Hz), 3.76 (1H, br d, J=14.4 Hz), 4.53 (1H, br d, J=14.4 Hz), 6.27 (1H, s), 7.0-7.4 (9H, m)

EXAMPLE 284

1-Acetyl-N-(3-chlorophenyl)-N-(3-{4-[hydroxy(diphenyl)methyl]-1-piperidinyl}propyl)-4-piperidinecarboxamide By a similar manner to Example 211, the titled compound was synthesized by using the compound obtained in Reference Example 12-2 and 4-[hydroxy(diphenyl)methyl]piperidine.

HPLC analysis (220 nm): Purity 98% (Retention time 5.267 minutes) MS (APCI$^+$) 588 (M+1) $^1$H NMR (CDCl$_3$) δ 1.3-2.0 (13H, m), 2.04 (3H, s), 2.2-2.5 (4H, m), 2.7-3.0 (3H, m), 3.6-3.9 (3H, m), 4.4-4.6 (1H, m), 7.0-7.1 (1H, m), 7.15-7.5 (13H, m)

EXAMPLE 285

1-Acetyl-N-(3-chlorophenyl)-N-[3-(inden-1-spiro-4'-piperidin-1'-yl)propyl]-4-piperidinecarboxamide By a similar manner to Example 211, the titled compound was synthesized by using the compound obtained in Reference Example 12-2, inden-1-spiro-4'-piperidine trifluoroacetate.

HPLC analysis (220 nm): Purity 98% (Retention time 4.637 minutes) MS (APCI$^+$) 520 (M+1) $^1$H NMR (CDCl$_3$) δ 1.32-1.39 (2H, m), 1.5-1.9 (4H, m), 2.05 (3H, s), 2.1-2.6 (10H, m), 2.7-3.1 (3H, m), 3.74 (2H, t, J=7.3 Hz), 3.78 (1H, br d, J=13.4 Hz), 4.53 (1H, br d, J=13.4 Hz), 6.74 (1H, d, J=5.8 Hz), 6.82 (1H, d, J=5.8 Hz), 7.1-7.4 (8H, m)

EXAMPLE 286

1-Acetyl-N-[3-(4-benzhydryl-1-piperazinyl)propyl]-N-(3-chlorophenyl)-4-piperidinecarboxamide By a similar manner to Example 211, the titled compound was synthesized by using the compound obtained in Reference Example 12-2 and 1-benzhydrylpiperazine.

HPLC analysis (220 nm): Purity 99% (Retention time 5.694 minutes) MS (APCI$^+$) 573 (M+1)

EXAMPLE 287

1-Acetyl-N-{3-[4-(4-chlorobenzyl)-1-piperazinyl]propyl}-N-(3-chlorophenyl)-4-piperidinecarboxamide By a similar manner to Example 211, the titled compound was synthesized by using the compound obtained in Reference Example 12-2 and 1-(4-chlorobenzyl)piperazine 2 hydrochloride.

HPLC analysis (220 nm): Purity 100% (Retention time 5.324 minutes) MS (APCI$^+$) 531 (M+1)

EXAMPLE 288

1-Acetyl-N-(3-chlorophenyl)-N-{3-[4-(4-fluorobenzyl)-1-piperazinyl]propyl}-4-piperidinecarboxamide By a similar manner to Example 211, the titled compound was synthesized by using the compound obtained in Reference Example 12-2 and 1-(4-fluorobenzyl)piperazine 2 hydrochloride.

HPLC analysis (220 nm): Purity 91% (Retention time 4.580 minutes) MS (APCI$^+$) 515 (M+1)

EXAMPLE 289

1-Acetyl-N-{3-[4-(1H-1,2,3-benzotriazol-1-yl)-1-piperidinyl]propyl}-N-(3-chlorophenyl)-4-piperidinecarboxamide By a similar manner to Example 211, the titled compound was synthesized by using the compound obtained in Reference Example 12-2 and 4-(1H-1,2,3-benzotriazol-1-yl)piperidine hydrochloride.

HPLC analysis (220 nm): Purity 98% (Retention time 4.440 minutes) MS (APCI$^+$) 523 (M+1)

EXAMPLE 290

1-Acetyl-N-(3-chlorophenyl)-N-{3-[4-(2-oxo-1,3-dihydro-2H-benzoimidazol-1-yl)-1-piperidinyl]propyl}-4-piperidinecarboxamide By a similar manner to Example 211, the titled compound was synthesized by using the compound obtained in Reference Example 12-2 and 4-(2-oxo-1,3-dihydro-2H-benzoimidazol-1-yl)piperidine.

HPLC analysis (220 nm): Purity 97% (Retention time 4.172 minutes) MS (APCI$^+$) 538 (M+1)

EXAMPLE 291

1-Acetyl-N-[3-(4-benzyl-4-cyano-1-piperidinyl)propyl]-N-(3-chlorophenyl)-4-piperidinecarboxamide By a similar manner to Example 211, the titled compound was synthesized by using the compound obtained in Reference Example 12-2 and 4-benzyl-4-cyanopiperidine hydrochloride.

HPLC analysis (220 nm): Purity 98% (Retention time 4.618 minutes) MS (APCI$^+$) 521 (M+1)

EXAMPLE 292

N-(3,4-Dichlorophenyl)-1-(methylsulfonyl)-N-(3-[4-(4-morpholinobenzyl)-1-piperidinyl]propyl}-4-piperidinecarboxamide By a similar manner to Example 215, the titled compound was synthesized by using 4-(4-morpholinobenzyl)piperidine hydrochloride (Reference Example 97).

HPLC analysis (220 nm): Purity 96% (Retention time 4.630 minutes) MS (APCI$^+$) 651 (M+1)

EXAMPLE 293

1-Acetyl-N-(3-chlorophenyl)-N-[3-(isoindolin-2-yl)propyl]-4-piperidinecarboxamide By a similar manner to Example 215, the titled compound was synthesized by using the compound obtained in Reference Example 12-2, isoindolin hydrobromate.

HPLC analysis (220 nm): Purity 90% (Retention time 4.076 minutes) MS (APCI$^+$) 440 (M+1)

EXAMPLE 294

1-Acetyl-N-(3-chlorophenyl)-N-[3-{4-[4-(1H-tetrazol-1-yl)benzyl]-1-piperidinyl}propyl]-4-piperidinecarboxamide By a similar manner to Example 215, the titled compound was synthesized by using the compound obtained in Reference Example 12-2 and 4-[4-(1H-tetrazol-1-yl)benzyl]piperidine hydrochloride (Reference Example 95-3).

HPLC analysis (220 nm): Purity 89% (Retention time 4.117 minutes) MS (APCI$^+$) 564 (M+1)

EXAMPLE 295

1-Acetyl-N-(3-chlorophenyl)-N-{3-[4-(4-cyanobenzyl)-1-piperidinyl]propyl)-4-piperidinecarboxamide By a similar manner to Example 215, the titled compound was synthesized by using the compound obtained in Reference Example 12-2 and 4-(4-cyanobenzyl)piperidine hydrochloride (Reference Example 93).

HPLC analysis (220 nm): Purity 93% (Retention time 4.298 minutes) MS (APCI$^+$) 521 (M+1)

EXAMPLE 296

1-Acetyl-N-(3-chlorophenyl)-N-[3-(4-piperonyl-1-piperidinyl)propyl]-4-piperidinecarboxamide By a similar manner to Example 215, the titled compound was synthesized by using the compound obtained in Reference Example 12-2 and 4-piperonylpiperidine hydrochloride (Reference Example 94).

HPLC analysis (220 nm): Purity 94% (Retention time 4.792 minutes) MS (APCI$^+$) 540 (M+1)

EXAMPLE 297

1-Acetyl-N-(3,4-dichlorophenyl)-N-(3-{4-[4-(1H-tetrazol-1-yl)benzyl]-1-piperazinyl}propyl)-4-piperidinecarboxamide By a similar manner to Example 215, the titled compound was synthesized by using 1-[4-(1H-tetrazol-1-yl)benzyl]piperazine 2 hydrochloride.

HPLC analysis (220 nm): Purity 99% (Retention time 4.085 minutes) MS (APCI$^+$) 599 (M+1)

EXAMPLE 298

1-Acetyl-N-{3-[4-(trans-cinnamyl)-1-piperazinyl]propyl}-N-(3,4-dichlorophenyl)-4-piperidinecarboxamide By a similar manner to Example 215, the titled compound was synthesized by using trans-1-cinnamylpiperazine.

HPLC analysis (220 nm): Purity 95% (Retention time 5.158 minutes) MS (APCI$^+$) 557 (M+1)

EXAMPLE 299

1-Acetyl-N-(3,4-dichlorophenyl)-N-[3-(4-piperonyl-1-piperazinyl)propyl]-4-piperidinecarboxamide By a similar manner to Example 215, the titled compound was synthesized by using 1-piperonylpiperazine.

HPLC analysis (220 nm): Purity 97% (Retention time 4.836 minutes) MS (APCI$^+$) 575 (M+1)

EXAMPLE 300

1-Acetyl-N-(3,4-dichlorophenyl)-N-(3-{4-[4-(1H-tetrazol-1-yl)benzyl]-1-piperidinyl}propyl)-4-piperidinecarboxamide By a similar manner to Example 215, the titled compound was synthesized by using 4-[4-(1H-tetrazol-1-yl)benzyl]piperidine hydrochloride (Reference Example 95-3).

HPLC analysis (220 nm): Purity 98% (Retention time 4.508 minutes) MS (APCI$^+$) 598 (M+1) $^1$H NMR (CDCl$_3$) δ 1.2-1.4 (2H, m), 1.4-2.0 (11H, m), 2.05 (3H, s), 2.24-2.5 (4H, m), 2.61 (2H, d, J=6.2 Hz), 2.75-3.0 (3H, m), 3.6-3.9 (3H, m), 4.4-4.6 (1H, m), 7.02 (1H, dd, J=8.6, 2.6 Hz), 7.27-7.35 (3H, m), 7.52 (1H, d, J=8.6 Hz), 7.60 (2H, d, J=8.6 Hz), 8.95 (1H, s)

EXAMPLE 301

1-Acetyl-N-(3,4-dichlorophenyl)-N-(3-{4-[2-(1H-tetrazol-1-yl)benzyl]-1-piperidinyl}propyl)-4-piperidinecarboxamide By a similar manner to Example 215, the titled compound was synthesized by using 4-[2-(1H-tetrazol-1-yl)benzyl]piperidine hydrochloride (Reference Example 96).

HPLC analysis (220 nm): Purity 98% (Retention time 4.352 minutes) MS (APCI$^+$) 598 (M+1)

EXAMPLE 302

1-Acetyl-N-(3,4-dichlorophenyl)-N-{3-[4-(4-nitrobenzyl)-1-piperidinyl]propyl}-4-piperidinecarboxamide By a similar manner to Example 215, the titled compound was synthesized by using 4-(4-nitrobenzyl)piperidine hydrochloride.

HPLC analysis (220 nm): Purity 98% (Retention time 4.604 minutes) MS (APCI$^+$) 575 (M+1)

EXAMPLE 303

1-Acetyl-N-{3-[4-(4-aminobenzyl)-1-piperidinyl]propyl}-N-(3,4-dichlorophenyl)-4-piperidinecarboxamide 1-Acetyl-N-(3,4-dichlorophenyl)-N-{3-[4-(4-nitrobenzyl)-1-piperidinyl]propyl}-4-piperidinecarboxamide (Example 302)(70 mg, 0.12 mmol) was dissolved in ethanol (0.4 mL). To the mixture was added stannic chloride 2 hydrate (135 mg, 0.61 mmol), and the mixture was heated for 30 minutes under reflux. The mixture was cooled, and to the mixture were added aqueous solution of 1N-sodium hydroxide (10 mL) and ethyl acetate (10 mL). The resulting white precipitates were filtered off with Celite. The filtrate was subjected to extraction procedure. The organic layer was washed with saturated aqueous solution of sodium chloride, dried over anhydrous sodium sulfate and concentrated under reduced pressure. The concentrate was subjected to column chromatography (alumina 10 g, ethyl acetate), and the desired fraction was concentrated under reduced pressure to give the titled compound (63 mg, 0.11 mmol, Yield 92%) as pale yellow oily substance.

HPLC analysis (220 nm): Purity 97% (Retention time 4.216 minutes) MS (APCI$^+$) 545 (M+1) $^1$H NMR (CDCl$_3$) δ 1.1-1.3 (2H, m), 1.3-1.9 (11H, m), 2.06 (3H, s), 2.26 (2H, t, J=7.5 Hz), 2.25-2.39 (1H, m), 2.40 (2H, d, J=7.0 Hz), 2.75-3.0 (3H, m), 3.4-3.85 (4H, m), 4.4-4.6 (1H, m), 6.61 (2H, d, J=8.4 Hz), 6.91 (2H, d, J=8.4 Hz), 7.03 (1H, dd, J=8.4, 2.4 Hz), 7.32 (1H, d, J=2.4 Hz), 7.52 (1H, d, J=8.4 Hz)

EXAMPLE 304

1-Acetyl-N-(3,4-dichlorophenyl)-N-[3-(4-{4-[(methylsulfonyl)amino]benzyl}-1-piperidinyl)propyl]-4-piperidinecarboxamide 1-Acetyl-N-{3-[4-(4-aminobenzyl)-1-piperidinyl]propyl}-N-(3,4-dichlorophenyl)-4-piperidinecarboxamide (Example 303) (18 mg, 0.033 mmol) was dissolved in tetrahydrofuran (0.3 mL). To the solution were added triethylamine (5.0 mg, 0.050 mmol) and methahesulfonyl chloride (4.9 mg, 0.043 mmol), and the mixture was stirred at room temperature for 30 minutes. To the reaction mixture was added aqueous solution of 1N-sodium hydroxide (5 mL), and the mixture was extracted with ethyl acetate (5 mL×2). The organic layer was dried over magnesium sulfate and concentrated under reduced pressure. The concentrate was subjected to alumina column chromatography (alumina 2 g, ethyl acetate), and the desired fraction was concentrated under reduced pressure to give the titled compound (16 mg, 0.026 mmol, Yield 78%) as a colorless oily substance.

HPLC analysis (220 nm): Purity 100% (Retention time 4.232 minutes) MS (APCI$^+$) 623 (M+1)

EXAMPLE 305

1-Acetyl-N-(3-{4-[4-(acetylamino)benzyl]-1-piperidinyl}propyl)-N-(3,4-dichlorophenyl)-4-piperidinecarboxamide 1-Acetyl-N-(3-[4-(4-aminobenzyl)-1-piperidinyl]propyl}-N-(3,4-dichlorophenyl)-4-piperidinecarboxamide (Example 303) (18 mg, 0.033 mmol) was dissolved in tetrahydrofuran (0.3 mL). To the solution were added triethylamine (5.0 mg, 0.050 mmol) and acetyl chloride (3.4 mg, 0.043 mmol), and the mixture was stirred at room temperature for 30 minutes. To the reaction mixture was added aqueous solution of 1N-sodium hydroxide (5 mL), and the mixture was extracted with ethyl acetate (5 mL×2). The organic layer was dried over magnesium sulfate and concentrated under reduced pressure. The concentrate was subjected to alumina column chromatography (alumina 2 g, ethyl acetate), and the desired fraction was concentrated under reduced pressure to give the titled compound (18 mg, 0.031 mmol, Yield 93%) as a colorless oily substance.

HPLC analysis (220 nm): Purity 99% (Retention time 4.363 minutes) MS (APCI$^+$) 587 (M+1)

EXAMPLE 306

N-(3,4-Dichlorophenyl)-1-(methylsulfonyl)-N-(3-{4-[4-(1H-tetrazol-1-yl)benzyl]-1-piperazinyl}propyl)-4-piperidinecarboxamide By a similar manner to Example 215, the titled compound was synthesized by using 1-[4-(1H-tetrazol-1-yl)benzyl]piperazine 2 hydrochloride.

HPLC analysis (220 nm): Purity 100% (Retention time 3.959 minutes) MS (APCI$^+$) 635 (M+1)

EXAMPLE 307

N-{3-[4-(trans-Cinnamyl)-1-piperazinyl]propyl}-N-(3,4-dichlorophenyl)-1-(methylsulfonyl)-4-piperidinecarboxamide By a similar manner to Example 215, the titled compound was synthesized by using trans-1-cinnamylpiperazine.

HPLC analysis (220 nm): Purity 100% (Retention time 4.565 minutes) MS (APCI$^+$) 593 (M+1)

EXAMPLE 308

N-(3,4-Dichlorophenyl)-1-(methylsulfonyl)-N-[3-(4-piperonyl-1-piperazinyl)propyl]-4-piperidinecarboxamide By a similar manner to Example 215, the titled compound was synthesized by using 1-piperonylpiperazine.

HPLC analysis (220 nm): Purity 98% (Retention time 4.392 minutes) MS (APCI$^+$) 611 (M+1)

EXAMPLE 309

N-(3,4-Dichlorophenyl)-1-(methylsulfonyl)-N-(3-{4-[4-(1H-tetrazol-1-yl)benzyl]-1-piperidinyl}propyl)-4-piperidinecarboxamide By a similar manner to Example 215, the titled compound was synthesized by using 4-[4-(1H-tetrazol-1-yl)benzyl]piperidine hydrochloride (Reference Example 95-3).

HPLC analysis (220 nm): Purity 100% (Retention time 4.429 minutes) MS (APCI⁺) 634 (M+1) ¹H NMR (CDCl₃) δ 1.2-1.4 (2H, m), 1.4-2.0 (11H, m), 2.15-2.3 (3H, m), 2.45-2.7 (2H, m), 2.62 (2H, d, J=6.6 Hz), 2.74 (3H, s), 2.8-2.9 (2H, m), 3.6-3.8 (4H, m), 7.03 (1H, dd, J=8.6, 2.6 Hz), 7.27-7.36 (3H, m), 7.52 (1H, d, J=8.6 Hz), 7.60 (2H, d, J=8.6 Hz), 8.95 (1H, s)

EXAMPLE 310

N-(3,4-Dichlorophenyl)-1-(methylsulfonyl)-N-(3-{4-[2-(1H-tetrazol-1-yl)benzyl]-1-piperidinyl}propyl)-4-piperidinecarboxamide By a similar manner to Example 215, the titled compound was synthesized by using 4-[2-(1H-tetrazol-1-yl)benzyl]piperidine hydrochloride (Reference Example 96).

HPLC analysis (220 nm): Purity 100% (Retention time 4.111 minutes) MS (APCI⁺) 634 (M+1)

EXAMPLE 311

N-(3,4-Dichlorophenyl)-1-(methylsulfonyl)-N-{3-[4-(4-nitrobenzyl)-1-piperidinyl]propyl}-4-piperidinecarboxamide By a similar manner to Example 215, the titled compound was synthesized by using 4-(4-nitrobenzyl)piperidine hydrochloride.

HPLC analysis (220 nm): Purity 100% (Retention time 4.444 minutes) MS (APCI⁺) 611 (M+1)

EXAMPLE 312

N-{3-[4-(4-Aminobenzyl)-1-piperidinyl]propyl}-N-(3,4-dichlorophenyl)-1-(methylsulfonyl)-4-piperidinecarboxamide By a similar manner to the synthesis of 1-acetyl-N-{3-[4-(4-aminobenzyl)-1-piperidinyl]propyl}-N-(3,4-dichlorophenyl)-4-piperidinecarboxamide (Example 303), the titled compound was obtained by using N-(3,4-dichlorophenyl)-1-(methylsulfonyl)-N-(3-[4-(4-nitrobenzyl)-1-piperidinyl]propyl}-4-piperidinecarboxamide (Example 311) as a starting material.

HPLC analysis (220 nm): Purity 99% (Retention time 4.363 minutes) MS (APCI⁺) 581 (M+1) ¹H NMR (CDCl₃) δ 1.3-1.9 (13H, m), 2.00 (2H, s), 2.05-2.35 (3H, m), 2.43 (2H, d, J=5.4 Hz), 2.45-2.65 (2H, m), 2.73 (3H, s), 3.13 (2H, br d, J=11.0 Hz), 3.63-3.76 (4H, m), 6.61 (2H, d, J=8.4 Hz), 6.91 (2H, d, J=8.4 Hz), 7.12 (1H, dd, J=8.4, 1.8 Hz), 7.35 (1H, d, J=1.8 Hz), 7.53 (1H, d, J=8.4 Hz)

EXAMPLE 313-1

N-[3-(4-{4-[Bis(methylsulfonyl)amino]benzyl}-1-piperidinyl)propyl]-N-(3,4-dichlorophenyl)-1-(methylsulfonyl)-4-piperidinecarboxamide

EXAMPLE 313-2

N-(3,4-Dichlorophenyl)-1-(methylsulfonyl)-N-[3-(4-{4-[(methylsulfonyl)amino]benzyl}-1-piperidinyl)propyl]-4-piperidinecarboxamide N-{3-[4-(4-aminobenzyl)-1-piperidinyl]propyl}-N-(3,4-dichlorophenyl)-1-(methylsulfonyl)-4-piperidinecarboxamide (Example 312)(30 mg, 0.052 mmol) was dissolved in tetrahydrofuran (0.3 mL). To the solution were added triethylamine (10.5 mg, 0.10 mmol) and methanesulfonyl chloride (8.9 mg, 0.078 mmol), and the mixture was stirred at room temperature for 30 minutes. To the solution were further added triethylamine (10.5 mg, 0.10 mmol) and methanesulfonyl chloride (8.9 mg, 0.078 mmol), and the mixture was stirred at room temperature for 30 minutes. To the reaction mixture was added aqueous solution of 1N-sodium hydroxide (7 mL), and the mixture was extracted with ethyl acetate (10 mL×2). The organic layer was dried over magnesium sulfate and concentrated under reduced pressure. The concentrate was subjected to alumina column chromatography (alumina 4 g, ethyl acetate), and the fraction firstly eluted was concentrated under reduced pressure to give N-[3-(4-{4-[bis(methylsulfonyl)amino]benzyl}-1-piperidinyl)propyl)-N-(3,4-dichlorophenyl)-1-(methylsulfonyl)-4-piperidinecarboxamide (12 mg, 0.016 mmol, 31%) as a colorless oily substance.

HPLC analysis (220 nm): Purity 95% (Retention time 3.886 minutes) ¹H NMR (CDCl₃) δ 1.1-1.4 (2H, m), 1.4-2.0 (10H, m), 2.1-2.4 (4H, m), 2.5-2.7 (2H, m), 2.74 (3H, s), 2.83 (2H, br d, J=10.4 Hz), 3.40 (6H, s), 3.6-3.8 (4H, m), 7.02 (1H, dd, J=8.4, 2.6 Hz), 7.17-7.4 (5H, m), 7.52 (1H, d, J=8.4 Hz)

The fraction lately eluted was concentrated under reduced pressure, N-(3,4-dichlorophenyl)-1-(methylsulfonyl)-N-[3-(4-{4-[(methylsulfonyl)amino]benzyl}-1-piperidinyl)propyl]-4-piperidinecarboxamide (13 mg, 0.020 mmol, 38%) as a colorless oily substance.

HPLC analysis (220 nm): Purity 98% (Retention time 4.125 minutes) ¹H NMR (CDCl₃) δ 1.1-1.3 (2H, m), 1.35-2.0 (10H, m), 2.1-2.35 (4H, m), 2.4-2.7 (2H, m), 2.50 (2H, d, J=6.2 Hz), 2.74 (3H, s), 2.83 (2H, br d, J=10.8 Hz), 2.99 (3H, s), 3.6-3.8 (4H, m), 7.03 (1H, dd, J=8.4, 2.6 Hz), 7.12-7.2 (3H, m), 7.2-7.4 (3H, m), 7.52 (1H, d, J=8.4 Hz)

EXAMPLE 314

1N-(3-{4-[4-(Acetylamino)benzyl]-1-piperidinyl}propyl)-N-(3,4-dichlorophenyl)-1-(methylsulfonyl)-4-piperidinecarboxamide By a similar manner to the synthesis of 1-acetyl-N-(3-{4-[4-(acetylamino)benzyl]-1-piperidinyl}propyl}-N-(3,4-dichlorophenyl)-4-piperidinecarboxamide (Example 305), the titled compound was obtained by using N-{3-[4-(4-aminobenzyl)-1-piperidinyl]propyl}-N-(3,4-dichlorophenyl)-1-(methylsulfonyl)-4-piperidinecarboxamide (Example 312) as a starting material.

HPLC analysis (220 nm): Purity 99% (Retention time 4.679 minutes) MS (APCI⁺) 623 (M+1)

EXAMPLE 315

1-Acetyl-N-{3-[4-(4-cyanobenzyl)-1-piperidinyl]propyl}-N-(3,4-dichlorophenyl)-4-piperidinecarboxamide By a similar manner to Example 211, the titled compound was synthesized by using 4-(4-cyanobenzyl)piperidine hydrochloride (Reference Example 93).

HPLC analysis (220 nm): Purity 92% (Retention time 4.607 minutes) MS (APCI⁺) 555 (M+1)

EXAMPLE 316

1-Acetyl-N-(3,4-dichlorophenyl)-N-[3-(4-{4-[methyl(methylsulfonyl)amino]benzyl}-1-piperidinyl)propyl]-4-piperidinecarboxamide By a similar manner to Example 211, the titled compound was synthesized by using 4-[methyl(methylsulfonyl)amino]benzyl}piperidine hydrochloride (Reference Example 98-3).

HPLC analysis (220 nm): Purity 99% (Retention time 4.338 minutes) MS (APCI$^+$) 637 (M+1)

EXAMPLE 317

1-Acetyl-N-(3,4-dichlorophenyl)-N-[3-(4-piperonyl-1-piperidinyl)propyl]-4-piperidinecarboxamide By a similar manner to Example 211, the titled compound was synthesized by using 4-piperonylpiperidine hydrochloride (Reference Example 94).

HPLC analysis (220 nm): Purity 96% (Retention time 4.916 minutes) MS (APCI$^+$) 574 (M+1)

EXAMPLE 318

1-Acetyl-N-(3,4-dichlorophenyl)-N-{3-[4-(4-morpholinobenzyl)-1-piperidinyl]propyl}-4-piperidinecarboxamide By a similar manner to Example 211, the titled compound was synthesized by using 4-(4-morpholinobenzyl)piperidine hydrochloride (Reference Example 97).

HPLC analysis (220 nm): Purity 87% (Retention time 4.634 minutes) MS (APCI$^+$) 615 (M+1)

EXAMPLE 319

N-{3-[4-(4-Cyanobenzyl)-1-piperidinyl]propyl}-N-(3,4-dichlorophenyl)-1-(methylsulfonyl)-4-piperidinecarboxamide By a similar manner to Example 215, the titled compound was synthesized by using 4-(4-cyanobenzyl)piperidine hydrochloride (Reference Example 93)

HPLC analysis (220 nm): Purity 99% (Retention time 4.236 minutes) MS (APCI$^+$) 591 (M+1)

EXAMPLE 320

N-(3,4-Dichlorophenyl)-N-[3-(4-{4-[methyl(methylsulfonyl)amino]benzyl}-1-piperidinyl)propyl]-1-(methylsulfonyl)-4-piperidinecarboxamide By a similar manner to Example 215, the titled compound was synthesized by using 4-[methyl(methylsulfonyl)amino]benzyl}piperidine hydrochloride (Reference Example 98-3).

HPLC analysis (220 nm): Purity 97% (Retention time 4.291 minutes) MS (APCI$^+$) 673 (M+1)

EXAMPLE 321

N-(3,4-Dichlorophenyl)-1-(methylsulfonyl)-N-[3-(4-piperonyl-1-piperidinyl)propyl]-4-piperidinecarboxamide By a similar manner to Example 215, the titled compound was synthesized by using 4-piperonylpiperidine hydrochloride (Reference Example 94).

HPLC analysis (220 nm): Purity 93% MS (APCI$^+$) 610 (M+1)

EXAMPLE 322

N-(3,4-Dichlorophenyl)-1-(methylsulfonyl)-N-[3-(4-oxo-1-piperidinyl)propyl]-4-piperidinecarboxamide The title compound was prepared using a similar procedure to that described for example 190 from 4-piperidone hydrochloride monohydrate, yield 43%.

$^1$H NMR (CDCl$_3$) δ 1.55-2.05 (6H, m), 2.15-2.75 (13H, m), 2.74 (3H, s), 3.65-3.8 (4H, m), 7.05 (1H, dd, J=2.5, 8.6 Hz), 7.33 (1H, d, J=2.5 Hz), 7.55 (1H, d, J=8.6 Hz)

EXAMPLE 323

N-(3,4-Dichlorophenyl)-N-{3-[4-(methylamino)-1-piperidinyl]propyl}-1-(methylsulfonyl)-4-piperidinecarboxamide The title compound was prepared using a similar procedure to that described for example 196 from the title compound of example 322, yield 97%.

$^1$H NMR (CDCl$_3$) δ 1.45-2.05 (12H, m), 2.1-2.4 (3H, m), 2.45-2.95 (5H, m), 2.51 (3H, s), 2.74 (3H, s), 3.6-3.8 (4H, m), 4.2 (1H, br), 7.06 (1H, dd, J=2.5, 8.4 Hz), 7.32 (1H, d, J=2.5 Hz), 7.54 (1H, d, J=8.4 Hz)

EXAMPLE 324

N-(3,4-Dichlorophenyl)-N-(3-(4-[[(4-fluorophenyl)sulfonyl](methyl)amino]-1-piperidinyl}propyl)-1-(methylsulfonyl)-4-piperidinecarboxamide The title compound was prepared using a similar procedure to that described for example 195 from the title compound of example 323, yield 88%.

$^1$H NMR (CDCl$_3$) δ 1.3-2.05 (12H, m), 2.1-2.35 (3H, m), 2.45-2.95 (4H, m), 2.74 (3H, s), 2.74 (3H, s), 3.55-3.9 (5H, m), 7.01 (1H, dd, J=2.2, 8.4 Hz), 7.1-7.25 (2H, m), 7.29 (1H, d, J=2.2 Hz), 7.52 (1H, d, J=8.4 Hz), 7.75-7.9 (2H, m)

EXAMPLE 325

N-(3,4-Dichlorophenyl)-N-(3-{4-[[(4-methoxyphenyl)sulfonyl](methyl)amino]-1-piperidinyl}propyl)-1-(methylsulfonyl)-4-piperidinecarboxamide The title compound was prepared using a similar procedure to that described for example 195 from the title compound of example 323 and 4-methoxybenzenesulfonyl chloride, yield 87%.

$^1$H NMR (CDCl$_3$) δ 1.3-2.05 (12H, m), 2.1-2.35 (3H, m), 2.45-2.9 (4H, m), 2.72 (3H, s), 2.74 (3H, s), 3.55-3.9 (5H, m), 3.87 (3H, s), 6.96 (2H, d, J=9.2 Hz), 7.01 (1H, dd, J=2.6, 8.4 Hz), 7.29 (1H, d, J=2.6 Hz), 7.52 (1H, d, J=8.4 Hz), 7.73 (2H, d, J=9.2 Hz)

EXAMPLE 326

N-(3,4-Dichlorophenyl)-N-(3-(4-[(4-fluorophenyl) sulfinyl]-1-piperidinyl}propyl)-1-(methylsulfonyl)-4-piperidinecarboxamide The title compound was prepared using a similar procedure to that described for example 190 from the title compound of reference example 62-2, yield 53%.

$^1$H NMR (CDCl$_3$) δ 1.4-2.05 (12H, m), 2.1-3.0 (8H, m), 2.74 (3H, s), 3.55-3.85 (4H, m), 7.02 (1H, dd, J=2.4, 8.4 Hz), 7.15-7.3 (2H, m), 7.29 (1H, d, J=2.4 Hz), 7.5-7.7 (2H, m), 7.53 (1H, d, J=8.4 Hz)

EXAMPLE 327

1-Acetyl-N-(3,4-dichlorophenyl)-N-(3-{4-[(4-ethoxyphenyl)sulfonyl]-1-piperidinyl}propyl)-4-piperidinecarboxamide The title compound was prepared using a similar procedure to that described for example 179 from the title compound of reference example 99, yield 88%.

$^1$H NMR (CDCl$_3$) δ 1.4-2.1 (12H, m), 1.46 (3H, t, J=7.0 Hz), 2.05 (3H, s), 2.2-2.5 (4H, m), 2.7-3.0 (4H, m), 3.55-3.9 (3H, m), 4.11 (2H, q, J=7.0 Hz), 4.4-4.65 (1H, m), 6.99 (2H, d, J=8.8 Hz), 7.01 (1H, dd, J=2.4, 8.5 Hz), 7.29 (1H, d, J=2.4 Hz), 7.52 (1H, d, J=8.5 Hz), 7.75 (2H, d, J=8.8 Hz)

EXAMPLE 328

N-(3,4-Dichlorophenyl)-N-(3-{4-[(4-ethoxyphenyl) sulfonyl]-1-piperidinyl}propyl)-1-(methylsulfonyl)-4-piperidinecarboxamide The title compound was prepared using a similar procedure to that described for example 190 from the title compound of reference example 99, yield 92%.

$^1$H NMR (CDCl$_3$) δ 1.4-2.1 (12H, m), 1.46 (3H, t, J=7.1 Hz), 2.1-2.35 (3H, m), 2.45-3.0 (5H, m), 2.73 (3H, s), 3.55-3.8 (4H, m), 4.11 (2H, q, J=7.1 Hz), 6.99 (2H, d, J=9.0 Hz), 7.01 (1H, dd, J=2.5, 8.4 Hz), 7.28 (1H, d, J=2.5 Hz), 7.52 (1H, d, J=8.4 Hz), 7.75 (2H, d, J=9.0 Hz)

EXAMPLE 329

N-(3,4-Dichlorophenyl)-1-(methylsulfonyl)-N-(3-{4-[4-(trifluoromethyl)benzyl]-1-piperidinyl}propyl)-4-piperidinecarboxamide A mixture of the title compound of reference example 57 (428 mg, 1.00 mmol), the title compound of reference example 28 (336 mg, 1.20 mmol), potassium iodide (199 mg, 1.20 mmol), and potassium carbonate (498 mg, 3.60 mmol) in acetonitrile (24 mL) was stirred at 80° C. for 13 hours. The reaction mixture was evaporated under reduced pressure, ethyl acetate (40 mL) was added to the residue, the organic layer was washed with water (10 mL), 1 N aqueous sodium hydroxide (2×5 mL), and brine (5 mL). The organic layer was dried over anhydrous magnesium sulfate, filtered, evaporated under reduced pressure, and the residue was subjected to column chromatography (silica gel 10 g, ethyl acetate). The fractions containing the product were collected and evaporated under reduced pressure. Diisopropyl ether was added to the residue, the resulting precipitate was collected by filtration, washed with diisopropyl ether, dried under reduced pressure to afford the title compound (393 mg, 0.62 mmol, 62%) as a white solid.

$^1$H NMR (CDCl$_3$) δ 1.1-2.05 (13H, m), 2.1-2.35 (3H, m), 2.45-2.9 (4H, m), 2.57 (2H, d, J=6.2 Hz), 2.74 (3H, s), 3.55-3.85 (4H, m), 7.02 (1H, dd, J=2.4, 8.4 Hz), 7.23 (2H, d, J=8.4 Hz), 7.31 (1H, d, J=2.4 Hz), 7.52 (1H, d, J=8.4 Hz), 7.52 (2H, d, J=8.4 Hz)

EXAMPLE 330

N-(3,4-Dichlorophenyl)-1-(methylsulfonyl)-N-[3-(4-{[4-(trifluoromethyl)phenyl]sulfonyl}-1-piperidinyl) propyl]-4-piperidinecarboxamide The title compound was prepared using a similar procedure to that described for example 329 from the title compound of reference example 100, yield 72%.

$^1$H NMR (CDCl$_3$) δ 1.5-2.05 (12H, m), 2.1-2.4 (3H, m), 2.4-3.0 (5H, m), 2.74 (3H, s), 3.55-3.8 (4H, m), 7.00 (1H, dd, J=2.6, 8.2 Hz), 7.28 (1H, d, J=2.6 Hz), 7.52 (1H, d, J=8.2 Hz), 7.84 (2H, d, J=8.6 Hz), 8.00 (2H, d, J=8.6 Hz)

EXAMPLE 331

N-(3,4-Dichlorophenyl)-N-(3-{4-[(4-isopropoxyphenyl)sulfonyl]-1-piperidinyl}propyl)-1-(methylsulfonyl)-4-piperidinecarboxamide The title compound was prepared using a similar procedure to that described for example 329 from the title compound of reference example 101, yield 84%.

$^1$H NMR (CDCl$_3$) δ 1.38 (6H, d, J=6.0 Hz), 1.5-2.05 (12H, m), 2.1-2.35 (3H, m), 2.45-3.0 (5H, m), 2.74 (3H, s), 3.55-3.8 (4H, m), 4.65 (1H, sept, J=6.0 Hz), 6.97 (2H, d, J=9.0 Hz), 7.01 (1H, dd, J=2.6, 8.4 Hz), 7.28 (1H, d, J=2.6 Hz), 7.52 (1H, d, J=8.4 Hz), 7.74 (2H, d, J=9.0 Hz)

EXAMPLE 332

N-(3-{4-[(4-tert-Butylphenyl)sulfonyl]-1-piperidinyl}propyl)-N-(3,4-dichlorophenyl)-1-(methylsulfonyl)-4-piperidinecarboxamide The title compound was prepared using a similar procedure to that described for example 329 from the title compound of reference example 102, yield 67%.

$^1$H NMR (CDCl$_3$) δ 1.35 (9H, s), 1.5-2.1 (12H, m), 2.1-2.35 (3H, m), 2.45-3.0 (5H, m), 2.74 (3H, s), 3.55-3.8 (4H, m), 7.01 (1H, dd, J=2.6, 8.2 Hz), 7.28 (1H, d, J=2.6 Hz), 7.52 (1H, d, J=8.2 Hz), 7.56 (2H, d, J=8.6 Hz), 7.77 (2H, d, J=8.6 Hz)

EXAMPLE 333

N-(3,4-Dichlorophenyl)-1-(methylsulfonyl)-N-[3-(4-{[4-(trifluoromethoxy)phenyl]sulfonyl}-1-piperidinyl)propyl]-4-piperidinecarboxamide The title compound was prepared using a similar procedure to that described for example 329 from the title compound of reference example 103, yield 74%.

$^1$H NMR (CDCl$_3$) δ 1.45-2.1 (12H, m), 2.1-2.35 (3H, m), 2.45-3.05 (5H, m), 2.74 (3H, s), 3.55-3.85 (4H, m), 7.01 (1H, dd, J=2.2, 8.4 Hz), 7.28 (1H, d, J=2.2 Hz), 7.39 (2H, d, J=8.6 Hz), 7.52 (1H, d, J=8.4 Hz), 7.91 (2H, d, J=8.6 Hz)

EXAMPLE 334

N-(3,4-Dichlorophenyl)-1-(methylsulfonyl)-N-[3-(4-{[4-(methylsulfonyl)phenyl]sulfonyl}-1-piperidinyl)propyl]-4-piperidinecarboxamide The title compound was prepared using a similar procedure to that described for example 329 from the title compound of reference example 104, yield 86%.

$^1$H NMR (CDCl$_3$) δ 1.45-2.1 (12H, m), 2.1-2.35 (3H, m), 2.45-2.65 (2H, m), 2.73 (3H, s), 2.8-3.05 (3H, m), 3.13 (3H, s), 3.55-3.8 (4H, m), 7.01 (1H, dd, J=2.6, 8.4 Hz), 7.28 (1H, d, J=2.6 Hz), 7.52 (1H, d, J=8.4 Hz), 8.07 (2H, d, J=8.6 Hz), 8.16 (2H, d, J=8.6 Hz)

EXAMPLE 335

N-(3,4-Dichlorophenyl)-N-{3-[4-(4-isobutyrylbenzyl)-1-piperidinyl]propyl}-1-(methylsulfonyl)-4-piperidinecarboxamide The title compound was prepared using a similar procedure to that described for example 329 from the title compound of reference example 105, yield 80%.

$^1$H NMR (CDCl$_3$) δ 1.05-2.05 (13H, m), 1.21 (6H, d, J=7.1 Hz), 2.1-2.35 (3H, m), 2.45-2.9 (4H, m), 2.57 (2H, d, J=6.6 Hz), 2.74 (3H, s), 3.54 (1H, sept, J=7.1 Hz), 3.55-3.8 (4H, m), 7.02 (1H, dd, J=2.4, 8.4 Hz), 7.21 (2H, d, J=8.1 Hz), 7.31 (1H, d, J=2.4 Hz), 7.52 (1H, d, J=8.4 Hz), 7.88 (2H, d, J=8.1 Hz)

EXAMPLE 336

N-(3,4-Dichlorophenyl)-N-(3-{4-[4-(1-hydroxy-2-methylpropyl)benzyl]-1-piperidinyl}propyl)-1-(methylsulfonyl)-4-piperidinecarboxamide To a stirred solution of the title compound of example 335 (318 mg, 0.50 mmol) in a mixture of methanol (5 mL) and THF (5 mL) was added sodium borohydride (38 mg, 1.0 mmol). The reaction mixture was stirred at room temperature for 16 hours before the addition of 1N hydrochloric acid (2 mL). After being stirred at room temperature for 30 minutes, 1N aqueous sodium hydroxide (4 mL) was added and the mixture was evaporated under reduced pressure. Water (15 mL) was added and extracted with dichloromethane (30 mL, 2×15 mL). The combined organic layers were dried over anhydrous magnesium sulfate, filtered, and evaporated under reduced pressure. A mixture of ethanol and ethyl acetate was added to the residue, the resulting precipitate, was collected by filtration, washed with ethyl acetate and dried under reduced pressure to afford the title compound (280 mg, 0.44 mmol, yield 88%) as a white solid.

$^1$H NMR (CDCl$_3$+CD$_3$OD) δ 0.77 (3H, d, J=7.0 Hz), 1.00 (3H, d, J=7.0 Hz), 1.1-2.05 (14H, m), 2.1-2.35 (3H, m), 2.45-2.9 (4H, m), 2.51 (2H, d, J=6.6 Hz), 2.75 (3H, s), 3.55-3.8 (4H, m), 4.29 (1H, d, J=7.0 Hz), 7.07 (1H, dd, J=2.4, 8.4 Hz), 7.08 (2H, d, J=8.1 Hz), 7.21 (2H, d, J=8.1 Hz), 7.35 (1H, d, J=2.4 Hz), 7.55 (1H, d, J=8.4 Hz)

EXAMPLE 337

N-(3,4-Dichlorophenyl)-N-(3-[4-(4-isobutylbenzyl)-1-piperidinyl]propyl}-1-(methylsulfonyl)-4-piperidinecarboxamide To a stirred solution of the title compound of example 335 (318 mg, 0.50 mmol) in trifluoroacetic acid (5 mL) was added triethylsilane (0.399 mL, 2.50 mmol), and the mixture was stirred at room temperature for 2 days. The reaction mixture was evaporated under reduced pressure, 1N aqueous sodium hydroxide (15 mL) was added and the aqueous layer was extracted with ethyl acetate (15 mL, 2×10 mL). The combined organic layers were dried over anhydrous magnesium sulfate, filtered and evaporated under reduced pressure. The residue was subjected to column chromatography (silica gel 10 g, ethyl acetate/methanol=1/0 to 9/1). The fractions containing the product were collected and evaporated under reduced pressure. Diisopropyl ether was added to the residue, the resulting precipitate was collected by filtration, washed with diisopropyl ether and dried under reduced pressure to afford the title compound (236 mg, 0.38 mmol, yield 76%) as a white solid.

$^1$H NMR (CDCl$_3$) δ 0.89 (6H, d, J=6.6 Hz), 1.1-2.05 (14H, m), 2.1-2.35 (3H, m), 2.35-2.9 (4H, m), 2.43 (2H, d, J=7.4 Hz), 2.47 (2H, d, J=6.6 Hz), 2.74 (3H, s), 3.55-3.8 (4H, m), 7.03 (1H, dd, J=2.4, 8.4 Hz), 7.03 (4H, s), 7.31 (1H, d, J=2.4 Hz), 7.52 (1H, d, J=8.4 Hz)

EXAMPLE 338

N-(3,4-Dichlorophenyl)-1-(methylsulfonyl)-N-(3-{4-[4-(methylsulfonyl)benzoyl]-1-piperidinyl}propyl)-4-piperidinecarboxamide The title compound was prepared using a similar procedure to that described for example 329 from the title compound of reference example 106, yield 69%.

$^1$H NMR (CDCl$_3$) δ 1.55-2.45 (15H, m)r, 2.45-3.0 (4H, m), 2.74 (3H, s), 3.09 (3H, s), 3.1-3.35 (1H, m), 3.6-3.85 (4H, m), 7.05 (1H, dd, J=2.4, 8.4 Hz), 7.32 (1H, d, J=2.4 Hz), 7.54 (1H, d, J=8.4 Hz), 8.0-8.15 (4H, m)

EXAMPLE 339

N-(3,4-Dichlorophenyl)-N-[3-(4-{hydroxy[4-(methylsulfonyl)phenyl]methyl}-1-piperidinyl)propyl]-1-(methylsulfonyl)-4-piperidinecarboxamide The title compound was prepared using a similar procedure to that described for example 336 from the title compound of example 338, yield 84%.

$^1$H NMR (CDCl$_3$) δ 1.1-2.35 (16H, m), 2.45-3.05 (4H, m), 2.74 (3H, s), 3.06 (3H, s), 3.55-3.8 (4H, m), 4.53 (1H, d, J=6.6 Hz), 7.02 (1H, dd, J=2.5, 8.3 Hz), 7.30 (1H, d, J=2.5 Hz), 7.51 (2H, d, J=8.4 Hz), 7.52 (1H, d, J=8.3 Hz), 7.91 (2H, d, J=8.4 Hz)

EXAMPLE 340

N-(3,4-Dichlorophenyl)-N-{3-[4-(ethyl{[4-(methylsulfanyl)phenyl]sulfonyl}amino)-1-piperidinyl]propyl}-1-(methylsulfonyl)-4-piperidinecarboxamide The title compound was prepared using a similar procedure to that described for example 329 from the title compound of reference example 107, yield 70%.

¹H NMR (CDCl₃) δ 1.22 (3H, t, J=7.3 Hz), 1.4-2.05 (12H, m), 2.1-2.35 (3H, m), 2.45-2.9 (4H, m), 2.52 (3H, s), 2.74 (3H, s), 3.21 (2H, q, J=7.3 Hz), 3.5-3.85 (5H, m), 7.01 (1H, dd, J=2.4, 8.4 Hz), 7.27 (2H, d, J=8.6 Hz), 7.29 (1H, d, J=2.4 Hz), 7.52 (1H, d, J=8.4 Hz), 7.70 (2H, d, J=8.6 Hz)

EXAMPLE 341

N-(3,4-Dichlorophenyl)-N-{3-[4-(ethyl{[4-(methylsulfonyl)phenyl]sulfonyl}amino)-1-piperidinyl]propyl}-1-(methylsulfonyl)-4-piperidinecarboxamide To a stirred solution of the title compound of example 340 (500 mg, 0.71 mmol) in a mixture of methanol (5 mL) and dichloromethane (5 mL) was added a solution of Oxone (653 mg, 1.06 mmol) in water (5 mL) at 0° C. The reaction mixture was stirred at room temperature for 8 hours. The organic solvent was removed under reduced pressure, 1N aqueous sodium hydroxide (10 mL), water (50 mL) was added and extracted with a mixture of ethyl acetate and THF (2/1) three times. The combined organic layers were washed with brine, dried over anhydrous sodium sulfate, filtered, and evaporated under reduced pressure. The residue was subjected to column chromatography (silica gel 10 g, ethyl acetate/methanol 1/0 to 9/1). The fractions containing the product were collected and evaporated under reduced pressure. Diisopropyl ether was added to the residue, the resulting precipitate was collected by filtration, washed with diisopropyl ether, dried under reduced pressure to afford the title compound (158 mg, 0.21 mmol, yield 30%) as a white solid.

¹H NMR (CDCl₃) δ 1.24 (3H, t, J=6.9 Hz), 1.4-2.05 (12H, m), 2.1-2.35 (3H, m), 2.45-2.95 (4H, m), 2.74 (3H, s), 3.10 (3H, s), 3.26 (2H, q, J=6.9 Hz), 3.5-3.85 (5H, m), 7.01 (1H, dd, J=2.6, 8.4 Hz), 7.29 (1H, d, J=2.6 Hz), 7.53 (1H, d, J=8.4 Hz), 7.95-8.15 (4H, m)

EXAMPLE 342

N-(3-Chlorophanyl)-1-(methylsulfonyl)-N-(3-{4-[4-(methylsulfonyl)benzyl]-1-piperidinyl)propyl)-4-piperidinecarboxamide A mixture of the title compound of reference example 165-4 (590 mg, 1.50 mmol), 4-[4-(methylsulfonyl)benzyl]piperidine (456 mg, 1.80 mmol), potassium iodide (249 mg, 1.50 mmol), and potassium carbonate (311 mg, 2.25 mmol) in acetonitrile (15 mL) was stirred at reflux temperature for 12 hours. The reaction mixture was evaporated under reduced pressure. Ethyl acetate (40 mL) was added to the residue, and the organic layer was washed with water (10 mL), 1 N aqueous sodium hydroxide (3×10 mL), brine (10 mL). The organic layer was dried over anhydrous magnesium sulfate, filtered and evaporated under reduced pressure. The residue was subjected to column chromatography (Daisogel IR-60-40/63-W 30 g, ethyl acetate/methanol 1/0 to 4/1). The fractions containing the product were collected and evaporated under reduced pressure to afford the title compound (690 mg, 1.13 mmol, 75%) as a colorless foam.

¹H NMR (CDCl₃) δ 1.1-2.05 (13H, m), 2.1-2.35 (3H, m), 2.45-2.9 (4H, m), 2.61 (2H, d, J=6.6 Hz), 2.73 (3H, s), 3.05 (31H, s), 3.55-3.8 (4H, m), 7.0-7.15 (1H, m), 7.19 (1H, br s), 7.32 (2H, d, J=8.6 Hz), 7.39 (2H, d, J=5.4 Hz), 7.85 (2H, d, J=8.6 Hz)

EXAMPLE 343

N-(3-Chloro-4-methylphenyl)-1-(methylsulfonyl)-N-(3-{4-[4-(methylsulfonyl)benzyl]-1-piperidinyl}propyl)-4-piperidinecarboxamide To a stirred solution of the title compound of reference example 108 (355 mg, 0.70 mmol) and triethylamine (0.585 mL) in dichloromethane (10 mL) was added 1-(methylsulfonyl)-4-piperidinecarbonylchloride (474 mg, 2.10 mmol) at 0° C., and the reaction mixture was stirred at 0° C. for 1 hour. The reaction mixture was quenched with water (5 mL), the organic solvent was removed under reduced pressure, and ethyl acetate was added to the residue. The organic layer was washed with 1N aqueous sodium hydroxide, brine, dried over anhydrous magnesium sulfate, filtered, and evaporated under reduced pressure. The residue was subjected to column chromatography (Fuji Silysia Chromatorex NH-DM1020 30 g, ethyl acetate/hexane 1/1 to 3/1). The fractions containing the product were collected and evaporated under reduced pressure to afford the title compound (416 mg, 0.67 mmol, 95%) as a colorless foam.

¹H NMR (CDCl₃) δ 1.1-2.0 (13H, m), 2.15-2.35 (3H, m), 2.41 (3H, s), 2.45-2.9 (4H, m), 2.61 (2H, d, J=6.6 Hz), 2.73 (3H, s), 3.05 (3H, s), 3.55-3.8 (4H, m), 6.95 (1H, dd, J=2.2 Hz, 7.8 Hz), 7.17 (1H, d, J=2.2 Hz), 7.28 (1H, d, J=7.8 Hz), 7.32 (2H, d, J=8.4 Hz), 7.84 (2H, d, J=8.4 Hz)

EXAMPLE 344

N-[3-(Methylsulfanyl)phenyl]-1-(methylsulfonyl)-N-(3-{4-[4-(methylsulfonyl)benzyl]-1-piperidinyl}propyl)-4-piperidinecarboxamide The title compound was prepared using a similar procedure to that described for example 343 from the title compound of reference example 109, yield 94%.

¹H NMR (CDCl₃) δ 1.1-2.0 (13H, m), 2.15-2.4 (3H, m), 2.4-2.95 (4H, m), 2.50 (3H, s), 2.61 (2H, d, J=6.4 Hz), 2.73 (3H, s), 3.05 (3H, s), 3.55-3.8 (4H, m), 6.89 (1H, ddd, J=1.3 Hz, 1.9 Hz, 7.5 Hz), 7.00 (1H, t, J=1.9 Hz), 7.15-7.4 (2H, m), 7.32 (2H, d, J=8.6 Hz), 7.84 (2H, d, J=8.6 Hz)

EXAMPLE 345

1-(Methylsulfonyl)-N-(3-{4-[4-(methylsulfonyl)benzyl]-1-piperidinyl}propyl)-N-[3-(methylsulfonyl)phenyl]-4-piperidinecarboxamide The title compound was prepared using a similar procedure to that described for example 341 from the title compound of example 344, yield 43%.

¹H NMR (CDCl₃) δ 1.1-2.05 (13H, m), 2.05-2.4 (3H, m), 2.4-2.95 (4H, m), 2.62 (2H, d, J=6.4 Hz), 2.73 (3H, s), 3.05 (3H, s), 3.13 (3H, s), 3.6-3.8 (4H, m), 7.33 (2H, d, J=8.3 Hz), 7.49 (1H, ddd, J=1.1 Hz, 1.9 Hz, 7.9 Hz), 7.69 (1H, br t, J=7.9 Hz), 7.79 (1H, t, J=1.9 Hz), 7.84 (2H, d, J=8.3 Hz), 7.97 (1H, br d, J=7.6 Hz)

EXAMPLE 346

N-[4-(Methylsulfanyl)phenyl]-1-(methylsulfonyl)-N-(3-{4-[4-(methylsulfonyl)benzyl]-1-piperidinyl}propyl)-4-piperidinecarboxamide The title compound was prepared using a similar procedure to that described for example 343 from the title compound of reference example 110, yield 90%.

¹H NMR (CDCl₃) δ 1.1-2.0 (13H, m), 2.15-2.35 (3H, m), 2.4-2.95 (4H, m), 2.52 (3H, s), 2.61 (2H, d, J=6.4 Hz), 2.72 (3H, s), 3.05 (3H, s), 3.55-3.8 (4H, m), 7.06 (2H, d, J=8.4 Hz), 7.27 (2H, d, J=8.4 Hz), 7.32 (2H, d, J=8.4 Hz), 7.84 (2H, d, J=8.4 Hz)

EXAMPLE 347

1-(Methylsulfonyl)-N-(3-{4-[4-(methylsulfonyl)benzyl]-1-piperidinyl}propyl)-N-[4-(methylsulfonyl)phenyl]-4-piperidinecarboxamide The title compound was prepared using a similar procedure to that described for example 341 from the title compound of example 346, yield 46%.

¹H NMR (CDCl₃) δ 1.1-2.05 (13H, m), 2.1-2.35 (3H, m), 2.45-2.9 (4H, m), 2.61 (2H, d, J=6.2 Hz), 2.73 (3H, s), 3.05 (3H, s), 3.14 (3H, s), 3.6-3.8 (4H, m), 7.32 (2H, d, J=8.3 Hz), 7.39 (2H, d, J=8.4 Hz), 7.85 (2H, d, J=8.3 Hz), 8.04 (2H, d, J=8.4 Hz)

EXAMPLE 348

N-(3-Chloro-4-fluorophenyl)-1-(methylsulfonyl)-N-(3-{4-[4-(methylsulfonyl)benzyl]-1-piperidinyl}propyl)-4-piperidinecarboxamide The title compound was prepared using a similar procedure to that described for example 343 from the title compound of reference example 111, yield 95%.

¹H NMR (CDCl₃) δ 1.1-2.0 (13H, m), 2.1-2.35 (3H, m), 2.45-2.9 (4H, m), 2.61 (2H, d, J=5.8 Hz), 2.73 (3H, s), 3.05 (3H, s), 3.55-3.8 (4H, m), 7.05 (1H, ddd, J=2.6 Hz, 4.4 Hz, 8.8 Hz), 7.15-7.4 (2H, m), 7.32 (2H, d, J=8.4 Hz), 7.84 (2H, d, J=8.4 Hz)

EXAMPLE 349

N-(3,4-Difluorophenyl)-1-(methylsulfonyl)-N-(3-{4-[4-(methylsulfonyl)benzyl]-1-piperidinyl}propyl)-4-piperidinecarboxamide The title compound was prepared using a similar procedure to that described for example 343 from the title compound of reference example 112, yield 70%.

¹H NMR (CDCl₃) δ 1.1-2.05 (13H, m), 2.1-2.35 (3H, m), 2.45-2.9 (4H, m), 2.61 (2H, d, J=6.2 Hz), 2.74 (3H, s), 3.05 (3H, s), 3.55-3.8 (4H, m), 6.85-7.4 (3H, m), 7.32 (2H, d, J=8.6 Hz), 7.85 (2H, d, J=8.6 Hz)

EXAMPLE 350

N-(2,3-Dihydro-1H-inden-5-yl)-1-(methylsulfonyl)-N-(3-{4-[4-(methylsulfonyl)benzyl]-1-piperidinyl}propyl)-4-piperidinecarboxamide The title compound was prepared using a similar procedure to that described for example 343 from the title compound of reference example 113, yield 96%.

¹H NMR (CDCl₃) δ 1.1-2.0 (13H, m), 2.0-2.4 (5H, m), 2.45-3.0 (8H, m), 2.61 (2H, d, J=6.6 Hz), 2.73 (3H, s), 3.05 (3H, s), 3.55-3.8 (4H, m), 6.86 (1H, dd, J=2.0 Hz, 7.9 Hz), 6.96 (1H, br s), 7.23 (1H, d, J=7.9 Hz), 7.32 (2H, d, J=8.0 Hz), 7.84 (2H, d, J=8.0 Hz)

EXAMPLE 351

N-(3,4-Dimethylphenyl)-1-(methylsulfonyl)-N-(3-{4-[4-(methylsulfonyl)benzyl]-1-piperidinyl}propyl)-4-piperidinecarboxamide The title compound was prepared using a similar procedure to that described for example 343 from the title compound of reference example 114, yield 95%.

¹H NMR (CDCl₃) δ 1.1-2.0 (13H, m), 2.1-2.4 (3H, m), 2.27 (3H, s), 2.29 (3H, s), 2.4-2.95 (4H, m), 2.61 (2H, d, J=6.4 Hz), 2.73 (3H, s), 3.05 (3H, s), 3.55-3.8 (4H, m), 6.8-6.9 (2H, m), 7.15 (1H, d, J=7.6 Hz), 7.32 (2H, d, J=8.2 Hz), 7.84 (2H, d, J=8.2 Hz)

EXAMPLE 352

N-(3-Chloro-4-isopropylphenyl)-N-(3-[4-(4-fluorobenzyl)-1-piperidinyl]propyl}-1-(methylsulfonyl)-4-piperidinecarboxamide The title compound was prepared from the title compound of reference example 115 using a similar method to that described for example 25. Yield 33%.

¹H NMR (CDCl₃) δ 1.10-1.30 (2H, m), 1.28 (6H, d, J=7.0 Hz), 1.50-2.00 (9H, m), 2.23-2.30 (3H, m), 2.48 (2H, d, J=6.6 Hz), 2.50-2.70 (2H, m), 2.74 (3H, s), 2.80-2.90 (3H, m), 3.42 (1H, septet, J=7.0 Hz), 3.57-3.74 (5H, m), 6.90-7.11 (5H, m), 7.16 (1H, d, J=2.2 Hz), 7.33 (1H, d, J=8.6 Hz)

EXAMPLE 353

1-Acetyl-N-(3-chloro-4-isopropylphenyl)-N-{3-[4-(4-fluorobenzyl)-1-piperidinyl]propyl}-4-piperidinecarboxamide The title compound was prepared from the title compound of reference example 115 using a similar method to that described for example 16. Yield 87%.

¹H NMR (CDCl₃) δ 1.10-1.40 (2H, m), 1.28 (6H, d, J=7.0 Hz), 1.50-1.97 (11H, m), 2.05 (3H, s), 2.23-2.42 (4H, m), 2.48 (2H, d, J=6.6 Hz), 2.80-2.93 (3H, m), 3.42 (1H, septet, J=7.0 Hz), 3.60-3.80 (3H, m), 4.47-4.54 (1H, m), 6.70-7.10 (5H, m), 7.16 (1H, d, J=2.2 Hz), 7.33 (1H, d, J=8.4 Hz)

EXAMPLE 354

N-(3,4-Dichlorophenyl)-1-(methylsulfonyl)-N-[3-(4-{4-[(propylamino)sulfonyl]benzyl}-1-piperidinyl)propyl]-4-piperidinecarboxamide A mixture of the title compound of reference example 116-2 (216 mg, 0.5 mmol), the title compound of reference example 57 (214 mg, 0.65 mmol), potassium iodide (83 mg, 0.5 mmol), potassium carbonate (276 mg, 2 mmol) and acetonitrile (3 ml) was stirred at 80° C. for 8 h. The solvent was removed in vacuo. Dichloromethane (5 ml) was added to the residue and the whole was washed with water (5 ml). The organic layer was concentrated in vacuo. The residue was purified by flash column chromatography (silica gel 8 g, ethyl acetate to ethyl acetate/methanol=4/1) to give the title compound (224 mg, 65%) as a colorless amorphous powder.

¹H NMR (CDCl₃) δ 0.87 (3H, t, J=7.2 Hz), 1.10-1.40 (2H, m), 1.41-21.97 (13H, m), 2.10-2.31 (3H, m), 2.51-2.60 (2H, m), 2.59 (2H, d, J=6.6 Hz), 2.74 (3H, s), 2.80-2.90 (2H, m), 2.92 (2H, q, J=7.2 Hz), 3.61-3.76 (4H, m), 4.39 (1H, t, J=6.2 Hz), 7.03 (1H, dd, J=8.4 Hz, 2.6 Hz), 7.26 (2H, d, J=8.0 Hz), 7.31 (1H, d, J=2.6 Hz), 7.52 (1H, d, J=8.4 Hz), 7.76 (2H, d, J=8.0 Hz)

EXAMPLE 355

N-[3-(4-{4-[(Cyclohexylamino)sulfonyl]benzyl}-1-piperidinyl)propyl]-N-(3,4-dichlorophenyl)-1-(methylsulfonyl)-4-piperidinecarboxamide The title compound was prepared from the title compound of reference example 117-2 using a similar method to that described for example 354. Yield 59%.

$^1$H NMR (CDCl$_3$) δ 1.00-1.40 (6H, m), 1.40-2.00 (17H, m), 2.20-2.31 (3H, m), 2.50-2.70 (2H, m), 2.58 (2H, d, J=6.2 Hz), 2.74 (3H, s), 2.80-2.85 (2H, m), 3.00-3.20 (1H, m), 3.61-3.76 (4H, m), 4.38 (1H, d, J=8.0 Hz), 7.03 (1H, dd, J=8.4 Hz, 2.2 Hz), 7.25 (2H, d, J=8.4 Hz), 7.31 (1H, d, J=2.2 Hz), 7.52 (1H, d, J=8.4 Hz), 7.77 (2H, d, J=8.4 Hz)

EXAMPLE 356

N-(3,4-Dichlorophenyl)-1-(methylsulfonyl)-N-(3-{4-[4-(4-morpholinylsulfonyl)benzyl]-1-piperidinyl}propyl)-4-piperidinecarboxamide A mixture of the title compound of reference example 118-3 (886 mg, 2.7 mmol), the title compound of reference example 57 (974 mg, 2.3 mmol), potassium iodide (378 mg, 2.3 mmol), potassium carbonate (473 mg, 3.4 mmol) and acetonitrile (20 ml) was refluxed for 8.5 h. The resulting mixture was diluted with ethyl acetate (50 ml) and the whole was washed with water (50 ml), 1N aqueous sodium hydroxide (50 ml×2) and saturated sodium chloride solution (50 ml×2) successively. The organic layer was dried over anhydrous sodium sulfate and concentrated in vacuo. The residue was purified by flash column chromatography (silica gel 30 g, ethyl acetate to ethyl acetate/methanol=8/1) to give the title compound (1.41 g, 86%) as a pale yellow amorphous powder.

$^1$H NMR (CDCl$_3$) δ 1.10-1.40 (2H, m), 1.50-2.00 (11H, m), 2.10-2.30 (3H, m), 2.52-2.70 (2H, m), 2.60 (2H, d, J=6.6 Hz), 2.74 (3H, m), 2.80-2.86 (2H, m), 2.70-3.02 (4H, m), 3.62-3.77 (8H, m), 7.07 (1H, dd, J=8.4 Hz, 2.2 Hz), 7.30 (2H, d, J=8.0 Hz), 7.31 (1H, d, J=2.6 Hz), 7.52 (1H, d, J=8.4 Hz), 7.65 (2H, d, J=8.0 Hz)

EXAMPLE 357

N-(3,4-Dichlorophenyl)-1-(methylsulfonyl)-N-(3-{4-[4-(2-trityl-2H-tetrazol-5-yl)benzyl]-1-piperidinyl}propyl)-4-piperidinecarboxamide The title compound was prepared from the title compound of reference example 119-4 using a similar method to that described for example 354. Yield 36%.

$^1$H NMR (CDCl$_3$) δ 1.20-1.40 (2H, m), 1.40-2.00 (11H, m), 2.10-2.40 (3H, m), 2.50-2.70 (2H, m), 2.56 (2H, d, J=6.6 Hz), 2.73 (3H, s), 2.80-2.85 (2H, m), 3.61-3.76 (4H, m), 7.03 (1H, dd, J=8.4 Hz, 2.6 Hz), 7.13-7.36 (18H, m), 7.51 (1H, d, J=8.0 Hz), 8.04 (2H, d, J=8.0 Hz)

EXAMPLE 358

N-(3,4-Dichlorophenyl)-1-(methylsulfonyl)-N-(3-{4-[4-(2H-tetrazol-5-yl)benzyl]-1-piperidinyl}propyl)-4-piperidinecarboxamide hydrochloride A solution of 4N hydrogen chloride in ethyl acetate (15 ml) was to a solution of the title compound of example 357 (263 mg, 0.3 mmol) in ethyl acetate-methanol (2/5, 7 ml) and this solution was stirred at room temperature for 1 h. The resulting mixture was concentrated in vacuo. The residue was crystallized from methanol-ethyl acetate (1/1) to give the title compound (196 mg, 97%) as colorless crystalline powder.

$^1$H NMR (CD$_3$OD) δ 1.50-2.01 (10H, m), 2.25-2.40 (1H, m), 2.45-2.60 (2H, m), 2.70-2.80 (2H, m), 2.73 (3H, s), 2.88-3.16 (5H, m), 3.54-3.67 (4H, m), 3.72-3.81 (2H, m), 7.34-7.46 (4H, m), 7.69 (1H, d, J=8.4 Hz), 7.70 (1H, d, J=2.2 Hz), 7.97 (2H, d, J=8.4 Hz)

EXAMPLE 359

N-(3,4-Dichlorophenyl)-N-[3-(4-{4-[(diethylamino)sulfonyl]benzyl}-1-piperidinyl)propyl]-1-(methylsulfonyl)-4-piperidinecarboxamide The title compound was prepared from the title compound of reference example 120-2 using a similar method to that described for example 356. Yield 80%.

$^1$H NMR (CDCl$_3$) δ 1.13 (6H, t, J=7.0 Hz), 1.20-1.40 (2H, m), 1.45-2.00 (11H, m), 2.19-2.31 (3H, m), 2.51-2.65 (2H, m), 2.57 (2H, d, J=5.8 Hz), 2.74 (3H, s), 2.79-2.85 (2H, m), 3.23 (4H, q, J=7.0 Hz), 3.61-3.76 (4H, m), 7.02 (1H, dd, J=8.4 Hz, 2.6 Hz), 7.24 (2H, d, J=8.4 Hz), 7.31 (1H, d, J=2.6 Hz), 7.52 (1H, d, J=8.4 Hz), 7.70 (2H, d, J=8.4 Hz)

EXAMPLE 360

N-(3,4-Dichlorophenyl)-1-(methylsulfonyl)-N-(3-{4-[4-(1-piperidinylsulfonyl)benzyl]-1-piperidinyl}propyl)-4-piperidinecarboxamide The title compound was prepared from the title compound of reference example 121-2 using a similar method to that described for example 356. Yield 97%.

$^1$H NMR (CDCl$_3$) δ 1.20-2.00 (19H, m), 2.10-2.31 (3H, m), 2.50-2.70 (2H, m), 2.59 (2H, d, J=6.2 Hz), 2.74 (3H, s), 2.80-2.86 (2H, m), 2.95-3.01 (4H, m), 3.62-3.76 (4H, m), 7.03 (1H, dd, J=8.4 Hz, 2.6 Hz), 7.26 (2H, d, J=8.0 Hz), 7.31 (1H, d, J=2.6 Hz), 7.52 (1H, d, J=8.4 Hz), 7.65 (2H, d, J=8.0 Hz)

EXAMPLE 361

N-(3,4-Dichlorophenyl)-1-(methylsulfonyl)-N-(3-{4-[4-(1-pyrrolidinylsulfonyl)benzyl]-1-piperidinyl}propyl)-4-piperidinecarboxamide The title compound was prepared from the title compound of reference example 122-2 using a similar method to that described for example 356. Yield 79%.

$^1$H NMR (CDCl$_3$) δ 1.10-1.40 (2H, m), 1.50-2.00 (15H, m), 2.10-2.31 (3H, m), 2.50-2.60 (2H, m), 2.59 (2H, d, J=6.4 Hz), 2.74 (3H, s), 2.80-2.85 (2H, m), 3.21-3.28 (4H, m), 3.61-3.76 (4H, m), 7.02 (1H, dd, J=8.4 Hz, 2.6 Hz), 7.27 (2H, d, J=8.4 Hz), 7.31 (1H, d, J=2.6 Hz), 7.52 (1H, d, J=8.4 Hz), 7.73 (2H, d, J=8.4 Hz)

EXAMPLE 362

N-(3-{4-[4-(Aminocarbonyl)benzyl]-1-piperidinyl}propyl)-N-(3,4-dichlorophenyl)-1-(methylsulfonyl)-4-piperidinecarboxamide A mixture of the title compound of reference example 123-4 (287 mg, 1.13 mmol), the title compound of reference example 57 (428 mg, 1 mmol), potassium iodide (187 mg, 1.13 mmol), potassium carbonate (415 mg, 3 mmol), acetonitrile (5 ml) and DMF (5 ml) was stirred at 80° C. for 18 h. The solvent was removed in vacuo. The resulting residue was dissolved in ethyl acetate (20 ml) and the solution was washed with water (30 ml), 1N aqueous sodium hydroxide (30 ml) and saturated sodium chloride solutions (50 ml) successively. The organic layer was dried over anhydrous sodium sulfate and concentrated in vacuo. The residue was purified by flash column chromatography (silica gel 25 g, ethyl acetate to ethyl acetate/methanol=8/1) followed by crystallization from diisopropyl ether to give the title compound (317 mg, 52%) as a colorless crystalline, powder.

$^1$H NMR (CDCl$_3$) δ 1.21-1.34 (2H, m), 1.40-1.97 (11H, m), 2.10-2.30 (3H, m), 2.50-2.65 (2H, m), 2.57 (2H, d, J=5.8 Hz), 2.74 (3H, s), 2.78-2.84 (2H, m), 3.61-3.76 (4H, m), 5.40-6.20 (2H, m), 7.02 (1H, dd, J=8.4 Hz, 2.6 Hz), 7.21 (2H, d, J=8.4 Hz), 7.31 (1H, d, J=2.6 Hz), 7.52 (1H, d, J=8.4 Hz), 7.72 (2H, d, J=8.4 Hz)

EXAMPLE 363

N-(3,4-dichlorophenyl)-N-{3-[4-(4-{[isopropyl(methyl)amino]sulfonyl}benzyl)-1-piperidinyl]propyl}-1-(methylsulfonyl)-4-piperidinecarboxamide The title compound was prepared from the title compound of reference example 125-2 using a similar method to that described for example 356. Yield 67%.

$^1$H NMR (CDCl$_3$) δ 0.98 (6H, m), 1.10-1.3 (2H, m)1, 1.40-2.00 (11H, m), 2.10-2.31 (3H, m), 2.50-2.70 (2H, m), 2.57 (2H, d, J=6.6 Hz), 2.71 (3H, s), 2.74 (3H, s), 2.79-2.85 (2H, m), 3.61-3.76 (4H, m), 4.21 (1H, septet, J=6.8 Hz), 7.02 (1H, dd, J=8.4 Hz, 2.2 Hz), 7.24 (2H, d, J=8.4 Hz), 7.31 (1H, d, J=2.2 Hz), 7.52 (1H, d, J=8.4 Hz), 7.70 (2H, d, J=8.4 Hz)

EXAMPLE 364

N-(3,4-Dichlorophenyl)-N-[3-(4-{4-[(dimethylamino)carbonyl]benzyl}-1-piperidinyl)propyl]-1-(methylsulfonyl)-4-piperidinecarboxamide The title compound was prepared from the title compound of reference example 124-2 using a similar method to that described for example 356. Yield 30%.

$^1$H NMR (CDCl$_3$) δ 1.12-1.40 (2H, m), 1.40-2.00 (11H, m), 2.10-2.40 (3H, m), 2.40-2.63 (2H, m), 2.53 (2H, d, J=6.6 Hz), 2.74 (3H, s), 2.74-2.90 (2H, m), 3.00 (3H, brs), 3.10 (3H, brs), 3.62 (4H, m), 7.02-7.06 (1H, m), 7.15 (2H, d, J=6.2 Hz), 7.32 (1H d, J=2.0 Hz), 7.34 (2H, d, J=6.2 Hz), 7.52 (1H, d, J=8.4 Hz)

EXAMPLE 365

N-(3,4-Dichlorophenyl)-N-[3-(4-{4-[(isopropylamino)sulfonyl]benzyl}-1-piperidinyl)propyl]-1-(methylsulfonyl)-4-piperidinecarboxamide The title compound was prepared from the title compound of reference example 126-2 using a similar method to that described for example 362. Yield 58%.

$^1$H NMR (CDCl$_3$) δ 1.08 (6H, m), 1.16-1.40 (2H, m), 1.40-1.99 (10H, m), 2.10-2.31 (4H, m), 2.50-2.70 (2H, m), 2.58 (2H, d, J=6.2 Hz), 2.70 (3H, s), 2.80-2.89 (2H, m), 3.42-3.55 (1H, m), 3.62-3.76 (4H, m), 4.35 (1H, d, J=7.6 Hz), 7.03 (1H, dd, J=8.4 Hz, 2.2 Hz), 7.25 (2H, d, J=8.6 Hz), 7.31 (1H, d, J=2.2 Hz), 7.52 (1H, d, J=8.4 Hz), 7.78 (2H, d, J=8.6 Hz)

EXAMPLE 366

N-(3,4-Dichlorophenyl)-N-[3-(4-{4-[(4-fluoroanilino)sulfonyl]benzyl}-1-piperidinyl)propyl]-1-(methylsulfonyl)-4-piperidinecarboxamide The title compound was prepared from the title compound of reference example 127-2 using a similar method to that described for example 362. Yield 8.4%.

$^1$H NMR (CDCl$_3$) δ 1.10-1.40 (2H, m), 1.40-2.00 (11H, m), 2.10-2.20 (3H, m), 2.50-2.70 (2H, m), 2.55 (2H, d, J=6.2 Hz), 2.74 (3H, s), 2.80-2.90 (2H, m), 3.61-3.76 (5H, m), 6.89-7.06 (5H, m), 7.19 (2H, d, J=8.6 Hz), 7.31 (1H, d, J=2.6 Hz), 7.52 (1H, d, J=8.6 Hz), 7.60 (2H, d, J=8.0 Hz)

EXAMPLE 367

N-(3,4-Dichlorophenyl)-N-{3-[4-(4-{[methoxy(methyl)amino]sulfonyl)benzyl)-1-piperidinyl]propyl}-1-(methylsulfonyl)-4-piperidinecarboxamide The title compound was prepared from the title compound of reference example 128-2 using a similar method to that described for example 356. Yield 62%.

$^1$H NMR (CDCl$_3$) δ 1.23-1.30 (2H, m), 1.56-1.97 (10H, m), 2.20-2.31 (3H, m), 2.52-2.70 (2H, m), 2.60 (2H, d, J=6.6 Hz), 2.74 (3H, s), 2.70-2.90 (2H, m), 2.78 (3H, s), 3.62-3.80 (5H, m), 3.82 (3H, s), 7.03 (1H, dd, J=8.4 Hz, 2.2 Hz), 7.30 (1H, d, J=2.2 Hz), 7.31 (2H, d, J=8.4 Hz), 7.52 (1H, d, J=8.4 Hz), 7.78 (2H, d, J=8.4 Hz)

EXAMPLE 368

N-(3,4-Dichlorophenyl)-N-[3-(4-{4-[(methylamino)carbonyl]benzyl}-1-piperidinyl)propyl]-1-(methylsulfonyl)-4-piperidinecarboxamide The title compound was prepared from the title compound of reference example 129-2 using a similar method to that described for example 362. Yield 63%.

$^1$H NMR (CDCl$_3$) δ 1.20-1.40 (2H, m), 1.40-2.00 (11H, m), 2.10-2.40 (3H, m), 2.54-2.62 (2H, m), 2.55 (2H, d, J=6.4 Hz), 2.74 (3H, s), 2.80-2.85 (2H, m), 3.01 (3H, d, J=Hz), 3.61-3.76 (4H, m), 6.12 (1H, brq, J=4.8 Hz), 7.03 (1H, dd, J=8.0 Hz, 2.2 Hz), 7.18 (2H, d, J=8.4 Hz), 7.31 (1H, d, J=2.2 Hz), 7.53 (1H, d, J=8.4 Hz), 7.66 (2H, d, J=8.0 Hz)

EXAMPLE 369

N-[3-(4-{4-[(tert-Butylamino)carbonyl]benzyl}-1-piperidinyl)propyl]-N-(3,4-dichlorophenyl)-1-(methylsulfonyl)-4-piperidinecarboxamide The title compound was prepared from the title compound of reference example 130-2 using a similar method to that described for example 362. Yield 67%.

$^1$H NMR (CDCl$_3$) δ 1.20-1.40 (2H, m), 1.47 (9H, s), 1.55-2.00 (11H, m), 2.20-2.30 (3H, m), 2.50-2.70 (2H, m), 2.55 (2H, d, J=6.2 Hz), 2.74 (3H, s), 2.75-2.84 (2H, m), 3.59-3.76 (4H, m), 5.91 (1H, brs), 7.03 (1H, dd, J=8.4 Hz, 2.6 Hz), 7.16 (2H, d, J=8.0 Hz), 7.31 (1H, d, J=2.6 Hz), 7.53 (1H, d, J=8.4 Hz). 7.63 (2H, d, J=8.0 Hz)

EXAMPLE 370

N-(3,4-Dichlorophenyl)-1-(methylsulfonyl)-N-(3-{4-[4-(4-morpholinylcarbonyl)benzyl]-1-piperidinyl}propyl)-4-piperidinecarboxamide The title compound was prepared from the title compound of reference example 131-2 using a similar method to that described for example 362. Yield 65%.

$^1$H NMR (CDCl$_3$) δ 1.10-1.20 (2H, m), 1.50-2.00 (11H, m), 2.20-2.32 (3H, m), 2.54 (2H, d, J=6.2 Hz), 2.50-2.62 (2H, m), 2.74 (3H, s), 2.80-2.86 (2H, m), 3.50-3.80 (12H, m), 7.07 (1H, dd, J=8.4 Hz, 2.6 Hz), 7.16 (2H, d, J=8.0 Hz), 7.31 (1H, d, J=2.6 Hz), 7.32 (2H, d, J=8.0 Hz), 7.52 (1H, d, J=8.4 Hz)

EXAMPLE 371

N-(3,4-Dichlorophenyl)-1-(methylsulfonyl)-N-(3-{4-[4-(1-pyrrolidinylcarbonyl)benzyl]-1-piperidinyl}propyl)-4-piperidinecarboxamide The title compound was prepared from the title compound of reference example 132-2 using a similar method to that described for example 362. Yield 52%.

$^1$H NMR (CDCl$_3$) δ 1.20-1.40 (2H, m), 1.40-2.00 (16H, m), 2.10-2.40 (3H, m), 2.50-2.70 (2H, m), 2.53 (2H, d, J=6.6 Hz), 2.74 (3H, s), 2.83-2.89 (2H, m), 3.41-3.47 (2H, m), 3.61-3.76 (5H, m), 7.05 (1H, dd, J=8.4 Hz, 2.2 Hz), 7.14 (2H, d, J=8.0 Hz), 7.32 (1H, d, J=2.2 Hz), 7.43 (2H, d, J=8.0 Hz), 7.52 (1H, d, J=8.4 Hz)

EXAMPLE 372

N-(3,4-Dichlorophenyl)-N-{3-[4-(4-{[(5-methyl-3-isoxazolyl)amino]sulfonyl}benzyl)-1-piperidinyl]propyl}-1-(methylsulfonyl)-4-piperidinecarboxamide The title compound was prepared from the title compound of reference example 133-2 using a similar method to that described for example 362. Yield 10%.

$^1$H NMR (CDCl$_3$) δ 1.50-2.00 (8H, m), 2.10-2.40 (3H, m), 2.27 (3H, s), 2.40-2.60 (4H, m), 2.72 (3H, s), 2.75-2.90 (2H, m), 3.30-3.80 (10H, m), 6.08 (1H, s), 7.13 (2H, d, J=8.0 Hz), 7.20 (1H, dd, J=8.4 Hz, 2.6 Hz), 7.29 (1H, d, J=2.6 Hz), 7.34 (1H, d, J=8.4 Hz), 7.74 (2H, d, J=8.0 Hz)

EXAMPLE 373

N-(3,4-Dichlorophenyl)-N-(3-{4-[4-(methylsulfanyl)phenoxy]-1-piperidinyl}propyl)-1-(methylsulfonyl)-4-piperidinecarboxamide The title compound was prepared from the title compound of reference example 134-2 using a similar method to that described for example 362. Yield 30%.

$^1$H NMR (CDCl$_3$) δ 1.60-2.00 (10H, m), 2.10-2.37 (5H, m), 2.44 (3H, s), 2.52-2.74 (4H, m), 2.74 (3H, s), 3.64-3.76 (4H, m), 4.20-4.30 (1H, m), 6.84 (2H, d, J=8.8 Hz), 7.04 (1H, dd, J=8.4 Hz, 2.6 Hz), 7.24 (2H, d, J=8.8 Hz), 7.32 (1H, d, J=2.6 Hz), 7.53 (1H, d, J=8.4 Hz)

EXAMPLE 374

N-(3,4-Dichlorophenyl)-1-(methylsulfonyl)-N-(3-{4-[4-(methylsulfonyl)phenoxy]-1-piperidinyl}propyl)-4-piperidinecarboxamide The title compound was prepared from the title compound of reference example 135-2 using a similar method to that described for example 362. Yield 54%.

$^1$H NMR: (CDCl$_3$) δ 1.66-2.05 (10H, m), 2.10-2.39 (5H, m), 2.50-2.74 (4H, m), 2.74 (3H, s), 3.03 (3H, s), 3.65-3.77 (4H, m), 4.30-4.50 (1H, m), 7.00 (2H, d, J=8.8 Hz), 7.04 (1H, dd, J=8.4 Hz, 2.6 Hz), 7.32 (1H, d, J=2.6 Hz), 7.54 (1H, d, J=8.4 Hz), 7.84 (2H, d, J=8.4 Hz)

EXAMPLE 375

N-[3-(4-{4-[(tert-Butylamino)sulfonyl]benzyl}-1-piperidinyl)propyl]-N-(3,4-dichlorophenyl)-1-(methylsulfonyl)-4-piperidinecarboxamide The title compound was prepared from the title compound of reference example 136-2 using a similar method to that described for example 362. Yield 54%.

$^1$H NMR (CDCl$_3$) δ 1.20-1.40 (2H, m), 1.22 (9H, s), 1.49-2.05 (11H, m), 2.24-2.28 (3H, m), 2.51-2.70 (2H, m), 2.57 (2H, d, J=6.2 Hz), 2.74 (3H, s), 2.75-2.89 (2H, m), 3.62-3.76 (4H, m), 4.60 (1H, s), 7.03 (1H, dd, J=8.4 Hz, 2.6 Hz), 7.23 (2H, d, J=8.0 Hz), 7.31 (1H, d, J=2.6 Hz), 7.52 (1H, d, J=8.4 Hz), 7.79 (2H, d, J=8.0 Hz)

EXAMPLE 376

1-Acetyl-N-(3-{4-[4-(aminocarbonyl)benzyl]-1-piperidinyl}propyl)-N-(3-chloro-4-methylphenyl)-4-piperidinecarboxamide A mixture of the title compound of reference example 123-4 (280 mg, 1.1 mmol), the title compound of reference example 11-2 (371 mg, 1 mmol), potassium iodide (183 mg, 1.1 mmol), potassium carbonate (415 mg, 3 mmol), acetonitrile (3 ml) and DMF (3 ml) was stirred at 80° C. for 20 h. The resulting mixture was diluted with ethyl acetate (20 ml) and the whole was washed with water (20 ml×2), 1N aqueous sodium hydroxide (20 ml×2), water (20 ml) and saturated sodium chloride solution (20 ml) successively. The organic layer was dried over anhydrous sodium sulfate and concentrated in vacuo. The residue was purified by flash column chromatography (silica gel 20 g, ethyl acetate to ethyl acetate/methanol=8/1 to 3/2) followed by crystallization from diethyl ether to give the title compound (252 mg, 46%) as a colorless crystalline powder.

$^1$H NMR (CDCl$_3$) δ 1.18-1.45 (2H, m), 1.56-1.87 (1H, m), 2.04 (3H, s), 2.23-2.40 (4H, m), 2.42 (3H, s), 2.57 (2H, d, J=6.2 Hz), 2.80-2.90 (3H, m), 3.60-3.79 (3H, m), 4.47-4.54 (1H, m), 5.40-6.20 (2H, m), 6.95 (1H, dd, J=8.0 Hz, 2.2 Hz), 7.35 (1H, d, J=2.2 Hz), 7.20 (2H, d, J=8.4 Hz), 7.28 (1H, d, J=8.0 Hz), 7.72 (2H, d, J=8.4 Hz)

EXAMPLE 377

1-Acetyl-N-(3-{4-[4-(aminocarbonyl)benzyl]-1-piperidinyl}propyl)-N-(3,4-dichlorophenyl)-4-piperidinecarboxamide A mixture of the title compound of reference example 123-4 (280 mg, 1.1 mmol), the title compound of reference example 56-3 (392 mg, 1 mmol), potassium iodide (183 mg, 1.1 mmol), potassium carbonate (415 mg, 3 mmol), acetonitrile (3 ml) and DMF, (3 ml) was stirred at 80° C. for 20 h. The resulting mixture was diluted with ethyl acetate (20 ml) and the whole was washed with water (20 ml×2), 1N aqueous sodium hydroxide (20 ml×2), water (20 ml) and saturated sodium chloride solution (20 ml) successively. The organic layer was dried over anhydrous sodium sulfate and concentrated in vacuo. The residue was purified by flash column chromatography (silica gel 20 g, ethyl acetate to ethyl acetate/methanol=8/1 to 3/2) followed by crystallization from diethyl ether to give the title compound (320 mg, 55%) as a colorless crystalline powder $^1$H NMR (CDCl$_3$) δ 1.19-1.34 (2H, m), 1.40-1.87 (11H, m), 2.05 (3H, s), 2.23-2.42 (4H, m), 2.57 (2H, d, J=6.2 Hz), 2.79-2.92 (3H, m), 3.61-3.81 (3H, m), 4.49-4.55 (1H, m), 5.60-6.120 (2H, m), 7.03 (1H, dd, J=8.4 Hz, 2.6 Hz), 7.20 (2H, d, J=8.0 Hz), 7.31 (1H, d, J=2.6 Hz), 7.52 (1H, d, J=8.4 Hz), 7.73 (2H, d, J=8.0 Hz)

EXAMPLE 378

N-[3-(4-{4-[(tert-Butylamino)sulfonyl]benzyl}-1-piperidinyl)propyl]-1-(methylsulfonyl)-N-phenyl-4-piperidinecarboxamide A mixture of the title compound of reference example 136-2 (382 mg, 1.1 mmol), the title compound of reference example 159 (359 mg, 1 mmol), potassium iodide (183 mg, 1.1 mmol), potassium carbonate (415 mg, 3 mmol), acetonitrile (5 ml) and DMF (5 ml) was stirred at 80° C. for 15 h. The solvent was removed in vacuo. The resulting residue was dissolved in ethyl acetate (20 ml) and this solution was washed with water (20 ml) and saturated sodium chloride solution (20 ml) successively. The organic layer was dried over anhydrous sodium sulfate and concentrated in vacuo. The residue was purified by flash column chromatography (silica gel 20 g, ethyl acetate to ethyl acetate/methanol=8/1; Alumina 10 g, ethyl acetate) to give the title compound (326 mg, 52%) as a colorless amorphous powder.

$^1$H NMR(CDCl$_3$) δ 1.23 (6H, s), 1.20-1.40 (2H, m), 1.43-1.96 (14H, m), 2.20-2.31 (3H, m), 2.44-2.58 (2H, m), 2.56 (2H, d, J=6.0 Hz), 2.72 (3H, s), 2.80-2.92 (2H, m), 3.64-3.73 (4H, m), 4.50 (1H, s), 7.13-7.17 (2H, m), 7.22 (2H, d, J=8.4 Hz), 7.34-7.49 (3H, m), 7.78 (2H, d, J=8.4 Hz)

EXAMPLE 379

1-Acetyl-N-(3,4-dichlorophenyl)-N-(3{4-[4-(methylsulfonyl)benzyl]-1-piperidinyl}propyl)-4-piperidinecarboxamide The title compound was prepared using a similar procedure to that described in example 179 from the title compound of reference example 86-2. Yield 77%.

$^1$H NMR (CDCl$_3$) δ 1.20-1.38 (2H, m), 1.41-1.92 (11H, m), 2.06 (3H, s), 2.22-2.47 (4H, m), 2.62 (2H, d, J=6.2 Hz), 2.75-2.95 (3H, m), 3.05 (3H, s), 2.60-2.84 (3H, m), 4.47-4.60 (1H, m), 7.04 (1H, dd, J=2.2, 8.4 Hz), 7.30-7.35 (3H, m), 7.52 (1H, d, J=8.4 Hz), 7.84 (2H, d, J=8.4 Hz).

EXAMPLE 380

N-(3-{4-[4-(Butylsulfonyl)benzyl]-1-piperidinyl}propyl)-N-(3,4-dichlorophenyl)-1-(methylsulfonyl)-4-piperidinecarboxamide The title compound was prepared using a similar procedure to that described in example 190 from the title compound of reference example 139-2. Yield 75%.

$^1$H NMR (CDCl$_3$) δ 0.89 (3H, t, J=7.2 Hz), 1.20-2.00 (17H, m), 2.10-2.35 (3H, m), 2.47-2.68 (4H, m), 2.74 (3H, s), 2.75-2.85 (2H, m), 3.00-3.12 (2H, m), 3.60-3.80 (4H, m), 7.04 (1H, dd, J=2.4, 8.6 Hz), 7.28-7.35 (3H, m), 7.52 (1H, d, J=8.6 Hz), 7.80 (2H, d, J=8.6 Hz).

EXAMPLE 381

N-(3,4-Dichlorophenyl)-N-{3-[4-({4-[(dimethylamino)sulfonyl]phenyl}sulfonyl)-1-piperidinyl]propyl}-1-(methylsulfonyl)-4-piperidinecarboxamide The title compound was prepared using a similar procedure to that described in example 190 from the title compound of reference example 144-7. Yield 30%.

$^1$H NMR (CDCl$_3$) (1.58-2.03 (12H, m), 2.10-2.35 (3H, m), 2.45-2.65 (2H, m), 2.74 (3H, s), 2.78 (6H, s), 2.85-3.00 (3H, m), 3.55-3.80 (4H, m), 7.02 (1H, dd, J=2.6, 8.4 Hz), 7.27 (1H, d, J=2.6 Hz), 7.53 (1H, d, J=8.4 Hz), 7.97 (2H, d, J=8.8 Hz), 8.05 (2H, d, J=8.8 Hz).

EXAMPLE 382

N-(3,4-Dichlorophenyl)-N-(3-{4-[4-(ethylsulfonyl)benzyl]-1-piperidinyl}propyl)-1-(methylsulfonyl)-4-piperidinecarboxamide The title compound was prepared using a similar procedure to that described in example 190 from the title compound of reference example 137-2. Yield 88%.

$^1$H NMR (CDCl$_3$) δ 1.20-1.40 (2H, m), 1.28 (3H, t, J=7.6), 1.40-2.00 (11H, m), 2.10-2.35 (3H, m), 2.45-2.70 (4H, m), 2.74 (3H, s), 2.75-2.90 (2H, m), 3.10 (2H, q, J=7.6 Hz), 3.60-3.80 (4H, m), 7.03 (1H, dd, J=2.6, 8.4 Hz), 7.27-7.35 (3H, m), 7.52 (1H, d, J=8.4 Hz), 7.80 (2H, d, J=8.0 Hz).

EXAMPLE 383

N-(3,4-Dichlorophenyl)-N-(3-{4-[4-(propylsulfonyl)benzyl]-1-piperidinyl}propyl)-1-(methylsulfonyl)-4-piperidinecarboxamide The title compound was prepared using a similar procedure to that described in example 190 from the title compound of reference example 138-2. Yield 75%.

$^1$H NMR (CDCl$_3$) δ 1.00 (3H, t, J=7.6 Hz), 1.20-1.40 (2H, m), 1.50-2.00 (13H, m), 2.15-2.35 (3H, m), 2.48-2.70 (4H, m), 2.74 (3H, s), 2.74-2.90 (2H, m), 3.00-3.10 (2H, m), 3.60-3.80 (4H, m), 7.03 (1H, dd, J=2.4, 8.4 Hz), 7.28-7.35 (3H, m), 7.52 (1H, d, J=8.4 Hz), 7.80 (2H, d, J=8.2 Hz).

EXAMPLE 384

N-(3,4-Dichlorophenyl)-N-(3-{4-[4-(isopropylsulfonyl)benzyl]-1-piperidinyl}propyl)-1-(methylsulfonyl)-4-piperidinecarboxamide The title compound was prepared using a similar procedure to that described in example 190 from the title compound of reference example 140-4. Yield 82%.

$^1$H NMR (CDCl$_3$) δ 1.22-1.35 (2H, m), 1.30 (6H, d, J=6.8 Hz), 1.45-2.00 (11H, m), 2.15-2.35 (3H, m), 2.48-2.68 (4H, m), 2.74 (3H, s), 2.79-2.91 (2H, m), 3.09-3.29 (1H, m), 3.60-3.80 (4H, m), 7.03 (1H, dd, J=2.2, 8.6 Hz), 7.28-7.34 (3H, m), 7.52 (1H, d, J=8.6 Hz), 7.78 (2H, d, J=8.4 Hz).

EXAMPLE 385

N-(3,4Dichlorophenyl)-N-(3-{4-[(4-{[methoxy(methyl)amino]sulfonyl}phenyl)sulfonyl]-1-piperidinyl}propyl)-1-(methylsulfonyl)-4-piperidinecarboxamide The title compound was prepared using a similar procedure to that described in example 190 from the title compound of reference example 145-3. Yield 59%.

$^1$H NMR (CDCl$_3$) δ 1.57-2.02 (12H, m), 2.15-2.35 (3H, m), 2.47-2.65 (2H, m), 2.74 (3H, s), 2.82 (3H, s), 2.90-3.01 (3H, m), 3.58-3.80 (4H, m), 3.85 (3H, s), 7.02 (1H, dd, J=2.2, 8.4 Hz), 7.28 (1H, d, J=2.2 Hz), 7.52 (1H, d, J=8.4 Hz), 8.06 (4H, s).

EXAMPLE 386

N-(3,4-Dichlorophenyl)-N-{3-[4-({4-[(diethylamino)sulfonyl]phenylsulfonyl)-1-piperidinyl]propyl)-1-(methylsulfonyl)-4-piperidinecarboxamide The title compound was prepared using a similar procedure to that described in example 190 from the title compound of reference example 146-3. Yield 74%.

$^1$H NMR (CDCl$_3$) δ 1.56 (6H, t, J=7.0 Hz), 1.60-2.02 (12H, m), 2.10-2.34 (3H, m), 2.48-2.65 (2H, m), 2.74 (3H, s), 2.85-3.00 (3H, m), 3.29 (4H, q, J=7.0 Hz), 3.57-3.80 (4H, m), 7.01 (1H, dd, J=2.6, 8.4 Hz), 7.28 (1H, d, J=2.6 Hz), 7.52 (1H, d, J=8.4 Hz), 7.91 (4H, s).

EXAMPLE 387

N-(3,4-Dichlorophenyl)-N-(3-{4-[4-(cyclopentylsulfonyl)benzyl]-1-piperidinyl}propyl)-1-(methylsulfonyl)-4-piperidinecarboxamide The title compound was prepared using a similar procedure to that described in example 190 from the title compound of reference example 141-3. Yield 89%.

$^1$H NMR (CDCl$_3$) δ 1.18-1.40 (2H, m), 1.45-2.15 (19H, m), 2.18-2.35 (3H, m), 2.49-2.65 (4H, m), 2.70-2.95 (2H, m), 2.74 (3H, s), 3.40-3.58 (1H, m), 3.60-3.80 (4H, m), 7.03 (1H, dd, J=2.2, 8.4 Hz), 7.25-7.32 (3H, m), 7.52 (1H, d, J=8.4 Hz), 7.80 (2H, d, J=8.4 Hz).

EXAMPLE 388

N-(3,4-Dichlorophenyl)-N-(3-{4-[4-(isobutylsulfonyl)benzyl]-1-piperidinyl}propyl)-1-(methylsulfonyl)-4-piperidinecarboxamide The title compound was prepared using a similar procedure to that described in example 190 from the title compound of reference example 142-3. Yield 84%.

$^1$H NMR (CDCl$_3$) δ 1.06 (6H, d, J=6.6 Hz), 1.20-1.40 (2H, m), 1.45-2.00 (12H, m), 2.10-2.35 (4H, m), 2.48-2.65 (4H, m), 2.74 (3H, s), 2.77-2.90 (2H, m), 2.98 (2H, d, J=6.6 Hz), 3.60-3.80 (4H, m), 7.15 (1H, dd, J=2.6, 8.4 Hz), 7.306 (1H, d, J=8.2 Hz), 7.308 (1H, d, J=2.6 Hz), 7.52 (1H, d, J=8.4 Hz), 7.80 (2H, d, J=8.2 Hz).

EXAMPLE 389

N-(3,4-Dichlorophenyl)-N-[3-(4-{[(4-fluorophenyl)sulfanyl]methyl}-1-piperidinyl)propyl]-1-(methylsulfonyl)-4-piperidinecarboxamide The title compound was prepared using a similar procedure to that described in example 190 from the title compound of reference example 149-2. Yield 90%.

$^1$H NMR (CDCl$_3$) δ 1.15-2.00 (13H, m), 2.15-2.34 (3H, m), 2.50-2.65 (2H, m), 2.74 (3H, s), 2.75-2.90 (2H, m), 2.78 (2H, d, J=6.6 Hz), 3.60-3.80 (4H, m), 6.92-7.07 (3H, m), 7.27-7.35 (3H, m), 7.52 (1H, d, J=8.4 Hz).

EXAMPLE 390

N-(3,4-Dichlorophenyl)-N-[3-(4-{[(4-fluorophenyl)sulfonyl]methyl}-1-piperidinyl)propyl]-1-(methylsulfonyl)-4-piperidinecarboxamide The title compound was prepared using a similar procedure to that described in example 190 from the title compound of reference example 150-2. Yield 77%.

$^1$H NMR (CDCl$_3$) δ 1.22-1.45 (2H, m), 1.57-2.05 (11H, m), 2.14-2.33 (3H, m), 2.44-2.67 (2H, m), 2.70-2.85 (2H, m), 2.74 (3H, s), 2.99 (2H, d, J=6.2 Hz), 2.59-2.80 (4H, m), 7.02 (1H, dd, J=2.6, 8.4 Hz), 7.20-7.31 (3H, m), 7.52 (1H, d, J=8.4 Hz), 7.88-7.96 (2H, m).

EXAMPLE 391

N-(3,4-Dichlorophenyl)-N-(3-{4-[4-(methylsulfanyl)benzyl]-1-piperidinyl}propyl)-1-(methylsulfonyl)-4-piperidinecarboxamide The title compound was prepared using a similar procedure to that described in example 190 from the title compound of reference example 143-2. Yield 92%.

$^1$H NMR (CDCl$_3$) δ 1.18-1.35 (2H, m), 1.55-2.00 (11H, M), 2.15-2.33 (3H, m), 2.43-2.66 (4H, m), 2.47, (3H, s), 2.74 (3H, s), 2.75-2.88 (2H, m), 3.60-3.80 (4H, m), 7.00-7.10 (3H, m), 7.19 (2H, d, J=8.4 Hz), 7.32 (1H, d, J=2.6 Hz), 7.52 (1H, d, J=8.6 Hz).

EXAMPLE 392

N-(3,4-Dichlorophenyl)-1-(methylsulfonyl)-N-[3-(4-{[4-(1-pyrrolidinylsulfonyl)phenyl]sulfonyl}-1-piperidinyl)propyl]-4-piperidinecarboxamide The title compound was prepared using a similar procedure to that described in example 190 from the title compound of reference example 147-3. Yield 78%.

$^1$H NMR (CDCl$_3$) δ 1.57-2.05. (17H, m), 2.20-2.34 (3H, m), 2.46-2.66 (2H, m), 2.74 (3H, s), 2.82-3.02 (3H, m), 3.25-3.33 (3H, m), 3.57-3.80 (4H, m), 7.02 (1H, dd, J=2.2, 8.4 Hz), 7.29 (1H, d, J=2.2 Hz), 7.53 (1H, d, J=8.4 Hz), 8.02 (4H, s).

EXAMPLE 393

N-(3-{4-[4-(Cyclopentylsulfonyl)benzyl]-1-piperidinyl}propyl)-1-(methylsulfonyl)-N-phenyl-4-piperidinecarboxamide The title compound was prepared using a similar procedure to that described in example 403 from the title compound of reference example 141-3. Yield 85%.

$^1$H NMR (CDCl$_3$) δ 1.20-1.40 (2H, m), 1.45-2.10 (19H, m), 2.20-2.35 (3H, m), 2.42-2.63 (4H, m), 2.74 (3H, s), 2.75-2.90 (2H, m), 3.40-3.53 (1H, m), 3.62-3.79 (4H, m), 7.10-7.19 (2H, m), 7.20 (2H, d, J=8.4 Hz), 7.35-7.50 (3H, m), 7.79 (2H, d, J=8.4 Hz).

EXAMPLE 394

N-(3-Chlorophenyl)-N-(3-{4-[4-(cyclopentylsulfonyl)benzyl]-1-piperidinyl}propyl)-1-(methylsulfonyl)-4-piperidinecarboxamide The title compound was prepared using a similar procedure to that described in example 412 from the title compound of reference example 141-3. Yield 78%.

$^1$H NMR (CDCl$_3$) δ 1.20-1.40 (2H, m), 1.45-2.14 (19H, m), 2.20-2.35 (3H, m), 2.45-2.65 (4H, m), 2.73 (3H, s), 2.79-2.90 (2H, m), 3.40-3.59 (1H, m), 3.61-3.80 (4H, m), 7.02-7.10 (1H, m), 7.16-7.21 (1H, m), 7.26-7.40 (4H, m), 7.79 (2H, d, J=8.0 Hz).

EXAMPLE 395

N-(4-Fluorophenyl)-1-(methylsulfonyl)-N-(3-{4-[4-(methylsulfonyl)benzyl]-1-piperidinyl}propyl)-4-piperidinecarboxamide The title compound was prepared using a similar procedure to that described in example 343 from the title compound of reference example 151. Yield 34%.

$^1$H NMR (CDCl$_3$) δ 1.23-1.45 (2H, m), 1.50-2.05 (11H, m), 2.15-2.65 (7H, m), 2.72 (3H, s), 2.88-3.00 (2H, m), 3.05 (3H, s), 3.60-3.80 (4H, m), 7.15 (4H, d, J=6.6 Hz), 7.32 (2H, d, J=8.4 Hz), 7.85 (2H, d, J=8.4 Hz).

EXAMPLE 396

N-(3,4-Dichlorophenyl)-N-{3-[4-({4-[methyl(methylsulfonyl)amino]phenyl}sulfonyl)-1-piperidinyl]propyl}-1-(methylsulfonyl)-4-piperidinecarboxamide The title compound was prepared using a similar procedure to that described in example 190 from the title compound of reference example 148-6. Yield 72%.

$^1$H NMR (CDCl$_3$) δ 1.55-2.05 (13H, m), 2.10-2.35 (3H, m), 2.45-2.65 (2H, m), 2.74 (3H, s), 2.80-3.00 (2H, m), 2.92 (3H, s), 3.40 (3H, s), 3.58-3.85 (4H, m), 7.02 (1H, dd, J=2.6, 8.4 Hz), 7.29 (1H, d, J=2.6 Hz), 7.48-7.61 (3H, m), 7.85 (2H, d, J=8.8 Hz).

EXAMPLE 397

N-(4-Ethylphenyl)-1-(methylsulfonyl)-N-(3-{4-[4-(methylsulfonyl)benzyl]-1-piperidinyl}propyl)-4-piperidinecarboxamide The title compound was prepared using a similar procedure to that described in example 343 from the title compound of reference example 153. Yield 90%.

$^1$H NMR (CDCl$_3$) δ 1.20-1.40 (2H, m), 1.27 (3H, t, J=7.6 Hz), 1.42-2.00 (11H, m), 2.20-2.35 (3H, m), 2.45-2.75 (6H, m), 2.72 (3H, s), 2.78-2.90 (2H, m), 3.05 (3H, s), 3.60-3.78 (4H, m), 7.03 (2H, d, J=8.0 Hz), 7.25 (2H, d, J=8.0 Hz), 7.31 (2H, d, J=8.0 Hz), 7.84 (2H, d, J=8.0 Hz).

EXAMPLE 398

N-(3-Ethylphenyl)-1-(methylsulfonyl)-N-(3-{4-[4-(methylsulfonyl)benzyl]-1-piperidinyl}propyl)-4-piperidinecarboxamide The title compound was prepared using a similar procedure to that described in example 343 from the title compound of reference example 152. Yield 46%.

$^1$H NMR (CDCl$_3$) δ 1.20-1.40 (2H, m), 1.24 (3H, t, J=7.6 Hz), 1.50-1.98 (11H, m), 2.17-2.35 (3H, m), 2.42-2.75 (6H, m), 2.72 (3H, s), 2.79-2.91 (2H, m), 3.05 (3H, s), 3.60-3.77 (4H, m), 6.92-9.98 (2H, m), 7.17-7.38 (4H, m), 7.84 (2H, d, J=8.4 Hz).

EXAMPLE 399

N-(4-Butylphenyl)-1-(methylsulfonyl)-N-(3-{4-[4-(methylsulfonyl)benzyl]-1-piperidinyl}propyl)-4-piperidinecarboxamide The title compound was prepared using a similar procedure to that described in example 343 from the title compound of preparartion 155. Yield 95%.

$^1$H NMR (CDCl$_3$) δ 0.95 (3H, t, J=7.2 Hz). 1.20-2.03 (17H, m), 2.20-2.35 (3H, m), 2.45-2.72 (6H, m), 2.72 (3H, s), 2.78-2.90 (2H, m), 3.05 (3H, s), 3.60-3.79 (4H, m), 7.03 (2H, d, J=8.4 Hz), 7.22 (2H, d, J=8.4 Hz), 7.32 (2H, d, J=8.5 Hz), 7.84 (2H, d, J=8.5 Hz).

EXAMPLE 400

N-(4-tert-Butylphenyl)-1-(methylsulfonyl)-N-(3-{4-[4-(methylsulfonyl)benzyl]-1-piperidinyl}propyl)-4-piperidinecarboxamide The title compound was prepared using a similar procedure to that described in example 343 from the title compound of preparartion 156. Yield 94%.

¹H NMR (CDCl₃) δ 1.22-1.38 (2H, m), 1.35 (9H, s), 1.50-2.00 (11H, m), 2.21-2.33 (3H, m), 2.50-2.65 (4H, m), 2.74 (3H, s), 2.78-2.90 (2H, m), 3.05 (3H, s), 3.60-3.78 (4H, m), 7.05 (2H, d, J=8.4 Hz), 7.32 (2H, d, J=8.0 Hz), 7.42 (2H, d, J=8.4 Hz), 7.84 (2H, d, J=8.0 Hz).

EXAMPLE 401

N-(4-Cyclohexylphenyl)-1-(methylsulfonyl)-N-(3-{4-[4-(methylsulfonyl)benzyl]-1-piperidinyl}propyl)-4-piperidinecarboxamide The title compound was prepared using a similar procedure to that described in EXAMPLE 343 from the title compound of prepararion 157. Yield 96%.

¹H NMR (CDCl₃) δ 1.20-2.00 (24H, m), 2.20-2.35 (3H, m), 2.45-2.67 (4H, m), 2.72 (3H, s), 2.79-2.90 (2H, m), 3.05 (3H, s), 3.60-3.79 (4H, m), 7.03 (2H, d, J8.4 Hz), 7.24 (2H, d, J=8.4 Hz), 7.32 (2H, d, J=8.4 Hz), 7.84 (2H, d, J=8.4 Hz).

EXAMPLE 402

1-(Methylsulfonyl)-N-(3-{4-[4-(methylsulfonyl)benzyl]-1-piperidinyl}propyl)-N-(4-propylphenyl)-4-piperidinecarboxamide The title compound was prepared using a similar procedure to that described in Example 343 from the title compound of prepararion 154. Yield 89%.

¹H NMR (CDCl₃) δ 0.96 (3H, t, J=7.6 Hz), 1.20-1.40 (2H, m), 1.45-2.00 (13H, m), 2.20-2.35 (3H, m), 2.45-2.70 (6H, m), 2.72 (3H, s), 2.79-2.90 (2H, m), 3.05 (3H, s), 3.60-3.78 (4H, m), 7.03 (2H, d, J=8.4 Hz), 7.22 (2H, d, J=8.4 Hz), 7.32 (2H, d, J=8.2 Hz), 7.84 (2H, d, J=8.2 Hz).

EXAMPLE 403

1-(Methylsulfonyl)-N-phenyl-N-(3-{4-[4-(propylsulfonyl)benzyl]-1-piperidinyl}propyl)-4-piperidinecarboxamide A mixture of the compound of reference example 159 (0.36 g, 1.0 mmol), that of reference example 138-2 (0.34 g, 1.2 mmol), KI (0.17 g, 1.0 mmol), K₂CO₃ (0.21 g, 1.5 mmol) in acetonitrile (24 mL) was stirred at 80° C. for 12 h. The reaction mixture was concentrated under reduced pressure and then water (10 mL) and ethyl acetate (30 mL) was added to the residue. The organic layer was washed with 1N NaOH (5 mL×2) and with brine (5 mL), dried over MgSO₄, and concentrated under reduced pressure. The residue was purified by silica gel column chromatography (ethyl acetate-methanol, 10/1, v/v) to give the title compound (0.36 g, 0.60 mmol) as pale yellow paste. Yield: 60%.

¹H NMR (CDCl₃) δ 1.00 (3H, t, J=7.4 Hz), 1.15-1.40 (2H, m), 1.40-2.00 (13H, m), 2.15-2.35 (3H, m), 2.40-2.65 (4H, m), 2.72 (3H, s), 2.80-2.95 (2H, m), 3.00-3.15 (2H, m), 3.60-3.80 (4H, m), 7.10-7.20 (2H, m), 7.25-7.50 (5H, m), 7.75-7.85 (2H, m).

EXAMPLE 404

N-[3-(4-{4-[(2-Ethoxyethyl)sulfonyl]benzyl}-1-piperidinyl)propyl]-1-(methylsulfonyl)-N-phenyl-4-piperidinecarboxamide Reference Example of the title compound from the compound of reference example 159 and that of reference example 164-3 was carried out according to the procedure of Example 403. Yield: 42%.

¹H NMR (CDCl₃) δ 1.02 (3H, t, J=7.0 Hz), 1.15-1.40 (2H, m), 1.50-2.00 (11H, m), 2.20-2.65 (7H, m), 2.72 (3H, s), 2.80-2.95 (2H, m), 3.35-3.45 (2H, m), 3.37 (2H, q, J=7.0 Hz), 3.60-3.80 (4H, m), 3.78 (2H, t, J=6.2 Hz), 7.10-7.20 (2H, m), 7.25-7.50 (5H, m), 7.75-7.85 (2H, m).

EXAMPLE 405

N-(3-Chlorophenyl)-1-(methylsulfonyl)-N-(3-{4-[4-(propylsulfonyl)benzyl]-1-piperidinyl}propyl)-4-piperidinecarboxamide Reference Example of the title compound from the compound of reference example 165-4 and that of reference example 138-2 was carried out according to the procedure of Example 412. Yield: 69%.

¹H NMR (CDCl₃) δ 1.00 (3H, t, J=7.3 Hz), 1.15-1.40 (2H, m), 1.45-2.00 (13H, m), 2.20-2.35 (3H, m), 2.45-2.65 (4H, m), 2.73 (3H, s), 2.75-2.90 (2H, m), 3.00-3.10 (2H, m), 3.60-3.80 (4H, m), 7.00-7.25 (2H, m), 7.25-7.45 (4H, m), 7.75-7.85 (2H, m).

EXAMPLE 406

N-(3-Chlorophenyl)-N-[3-(4-{4-[(2-ethoxyethyl)sulfonyl]benzyl)-1-piperidinyl)propyl]-1-(methylsulfonyl)-4-piperidinecarboxamide Reference Example of the title compound from the compound of reference example 165-4 and that of reference example 164-3 was carried out according to the procedure of example 412. Yield: 37%.

¹H NMR (CDCl₃) δ 1.02 (3H, t, J=7.0 Hz), 1.15-1.40 (2H, m), 1.45-2.00 (11H, m), 2.20-2.35 (3H, m), 2.45-2.65 (4H, m), 2.73 (3H, s), 2.75-2.90 (2H, m), 3.30-3.45 (2H, m), 3.37 (2H, q, J=7.0 Hz), 3.60-3.80 (4H, m), 3.78 (2H, t, J=6.6 Hz), 7.00-7.10 (1H, m), 7.15-7.40 (5H, m), 7.75-7.85 (2H, m).

EXAMPLE 407

N-(3,4-Dichlorophenyl)-N-[3-(4-{4-[(2-ethoxyethyl)sulfonyl]benzyl}-1-piperidinyl)propyl]-1-(methylsulfonyl)-4-piperidinecarboxamide Reference Example of the title compound from the compound of reference example 57 and that of reference example 164-3 was carried out according to the procedure of example 356. Yield: 68%.

¹H NMR (CDCl₃) δ 1.02 (3H, t, J=7.0 Hz), 1.10-2.05 (13H, m), 2.15-2.35 (3H, m), 2.45-2.90 (6H, m), 2.74 (3H, s), 3.35-3.45 (2H, m), 3.37 (2H, q, J=7.0 Hz), 3.60-3.80 (4H, m), 3.78 (2H, t, J=6.2 Hz), 6.95-7.05 (1H, m), 7.15-7.35 (3H, m), 7.45-7.60 (1H, m), 7.75-7.85 (2H, m).

EXAMPLE 408

N-(3-Fluorophenyl)-1-(methylsulfonyl)-N-(3-{4-[4-(methylsulfonyl)benzyl]-1-piperidinyl}propyl)-4-piperidinecarboxamide Acylation of the compound of reference example 160 was carried out according to the procedure of Example 343 to give the title compound. Yield: 91%.

¹H NMR (CDCl₃) δ 1.10-1.40 (2H, m), 1.40-2.00 (11H, m), 2.20-2.35 (3H, m), 2.45-2.65 (4H, m), 2.73 (3H, s), 2.83

(2H, d, J=11.2 Hz), 3.05 (3H, s), 3.60-3.80 (4H, m), 6.85-7.00 (2H, m), 7.05-7.20 (1H, m), 7.25-7.50 (3H, m), 7.80-7.90 (2H, m).

EXAMPLE 409

1-(Methylsulfonyl)-N-(3-{4-[4-(methylsulfonyl)benzyl]-1-piperidinyl}propyl)-N-[4-(trifluoromethyl)phenyl]-4-piperidinecarboxamide Acylation of the compound of reference example 161 was carried out according to the procedure of Example 343 to give the title compound. Yield: 96%.

$^1$H NMR (CDCl$_3$) δ 1.10-1.40 (2H, m), 1.40-2.00 (11H, m), 2.10-2.35 (1H, m), 2.29 (2H, t, J=7.6 Hz), 2.45-2.65 (2H, m), 2.61 (2H, d, J=14.2 Hz), 2.73 (3H, s), 2.82 (2H, d, J=11.4 Hz), 3.05 (3H, s), 3.65-3.80 (2H, m), 3.71 (2H, t, J=7.6 Hz), 7.25-7.40 (4H, m), 7.65-7.80 (2H, m), 7.80-7.90 (2H, m).

EXAMPLE 410

N-(3-Isopropylphenyl)-1-(methylsulfonyl)-N-(3-{4-[4-(methylsulfonyl)benzyl]-1-piperidinyl}propyl)-4-piperidinecarboxamide Acylation of the compound of reference example 162 was carried out according to the procedure of Example 343 to give the title compound. Yield: 99%.

$^1$H NMR (CDCl$_3$) δ 1.10-1.40 (2H, m), 1.25 (6H, d, J=6.6 Hz), 1.40-2.00 (11H, m), 2.05-2.35 (3H, m), 2.40-2.65 (2H, m), 2.61 (2H, d, J=6.6 Hz), 2.73 (3H, s), 2.85 (2H, d, J=10.2 Hz), 2.85-3.05 (1H, m), 3.05 (3H, s), 3.60-3.80 (4H, m), 6.90-7.00 (2H, m), 7.15-7.40 (4H, m), 7.80-7.90 (2H, m).

EXAMPLE 411

N-(4-Methylphenyl)-1-(methylsulfonyl)-N-(3-{4-[4-(methylsulfonyl)benzyl]-1-piperidinyl}propyl)-4-piperidinecarboxamide Acylation of the compound of reference example 163 was carried out according to the procedure of Example 343 to give the title compound. Yield: 88%.

$^1$H NMR (CDCl$_3$) δ 1.10-1.40 (2H, m, 1.45-2.00 (11H, m), 2.20-2.35 (3H, m), 2.40 (3H, s), 2.40-2.65 (2H, m), 2.61 (2H, d, J=6.2 Hz), 2.72 (3H, s), 2.84 (2H, d, J=11.0 Hz), 3.05 (3H, s), 3.60-3.80 (4H, m), 6.95-7.05 (2H, m), 7.15-7.40 (4H, m), 7.80-7.90 (2H, m).

EXAMPLE 412

N-(3-Chlorophenyl)-N-(3-{4-[4-(isopropylsulfonyl)benzyl]-1-piperidinyl}propyl)-1-(methylsulfonyl)-4-piperidinecarboxamide hydrochloride A mixture of the compound obtained at reference example 165-4 (500 mg, 1.27 mmol), the compound obtained at reference example 140-4 (484 mg, 1.53 mmol), KI (254 mg, 1.53 mmol), K$_2$CO$_3$ (263 mg, 1.91 mmol) and acetonitrile (20 ml) was refluxed for 18 h. After being cooled to room temperature, the mixture was extracted with EtOAc-H$_2$O. The organic layer was washed with brine, dried over Na$_2$SO$_4$ and then concentrated. The residue was purified by silica gel column chromatography with EtOAc/MeOH (10/1) as an eluent. The fractions containing the target compound were combined and evaporated to give an amorphous solid. This solid was suspended in 4N HCl/EtOAc (5 ml) and stirred at room temperature for 30 min. After removal of solvent in vacuo, the residue was crystallized from iPr$_2$O to give the title compound (450 mg, 0.667 mmol, 53%) as a colorless solid.

$^1$H NMR (CD$_3$OD) δ 1.26 (6H, d, J=7.0 Hz), 1.40-2.10 (11H, m), 2.20-2.60 (3H, m), 2.74 (3H, s), 2.70-3.40 (7H, m), 3.50-3.90 (6H, m), 7.30-7.40 (1H, m), 7.45-7.60 (5H, m), 7.82 (2H, d, J=8.4 Hz)

free base: $^1$H NMR (CDCl$_3$) δ 1.29 (6H, d, J=6.6 Hz), 1.40-2.00 (13H, m), 2.15-2.35 (3H, m), 2.45-2.70 (4H, m), 2.73 (3H, s), 2.75-2.90 (2H, m), 3.10-3.30 (1H, m), 3.60-3.80 (4H, m), 7.00-7.10 (1H, m), 7.15-7.40 (5H, m), 7.77 (2H, d, J=8.0 Hz)

EXAMPLE 413

N-(3-Chlorophenyl)-N-(3-{4-[4-(ethylsulfonyl)benzyl]-1-piperidinyl}propyl)-1-(methylsulfonyl)-4-piperidinecarboxamide hydrochloride The title compound was prepared by a similar procedure that employed for example 412 using the compound obtained at reference example 166-3 in 35% yield.

$^1$H NMR (CD$_3$OD) δ 1.23 (3H, t, J=7.2 Hz), 1.30-2.10 (11H, m), 2.20-2.60 (3H, m), 2.74 (3H, s), 2.70-3.30 (8H, m), 3.40-3.90 (6H, m), 7.30-7.40 (1H, m), 7.45-7.60 (5H, m), 7.85 (2H, d, J=8.4 Hz)

free base: $^1$H NMR (CDCl$_3$) δ 1.28 (3H, t, J=7.4 Hz), 1.20-2.00 (13H, m), 2.10-2.40 (3H, m), 2.45-2.70 (4H, m), 2.73,(3H, s), 2.80-2.95 (2H, m), 3.10 (2H, q, J=7.4 Hz), 3.60-3.80 (4H, m), 7.00-7.40 (6H, m), 7.80 (2H, d, J=8.2 Hz)

EXAMPLE 414

N-(3-{4-[4-(Isopropylsulfonyl)benzyl]-1-piperidinyl}propyl)-1-(methylsulfonyl)-N-phenyl-4-piperidinecarboxamide hydrochloride The title compound was prepared by a similar procedure that employed for example 412 using the compounds obtained, at reference example 159 and reference example 140-4 in 64% yield.

$^1$H NMR (CD$_3$OD) δ 1.26 (6H, d, J=7.0 Hz), 1.40-2.10 (11H, m), 2.20-2.60 (3H, m), 2.72 (3H, s), 2.75-3.20 (7H, m), 3.50-3.90 (6H, m), 7.30-7.40 (2H, m), 7.45-7.60 (5H, m), 7.82 (2H, d, J=8.8 Hz)

free base: $^1$H NMR (CDCl$_3$) δ 1.29 (6H, d, J=6.6 Hz), 1.40-2.00 (13H, m), 2.10-2.35 (3H, m), 2.40-2.70 (4H, m), 2.72 (3H, s), 2.75-2.95 (2H, m), 3.10-3.30 (1H, m), 3.60-3.80 (4H, m), 7.10-7.50 (7H, m), 7.77 (2H, d, J=8.4 Hz)

EXAMPLE 415

N-(3-{4-[4-(Ethylsulfonyl)benzyl]-1-piperidinyl}propyl)-1-(methylsulfonyl)-N-phenyl-4-piperidinecarboxamide hydrochloride The title compound was prepared by a similar procedure that employed for example 412 using the compounds obtained at reference example 159 and reference example 166-3 in 46% yield.

$^1$H NMR (CD$_3$OD) δ 1.23 (3H, t, J=7.6 Hz), 1.20-2.10 (11H, m), 2.30-2.50 (3H, m), 2.73 (3H, s), 2.70-3.30 (8H, m), 3.40-3.90 (6H, m), 7.35 (2H, d, J=8.4 Hz), 7.40-7.60 (5H, m), 7.85 (2H, d, J=8.4 Hz)

free base: $^1$H NMR (CDCl$_3$) δ 1.10-2.00 (13H, m), 1.28 (3H, t, J=7.2 Hz), 2.15-2.38 (3H, m), 2.40-2.65 (4H, m), 2.72 (3H, s), 2.80-2.90 (2H, m), 3.11 (2H, q, J=7.2 Hz), 3.60-3.80 (4H, m), 7.10-7.50 (7H, m), 7.80 (2H, d, J=8.0 Hz)

EXAMPLE 416

1-(Methylsulfonyl)-N-(3-{4-[4-(methylsulfonyl)benzyl]-1-piperidinyl}propyl)-N-[3-(trifluoromethyl)phenyl]-4-piperidinecarboxamide hydrochloride To a solution of the compound obtained at reference example 167 (500 mg, 0.949 mmol), Et$_3$N (0.397 ml, 2.85 mmol) in CH$_2$Cl$_2$ (20 ml) was added dropwise a solution of the compound obtained at reference example 158 (428 mg, 1.90 mmol) in CH$_2$Cl$_2$ (10 ml) keeping the temperature at 0° C. After being stirred at 0° C. for 15 min, the reaction mixture was warmed to room temperature and stirred for additional 1 h. 1N NaOH (20 ml) was added to the reaction mixture. The organic layer was separated and washed with brine, dried over Na$_2$SO$_4$ and then concentrated. The residue was purified by silica gel column chromatography (Fuji Silysia Chromatorex NH-DM1020) with hexane/EtOAc (2/1) as an eluent. The fractions containing the target compound were combined and evaporated to give an amorphous solid. This solid was dissolved in EtOAc (1 ml) and 4N HCl/EtOAc (1 ml) was added to this solution. The resulting precipitates were collected by filtration to give the title compound (140 mg, 0.206 mmol, 22%) as a colorless solid.

$^1$H NMR (CD$_3$OD) δ 1.40-2.10 (11H, m), 2.15-2.60 (3H, m), 2.73 (3H, s), 2.70-3.20 (6H, m), 3.11 (3H, s), 3.50-3.90 (6H, m), 7.47 (2H, d, J=8.4 Hz), 7.60-7.80 (4H, m), 7.89 (2H, d, J=8.6 Hz)

EXAMPLE 417

N-(4-Isopropylphenyl)-1-(methylsulfonyl)-N-(3-{4-[4-(methylsulfonyl)benzyl]-1-piperidinyl}propyl)-4-piperidinecarboxamide hydrochloride The title compound was prepared from the compound obtained at reference example 168 using a similar procedure that employed for example 416 in 45% yield.

$^1$H NMR (CD$_3$OD) δ 1.28 (6H, d, J=6.6 Hz), 1.40-2.10 (11H, m), 2.15-2.60 (3H, m), 2.73 (3H, s), 2.70-3.20 (7H, m), 3.05 (3H, s), 3.40-3.90 (6H, m), 7.25 (2H, d, J=8.6 Hz), 7.39 (2H, d, J=8.6 Hz), 7.48 (2H, d, J=8.4 Hz), 7.89 (2H, d, J=8.4 Hz)

free base: $^1$H NMR (CDCl$_3$) δ 1.27 (6H, d, J=7.0 Hz), 1.20-2.00 (13H, m), 2.20-2.40 (3H, m), 2.45-2.70 (4H, m), 2.73 (3H, s), 2.80-3.00 (3H, m), 3.05 (3H, s), 3.60-3.80 (4H, m), 7.04 (2H, d, J=8.6 Hz), 7.26 (2H, d, J=8.6 Hz), 7.32 (2H, d, J=8.4 Hz), 7.84 (2H, d, J=8.4 Hz)

EXAMPLE 418

N-(4-Chlorophenyl)-1-(methylsulfonyl)-N-(3-{4-[4-(methylsulfonyl)benzyl]-1-piperidinyl}propyl)-4-piperidinecarboxamide hydrochloride The title compound was prepared from the compound obtained at reference example 169 using a similar procedure that employed for example 416 in 44% yield.

$^1$H NMR (CD$_3$OD) δ 1.40-2.10 (11H, m), 2.20-2.60 (3H, m), 2.73 (3H, s), 2.70-3.20 (6H, m), 3.11 (3H, s), 3.40-3.85 (6H, m), 7.36 (2H, d, J=8.8 Hz), 7.48 (2H, d, J=8.8 Hz), 7.53 (2H, d, J=8.8 Hz), 7.89 (2H, d, J=8.8 Hz)

free base: $^1$H NMR (CDCl$_3$) δ 1.10-2.00 (13H, m), 2.10-2.35 (3H, m), 2.40-2.70 (4H, m), 2.73 (3H, s), 2.75-2.90 (2H, m), 3.05 (3H, s), 3.55-3.80 (4H, m), 7.10 (2H, d, J=8.4 Hz), 7.32 (2H, d, J=8.4 Hz), 7.42 (2H, d, J=8.4 Hz), 7.84 (2H, d, J=8.4 Hz)

EXAMPLE 419

N-(3-Methylphenyl)-1-(methylsulfonyl)-N-(3-{4-[4-(methylsulfonyl)benzyl]-1-piperidinyl}propyl)-4-piperidinecarboxamide To a solution of the compound obtained at reference example 170 (600 mg, 1.26 mmol), Et$_3$N (0.708 ml, 5.08 mmol) in CH$_2$Cl$_2$ (20 ml) was added dropwise a solution of the compound obtained at reference example 158 (569 mg, 2.52 mmol) in CH$_2$Cl$_2$ (10 ml) keeping the temperature at 0° C. After being stirred at 0° C. for 1 h, the reaction mixture was warmed to room temperature and stirred for additional 1 h. 1N NaOH (10 ml) was added to the reaction mixture. The mixture was extracted with CH$_2$Cl$_2$ and the extract was washed with brine, dried over Na$_2$SO$_4$ and then concentrated. The residue was purified by silica gel column chromatography (Fuji Silysia Chromatorex NH-DM1020) with hexane/EtOAc (2/1) as an eluent. The fractions containing the target compound were combined and evaporated to give an amorphous solid, which was recrystallized from EtOAc-CH$_2$Cl$_2$ to give the title compound (420 mg, 0.712 mmol, 56%) as a colorless solid.

$^1$H NMR (CDCl$_3$) δ 1.15-2.00 (13H, m), 2.20-2.35 (3H, m), 2.38 (3H, s), 2.40-2.70 (4H, m), 2.72 (3H, s), 2.75-2.90 (2H, m), 3.05 (3H, s), 3.60-3.80 (4H, m), 6.92 (2H, d, J=7.0 Hz), 7.10-7.40 (4H, m), 7.84 (2H, d, J=8.0 Hz)

EXAMPLE 420

N-(3,4-Dichlorophenyl)-1-(methylsulfonyl)-N-(3-{4-[4-(methylsulfonyl)benzyl]-1-piperidinyl}propyl)-4-piperidinecarboxamide hydrochloride A mixture of the title compound of reference example 57 (705 mg), 4-[4-(methylsulfonyl)benzyl]piperidine (500 mg), potassium iodide (274 mg), potassium carbonate (342 mg) in acetonitrile (15 ml) was stirred and heated under reflux for 8 hours. Ethyl acetate (30 ml) and water (30 ml) were added to the reaction mixture. The separated organic layer was washed with brine (30 ml), dried over magnesium sulfate, filtered and concentrated under reduced pressure. The residue was subjected to column chromatography (silica gel, ethyl acetate/methanol=5/1). The fractions containing the product were collected and concentrated under reduced pressure to afford a colorless oil (964 mg).

To a solution of the above compound (500 mg) in methanol (5 ml) was added dropwise a solution of 4N hydrogen chloride in ethyl acetate (0.96 ml). After 10 minutes, the solvent was removed under reduced pressure and the residue was washed with diisopropyl ether and a small amount of ethyl acetate to afford the title compound (521 mg) as a colorless powder.

$^1$H NMR (CD$_3$OD) δ 1.4-2.1 (11H, m), 2.2-2.65 (3H, m), 2.65-3.2 (6H, m), 2.73 (3H, s), 3.10 (3H, s), 3.4-3.85 (6H, m), 7.36 (1H, dd, J=2.3 Hz, 8.5 Hz), 7.49 (2H, d, J=8.4 Hz), 7.69 (1H, d, J=8.5 Hz), 7.70 (1H, d, J=2.3 Hz), 7.90 (2H, d, J=8.4 Hz)

EXAMPLE 421

1-(Methylsulfonyl)-N-(3-{4-[4-(4-morpholinylsulfonyl)benzyl]-1-piperidinyl}propyl)-N-phenyl-4-piperidinecarboxamide hydrochloride To a stirred solution of the title compound of reference example 171 (0.6 g, 1.13 mmol) and triethylamine (556 ml, 4.0 mmol) in dichloromethane (10 ml) was added 1-(methylsulfonyl)-4-piperidinecarbonyl chloride (255 mg, 1.13 mmol) at 0° C. The mixture was stirred, being allowed to warm to room temperature, for 10 hours. The layers were separated with saturated aqueous sodium bicarbonate solution (10 ml) and dichloromethane (10 ml×2) and organics were washed with saturated aqueous sodium bicarbonate solution (10 ml×2) and brine (10 ml). The organic layer was dried over magnesium sulfate and the solvent was removed in vacuo. The oily residue was chromatographed on silica gel (40 g) with 4:1 ethyl acetate/methanol to give colorless oil.

$^1$H-NMR(CDCl$_3$) δ 1.10-1.95 (13H, m), 2.20-2.35 (3H, m), 2.41-2.53 (2H, m), 2.59 (2H, d, J=6.6 Hz), 2.72 (3H, s), 2.77-2.90 (2H, m), 2.96-3.02 (4H, m), 3.64-3.77 (8H, m), 7.15 (2H, dd, J=2.2, 5.8 Hz), 7.29 (2H, d, J=10.2 Hz), 7.38-7.45 (3H, m), 7.65 (2H, d, J=8.2 Hz)

This oil dissolved into 1:1 ethyl acetate/methanol (20 ml) was treated with 4N hydrogen chloride solution in ethyl acetate (500 ml). The white amorphous was filtered and washed with diisopropylether (10 ml) after solvent removal. The title compound was obtained as white amorphous (355 mg, yield 46%) after drying in vacuo.

EXAMPLE 422

N-(3-Chlorophenyl)-1-(methylsulfonyl)-N-(3-{4-[4-(4-morpholinylsulfonyl)benzyl]-1-piperidinyl}propyl)-4-piperidinecarboxamide hydrochloride The title compound (391 mg, yield 88%) was obtained by a similar procedure employed for example 421 from the title compound of reference example 172 (350 mg) and 1-(methylsulfonyl)-4-piperidinecarbonyl chloride (280 mg).

Free base: $^1$H-NMR (CDCl$_3$) δ 1.20-1.95 (13H, m), 2.22-2.38 (3H, m), 2.45-2.61 (2H, m), 2.60 (2H, d, J=6.2 Hz), 2.73 (3H, s), 2.77-2.90 (2H, m), 2.97-3.02 (4H, m), 3.64-3.77 (8H, m), 7.04-7.07 (1H, m), 7.19-7.32 (3H, m), 7.38 (2H, d, J=4.8 Hz), 7.65 (2H, d, J=8.0 Hz)

EXAMPLE 423

1-(Methylsulfonyl)-N-(3-{4-[4-(4-methylsulfonyl)benzyl]-1-piperidinyl}propyl)-N-phenyl-4-piperidinecarboxamide hydrochloride The title compound (167 mg, yield 63%) was obtained by a similar procedure employed for example 421 from the title compound of reference example 173 (200 mg).

Free base: $^1$H-NMR (CDCl$_3$) δ 1.10-1.40 (2H, m), 1.44-2.00 (11H, m), 2.16-2.36 (3H, m), 2.44-2.57 (2H, m), 2.61 (2H, d, J=6.2 Hz), 2.72 (3H, s), 2.81-2.86 (2H, brd), 3.05 (3H, s), 3.64-3.73 (4H, m), 7.15 (2H, dd, J=2.2, 8.0 Hz), 7.32 (2H, d, J=8.4 Hz), 7.37-7.45 (3H, m), 7.84 (2H, d, J=8.4 Hz)

EXAMPLE 424

N-(3-Chlorophenyl)-1-(methylsulfonyl)-N-(3-{4-[4-(4-methylsulfonyl)benzyl]-1-piperidinyl}propyl)-4-piperidinecarboxamide hydrochloride The title compound (206 mg, yield 52%) was obtained by a similar procedure employed for example 421 from the title compound of reference example 174 (300 mg).

EXAMPLE 425

N-(3-{4-[4-(Aminocarbonyl)benzyl]-1-piperidinyl}propyl)-1-(methylsulfonyl)-N-phenyl-4-piperidinecarboxamide The title compound (137 mg, yield 18%) was obtained by a similar procedure employed for example 179 from 4-(4-piperidinylmethyl)benzamide hydrochloride (390 mg) and N-(3-chloropropyl)-1-(methylsulfonyl)-N-phenyl-4-piperidinecarboxamide (500 mg).

$^1$H-NMR (CDCl$_3$) δ 1.10-1.20 (2H, m), 1.22-1.98 (11H, m), 2.15-2.38 (3H, m), 2.40-2.51 (2H, m), 2.57 (2H, d, J=6.0 Hz), 2.72 (3H, s), 2.82-2.87 (2H, brd), 3.64-3.72 (4H, m), 5.4-6.2 (2H, br), 7.13-7.22 (4H, m), 7.38-7.44 (3H, m), 7.72 (2H, d, J=8.4 Hz)

EXAMPLE 426

N-(3-{4-[4-(Aminocarbonyl)benzyl]-1-piperidinyl}propyl)-N-(3-chlorophenyl)-1-(methylsulfonyl) piperidinecarboxamide The title compound (235 mg, yield 32%) was obtained by a similar procedure employed for example 179 from 4-(4-piperidinylmethyl)benzamide hydrochloride (357 mg) and N-(3-chlorophenyl)-N-(3-chloropropyl)-1-(methylsulfonyl)-4-piperidinecarboxamide (500 mg).

$^1$H-NMR(CDCl$_3$) δ 1.10-1.39 (2H, m), 1.43-2.00 (11H, m), 2.13-2.36 (3H, m), 2.43-2.64 (2H, m), 2.57 (2H, d, J=6.2 Hz), 2.73 (3H, s), 2.78-2.85 (2H, brd), 3.62-3.75 (4H, m), 5.3-6.2 (2H, br), 7.04-7.07 (1H, m), 7.18-7.23 (3H, m), 7.37-7.39 (2H, m), 7.72 (2H, d, J=8.0 Hz)

EXAMPLE 427

N-(3,4-Dichlorophenyl)-N-[3-(4-{4-{(isopropylamino)carbonyl}benzyl}-1-piperidinyl)propyl]-1-(methylsulfonyl)-4-piperidinecarboxamide The title compound (481 mg, yield 63%) was obtained by a similar procedure employed for example 179 from N-isopropyl-4-(4-piperidinylmethyl)benzamide hydrochloride (386 mg) and N-(3-chloropropyl)-N-(3,4-dichlorophenyl)-1-(methylsulfonyl)-4-piperidinecarboxamide (506 mg).

$^1$H-NMR(CD$_3$OD) δ 1.24 (6H, d, J=6.6 Hz), 1.20-2.00 (13H, m), 2.23-2.39 (3H, m), 2.73 (3H, s), 2.42-2.64 (2H, m), 2.59 (2H, d, J=6.6 Hz), 2.82-2.97 (2H, br), 3.55-3.77 (4H, m), 4.20 (1H, septet, J=6.6 Hz), 7.22-7.32 (3H, m), 7.63-7.74 (4H, m)

EXAMPLE 428

N-(3,4-Dichlorophenyl)-N-{3-[4-(4-{[(2-hydroxyethyl)amino]carbonyl}benzyl)-1-piperidinyl]propyl}-1-(methylsulfonyl)-4-piperidinecarboxamide hydrochloride The title compound (433 mg, yield 54%) was obtained by a similar procedure employed for example 179 from N-(2-hydroxyethyl)-4-(4-piperidinylmethyl)benzamide hydrochloride (385 mg) and N-(3-chloropropyl)-N-(3,4-dichlorophenyl)-1-(methylsulfonyl)-4-piperidinecarboxamide (500 mg).

$^1$H-NMR(CD$_3$OD) δ 1.42-1.68 (2H, m), 1.70-2.04 (9H, m), 2.23-2.41 (1H, m), 2.44-2.62 (2H, m), 2.68-2.80 (2H, m), 2.73 (3H, s), 2.82-3.03 (2H, m), 3.06-3.14 (2H, m), 3.25-3.80 (6H, m), 3.50 (2H, t, J=5.6 Hz), 3.71 (2H, t, J=5.6 Hz), 7.30 (2H, d, J=8.4 Hz), 7.36 (1H, dd, J=2.4, 8.8 Hz), 7.69 (1H, d, J=8.8 Hz), 7.69 (1H, d, J=2.4 Hz), 7.79 (2H, d, J=8.4 Hz)

EXAMPLE 429

Benzyl 3-[(3,4-dichloro{3-[4-(4-fluorobenzyl)-1-piperidinyl]propyl}anilino)carbonyl]-1-pyrrolidinecarboxylate The title compound was obtained by a similar procedure, employed for example 1 from the title compound of reference example 3-3 and 1-[(benzyloxy)carbonyl]-3-pyrrolidinecarboxylic acid, yield 85%.

$^1$H-NMR (CDCl$_3$) δ 1.19-1.82 (12H, m), 1.93-2.01 (2H, m), 2.05-2.30 (1H, m), 2.34 (2H, d, J=6.0 Hz), 2.43-2.63 (1H, m), 2.68-2.89 (1H, m), 2.95-3.13 (1H, m), 3.57 (2H, t, J=7.0 Hz), 3.90-4.08 (2H, m), 5.03 (2H, s), 6.84-7.04 (5H, m), 7.18-7.25 (6H, m), 7.37 (1H, d, J=8.2 Hz)

EXAMPLE 430

N-(3,4-Dichlorophenyl)-N-(3-[4-(4-fluorobenzyl)-1-piperidinyl]propyl)-3-pyrrolidinecarboxamide The title compound was obtained by a similar procedure employed for example 66 from the title compound of example 429, yield 79%.

$^1$H-NMR (CDCl$_3$) δ 1.21-1.90 (12H, m), 2.33 (2H, t, J=7.8 Hz), 2.41 (2H, br), 2.48 (2H, d, J=6.6 Hz), 2.87 (2H, d, J=11.2 Hz), 3.12 (2H, d, J=12.0 Hz), 3.65 (2H, d, J=7.8 Hz), 3.94 (1H, br), 6.95-7.08 (5H, m), 7.31 (1H, d, J=2.2 Hz), 7.50 (1H, d, J=8.4 Hz)

EXAMPLES 431-446

The compounds of the following examples 431-442 were obtained using a similar procedure employed for example 145 from the title compound of example 430 and corresponding acids.

The compounds of the following examples 443-446 were obtained using a similar procedure employed for example 91 from the title compound of example 430 and corresponding acid chlorides.

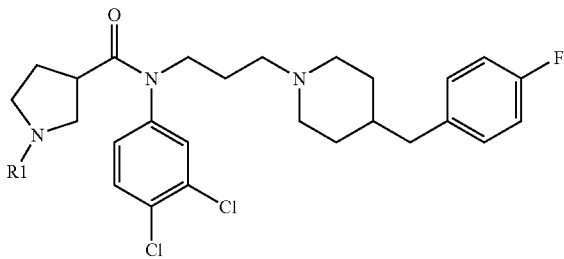

| Example | R1 | Additive | Yield (mg) | MS (APCI+) (M + 1) | HPLC Retention time and Purity |
|---|---|---|---|---|---|
| 431 | | CF$_3$COOH | 3.7 | 563 | 3.085 min 94% |
| 432 | | CF$_3$COOH | 2.4 | 675 | 3.854 min 96% |
| 433 | | CF$_3$COOH | 2.3 | 653 | 3.871 min 99% |

-continued
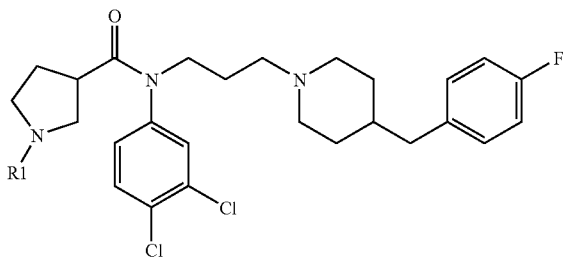
| Example | R1 | Additive | Yield (mg) | MS (APCI+) (M + 1) | HPLC Retention time and Purity |
|---|---|---|---|---|---|
| 434 | (4-fluorobenzyl)carbonyl | CF₃COOH | 2.2 | 628 | 3.881 min 98% |
| 435 | (4-hydroxyphenyl)(hydroxy)acetyl | CF₃COOH | 1.4 | 642 | 3.661 min 100% |
| 436 | methoxyacetyl | CF₃COOH | 3.9 | 564 | 3.504 min 94% |
| 437 | (acetyloxy)acetyl | CF₃COOH | 1.9 | 592 | 3.382 min 97% |
| 438 | 4-chloro-3-sulfamoylbenzoyl | CF₃COOH | 1.6 | 709 | 3.875 min 99% |
| 439 | (benzoylamino)acetyl | CF₃COOH | 1.9 | 653 | 3.894 min 98% |
| 440 | tetrahydrofuran-2-ylcarbonyl | CF₃COOH | 1.7 | 590 | 3.479 min 96% |

-continued

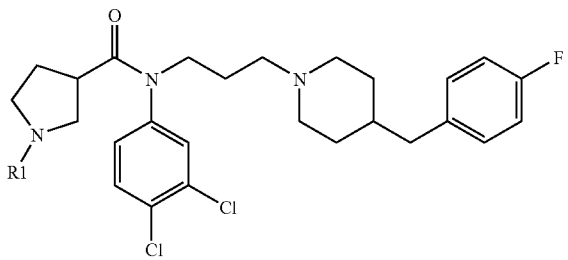

| Example | R1 | Additive | Yield (mg) | MS (APCI+) (M + 1) | HPLC Retention time and Purity |
|---|---|---|---|---|---|
| 441 | *-C(O)-CH₂-OH | CF₃COOH | 1.1 | 550 | 3.506 min 97% |
| 442 | pyridine-3-C(O)-NH-(CH₂)₃-C(O)-* | 2CF₃COOH | 2.2 | 682 | 3.784 min 99% |
| 443 | *-C(O)-CH₃ | CF₃COOH | 3.3 | 534 | 3.615 min 100% |
| 444 | *-S(O)₂-CH₃ | CF₃COOH | 5.5 | 570 | 3.532 min 98% |
| 445 | (1H-indol-3-yl)-C(O)-C(O)-* | 2CF₃COOH | 2.1 | 663 | 3.655 min 92% |
| 446 | 1-acetylpiperidin-4-yl-C(O)-* | CF₃COOH | 1 | 645 | 3.684 min 96% |

1-Acetyl-N-(3,4-dichlorophenyl-N-{3-[4-(4-fluorobenzyl)-1-piperidinyl]propyl}-3-pyrrolidinecarboxamide trifluoroacetic acid salt (example 443)

¹H-NMR (CDCl₃) δ 1.16-1.85 (12H, m), 1.89-2.00 (2H, m), 2.02-2.33 (1H, m), 2.06 (3H, s), 2.35 (2H, d, J=6.0 Hz), 2.43-2.67 (1H, m), 2.71-2.89 (1H, m), 2.93-3.14 (1H, m), 3.55 (2H, t, J=7.0 Hz), 3.92-4.08 (2H, m), 6.96-7.09 (5H, m), 7.33 (1H, d, J=2.0 Hz), 7.52 (1H, d, J=8.2 Hz)

EXAMPLES 447-456

The compounds of the following examples 447-456 were obtained using a similar procedure employed for example 145 from corresponding acids.

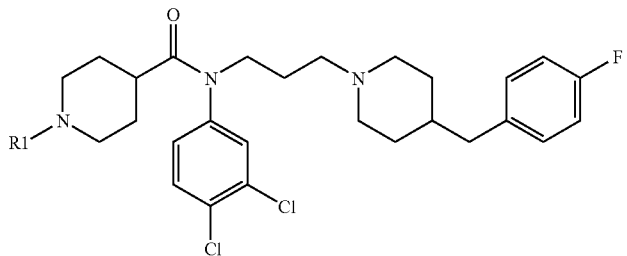
| Example | R1 | Additive | Yield (mg) | MS (APCI+) (M + 1) | HPLC Retention time and Purity |
|---|---|---|---|---|---|
| 447 | (*C(=O)CH(OH)-C6H4-OH) | CF3COOH | 2 | 656 | 3.438 min 94% |
| 448 | (*C(=O)CH2-O-C(=O)CH3) | CF3COOH | 20.2 | 606 | 3.238 min 96% |
| 449 | (2-SO2NH2-4-Cl-C6H3-C(=O)*) | CF3COOH | 17.3 | 723 | 3.343 min 98% |
| 450 | (*C(=O)CH2-NH-C(=O)-C6H5) | CF3COOH | 16.3 | 667 | 3.249 min 96% |
| 451 | (tetrahydrofuran-2-yl-C(=O)*) | CF3COOH | 19.3 | 604 | 3.597 min 92% |
| 452 | (*C(=O)CH2OH) | CF3COOH | 13.4 | 564 | 3.259 min 97% |
| 453 | (pyridin-3-yl-C(=O)NH-CH2CH2CH2-C(=O)*) | 2CF3COOH | 7.7 | 696 | 2.956 min 93% |
| 454 | (1-acetylpiperidin-4-yl-C(=O)*) | CF3COOH | 1.2 | 659 | 3.486 min 95% |

-continued

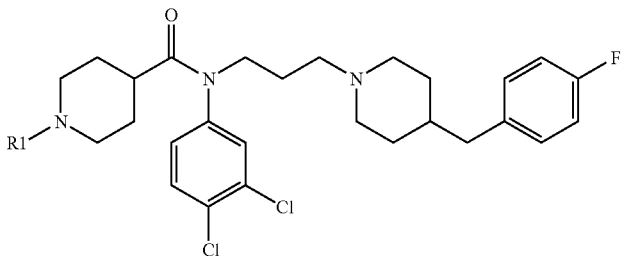

| Example | R1 | Additive | Yield (mg) | MS (APCI+) (M + 1) | HPLC Retention time and Purity |
|---|---|---|---|---|---|
| 455 | (2-acetamidobenzoyl) | CF$_3$COOH | 8.9 | 667 | 3.371 min 99% |
| 456 | (4-acetamidobenzoyl) | CF$_3$COOH | 15.2 | 667 | 3.354 min 97% |

2-{4-[(3,4-Dichloro{3-[4-(4-fluorobenzyl)-1-piperidinyl]propyl}anilino)carbonyl]-1-piperidinyl}-2-oxoethylacetate trifluoroacetic acid salt (example 448)

$^1$H NMR (CDCl$_3$) δ 1.10-1.84 (14H, m), 1.91-2.06 (2H, m), 2.00-2.26 (1H, br), 2.18 (3H, s), 2.31-2.63 (4H, br), 2.66-2.86 (1H, br), 2.91-3.11 (1H, d, J=11.8 Hz), 3.54 (1H, t, J=6.8 Hz), 3.80-4.19 (2H, br), 4.72 (2H, s), 6.92-7.13 (5H, m), 7.32 (1H, d, J=2.4 Hz), 7.53 (1H, d, J=8.6 Hz)

EXAMPLE 457

N'-(1-Acetyl-3-piperidinyl)-N-[3-(4-benzyl-1-piperidinyl)propyl]-N-phenylurea hydrochloride The title compound was prepared using a similar procedure to that described in example 12 from 1-acetyl-3-piperidinecarboxylic acid. Yield 51%.

Free base: $^1$H NMR (CDCl$_3$) δ 1.1-2.1 (16H, m), 2.2-2.55 (3H, m), 2.50 (2H, d, J=6.6 Hz), 2.7-2.9 (2H, m), 3.0-3.4 (2H, m), 3.5-3.9 (4H, m), 4.2-4.4 (1H, m), 7.05-7.5 (10H, m)

EXAMPLE 458

1-Acetyl-N-[3-(4-benzyl-4-cyano-1-piperidinyl)propyl]-N-(3,4-dichlorophenyl)-4-piperidinecarboxamide hydrochloride The title compound was prepared using a similar procedure to that described in example 179 from 4-benzyl-4-cyanopiperidine hydrochloride. Yield 80%.

Free base: $^1$H NMR (CDCl$_3$) δ 1.45-1.95 (10H, m), 2.05 (3H, s), 2.1-2.5 (6H, m), 2.7-3.0 (3H, m), 2.84 (2H, s), 3.5-3.9 (3H, m), 4.45-4.6 (1H, m), 7.04 (1H, dd, J=2.6, 8.5 Hz), 7.2-7.4 (6H, m), 7.53 (1H, d, J=8.5 Hz)

EXAMPLE 459

1-Acetyl-N-(3-{4-[allyl(benzyloxycarbonyl)amino]-1-piperidinyl}propyl)-N-(3,4-chlorophenyl)-4-piperidinecarboxamide methanesulfonate The title compound was prepared using a similar procedure to that described in example 211 from the title compound of reference example 12-2 and 4-[allyl(benzyloxycarbonyl)amino]piperidine.

HPLC purity (220 nm) 95% (retention time 4.535 min) MS (APCI$^+$) 595 (M+1)

EXAMPLE 460

1-Acetyl-N-(3-{4-[allyl(benzyloxycarbonyl)amino]-1-piperidinyl}propyl)-N-(3,4-dichlorophenyl)-4-piperidinecarboxamide methanesulfonate The title compound was prepared using a similar procedure to that described in example 179 from 4-[allyl(benzyloxycarbonyl)amino]piperidine. Yield 33%.

Free base: $^1$H NMR (CDCl$_3$) δ 1.5-2.1 (12H, m), 2.06 (3H, s), 2.2-2.5 (4H, m), 2.75-3.0 (3H, m), 3.5-4.2 (6H, m), 4.45-4.65 (1H, m), 5.0-5.2 (2H, m), 5.14 (2H, s), 5.65-5.95 (1H, m), 7.05 (1H, dd, J=2.2, 8.4 Hz), 7.25-7.4 (6H, m), 7.53 (1H, d, J=8.4 Hz)

EXAMPLE 461

1-Acetyl-N-{3-[4-(acetyl-4-fluoroanilino)-1-piperidinyl]propyl}-N-(3,4-dichlorophenyl)-4-piepridinecarboxamide hydrochloride The title compound was prepared using a similar procedure to that described in example 179 from N-(4-fluorophenyl)-N-(4-piperidinyl)acetamide. Yield 21%.

Free base: $^1$H NMR (CDCl$_3$) δ 1.1-2.5 (16H, m), 1.74 (3H, s), 2.05 (3H, s), 2.7-3.0 (3H, m), 3.5-3.9 (3H, m), 4.4-4.7 (2H, m), 6.95-7.15 (5H, m), 7.27 (1H, d, J=2.2 Hz), 7.49 (1H, d, J=8.4 Hz)

EXAMPLE 462

N-(3,4-Dichlorophenyl)-N-{3-[4-(4-fluorobenzyl)-1-piperidinyl]propyl}-N'-1-(methylsulfonyl)-4-piperidinyl]urea hydrochloride The title compound was prepared using a similar procedure to that described in example 12 from 1-(methylsulfonyl)-4-piperidinecarboxylic acid and the title compound of reference example 3-3. Yield 66%.

$^1$H NMR (CDCl$_3$) δ 1.25-2.25 (11H, m), 2.4-2.85 (4H, m), 2.60 (2H, d, J=7.4 Hz), 2.76 (3H, s), 2.9-3.1 (2H, m), 3.45-3.85 (7H, m), 4.29 (1H, br d, J=7.0 Hz), 6.9-7.15 (4H, m), 7.33 (1H, dd, J=2.4, 8.5 Hz), 7.41 (1H, d, J=2.4 Hz), 7.58 (1H, d, J=8.5 Hz)

EXAMPLE 463

N-[3-(4-Benzyl-1-piperidinyl)propyl]-N-(3-chloro-4-methylphenyl)-N'-[1-(methylsulfonyl)-4-pipeidinyl]urea hydrochloride The title compound was prepared using a similar procedure to that described in example 12 from 1-(methylsulfonyl)-4-piperidinecarboxylic acid and the title compound of reference example 9. Yield 94%.

$^1$H NMR (CDCl$_3$) δ 1.2-2.25 (11H, m), 2.40 (3H, s), 2.4-2.9 (4H, m), 2.63 (2H, d, J=7.0 Hz), 2.76 (3H, s), 2.9-3.1 (2H, m), 3.45-3.8 (7H, m), 4.05-4.25 (1H, m), 7.05-7.4 (8H, m)

EXAMPLE 464

1-Acetyl-N-[3-(4-benzyl-1-piperidinyl)propyl]-N-(3-pyridinyl)-4-piperidinecarboxamide hydrochloride To a solution of N-[3-(4-Benzyl-1-piperidinyl)propyl]-3-pyridinamine (400 mg) in 6 ml of tetrahyfrofuran, triethylamine (0.719 ml) and 1-acetyl-4-piperidinecarbonyl chloride (180 mg) were added at 0° C., and the mixture was stirred for 2 h at 0° C. AcOEt (15 ml) and aq. NaHCO$_3$ (15 ml) were added and the organic layer was separated. The aqueous layer was extracted with AcOEt (10 ml) twice. The combined AcOEt layer was washed with aq. NaHCO$_3$ (10 ml) twice and brine (10 ml), dried over anhydrous MgSO$_4$. After concentration, the residue was purified on Al$_2$O$_3$ column chromatography (hexane-AcOEt 1:1). After evaporation, to the residue 4N HCl in AcOEt (1.0 ml) was added and the resulting precipitate was collcted by filtration to give the title compound (251 mg, yield 39.0%).

Free base: $^1$H NMR (CDCl$_3$) δ 1.25 (2H, d, J=4.0 Hz, 11.6 Hz), 1.43-1.86 (11H, m), 2.04 (3H, s), 2.20-2.40 (4H, m), 2.50 (2H, d, J=6.6 Hz), 2.80 (3H, m), 3.66-3.79 (3H, m), 4.51 (1H, m), 7.10-7.57 (7H, m), 8.49 (1H, m), 8.65 (1H, m).

EXAMPLE 465

1-Acetyl-N-[3-(4-benzyl-1-piperidinyl)propyl]-N-(2-pyridinyl)-4-piperidinecarboxamide hydrochloride The title compound (320 mg, yield 49.7%) was obtained by a similar procedure employed for example 464 from N-[3-(4-Benzyl-1-piperidinyl)propyl]-2-pyridinamine (400 mg).

Free base: $^1$H NMR (CDCl$_3$) δ 1.25 (2H, m), 1.43-1.84 (11H, m), 2.05 (3H, s), 2.28 (2H, dd, J=6.6 Hz and 7.4 Hz), 2.30-2.41 (2H, m), 2.50 (2H, d, J=6.6 Hz), 2.77-2.90 (3H, m), 3.73-3.85 (3H, m), 4.50 (1H, m), 7.10-7.31 (7H, m), 7.79 (1H, dt, J=1.8 Hz and 7.6 Hz), 8.52 (1H, m).

EXAMPLE 466

1-Acetyl-N-[3-(4-benzyl-1-piperidinyl)propyl]-N-(1H-indazol-6-yl)-4-piperidinecarboxamide hydrochloride The title compound (332 mg, yield 53.6%) was obtained by a similar procedure employed for example 464 from N-[3-(4-Benzyl-1-piperidinyl)propyl]-1H-indazol-6-amine (400 mg).

Free base: $^1$H NMR (CDCl$_3$) δ 1.26 (2H, m), 1.40-1.87 (11H, m), 2.05 (3H, s), 2.20-2.38 (4H, m), 2.50 (2H, d, J=6.6 Hz), 2.71-2.86 (3H, m), 3.69-3.77 (3H, m), 4.49 (1H, m), 6.95 (1H, dd, J=1.8 Hz and 8.4 Hz), 7.09-7.31 (6H, m), 7.80 (1H, d, J=8.4 Hz), 8.13 (1H, s).

EXAMPLE 467

1-Acetyl-N-[3-(4-benzyl-1-piperidinyl)propyl]-N-(1-phenylethyl)-4-piperidinecarboxamide hydrochloride The title compound (355 mg, yield 56.7%) was obtained by a similar procedure employed for example 464 from 3-(4-Benzyl-1-piperidinyl)-N-(1-phenylethyl)-1-propanamine (400 mg).

Free base: $^1$H NMR (CDCl$_3$) δ 1.25-2.04 (13H, m), 1.75 (3H, d, J=6.6 Hz), 2.09 (3H, s), 2.40-2.70 (4H, m), 2.60 (2H, d, J=7.0 Hz), 2.75-2.80 (3H, m), 3.27-3.40 (2H, m), 3.87 (1H, m), 4.63 (1H, m), 5.17 (1H, q, J=6.6 Hz), 7.09-7.42 (10H, m).

EXAMPLE 468

1-Acetyl-N-(3,4-dichlorophenyl)-N-{3-[4-(4-fluorobenzyl)-1-piperidinyl]propyl}-4-piperidinecarboxamide hydrochloride The title compound of example 17 (1096 mg) dissolved in methanol was treated with 4N hydrogen chloride solution in ethyl acetate (0.75 mL) and the solvent was removed under reduced pressure. Diethyl ether was added to the residue, the resulting precipitate was collected by filtration, washed with diethyl ether, and dried under reduced pressure to afford the title compound (1060 mg) as a white amorphous solid.

$^1$H NMR (CD$_3$OD) δ 1.35-2.15 (11H, m), 2.06 (3H, s), 2.3-2.7 (2H, m), 2.62 (2H, d, J=6.6 Hz), 2.8-3.2 (5H, m), 3.4-3.65 (2H, m), 3.65-3.95 (3H, m), 4.35-4.5 (1H, m), 6.95-7.1 (2H, m), 7.1-7.3 (2H, m), 7.37 (11H, dd, J=2.3 Hz, 8.5 Hz), 7.70 (1H, d, J=8.5 Hz), 7.70 (1H, d, J=2.3 Hz)

EXAMPLE 469

1-Acetyl-N-(3-chlorophenyl)-N-[3-[4-(2-benzthiazolylthio)-1-piperidinyl]propyl]-4-piperidinecarboxamide hydrochloride To a solution of 1-tert-butoxycarbonyl-4-(2-benzothiazolylthio)piperidine (505 mg, 1.44 mmol) in dry dichloromethane (4 ml) was added trifluoroacetic acid (4 ml) and stirred at room temperature for 30 min. After the solvent was removed in vacuo, the residue was dissolved in methanol (4 ml) and evaporated. The residue was dissolved in dry acetonitrile (12 ml) followed by addition of 1-acetyl-N-(3-chlorophenyl)-N-(3-chloropropyl)-4-piperidinecarboxamide (400 mg, 1.12 mmol), potassium carbonate (0.77 g, 5.6 mmol), and potassium iodide (186 mg, 1.12 mmol). After stirred at 80° C. for 8 h, the mixture was diluted with ethyl acetate (60 ml), washed with brine (60 ml), dried over anhydrous magnesium sulfate, and evaporated. The residue was purified by preparative HPLC eluting water-acetonitrile containing 0.1% TFA. To the TFA salt was added 5% aqueous solution of potassium carbonate, extracted with ethyl acetate (30 ml), washed with brine, dried over anhydrous magnesium sulfate, and evaporated. The residue dissolved in ethyl acetate (20 ml) was treated with 4N hydrogen chloride in ethyl acetate (0.72 ml). After the solvent was removed in vacuo, the residue was washed with ether and dried in vacuo to give the title compound (230 mg, 34%) as a white solid.

IR (KBr) 2953, 1643, 1589 cm$^{-1}$ $^1$H-NMR (CD$_3$OD) δ 1.6-1.8 (5H, m), 2.0-2.2 (5H, m), 2.10 (3H, s), 2.4-2.6 (5H, m), 3.1-4.0 (9H, m), 7.3-7.6 (6H, m), 7.8-7.9 (2H, m) HPLC purity (220 nm) 99% (t$_R$3.181 min) MS (APCI+) 571 (M+1), 573 (M+3)

EXAMPLE 470

N-(3-{4-[4-(Aminocarbonyl)benzyl]-1-piperidinyl}propyl)-N-(3-chloro-4-methylphenyl)-1-(methylsulfonyl)-4-piperidinecarboxamide 1-(Methylsulfonyl)-4-piperidinecarbonylchloride (677.1 mg, 3 mmol) was added to a mixture of the title compound of reference example 181-2 (472.9 mg, 1 mmol), triethylamine (607 mg, 6 mmol) and dichloromethane (10 ml) at 0° C. and the mixture was stirred at 0° C. for 1 h. The resulting mixture was poured into 5% aqueous sodium bicarbonate (20 ml) and the whole was extracted with dichloromethane (20 ml×2). The extracts were washed with saturated sodium chloride solution (20 ml) and dried over anhydrous sodium sulfate. The solvent was removed in vacuo and the residue was purified by flash column chromatography (silica gel 25 g, ethyl acetate to ethyl acetate/methanol=10/1) to give the title compound (464 mg, 79%) as colorless crystalline powder.

$^1$H NMR (CDCl$_3$) δ 1.10-1.40 (2H, m), 1.50-2.00 (11H, m), 2.23-2.30 (3H, m), 2.42 (3H, s), 2.51-2.62 (4H, m), 2.73 (3H, s), 2.80-2.85 (2H, m), 3.60-3.74 (4H, m), 5.57-5.97 (2H, br), 6.95 (1H, dd, J=8.0 Hz, 2.0 Hz), 7.17 (1H, d, J=2.0 Hz), 7.21 (2H, d, J=8.2 Hz), 7.28 (1H, d, J=8.0 Hz), 7.73 (2H, d, J=8.2 Hz)

EXAMPLE 471

1-Acetyl-N-(3,4-dichlorophenyl)-N-{3-[4-(4-fluorobenzyl)-1-piperidinyl]propyl)-3-azetidinecarboxamide The title compound was prepared using a similar procedure to that described for example 25 from 1-acetyl-3-azetidinecarboxylic acid (yield 28%).

$^1$H NMR (CDCl$_3$) δ 1.05-2.1 (9H, m), 1.82 (3H, s), 2.2-2.4 (2H, m), 2.48 (2H, d, J=6.6 Hz), 2.7-2.9 (2H, m), 3.1-3.35 (1H, m), 3.6-3.85 (3H, m), 3.85-4.05 (2H, m)), 4.35-4.5 (11H, m), 6.85-7.15 (5H, m), 7.24 (1H, d, J=2.2 Hz), 7.51 (1H, d, J=8.4 Hz)

EXAMPLE 472

N-(3,4-Dichlorophenyl)-N-{3-[4-({4-[ethyl(methylsulfonyl)amino]phenyl}sulfonyl)-1-piperidinyl]propyl)-1-(methylsulfonyl)-4-piperidinecarboxamide The title compound was prepared using a similar procedure to that described in reference example 190 from the title compound of reference example 182-2. Yield 34%.

$^1$H NMR (CDCl$_3$) δ 1.20 (3H, t, J=7.2 Hz), 1.53-2.05 (13H, m), 2.15-2.35 (3H, m), 2.46-2.67 (2H, m), 2.74 (3H, s), 2.80-3.01 (2H, m), 2.95 (3H, s), 3.56-3.80 (4H, m), 3.84 (2H, q, J=7.2 Hz), 7.02 (1H, dd, J=2.6, 8.4 Hz), 7.29 (1H, d, J=2.6 Hz), 7.50-7.58 (3H, m), 7.89 (2H, d, J=8.4 Hz).

EXAMPLE 473

N-(3-{4-[4-(Aminocarbonyl)benzyl]-1-piperidinyl}propyl)-N-(3,4-dichlorophenyl)-1-(methylsulfonyl)-4-piperidinecarboxamide hydrochloride To a solution of the title compound of example 362 (195.3 mg, 0.32 mmol) in methanol (20 ml) was added a solution of 4N hydrogen chloride in ethyl acetate (0.4 ml) at room temperature. The resulting solution was concentrated in vacuo. The residue was crystallized from ethanol (10 ml) to give the title compound (165.6 mg, 80%) as colorless crystalline powder.

$^1$H NMR (CD$_3$OD) δ 1.40-1.70 (2H, m), 1.70-2.00 (9H, m), 2.20-2.40 (1H, m), 2.42-2.62 (2H, m), 2.69-2.73 (2H, m), 2.73 (3H, s), 2.80-3.00 (2H, m), 3.05-3.13 (2H, m), 3.49-3.80 (6H, m), 7.31 (2H, d, J=8.0 Hz), 7.35 (1H, dd, J=8.6 Hz, 2.2 Hz), 7.69 (1H, d, J=8.6 Hz), 7.70 (1H, d, J=2.2 Hz), 7.82 (2H, d, J=8.0 Hz)

EXAMPLE 474

N-(3,4-Dichlorophenyl)-N-(3-{4-[(4-fluorobenzoyl)amino]-1-piperidinyl}propyl)-1-(methylsulfonyl)-4-piperidinecarboxamide The title compound was prepared using a similar procedure to that described in example 195 from the title compound of example 199 and 4-fluorobenzoyl chloride. Yield 34%.

$^1$H NMR (CDCl$_3$) δ 1.40-2.40 (15H, m), 2.48-2.67 (2H, m), 2.74 (3H, s), 2.77-2.90 (2H, m), 3.62-3.80 (4H, m), 3.85-4.07 (1H, m), 5.82-5.93 (1H, m), 7.01-7.16 (3H, m), 7.32 (1H, d, J=2.2 Hz), 7.54 (1H, d, J=8.4 Hz), 7.70-7.80 (2H, m).

TEST EXAMPLE

(1) Cloning of Human CCR5 Chemokine Receptor

Cloning of CCR5 gene was carried out by PCR (polymerase chain reaction) from human spleen cDNA. With using 0.5 ng of spleen cDNA (Toyobo, QUICK-Clone cDNA) as template, PCR was performed in DNA Thermal Cycler 480 (Perkin-Elmer) (reaction conditions: 30 cycles of 95° C. for 1 minute, 60° C. for 1 minute, and 75° C. for 5 minutes) by adding primer set,
5'-CAGGATCCGATGGATTATCAAGTGT-CAAGTCCAA-3' (25 pmol) and
5'-TCTAGATCACAAGCCCACAGATATTTCCTGCTCC-3' (25 pmol),
which were designed referring to nucleotide sequence of CCR5 gene reported by Samson et al. (Biochemistry, 35 (11), 3362-3367 (1996)) and by using TaKaRa EX Taq (Takara Shuzo). The resultant PCR product was subjected to agarose gel electrophoresis to collect about 1.0 kb DNA fragment, which was subjected to Original TA Cloning Kit (Funakoshi) to carry out cloning of CCR5 gene.

(2) Preparation of Plasmid for Expression of Human 5

The plasmid obtained in the above (1) was digested with restriction enzymes XbaI (Takara Shuzo) and BamHI (Takara Shuzo) and subjected to agarose gel electrophoresis to collect about 1.0 kb DNA fragment. The DNA fragment was mixed with plasmid pcDNA3.1 (Funakoshi) for expression in animal cells, said plasmid being digested with XbaI and BamHI, and they were ligated with DNA Ligation Kit Ver.2 (Takara Shuzo). The resulting plasmid was subjected to transformation of competent cell of *E. coli* JM109 (Takara Shuzo) to obtain plasmid pCKR5.

(3) Introduction of Plasmid for Expression of Human CCR5 Into CHO-K1Cell and Expression of Said Plasmid in CHO-K1 Cell CHO-K1 cells were grown in 750 ml of tissue culture flask (Becton Dickinson) using Ham's F12 medium (Nihon Pharmaceutical) containing 10% fetal calf serum (Life Tech Oriental) and took off with 0.5 g/L trypsin-0.2 g/L EDTA (Life Tech Oriental). The cells were washed with PBS (Life Tech Oriental), centrifuged (1000 rpm, 5 minutes), and suspended in PBS. With using Gene Pulser (Bio-Rad Laboratories), DNA was introduced into the cells under the conditions shown below. That is, to the cuvette of 0.4 cm gap were added $8 \times 10^6$ cells and 10 µg of plasmid pCKR5 for expression of human CCR5, and electroporation was carried out under 0.25 kV of voltage and 960 µg of capacitance. The cells were transferred into Ham's F12 medium (Nihon Pharmaceutical) containing 10% fetal calf serum, and cultivated for 24 hours. The cells were again took off and centrifuged, and suspended in Ham's F12 medium (Nihon Pharmaceutical) containing 10% fetal calf serum and 500 µg/ml of geneticin (Life Tech Oriental). The suspension was diluted to give $10^4$ cells/ml of the suspension, which was inoculated on 96 well plate (Becton Dickinson) to give geneticin resistant cells. The resulting geneticin resistant cells were cultivated in 96 well plate (Becton Dickinson), and cells expressing CCR5 were selected from the geneticin resistant cells. That is, in assay buffer (Ham's F12 medium containing 0.5% BSA and 20 mM HEPES (Wako Pure Chemical, pH7.2) to which was added 200 pM of $[^{125}I]$-RANTES (Amersham) as ligand, binding reaction was carried out at room temperature for 40 minutes, and the buffer was washed with cooled PBS. To the buffer was added 50 µl/well of 1M NaOH, and the mixture was stirred. Radio-activity was determined with γ-counter to select CHO/CCR5 cells which specifically bind to the ligand.

(4) Evaluation of Test Compounds Based on CCR5 Antagonistic Activity

The CHO/CCR5 were inoculated on 96 well microplate ($5 \times 10^4$ cells/well) and cultivated for 24 hours. The medium was removed by means of suction, and to each well was added assay buffer containing Test Compound (1 µl) and then 100 pM of $[^{125}I]$-RANTES (Amersham) as ligand. Binding assay was carried out at room temperature for 40 minutes, and assay buffer was removed by means of suction. Each well was washed twice with cooled PBS, and 200 µl of Micrbscint-20 (Packard Instrument, Inc.) was added to each well. Radio-activity was determined with Top-Count Micro Scintillation Counter (Packard Instrument, Inc.).

According to the method described above, inhibition rate of Test Compound (whose number is referred to in the following Examples) to CCR5 binding.

The results are shown in Table 1.

TABLE 1

| Inhibition Rate (%) at 1.0 µM | | | |
|---|---|---|---|
| Example Number | Inhibition Rate (%) at 1.0 µM | Example Number | Inhibition Rate (%) at 1.0 µM |
| 3 | 98 | 15 | 97 |
| 18 | 87 | 27 | 99 |
| 40 | 98 | 57 | 96 |
| 79 | 90 | 88 | 99 |
| 92 | 92 | 150 | 98 |
| 158 | 97 | 168 | 82 |
| 189 | 100 | 190 | 100 |
| 211 | 90 | 214 | 92 |
| 224 | 97 | 243 | 99 |
| 244 | 100 | 249 | 94 |
| 250 | 96 | 261 | 98 |
| 272 | 96 | 289 | 83 |
| 291 | 84 | 292 | 97 |
| 300 | 100 | 304 | 99 |
| 309 | 92 | 313-2 | 97 |
| 318 | 100 | 334 | 100 |
| 341 | 98 | 356 | 100 |
| 362 | 95 | 372 | 97 |
| 374 | 92 | 376 | 97 |
| 384 | 100 | 413 | 99 |
| 420 | 98 | 470 | 99 |

(5) Inhibitory Effect on HIV-1 Infection to MAGI-CCR5 Cell

The plasmid where β-galactosidase gene was ligated downstream HIV-1 LTR was introduced into CD4 positive HeLa cell, to which human CCR5 was further introduced to obtain transformant MAGI-CCR5. By using said transformant MAGI-CCR5, degree of HIV-1 infection was calculated from β-galactosidase activity (blue color due to decomposition of 5-bromo-4-chloro-3-indolyl-β-D-galactopyranoside). Specifically, MAGI-CCR5 cells were suspended in DMEM medium containing 10% serum to prepare $5 \times 10^4$ cells/ml suspension. To each well of 96 well plate was inoculated 200 µM of the suspension, and the cells were cultivated at 37° C. overnight. The medium was removed by means of suction, and to the residue was added 100 μM of the above medium containing 0.064 μM of Test Compound and 100 μM of the above medium containing 300 PFU of HIV-1 Ba-L cells. The final concentration of Test Compound was 0.032 μM. The cells were cultivated at 37° C. for 2 days. The medium was removed by means of suction. To the residue was added 200 μM of cell fixative (PBS containing 1% formaldehyde and 0.2% glutaraldehyde), and the mixture was allowed to stand at room temperature for 5 minutes and washed twice with PBS. To the mixture was added 100 μl of staining solution (PBS containing 4 μM potassium ferrocyanide, 4 μM potassium ferricyanade, 2 μM $MgCl_2$ and 0.4 mg/ml X-gal), and the mixture was allowed to stand at 37° C. for 50 minutes and washed twice with PBS. The number of blue cells was counted by microscope and defined as the number of cells infected with HIV-1. According to this method, inhibition rate on HIV-1 infection was determined and found that Compounds 468 and 469 respectively show 97% and 96% inhibition on HIV-1 infection.

The pharmaceutical composition for antagonizing CCR5 (e.g. a medicament for the treatment or prevention of infectious disease of HIV, a medicament for the treatment or prevention of AIDS, etc.) comprising the compound (I) of the present invention, as an active ingredient, can be prepared, for example, by the following prescriptions:

Preparations

1. Capsule

| (1) Compound obtained in Working Example 3 | 40 mg |
| (2) lactose | 70 mg |
| (3) fine crystalline cellulose | 9 mg |
| (4) magnesium stearate | 1 mg |

1 capsule 120 mg (1), (2), (3) and ½ of (4) are mixed and then granulated. To the granules is added the remainder of (4), and the whole is filled into a gelatin capsule.

2. Tablet

| (1) Compound obtained in Working Example 27 | 40 mg |
| (2) lactose | 58 mg |
| (3) corn starch | 18 mg |
| (4) fine crystalline cellulose | 3.5 mg |
| (5) magnesium stearate | 0.5 mg |

1 tablet 120 mg (1), (2), (3), ⅔ of (4) and ½ of (5) are mixed and then granulated. To the granules are added the remainders of (4) and (5), followed by subjecting the mixture to compression molding.

INDUSTRIAL APPLICABILITY

The compound of the formula (I) or salt thereof of the present invention has potent CCR5 antagonistic activity and can be advantageously used for the treatment or prevention of infectious disease of various HIV in human (e.g. AIDS).

The invention claimed is:

1. A compound of the formula:

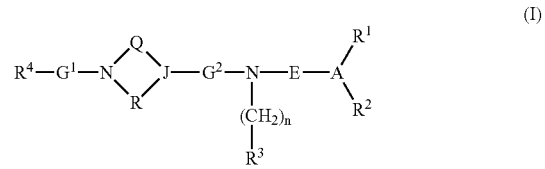

wherein $R^1$ and $R^2$ combine with each other together with A to form a piperidinyl group which may be substituted; A is N or $N^+$—$R^5 \cdot Y^-$ wherein $R^5$ is a hydrocarbon group and $Y^-$ is a counter anion; $R^3$ is a cyclic hydrocarbon group which may be substituted or a heterocyclic group which may be substituted; n is 0 or 1; $R^4$ is a hydrogen atom, a hydrocarbon group which may be substituted, a heterocyclic group which may be substituted, an alkoxy group which may be substituted, an aryloxy group which may be substituted, or an amino group which may be substituted; E is a divalent aliphatic hydrocarbon group which may be substituted by group(s) other than oxo; $G^1$ is a bond, CO or $SO_2$; $G^2$ is CO, $SO_2$, NHCO, CONH or OCO; -Q-J-R- combine with the nitrogen to which they are attached to form a piperidinyl group, or a salt thereof, provided that the compound is not N-(3-{4-[4-(Aminocarbonyl)benzyl]-1-piperidinyl}propyl)-N-(3,4-dichlorophenyl)-1-(methylsulfonyl)-4-piperidinecarboxamide or a salt thereof, 1-Acetyl-N-(3-{4-[4-(aminocarbonyl)benzyl]-1-piperidinyl}propyl)-N-(3-chloro-4-methylphenyl)-4-piperidinecarboxamide or a salt thereof, and N-(3-{4-[4-(Aminocarbonyl)benzyl]-1-piperidinyl}propyl)-N-(3-chloro-4-methylphenyl)-1-(methylsulfonyl)-4-piperidinecarboxamide or a salt thereof.

2. A compound as claimed in claim 1, wherein the piperidinyl group formed by -A$R^1R^2$ may be substituted by member(s) selected from Group 3; A is N or $N^+$—$R^5 \cdot Y^{31}$ wherein $Y^-$ is $Cl^{31}$, $Br^{31}$, $I^-$, $NO_3^-$, $SO_4^{2-}$, $PO_4^{3-}$ or $CH_3SO_3^-$ and $R^5$ is a hydrocarbon group selected from Group 2; $R^3$ is a cyclic hydrocarbon group selected from Group 5 which may be substituted by member(s) selected from Group 1 or a heterocyclic group selected from Group 6 which may be substituted by member(s) selected from Group 1; $R^4$ is a hydrogen atom, a hydrocarbon group selected from Group 2 which may be substituted by member(s) selected from Group 1, a heterocyclic group selected from Group 6 which may be substituted by member(s) selected from Group 1, a $C_{1-6}$ alkoxy group which may be substituted by member(s) selected from Group 7, a $C_{6-14}$ aryloxy group which may be substituted by member(s) selected from Group 8, an amino group which may be substituted by member(s) selected from Group 9 or a cyclic-amino group selected from Group 10; E is a divalent aliphatic hydrocarbon group selected from Group 12 which may be substituted by member(s) other than oxo and selected from Group 11;

wherein Group 1 consists of:
(1) a $C_{1-6}$ alkyl group which may be substituted by member(s) selected from Group 14, (2) a $C_{2-6}$ alkenyl group which may be substituted by member(s) selected from Group 14, (3) a $C_{2-6}$ alkynyl group which may be substituted by member(s) selected from Group 14, (4) a $C_{6-14}$ aryl group which may be substituted by member(s) selected from Group 14, (5) a $C_{3-7}$ cycloalkyl group which may be substituted by member(s) selected from Group 14, (6) a $C_{3-6}$ cycloalkenyl group which may be substituted by member(s) selected from Group 14, (7) a heterocyclic group selected from Group 16 which may be substituted by member(s) selected from Group 15, (8) an amino group which may be substituted by $C_{1-6}$ alkyl-imidoyl(s), formyl-imidoyl(s), amidino(s) or member(s) selected from Group 17, (9) a cyclic-amino group which may be substituted by member(s) selected from Group 10, (10) an imidoyl group which may be substituted by member(s) selected from Group 17, (11) an amidino group which may be substituted by member(s) selected from Group 17, (12) a hydroxyl group which may be substituted by a member selected from Group 17, (13) a thiol group which may be substituted by a member selected from Group 17, (14) a carboxyl group, (15) a $C_{1-6}$ alkoxy-carbonyl group which may be substituted by member(s) selected from Group 18, (16) a $C_{7-12}$ aryloxy-carbonyl group which may be substituted by member(s) selected from Group 18, (17) a $C_{7-10}$ aralkyl-oxy-carbonyl group which may be substituted by member(s) selected from Group 18, (18) a carbamoyl group, (19) a mono-substituted carbamoyl group which may be substituted by a member selected from Group 19, (20) a di-substituted carbamoyl group substituted by a member selected from Group 19 and a member selected from Group 20, (21) a cyclic-aminocarbamoyl group selected from Group 21, (22) a thiocarbamoyl group, (23) a mono-substituted thiocarbamoyl group which may be substituted by a member selected from Group 19, (24) a di-substituted thiocarbamoyl group substituted by a member selected from Group 19 and a member selected from Group 20, (25) a cyclic-aminothiocarbamoyl group which may be substituted by member(s) selected from Group 21, (26) a sulfamoyl group, (27) a N-mono-substituted sulfamoyl group substituted by a member selected from Group 19, (28) a N,N-di-substituted sulfamoyl group substituted by a member selected from Group 19 and a member selected from Group 20, (29) a cyclic-aminosulfonyl group (30) a halogen atom, (31) a cyano group, (32) a nitro group, (33) an acyl group derived from a sulfonic acid selected from Group 22, (34) a formyl group, (35) a $C_{2-6}$ alkanoyl group, (36) a $C_{7-12}$ aryl-carbonyl group, (37) a $C_{1-6}$ alkyl-sulfinyl group which may be substituted by member(s) selected from Group 23 and (38) a $C_{6-14}$ aryl-sulfinyl group which may be substituted by member(s) selected from Group 23;

wherein Group 2 consists of:
(1) a $C_{1-10}$ alkyl group, (2) a $C_{2-6}$ alkenyl group, (3) a $C_{2-6}$ alkynyl group, (4) a $C_{3-9}$ cycloalkyl group which may be condensed with benzene, (5) a $C_{3-6}$ cycloalkenyl group, (6) a $C_{4-6}$ cycloalkadienyl group and (7) a $C_{6-14}$ aryl group;

wherein Group 3 consists of:
(1) a hydroxy group, (2) a cyano group, (3) a nitro group, (4) an amino group, (5) an oxo group, (6) a halogen atom and (7) a group represented by the formula: —$B^1R^a$ wherein $R^a$ is a hydrocarbon group selected from Group 2 which may be substituted by member(s) selected from Group 1, or a heterocyclic group selected from Group 6 which may be substituted by member(s) selected from Group 1, $B^1$ is a bond, —$CR^bR^c$—, —COO—, —CO—, —$CR^b$(OH)—, —$CR^bR^c$—S—, —$CR^bR^c$—$SO_2$—, —CO—$NR^b$—, —CS—$NR^b$—, —CO—S—, —CS—S—, —CO—$NR^b$—CO—$NR^c$—, —C(=NH)—$NR^b$—, —$NR^b$—, —$NR^b$CO—, —$NR^b$—CS—, —$NR^b$—CO—$NR^c$—, —$NR^b$—CS—$NR^c$—, —$NR^b$—CO—O—, —$NR^b$—CS—O—, —$NR^b$—CO—S—, —$NR^b$—CS—S—, —$NR^b$—C(=NH)—$NR^c$—, —$NR^b$—$SO_2$—, —$NR^b$—$NR^c$—, —O—, —O—CO—, —O—CS—, —O—CO—O, —O—CO—$NR^b$—, —O—C(=NH)—$NR^b$—, —S—, —SO—, —$SO_2$—, —$SO_2$—$NR^b$—, —S—CO—, —S—CS—, —S—CO—$NR^b$—, —S—CS—$NR^b$- and -S—C(=NH)—$NR^b$, wherein each of $R^b$ and $R^c$ is a hydrogen atom, a $C_{1-6}$ alkyl group which may be substituted by member(s) selected from Group 14, a $C_{2-6}$ alkenyl group which may be substituted by member(s) selected from Group 14, a $C_{2-6}$ alkynyl group which may be substituted by member(s) selected from Group 14, a $C_{6-14}$ aryl group which may be substituted by member(s) selected from Group 14, a $C_{3-7}$ cycloalkyl group which may be substituted by member(s) selected from Group 14, a $C_{3-6}$ cycloalkenyl group which may be substituted by member(s) selected from Group 14, a heterocyclic group selected from Group 6 which may be substituted by member(s) selected from Group 1, an acyl group derived from a sulfonic acid selected from Group 22, formyl, a $C_{2-6}$ alkanoyl, a $C_{7-12}$ aryl-carbonyl group;

wherein Group 4 consists of:
(1) a monocyclic heterocyclic group, (2) a heterocyclic group condensed with benzene and (3) a heterocyclic spiro compound, each of which contains one nitrogen atom and may further contain one or more atoms selected from the group consisting of a nitrogen atom, a oxygen atom and a sulfur atom;

wherein Group 5 consists of:
(1) a $C_{3-9}$ cycloalkyl which may be condensed with benzene, (2) a $C_{3-6}$ cycloalkenyl group, (3) a $C_{4-6}$ cycloalkadienyl group and (4) a $C_{6-14}$ aryl group;

wherein Group 6 consists of:
(1) a 5- to 6-membered aromatic monocyclic heterocyclic group selected from Group 24, (2) a 8- to 12-membered aromatic condensed heterocyclic group selected from Group 26 and (3) a 3- to 8-membered saturated or unsaturated non-aromatic heterocyclic group selected from Group 25, each of which contains at least one hetero atom selected from the group consisting of an oxygen atom, a sulfur atom and a nitrogen atom;

wherein Group 7 consists of:
a $C_{3-6}$ cycloalkyl group which may be substituted by member(s) selected from Group 18, a $C_{6-10}$ aryl group which may be substituted by member(s) selected from Group 18, a $C_{7-10}$ aralkyl group which may be substituted by member(s) selected from Group 18 and a heterocyclic group selected from Group 16 which may be substituted by member(s) selected from Group 18;

wherein Group 8 consists of:
a $C_{1-6}$ alkoxy group, a halogen atom, a $C_{1-6}$ alkyl group, an amino group, a hydroxyl group, a cyano group and an amidino group;

wherein Group 9 consists of:
(1) a $C_{1-6}$ alkyl group, (2) formyl, a $C_{2-6}$ alkanoyl, (3) benzoyl, (4) a $C_{1-6}$ alkoxy-carbonyl group which may be substituted by halogen(s), (5) a $C_{1-6}$ alkyl-imidoyl, (6) formyl-imidoyl and (7) amidino;

wherein Group 10 consists of:
(1) 1-azetidinyl, (2) 1-pyrrolidinyl, (3) 1-piperidinyl, (4) 4-morpholinyl and (5) a 1-piperazinyl which may be substituted by member(s) selected from Group 27;

wherein Group 11 consists of:
(1) a $C_{1-6}$ alkyl group which may be substituted by member(s) selected from Group 14, (2) a $C_{6-14}$ aryl group which may be substituted by member(s) selected from Group 14, (3) a $C_{3-7}$ cycloalkyl group which may be substituted by member(s) selected from Group 14, (4) a $C_{3-6}$ cycloalkenyl group which may be substituted by member(s) selected from Group 14, (5) a carboxyl group, (6) a $C_{1-6}$ alkoxy-carbonyl group which may be substituted by member(s) selected from Group 18, (7) a $C_{7-12}$ aryloxy-carbonyl group which may be substituted by member(s) selected from Group 18, (8) a $C_{7-10}$ aralkyl-oxy-carbonyl group which may be substituted by member(s) selected from Group 18, (9) a carbamoyl group, (10) a mono-substituted carbamoyl group which may be substituted by a member selected from Group 19, (11) a di-substituted carbamoyl group substituted by a member selected from Group 19 and a member selected from Group 20, (12) a cyclic-aminocarbamoyl group selected from Group 21, (13) a thiocarbamoyl group, (14) a mono-substituted thiocarbamoyl group which may be substituted by a member selected from Group 19, (15) a di-substituted thiocarbamoyl group substituted by a member selected from Group 19 and a member selected from Group 20, (16) a cyclic-aminothiocarbamoyl group selected from Group 21, (17) an amino group which may be substituted by $C_{1-6}$ alkyl-imidoyl(s), formyl-imidoyl(s), amidino(s) or member(s) selected from Group 17, (18) a cyclic-amino group selected from Group 10, (19) a hydroxyl group which may be substituted by a member selected from Group 17, (20) a thiol group which may be substituted by a member selected from Group 17, (21) formyl, a $C_{2-6}$ alkanoyl, (22) a $C_{7-12}$ aryl-carbonyl group, (23) an acyl group derived from a sulfonic acid selected from Group 22, (24) a halogen atom, (25) nitro and (26) cyano;

wherein Group 12 consists of:
a $C_{1-6}$ alkylene, a $C_{2-6}$ alkenylene and a $C_{2-6}$ alkynylene;

wherein Group 13 consists of:
a $C_{1-3}$ alkylene, a $C_{2-3}$ alkenylene and a $C_{2-3}$ alkynylene;

wherein Group 14 consists of:
(1) a $C_{1-6}$ alkoxy group which may be substituted by halogen(s), (2) a phenoxy group which may be substituted by halogen(s) or carbamoyl(s), (3) a halogen atom, (4) a $C_{1-6}$ alkyl group, (5) a $C_{1-4}$ alkyl group substituted by halogen(s), (6) $C_{3-8}$ cycloalkyl, (7) an amino group substituted by one or two members selected from the group consisting of carbamoyl, $C_{1-4}$ alkyl and $C_{1-4}$ alkyl-sulfonyl, (9) a carbamoyl group which may be substituted by $C_{1-6}$ alkyl(s), (10) formyl, (11) a $C_{2-6}$ alkanoyl group, (12) a $C_{6-14}$ aryl group, (13) a $C_{6-14}$ aryl-carbonyl group, (14) a $C_{7-13}$ aralkyl-carbonyl group, (15) a hydroxyl group, (16) a $C_{2-5}$ alkanoyl-oxy group, (17) a $C_{7-13}$ aralkyl-carbonyloxy group, (18) a nitro group, (19) a sulfamoyl group, (20) a N—$C_{1-4}$ alkyl-sulfamoyl group, (21) a phenylthio group, (22) a $C_{1-4}$ alkyl-phenylthio group, (23) —N=N-phenyl group, (24) a cyano group, (25) an oxo group, (26) an amidino group, (27) a carboxyl group, (28) a $C_{1-4}$ alkoxy-carbonyl group, (29) a $C_{1-6}$ alkylthio group, (30) a $C_{1-6}$ alkyl-sulfinyl group, (31) a $C_{1-6}$ alkyl-sulfonyl group, (32) a $C_{6-14}$ arylthio group, (33) a $C_{6-14}$ aryl-sulfinyl group, (34) a $C_{6-14}$ aryl-sulfonyl group and (35) a heterocyclic group selected from Group 6;

wherein Group 15 consists of:
a $C_{1-6}$ alkyl group, formyl, a $C_{2-6}$ alkanoyl, a $C_{7-13}$ aryl-carbonyl group, a $C_{1-6}$ alkyl-sulfonyl group, an aminosulfonyl group, a mono-$C_{1-6}$ alkylaminosulfonyl group, a di-$C_{1-6}$ alkylaminosulfonyl group and a $C_{1-4}$ alkyl group substituted by halogen;

wherein Group 16 consists of:
(1) an aromatic heterocyclic group selected from Groups 24 and 26, and (2) a saturated or unsaturated non-aromatic heterocyclic group selected from Group 25, each of which contains at least one hetero atom selected from the group consisting of an oxygen atom, a sulfur atom and a nitrogen atom;

wherein Group 17 consists of:
(1) a $C_{1-6}$ alkyl group which may be substituted by halogen or a $C_{1-6}$ alkoxy, (2) a $C_{6-12}$ aryl group, (3) a $C_{6-12}$ aryl group substituted by $C_{1-4}$ alkyl(s), (4) a $C_{3-8}$ cycloalkyl group which may be substituted by halogen(s) or $C_{1-6}$ alkoxy(s), (5) a $C_{1-6}$ alkoxy group, (6) formyl, a $C_{2-6}$ alkanoyl, (7) a $C_{7-13}$ aryl-carbonyl group, (8) a $C_{7-13}$ aryl-carbonyl group substituted by $C_{1-4}$ alkyl(s), (9) a $C_{1-6}$ alkyl-sulfonyl group, (10) a $C_{6-14}$ aryl-sulfonyl group, (11) a aminosulfonyl group, (12) a mono- or di-substituted aminosulfonyl group substituted by $C_{1-4}$ alkyl(s) and (13) a $C_{1-6}$ alkoxy-carbonyl group which may be substituted by halogen(s);

wherein Group 18 consists of:
(1) a hydroxyl group, (2) an amino group, (3) a mono or di-substituted amino group which may be substituted by member(s) selected from Group 28, (4) a halogen atom, (5) a nitro group, (6) a cyano group, (7) a $C_{1-6}$ alkyl group which may be substituted by halogen(s) and (8) a $C_{1-6}$ alkoxy group which may be substituted by halogen(s);

wherein Group 19 consists of:
a $C_{1-6}$ alkyl group which may be substituted by member(s) selected from Group 18, a $C_{3-6}$ cycloalkyl group which may be substituted by member(s) selected from Group 18, a $C_{6-10}$ aryl group which may be substituted by member(s) selected from Group 18, a $C_{7-10}$ aralkyl group which may be substituted by member(s) selected from Group 18, a $C_{1-6}$ alkoxy group which may be substituted by member(s) selected from Group 18 and a heterocyclic group selected from Group 16 which may be substituted by member(s) selected from Group 18;

wherein Group 20 consists of:
a $C_{1-6}$ alkyl group, a $C_{3-6}$ cycloalkyl group and a $C_{7-10}$ aralkyl group;

wherein Group 21 consists of:
a 1-azetidinyl-carbonyl group, a 1-pyrrolidinyl-carbonyl group, a 1-piperidinyl-carbonyl group, a 4-morpholinyl-carbonyl group and a 1-piperazinyl-carbonyl group which may be substituted by member(s) selected from Group 27;

wherein Group 22 consists of:
a $C_{1-10}$ alkyl-sulfonyl group which may be substituted by member(s) selected from Group 18, a $C_{2-6}$ alkenyl-sulfonyl group which may be substituted by member(s) selected from Group 18, a $C_{2-6}$ alkynyl-sulfonyl group which may be substituted by member(s) selected from Group 18, a $C_{3-9}$ cycloalkyl-sulfonyl group which may be substituted by member(s) selected from Group 18, a $C_{3-9}$ cycloalkenyl-sulfonyl group which may be substituted by member(s) selected from Group 18, a $C_{6-14}$ aryl-sulfonyl group and a $C_{7-10}$ aralkyl-sulfonyl group which may be substituted by member(s) selected from Group 18;

wherein Group 23 consists of:
a $C_{1-6}$ alkoxy group, a halogen atom, a $C_{1-6}$ alkyl group, an amino group, a hydroxyl group, a cyano group and an amidino group;

wherein Group 24 consists of:
furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl;

wherein Group 25 consists of:
oxylanyl, azetidinyl, oxetanyl, thietanyl, pyrrolidinyl, tetrahydro furyl, thiolanyl, piperidinyl, tetrahydro pyranyl, morpholinyl, thiomorpholinyl and piperazinyl;

wherein Group 26 consists of:
benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, benzodioxolyl, benzimidazolyl, 2,1,1-benzoxadiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo(1,2-b)pyridazinyl, pyrazolo(1,5-a)pyridyl, pyrazolo[3,4-b]pyridyl, imidazo(1,2-a)pyridyl, imidazo(1,5-a)pyridyl, imidazo(1,2-b)pyridazinyl, imidazo(1,2-a)pyrimidinyl, 1,2,4-triazolo(4,3-a)pyridyl and 1,2,4-triazolo(4,3-b)pyridazinyl;

wherein Group 27 consists of:
a $C_{1-6}$ alkyl group, a $C_{7-10}$ aralkyl group and a $C_{6-10}$ aryl group; and wherein Group 28 consists of:
a $C_{1-6}$ alkyl group, formyl, a $C_{2-6}$ alkanoyl, a $C_{7-13}$ aryl-carbonyl group and a $C_{1-6}$ alkyl-sulfonyl group.

3. A compound as claimed in claim 2, wherein the piperidinyl group formed by combining $R^1$ and $R^2$ together with A, which may be substituted by member(s) selected from Group 3, is 1-piperidinyl.

4. A compound as claimed in claim 2, wherein the piperidinyl group represented by -$AR^1R^2$ is a group represented by the formula:

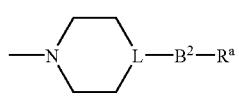

(1)

wherein L is methine, $B^2$ is a bond, —$CH_2$—, —$SO_2$—, —SO—, —S—, —O—, —CO—, —$NR^{b1}$—$SO_2$— (wherein $R^{b1}$ is a hydrogen atom, a $C_{1-6}$ alkyl group, a $C_{2-6}$ alkenyl group, a alkynyl group, or a $C_{3-6}$ cycloalkyl group), —CH(OH)—, —$NR^{b2}$— (wherein $R^{b2}$ is a hydrogen atom or a $C_{2-4}$ alkanoyl group), —$NR^{b1}$—CO— (wherein $R^{b1}$ has the meaning given above), —$NR^{b1}$—CO—O— (wherein $R^{b1}$ has the meaning given above), —$CH_2SO_2$— or —$CH_2S$—, $R^a$ is a hydrocarbon group selected from Group 2 which may be substituted by member(s) selected from Group 1 or a heterocyclic group selected from Group 6 which may be substituted by member(s) selected from Group 1.

5. A compound as claimed in claim 2, wherein the piperidinyl group represented by the formula-$AR^1R^2$ is a group represented by the formula:

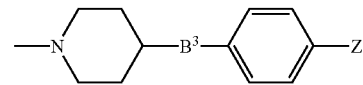

(2)

wherein $B^3$ is —$CH_2$—, —$SO_2$—, —SO—, —S—, —O—, —CO—, —$NR^{b1}$—$SO_2$— (wherein $R^{b1}$ is a hydrogen atom, a $C_{1-6}$ alkyl group, a $C_{2-4}$ alkenyl group, a $C_{2-6}$ alkynyl group, or a $C_{3-6}$ cycloalkyl group), —$NR^{b1}$—CO— (wherein $R^{b1}$ has the meaning given above), —$NR^{b1}$—CO—O— (wherein $R^{b1}$ has the meaning given above), Z is a halogen, $SO_2NR^{b3}R^{b4}$ (wherein each of $R^{b3}$ and $R^{b4}$ is (1) a $C_{1-6}$ alkyl group which may be substituted by halogen(s), hydroxyl(s) or $C_{1-6}$ alkoxy(s), (2) a $C_{3-6}$ cycloalkyl group which may be substituted by halogen(s) or $C_{1-6}$ alkoxy(s), (3) a $C_{1-4}$ alkoxy group, (4) a hydrogen atom or, $R^{b3}$ and $R^{b4}$ are combined with each other together with a nitrogen atom to form a cyclic-amino group), $SO_2R^{b5}$ (wherein $R^{b5}$ is (1) a $C_{1-6}$ alkyl group which may be substituted by halogen(s), hydroxyl(s) or $C_{1-6}$ alkoxy(s), (2) a $C_{3-8}$ cycloalkyl group which may be substituted by halogen(s) or $C_{1-6}$ alkoxy(s)), a $CONR^{b3}R^{b4}$ (wherein each of $R^{b3}$ and $R^{b4}$ has the meaning given above) or —$NR^{b7}$—$SO_2R^{b6}$ (wherein $R^{b6}$ is (1) a $C_{1-6}$ alkyl, $R^{b7}$ is (1) a $C_{1-6}$ alkyl group which may be substituted by halogen(s) or $C_{1-6}$ alkoxy(s), (2) a $C_{3-8}$ cycloalkyl group which may be substituted by halogen(s) or $C_{1-6}$ alkoxy(s) or (3) a hydrogen atom), a $C_{1-6}$ alkoxy group, an amino group which may be substituted by $C_{2-4}$ alkanoyl(s), nitro(s), cyano(s), tetrazolyl(s) or morpholinyl(s).

6. A compound as claimed in claim 2, wherein $R^3$ is a $C_{6-14}$ aryl group which may be substituted by member(s) selected from Group 1.

7. A compound as claimed in claim 2, wherein $R^3$ is a phenyl group which may be substituted by member(s) selected from Group 1.

8. A compound as claimed in claim 1, wherein E is —$CH_2CH_2$—, —$CH_2CH_2CH_2$—, —$CH_2CH_2CH_2CH_2$— or —$CH_2CH_2CH_2CH_2CH_2$—.

9. A compound as claimed in claim 1, wherein E is —$CH_2CH_2CH_2$—.

10. A compound as claimed in claim 1, wherein $G^2$ is CO, $SO_2$, CONH or OCO.

11. A compound as claimed in claim 1, wherein $G^2$ is CO or NHCO.

12. A compound as claimed in claim 1, wherein $G^2$ is CO.

13. A compound as claimed in claim 1, wherein $G^1$ is CO or $SO_2$.

14. A compound as claimed in claim 2, wherein $R^4$ is a hydrocarbon group selected from Group 2 which may be substituted by member(s) selected from Group 1, a heterocyclic group selected from Group 6 which may be substituted by member(s) selected from Group 1, a $C_{1-6}$ alkoxy group which may be substituted by member(s) selected from Group 7, or an amino group which may be substituted by member(s) selected from Group 9.

15. A compound as claimed in claim 1, wherein $R^4$ is a $C_{1-3}$ alkyl.

16. A compound as claimed in claim 1, wherein $R^4$ is methyl.

17. A compound as claimed in claim 1, wherein n is zero.

18. A compound represented by the formula:

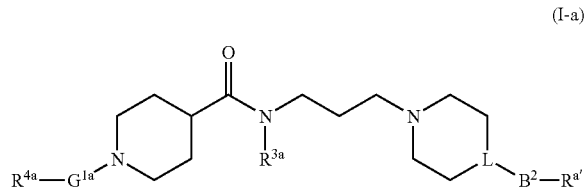

(I-a)

wherein $R^{4a}$ is (1) a $C_{1-6}$ alkyl group which may be substituted by halogen(s), $C_{1-6}$ alkoxy(s), oxo(s), amino(s), phenyl(s), pyridyl(s) or tetrazolyl(s), (2) a $C_{2-6}$ alkenyl group, (3) a $C_{3-8}$ cycloalkyl group which may be substituted by halogen(s), $C_{1-6}$ alkyl(s) or $C_{1-6}$ alkoxy(s), (4) a phenyl group which may be substituted by halogen(s), $C_{1-6}$ alkyl(s), $C_{1-6}$ alkoxy(s), nitro(s), cyano(s), hydroxyl(s), formyl-amino(s), $C_{2-4}$ alkanoyl-amino(s), carbamoyls(s) or sulfamoyl(s), (5) an amino group which may be substituted by $C_{1-6}$ alkyl(s), (6) a $C_{1-6}$ alkoxy group which may be substituted by phenyl(s), (7) a $C_{3-8}$ cycloalkyloxy group (8) a heterocyclic group which may be substituted by halogen(s), $C_{1-6}$ alkyl(s) or hydroxyl(s), $G^{1a}$ is CO or $SO_2$, $R^{3a}$ is a $C_{6-10}$ aryl group which may be substituted by (1)halogen(s), (2) $C_{1-6}$ alkyl(s) which may be substituted by halogen(s), (3) $C_{1-6}$ alkoxy(s) which may be substituted by halogen(s), (4) $C_{1-6}$ alkyl-thio(s), or (5) $C_{1-6}$ alkyl-sulfonyl(s), L is methine, $B^2$ is a bond, —$CH_2$—, —$SO_2$—, —SO—, —S—, —O—, —CO—, —$NR^{b1}$—$SO_2$— (wherein $R^{b1}$ is a hydrogen atom, a $C_{1-6}$ alkyl group, a $C_{2-6}$ alkenyl group, a $C_{2-6}$ alkynyl group or a $C_{3-6}$ cycloalkyl group), —CH(OH)—, —$NR^{b2}$— (wherein $R^{b2}$ is a hydrogen atom or a $C_{2-4}$ alkanoyl group), —$NR^{b1}$—CO— (wherein $R^{b1}$ has the meaning given above), —$NR^{b1}$—CO—O— (wherein $R^{b1}$ has the meaning given above), —$CH_2SO_2$— or —$CH_2S$—, $R^{a'}$ is ① an aromatic hydrocarbon group which may be substituted by halogen(s), $SO_2NR^{b3}R^{b4}$ (wherein each of $R^{b3}$ and $R^{b4}$ is (1) a $C_{1-6}$ alkyl group which may be substituted by 1) halogen(s), 2) hydroxyl(s) or 3) $C_{1-6}$ alkoxy(s), (2) a $C_{3-8}$ cycloalkyl group which may be substituted by 1) halogen(s), or 2) $C_{1-6}$ alkoxy(s), (3) a $C_{1-6}$ alkoxy group or (4) a hydrogen atom, or $R^{b3}$ and $R^{b4}$ may combine with each other together with a nitrogen atom to form a cyclic-amino group), $SO_2R^{b5}$ (wherein $R^{b5}$ is (1) a $C_{1-6}$ alkyl group which may be substituted by halogen(s), hydroxyl(s) or $C_{1-6}$ alkoxy(s), (2) a $C_{3-8}$ cycloalkyl group which may be substituted by halogen(s) or $C_{1-6}$ alkoxy(s)), $CONR^{b3}R^{b4}$ (wherein $R^{b3}$ and $R^{b4}$ have the meanings given above) or-$NR^{b7}$—$SO_2R^{b6}$ (wherein $R^{b6}$ is (1) a $C_{1-6}$ alkyl group which may be substituted by halogen(s) or $C_{1-6}$ alkoxy(s), (2) a $C_{3-8}$ cycloalkyl group which may be substituted by halogen(s) or $C_{1-6}$ alkoxy(s), $R^{b7}$ is (1) a $C_{1-6}$ alkyl group which may be substituted by halogen(s) or $C_{1-6}$ alkoxy(s), (2) a $C_{3-8}$ cycloalkyl group which may be substituted by halogen(s) or $C_{1-6}$ alkoxy(s) or (3) a hydrogen atom), a $C_{1-6}$ alkoxy group, an amino group which may be substituted by a $C_{2-4}$ alkanoyl(s), nitro group, cyano group, tetrazolyl group or morpholinyl group or ② an aromatic heterocyclic group which may be substituted by substituent(s) selected from the above mentioned substituents of aromatic hydrocarbon group or a salt thereof, provided that the compound is not N-(3-{4-[4-(Aminocarbonyl)benzyl]-1-piperidinyl}propyl)-N-(3,4-dichlorophenyl)-1-(methylsulfonyl)-4-piperidinecarboxamide or a salt thereof, 1-Acetyl-N-(3-{4-[4-(aminocarbonyl)benzyl]-1-piperidinyl}propyl)-N-(3-chloro-4-methylphenyl)-4-piperidinecarboxamide or a salt thereof, and N-(3-{4-[4-(Aminocarbonyl)benzyl]-1-piperidinyl}propyl)-N-(3-chloro-4-methylphenyl)-1-(methylsulfonyl)-4-piperidinecarboxamide or a salt thereof.

19. A compound as claimed in claim 18, wherein $R^{3a}$ is a phenyl group which may be substituted by halogen(s), trifluoromethyl(s) or $C_{1-6}$ alkyl(s).

20. A compound as claimed in claim 18, wherein $B^2$ is —$CH_2$—, —$SO_2$—, —SO—, —S—, —O—, —CO—, —$NR^{b1}$—$SO_2$—, —$NR^{b1}$—CO— or $NR^{b1}$—CO—O— (wherein $R^{b1}$ is a hydrogen atom, a $C_{1-4}$ alkyl group, a $C_{2-6}$ alkenyl group, a $C_{2-6}$ alkynyl group or a $C_{3-6}$ cycloalkyl group).

21. A compound as claimed in claim 18, wherein $R^{a'}$ is a phenyl group which may be substituted by (1) halogen(s), (2) $SO_2R^c$ (wherein $R^c$ is a $C_{1-6}$ alkyl group or a $C_{3-8}$ cycloalkyl group), (3) $N(R^d)SO_2R^c$ (wherein $R^d$ is a hydrogen atom or a $C_{1-4}$ alkyl group, $R^e$ has the meaning given above), (4) $SO_2NR^fR^g$ (wherein each of $R^f$ and $R^g$ is a hydrogen atom or a $C_{1-6}$ alkyl group or $R^f$ and $R^g$ may combine with each other together with a nitrogen atom to form a cyclic-amino group) or (5) $CONR^fR^g$ (wherein each of $R^f$ and $R^g$ is a hydrogen atom or a $C_{1-6}$ alkyl group, or $R^f$ and $R^g$ may combine with each other together with a nitrogen atom to form a cyclic-amino group).

22. A compound as claimed in claim 18, wherein $B^2$ is $SO_2$, $CH_2$ or $N(R^d)$—$SO_2$ (wherein $R^d$ is a hydrogen atom or a $C_{1-4}$ alkyl group); $R^{a'}$ is a phenyl group which may be substituted by (1) halogen(s), (2) $SO_2R^e$ (wherein $R^e$ is a $C_{1-6}$ alkyl group or a $C_{3-8}$ cycloalkyl group), (3) $N(R^d)SO_2R^e$ (wherein $R^d$ is a hydrogen atom or a $C_{1-4}$ alkyl group, and $R^e$ has the meaning given above), (4) $SO_2NR^fR^g$ (wherein each of $R^f$ and $R^g$ is a hydrogen atom or a $C_{1-6}$ alkyl group or $R^f$ and $R^g$ may combine with each other together with a nitrogen atom to form a cyclic-amino group) or (5) $CONR^fR^g$ (wherein each of $R^f$ and $R^g$ is a hydrogen atom or a $C_{1-6}$ alkyl group or $R^f$ and $R^g$ may combine with each other together with a nitrogen atom to form a cyclic-amino group); $R^{3a}$ is a phenyl group substituted by one or two members selected from the group of halogen atom and a $C_{1-4}$ alkyl.

23. A compound as claimed in claim 18, wherein $G^{1a}$ is $SO_2$ or CO, L is methine, $B^2$ is $SO_2$ or $CH_2$, $R^{a'}$ is a group represented by the formula:

(3)

(wherein Z is a $C_{1-4}$ alkylsulfonyl group, a sulfamoyl group which may be substituted by $C_{1-4}$ alkyl(s), or carbamoyl group); $R^{3a}$ is a phenyl group which may be substituted by one or two members selected from the group consisting of halogen(s) and $C_{1-4}$ alkyl(s); $R^{4a}$ is methyl.

24. A compound as claimed in claim 1, which is N-(3,4-dichlorophenyl)-1-(methylsulfonyl)-N-{3-[4-({4-[(methylsulfonyl)amino]phenyl}sulfonyl)-1-piperidinyl]propyl}-4-piperidinecarboxainide or a salt thereof.

25. A compound as claimed in claim 1, which is N-(3-chlorophenyl)-1-(methylsulfonyl)-N-(3-{4-[4-(methylsulfonyl)benzyl]-1-piperidinyl}propyl)-4-piperidinecarboxamide or a salt thereof.

26. A compound as claimed in claim 1, which is N-(3,4-dichlorophenyl)-N-(3-{4-[4-(ethylsulfonyl)benzyl]-1-piperidinyl}propyl)-1-(methylsulfonyl)-4-piperidinecarboxamide or a salt thereof.

27. A compound as claimed in claim 1, which is N-(3,4-dichlorophenyl)-N-(3-{4-[4-(isopropylsulfonyl)benzyl]-1-piperidinyl}propyl)-1-(methylsulfonyl)-4-piperidinecarboxamide or a salt thereof.

28. A compound as claimed in claim 1, which is N-(3-chlorophenyl)-N-(3-{4-[4-(isopropylsulfonyl)benzyl]-1-piperidinyl}propyl)-1-(methylsulfonyl)-4-piperidinecarboxamide or a salt thereof.

29. A compound as claimed in claim 1, which is N-(3-chlorophenyl)-N-(3-{4-[4-(ethylsulfonyl)benzyl]-1-piperidinyl}propyl)-1-(methylsulfonyl)-4-piperidinecarboxamide or a salt thereof.

30. A compound as claimed in claim 1, which is N-(3,4-dichlorophenyl)-1-(methylsulfonyl)-N-(3-{4-[4-(methylsulfonyl)benzyl]-1-piperidinyl}propyl)-4-piperidinecarboxamide or a salt thereof.

31. A pharmaceutical composition comprising a compound represented by the formula:

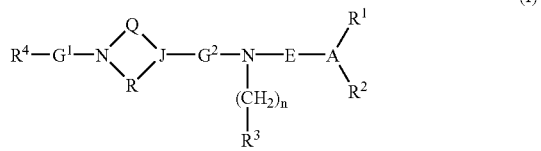

(I)

wherein $R^1$ and $R^2$ combine with each other together with A to form a piperidinyl group which may be substituted; A is N or $N^+—R^5.Y^-$ wherein $R^5$ is a hydrocarbon group and $Y^-$ is a counter anion; $R^3$ is a cyclic hydrocarbon group which may be substituted or a heterocyclic group which may be substituted; n is 0 or 1; $R^4$ is a hydrogen atom, a hydrocarbon group which may be substituted, a heterocyclic group which may be substituted, an alkoxy group which may be substituted, an aryloxy group which may be substituted, or an amino group which may be substituted; E is a divalent aliphatic hydrocarbon group which may be substituted by group(s) other than oxo; $G^1$ is a bond, CO or $SO_2$; $G^2$ is CO, $SO_2$, NHCO, CONH or OCO; -Q-J-R- combine with the nitrogen to which they are attached to form a piperidinyl group, or a salt thereof, provided that the compound is not N-(3-{4-[4-(Aminocarbonyl)benzyl]-1-piperidinyl}propyl)-N-(3,4-dichlorophenyl)-1-(methylsulfonyl)-4-piperidinecarboxamide or a salt thereof, 1-Acetyl-N-(3-{4-[4-(aminocarbonyl)benzyl]-1-piperidinyl}propyl)-N-(3-chloro-4-methylphenyl)-4-piperidinecarboxamide or a salt thereof, and N-(3-{4-[4-(Aminocarbonyl)benzyl]-1-piperidinyl}propyl)-N-(3-chloro-4-methylphenyl)-1-(methylsulfonyl)-4-piperidinecarboxamide or a salt thereof.

32. A method for the treatment of infectious disease of HIV, which comprises administering to a mammal in need thereof an effective amount of the compound as claimed in claim 1.

33. A method for the treatment of AIDS, which comprises administering to a mammal in need thereof an effective amount of the compound as claimed in claim 1.

34. A method for producing a compound of the formula:

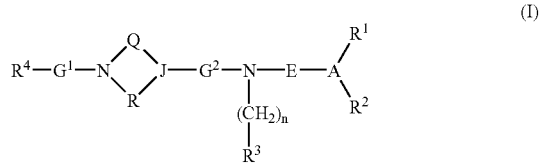

(I)

wherein $R^1$ and $R^2$ combine with each other together with A to form a piperidinyl group which may be substituted; A is N or $N^+—R^5.Y^-$ wherein $R^5$ is a hydrocarbon group and $Y^-$ is a counter anion; $R^3$ is a cyclic hydrocarbon group which may be substituted or a heterocyclic group which may be substituted; n is 0 or 1; $R^4$ is a hydrogen atom, a hydrocarbon group which may be substituted, a heterocyclic group which may be substituted, an alkoxy group which may be substituted, an aryloxy group which may be substituted, or an amino group which may be substituted; E is a divalent aliphatic hydrocarbon group which may be substituted by group(s) other than oxo; $G^1$ is a bond, CO or $SO_2$; $G^2$ is CO, $SO_2$, or NHCO; -Q-J-R- combine with the nitrogen to which they are attached to form a piperidinyl group or a salt thereof, which comprises reacting a compound of the formula:

(II)

wherein each symbol has the meaning given above or a salt thereof with a compound of the formula:

(III)

wherein $R^6$ is a carboxyl group, or sulfonic acid group, or a salt thereof, or a reactive derivative of a carboxyl group selected from the group consisting of an acid halide, an acid azide, an acid anhydride, a mixed acid anhydride, an active amide, an active ester, an active thio ester, and an isocyanate, and the other symbols have the meanings given above or a salt thereof.

35. A method for making a pharmaceutical composition, which comprises mixing the compound as claimed in claim 1 with a pharmaceutically acceptable carrier, excipient, binder or diluent.

* * * * *